United States Patent
Alfaro et al.

(10) Patent No.: US 12,325,702 B2
(45) Date of Patent: *Jun. 10, 2025

(54) ATF6 INHIBITORS AND USES THEREOF

(71) Applicant: Altos Labs, Inc., Redwood City, CA (US)

(72) Inventors: Jennifer Alfaro, Santiago (CL); Sebastian Belmar, Santiago (CL); Gonzalo Esteban Núñez Vasquez, Santiago (CL); Brahmam Pujala, Greater Noida (IN); Balaji Dashrath Sathe, Greater Noida (IN); Pooja Thakral, New Delhi (IN); Rajesh Kumar Patidar, Uttar Pradesh (IN); Sebastian Bernales, San Francisco, CA (US); Sarvajit Chakravarty, Edmond, OK (US)

(73) Assignee: Altos Labs, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/324,826

(22) Filed: May 26, 2023

(65) Prior Publication Data

US 2024/0124434 A1 Apr. 18, 2024

Related U.S. Application Data

(63) Continuation of application No. 16/992,000, filed on Aug. 12, 2020, now abandoned, which is a continuation of application No. 16/377,156, filed on Apr. 6, 2019, now Pat. No. 10,829,485.

(60) Provisional application No. 62/654,263, filed on Apr. 6, 2018.

(51) Int. Cl.
| | |
|---|---|
| *C07D 413/14* | (2006.01) |
| *A61P 35/00* | (2006.01) |
| *C07D 401/12* | (2006.01) |
| *C07D 401/14* | (2006.01) |
| *C07D 405/12* | (2006.01) |
| *C07D 405/14* | (2006.01) |
| *C07D 413/12* | (2006.01) |
| *C07D 417/14* | (2006.01) |

(52) U.S. Cl.
CPC ............ *C07D 413/14* (2013.01); *A61P 35/00* (2018.01); *C07D 401/12* (2013.01); *C07D 401/14* (2013.01); *C07D 405/12* (2013.01); *C07D 405/14* (2013.01); *C07D 413/12* (2013.01); *C07D 417/14* (2013.01)

(58) Field of Classification Search
CPC .................................................. C07D 413/14
USPC ......................................................... 514/256
See application file for complete search history.

(56) References Cited

U.S. PATENT DOCUMENTS

| | | | |
|---|---|---|---|
| 6,458,951 B2 | 10/2002 | Bunnage | |
| 7,151,113 B2 | 12/2006 | Dyckman | |
| 7,285,666 B2 | 10/2007 | Hibi et al. | |
| 8,288,419 B2 | 10/2012 | Bur | |
| 8,642,660 B2 | 2/2014 | Goldfarb | |
| 8,907,306 B2 | 12/2014 | Yoshikawa | |
| 10,825,485 B2 * | 11/2020 | Hollis | G11C 7/1057 |
| 2015/0272959 A1 | 10/2015 | Smith | |
| 2017/0166552 A1 | 6/2017 | Ban et al. | |
| 2022/0389001 A1 | 12/2022 | Pujala et al. | |
| 2023/0028584 A1 | 1/2023 | Pujala et al. | |

FOREIGN PATENT DOCUMENTS

| | | |
|---|---|---|
| RU | 2308457 | 10/2007 |
| WO | 2007073300 | 6/2007 |
| WO | 2011/08776 A1 | 7/2011 |
| WO | 2014/023258 A1 | 2/2014 |
| WO | 2016172560 | 10/2016 |
| WO | 2016/208591 A1 | 12/2016 |
| WO | 2017/103611 A1 | 6/2017 |
| WO | 2017/146128 A1 | 8/2017 |
| WO | 2019195810 | 10/2019 |
| WO | 2019209962 | 10/2019 |
| WO | 2021069701 | 4/2021 |
| WO | 2021069721 | 4/2021 |

OTHER PUBLICATIONS

International Search Report and Written Opinion mailed on Jan. 25, 2021, for PCT Application No. PCT/EP2020/078507, filed on Oct. 9, 2020, 17 pages.
International Search Report and Written Opinion mailed on Jan. 29, 2021, for PCT Application No. PCT/EP2020/0784 78, filed on Oct. 9, 2020, 18 pages.
Kummerer, K. (2010). "Pharmaceuticals in the Environment," Annual Review of Environment and Resources 35:57-75.
Adachi, Y. et al. (2008). "ATF6 Is A Transcription Factor Specializing in the Regulation of Quality Control Proteins in the Endoplasmic Reticulum," Cell Structure and Function 33(1):75-89.
Ambrose, R. et al. (Feb. 2013, e-pub. Dec. 2012). "ATF6 Signaling Is Required for Efficient West Nile Virus Replication by Promoting Cell Survival and Inhibition of Innate immune Responses," J. Virol. 87(4):2206-2214.

(Continued)

*Primary Examiner* — Niloofar Rahmani
(74) *Attorney, Agent, or Firm* — Meunier Carlin & Curfman LLC

(57) ABSTRACT

Compounds as inhibitors of Activating Transcription Factor 6 (ATF6) are provided. The compounds may find use as therapeutic agents for the treatment of diseases or disorders mediated by ATF6 and may find particular use in the treatment of viral infections, neurodegenerative diseases, vascular diseases, or cancer.

38 Claims, 4 Drawing Sheets

Specification includes a Sequence Listing.

(56) References Cited

OTHER PUBLICATIONS

Birdsey, G.M. et al. (Apr. 2008, e-pub, Jan. 14, 2008). "Transcription Factor Erg Regulates Angiogenesis and Endothelial Apoptosis Though VE-cadherin," Blood, 2008, 111 3498-3506.
Cai, JW et al. (1993). "Induction of Glucose Regulated Proteins During Growth of a Murine Tumor," J Cell Physiol. 154(2):229-237.
Chu, Ws., et al. (Mar. 2007). "Activating Transcription Factor 6 (ATF6) Sequence Polymorphisms in Type 2 Diabetes and Pre-Diabetic Traits," Diabetes 56(3):856-862.
Dadey, DY et al. (Dec. 21, 2015). "The ATF6 Pathway Of The ER Stress Response Contributes To Enllaneed Viability in Glioblastoma" Oncotarget 7(2):2080-2092.
Fitzpatrick, J.M. et al. (Aug. 29, 2014), "Small Molecule inhibition of the Na+/H+ Exchange Regulatory Factor • 1 and Parathyroid Hormone 1 Receptor Interaction," Biochemistry 53(37):5916-5922.
Galindo L et al. (Jul. 2012). "The ATF6 Branch Of Unfolded Protein Response and Apoptosis Are Activated To Promote African Swine Fever Virus Infection," Ceil Death Dis 5:3:e341, 10 pages.
Gallagher, C.M. et al. (Jul. 20, 2016). "Ceapins are a New Class Of Unfolded Protein Response Inhibitors, Selectively Targeting the ATF6 [alpha] branch," elife 5:e11878, 33 pages.
Hardy, J. et al. (Nov. 2, 1998, e-pub. Apr. 7, 2009). "Genetic Classification of Primary Neurodegenerative Disease," Science 282(5391) 1075-1079.
Hensel, JA et al. (Jan. 2013, e-pub. Nov. 27, 2012). "Clinical opportunities and challenges in targeting tumour dormancy," Nat Rev Clin Oncol. 10(1):41-51.
International Preliminary Report on Patentability mailed Oct. 15, 2020, for Patent Application No. PCT/US2019/026196, filed Apr. 6, 2019, 7 pages.
International Search Report mailed Sep. 30, 2019, for Patent Application No. PCT/US2019/026196, filed Apr. 6, 2019, 5 pages.
Jamora, C. et al. (Jul. 1996) "Inhibition of Tumor Progression By Suppression Of Stress Protein GRP78IBiP Induction In Fibrosarcoma B/C10ME," PNAS USA 93(15): 7690-7694.
Johnson, WG. (2000). "Late-Onset Neurodegenerative Diseases the Role of Protein Insolubility," J. Anal. 196 (part4):609-616.
Karau, E. et al. (May 22, 2014). "VEGF Signals through ATF6 and PERK to Promote Endothelial Cell Survival and Angiogenesis in the Absence of ER Stress," Molecular Cell 54:559-572.
Liu, C.L. et al. (2016). "High-content screening identifies inhibitors of tlle nuclear translocation of ATF6," Int J Mol Med 37(2):407-414.
McKimpson, WM. et al. (Mar. 3, 2017). A New Role for the ER Unfold Protein Response Mediator ATF6: Induction of a Generalized Antioxidant Program, Circ Res. 120(5):759-761, 6 pages.
Meng, S. et al. (Dec. 15, 2004). "'Circulating Tumor Cells in Patients with Breast Cancer Dormancy," Clin Cancer Res 10(24):8152-8162.
Niu, T. et al. (Dec. 2012). "Chemo selective Preparation of Unsymmetrical Bis(1,2,3-triazole) Derivatives and Application in Bis(1,2,3-trazole)-Modified Peptidomimetic Synthesis," European Journal of Organic Chemistry (34):6767-6776.

Ott, PA et al. (Sep. 22, 2015). Inhibition of Immune Checkpoints and Vascular Endothelial Growth Factor as Combination Therapy for Metastatic Melanoma: An Overview of Rationale, Preclinical Evidence, and Initial Clinical Data, Front Oncol 5202, 7 pages.
Ramaswamy, S. et al. (Dec. 18, 2001). "Multiclass Cancer Diagnosis Using Tumor Gene Expression Signatures," PNAS USA 98(26): 15149-15154.
Schewe, D.M. et al. (Jul. 29, 2008). "ATF6α-Rheb-mTOR Signaling Promotes Survival of Dormant Tumor Cells In Vivo," PNAS USA 105(30):10519-10524.
Sugawara, S. et al. (Dec. 15, 1993). "Suppression of Stress Protein GRP78 Induction in Tumor B/C10ME Eliminates Resistance to Cell Mediated Cytotoxicity" Cancer Res 53(24) 6001-6005.
Tay, K.H. et al. (Feb. 2014, e-pub. Nov. 12, 2013) "Sustained IRE. 1 and ATF6 signaling is important for survival of melanoma cells under ioing ER stress," Celi Signal 26(2):287-294.
Vekich, J. A. et al. (Aug. 2012, e-pub. May 8, 2012). "Protein Disulfide Isomerase-Associated 6 is an ATF6-Inducible ER Stress Response Protein That Protects Cardiac Myocytes From ischemia/Reperfusion-tlediated Cell Death," J. Mol. Cell. Cardiol. 53(2)259-267, 23 pages.
Written Opinion of the International Searching Authority mailed Sep. 30, 2019, for Patent Application No. PCT/US2019/026196, filed Apr. 6, 2019, 5 pages.
I/VU, J. et al. (Sep. 2007). "ATF6a Optimizes Long-Term Endoplasmic Reticulum Function to Protect Cells from Chronic Stress," Dev Cell 13(3):351-364.
Wu, Y. et al. (Mar. 1, 2012), "Dynamic modeling of Human 5-Upoxygenase-inhibitor interactions Helps to Discovery Novel Inhibitors," Journal of Medicinal Chemistry 55(6):2597-2605.
Yang, W. et al. (2013, e-pub. Nov. 23, 2012). Genomics of Drug Sensitivity in Cancer (GDSC): a resource for therapeutic biomarker discovery in cancer cells: Nucleic Acids Research 41(D1):D955-D961.
Ye, J. et al. (Dec. 2000). ER Stress Induces Cleavage of Membrane-Bound ATF6 by the Same Proteases that Process SREBPs' Mol Cell 6(6): 1355-1364.
Yoshida, H. et al. (Dec. 28, 2001). "XBP1 mRNA is induced by ATF6 and Spliced by iRE1 in Response to ER Stress to Produce a Highly Active Transcription Factor," Cell 107(7) 881-891.
Examination Report issued on May 19, 2023, in Australian Patent Application No. 2019247533.
Communication under Rule 71(3) EPC issued on Sep. 18, 2024, in European Patent Application No. 19719005.1.
Registry(STN)[online], 2011, p. 1, CAS login No. 13232 58-07-6.
Registry(STN)[online], 2007, pp. 1-6, CAS registration No. 195-5888-36-5, 942781-79-5, 942762-90-5, 942752-21-8, 942730-1 7-8, 942729-50-2, 942715-39-1, 942.
Registry(STN)[online], 2003, pp. 1-2, CAS login No. 89804 8-33-4, 898048-28-7.
Registry(STN)[online], 2003, pp. 1-2, CAS registration No. 51 5850-00-7, 515849-63-5, 515848-81-4.
Office Action mailed Mar. 11, 2025, in Japanese Patent Application No. 2024-066563

\* cited by examiner

ATF6 INHIBITORS AND USES THEREOF

CROSS-REFERENCE TO RELATED APPLICATIONS

This application is a continuation of U.S. patent application Ser. No. 16/992,000, filed Aug. 12, 2020, which is a continuation of U.S. patent application Ser. No. 16/377,156, filed Apr. 6, 2019, now U.S. Pat. No. 10,829,485, issued Nov. 10, 2020, which claims prior benefit of U.S. Provisional Patent Application No. 62/654,263, filed Apr. 6, 2018, the disclosures of each of which are hereby incorporated herein by reference in their entirety.

REFERENCE TO AN ELECTRONIC SEQUENCE LISTING

The contents of the electronic sequence listing (263232000202SEQLIST.xml; Size: 2,303 bytes; and Date of Creation: May 25, 2023) is herein incorporated by reference in its entirety.

FIELD OF THE INVENTION

This disclosure relates generally to therapeutic agents that may be useful as inhibitors of Activating Transcription Factor 6 (ATF6).

BACKGROUND

Multiple myeloma (MM) remains a predominantly incurable malignancy despite high-dose chemotherapy, autologous stem cell transplant and novel agents. Proteasome inhibitors (PI) such as Bortezomib have increased the response rate and survival of patients with MM. The overall patient response rate of newly diagnosed MM to Bortezomib and Dexamethasone is about 67%. In relapsed refractory MM, the response rate is reduced to about 40-60%. Therefore, there are a significant number of MM patients who are resistant to Bortezomib. MM cells are inherently sensitive to PIs because of their large volume of immunoglobulin production, which requires the constitutive expression of physiologic unfolded protein response (UPR) genes. This appears to lower their threshold for the induction of a proapoptotic/terminal UPR in response to PI-induced endoplasmic reticulum (ER) stress. One of the hallmarks of UPR induction is the increased transcription and translation of ER molecular chaperones. These genes are induced by the UPR transcription factors XBP1 and ATF6. Although XBP1 splicing and its resulting activation have been shown to be inhibited in PI-treated MM cells, findings show that the high constitutive expression of 2 XBP1 target genes products, GRP78 and GRP94, is not reduced by PI treatment and the observation that the XBP1-dependent UPR target gene ERdj4 was normally induced by PIs suggest that the UPR remains functional in PI-treated MM cells. Because both XBP1 and ATF6 can bind to ER stress response elements in the promoters of UPR target genes, it has been suggested that ATF6 may compensate for decreased XBP1 activity in PI-treated MM cells. Consistent with this, it has been shown that the induction of GRP78 and GRP94 is only slightly impaired in XBP1' B cells and that the expression of GRP94 requires either, but not both, ATF6 or XBP1. Interestingly previous studies have shown that XBP1 predicts sensitivity to Bortezomib and its level correlates proportionally with sensitivity to Bortezomib. Recently Harnoss J M et al. demonstrated using genetic and pharmacologic disruption that in vitro and in vivo the IRE1a-XBP1s pathway plays a critical role in MM growth. Indeed, the inhibition of IRE1α kinase activity using a small molecule was demonstrated to be a potential effective and safe therapy for treating MM clinically.

In addition to the amount, PI sensitivity also appears to involve the efficiency of immunoglobulin folding within MM cells. The high constitutive expression of the ER resident chaperones GRP78 and GRP94 in MM cell lines is consistent with reports that physiologic UPR gene expression is required for professional secretory cell function. Elevated levels of ER chaperones are characteristic of plasma cells and their expression is essential for proper antibody assembly and secretion. GRP78 has been shown to stably bind to immunoglobulin heavy chains that have not yet associated with immunoglobulin light chains and to assist in immunoglobulin assembly. Furthermore, both GRP78 and GRP94 are important for immunoglobulin light chain folding and targeting unassembled subunits for degradation. The fact that the expression of GRP78 and GRP94 is only slightly increased in MM cells treated with PIs and classical ER stress agents suggests they already express near-maximal levels of cytoprotective UPR proteins to function as secretory cells. Thus, these cells may have a lower threshold (compared with non-secretory cells) for induction of the terminal UPR following any additional stress to the ER. Hence more resistant myeloma clones as well as other non-secretory malignancies may be sensitized to bortezomib by combining it with agents that interfere with the UPR, such as modulators of ATF6 signaling pathway.

The accumulation of misfolded proteins in the EP of mammalian cells causes the folding machinery to become overwhelmed and leads to a stress response. Cells attempt to decrease the ER protein load by sending signals from the ER to the nucleus, activating a vast gene expression program that increases the protein-folding capacity in the ER. However, if this system fails and homeostasis cannot be re-established, cells die by engaging apoptosis. The UPR is an evolutionarily conserved signal transduction pathway that maintains protein homeostasis in response to ER stress.

Three intertwined signaling pathways comprise the UPR: (1) PERK (protein kinase RNA-like ER kinase); (2) IRE1 (inositol-requiring enzyme 1α); and (3) ATF6 (Activating transcription factor 6) (McKimpson, W. M. et al, Circ Res, 2017, 120(5): 759-761). Activation of the ATF6 pathway leads to the upregulation of genes, such as BIP (Grp78), CHOP or XBP-1, that enhance the capacity of the endoplasmic reticulum to fold proteins or mediate quality control. ATF6 works in partnership with IRE1, as one of the target genes of ATF6 is XBP1, the key substrate of IRE1 (Yoshida, H., et al., Cell, 2001, 107(7): 881-891). PERK performs several other roles including pausing the production of new proteins to temporarily lower the protein-folding burden.

ATF6 is a type-II transmembrane protein localized in the ER that functions as an ER stress sensor and transcription factor (Adachi, Y., et al., Cell Struct Funct, 2008, 33(1): 75-89; Wu, J., et al., Dev Cell, 2007, 13(3): 351-64). When demand exceeds the folding capacity of the ER, ATF6 is transported from the ER to the Golgi apparatus, where sequential cleavage by two Golgi-resident proteases, site-1 and site-2 proteases (S1P and S2P), releases its N-terminal domain (ATF6N) from the Golgi membrane to be imported into the nucleus where it activates transcription of its target genes (Ye, J., et al., Mol Cell, 2000, 6(6): 1355-64). This activation involves binding of ATF6 to a consensus sequence called the ER-stress responsive element (ERSE). The consensus sequence of ERSE is CCAATCGGCGGCGGC-CACG (SEQ ID NO. 1).

ATF6—activated transcription targets play a role in the pathogenesis and development of various diseases, including viral infection, cancer, neurodegeneration, Alzheimer's disease, cerebral ischemia, hereditary cerebellar atrophy and ataxia, type 2 diabetes mellitus, and diabetic nephropathy, as well as cardiovascular diseases, such as myocardial atrophy, heart failure, ischemic heart disease and atherosclerosis (Chu, W. S., et al., Diabetes, 2007, 56(3): 856-62; Vekich, J. A., et al., J Mol Cell Cardiol, 2012, 53(2): 259-67, Liu, C. L., et al., Int J Mol Med, 2016, 37(2): 407-14). Therefore, inhibition of ATF6-mediated transcription may provide a therapeutic strategy for these and other diseases in which modulation of ATF6 is implicated.

BRIEF SUMMARY

In one aspect, provided is a compound of the Formula (A):

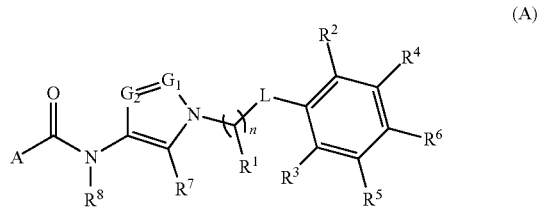

or a pharmaceutically acceptable salt thereof, wherein A, $R^1$, n, L, $R^2$, $R^3$, $R^4$, $R^5$, $R^6$, $R^7$, $R^8$, $G_1$, and $G_2$ are as detailed herein.

In some embodiments, provided is a compound of the formula (I):

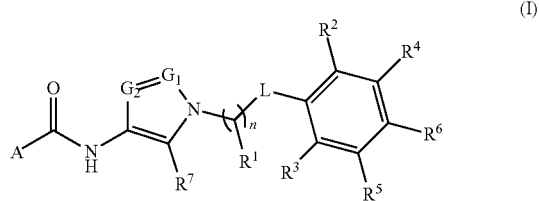

or a pharmaceutically acceptable salt thereof, wherein A, $R^1$, n, L, $R^2$, $R^3$, $R^4$, $R^5$, $R^6$, $R^7$, $G_1$, and $G_2$ are as detailed herein.

In some embodiments, the compound of Formula (A), (I), or a pharmaceutically acceptable salt thereof, is of the Formula (Ia), (Ib), (Ic), (Id), (Ie), (If), (Ig), (Ih), (Ii), (Ij), or (Ik), as detailed herein.

In another aspect, provided is a method of treating a disease or disorder mediated by activating transcription factor 6 (ATF6) in an individual in need thereof, wherein the method comprises administering to the individual an effective amount of a compound of Formula (A), (I) or a pharmaceutically acceptable salt thereof or a pharmaceutical composition comprising the compound. In a further aspect of the methods, the compound of Formula (A), (I) or a salt thereof is a compound of the Formula (Ia), (Ib), (Ic), (Id), (Ie), (If), (Ig), (Ih), (Ii), (Ij), or (Ik), or a pharmaceutically acceptable salt of any of the foregoing or a pharmaceutical composition comprising the compound. In some embodiments, the disease or disorder mediated by activating transcription factor 6 (ATF6) is viral infection, cancer, a neurodegenerative disease, or a vascular disease. In certain embodiments, the disease or disorder is viral infection, hereditary cerebellar atrophy and ataxia, Alzheimer's disease, type 2 diabetes mellitus, diabetic nephropathy, myocardial atrophy, heart failure, atherosclerosis, ischemia, ischemic heart disease, or cerebral ischemia. In some embodiments, the disease or disorder characterized by activating transcription factor 6 (ATF6) is cancer. In some embodiments, ATF6 is ATF6a.

In another aspect, provided is a method of treating a disease or disorder characterized by activating transcription factor 6 (ATF6) in an individual in need thereof, wherein the method comprises administering to the individual an effective amount of a compound of Formula (A), (I) or a pharmaceutically acceptable salt thereof or a pharmaceutical composition comprising the compound. In a further aspect of the methods, the compound of Formula (A), (I) or a salt thereof is a compound of the Formula (Ia), (Ib), (Ic), (Id), (Ie), (If), (Ig), (Ih), (Ii), (Ij), or (Ik), or a pharmaceutically acceptable salt of any of the foregoing or a pharmaceutical composition comprising the compound. In some embodiments, the disease or disorder characterized by activation of ATF6 is viral infection, cancer, a neurodegenerative disease, or a vascular disease. In certain embodiments, the disease or disorder is viral infection, hereditary cerebellar atrophy and ataxia, Alzheimer's disease, type 2 diabetes mellitus, diabetic nephropathy, myocardial atrophy, heart failure, atherosclerosis, ischemia, ischemic heart disease, or cerebral ischemia. In some embodiments, the disease or disorder characterized by activating transcription factor 6 (ATF6) is cancer. In some embodiments, ATF6 is ATF6a.

In another aspect, provided is a method of treating cancer in an individual in need thereof, comprising administering to the individual a therapeutically effective amount of a compound of Formula (A), (I) or a pharmaceutically acceptable salt thereof or a pharmaceutical composition comprising the compound. In a further aspect of the methods, the compound of Formula (A), (I) or a salt thereof is a compound of the Formula (Ia), (Ib), (Ic), (Id), (Ie), (If), (Ig), (Ih), (Ii), (Ij), or (Ik), or a pharmaceutically acceptable salt of any of the foregoing or a pharmaceutical composition comprising the compound.

In some embodiments, the cancer is breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma. In some embodiments, one or more cancer cells in the individual are dormant cancer cells.

In some embodiments, the individual has had a prior treatment. In some embodiments, the cancer is resistant or refractory to the prior treatment. In some embodiments, the cancer is resistant to treatment with a ubiquitin-proteasome pathway inhibitor, a taxane, a Cox-2 inhibitor, a platinum-based antineoplastic drug, an anthracycline, a pyrimidine analog, a topoisomerase inhibitor, an mTOR inhibitor, an immune-check point inhibitor, or an agent that is used in immune oncology.

In some embodiments, the method further comprises administering radiation. In some embodiments, the method further comprises administering a second anticancer agent. In some embodiments, the second anticancer agent targets an immune checkpoint protein.

In another aspect, provided is a method of treating a disease or disorder associated with angiogenesis in an individual in need thereof, wherein the method comprises administering to the individual an effective amount of a compound of Formula (A), (I) or a pharmaceutically acceptable salt thereof or a pharmaceutical composition comprising the compound. In a further aspect of the methods, the compound of Formula (I) or a salt thereof is a compound of the Formula (Ia), (Ib), (Ic), (Id), (Ie), (If), (Ig), (Ih), (Ii), (Ij), or (Ik), or a pharmaceutically acceptable salt of any of the foregoing or a pharmaceutical composition comprising the compound. In some embodiments, the method further comprises administering a second anti-angiogenesis agent.

In some embodiments of the methods disclosed herein, the method further comprises administering a second agent that modulates the Unfolded Protein Response or the Integrated Stress Response. In some embodiments, the second agent inhibits the IRE1/XBP1 pathway.

In another aspect, provided is a method of inhibiting ATF6 in an individual comprising administering to the individual a compound of Formula (A), (I) or a pharmaceutically acceptable salt thereof or a pharmaceutical composition comprising the compound. In a further aspect of the methods, the compound of Formula (A), (I) or a salt thereof is a compound of the Formula (Ia), (Ib), (Ic), (Id), (Ie), (If), (Ig), (Ih), (Ii), (Ij), or (Ik), or a pharmaceutically acceptable salt of any of the foregoing or a pharmaceutical composition comprising the compound.

In another aspect, provided is a method of inhibiting ATF6 in a cell comprising delivering to the cell a compound of Formula (A), (I) or a pharmaceutically acceptable salt thereof or a pharmaceutical composition comprising the compound. In a further aspect of the methods, the compound of Formula (A), (I) or a salt thereof is a compound of the Formula (Ia), (Ib), (Ic), (Id), (Ie), (If), (Ig), (Ih), (Ii), (Ij), or (Ik), or a pharmaceutically acceptable salt of any of the foregoing or a pharmaceutical composition comprising the compound.

Also provided are pharmaceutical compositions comprising: (A) a compound detailed herein, such as a compound of Formula (A), (I) or a pharmaceutically acceptable salt thereof, or a compound of Formula (Ia), (Ib), (Ic), (Id), (Ie), (If), (Ig), (Ih), (Ii), (Ij), or (Ik) or a pharmaceutically acceptable salt thereof; and (B) a pharmaceutically acceptable carrier or excipient. Kits comprising a compound detailed herein or a salt thereof and optionally instructions for use are also provided. Compounds as detailed herein or a pharmaceutically acceptable salt thereof are also provided for the manufacture of a medicament for the treatment of a disease or disorder characterized by activation of ATF6. In some embodiments, the disease or disorder is cancer, a neurodegenerative disease, or a vascular disease. In certain embodiments, the disease or disorder is viral infection, hereditary cerebellar atrophy and ataxia, Alzheimer's disease, type 2 diabetes mellitus, diabetic nephropathy, myocardial atrophy, heart failure, atherosclerosis, ischemia, ischemic heart disease, or cerebral ischemia.

DETAILED DESCRIPTION

Definitions

Figure 1:
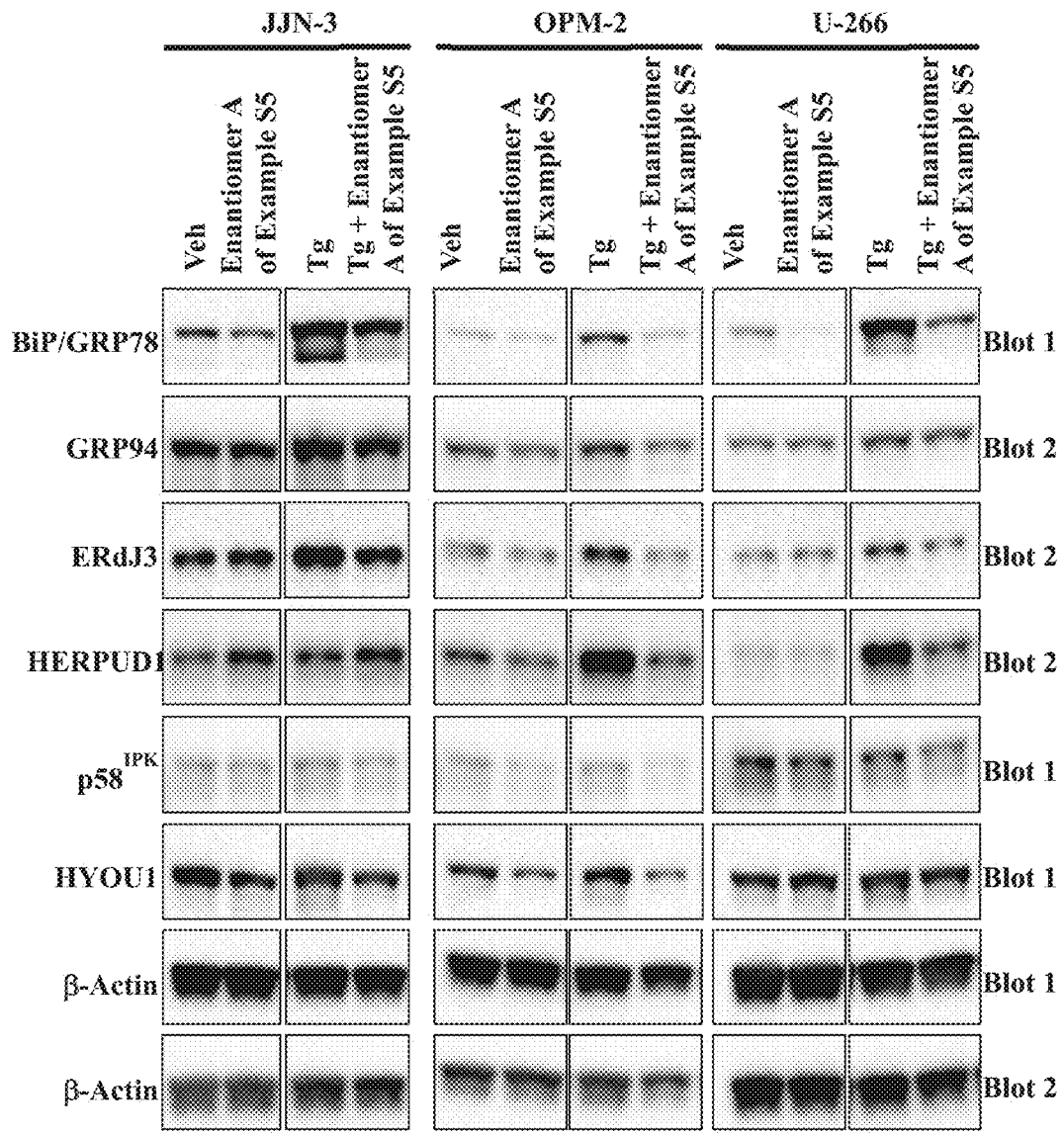
FIG. 1 depicts modulation of ATF6-dependent molecular machinery from endoplasmic reticulum (ER) proteostasis network in multiple myeloma (MM) cell lines.

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkoxy" refers to the group R—O—, where R is alkyl; and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl (—CF$_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

The term "haloalkyl" refers to an alkyl group with one or more halo substituents, or one, two, or three halo substituents. Examples of haloalkyl groups include —CF$_3$, —(CH$_2$)F, —CHF$_2$, CH$_2$Br, —CH$_2$CF$_3$, and —CH$_2$CH$_2$F.

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof, but excludes heteroaryl groups. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of an individual. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying recurrence, such as of unwanted cell proliferation.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations, in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

It is understood that aspects and variations described herein also include "consisting" and/or "consisting essentially of" aspects and variations.

All references throughout, such as publications, patents, patent applications and published patent applications, are incorporated herein by reference in their entireties.

Compounds

In one aspect, provided is a compound of the Formula (A):

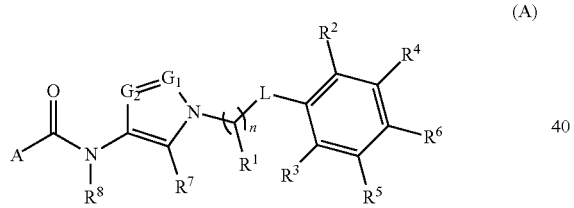

(A)

or a pharmaceutically acceptable salt thereof, wherein:
one of $G_1$ and $G_2$ is N and one of $G_1$ and $G_2$ is $CR^d$,
  wherein $R^d$ is H or $C_1$-$C_6$alkyl;
$R^1$ is H, $C_1$-$C_6$alkyl, $C_3$-$C_8$cycloalkyl, or $C_1$-$C_6$haloalkyl;
$R^8$ is H or $C_1$-$C_6$alkyl,
n is 0 or 1;
L is —$CH_2$— or is absent;
$R^2$, $R^3$, $R^4$, $R^5$, and $R^6$ are each independently H, halo, CN, $C_1$-$C_6$alkyl, or $C_1$-$C_6$haloalkyl;
or $R^2$, $R^4$, $R^5$, and $R^6$ are each independently H, halo, CN, $C_1$-$C_6$alkyl, or $C_1$-$C_6$haloalkyl and $R^3$ is taken together with an $R^1$ and the atoms to which they are attached to form a 5- or 6-membered ring, wherein the 5- or 6-membered ring is unsubstituted or substituted with one to three groups selected from the group consisting of halo, CN, —OH, $C_1$-$C_6$alkyl, and $C_1$-$C_6$haloalkyl;
provided that either:
  $R^3$ is taken together with $R^1$ and the atoms to which they are attached to form a 5- or 6-membered ring; or
  at least two of $R^2$, $R^3$, $R^4$, $R^5$, and $R^6$ are other than H; or
  one of $R^2$, $R^3$, $R^4$, $R^5$, and $R^6$ is cyano;

A is

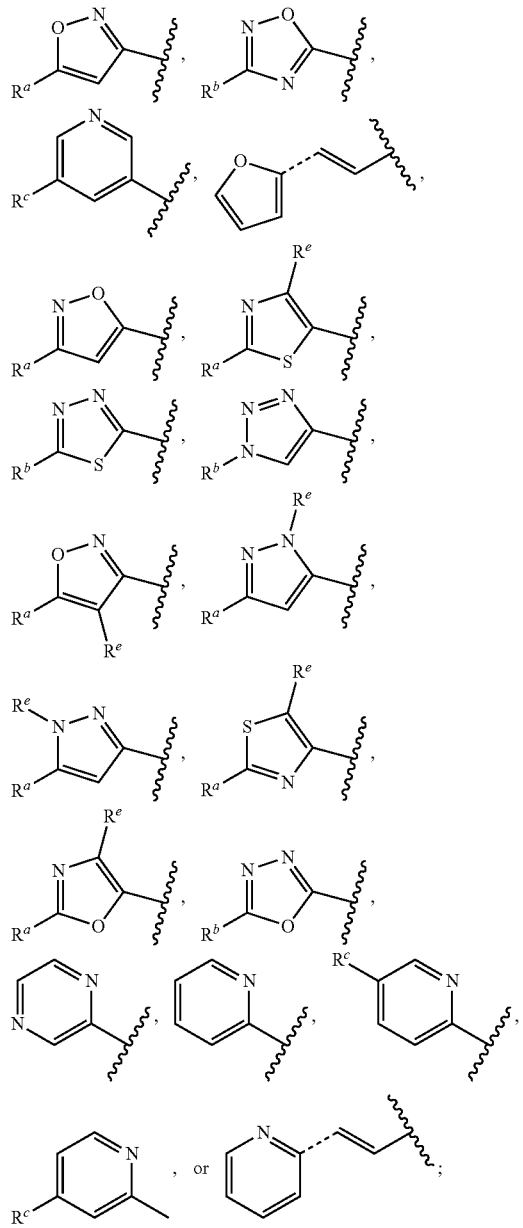

wherein --- indicates that

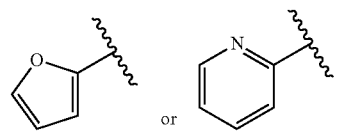 [SMILES: *c1ccco1 ; *c1ccccn1]

is attached in either an E or Z configuration;

$R^a$ and $R^b$ are each independently H, $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^a$ and $R^b$ are unsubstituted or substituted with one to four groups selected from OH, halo, $C_1$-$C_6$alkyl and $C_1$-$C_6$alkoxy;

$R^c$ is $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^c$ is unsubstituted or substituted with one to four groups selected from the group consisting of OH, halo, and $C_1$-$C_6$alkyl;

$R^e$ is H, $C_1$-$C_6$alkyl or $C_1$-$C_6$haloalkyl;

provided that when A is

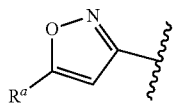

and $R^a$ is H, methyl, ethyl, n-Pr, i-Pr, i-Bu, 2-thiofuryl, 2-furyl, unsubstituted phenyl, 2-methoxyphenyl, 3-methoxyphenyl, 3,4-dimethoxyphenyl, 3-hydroxyphenyl, 4-hydroxyphenyl, 4-fluorophenyl, or 2,4-dichlorophenyl, at least one of (i)-(ix) applies:

(i) $G_2$ is N;
(ii) n is 1, L is absent, and $R^1$ is $C_1$-$C_6$alkyl;
(iii) n is 0, L is absent, and at least one of $R^2$, $R^3$, $R^4$, $R^5$, and $R^6$ is halo, CN, or $C_1$-$C_6$haloalkyl;
(iv) n is 1, and $R^3$ is taken together with $R^1$ and the atoms to which they are attached to form a 5- or 6-membered ring;
(v) one of $R^2$, $R^3$, $R^4$, $R^5$, and $R^6$ is CN; and
(vi) $R^4$ and $R^5$ are each independently Cl, Br, I, CN, $C_1$-$C_6$alkyl, or $C_1$-$C_6$haloalkyl;
(vii) one of $R^d$ and $R^7$ is $C_1$-$C_6$alkyl;
(viii) $R^2$ and $R^3$ are each $C_1$;
(ix) at least one of $R^2$, $R^3$, $R^4$, $R^5$, and $R^6$ is F, Br, I, CN, or $C_1$-$C_6$haloalkyl and $R^a$ is H or 2-thiofuryl;

provided that when A is

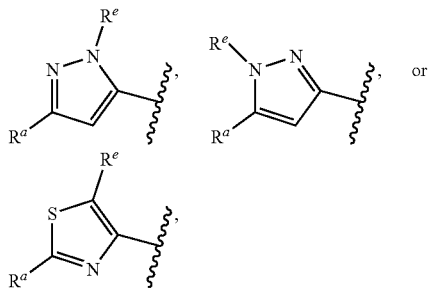

and n is 1, then $R^1$ is other than H;
provided that when A is

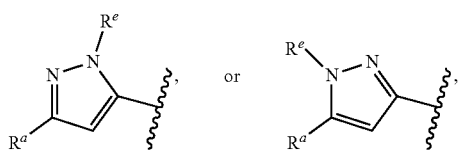

n is 0 and L is absent, then $R^a$ is other than H;

provided that when A is

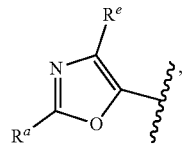

and $R^e$ is methyl, then $R^a$ is other than unsubstituted phenyl;

provided that when A is

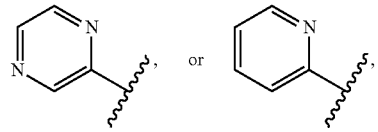 [SMILES: *c1cnccn1 ; *c1ccccn1]

n is 1 and L is absent, then $R^1$ is other than H;
and
$R^7$ is H or $C_1$-$C_6$alkyl,
provided that when $R^d$ is $C_1$-$C_6$alkyl, $R^7$ is H, and when $R^7$ is $C_1$-$C_6$alkyl, $R^d$ is H.

In one variation is provided a compound of the formula (A), or a salt thereof, wherein the carbon bearing $R^1$ when $R^1$ is other than H (i.e., $C_1$-$C_6$alkyl, $C_3$-$C_8$cycloalkyl or $C_1$-$C_6$haloalkyl), is in the "S" configuration. In another variation is provided a compound of the formula (A), or a salt thereof, wherein the carbon bearing $R^1$ when $R^1$ is other than H (i.e., $C_1$-$C_6$alkyl, $C_3$-$C_8$cycloalkyl or $C_1$-$C_6$haloalkyl), is in the "R" configuration. Mixtures of a compound of the formula (A) are also embraced, including racemic or non-racemic mixtures of a given compound, and mixtures of two or more compounds of different chemical formulae.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to $R^1$ of formula (A) may be combined with every description, variation, embodiment or aspect of A the same as if each and every combination were specifically and individually listed. Likewise, every description of $R^1$ may be combined with every description of A and $G_1$ and $G_2$ the same as if each and every description were specifically and individually listed.

In some embodiments, provided is a compound of the Formula (A), wherein A is

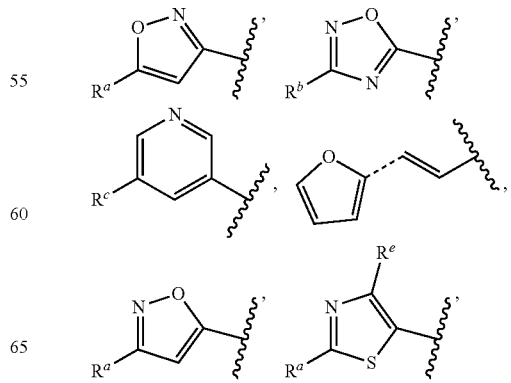

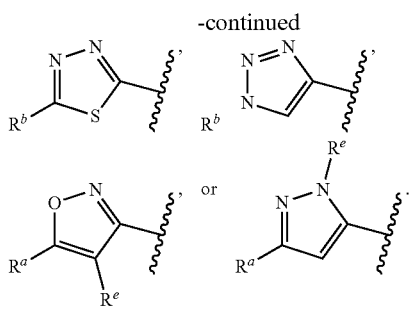

In some embodiments, provided is a compound of the Formula (A), wherein A is

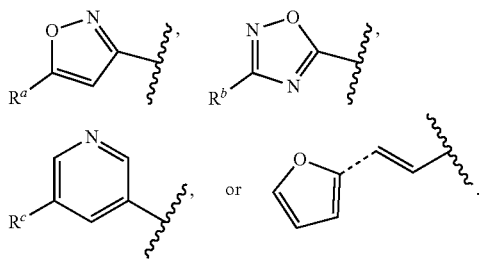

In some embodiments, provided is a compound of the Formula (I):

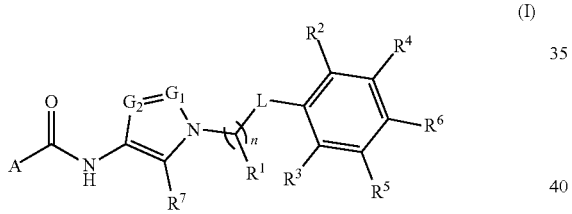

(I)

or a pharmaceutically acceptable salt thereof, wherein:
one of $G_1$ and $G_2$ is N and one of $G_1$ and $G_2$ is $CR^d$, wherein $R^d$ is H or $C_1$-$C_6$alkyl;
$R^1$ is H, $C_1$-$C_6$alkyl, or $C_3$-$C_8$cycloalkyl;
n is 0 or 1;
L is —$CH_2$— or is absent;
$R^2$, $R^3$, $R^4$, $R^5$, and $R^6$ are each independently H, halo, CN, $C_1$-$C_6$alkyl, or $C_1$-$C_6$haloalkyl;
or $R^2$, $R^4$, $R^5$, and $R^6$ are each independently H, halo, CN, $C_1$-$C_6$alkyl, or $C_1$-$C_6$haloalkyl and $R^3$ is taken together with an $R^1$ and the atoms to which they are attached to form a 5- or 6-membered ring, wherein the 5- or 6-membered ring is unsubstituted or substituted with one to three groups selected from the group consisting of halo, CN, —OH, $C_1$-$C_6$alkyl, and $C_1$-$C_6$haloalkyl;
provided that either:
$R^3$ is taken together with $R^1$ and the atoms to which they are attached to form a 5- or 6-membered ring; or
at least two of $R^2$, $R^3$, $R^4$, $R^5$, and $R^6$ are other than H; or
one of $R^2$, $R^3$, $R^4$, $R^5$, and $R^6$ is cyano;

A is

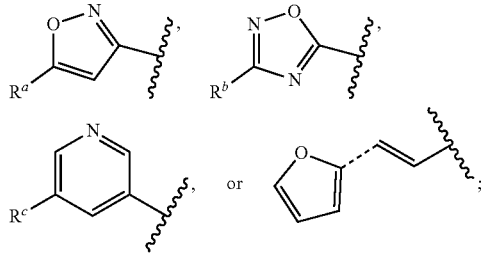

wherein --- indicates that

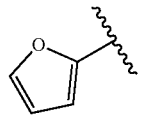

is attached in either an E or Z configuration;
$R^a$ and $R^b$ are each independently H, $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^a$ and $R^b$ are unsubstituted or substituted with one to four groups selected from the group consisting of OH, halo, and $C_1$-$C_6$alkyl;
$R^c$ is $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^c$ is unsubstituted or substituted with one to four groups selected from the group consisting of OH, halo, and $C_1$-$C_6$alkyl;
provided that when A is

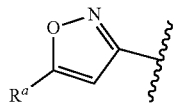

and $R^a$ is H, methyl, ethyl, n-Pr, i-Pr, i-Bu, 2-thiofuryl, 2-furyl, unsubstituted phenyl, 3-hydroxyphenyl, 4-hydroxyphenyl, 4-fluorophenyl, or 2,4-dichlorophenyl, at least one of (i)-(ix) applies:
(i) $G_2$ is N;
(ii) n is 1, L is absent, and $R^1$ is $C_1$-$C_6$alkyl;
(iii) n is 0, L is absent, and at least one of $R^2$, $R^3$, $R^4$, $R^5$, and $R^6$ is halo, CN, or $C_1$-$C_6$haloalkyl;
(iv) n is 1, and $R^3$ is taken together with $R^1$ and the atoms to which they are attached to form a 5- or 6-membered ring;
(v) one of $R^2$, $R^3$, $R^4$, $R^5$, and $R^6$ is CN; and
(vi) $R^4$ and $R^5$ are each independently Cl, Br, I, CN, $C_1$-$C_6$alkyl, or $C_1$-$C_6$haloalkyl;
(vii) one of $R^d$ or $R^7$ is $C_1$-$C_6$alkyl;
(viii) $R^2$ and $R^3$ are each $C_1$;
(ix) at least one of $R^2$, $R^3$, $R^4$, $R^5$, and $R^6$ is F, Br, I, CN, or $C_1$-$C_6$haloalkyl and $R^a$ is H or 2-thiofuryl; and
$R^7$ is H or $C_1$-$C_6$alkyl,
provided that when $R^d$ is $C_1$-$C_6$alkyl, $R^7$ is H, and when $R^7$ is $C_1$-$C_6$alkyl, $R^a$ is H.

In some embodiments of Formula (I), when A is

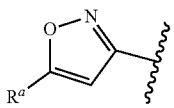

and $R^a$ is 2-methoxyphenyl, 3-methoxyphenyl, or 3,4-dimethoxyphenyl, at least one of (i)-(ix) applies.

In some embodiments, provided is a compound of Formula (Ia):

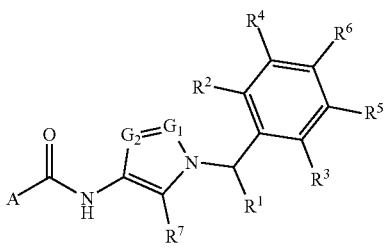

(Ia)

or a pharmaceutically acceptable salt thereof, wherein: A, $R^1$, $R^2$, $R^3$, $R^4$, $R^5$, $R^6$, $R^7$, $G_1$, and $G_2$ are as defined for Formula (I).

In some embodiments, the provided is a compound of Formula (Ib):

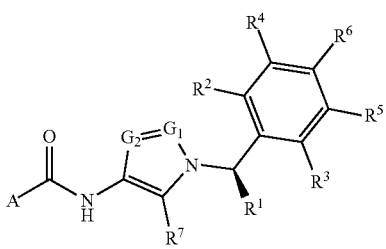

(Ib)

or a pharmaceutically acceptable salt thereof, wherein: A, $R^1$, $R^2$, $R^3$, $R^4$, $R^5$, $R^6$, $R^7$, $G_1$, and $G_2$ are as defined for Formula (I).

In some embodiments, provided is a compound of Formula (Ic):

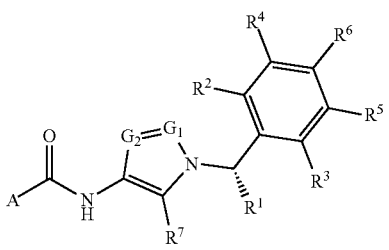

(Ic)

or a pharmaceutically acceptable salt thereof, wherein: A, $R^1$, $R^2$, $R^3$, $R^4$, $R^5$, $R^6$, $R^7$, $G_1$, and $G_2$ are as defined for Formula (I).

In some embodiments, provided is a compound of Formula (Id):

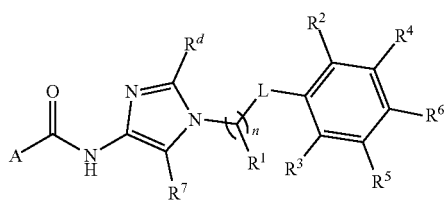

(Id)

or a pharmaceutically acceptable salt thereof, wherein: A, $R^d$, n, L, $R^1$, $R^2$, $R^3$, $R^4$, $R^5$, $R^6$, and $R^7$, are as defined for Formula (I).

In one embodiment of Formula (Id), L is absent. In one embodiment of Formula (Id), L is absent and n is 0. In one embodiment of Formula (Id), L is absent, n is 1 and $R^1$ is H, $C_1$-$C_6$alkyl, or $C_3$-$C_8$cycloalkyl. In one embodiment of Formula (Id), L is absent, n is 1 and $R^1$ is $C_1$-$C_6$alkyl, or $C_3$-$C_8$cycloalkyl. In one such embodiment, the carbon bearing $R^1$ is in the S-configuration. In another such embodiment, the carbon bearing $R^1$ is in the R-configuration.

In some embodiments, provided is a compound of Formula (Ie):

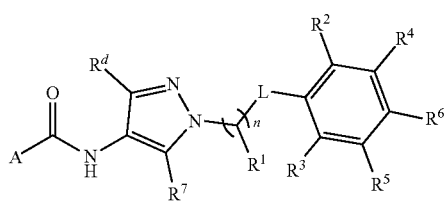

(Ie)

or a pharmaceutically acceptable salt thereof, wherein: A, R d, n, L, $R^1$, $R^2$, $R^3$, $R^4$, $R^5$, $R^6$, and $R^7$, are as defined for Formula (I). In one embodiment of Formula (Ie), L is absent.

In one embodiment of Formula (Ie), L is absent and n is 0. In one embodiment of Formula (Ie), L is absent, n is 1 and $R^1$ is H, $C_1$-$C_6$alkyl, or $C_3$-$C_8$cycloalkyl. In one embodiment of Formula (Ie), L is absent, n is 1 and $R^1$ is $C_1$-$C_6$alkyl, or $C_3$-$C_8$cycloalkyl. In one such embodiment, the carbon bearing $R^1$ is in the S-configuration. In another such embodiment, the carbon bearing $R^1$ is in the R-configuration.

In some embodiments, provided is a compound of Formula (If):

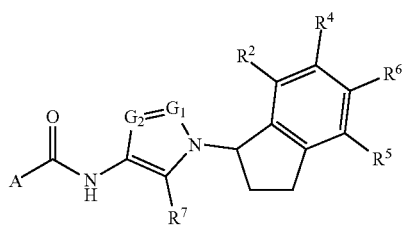

(If)

or a pharmaceutically acceptable salt thereof, wherein: A, $R^2$, $R^4$, $R^5$, $R^6$, $R^7$, $G_1$, and $G_2$ are as defined for Formula (I).

In some embodiments, provided is a compound of Formula (Ig):

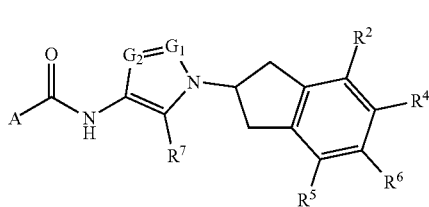

(Ig)

or a pharmaceutically acceptable salt thereof, wherein: A, $R^2$, $R^4$, $R^5$, $R^6$, $R^7$, $G_1$, and $G_2$ are as defined for Formula (I).

In some embodiments, provided is a compound of Formula (Ih):

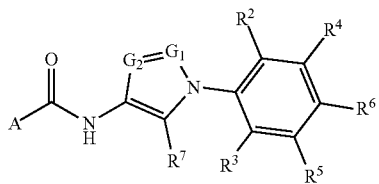

(Ih)

or a pharmaceutically acceptable salt thereof, wherein: A, $R^2$, $R^3$, $R^4$, $R^5$, $R^6$, $R^7$, $G_1$, and $G_2$ are as defined for Formula (I).

In some embodiments, provided is a compound of Formula (Ii):

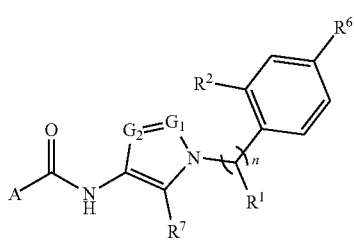

(Ii)

or a pharmaceutically acceptable salt thereof, wherein: A, n, $R^1$, $R^2$, $R^6$, $R^7$, $G_1$, and $G_2$ are as defined for Formula (I).

In some embodiments, provided is a compound of Formula (Ij):

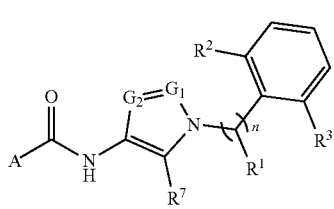

(Ij)

or a pharmaceutically acceptable salt thereof, wherein: A, n, $R^1$, $R^2$, $R^3$, $R^7$, $G_1$, and $G_2$ are as defined for Formula (I).

In some embodiments, provided is a compound of Formula (Ik):

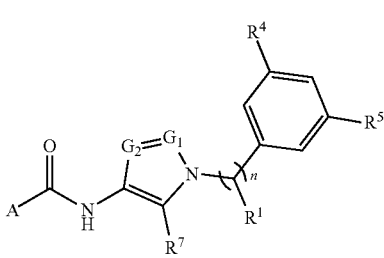

(Ik)

or a pharmaceutically acceptable salt thereof, wherein: A, n, $R^1$, $R^4$, $R^5$, $R^7$, $G_1$, and $G_2$ are as defined for Formula (I).

Any of the embodiments detailed herein with respect to Formula (A) or (I), where applicable, apply equally to Formula (Ia), (Ib), (Ic), (Id), (Ie), (If), (Ig), (Ih), (Ii), (Ij), and (Ik). It is also understood that the descriptions of any variable of Formula (A), (I), (Ia), (Ib), (Ic), (Id), (Ie), (If), (Ig), (Ih), (Ii), (Ij), or (Ik) may, where applicable, be combined with one or more descriptions of any other variable, the same as if each and every combination of variables were specifically and individually listed. For example, every description of $R^1$ may be combined with every description of A the same as if each and every combination were specifically and individually listed. Likewise, every description of $R^1$ may be combined with every description of A and $G_1$ and $G_2$ the same as if each and every description were specifically and individually listed.

In some embodiments of a compound of Formula (A), $R^8$ is $C_1$-$C_6$alkyl. In some embodiments of a compound of Formula (A), $R^8$ is methyl. In some embodiments of a compound of Formula (A), $R^8$ is H.

In some embodiments of a compound of Formula (A), (I), (Id), (Ie), (Ii), (Ij), or (Ik), n is 1 and $R^1$ is H. In some embodiments, n is 1 and $R^1$ is $C_1$-$C_6$alkyl. In other embodiments, n is 1 and $R^1$ is $C_3$-$C_8$cycloalkyl. In some embodiments, n is 1 and $R^1$ is $C_1$-$C_6$haloalkyl. In certain embodiments, n is 1 and $R^1$ is methyl, ethyl, n-propyl, isopropyl, n-butyl, isobutyl, sec-butyl, or tert-butyl. In some embodiments, n is 1 and $R^1$ methyl. In some embodiments, n is 1 and $R^1$ ethyl. In some embodiments, n is 1 and $R^1$ cyclopropyl, cyclobutyl, cyclopentyl, or cyclohexyl. In some embodiments, n is 1 and $R^1$ is cyclopropyl. In some embodiments of a compound of Formula (A), (I), (Id), (Ie), or (Ij), n is 1 and $R^3$ is taken together with $R^1$ and the atoms to which they are attached to form a 5- or 6-membered ring. In some embodiments, n is 1 and $R^3$ is taken together with $R^1$ and the atoms to which they are attached to form an unsubstituted 5-membered carbocyclic ring. In some embodiments, n is 1 and $R^3$ is taken together with $R^1$ and the atoms to which they are attached to form an unsubstituted 6-membered carbocyclic ring. In some embodiments, n is 1 and $R^3$ is taken together with $R^1$ and the atoms to which they are attached to form a 5-membered carbocyclic ring substituted with one to three groups selected from the group consisting of halo, CN, —OH, $C_1$-$C_6$alkyl, and $C_1$-$C_6$haloalkyl. In some embodiments, n is 1 and $R^3$ is taken together with $R^1$ and the atoms to which they are attached to form a 6-membered carbocyclic ring substituted with one to three groups selected from the group consisting of halo, CN, —OH, $C_1$-$C_6$alkyl, and $C_1$-$C_6$haloalkyl. In some embodiments, n is 1 and $R^3$ is taken together with $R^1$ and the atoms to which they are attached to form a 5- or 6-membered heterocyclic ring, wherein the 5- or 6-membered heterocyclic ring is unsubstituted or substituted with one to three groups selected from the group consisting of halo, CN, —OH, $C_1$-$C_6$alkyl, and $C_1$-$C_6$haloalkyl. In some embodiments of a compound of Formula (A), (I), (Id), (Ie), (Ii), (Ij), or (Ik), n is 0.

In some embodiments of a compound of Formula (A), (I), (Id), or (Ie), L is absent. In other embodiments, L is —$CH_2$—. In some embodiments, n is 1, L is absent, and $R^1$ is H. In some embodiments, n is 1, L is absent, and $R^1$ is $C_1$-$C_6$alkyl. In other embodiments, n is 1, L is absent, and $R^1$ is $C_3$-$C_8$cycloalkyl. In some embodiments, n is 1, L is absent, and $R^1$ is $C_1$-$C_6$haloalkyl. In certain embodiments, n is 1, L is absent, and $R^1$ is methyl, ethyl, n-propyl, isopropyl, n-butyl, isobutyl, sec-butyl, or tert-butyl. In some embodiments, n is 1, L is absent, and $R^1$ is methyl. In some embodiments, n is 1, L is absent, and $R^1$ is ethyl. In some embodiments, n is 1, L is absent, and $R^1$ is cyclopropyl, cyclobutyl, cyclopentyl, or cyclohexyl. In some embodiments, n is 1, L is absent, and $R^1$ is cyclopropyl.

In some embodiments of a compound of Formula (A), (I), (Id), or (Ie), n is 1, L is absent, and $R^3$ is taken together with $R^1$ and the atoms to which they are attached to form a 5- or 6-membered ring. In some embodiments, n is 1, L is absent, and $R^3$ is taken together with $R^1$ and the atoms to which they are attached to form an unsubstituted 5-membered carbocyclic ring. In some embodiments, n is 1, L is absent, and $R^3$ is taken together with $R^1$ and the atoms to which they are attached to form an unsubstituted 6-membered carbocyclic ring. In some embodiments, n is 1, L is absent, and $R^3$ is taken together with $R^1$ and the atoms to which they are attached to form a 5-membered carbocyclic ring substituted with one to three groups selected from the group consisting of halo, CN, —OH, $C_1$-$C_6$alkyl, and $C_1$-$C_6$haloalkyl. In some embodiments, n is 1, L is absent, and $R^3$ is taken together with $R^1$ and the atoms to which they are attached to form a 6-membered carbocyclic ring substituted with one to three groups selected from the group consisting of halo, CN, —OH, $C_1$-$C_6$alkyl, and $C_1$-$C_6$haloalkyl. In some embodiments, n is 1, L is absent, and $R^3$ is taken together with $R^1$ and the atoms to which they are attached to form a 5- or 6-membered heterocyclic ring, wherein the 5- or 6-membered heterocyclic ring is unsubstituted or substituted with one to three groups selected from the group consisting of halo, CN, —OH, $C_1$-$C_6$alkyl, and $C_1$-$C_6$haloalkyl. In some embodiments, n is 1, L is absent, and $R^3$ is taken together with $R^1$ and the atoms to which they are attached to form a 5-membered carbocyclic ring, wherein the 5-membered carbocyclic ring is unsubstituted or substituted with halo, CN, —OH, $C_1$-$C_6$alkyl, or $C_1$-$C_6$haloalkyl and one or two of $R^2$, $R^4$, $R^5$, and $R^6$ are independently selected from halo, CN, $C_1$-$C_6$alkyl, and $C_1$-$C_6$haloalkyl. In certain embodiments, n is 1, L is absent, and $R^3$ is taken together with $R^1$ and the atoms to which they are attached to form an unsubstituted 5-membered carbocyclic ring, and $R^2$, $R^4$, $R^5$, and $R^6$ are each H. In one variation, n is 1, L is absent, and $R^3$ is taken together with $R^1$ and the atoms to which they are attached to form a 5-membered carbocyclic ring, when the carbon bearing $R^1$ is in the "S" configuration. In another variation, n is 1, L is absent, and $R^3$ is taken together with $R^1$ and the atoms to which they are attached to form a 5-membered carbocyclic ring, when the carbon bearing $R^1$ is in the "R" configuration.

In some embodiments of a compound of Formula (A), (I), (Id), or (Ie), n is 0 and L is absent.

In some embodiments of a compound of Formula (A), (I), (Id), or (Ie), n is 1, L is —$CH_2$—, and $R^1$ is H. In some embodiments, n is 1, L is —$CH_2$—, and $R^1$ is $C_1$-$C_6$alkyl. In other embodiments, n is 1, L is —$CH_2$—, and $R^1$ is $C_3$-$C_8$cycloalkyl. In some embodiments, n is 1, L is —$CH_2$—, and $R^1$ is $C_1$-$C_6$haloalkyl. In certain embodiments, n is 1, L is —$CH_2$—, and $R^1$ is methyl, ethyl, n-propyl, isopropyl, n-butyl, isobutyl, sec-butyl, or tert-butyl. In some embodiments, n is 1, L is —$CH_2$—, and $R^1$ methyl. In some embodiments, n is 1, L is —$CH_2$—, and $R^1$ ethyl. In some embodiments, n is 1, L is —$CH_2$—, and $R^1$ is cyclopropyl, cyclobutyl, cyclopentyl, or cyclohexyl. In some embodiments, n is 1, L is —$CH_2$—, and $R^1$ is cyclopropyl. In some embodiments of a compound of Formula (A), (I), (Id), or (Ie), n is 1, L is —$CH_2$—, and $R^3$ is taken together with $R^1$ and the atoms to which they are attached to form a 5- or 6-membered ring. In some embodiments, n is 1, L is —$CH_2$—, and $R^3$ is taken together with $R^1$ and the atoms to which they are attached to form an unsubstituted 5-membered carbocyclic ring. In some embodiments, n is 1, L is —$CH_2$—, and $R^3$ is taken together with $R^1$ and the atoms to which they are attached to form an unsubstituted 6-membered carbocyclic ring. In some embodiments, n is 1, L is —$CH_2$—, and $R^3$ is taken together with $R^1$ and the atoms to which they are attached to form a 5-membered carbocyclic ring substituted with one to three groups selected from the group consisting of halo, CN, —OH, $C_1$-$C_6$alkyl, and $C_1$-$C_6$haloalkyl. In some embodiments, n is 1, L is —$CH_2$—, and $R^3$ is taken together with $R^1$ and the atoms to which they are attached to form a 6-membered carbocyclic ring substituted with one to three groups selected from the group consisting of halo, CN, —OH, $C_1$-$C_6$alkyl, and $C_1$-$C_6$haloalkyl. In some embodiments, n is 1, L is —$CH_2$—, and $R^3$ is taken together with $R^1$ and the atoms to which they are attached to form a 5- or 6-membered heterocyclic ring, wherein the 5- or 6-membered heterocyclic ring is unsubstituted or substituted with one to three groups selected from the group consisting of halo, CN, —OH, $C_1$-$C_6$alkyl, and $C_1$-$C_6$haloalkyl. In some embodiments, n is 1, L is —$CH_2$—, and $R^3$ is taken together with $R^1$ and the atoms to which they are attached to form a 5-membered carbocyclic ring, wherein the 5-membered carbocyclic ring is unsubstituted or substituted with halo, CN, —OH, $C_1$-$C_6$alkyl, or $C_1$-$C_6$haloalkyl and one or two of $R^2$, $R^4$, $R^5$, and $R^6$ are independently selected from halo, CN, $C_1$-$C_6$alkyl, and $C_1$-$C_6$haloalkyl. In certain embodiments, n is 1, L is —$CH_2$—, and $R^3$ is taken together with $R^1$ and the atoms to which they are attached to form an unsubstituted 5-membered carbocyclic ring, and $R^2$, $R^4$, $R^5$, and $R^6$ are each H. In one variation, n is 1, L is —$CH_2$—, and $R^3$ is taken together with $R^1$ and the atoms to which they are attached to form a 5-membered carbocyclic ring, when the carbon bearing $R^1$ is in the "S" configuration. In another variation, n is 1, L is —$CH_2$—, and $R^3$ is taken together with $R^1$ and the atoms to which they are attached to form a 5-membered carbocyclic ring, when the carbon bearing $R^1$ is in the "R" configuration.

In some embodiments of a compound of Formula (A), (I), (Id), or (Ie), n is 0 and L is —$CH_2$—.

In some embodiments of a compound of Formula (A), (I), (Ia), (Ib), (Ic), (If), (Ig), (Ih), (Ii), (Ij), or (Ik), $G_1$ is N and $G_2$ is $CR^d$. In some embodiments, $G_1$ is N and $G_2$ is CH. In some embodiments, $G_1$ is N and $G_2$ is $CC_1$-$C_6$alkyl. In some embodiments, $G_1$ is N and $G_2$ is $CCH_3$. In some embodiments of a compound of Formula (A), (I), (Ia), (Ib), (Ic), (If), (Ig), (Ih), (Ii), (Ij), or (Ik), $G_1$ is $CR^d$ and $G_2$ is N. In some embodiments, $G_1$ is CH and $G_2$ is N. In some embodiments, $G_1$ is $CC_1-C_6$alkyl and $G_2$ is N. In some embodiments, $G_1$ is $CCH_3$ and $G_2$ is N.

In some embodiments of a compound of Formula (A), (I), (Ia), (Ib), (Ic), (Id), (Ie), (Ii), (Ij), or (Ik), $R^1$ is H. In some embodiments, $R^1$ is $C_1-C_6$alkyl. In other embodiments, $R^1$ is $C_3-C_8$cycloalkyl. In some embodiments, $R^1$ is $C_1-C_6$haloalkyl. In certain embodiments, $R^1$ is methyl, ethyl, n-propyl, isopropyl, n-butyl, isobutyl, sec-butyl, or tert-butyl. In some embodiments, $R^1$ is methyl. In some embodiments, $R^1$ is ethyl. In some embodiments, $R^1$ is cyclopropyl, cyclobutyl, cyclopentyl, or cyclohexyl. In some embodiments, $R^1$ is cyclopropyl. In some embodiments of a compound of Formula (A), (I), (Ia), (Ib), (Ic), (Id), (Ie), or (Ih), or (Ij), $R^3$ is taken together with $R^1$ and the atoms to which they are attached to form a 5- or 6-membered ring. In some embodiments, $R^3$ is taken together with $R^1$ and the atoms to which they are attached to form a 5-membered carbocyclic ring. In certain embodiments, $R^3$ is taken together with $R^1$ and the atoms to which they are attached to form a 5-membered carbocyclic ring, and $R^2$, $R^4$, $R^5$, and $R^6$ are each H.

In some embodiments of a compound of Formula (A), (I), (Ia), (Ib), (Ic), (Id), (Ie), (If), (Ig), or (Ih), $R^2$, $R^3$, $R^4$, $R^5$, and $R^6$ are each independently H, halo, CN, $C_1-C_6$alkyl, or $C_1-C_6$haloalkyl. In some embodiments, $R^2$, $R^3$, $R^4$, $R^5$, and $R^6$ are each independently H, Cl, CN, or $CF_3$. In some embodiments, $R^4$ and $R^5$ are each independently Cl, Br, I, CN, $C_1-C_6$alkyl, or $C_1-C_6$haloalkyl. In some embodiments, one of $R^2$, $R^3$, $R^4$, $R^5$, and $R^6$ is other than H. In some embodiments, two of $R^2$, $R^3$, $R^4$, $R^5$, and $R^6$ are other than H. In some embodiments, at least two of $R^2$, $R^3$, $R^4$, $R^5$, and $R^6$ are other than H. In some embodiments, one of $R^2$, $R^3$, $R^4$, $R^5$, and $R^6$ is CN. In some embodiments, $R^6$ is CN. In some embodiments, one of $R^2$, $R^3$, $R^4$, $R^5$, and $R^6$ is $CF_3$. In some embodiments, two of $R^2$, $R^3$, $R^4$, $R^5$, and $R^6$ are $CF_3$. In some embodiments, $R^2$ and $R^6$ are each $CF_3$, or $R^4$ and $R^5$ are each $CF_3$, or $R^3$ and $R^6$ are each $CF_3$. In some embodiments, one or two of $R^2$, $R^3$, $R^4$, $R^5$, and $R^6$ is $C_1$. In some embodiments, $R^4$ and $R^5$ are each $C_1$. In some embodiments, $R^2$, $R^4$, $R^5$, and $R^6$ are each H.

In some embodiments of Formula (A), (I), (Ia), (Ib), (Ic), (Id), (Ie), (If), (Ig), or (Ih),

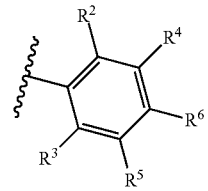

is

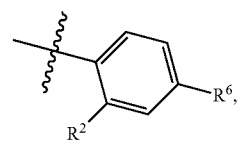

wherein $R^2$ and $R^6$ are each $C_1-C_6$ haloalkyl. In some embodiments,

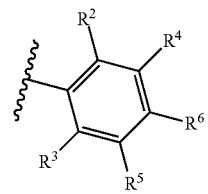

is

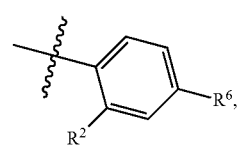

wherein $R^2$ and $R^6$ are each independently selected from the group consisting of halo, $C_1-C_6$alkyl, and $C_1-C_6$haloalkyl. In some embodiments,

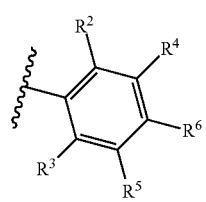

is

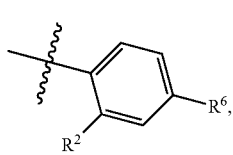

wherein $R^2$ and $R^6$ are each independently selected from the group consisting of Cl, $C_1-C_6$alkyl, and $C_1-C_6$haloalkyl. In some embodiments,

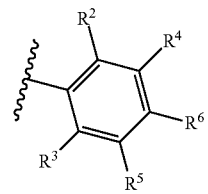

is

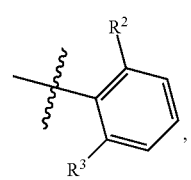

wherein $R^2$ and $R^3$ are each halo. In some embodiments,

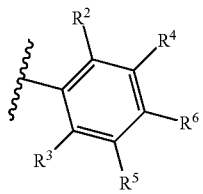

is

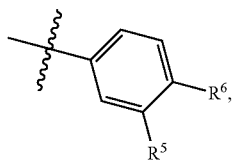

wherein $R^5$ and $R^6$ are each independently selected from the group consisting of Cl, Br, I, CN, $C_1$-$C_6$alkyl, and $C_1$-$C_6$haloalkyl. In some embodiments,

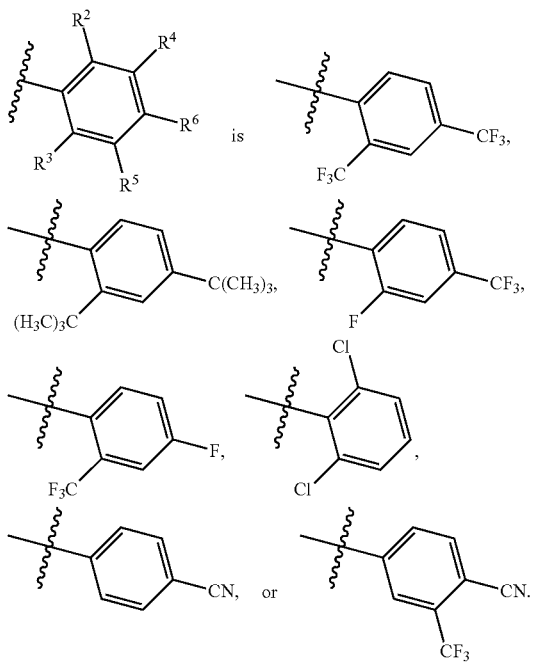

In some embodiments of a compound of Formula (A), (I), (Ia), (Ib), (Ic), (Id), (Ie), (If), (Ig), (Ih), (Ii), (Ij), or (Ik), $R^a$, $R^b$ and $R^c$ are each independently 6-membered aryl, or 5- or 6-membered heteroaryl, wherein the 6-membered aryl, or 5- or 6-membered heteroaryl is unsubstituted or substituted with one to four groups selected from OH, halo, $C_1$-$C_6$alkyl and $C_1$-$C_6$alkoxy. In some embodiments, $R^a$, $R^b$ and $R^c$ are each independently 6-membered aryl, or 5- or 6-membered heteroaryl, wherein the 6-membered aryl, or 5- or 6-membered heteroaryl is unsubstituted or substituted with one to four groups selected from OH, halo, and $C_1$-$C_6$alkyl. In some embodiments, $R^a$, $R^b$ and $R^c$ are each independently 5- or 6-membered heteroaryl, wherein the 5- or 6-membered heteroaryl is unsubstituted or substituted with one to four groups selected from OH, halo, $C_1$-$C_6$alkyl and $C_1$-$C_6$alkoxy. In some embodiments, $R^a$, $R^b$ and $R^c$ are each independently 5- or 6-membered heteroaryl, wherein the 5- or 6-membered heteroaryl is unsubstituted or substituted with one to four groups selected from OH, halo, and $C_1$-$C_6$alkyl.

In some embodiments of a compound of Formula (A), (I), (Ia), (Ib), (Ic), (Id), (Ie), (If), (Ig), (Ih), (Ii), (Ij), or (Ik), $R^a$ and $R^b$ are each independently selected from the group consisting of H, $C_1$-$C_6$alkyl,

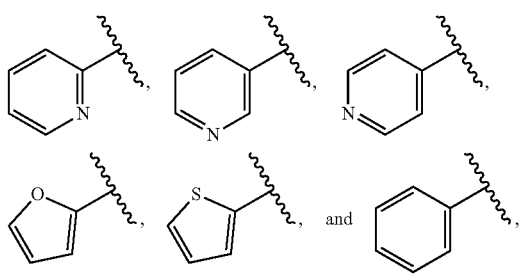

each of which is unsubstituted or is substituted with one to four groups selected from the group consisting of OH, halo, $C_1$-$C_6$alkyl, and $C_1$-$C_6$alkoxy. In some embodiments, $R^a$ and $R^b$ are each independently selected from the group consisting of H, $C_1$-$C_6$alkyl,

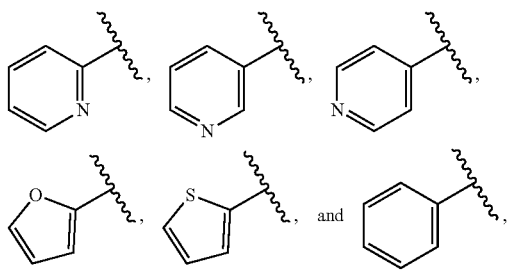

each of which is unsubstituted or is substituted with one to four groups selected from the group consisting of OH, halo, and $C_1$-$C_6$alkyl. In some embodiments, $R^a$ and $R^b$ are each independently selected from the group consisting of H,

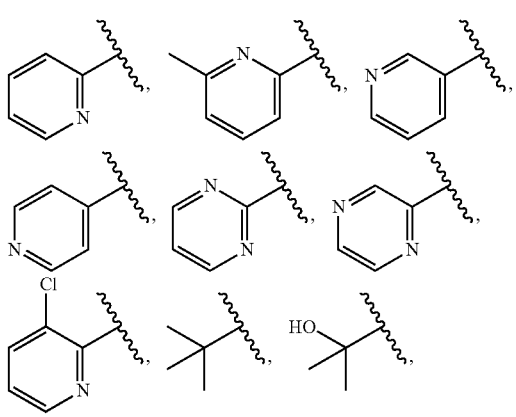

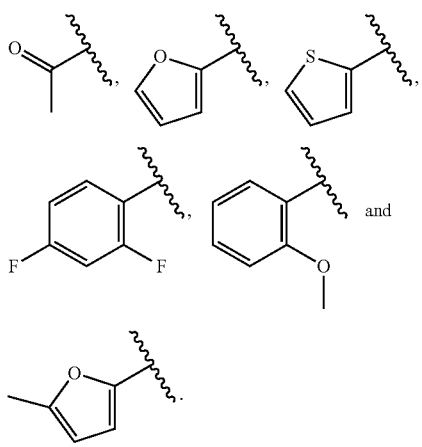

In some embodiments of a compound of Formula (A), (I), (Ia), (Ib), (Ic), (Id), (Ie), (If), (Ig), (Ih), (Ii), (Ij), or (Ik), $R^c$ is selected from the group consisting of $C_1$-$C_6$alkyl,

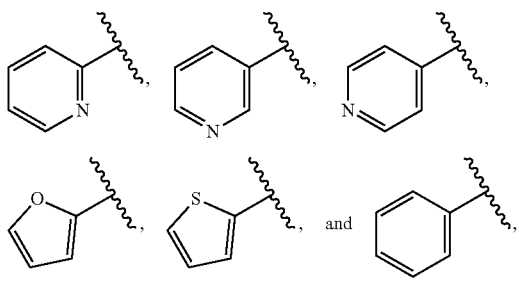

each of which is unsubstituted or is substituted with one to four groups selected from the group consisting of OH, halo, and $C_1$-$C_6$alkyl. In some embodiments, $R^c$ is selected from the group consisting of

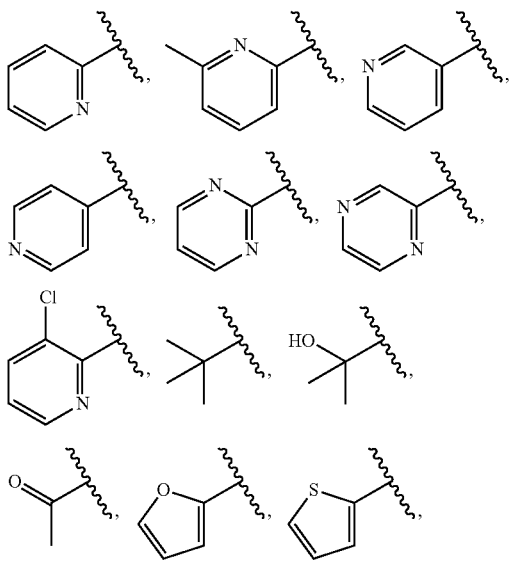

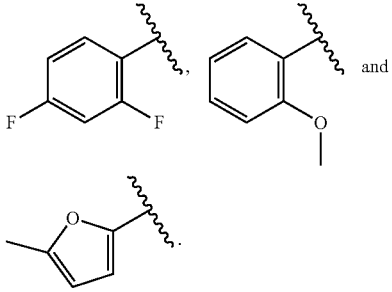

In some embodiments of a compound of Formula (A), (I), (Ia), (Ib), (Ic), (Id), (Ie), (If), (Ig), (Ih), (Ii), (Ij), or (Ik), A is

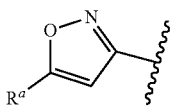

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ are unsubstituted or substituted with one to four groups selected from the group consisting of OH, halo, and $C_1$-$C_6$alkyl. In some embodiments, A is

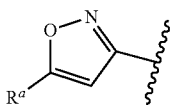

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ are unsubstituted or substituted with one to four groups selected from the group consisting of OH, halo, $C_1$-$C_6$alkyl and $C_1$-$C_6$alkoxy.

In some embodiments, A is

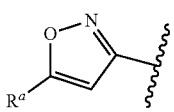

and $R^a$ is a 5- or 6-membered heteroaryl that is unsubstituted or is substituted with one to four groups selected from the group consisting of OH, halo, and $C_1$-$C_6$alkyl. In some embodiments, A is

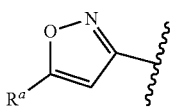

and $R^a$ is a 5- or 6-membered heteroaryl that is unsubstituted or is substituted with one to four groups selected from the group consisting of OH, halo, $C_1$-$C_6$alkyl and $C_1$-$C_6$alkoxy. In some embodiments, A is

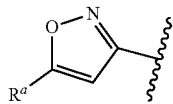

and $R^a$ is pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, or tetrazinyl, each unsubstituted or substituted with one to four groups selected from the group consisting of OH, halo, and $C_1$-$C_6$alkyl. In some embodiments, A is

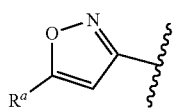

and $R^a$ is pyridyl, wherein the pyridyl is unsubstituted or substituted with one to four groups selected from the group consisting of OH, halo, and $C_1$-$C_6$alkyl. In some embodiments, A is

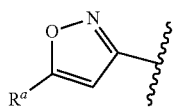

and $R^a$ is furanyl, wherein the furanyl is unsubstituted or substituted with one to four groups selected from the group consisting of OH, halo, and $C_1$-$C_6$alkyl. In some embodiments, A is

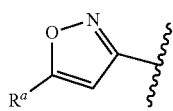

and $R^a$ is thiophenyl, wherein the thiophenyl is unsubstituted or substituted with one to four groups selected from the group consisting of OH, halo, and $C_1$-$C_6$alkyl.

In some embodiments, A is

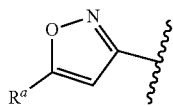

and $R^a$ is selected from the group consisting of H, $C_1$-$C_6$alkyl,

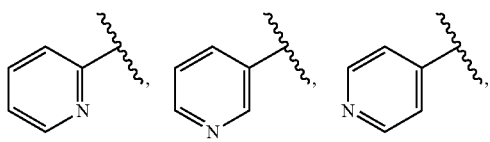

-continued

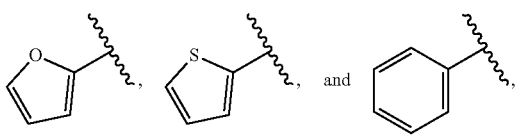

each of which is unsubstituted or is substituted with one to four groups selected from the group consisting of OH, halo, $C_1$-$C_6$alkyl and $C_1$-$C_6$alkoxy. In some embodiments, A is

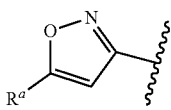

and $R^a$ is selected from the group consisting of H,

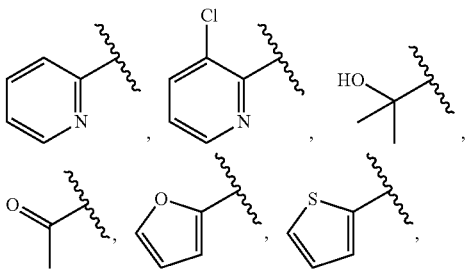

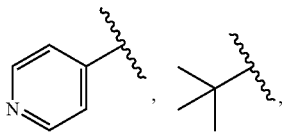

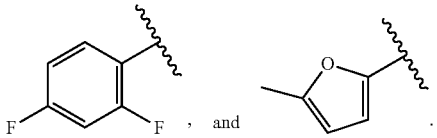

, and

In some embodiments, A is

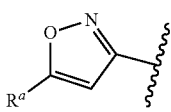

and $R^a$ is selected from the group consisting of H,

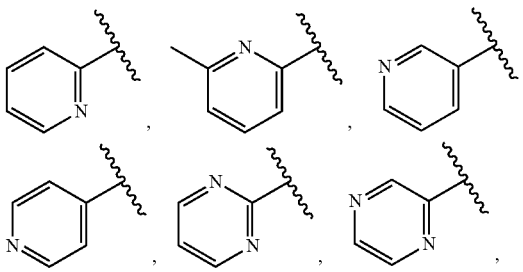

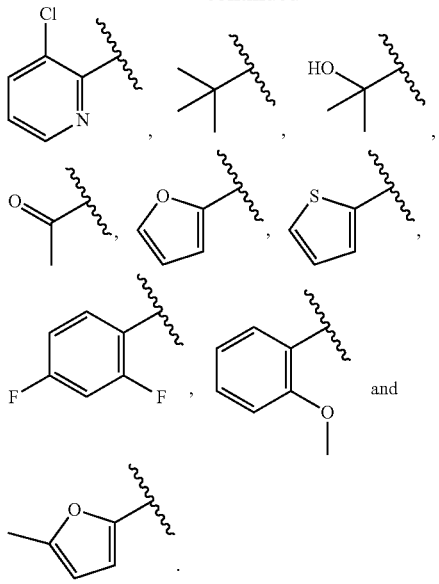

In some embodiments of a compound of Formula (A), (I), (Ia), (Ib), (Ic), (Id), (Ie), (If), (Ig), (Ih), (Ii), (Ij), or (Ik), A is

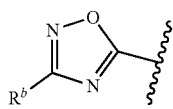

and $R^b$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^b$ is unsubstituted or is substituted with one to four groups selected from the group consisting of OH, halo, and $C_1$-$C_6$alkyl. In some embodiments, A is

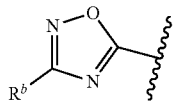

and $R^b$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^b$ is unsubstituted or is substituted with one to four groups selected from the group consisting of OH, halo, $C_1$-$C_6$alkyl and $C_1$-$C_6$alkoxy. In some embodiments, A is

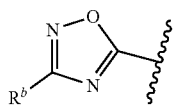

and $R^b$ is a 6-membered aryl or a 5- or 6-membered heteroaryl, wherein each 6-membered aryl and 5- or 6-membered heteroaryl of $R^b$ is unsubstituted or is substituted with one to four groups selected from the group consisting of OH, halo, and $C_1$-$C_6$alkyl. In some embodiments, A is

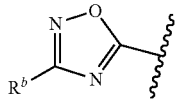

and $R^b$ is a 6-membered aryl or a 5- or 6-membered heteroaryl, wherein each 6-membered aryl and 5- or 6-membered heteroaryl of $R^b$ is unsubstituted or is substituted with one to four groups selected from the group consisting of OH, halo, $C_1$-$C_6$alkyl and $C_1$-$C_6$alkoxy. In some embodiments, A is

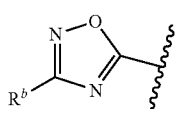

and $R^b$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, and $C_1$-$C_6$alkyl.

In some embodiments, A is

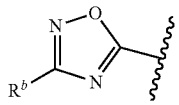

and $R^b$ is selected from the group consisting of H, $C_1$-$C_6$alkyl,

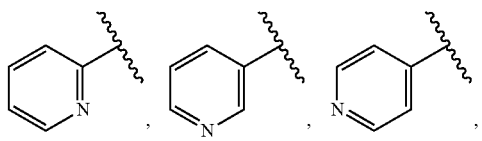

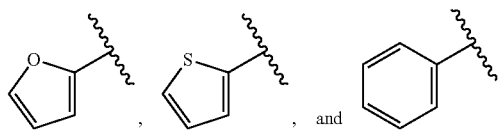

each of which is unsubstituted or is substituted with one to four groups selected from the group consisting of OH, halo, and $C_1$-$C_6$alkyl. In some embodiments, A is

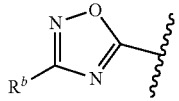

and $R^b$ is selected from the group consisting of H,

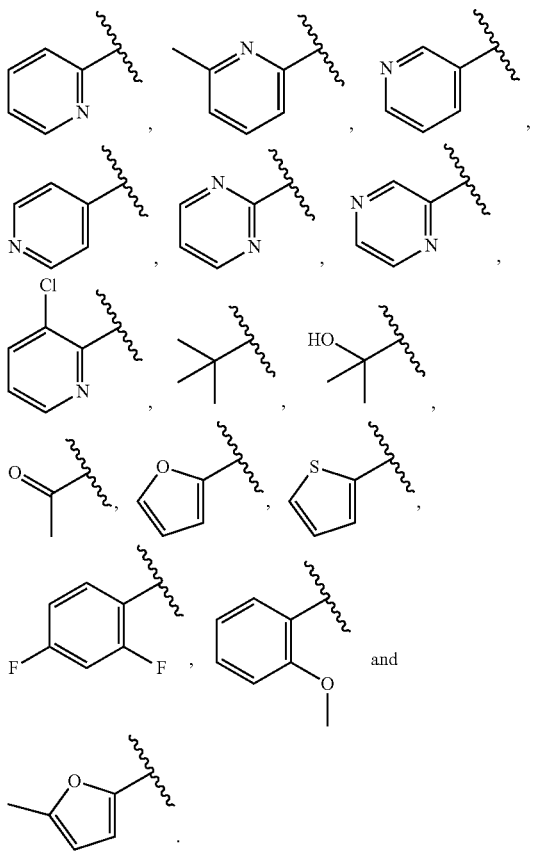

In some embodiments, A is

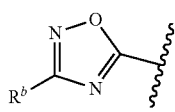

and $R^b$ is

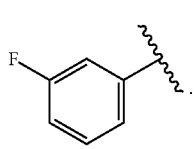

In some embodiments of a compound of Formula (A), (I), (Ia), (Ib), (Ic), (Id), (Ie), (If), (Ig), (Ih), (Ii), (Ij), or (Ik), A is

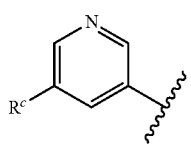

and $R^c$ is selected from the group consisting of $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^c$ is unsubstituted or is substituted with one to four groups selected from the group consisting of OH, halo, and $C_1$-$C_6$alkyl. In some embodiments, A is

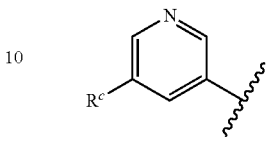

and $R^c$ is a 6-membered aryl or a 5- or 6-membered heteroaryl, wherein the 6-membered aryl and 5- or 6-membered heteroaryl of $R^c$ are unsubstituted or are substituted with one to four groups selected from the group consisting of OH, halo, and $C_1$-$C_6$alkyl. In some embodiments, A is

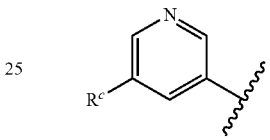

and $R^c$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, and $C_1$-$C_6$alkyl.

In some embodiments, A is

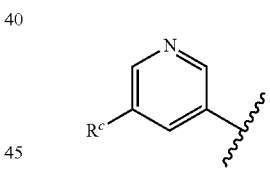

and $R^c$ is selected from the group consisting of $C_1$-$C_6$alkyl,

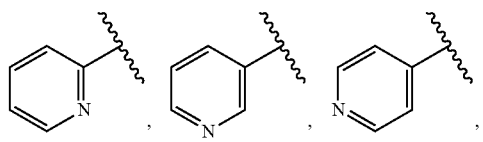

each of which is unsubstituted or is substituted with one to four groups selected from the group consisting of OH, halo, and $C_1$-$C_6$alkyl. In some embodiments, A is

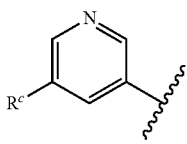

and $R^c$ is selected from the group consisting of

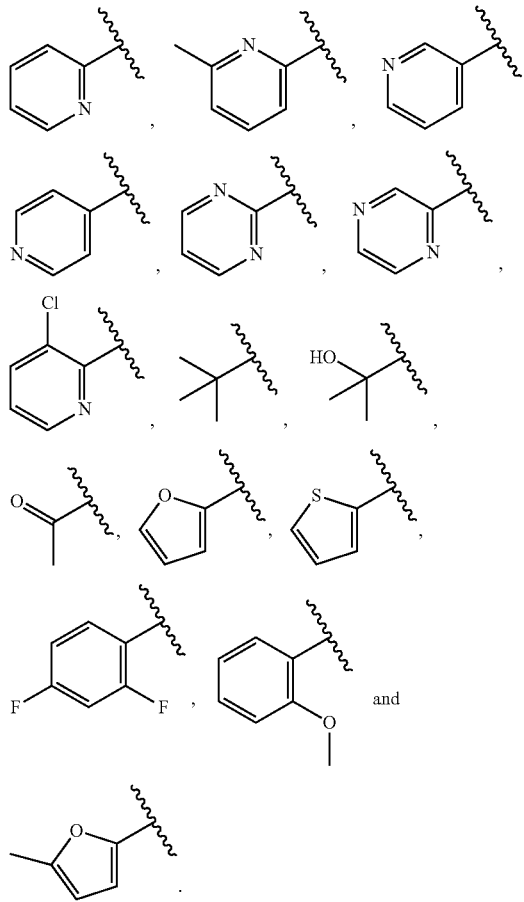

In some embodiments, A is

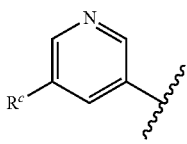

and $R^c$ is selected from the group consisting of

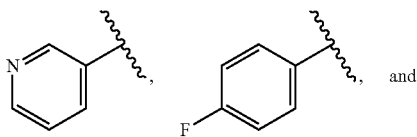

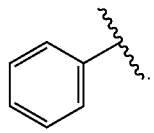

In some embodiments of a compound of Formula (A), (I), (Ia), (Ib), (Ic), (Id), (Ie), (If), (Ig), (Ih), (Ii), (Ij), or (Ik), A is

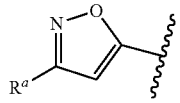

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ is unsubstituted or is substituted with one to four groups selected from the group consisting of OH, halo, and $C_1$-$C_6$alkyl. In some embodiments, A is

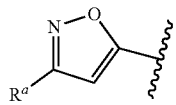

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ is unsubstituted or is substituted with one to four groups selected from the group consisting of OH, halo, $C_1$-$C_6$alkyl and $C_1$-$C_6$alkoxy.

In some embodiments, A is

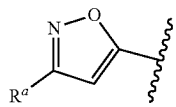

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, and $C_1$-$C_6$alkyl. In some embodiments, A is

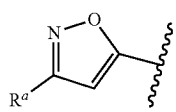

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, $C_1$-$C_6$alkyl and $C_1$-$C_6$alkoxy. In some embodiments, A is

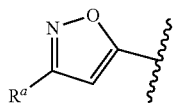

and R$^a$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, C$_1$-C$_6$alkyl and C$_1$-C$_6$alkoxy.

In some embodiments, A is

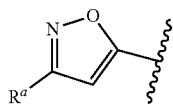

and R$^a$ is selected from the group consisting of C$_1$-C$_6$alkyl,

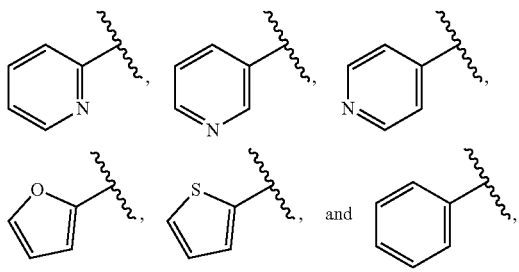

each of which is unsubstituted or is substituted with one to four groups selected from the group consisting of OH, halo, C$_1$-C$_6$alkyl and C$_1$-C$_6$alkoxy. In some embodiments, A is

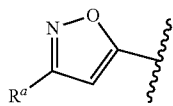

and R$^a$ is selected from the group consisting of H,

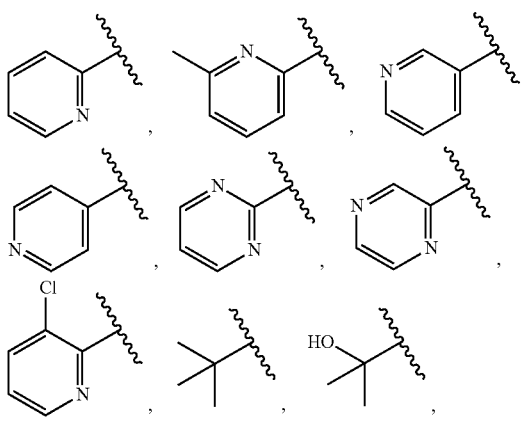

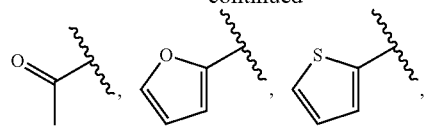

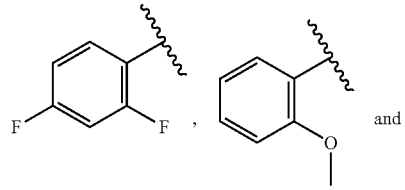

In some embodiments of a compound of Formula (A), (I), (Ia), (Ib), (Ic), (Id), (Ie), (If), (Ig), (Ih), (Ii), (Ij), or (Ik), A is

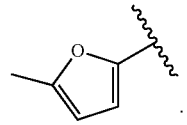

and R$^a$ is selected from the group consisting of H, C$_1$-C$_6$alkyl, —C(O)C$_1$-C$_6$alkyl, 6-membered aryl, and 5- or 6-membered heteroaryl, wherein each C$_1$-C$_6$alkyl, —C(O)C$_1$-C$_6$alkyl, 6-membered aryl, or 5- or 6-membered heteroaryl of R$^a$ is unsubstituted or is substituted with one to four groups selected from the group consisting of OH, halo, and C$_1$-C$_6$alkyl. In some embodiments, A is

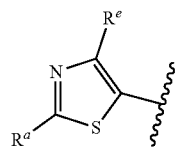

and R$^a$ is selected from the group consisting of H, C$_1$-C$_6$alkyl, —C(O)C$_1$-C$_6$alkyl, 6-membered aryl, and 5- or 6-membered heteroaryl, wherein each C$_1$-C$_6$alkyl, —C(O)C$_1$-C$_6$alkyl, 6-membered aryl, or 5- or 6-membered heteroaryl of R$^a$ is unsubstituted or is substituted with one to four groups selected from the group consisting of OH, halo, C$_1$-C$_6$alkyl and C$_1$-C$_6$alkoxy.

In some embodiments, A is

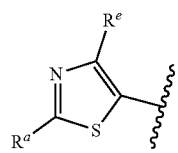

and R$^a$ is a 6-membered aryl or a 5- or 6-membered heteroaryl, wherein the 6-membered aryl and 5- or 6-membered heteroaryl of R$^a$ are unsubstituted or are substituted with one to four groups selected from the group consisting of OH, halo, and C$_1$-C$_6$alkyl. In some embodiments, A is

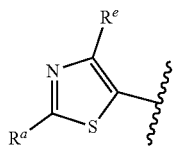

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, $C_1$-$C_6$alkyl and $C_1$-$C_6$alkoxy. In some embodiments, A is

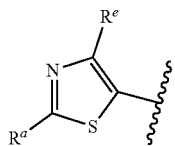

and $R^a$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, $C_1$-$C_6$alkyl and $C_1$-$C_6$alkoxy.

In some embodiments, A is

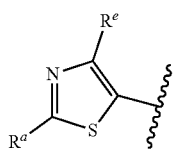

and $R^a$ is selected from the group consisting of $C_1$-$C_6$alkyl,

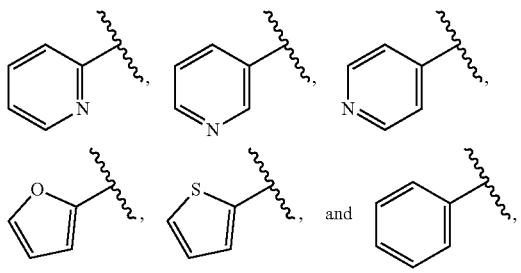

each of which is unsubstituted or is substituted with one to four groups selected from the group consisting of OH, halo, $C_1$-$C_6$alkyl and $C_1$-$C_6$alkoxy. In some embodiments, A is

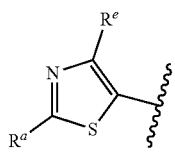

and $R^a$ is selected from the group consisting of H,

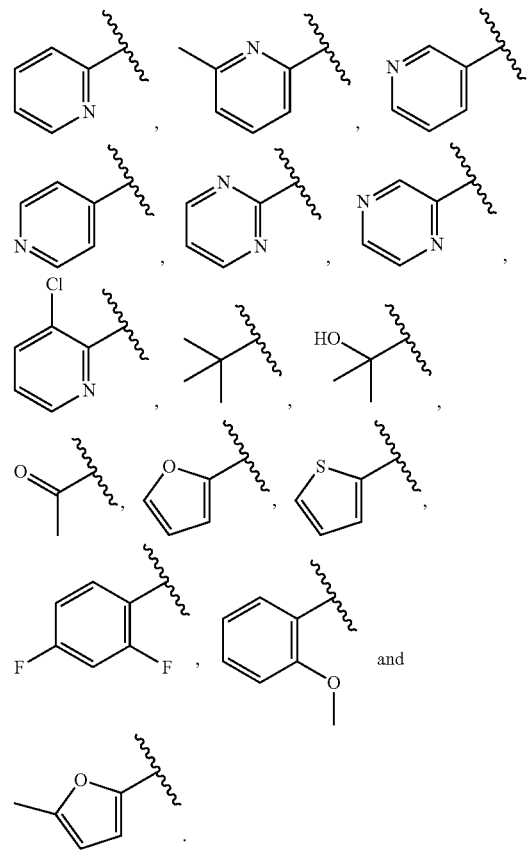

In some embodiments of a compound of Formula (A), (I), (Ia), (Ib), (Ic), (Id), (Ie), (If), (Ig), (Ih), (Ii), (Ij), or (Ik), A is

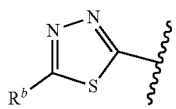

and $R^b$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^b$ is unsubstituted or is substituted with one to four groups selected from the group consisting of OH, halo, and $C_1$-$C_6$alkyl. In some embodiments, A is

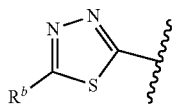

and $R^b$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^b$ is unsubstituted or is substituted with one to four groups selected from the group consisting of OH, halo, $C_1$-$C_6$alkyl and $C_1$-$C_6$alkoxy.

In some embodiments, A is

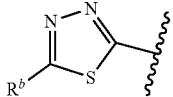

and $R^b$ is a 6-membered aryl or a 5- or 6-membered heteroaryl, wherein the 6-membered aryl and 5- or 6-membered heteroaryl of $R^b$ are unsubstituted or are substituted with one to four groups selected from the group consisting of OH, halo, and $C_1$-$C_6$alkyl. In some embodiments, A is

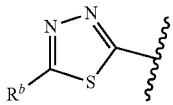

and $R^b$ is a 6-membered aryl or a 5- or 6-membered heteroaryl, wherein the 6-membered aryl and 5- or 6-membered heteroaryl of $R^b$ are unsubstituted or are substituted with one to four groups selected from the group consisting of OH, halo, $C_1$-$C_6$alkyl and $C_1$-$C_6$alkoxy. In some embodiments, A is

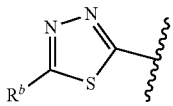

and $R^b$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, $C_1$-$C_6$alkyl and $C_1$-$C_6$alkoxy.

In some embodiments, A is

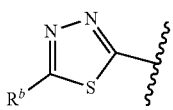

and $R^b$ is selected from the group consisting of $C_1$-$C_6$alkyl,

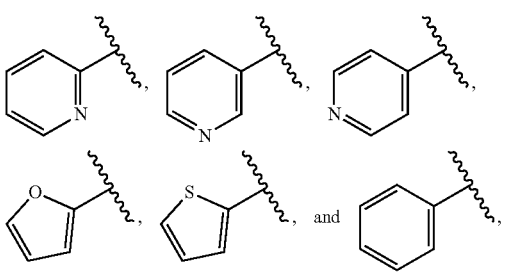

each of which is unsubstituted or is substituted with one to four groups selected from the group consisting of OH, halo, $C_1$-$C_6$alkyl and $C_1$-$C_6$alkoxy. In some embodiments, A is

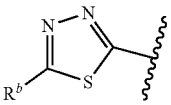

and $R^b$ is selected from the group consisting of H,

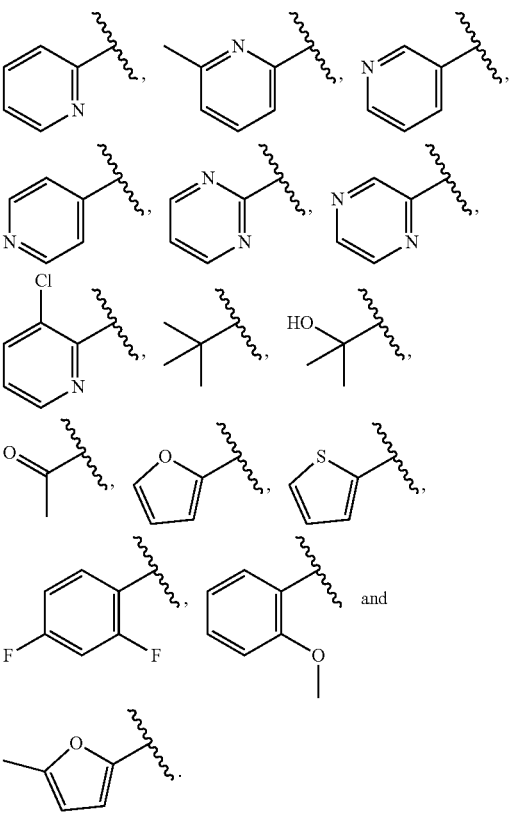

In some embodiments of a compound of Formula (A), (I), (Ia), (Ib), (Ic), (Id), (Ie), (If), (Ig), (Ih), (Ii), (Ij), or (Ik), A is

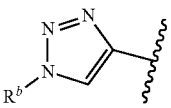

and $R^b$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^b$ is unsubstituted or is substituted with one to four groups selected from the group consisting of OH, halo, and $C_1$-$C_6$alkyl. In some embodiments, A is

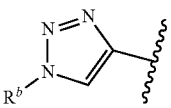

and $R^b$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^b$ is unsubstituted or is substituted with one to four groups selected from the group consisting of OH, halo, $C_1$-$C_6$alkyl and $C_1$-$C_6$alkoxy.

In some embodiments, A is

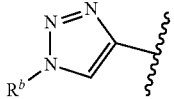

and $R^b$ is a 6-membered aryl or a 5- or 6-membered heteroaryl, wherein the 6-membered aryl and 5- or 6-membered heteroaryl of $R^b$ are unsubstituted or are substituted with one to four groups selected from the group consisting of OH, halo, and $C_1$-$C_6$alkyl. In some embodiments, A is

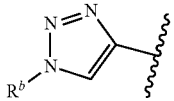

and $R^b$ is a 6-membered aryl or a 5- or 6-membered heteroaryl, wherein the 6-membered aryl and 5- or 6-membered heteroaryl of $R^b$ are unsubstituted or are substituted with one to four groups selected from the group consisting of OH, halo, $C_1$-$C_6$alkyl and $C_1$-$C_6$alkoxy. In some embodiments, A is

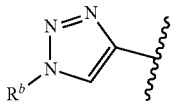

and $R^b$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, $C_1$-$C_6$alkyl and $C_1$-$C_6$alkoxy.

In some embodiments, A is

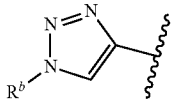

and $R^b$ is selected from the group consisting of $C_1$-$C_6$alkyl,

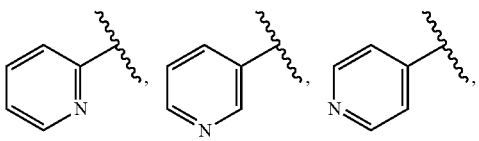

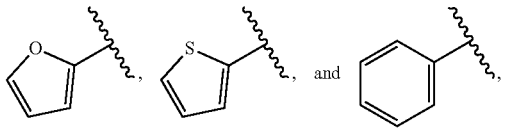

each of which is unsubstituted or is substituted with one to four groups selected from the group consisting of OH, halo, $C_1$-$C_6$alkyl and $C_1$-$C_6$alkoxy. In some embodiments, A is

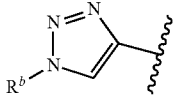

and $R^b$ is selected from the group consisting of H,

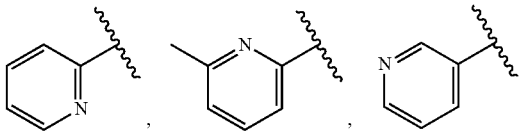

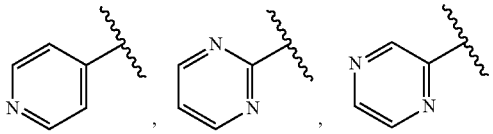

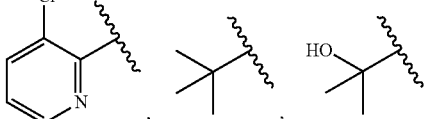

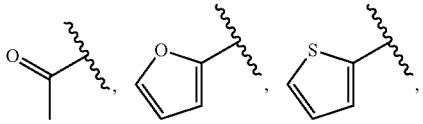

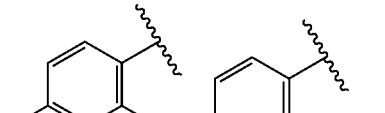

and

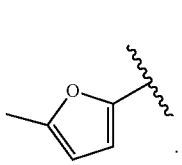

In some embodiments of a compound of Formula (A), (I), (Ia), (Ib), (Ic), (Id), (Ie), (If), (Ig), (Ih), (Ii), (Ij), or (Ik), A is

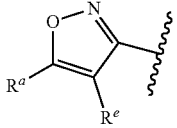

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)

$C_1$-$C_6$alkyl, 6-membered aryl, or 5- or 6-membered heteroaryl of $R^a$ is unsubstituted or is substituted with one to four groups selected from the group consisting of OH, halo, and $C_1$-$C_6$alkyl. In some embodiments, A is

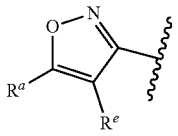

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ is unsubstituted or is substituted with one to four groups selected from the group consisting of OH, halo, $C_1$-$C_6$alkyl and $C_1$-$C_6$alkoxy.

In some embodiments, A is

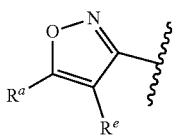

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, and $C_1$-$C_6$alkyl. In some embodiments, A is

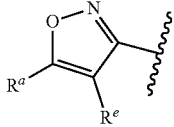

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, $C_1$-$C_6$alkyl and $C_1$-$C_6$alkoxy. In some embodiments, A is

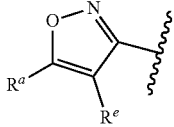

and $R^a$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, $C_1$-$C_6$alkyl and $C_1$-$C_6$alkoxy.

In some embodiments, A is

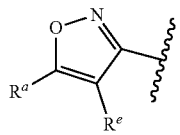

and $R^a$ is selected from the group consisting of $C_1$-$C_6$alkyl

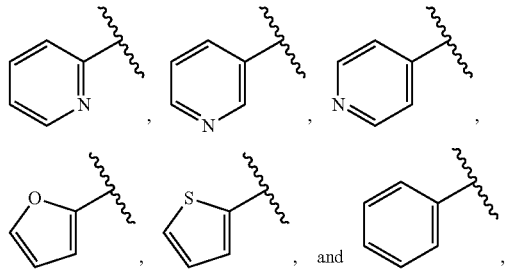

each of which is unsubstituted or is substituted with one to four groups selected from the group consisting of OH, halo, $C_1$-$C_6$alkyl and $C_1$-$C_6$alkoxy. In some embodiments, A is

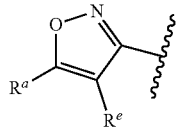

and $R^a$ is selected from the group consisting of H,

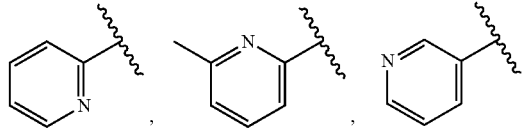

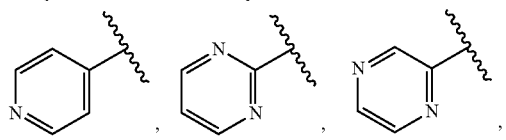

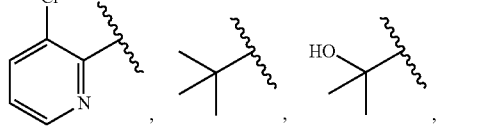

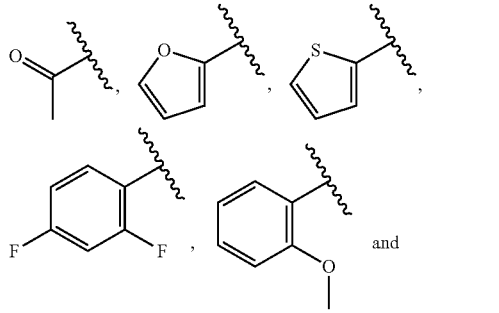

-continued

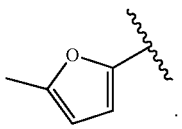

In some embodiments of a compound of Formula (A), (I), (Ia), (Ib), (Ic), (Id), (Ie), (If), (Ig), (Ih), (Ii), (Ij), or (Ik), A is

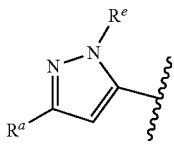

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ is unsubstituted or is substituted with one to four groups selected from the group consisting of OH, halo, and $C_1$-$C_6$alkyl. In some embodiments, A is

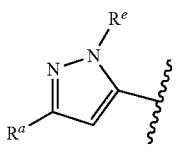

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ is unsubstituted or is substituted with one to four groups selected from the group consisting of OH, halo, $C_1$-$C_6$alkyl and $C_1$-$C_6$alkoxy.

In some embodiments, A is

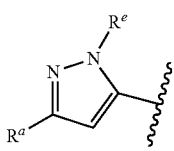

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, and $C_1$-$C_6$alkyl. In some embodiments, A is

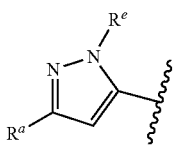

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, $C_1$-$C_6$alkyl and $C_1$-$C_6$alkoxy. In some embodiments, A is

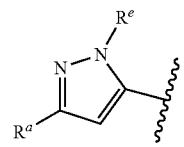

and $R^a$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, $C_1$-$C_6$alkyl and $C_1$-$C_6$alkoxy.

In some embodiments, A is

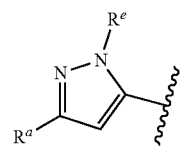

and $R^a$ is selected from the group consisting of $C_1$-$C_6$alkyl,

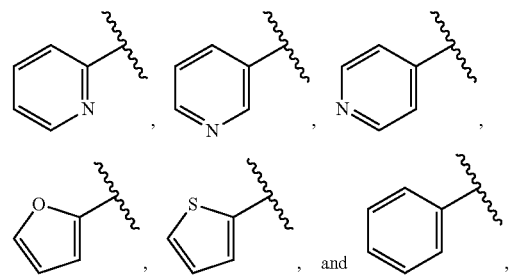

each of which is unsubstituted or is substituted with one to four groups selected from the group consisting of OH, halo, $C_1$-$C_6$alkyl and $C_1$-$C_6$alkoxy. In some embodiments, A is

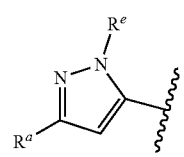

and $R^a$ is selected from the group consisting of H,

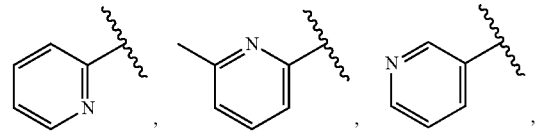

-continued

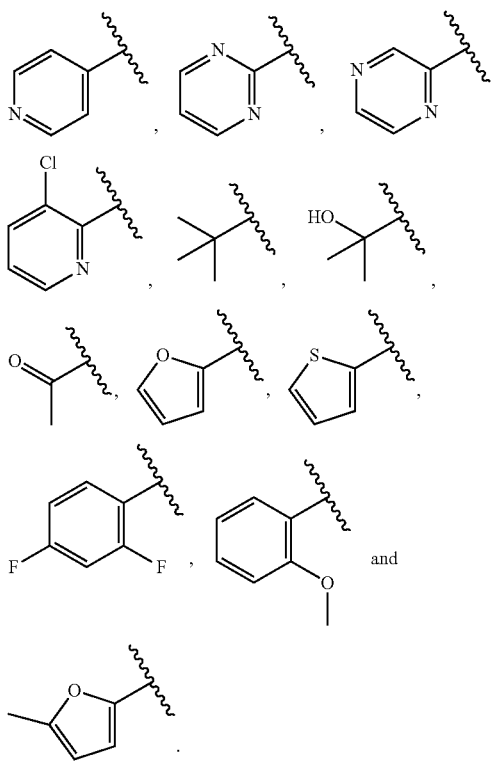

In some embodiments of a compound of Formula (A), (I), (Ia), (Ib), (Ic), (Id), (Ie), (If), (Ig), (Ih), (Ii), (Ij), or (Ik), A is

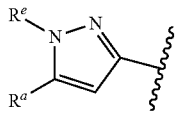

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ is unsubstituted or is substituted with one to four groups selected from the group consisting of OH, halo, and $C_1$-$C_6$alkyl. In some embodiments, A is

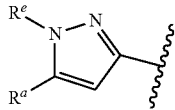

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ is unsubstituted or is substituted with one to four groups selected from the group consisting of OH, halo, $C_1$-$C_6$alkyl and $C_1$-$C_6$alkoxy.

In some embodiments, A is

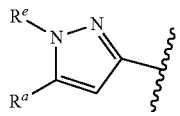

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, and $C_1$-$C_6$alkyl. In some embodiments, A is

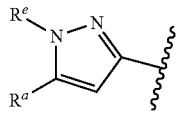

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, $C_1$-$C_6$alkyl and $C_1$-$C_6$alkoxy. In some embodiments, A is

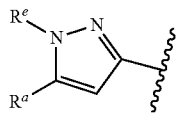

and $R^a$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, $C_1$-$C_6$alkyl and $C_1$-$C_6$alkoxy.

In some embodiments, A is

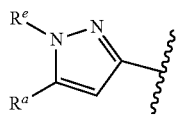

and $R^a$ is selected from the group consisting of $C_1$-$C_6$alkyl,

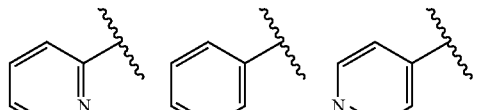

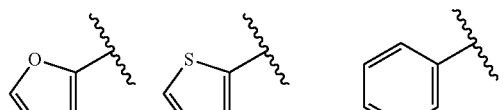

each of which is unsubstituted or is substituted with one to four groups selected from the group consisting of OH, halo, $C_1$-$C_6$alkyl and $C_1$-$C_6$alkoxy. In some embodiments, A is

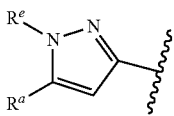

and R$^a$ is selected from the group consisting of H,

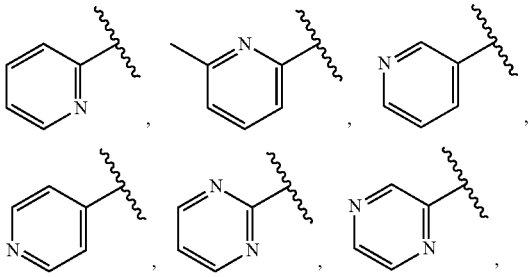

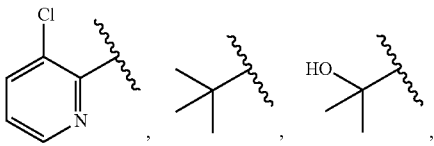

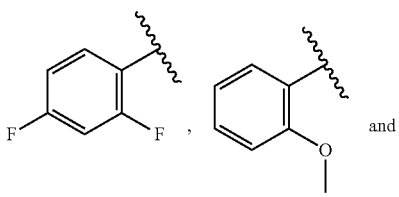 and

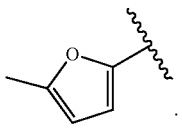

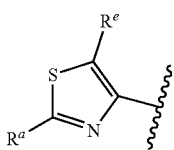.

In some embodiments of a compound of Formula (A), (I), (Ia), (Ib), (Ic), (Id), (Ie), (If), (Ig), (Ih), (Ii), (Ij), or (Ik), A is

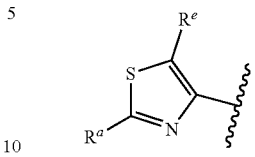

and R$^a$ is selected from the group consisting of H, C$_1$-C$_6$alkyl, —C(O)C$_1$-C$_6$alkyl, 6-membered aryl, and 5- or 6-membered heteroaryl, wherein each C$_1$-C$_6$alkyl, —C(O)C$_1$-C$_6$alkyl, 6-membered aryl, or 5- or 6-membered heteroaryl of R$^a$ is unsubstituted or is substituted with one to four groups selected from the group consisting of OH, halo, and C$_1$-C$_6$alkyl. In some embodiments, A is

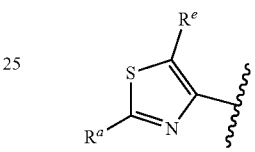

and R$^a$ is selected from the group consisting of H, C$_1$-C$_6$alkyl, —C(O)C$_1$-C$_6$alkyl, 6-membered aryl, and 5- or 6-membered heteroaryl, wherein each C$_1$-C$_6$alkyl, —C(O)C$_1$-C$_6$alkyl, 6-membered aryl, or 5- or 6-membered heteroaryl of R$^a$ is unsubstituted or is substituted with one to four groups selected from the group consisting of OH, halo, C$_1$-C$_6$alkyl and C$_1$-C$_6$alkoxy.

In some embodiments, A is

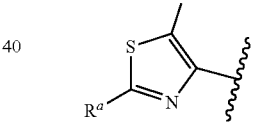

and R$^a$ is a 6-membered aryl or a 5- or 6-membered heteroaryl, wherein the 6-membered aryl and 5- or 6-membered heteroaryl of R$^a$ are unsubstituted or are substituted with one to four groups selected from the group consisting of OH, halo, and C$_1$-C$_6$alkyl. In some embodiments, A is

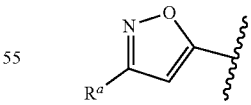

and R$^a$ is a 6-membered aryl or a 5- or 6-membered heteroaryl, wherein the 6-membered aryl and 5- or 6-membered heteroaryl of R$^a$ are unsubstituted or are substituted with one to four groups selected from the group consisting of OH, halo, C$_1$-C$_6$alkyl and C$_1$-C$_6$alkoxy. In some embodiments, A is and R$^a$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, C$_1$-C$_6$alkyl and C$_1$-C$_6$alkoxy.

In some embodiments, A is

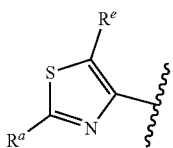

and $R^a$ is selected from the group consisting of $C_1$-$C_6$alkyl,

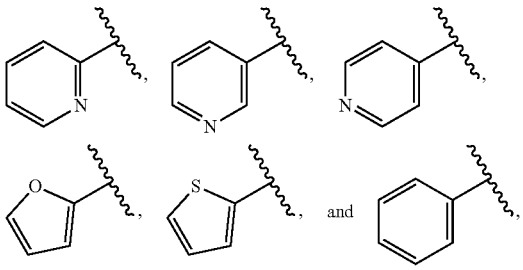

each of which is unsubstituted or is substituted with one to four groups selected from the group consisting of OH, halo, $C_1$-$C_6$alkyl and $C_1$-$C_6$alkoxy. In some embodiments, A is

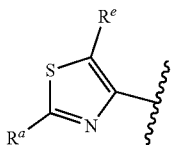

and $R^a$ is selected from the group consisting of H,

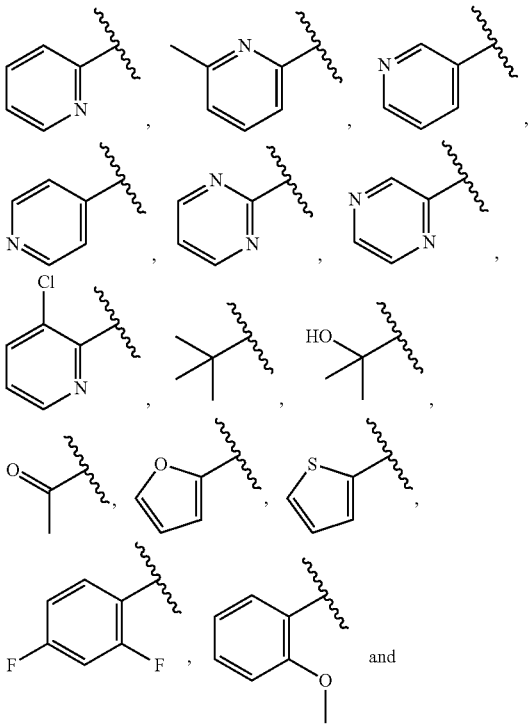

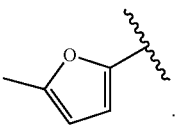

In some embodiments of a compound of Formula (A), (I), (Ia), (Ib), (Ic), (Id), (Ie), (If), (Ig), (Ih), (Ii), (Ij), or (Ik), A is

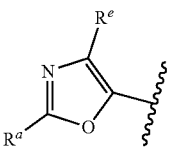

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O) $C_1$-$C_6$alkyl, 6-membered aryl, or 5- or 6-membered heteroaryl of $R^a$ is unsubstituted or is substituted with one to four groups selected from the group consisting of OH, halo, and $C_1$-$C_6$alkyl. In some embodiments, A is

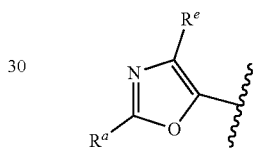

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O) $C_1$-$C_6$alkyl, 6-membered aryl, or 5- or 6-membered heteroaryl of $R^a$ is unsubstituted or is substituted with one to four groups selected from the group consisting of OH, halo, $C_1$-$C_6$alkyl and $C_1$-$C_6$alkoxy.

In some embodiments, A is

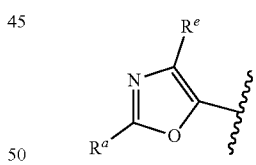

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, and $C_1$-$C_6$alkyl. In some embodiments, A is

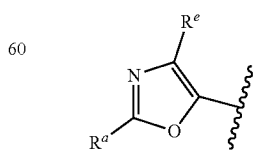

and $R^a$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, $C_1$-$C_6$alkyl and $C_1$-$C_6$alkoxy. In some embodiments, A is

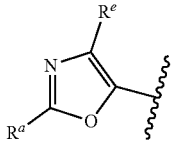

and $R^a$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, $C_1$-$C_6$alkyl and $C_1$-$C_6$alkoxy.

In some embodiments, A is

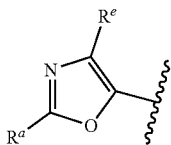

and $R^a$ is selected from the group consisting of $C_1$-$C_6$alkyl,

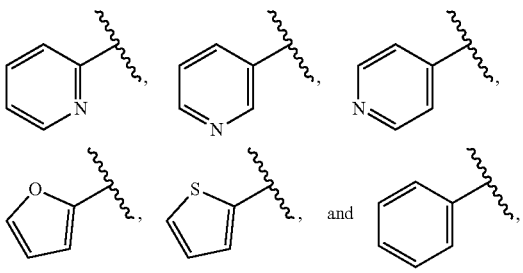

each of which is unsubstituted or is substituted with one to four groups selected from the group consisting of OH, halo, $C_1$-$C_6$alkyl and $C_1$-$C_6$alkoxy. In some embodiments, A is

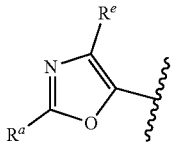

and $R^a$ is selected from the group consisting of H,

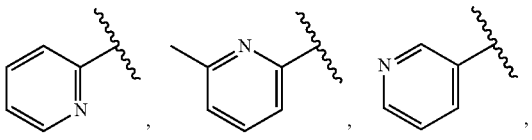

-continued

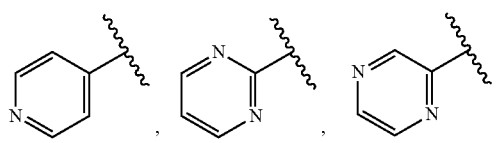

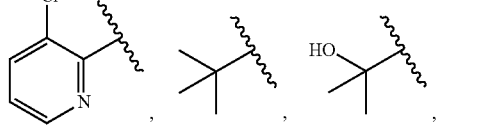

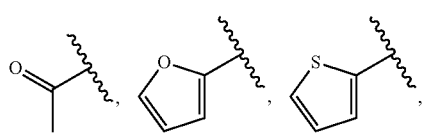

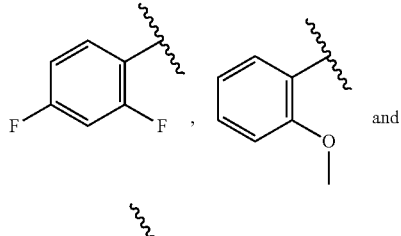 and

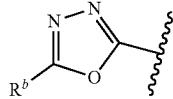

In some embodiments of a compound of Formula (A), (I), (Ia), (Ib), (Ic), (Id), (Ie), (If), (Ig), (Ih), (Ii), (Ij), or (Ik), A is

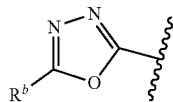

and $R^b$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^b$ is unsubstituted or is substituted with one to four groups selected from the group consisting of OH, halo, and $C_1$-$C_6$alkyl. In some embodiments, A is

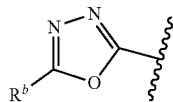

and $R^b$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^b$ is unsubstituted or is substituted with one to four groups selected from the group consisting of OH, halo, $C_1$-$C_6$alkyl and $C_1$-$C_6$alkoxy.

In some embodiments, A is

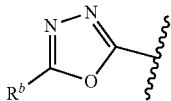

and $R^b$ is a 6-membered aryl or a 5- or 6-membered heteroaryl, wherein the 6-membered aryl and 5- or 6-membered heteroaryl of $R^b$ are unsubstituted or are substituted with one to four groups selected from the group consisting of OH, halo, and $C_1$-$C_6$alkyl. In some embodiments, A is

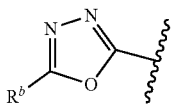

and $R^b$ is a 6-membered aryl or a 5- or 6-membered heteroaryl, wherein the 6-membered aryl and 5- or 6-membered heteroaryl of $R^a$ are unsubstituted or are substituted with one to four groups selected from the group consisting of OH, halo, $C_1$-$C_6$alkyl and $C_1$-$C_6$alkoxy. In some embodiments, A is

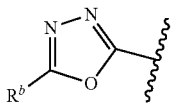

and $R^b$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, $C_1$-$C_6$alkyl and $C_1$-$C_6$alkoxy.

In some embodiments, A is

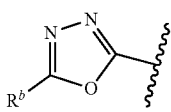

and $R^b$ is selected from the group consisting of $C_1$-$C_6$alkyl,

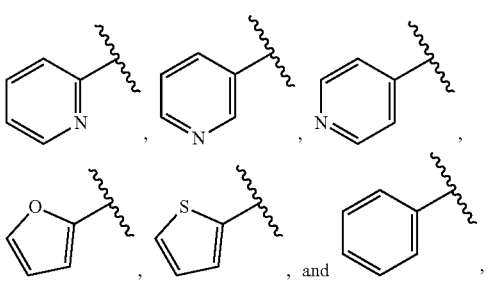

each of which is unsubstituted or is substituted with one to four groups selected from the group consisting of OH, halo, $C_1$-$C_6$alkyl and $C_1$-$C_6$alkoxy. In some embodiments, A is

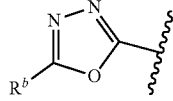

and $R^b$ is selected from the group consisting of H,

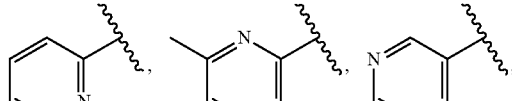

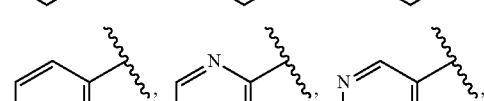

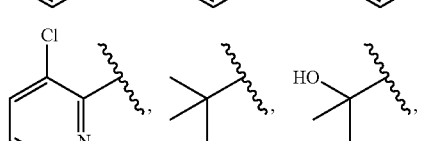

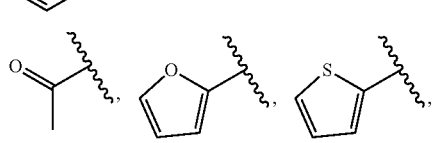

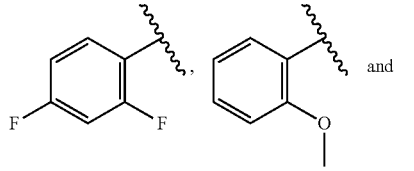

In some embodiments of a compound of Formula (A), (I), (Ia), (Ib), (Ic), (Id), (Ie), (If), (Ig), (Ih), (Ii), (Ij), or (Ik), A is

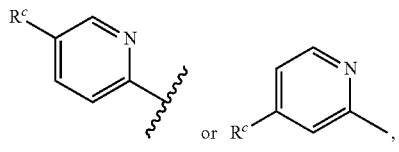

and $R^c$ is selected from the group consisting of $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^c$ is unsubstituted or is substituted with one to four groups selected from the group consisting of OH, halo, and $C_1$-$C_6$alkyl.

In some embodiments, A is

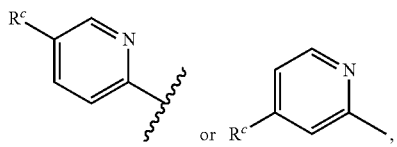

and $R^c$ is a 6-membered aryl or a 5- or 6-membered heteroaryl, wherein the 6-membered aryl and 5- or 6-membered heteroaryl of $R^c$ are unsubstituted or are substituted with one to four groups selected from the group consisting of OH, halo, and $C_1$-$C_6$alkyl. In some embodiments, A is

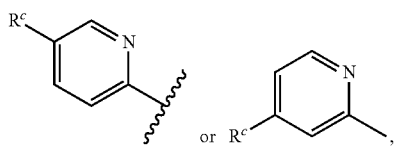

and $R^c$ is selected from the group consisting of phenyl, pyrrolyl, pyrazolyl, imidazolyl, triazolyl, tetrazolyl, furanyl, isoxazolyl, oxazolyl, oxadiazolyl, thiophenyl, isothiazolyl, thiazolyl, thiadiazolyl, pyridyl, pyridazinyl, pyrimidinyl, pyrazinyl, triazinyl, and tetrazinyl, each unsubstituted or substituted with one to four groups selected from the group consisting of OH, halo, and $C_1$-$C_6$alkyl.

In some embodiments, A is

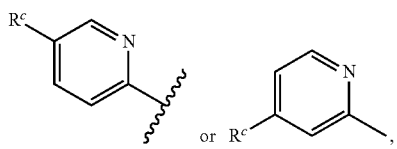

and $R^c$ is selected from the group consisting of $C_1$-$C_6$alkyl,

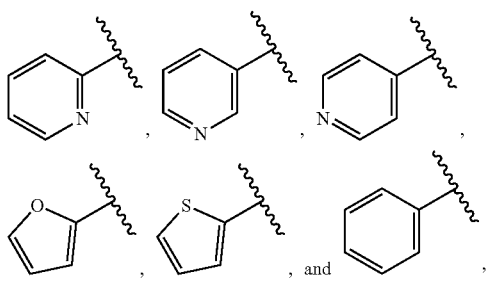

each of which is unsubstituted or is substituted with one to four groups selected from the group consisting of OH, halo, and $C_1$-$C_6$alkyl. In some embodiments, A is

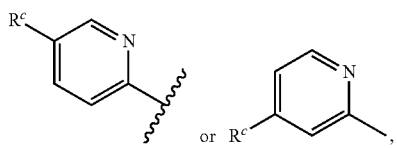

and $R^c$ is selected from the group consisting of

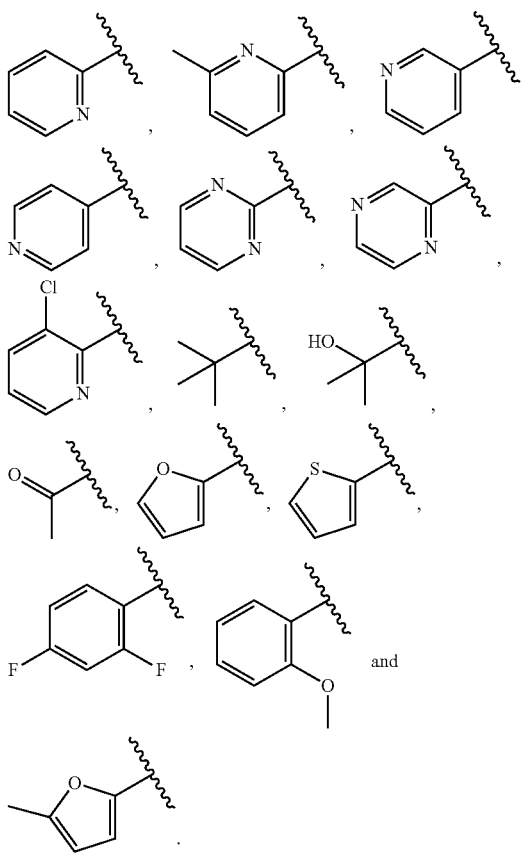

In some embodiments of a compound of Formula (A), (I), (Ia), (Ib), (Ic), (Id), (Ie), (If), (Ig), (Ih), (Ti), (Ij), or (Ik), A is

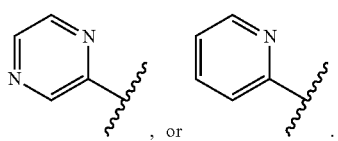 [SMILES: *c1cnccn1 ; *c1ccccn1]

In some embodiments of a compound of Formula (A), (I), (Ia), (Ib), (Ic), (Id), (Ie), (If), (Ig), (Ih), (Ii), (Ij), or (Ik), A is

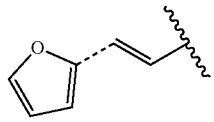

In other embodiments, A is

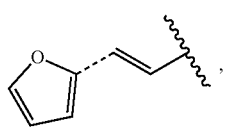

wherein

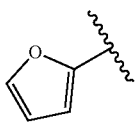

is attached in an E configuration. In other embodiments, A is

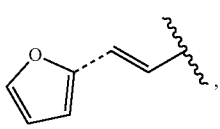

wherein

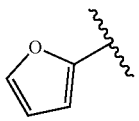

is attached in a Z configuration. For instance, in some embodiments, A is

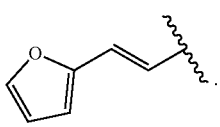 [SMILES: */C=C/c1ccco1]

In another embodiment, A is

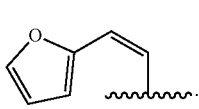 [SMILES: */C=C\c1ccco1]

In some embodiments of a compound of Formula (A), (I), (Ia), (Ib), (Ic), (Id), (Ie), (If), (Ig), (Ih), (Ii), (Ij), or (Ik), A is

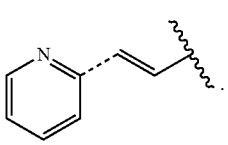

In some embodiments, A is

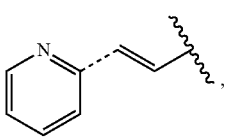

wherein

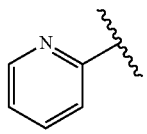 [SMILES: *c1ccccn1]

is attached in an E configuration. In other embodiments, A is

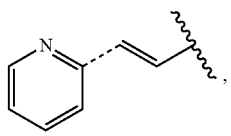

wherein

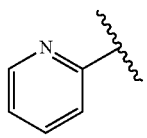 [SMILES: *c1ccccn1]

is attached in a Z configuration. For instance, in some embodiments, A is

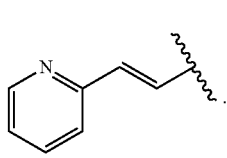

In other embodiments, A is

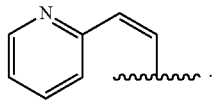

It is understood that each description of A may be combined with each description of $R^2$, $R^3$, $R^4$, $R^5$, and/or $R^6$ the same as if each and every combination were specifically and individually listed. For example, in one aspect, it is understood that each description of A may be combined in one aspect with a variation in which $R^2$ and $R^6$ are each $CF_3$ and $R^3$, $R^4$, and $R^5$ are each hydrogen. Each description of A may also be combined with each description of $R^1$ and n the same as if each and every combination were specifically and individually listed. It is similarly understood that each description of A may be combined with each description of $G_1$, $G_2$, and $R^7$ the same as if each and every combination were specifically and individually listed.

In some embodiments of a compound of Formula (A), (I), (Ia), (Ib), (Ic), (Id), (Ie), (If), (Ig), (Ii), (Ij), or (Ik), $R^7$ is H. In some embodiments, $R^7$ is H. In some embodiments, $R^7$ is $C_1$-$C_6$alkyl. In some embodiments, $R^7$ is methyl, ethyl, n-propyl, isopropyl, n-butyl, isobutyl, sec-butyl, or tert-butyl. In certain embodiments, $R^7$ is methyl.

In some embodiments of a compound of Formula (A), (I), (Ia), (Ib), (Ic), (Id), (Ie), (If), (Ig), (Ii), (Ij), or (Ik), $R^7$ and $R^d$ are both H. In some embodiments, $R^d$ is $C_1$-$C_6$alkyl and $R^7$ is H. In other embodiments, $R^d$ is H and $R^7$ is $C_1$-$C_6$alkyl. In certain embodiments, $R^d$ is methyl and $R^7$ is H. In other embodiments, $R^d$ is H and $R^7$ is methyl.

In some embodiments, A is

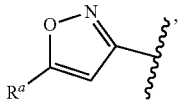

$R^a$ is furanyl, wherein the furanyl of $R^a$ is unsubstituted or substituted with OH, halo, or $C_1$-$C_6$alkyl. In some embodiments, A is

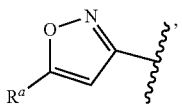

$R^a$ is furanyl, wherein the furanyl of $R^a$ is unsubstituted or substituted with OH, halo, or $C_1$-$C_6$alkyl, $R^2$ is $C_1$-$C_6$haloalkyl, and $R^6$ is $C_1$-$C_6$haloalkyl. In some embodiments, A is

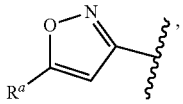

$R^a$ is

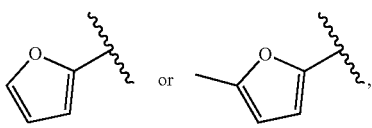

$R^2$ is $C_1$-$C_6$haloalkyl, and $R^6$ is $C_1$-$C_6$haloalkyl. In some embodiments, A is

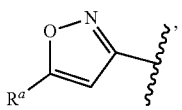

$R^a$ is

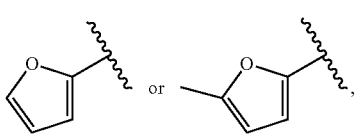

$R^2$ is $CF_3$, and $R^6$ is $CF_3$. In some embodiments, A is

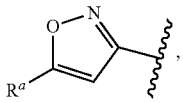

$R^a$ is

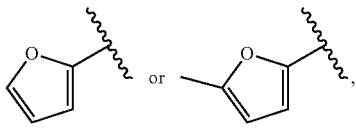

$R^2$ is halo, and $R^3$ is halo. In certain embodiments, A is

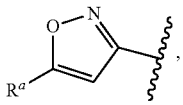

$R^a$ is

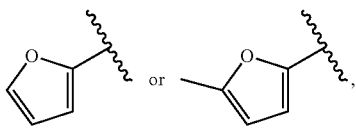

$R^2$ is Cl, and $R^3$ is Cl. In certain embodiments, A is

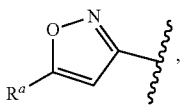

$R^a$ is

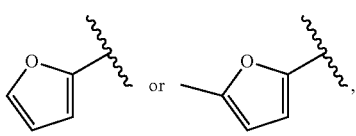

and $R^3$ is taken together with $R^1$ and the atoms to which they are attached to form a 5- or 6-membered carbocyclic ring. In some embodiments, A is

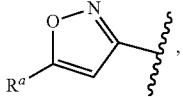

$R^a$ is

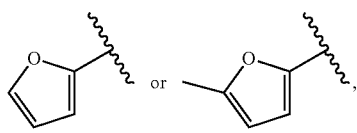

and $R^6$ is CN. In some embodiments, A is

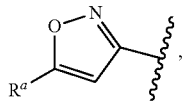

$R^a$ is

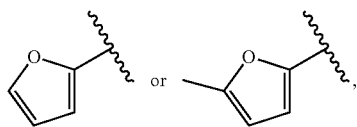

$R^6$ is CN, and $R^4$ is halo. In certain embodiments, A is

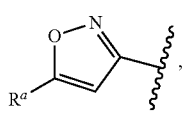

$R^a$ is

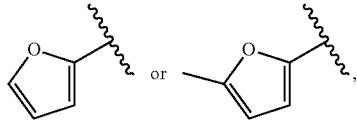

$R^2$ is $CF_3$, $R^6$ is $CF_3$, and $R^1$ is $C_1$-$C_6$alkyl or $C_1$-$C_6$cycloalkyl. In some embodiments, A is

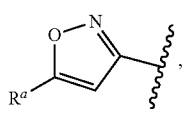

$R^a$ is

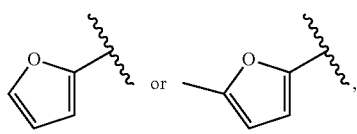

$R^2$ is $CF_3$, $R^6$ is $CF_3$, and $R^7$ or $R^d$ is $C_1$-$C_6$alkyl.

In some embodiments, A is

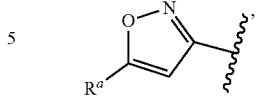

$R^a$ is thiophenyl, wherein the thiophenyl of $R^a$ is unsubstituted or substituted with OH, halo, or $C_1$-$C_6$alkyl. In some embodiments, A is

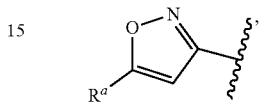

$R^a$ is thiophenyl, wherein the thiophenyl of $R^a$ is unsubstituted or substituted with OH, halo, or $C_1$-$C_6$alkyl, $R^2$ is $C_1$-$C_6$haloalkyl, and $R^6$ is $C_1$-$C_6$haloalkyl. In some embodiments, A is

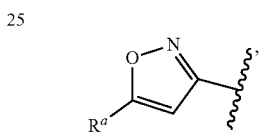

$R^a$ is

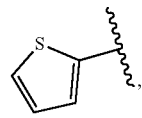 [SMILES: *c1cccs1]

$R^2$ is $C_1$-$C_6$haloalkyl, and $R^6$ is $C_1$-$C_6$haloalkyl. In some embodiments, A is

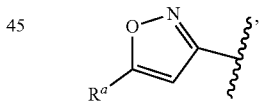

$R^a$ is

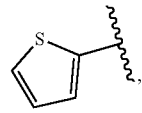

$R^2$ is $CF_3$, and $R^6$ is $CF_3$. In certain embodiments, A is

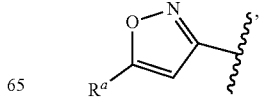

$R^a$ is

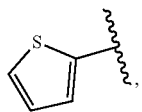, $R^2$ is $CF_3$, $R^6$ is $CF_3$, and $R^1$ is $C_1$-$C_6$alkyl or $C_1$-$C_6$cycloalkyl. In some embodiments, A is

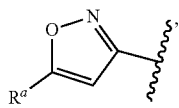

$R^a$ is

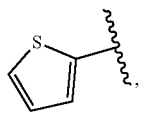, $R^2$ is $CF_3$, $R^6$ is $CF_3$, and $R^7$ or $R^d$ is $C_1$-$C_6$alkyl.

In some embodiments, A is

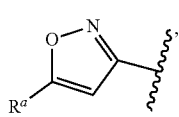

$R^a$ is pyridyl, wherein the pyridyl of $R^a$ is unsubstituted or substituted with OH, halo, or $C_1$-$C_6$alkyl. In some embodiments, A is

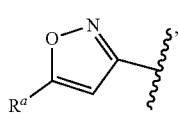

$R^a$ is pyridyl, wherein the pyridyl of $R^a$ is unsubstituted or substituted with OH, halo, or $C_1$-$C_6$alkyl, $R^2$ is $C_1$-$C_6$haloalkyl, and $R^6$ is $C_1$-$C_6$haloalkyl. In some embodiments, A is

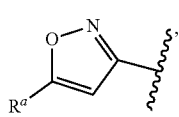

$R^a$ is

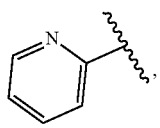 

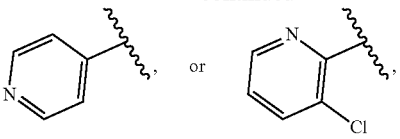

$R^2$ is $CF_3$, and $R^6$ is $CF_3$. In certain embodiments, A is

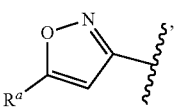

$R^a$ is

 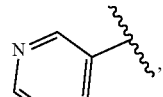

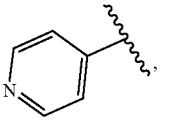 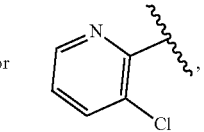

$R^2$ is $CF_3$, $R^6$ is $CF_3$, and $R^1$ is $C_1$-$C_6$alkyl or $C_1$-$C_6$cycloalkyl. In some embodiments, A is

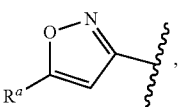

$R^a$ is

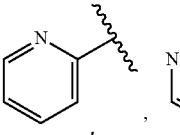

$R^2$ is $CF_3$, $R^6$ is $CF_3$, and $R^7$ or $R^d$ is $C_1$-$C_6$alkyl.

In some embodiments, A is

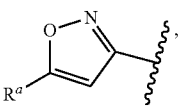

$R^a$ is phenyl, wherein the phenyl of $R^a$ is unsubstituted or substituted with OH, halo, or $C_1$-$C_6$alkyl. In some embodiments, A is

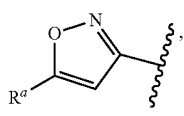

$R^a$ is phenyl, wherein the phenyl of $R^a$ is unsubstituted or substituted with OH, halo, or $C_1$-$C_6$alkyl, $R^2$ is $C_1$-$C_6$haloalkyl, and $R^6$ is $C_1$-$C_6$haloalkyl. In some embodiments, A is

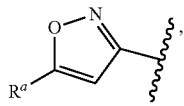

$R^a$ is

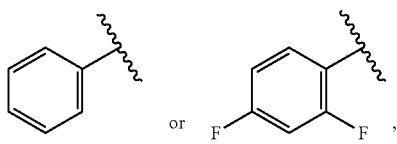 [SMILES: *c1ccccc1 ; *c1ccc(F)cc1F]

$R^2$ is $CF_3$, and $R^6$ is $CF_3$. In certain embodiments, A is

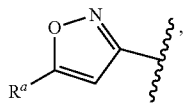

$R^a$ is

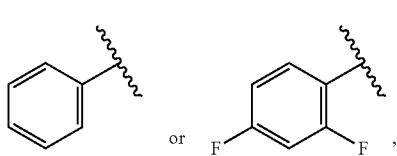 [SMILES: *c1ccccc1 ; *c1ccc(F)cc1F]

$R^2$ is $CF_3$, $R^6$ is $CF_3$, and $R^1$ is $C_1$-$C_6$alkyl or $C_1$-$C_6$cycloalkyl. In some embodiments, A is

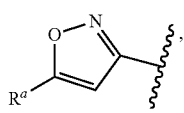

$R^a$ is

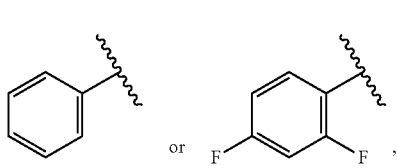 [SMILES: *c1ccccc1 ; *c1ccc(F)cc1F]

$R^2$ is $CF_3$, $R^6$ is $CF_3$, and $R^7$ or $R^d$ is $C_1$-$C_6$alkyl.

In some embodiments, A is

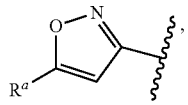

$R^a$ is

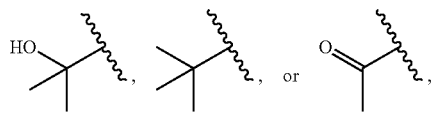

$R^2$ is $C_1$-$C_6$haloalkyl, and $R^6$ is $C_1$-$C_6$haloalkyl. In some embodiments, A is

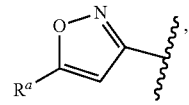

$R^a$ is

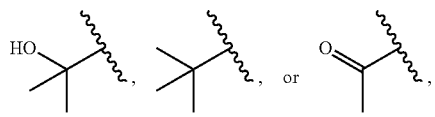

$R^2$ is $CF_3$, and $R^6$ is $CF_3$. In certain embodiments, A is

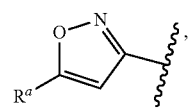

$R^a$ is

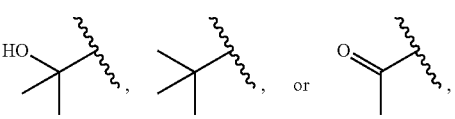

$R^2$ is $CF_3$, $R^6$ is $CF_3$, and $R^1$ is $C_1$-$C_6$alkyl or $C_1$-$C_6$cycloalkyl. In some embodiments, A is

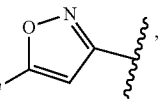

$R^a$ is

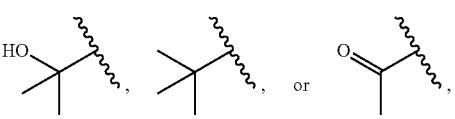

$R^2$ is $CF_3$, $R^6$ is $CF_3$, and $R^7$ or $R^d$ is $C_1$-$C_6$alkyl.

In some embodiments, A is

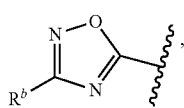, $R^b$ is phenyl, wherein the phenyl of $R^b$ is unsubstituted or substituted with OH, halo, or $C_1$-$C_6$alkyl. In some embodiments, A is

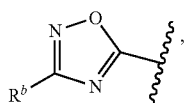, $R^b$ is phenyl, wherein the phenyl of $R^b$ is unsubstituted or substituted with OH, halo, or $C_1$-$C_6$alkyl, $R^2$ is $C_1$-$C_6$haloalkyl, and $R^6$ is $C_1$-$C_6$haloalkyl. In some embodiments, A is

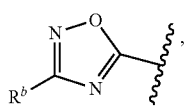, $R^b$ is

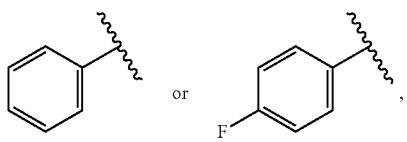 [SMILES: *c1ccccc1 ; *c1ccc(F)cc1], $R^2$ is $CF_3$, and $R^6$ is $CF_3$. In certain embodiments, A is

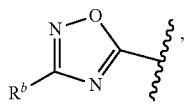, $R^b$ is

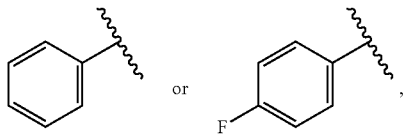 [SMILES: *c1ccccc1 ; *c1ccc(F)cc1], $R^2$ is $CF_3$, $R^6$ is $CF_3$, and $R^1$ is $C_1$-$C_6$alkyl or $C_1$-$C_6$cycloalkyl. In some embodiments, A is

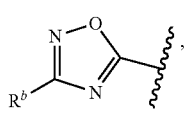, $R^b$ is

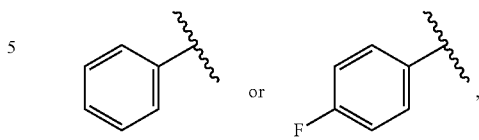, $R^2$ is $CF_3$, $R^6$ is $CF_3$, and $R^7$ or $R^d$ is $C_1$-$C_6$alkyl.

In some embodiments, A is

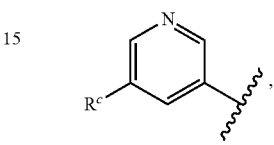, $R^c$ is furanyl, wherein the furanyl of $R^c$ is unsubstituted or substituted with OH, halo, or $C_1$-$C_6$alkyl. In some embodiments, A is

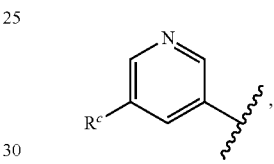, $R^c$ is furanyl, wherein the furanyl of $R^c$ is unsubstituted or substituted with OH, halo, or $C_1$-$C_6$alkyl, $R^2$ is $C_1$-$C_6$haloalkyl, and $R^6$ is $C_1$-$C_6$haloalkyl. In some embodiments, A is

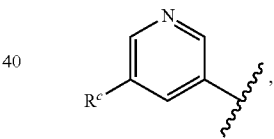, $R^c$ is 2-furanyl, $R^2$ is $CF_3$, and $R^6$ is $CF_3$. In certain embodiments, A is

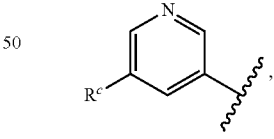, $R^c$ is 2-furanyl, $R^2$ is $CF_3$, $R^6$ is $CF_3$, and $R^1$ is $C_1$-$C_6$alkyl or $C_1$-$C_6$cycloalkyl. In some embodiments, A is

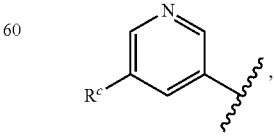, $R^c$ is 2-furanyl, $R^2$ is $CF_3$, $R^6$ is $CF_3$, and $R^7$ or $R^d$ is $C_1$-$C_6$alkyl.

In some embodiments, A is

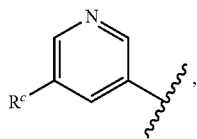

$R^c$ is pyridyl or phenyl, wherein the pyridyl or phenyl of $R^c$ is unsubstituted or substituted with OH, halo, or $C_1$-$C_6$alkyl. In some embodiments, A is

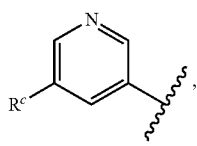

$R^c$ is pyridyl or phenyl, wherein the pyridyl or phenyl of $R^c$ is unsubstituted or substituted with OH, halo, or $C_1$-$C_6$alkyl, $R^2$ is $C_1$-$C_6$haloalkyl, and $R^6$ is $C_1$-$C_6$haloalkyl. In some embodiments, A is

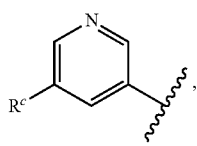

$R^c$ is

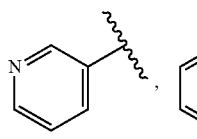

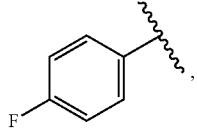

$R^2$ is $CF_3$, and $R^6$ is $CF_3$. In certain embodiments, A is

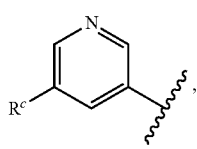

$R^c$ is

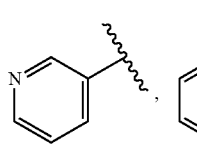

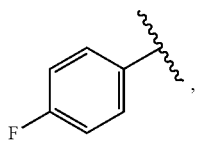

$R^2$ is $CF_3$, $R^6$ is $CF_3$, and $R^1$ is $C_1$-$C_6$alkyl or $C_1$-$C_6$cycloalkyl. In some embodiments, A is

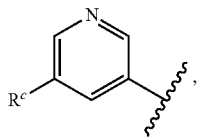
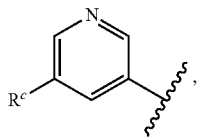

$R^c$ is

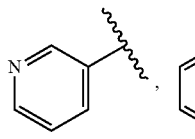

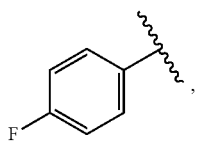

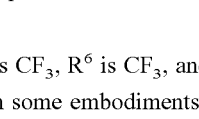

$R^2$ is $CF_3$, $R^6$ is $CF_3$, and $R^7$ or $R^d$ is $C_1$-$C_6$alkyl.

In some embodiments, A is

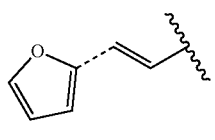

$R^2$ is $C_1$-$C_6$haloalkyl, and $R^6$ is $C_1$-$C_6$haloalkyl. In some embodiments, A is

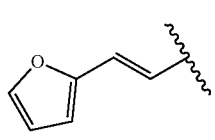

$R^2$ is $CF_3$, and $R^6$ is $CF_3$. In certain embodiments, A is

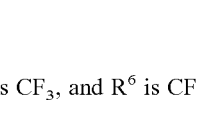

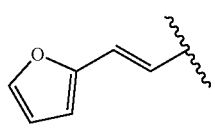

$R^2$ is $CF_3$, $R^6$ is $CF_3$, and $R^1$ is $C_1$-$C_6$alkyl or $C_1$-$C_6$cycloalkyl. In some embodiments, A is

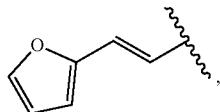, $R^2$ is $CF_3$, $R^6$ is $CF_3$, and $R^7$ or $R^a$ is $C_1$-$C_6$alkyl.
In some embodiments, A is

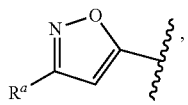, $R^a$ is furanyl, wherein the furanyl of $R^a$ is unsubstituted or substituted with OH, halo, $C_1$-$C_6$alkyl or $C_1$-$C_6$alkoxy. In some embodiments, A is

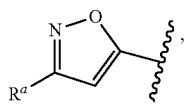, $R^a$ is furanyl, wherein the furanyl of $R^a$ is unsubstituted or substituted with OH, halo, $C_1$-$C_6$alkyl or $C_1$-$C_6$alkoxy, $R^2$ is $C_1$-$C_6$haloalkyl, and $R^6$ is $C_1$-$C_6$haloalkyl. In certain embodiments, A is

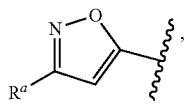, $R^a$ is

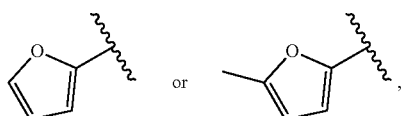, $R^2$ is $CF_3$, and $R^6$ is $CF_3$. In certain embodiments, A is

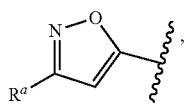, $R^a$ is

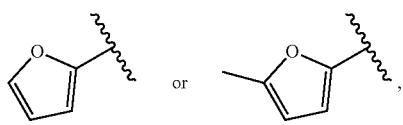, and $R^3$ is taken together with $R^1$ and the atoms to which they are attached to form a 5- or 6-membered carbocyclic ring.

In some embodiments, A is

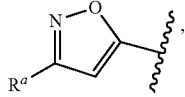, $R^a$ is pyridyl, wherein the pyridyl of $R^a$ is unsubstituted or substituted with OH, halo, $C_1$-$C_6$alkyl or $C_1$-$C_6$alkoxy. In some embodiments, A is

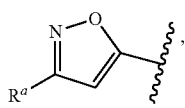, $R^a$ is pyridyl, wherein the pyridyl of $R^a$ is unsubstituted or substituted with OH, halo, $C_1$-$C_6$alkyl or $C_1$-$C_6$alkoxy, $R^2$ is $C_1$-$C_6$haloalkyl, and $R^6$ is $C_1$-$C_6$haloalkyl. In certain embodiments, A is

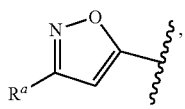, $R^a$ is

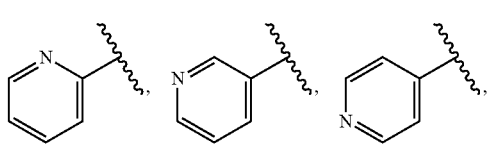

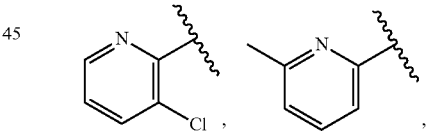

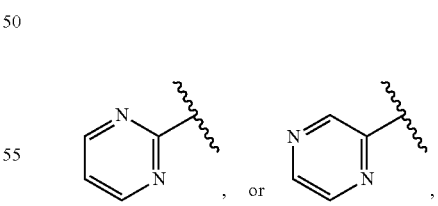, $R^2$ is $CF_3$, and $R^6$ is $CF_3$. In certain embodiments, A is

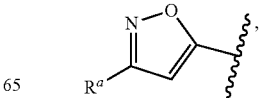, $R^a$ is

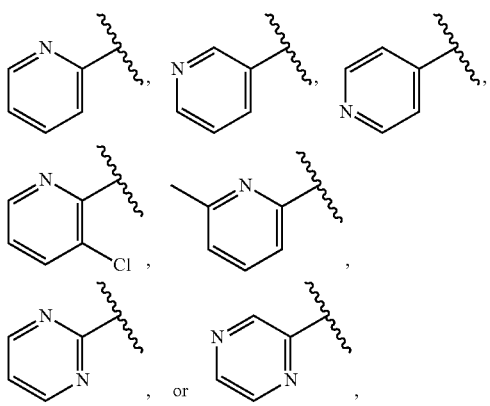

and $R^3$ is taken together with $R^1$ and the atoms to which they are attached to form a 5- or 6-membered carbocyclic ring.

In some embodiments, A is

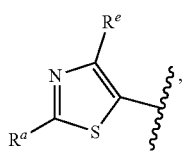

$R^a$ is furanyl, wherein the furanyl of $R^a$ is unsubstituted or substituted with OH, halo, $C_1$-$C_6$alkyl or $C_1$-$C_6$alkoxy. In some embodiments, A is

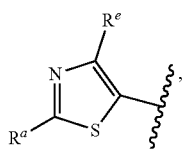

$R^a$ is furanyl, wherein the furanyl of $R^a$ is unsubstituted or substituted with OH, halo, $C_1$-$C_6$alkyl or $C_1$-$C_6$alkoxy, $R^2$ is $C_1$-$C_6$haloalkyl, and $R^6$ is $C_1$-$C_6$haloalkyl. In certain embodiments, A is

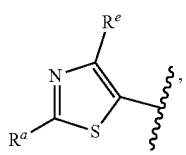

$R^a$ is

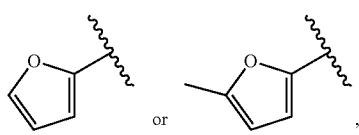

$R^2$ is $CF_3$, and $R^6$ is $CF_3$. In certain embodiments, A is

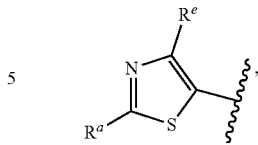

$R^a$ is

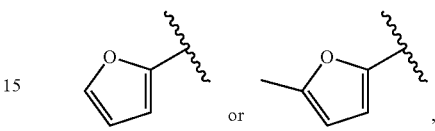

and $R^3$ is taken together with $R^1$ and the atoms to which they are attached to form a 5- or 6-membered carbocyclic ring. In some embodiments, A is

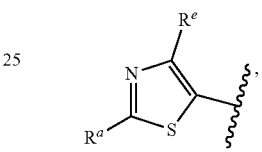

$R^a$ is pyridyl, wherein the pyridyl of $R^a$ is unsubstituted or substituted with OH, halo, $C_1$-$C_6$alkyl or $C_1$-$C_6$alkoxy. In some embodiments, A is

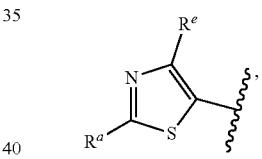

$R^a$ is pyridyl, wherein the pyridyl of $R^a$ is unsubstituted or substituted with OH, halo, $C_1$-$C_6$alkyl or $C_1$-$C_6$alkoxy, $R^2$ is $C_1$-$C_6$haloalkyl, and $R^6$ is $C_1$-$C_6$haloalkyl. In certain embodiments, A is

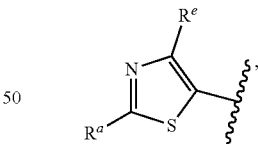

$R^a$ is

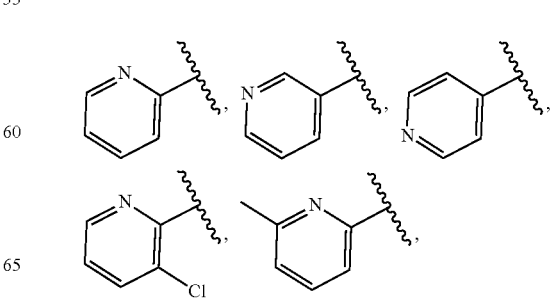

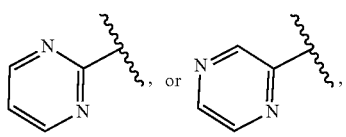

$R^2$ is $CF_3$, and $R^6$ is $CF_3$. In certain embodiments, A is

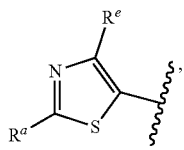

$R^a$ is

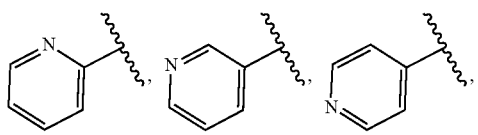

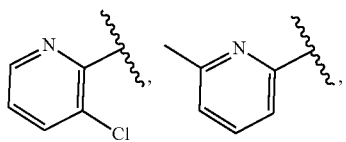

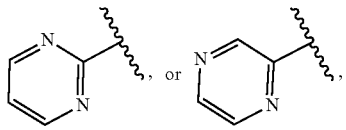

and $R^3$ is taken together with $R^1$ and the atoms to which they are attached to form a 5- or 6-membered carbocyclic ring.

In some embodiments, A is

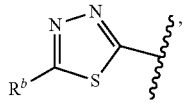

$R^b$ is furanyl, wherein the furanyl of $R^b$ is unsubstituted or substituted with OH, halo, $C_1$-$C_6$alkyl or $C_1$-$C_6$alkoxy. In some embodiments, A is

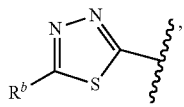

$R^b$ is furanyl, wherein the furanyl of $R^b$ is unsubstituted or substituted with OH, halo, $C_1$-$C_6$alkyl or $C_1$-$C_6$alkoxy, $R^2$ is $C_1$-$C_6$haloalkyl, and $R^6$ is $C_1$-$C_6$haloalkyl. In certain embodiments, A is

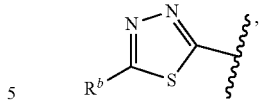

$R^b$ is

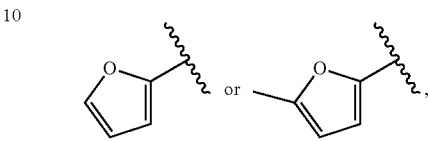

$R^2$ is $CF_3$, and $R^6$ is $CF_3$. In certain embodiments, A is

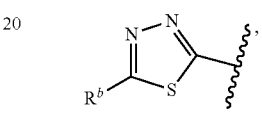

$R^b$ is

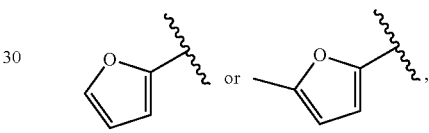

and $R^3$ is taken together with $R^1$ and the atoms to which they are attached to form a 5- or 6-membered carbocyclic ring.

In some embodiments, A is

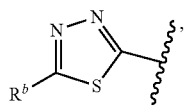

$R^b$ is pyridyl, wherein the pyridyl of $R^b$ is unsubstituted or substituted with OH, halo, $C_1$-$C_6$alkyl or $C_1$-$C_6$alkoxy. In some embodiments, A is

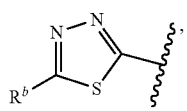

$R^b$ is pyridyl, wherein the pyridyl of $R^b$ is unsubstituted or substituted with OH, halo, $C_1$-$C_6$alkyl or $C_1$-$C_6$alkoxy, $R^2$ is $C_1$-$C_6$haloalkyl, and $R^6$ is $C_1$-$C_6$haloalkyl. In certain embodiments, A is

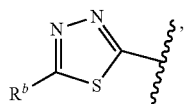

$R^b$ is

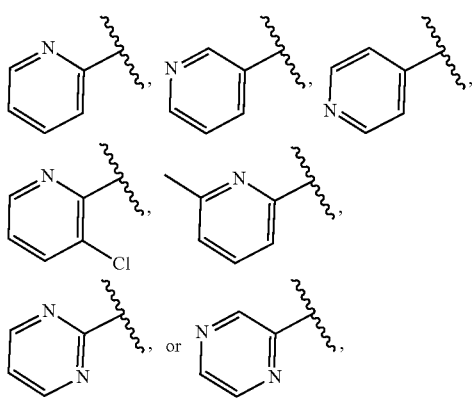

$R^2$ is $CF_3$, and $R^6$ is $CF_3$. In certain embodiments, A is

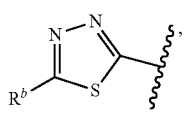

$R^b$ is

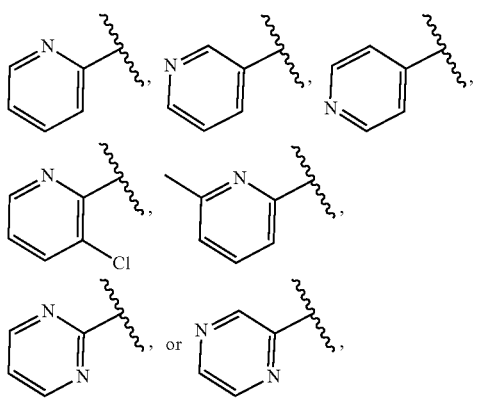

and $R^3$ is taken together with $R^1$ and the atoms to which they are attached to form a 5- or 6-membered carbocyclic ring.

In some embodiments, A is

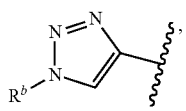

$R^b$ is furanyl, wherein the furanyl of $R^b$ is unsubstituted or substituted with OH, halo, $C_1$-$C_6$alkyl or $C_1$-$C_6$alkoxy. In some embodiments, A is

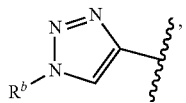

$R^b$ is furanyl, wherein the furanyl of $R^b$ is unsubstituted or substituted with OH, halo, $C_1$-$C_6$alkyl or $C_1$-$C_6$alkoxy, $R^2$ is $C_1$-$C_6$haloalkyl, and $R^6$ is $C_1$-$C_6$haloalkyl. In certain embodiments, A is

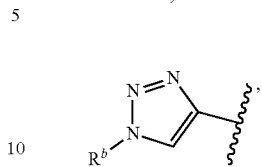

$R^b$ is

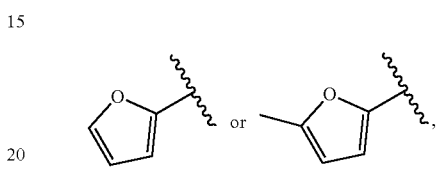

$R^2$ is $CF_3$, and $R^6$ is $CF_3$. In certain embodiments, A is

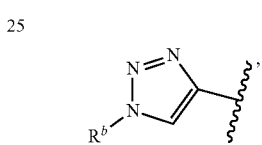

$R^b$ is

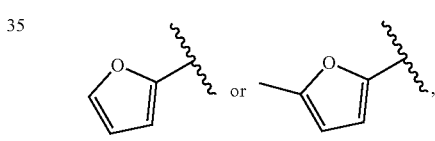

and $R^3$ is taken together with $R^1$ and the atoms to which they are attached to form a 5- or 6-membered carbocyclic ring.

In some embodiments, A is

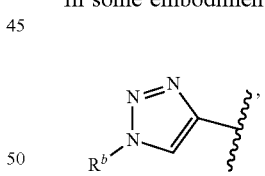

$R^b$ is pyridyl, wherein the pyridyl of $R^b$ is unsubstituted or substituted with OH, halo, $C_1$-$C_6$alkyl or $C_1$-$C_6$alkoxy. In some embodiments, A is

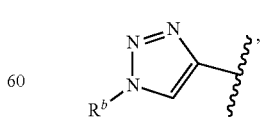

$R^b$ is pyridyl, wherein the pyridyl of $R^b$ is unsubstituted or substituted with OH, halo, $C_1$-$C_6$alkyl or $C_1$-$C_6$alkoxy, $R^2$ is $C_1$-$C_6$haloalkyl, and $R^6$ is $C_1$-$C_6$haloalkyl. In certain embodiments, A is

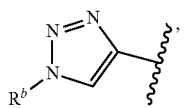

R$^b$ is

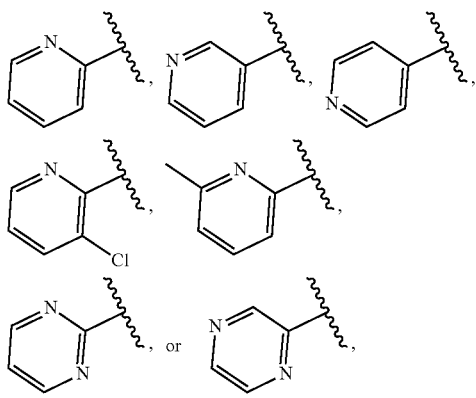

R$^2$ is CF$_3$, and R$^6$ is CF$_3$. In certain embodiments, A is

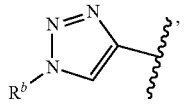

R$^b$ is

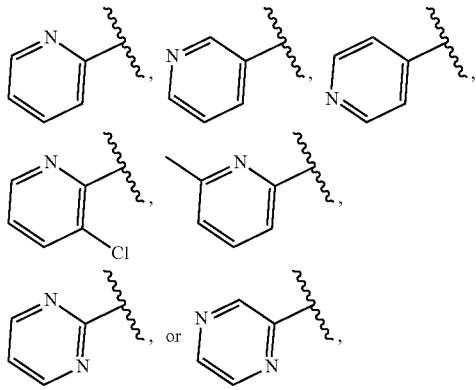

and R$^3$ is taken together with R$^1$ and the atoms to which they are attached to form a 5- or 6-membered carbocyclic ring.

In some embodiments, A is

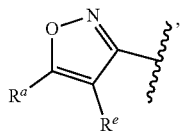

R$^a$ is furanyl, wherein the furanyl of R$^a$ is unsubstituted or substituted with OH, halo, C$_1$-C$_6$alkyl or C$_1$-C$_6$alkoxy. In some embodiments, A is

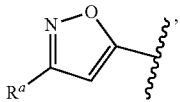

R$^a$ is furanyl, wherein the furanyl of R$^a$ is unsubstituted or substituted with OH, halo, C$_1$-C$_6$alkyl or C$_1$-C$_6$alkoxy, R$^2$ is C$_1$-C$_6$haloalkyl, and R$^6$ is C$_1$-C$_6$haloalkyl. In certain embodiments, A is

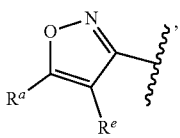

R$^a$ is

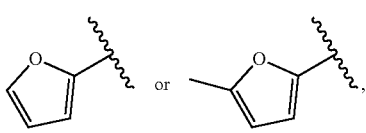

R$^2$ is CF$_3$, and R$^6$ is CF$_3$. In certain embodiments, A is

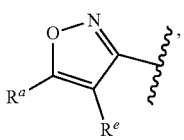

R$^a$ is

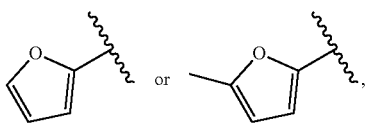

and R$^3$ is taken together with R$^1$ and the atoms to which they are attached to form a 5- or 6-membered carbocyclic ring.

In some embodiments, A is

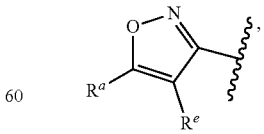

R$^a$ is pyridyl, wherein the pyridyl of R$^a$ is unsubstituted or substituted with OH, halo, C$_1$-C$_6$alkyl or C$_1$-C$_6$alkoxy. In some embodiments, A is

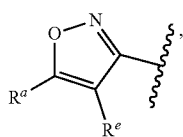

R$^a$ is pyridyl, wherein the pyridyl of R$^a$ is unsubstituted or substituted with OH, halo, C$_1$-C$_6$alkyl or C$_1$-C$_6$alkoxy, R$^2$ is C$_1$-C$_6$haloalkyl, and R$^6$ is C$_1$-C$_6$haloalkyl. In certain embodiments, A is

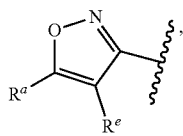

R$^a$ is

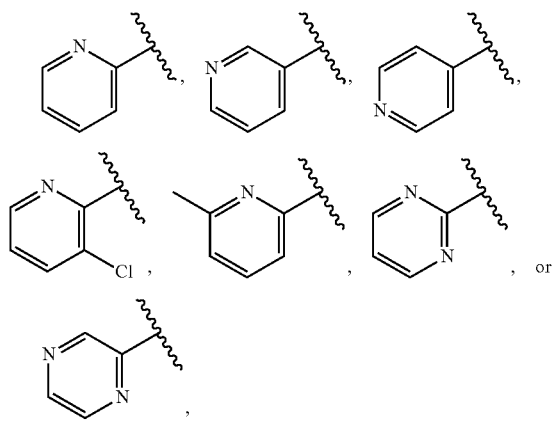

R$^2$ is CF$_3$, and R$^6$ is CF$_3$. In certain embodiments, A is

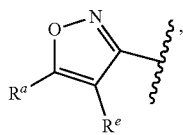

R$^a$ is

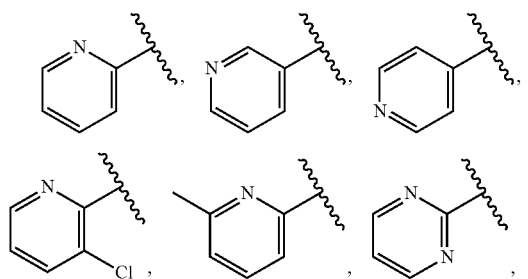

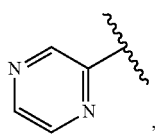

and R$^3$ is taken together with R$^1$ and the atoms to which they are attached to form a 5- or 6-membered carbocyclic ring.

In some embodiments, A is

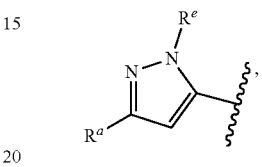

R$^a$ is furanyl, wherein the furanyl of R$^a$ is unsubstituted or substituted with OH, halo, C$_1$-C$_6$alkyl or C$_1$-C$_6$alkoxy. In some embodiments, A is

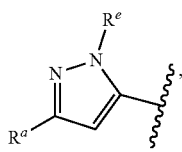

R$^a$ is furanyl, wherein the furanyl of R$^a$ is unsubstituted or substituted with OH, halo, C$_1$-C$_6$alkyl or C$_1$-C$_6$alkoxy, R$^2$ is C$_1$-C$_6$haloalkyl, and R$^6$ is C$_1$-C$_6$haloalkyl. In certain embodiments, A is

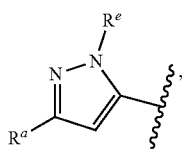

R$^a$ is

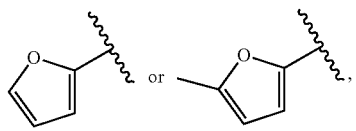

R$^2$ is CF$_3$, and R$^6$ is CF$_3$. In certain embodiments, A is

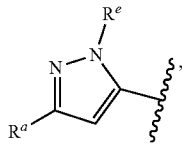

$R^a$ is

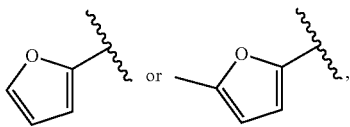

and $R^3$ is taken together with $R^1$ and the atoms to which they are attached to form a 5- or 6-membered carbocyclic ring.

In some embodiments, A is

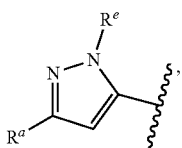

$R^a$ is pyridyl, wherein the pyridyl of $R^a$ is unsubstituted or substituted with OH, halo, $C_1$-$C_6$alkyl or $C_1$-$C_6$alkoxy. In some embodiments, A is

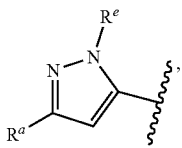

$R^a$ is pyridyl, wherein the pyridyl of $R^a$ is unsubstituted or substituted with OH, halo, $C_1$-$C_6$alkyl or $C_1$-$C_6$alkoxy, $R^2$ is $C_1$-$C_6$haloalkyl, and $R^6$ is $C_1$-$C_6$haloalkyl. In certain embodiments, A is

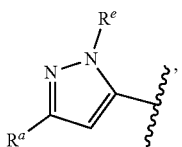

$R^a$ is

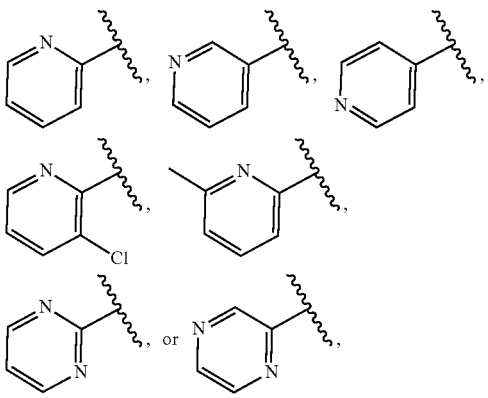

$R^2$ is $CF_3$, and $R^6$ is $CF_3$. In certain embodiments, A is

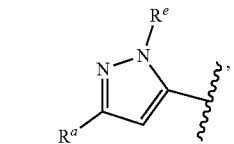

$R^a$ is

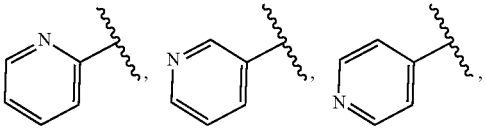
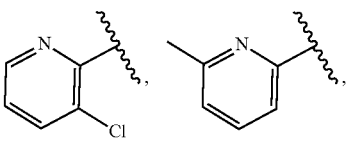
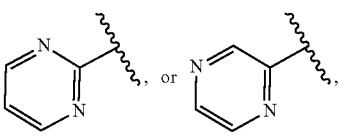

and $R^3$ is taken together with $R^1$ and the atoms to which they are attached to form a 5- or 6-membered carbocyclic ring.

In some embodiments of a compound of Formula (A), (I), (Id), (Ie), (Ii), (Ij), or (Ik), $R^e$ is $C_1$-$C_6$alkyl. In some embodiments, $R^e$ is methyl. In some embodiments, $R^e$ is $C_1$-$C_6$haloalkyl. In some embodiments, $R^e$ is H.

In certain variations, the compounds of Formula (A), (I), (Ia), (Ib), (Ic), (Id), (Ie), (If), (Ig), (Ih), (Ii), (Ij), or (Ik) have one or more of the following structural features: (A) A is

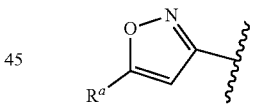

and $R^a$ is selected from the group consisting of H,

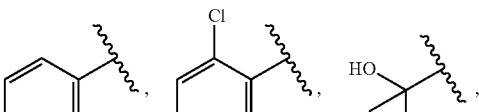
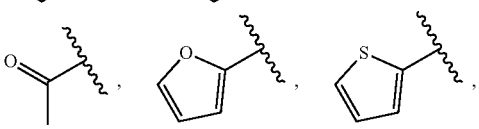

-continued
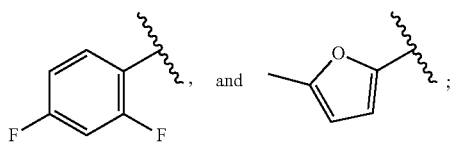
or A is
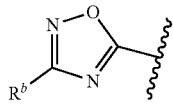
and $R^b$ is
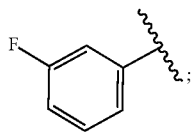
or A is
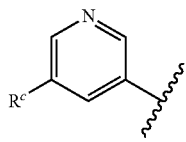
and $R^c$ is selected from the group consisting of
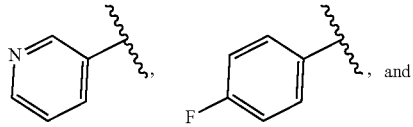
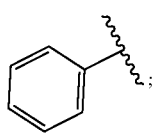
or A is
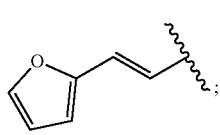 [SMILES: */C=C/c1ccco1]
and (B)
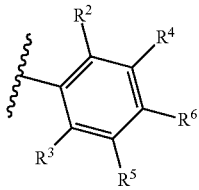
is
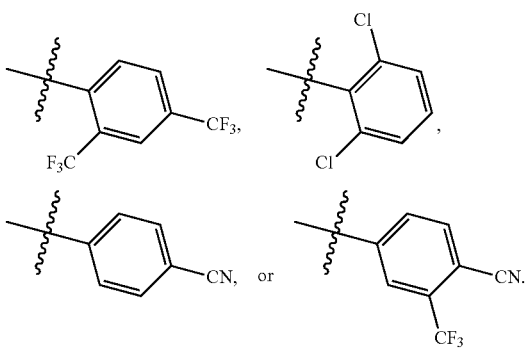
In certain variations, the compounds of Formula (A), (I), (Ia), (Ib), (Ic), (Id), (Ie), (If), (Ig), (Ih), (Ii), (Ij), or (Ik) have one or more of the following structural features: (A) A is
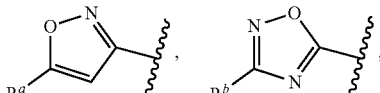
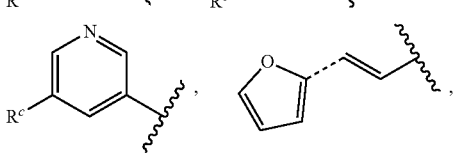
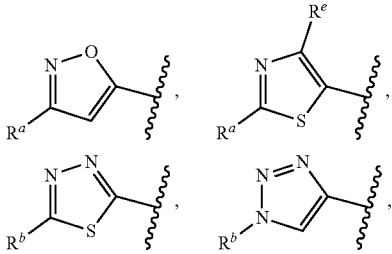
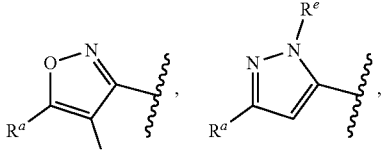
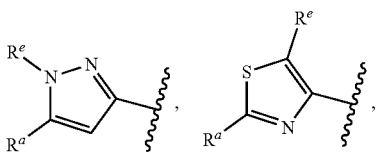

-continued
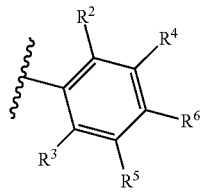
$R^a$, $R^b$ and $R^c$, when present, are each independently selected from the group consisting of
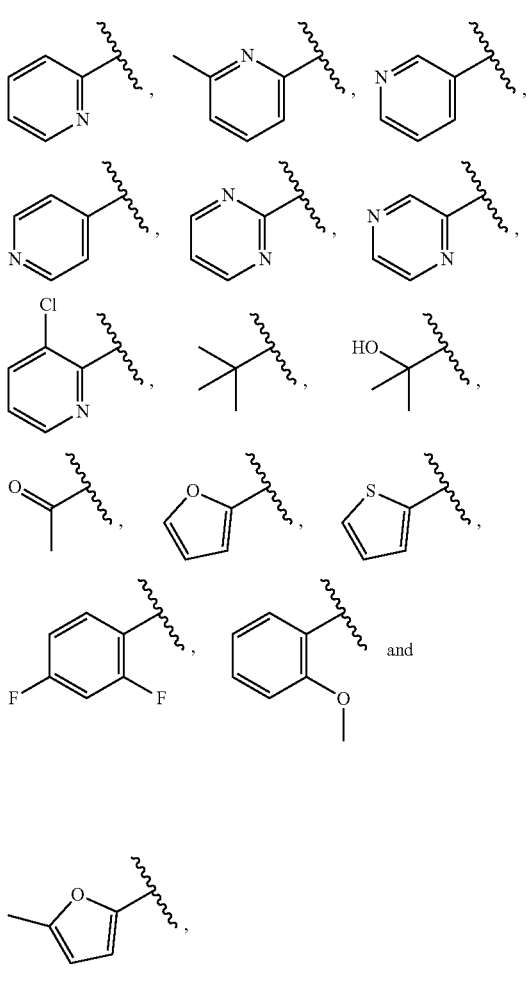
and $R^e$, when present, is H or methyl; (B)
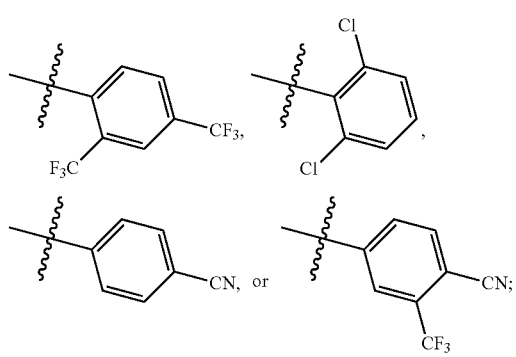
is
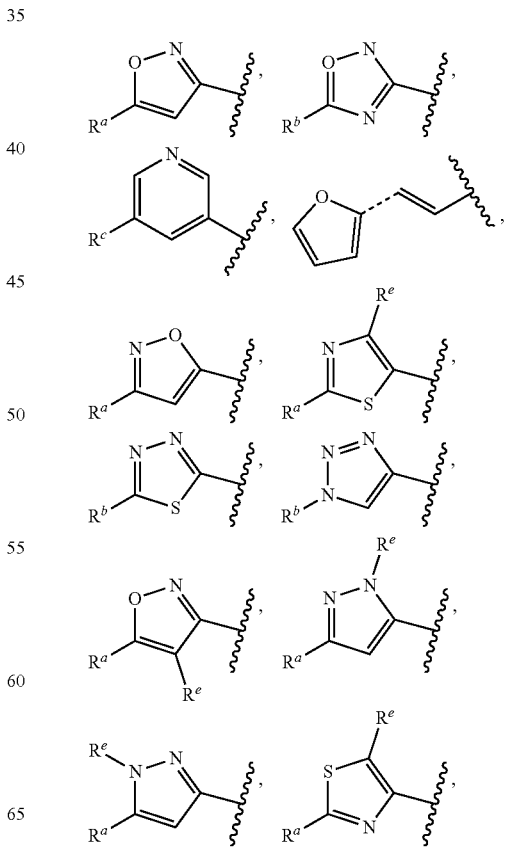
(C) n is 1; and (D) $R^1$ is H or methyl.
In certain variations, the compounds of Formula (A), (I), (Ia), (Ib), (Ic), (Id), (Ie), (If), (Ig), (Ih), (Ii), (Ij), or (Ik) have one or more of the following structural features: (A) A is
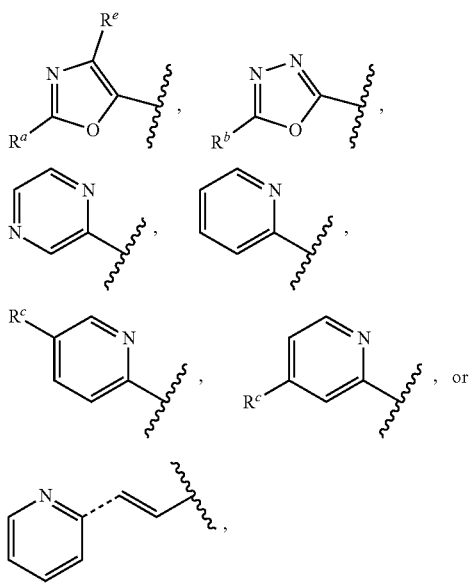

-continued

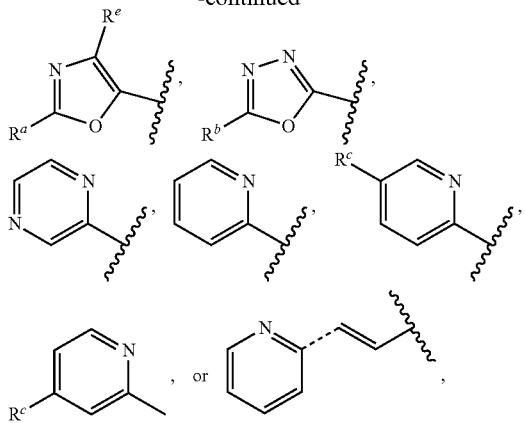

$R^a$, $R^b$ and $R^c$, when present, are each independently selected from the group consisting of

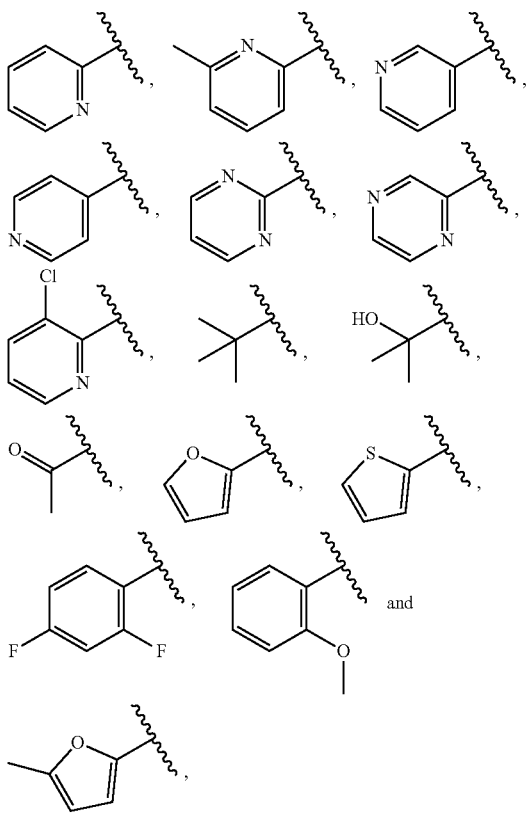

and $R^e$, when present, is H or methyl; (B) n is 1 and $R^3$ is taken together with $R^1$ and the atoms to which they are attached to form a 5- or 6-membered ring.

In some embodiments of any of the formulae provided herein, A is

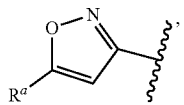

$R^a$ is 2-furyl, $G_1$ is N, $G_2$ is CH, n is 1, $R^1$ is H, L is absent, $R^2$ is Cl, $R^3$ is H, $R^4$ is H, $R^5$ is H, $R^7$ is H,

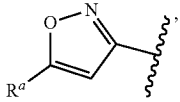

and $R^6$ is not $C_1$. In some embodiments, A is $R^a$ is methyl, $G_1$ is N, $G_2$ is CH, n is 1, $R^1$ is H, L is absent, $R^2$ is Cl, $R^3$ is H, $R^4$ is H, $R^5$ is H, $R^7$ is H, and $R^6$ is not $C_1$. In some embodiments, A is

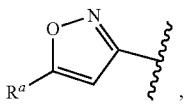

$R^a$ is phenyl, $G_1$ is N, $G_2$ is CH, n is 1, $R^1$ is H, L is absent, $R^2$ is Cl, $R^3$ is H, $R^4$ is H, $R^5$ is H, $R^7$ is H, and $R^6$ is not $C_1$. In some embodiments, A is

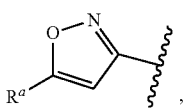

$R^a$ is 2-furyl, $G_1$ is N, $G_2$ is CH, n is 1, $R^1$ is H, L is absent, $R^2$ is H, $R^3$ is H, $R^4$ is H, $R^5$ is H, $R^7$ is H, and $R^6$ is not H. In some embodiments, A is

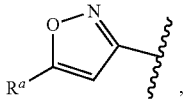

$G_1$ is N, $G_2$ is CH, n is 1, $R^1$ is H, L is absent, $R^2$ and $R^6$ are each Br, $R^3$ is H, $R^4$ is H, $R^5$ is H, $R^7$ is H, and $R^a$ is not 2-furyl. In some embodiments, A is

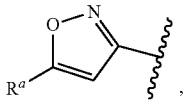

$G_1$ is N, $G_2$ is CH, n is 1, $R^1$ is H, L is absent, $R^2$ and $R^6$ are each $CF_3$, $R^3$ is H, $R^4$ is H, $R^5$ is H, $R^7$ is H, and $R^a$ is not 2-furyl. In some embodiments, A is

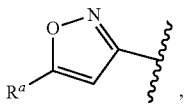

$G_1$ is N, $G_2$ is CH, n is 1, $R^1$ is H, L is absent, $R^2$ is H, $R^3$ is H, $R^4$ is H, $R^5$ is H, $R^6$ is $CF_3$, $R^7$ is H, and $R^a$ is not 2-furyl. In some embodiments, A is

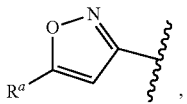, $G_1$ is N, $G_2$ is CH, n is 1, $R^1$ is H, L is absent, $R^2$ is Cl, $R^3$ is H, $R^4$ is H, $R^5$ is H, $R^6$ is F, $R^7$ is H, and $R^a$ is not phenyl. In some embodiments, A is

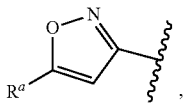, $R^a$ is phenyl, $G_1$ is N, $G_2$ is CH, n is 1, $R^1$ is H, L is absent, $R^2$ is Cl, $R^3$ is H, $R^4$ is H, $R^5$ is H, $R^7$ is H, and $R^6$ is not F. In some embodiments, A is

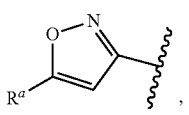, $G_1$ is N, $G_2$ is CH, n is 0, L is absent, $R^2$ is $CH_3$, $R^3$ is H, $R^4$ is H, $R^5$ is H, $R^6$ is $CH_3$, $R^7$ is H, and $R^a$ is not H. In some embodiments, A is

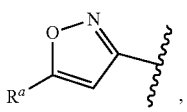, $R^a$ is H, $G_1$ is N, $G_2$ is CH, n is 0, L is absent, $R^2$ is $CH_3$, $R^3$ is H, $R^4$ is H, $R^5$ is H, $R^7$ is H, and $R^6$ is not $CH_3$.

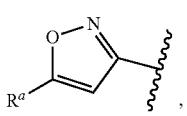,

In some embodiments of any of the formulae provided herein, A is $G_1$ is N, $G_2$ is CH, n is 1, $R^1$ is H, L is absent, $R^2$ is Cl, $R^3$ is H, $R^4$ is H, $R^5$ is H, $R^6$ is Cl, $R^7$ is H, and $R^a$ is not n-propyl, isopropyl, isobutyl, 2-furyl, methyl, ethyl, 4-fluorophenyl, 3-hydroxyphenyl, 4-hydroxyphenyl, phenyl, or 2-thiofuryl. In some embodiments, A is

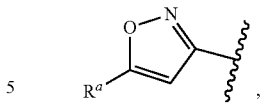, $R^a$ is n-propyl, isopropyl, isobutyl, 2-furyl, methyl, ethyl, 4-fluorophenyl, 3-hydroxyphenyl, 4-hydroxyphenyl, phenyl, or 2-thiofuryl, $G_1$ is N, $G_2$ is CH, n is 1, $R^1$ is H, L is absent, $R^2$ is Cl, $R^3$ is H, $R^4$ is H, $R^5$ is H, $R^7$ is H, and $R^6$ is not Cl.

In some embodiments of any of the formulae provided herein, A is

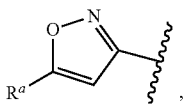, $G_1$ is N, $G_2$ is CH, n is 1, $R^1$ is H, L is absent, $R^2$ is F, $R^3$ is F, $R^4$ is F, $R^5$ is F, $R^6$ is Cl, $R^7$ is H, and $R^a$ is not 2,4-dichlorophenyl. In some embodiments, A is

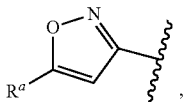, $G_1$ is N, $G_2$ is CH, n is 1, $R^1$ is H, L is absent, $R^2$ is Cl, $R^3$ is F, $R^4$ is H, $R^5$ is H, $R^6$ is H, $R^7$ is H, and $R^a$ is not phenyl. In some embodiments, A is

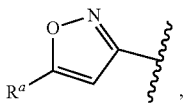, $R^a$ is not phenyl, $G_1$ is N, $G_2$ is CH, n is 1, $R^1$ is H, L is absent, $R^2$ is Cl, $R^4$ is H, $R^5$ is H, $R^6$ is H, $R^7$ is H, and $R^3$ is not F.

In some embodiments of any of the formulae provided herein, A is

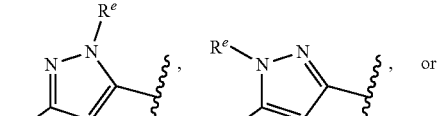, or

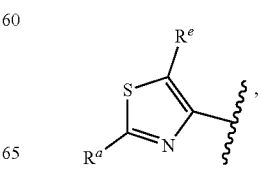

$G_1$ is N, $G_2$ is $CR^d$, and n is 1, then $R^1$ is other than H. In some embodiments, A is

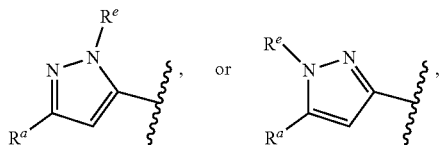

$G_1$ is N, $G_2$ is $CR^d$, n is 0, and L is absent, then $R^a$ is other than H. In some embodiments, A is

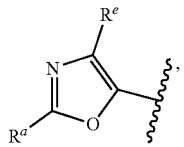

$G_1$ is N, $G_2$ is $CR^d$, and $R^e$ is methyl, then $R^a$ is other than unsubstituted phenyl. In some embodiments,

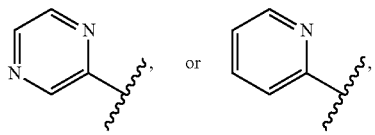 [SMILES: *c1cnccn1 ; *c1ccccn1]

$G_1$ is N, $G_2$ is $CR^d$, n is 1 and L is absent, then $R^1$ is other than H.

Representative compounds are listed in Table 1.

TABLE 1

| Cmpd No. | Structure | Chemical Name |
|---|---|---|
| 1 | 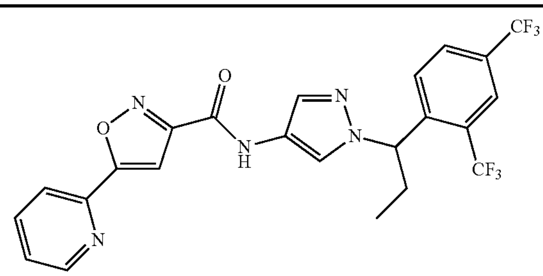 | N-(1-(1-(2,4-bis(trifluoromethyl)phenyl)propyl)-1H-pyrazol-4-yl)-5-(pyridin-2-yl)isoxazole-3-carboxamide |
| 2 | 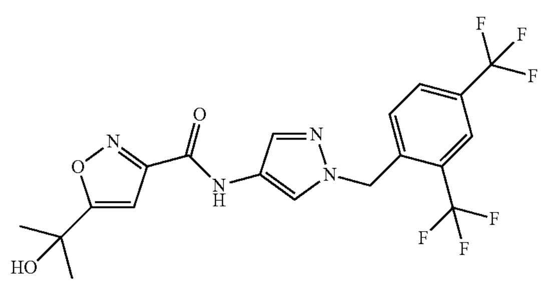 [SMILES: CC(C)(O)c1cc(C(=O)Nc2cnn(Cc3ccc(C(F)(F)F)cc3C(F)(F)F)c2)no1] | N-(1-(2,4-bis(trifluoromethyl)benzyl)-1H-pyrazol-4-yl)-5-(2-hydroxypropan-2-yl)isoxazole-3-carboxamide |
| 3 | 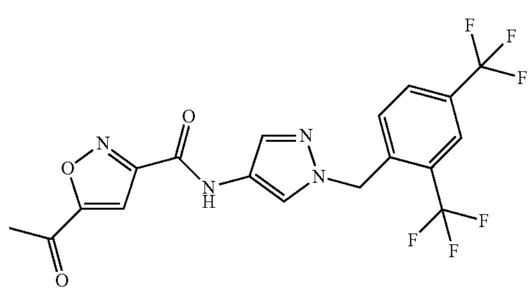 [SMILES: CC(=O)c1cc(C(=O)Nc2cnn(Cc3ccc(C(F)(F)F)cc3C(F)(F)F)c2)no1] | 5-acetyl-N-(1-(2,4-bis(trifluoromethyl)benzyl)-1H-pyrazol-4-yl)isoxazole-3-carboxamide |
| 4 | 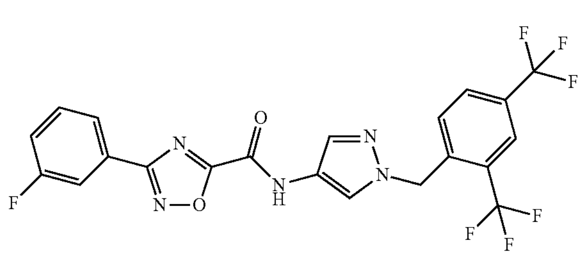 [SMILES: O=C(Nc1cnn(Cc2ccc(C(F)(F)F)cc2C(F)(F)F)c1)c1nc(-c2cccc(F)c2)no1] | N-(1-(2,4-bis(trifluoromethyl)benzyl)-1H-pyrazol-4-yl)-3-(3-fluorophenyl)-1,2,4-oxadiazole-5-carboxamide |

TABLE 1-continued

| Cmpd No. | Structure | Chemical Name |
|---|---|---|
| 5 | 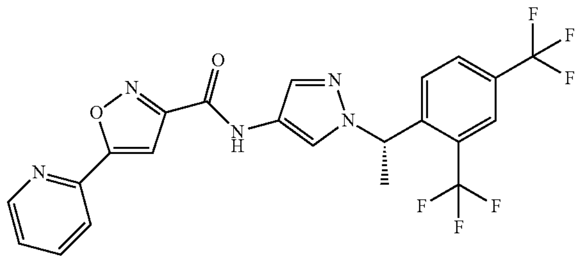 [SMILES: C[C@@H](c1ccc(C(F)(F)F)cc1C(F)(F)F)n1cc(NC(=O)c2cc(-c3ccccn3)on2)cn1] | (S)-N-(1-(1-(2,4-bis(trifluoromethyl)phenyl)ethyl)-1H-pyrazol-4-yl)-5-(pyridin-2-yl)isoxazole-3-carboxamide |
| 6 | 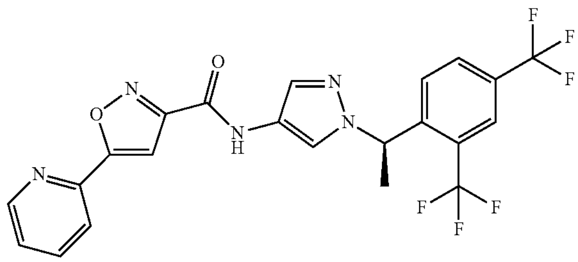 [SMILES: C[C@H](c1ccc(C(F)(F)F)cc1C(F)(F)F)n1cc(NC(=O)c2cc(-c3ccccn3)on2)cn1] | (R)-N-(1-(1-(2,4-bis(trifluoromethyl)phenyl)ethyl)-1H-pyrazol-4-yl)-5-(pyridin-2-yl)isoxazole-3-carboxamide |
| 7 | 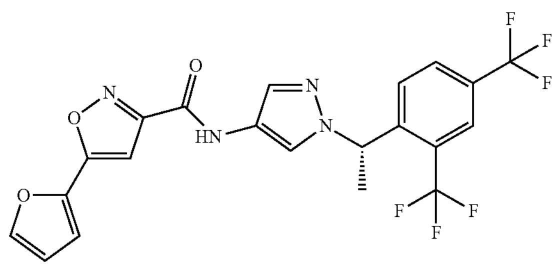 [SMILES: C[C@@H](c1ccc(C(F)(F)F)cc1C(F)(F)F)n1cc(NC(=O)c2cc(-c3ccco3)on2)cn1] | (S)-N-(1-(1-(2,4-bis(trifluoromethyl)phenyl)ethyl)-1H-pyrazol-4-yl)-5-(furan-2-yl)isoxazole-3-carboxamide |
| 8 | 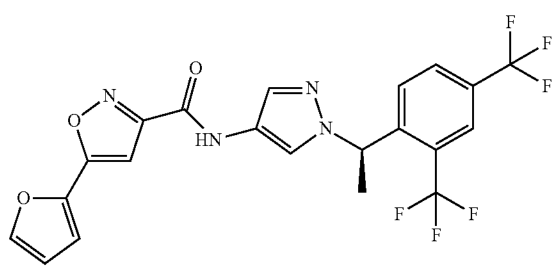 [SMILES: C[C@H](c1ccc(C(F)(F)F)cc1C(F)(F)F)n1cc(NC(=O)c2cc(-c3ccco3)on2)cn1] | (R)-N-(1-(1-(2,4-bis(trifluoromethyl)phenyl)ethyl)-1H-pyrazol-4-yl)-5-(furan-2-yl)isoxazole-3-carboxamide |
| 9 | 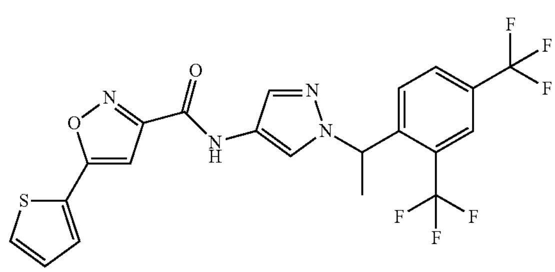 [SMILES: CC(c1ccc(C(F)(F)F)cc1C(F)(F)F)n1cc(NC(=O)c2cc(-c3cccs3)on2)cn1] | N-(1-(1-(2,4-bis(trifluoromethyl)phenyl)ethyl)-1H-pyrazol-4-yl)-5-(thiophen-2-yl)isoxazole-3-carboxamide |

TABLE 1-continued

| Cmpd No. | Structure | Chemical Name |
|---|---|---|
| 10 | 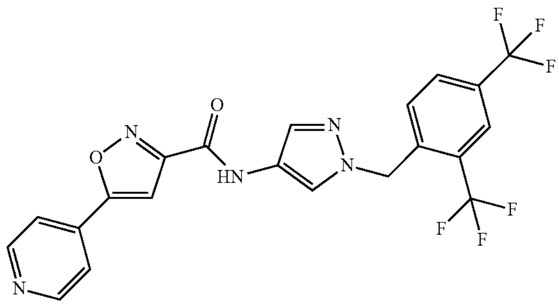 [SMILES: O=C(Nc1cnn(Cc2ccc(C(F)(F)F)cc2C(F)(F)F)c1)c1cc(-c2ccncc2)on1] | N-(1-(2,4-bis(trifluoromethyl)benzyl)-1H-pyrazol-4-yl)-5-(pyridin-4-yl)isoxazole-3-carboxamide |
| 11 | 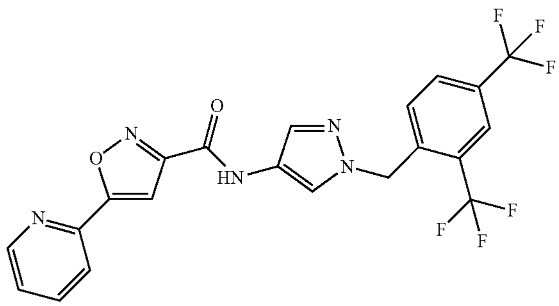 [SMILES: O=C(Nc1cnn(Cc2ccc(C(F)(F)F)cc2C(F)(F)F)c1)c1cc(-c2ccccn2)on1] | N-(1-(2,4-bis(trifluoromethyl)benzyl)-1H-pyrazol-4-yl)-5-(pyridin-2-yl)isoxazole-3-carboxamide |
| 12 | 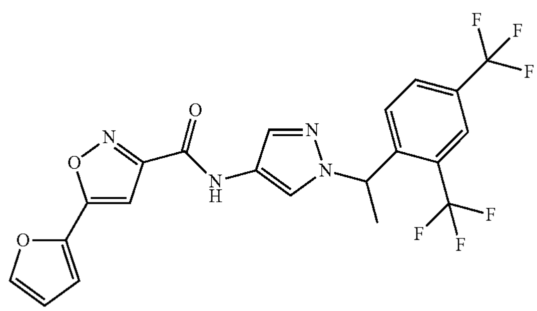 [SMILES: CC(c1ccc(C(F)(F)F)cc1C(F)(F)F)n1cc(NC(=O)c2cc(-c3ccco3)on2)cn1] | N-(1-{1-[2,4-bis(trifluoromethyl)phenyl]ethyl}-1H-pyrazol-4-yl)-5-(furan-2-yl)isoxazole-3-carboxamide |
| 13 | 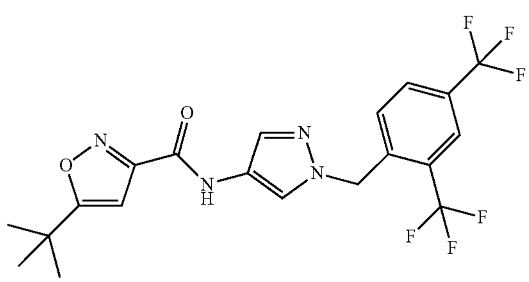 [SMILES: CC(C)(C)c1cc(C(=O)Nc2cnn(Cc3ccc(C(F)(F)F)cc3C(F)(F)F)c2)no1] | N-{1-[2,4-bis(trifluoromethyl)benzyl]-1H-pyrazol-4-yl}-5-tert-butyl-1,2-oxazole-3-carboxamide |
| 14 | 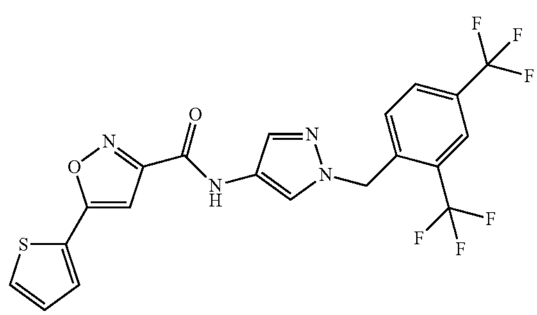 [SMILES: O=C(Nc1cnn(Cc2ccc(C(F)(F)F)cc2C(F)(F)F)c1)c1cc(-c2cccs2)on1] | N-(1-(2,4-bis(trifluoromethyl)benzyl)-1H-pyrazol-4-yl)-5-(thiophen-2-yl)isoxazole-3-carboxamide |

TABLE 1-continued

| Cmpd No. | Structure | Chemical Name |
|---|---|---|
| 15 | 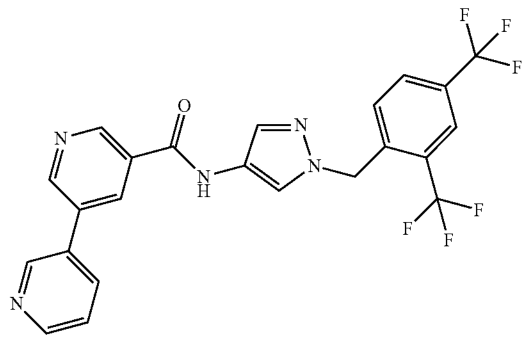 [SMILES: O=C(Nc1cnn(Cc2ccc(C(F)(F)F)cc2C(F)(F)F)c1)c1cncc(-c2cccnc2)c1] | N-(1-(2,4-bis(trifluoromethyl)benzyl)-1H-pyrazol-4-yl)-[3,3'-bipyridine]-5-carboxamide |
| 16 | 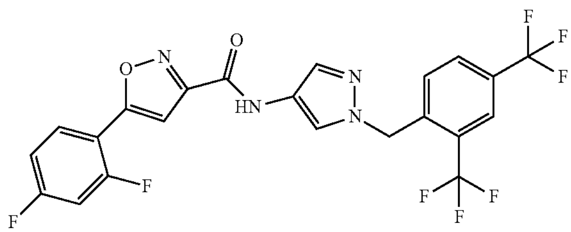 [SMILES: O=C(Nc1cnn(Cc2ccc(C(F)(F)F)cc2C(F)(F)F)c1)c1cc(-c2ccc(F)cc2F)on1] | N-(1-(2,4-bis(trifluoromethyl)benzyl)-1H-pyrazol-4-yl)-5-(2,4-difluorophenyl)isoxazole-3-carboxamide |
| 17 | 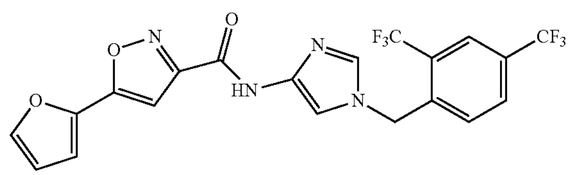 [SMILES: O=C(Nc1cn(Cc2ccc(C(F)(F)F)cc2C(F)(F)F)cn1)c1cc(-c2ccco2)on1] | N-(1-(2,4-bis(trifluoromethyl)benzyl)-1H-imidazol-4-yl)-5-(furan-2-yl)isoxazole-3-carboxamide |
| 18 | 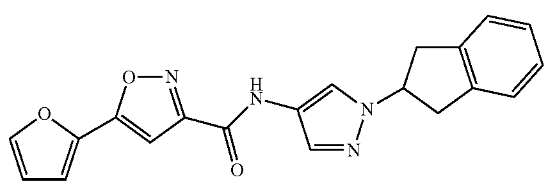 [SMILES: O=C(Nc1cnn(C2Cc3ccccc3C2)c1)c1cc(-c2ccco2)on1] | N-(1-(2,3-dihydro-1H-inden-2-yl)-1H-pyrazol-4-yl)-5-(furan-2-yl) isoxazole-3-carboxamide |
| 19 | 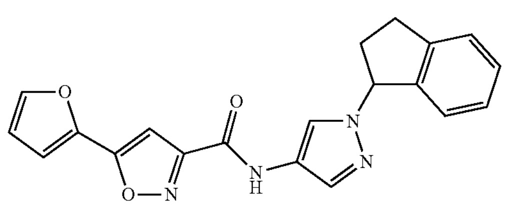 [SMILES: O=C(Nc1cnn(C2CCc3ccccc32)c1)c1cc(-c2ccco2)on1] | N-(1-(2,3-dihydro-1H-inden-1-yl)-1H-pyrazol-4-yl)-5-(furan-2-yl) isoxazole-3-carboxamide |
| 20 | 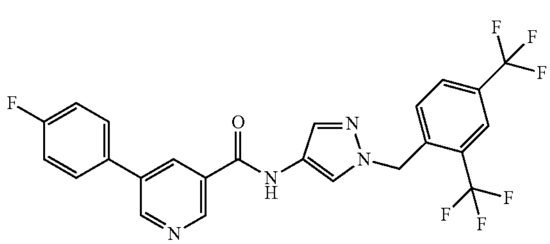 [SMILES: O=C(Nc1cnn(Cc2ccc(C(F)(F)F)cc2C(F)(F)F)c1)c1cncc(-c2ccc(F)cc2)c1] | N-(1-(2,4-bis(trifluoromethyl)benzyl)-1H-pyrazol-4-yl)-5-(4 fluorophenyl)nicotinamide |

TABLE 1-continued

| Cmpd No. | Structure | Chemical Name |
|---|---|---|
| 21 | 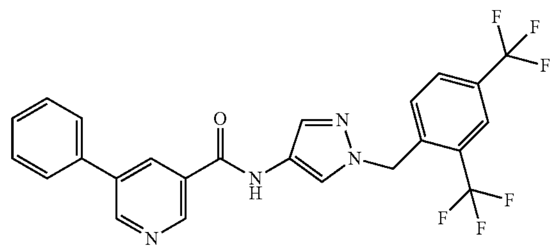 [SMILES: O=C(Nc1cnn(Cc2ccc(C(F)(F)F)cc2C(F)(F)F)c1)c1cncc(-c2ccccc2)c1] | N-(1-(2,4-bis(trifluoromethyl)benzyl)-1H-pyrazol-4-yl)-5-phenylnicotinamide |
| 22 | 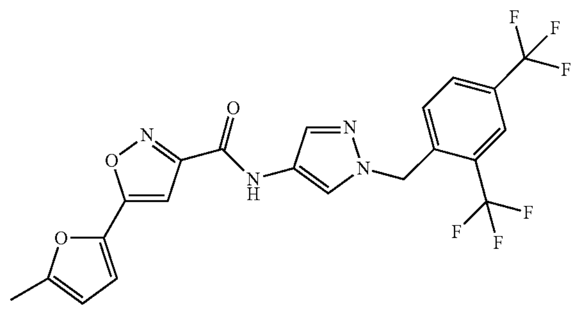 [SMILES: Cc1ccc(-c2cc(C(=O)Nc3cnn(Cc4ccc(C(F)(F)F)cc4C(F)(F)F)c3)no2)o1] | N-(1-(2,4-bis(trifluoromethyl)benzyl)-1H-pyrazol-4-yl)-5-(5-methylfuran-2-yl)isoxazole-3-carboxamide |
| 23 | 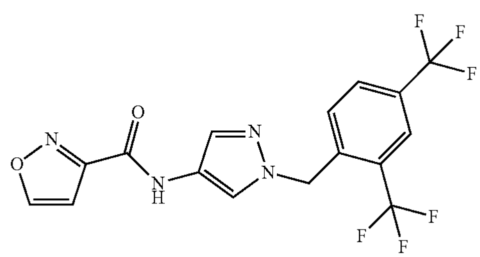 [SMILES: O=C(Nc1cnn(Cc2ccc(C(F)(F)F)cc2C(F)(F)F)c1)c1ccon1] | N-(1-(2,4-bis(trifluoromethyl)benzyl)-1H-pyrazol-4-yl)isoxazole-3-carboxamide |
| 24 | 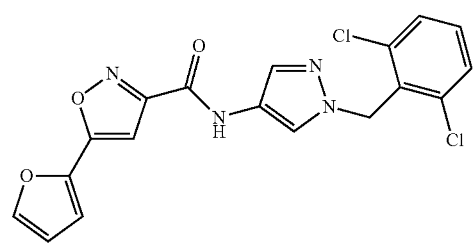 [SMILES: O=C(Nc1cnn(Cc2c(Cl)cccc2Cl)c1)c1cc(-c2ccco2)on1] | N-(1-(2,6-dichlorobenzyl)-1H-pyrazol-4-yl)-5-(furan-2-yl)isoxazole-3-carboxamide |
| 25 | 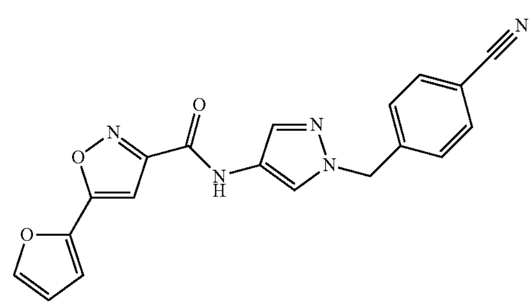 [SMILES: N#Cc1ccc(Cn2cc(NC(=O)c3cc(-c4ccco4)on3)cn2)cc1] | N-(1-(4-cyanobenzyl)-1H-pyrazol-4-yl)-5-(furan-2-yl)isoxazole-3-carboxamide |
| 26 | 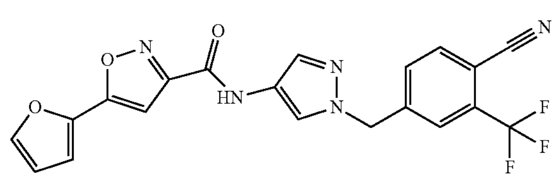 [SMILES: N#Cc1ccc(Cn2cc(NC(=O)c3cc(-c4ccco4)on3)cn2)cc1C(F)(F)F] | N-(1-(4-cyano-3-(trifluoromethyl)benzyl)-1H-pyrazol-4-yl)-5-(furan-2-yl)isoxazole-3-carboxamide |

TABLE 1-continued

| Cmpd No. | Structure | Chemical Name |
|---|---|---|
| 27 | 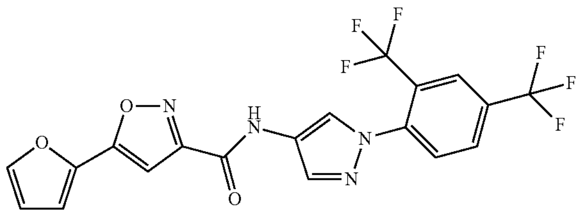 [SMILES: O=C(Nc1cnn(-c2ccc(C(F)(F)F)cc2C(F)(F)F)c1)c1cc(-c2ccco2)on1] | N-(1-(2,4-bis(trifluoromethyl)phenyl)-1H-pyrazol-4-yl)-5-(furan-2-yl)isoxazole-3-carboxamide |
| 28 | 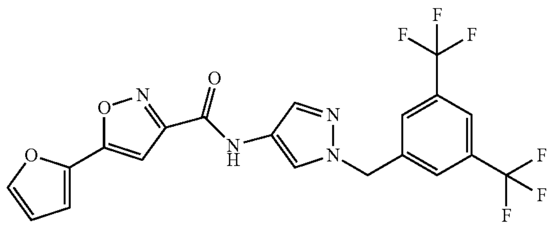 [SMILES: O=C(Nc1cnn(Cc2cc(C(F)(F)F)cc(C(F)(F)F)c2)c1)c1cc(-c2ccco2)on1] | N-(1-(3,5-bis(trifluoromethyl)benzyl)-1H-pyrazole-4-yl)-5-(furan-2- |
| 29 | 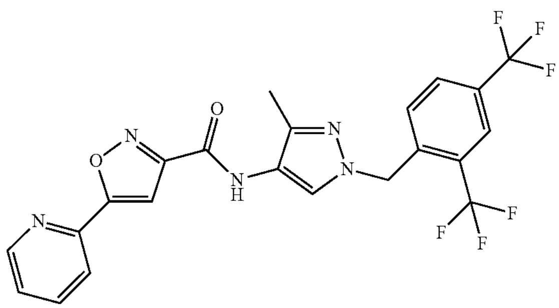 [SMILES: Cc1nn(Cc2ccc(C(F)(F)F)cc2C(F)(F)F)cc1NC(=O)c1cc(-c2ccccn2)on1] | N-(1-(2,4-bis(trifluoromethyl)benzyl)-3-methyl-1H-pyrazol-4-yl)-5-(pyridin-2-yl)isoxazole-3-carboxamide |
| 30 | 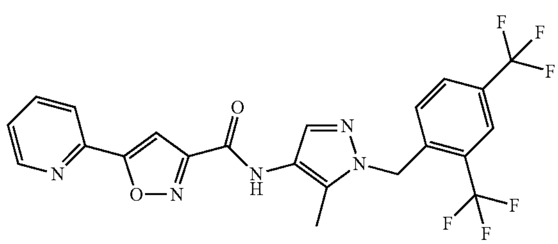 [SMILES: Cc1c(NC(=O)c2cc(-c3ccccn3)on2)cnn1Cc1ccc(C(F)(F)F)cc1C(F)(F)F] | N-(1-(2,4-bis(trifluoromethyl)benzyl)-5-methyl-1H-pyrazol-4-yl)-5-(pyridin-2-yl)isoxazole-3-carboxamide |
| 31 | 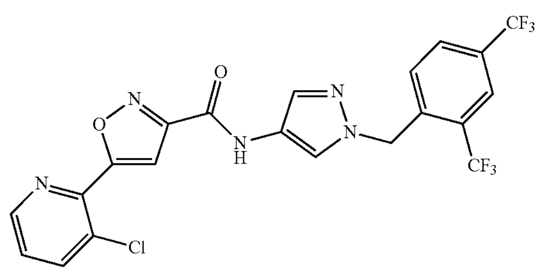 [SMILES: O=C(Nc1cnn(Cc2ccc(C(F)(F)F)cc2C(F)(F)F)c1)c1cc(-c2ncccc2Cl)on1] | N-(1-(2,4-bis(trifluoromethyl)benzyl)-1H-pyrazol-4-yl)-5-(3-chloropyridin-2-yl)isoxazole-3-carboxamide |
| 32 | 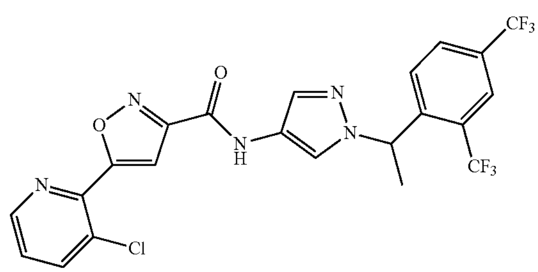 [SMILES: CC(c1ccc(C(F)(F)F)cc1C(F)(F)F)n1cc(NC(=O)c2cc(-c3ncccc3Cl)on2)cn1] | N-(1-(1-(2,4-bis(trifluoromethyl)phenyl)ethyl)-1H-pyrazol-4-yl)-5-(3-chloropyridin-2-yl)isoxazole-3-carboxamide |

TABLE 1-continued

| Cmpd No. | Structure | Chemical Name |
|---|---|---|
| 33 | 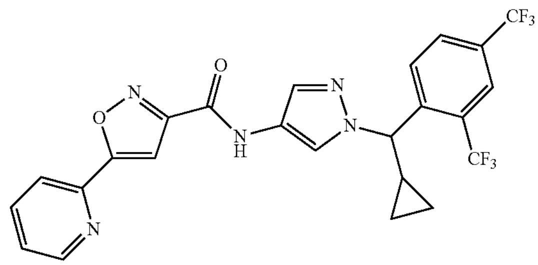 [SMILES: O=C(Nc1cnn(C(c2ccc(C(F)(F)F)cc2C(F)(F)F)C2CC2)c1)c1cc(-c2ccccn2)on1] | N-(1-((2,4-bis(trifluoromethyl)phenyl)(cyclopropyl)methyl)-1H-pyrazol-4-yl)-5-(pyridin-2-yl)isoxazole-3-carboxamide |
| 34 | 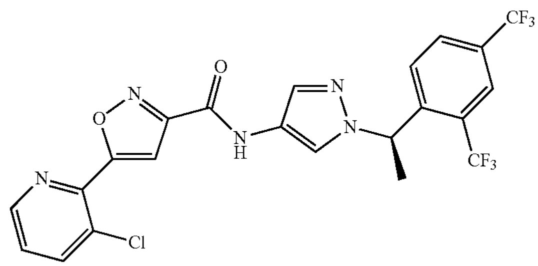 [SMILES: C[C@H](c1ccc(C(F)(F)F)cc1C(F)(F)F)n1cc(NC(=O)c2cc(-c3ncccc3Cl)on2)cn1] | (R)-N-(1-(1-(2,4-bis(trifluoromethyl)phenyl)ethyl)-1H-pyrazol-4-yl)-5-(3-chloropyridin-2-yl)isoxazole-3-carboxamide |
| 35 | 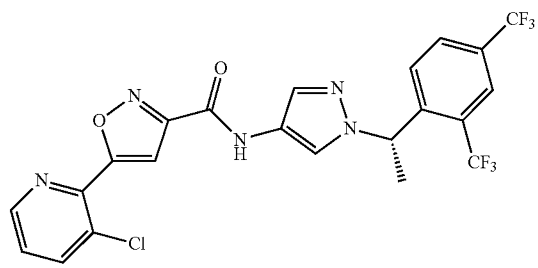 [SMILES: C[C@@H](c1ccc(C(F)(F)F)cc1C(F)(F)F)n1cc(NC(=O)c2cc(-c3ncccc3Cl)on2)cn1] | (S)-N-(1-(1-(2,4-bis(trifluoromethyl)phenyl)ethyl)-1H-pyrazol-4-yl)-5-(3-chloropyridin-2-yl)isoxazole-3-carboxamide |
| 36 | 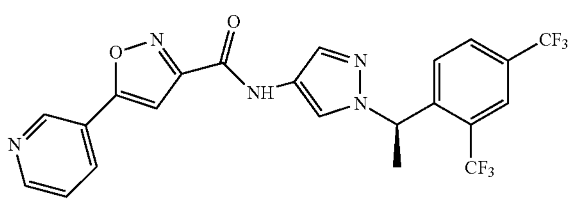 [SMILES: C[C@H](c1ccc(C(F)(F)F)cc1C(F)(F)F)n1cc(NC(=O)c2cc(-c3cccnc3)on2)cn1] | (R)-N-(1-(1-(2,4-bis(trifluoromethyl)phenyl)ethyl)-1H-pyrazol-4-yl)-5-(pyridin-3-yl)isoxazole-3-carboxamide |
| 37 | 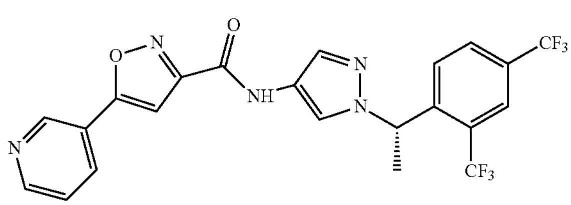 [SMILES: C[C@@H](c1ccc(C(F)(F)F)cc1C(F)(F)F)n1cc(NC(=O)c2cc(-c3cccnc3)on2)cn1] | (S)-N-(1-(1-(2,4-bis(trifluoromethyl)phenyl)ethyl)-1H-pyrazol-4-yl)-5-(pyridin-3-yl)isoxazole-3-carboxamide |
| 38 | 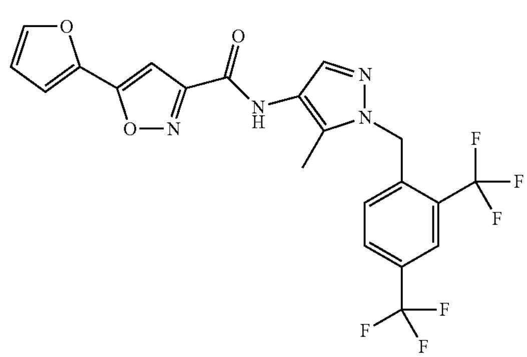 [SMILES: Cc1c(NC(=O)c2cc(-c3ccco3)on2)cnn1Cc1ccc(C(F)(F)F)cc1C(F)(F)F] | N-(1-(2,4-bis(trifluoromethyl)benzyl)-5-methyl-1H-pyrazol-4-yl)-5-(furan-2-yl)isoxazole-3-carboxamide |

TABLE 1-continued

| Cmpd No. | Structure | Chemical Name |
|---|---|---|
| 39 | 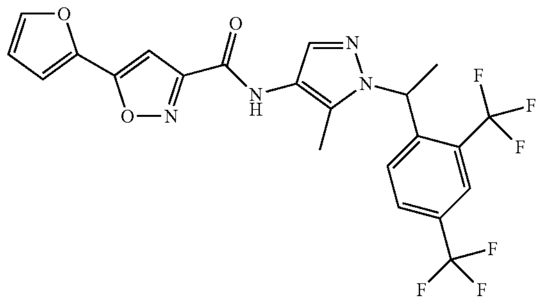 [SMILES: Cc1c(NC(=O)c2cc(-c3ccco3)on2)cnn1C(C)c1ccc(C(F)(F)F)cc1C(F)(F)F] | N-(1-(1-(2,4-bis(trifluoromethyl)phenyl)ethyl)-5-methyl-1H-pyrazol-4-yl)-5-(furan-2-yl)isoxazole-3-carboxamide |
| 40 | 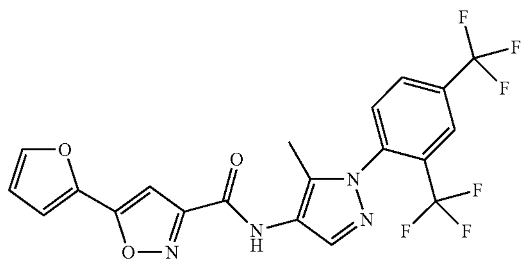 [SMILES: Cc1c(NC(=O)c2cc(-c3ccco3)on2)cnn1-c1ccc(C(F)(F)F)cc1C(F)(F)F] | N-(1-(2,4-bis(trifluoromethyl)phenyl)-5-methyl-1H-pyrazol-4-yl)-5-(furan-2-yl)isoxazole-3-carboxamide |
| 41 | 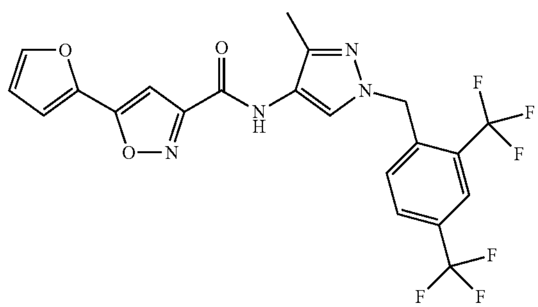 [SMILES: Cc1nn(Cc2ccc(C(F)(F)F)cc2C(F)(F)F)cc1NC(=O)c1cc(-c2ccco2)on1] | N-(1-(2,4-bis(trifluoromethyl)benzyl)-3-methyl-1H-pyrazol-4-yl)-5-(furan-2-yl)isoxazole-3-carboxamide |
| 42 | 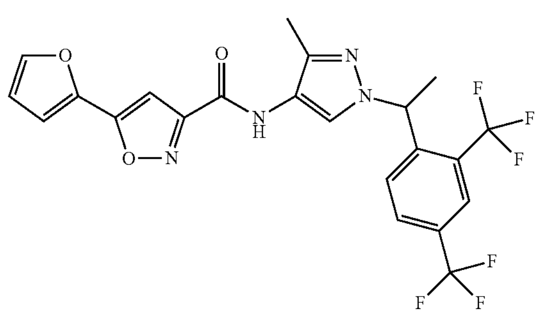 [SMILES: Cc1nn(C(C)c2ccc(C(F)(F)F)cc2C(F)(F)F)cc1NC(=O)c1cc(-c2ccco2)on1] | N-(1-(1-(2,4-bis(trifluoromethyl)phenyl)ethyl)-3-methyl-1H-pyrazol-4-yl)-5-(furan-2-yl)isoxazole-3-carboxamide |
| 43 | 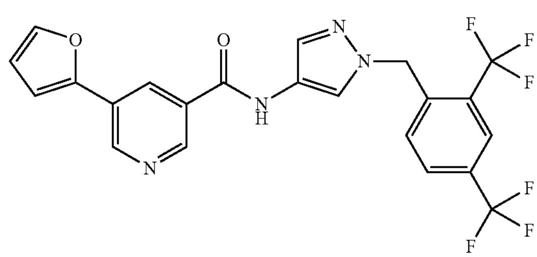 [SMILES: O=C(Nc1cnn(Cc2ccc(C(F)(F)F)cc2C(F)(F)F)c1)c1cncc(-c2ccco2)c1] | N-(1-(2,4-bis(trifluoromethyl)benzyl)-1H-pyrazol-4-yl)-5-(furan-2-yl)nicotinamide |

TABLE 1-continued

| Cmpd No. | Structure | Chemical Name |
|---|---|---|
| 44 | 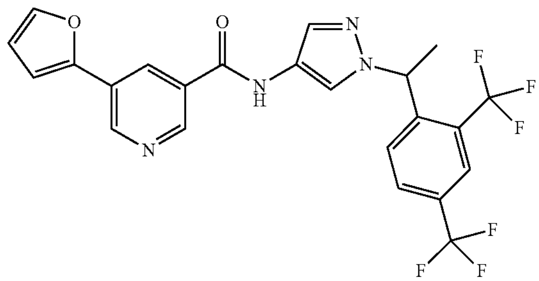 [SMILES: CC(c1ccc(C(F)(F)F)cc1C(F)(F)F)n1cc(NC(=O)c2cncc(-c3ccco3)c2)cn1] | N-(1-(1-(2,4-bis(trifluoromethyl)phenyl)ethyl)-1H-pyrazol-4-yl)-5-(furan-2-yl)nicotinamide |
| 45 | 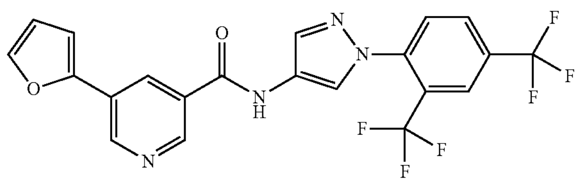 [SMILES: O=C(Nc1cnn(-c2ccc(C(F)(F)F)cc2C(F)(F)F)c1)c1cncc(-c2ccco2)c1] | N-(1-(2,4-bis(trifluoromethyl)phenyl)-1H-pyrazol-4-yl)-5-(furan-2-yl)nicotinamide |
| 46 | 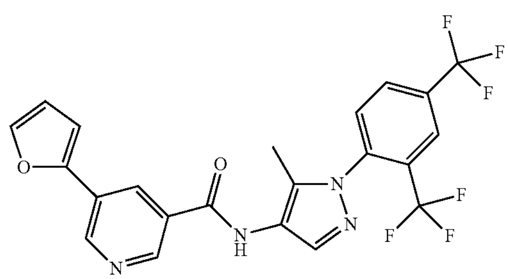 [SMILES: Cc1c(NC(=O)c2cncc(-c3ccco3)c2)cnn1-c1ccc(C(F)(F)F)cc1C(F)(F)F] | N-(1-(2,4-bis(trifluoromethyl)phenyl)-5-methyl-1H-pyrazol-4-yl)-5-(furan-2-yl)nicotinamide |
| 47 | 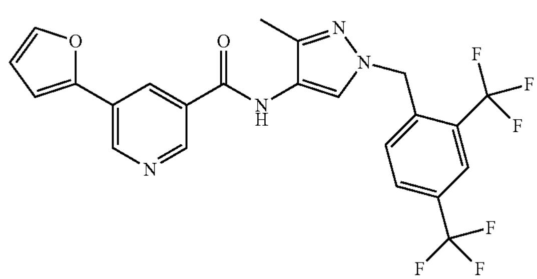 [SMILES: Cc1nn(Cc2ccc(C(F)(F)F)cc2C(F)(F)F)cc1NC(=O)c1cncc(-c2ccco2)c1] | N-(1-(2,4-bis(trifluoromethyl)benzyl)-3-methyl-1H-pyrazol-4-yl)-5-(furan-2-yl)nicotinamide |
| 48 | 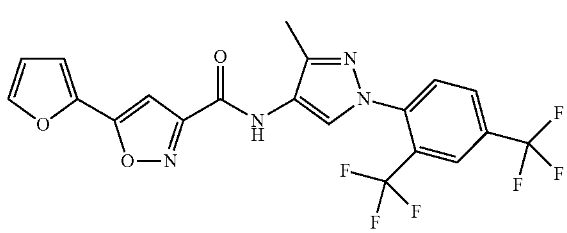 [SMILES: Cc1nn(-c2ccc(C(F)(F)F)cc2C(F)(F)F)cc1NC(=O)c1cc(-c2ccco2)on1] | N-(1-(2,4-bis(trifluoromethyl)phenyl)-3-methyl-1H-pyrazol-4-yl)-5-(furan-2-yl)isoxazole-3-carboxamide |
| 49 | 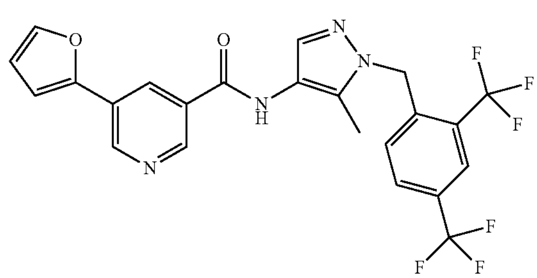 [SMILES: Cc1c(NC(=O)c2cncc(-c3ccco3)c2)cnn1Cc1ccc(C(F)(F)F)cc1C(F)(F)F] | N-(1-(2,4-bis(trifluoromethyl)benzyl)-5-methyl-1H-pyrazol-4-yl)-5-(furan-2-yl)nicotinamide |

TABLE 1-continued

| Cmpd No. | Structure | Chemical Name |
| --- | --- | --- |
| 50 | 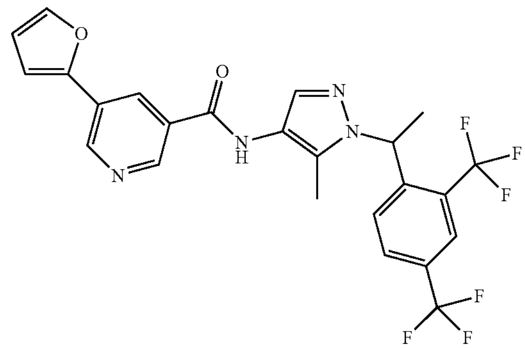 [SMILES: Cc1c(NC(=O)c2cncc(-c3ccco3)c2)cnn1C(C)c1ccc(C(F)(F)F)cc1C(F)(F)F] | N-(1-(1-(2,4-bis(trifluoromethyl)phenyl)ethyl)-5-methyl-1H-pyrazol-4-yl)-5-(furan-2-yl)nicotinamide |
| 51 | 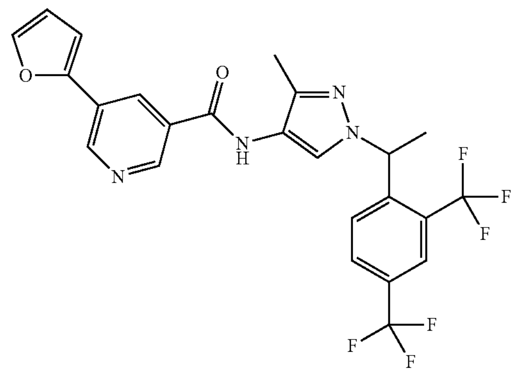 [SMILES: Cc1nn(C(C)c2ccc(C(F)(F)F)cc2C(F)(F)F)cc1NC(=O)c1cncc(-c2ccco2)c1] | N-(1-(1-(2,4-bis(trifluoromethyl)phenyl)ethyl)-3-methyl-1H-pyrazol-4-yl)-5-(furan-2-yl)nicotinamide |
| 52 | 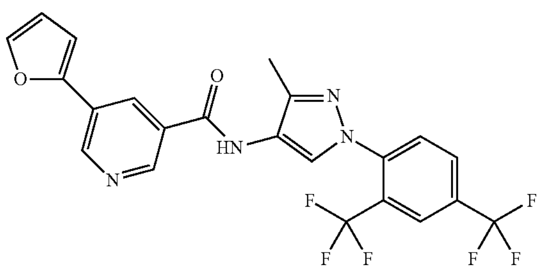 [SMILES: Cc1nn(-c2ccc(C(F)(F)F)cc2C(F)(F)F)cc1NC(=O)c1cncc(-c2ccco2)c1] | N-(1-(2,4-bis(trifluoromethyl)phenyl)-3-methyl-1H-pyrazol-4-yl)-5-(furan-2-yl)nicotinamide |
| 53 | 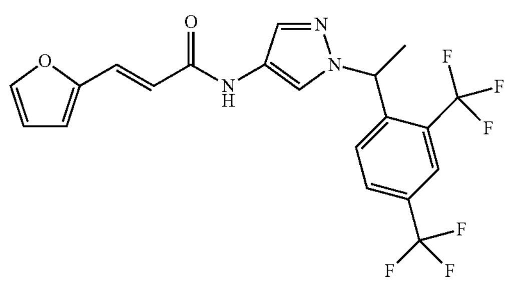 [SMILES: CC(c1ccc(C(F)(F)F)cc1C(F)(F)F)n1cc(NC(=O)/C=C/c2ccco2)cn1] | (E)-N-(1-(1-(2,4-bis(trifluoromethyl)phenyl)ethyl)-1H-pyrazol-4-yl)-3-(furan-2-yl)acrylamide |
| 54 | 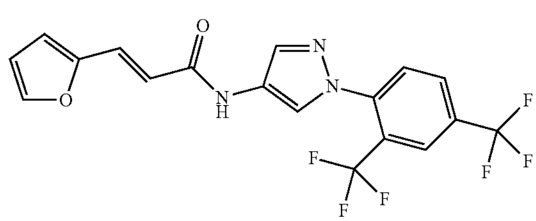 [SMILES: O=C(/C=C/c1ccco1)Nc1cnn(-c2ccc(C(F)(F)F)cc2C(F)(F)F)c1] | (E)-N-(1-(2,4-bis(trifluoromethyl)phenyl)-1H-pyrazol-4-yl)-3-(furan-2-yl)acrylamide |

TABLE 1-continued

| Cmpd No. | Structure | Chemical Name |
|---|---|---|
| 55 | 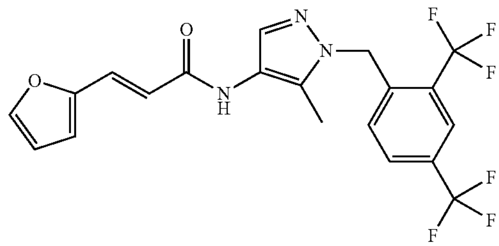 [SMILES: Cc1c(NC(=O)/C=C/c2ccco2)cnn1Cc1ccc(C(F)(F)F)cc1C(F)(F)F] | (E)-N-(1-(2,4-bis(trifluoromethyl)benzyl)-5-methyl-1H-pyrazol-4-yl)-3-(furan-2-yl)acrylamide |
| 56 | 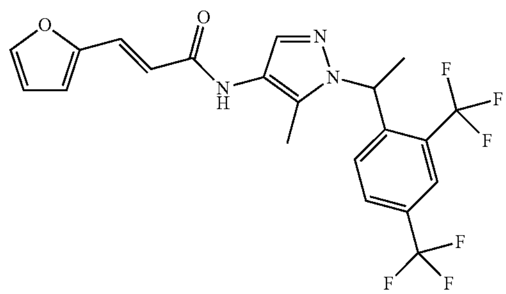 [SMILES: Cc1c(NC(=O)/C=C/c2ccco2)cnn1C(C)c1ccc(C(F)(F)F)cc1C(F)(F)F] | (E)-N-(1-(1-(2,4-bis(trifluoromethyl)phenyl)ethyl)-5-methyl-1H-pyrazol-4-yl)-3-(furan-2-yl)acrylamide |
| 57 | 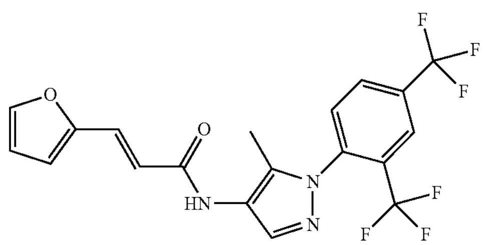 [SMILES: Cc1c(NC(=O)/C=C/c2ccco2)cnn1-c1ccc(C(F)(F)F)cc1C(F)(F)F] | (E)-N-(1-(2,4-bis(trifluoromethyl)phenyl)-5-methyl-1H-pyrazol-4-yl)-3-(furan-2-yl)acrylamide |
| 58 | 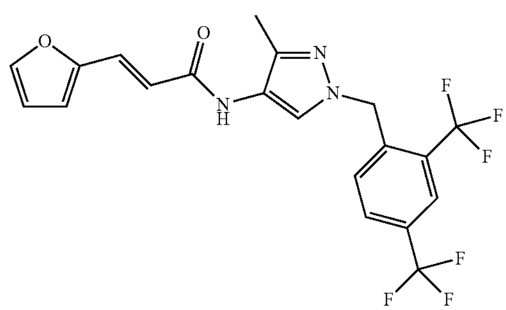 [SMILES: Cc1nn(Cc2ccc(C(F)(F)F)cc2C(F)(F)F)cc1NC(=O)/C=C/c1ccco1] | (E)-N-(1-(2,4-bis(trifluoromethyl)benzyl)-3-methyl-1H-pyrazol-4-yl)-3-(furan-2-yl)acrylamide |
| 59 | 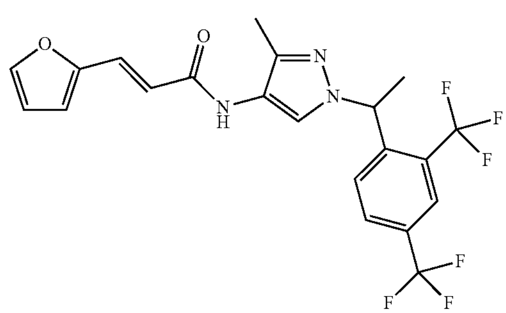 [SMILES: Cc1nn(C(C)c2ccc(C(F)(F)F)cc2C(F)(F)F)cc1NC(=O)/C=C/c1ccco1] | (E)-N-(1-(1-(2,4-bis(trifluoromethyl)phenyl)ethyl)-3-methyl-1H-pyrazol-4-yl)-3-(furan-2-yl)acrylamide |

TABLE 1-continued

| Cmpd No. | Structure | Chemical Name |
|---|---|---|
| 60 | 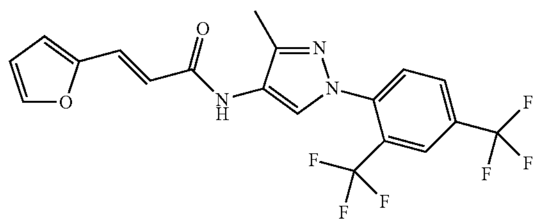 [SMILES: Cc1nn(-c2ccc(C(F)(F)F)cc2C(F)(F)F)cc1NC(=O)/C=C/c1ccco1] | (E)-N-(1-(2,4-bis(trifluoromethyl)phenyl)-3-methyl-1H-pyrazol-4-yl)-3-(furan-2-yl)acrylamide |
| 61 | 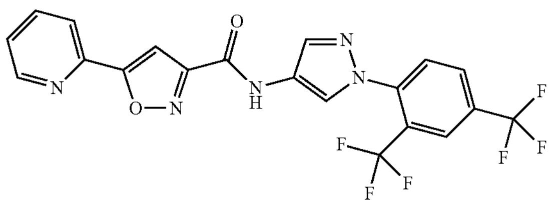 [SMILES: O=C(Nc1cnn(-c2ccc(C(F)(F)F)cc2C(F)(F)F)c1)c1cc(-c2ccccn2)on1] | N-(1-(2,4-bis(trifluoromethyl)phenyl)-1H-pyrazol-4-yl)-5-(pyridin-2-yl)isoxazole-3-carboxamide |
| 62 | 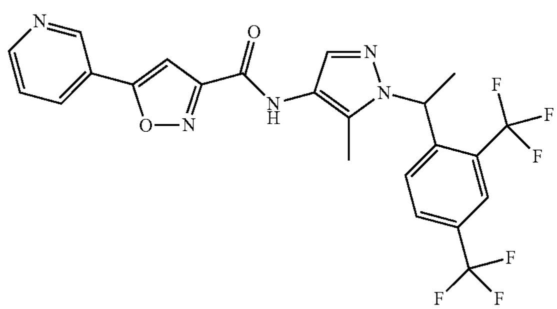 [SMILES: Cc1c(NC(=O)c2cc(-c3cccnc3)on2)cnn1C(C)c1ccc(C(F)(F)F)cc1C(F)(F)F] | N-(1-(1-(2,4-bis(trifluoromethyl)phenyl)ethyl)-5-methyl-1H-pyrazol-4-yl)-5-(pyridin-2-yl)isoxazole-3-carboxamide |
| 63 | 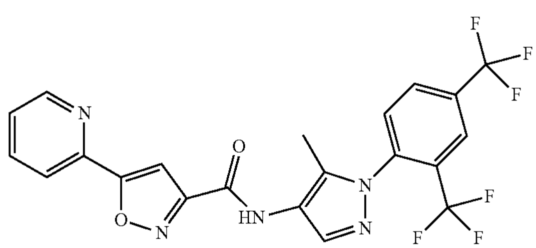 [SMILES: Cc1c(NC(=O)c2cc(-c3ccccn3)on2)cnn1-c1ccc(C(F)(F)F)cc1C(F)(F)F] | N-(1-(2,4-bis(trifluoromethyl)phenyl)-5-methyl-1H-pyrazol-4-yl)-5-(pyridin-2-yl)isoxazole-3-carboxamide |
| 64 | 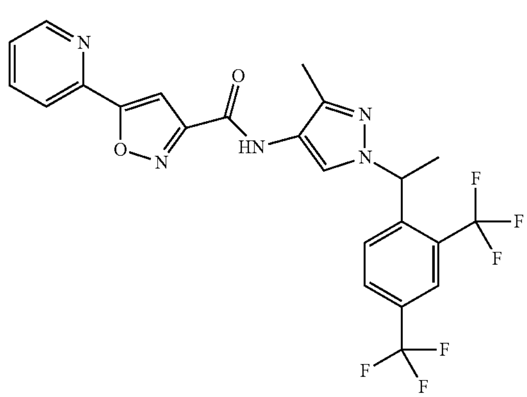 [SMILES: Cc1nn(C(C)c2ccc(C(F)(F)F)cc2C(F)(F)F)cc1NC(=O)c1cc(-c2ccccn2)on1] | N-(1-(1-(2,4-bis(trifluoromethyl)phenyl)ethyl)-3-methyl-1H-pyrazol-4-yl)-5-(pyridin-2-yl)isoxazole-3-carboxamide |

TABLE 1-continued

| Cmpd No. | Structure | Chemical Name |
|---|---|---|
| 65 | 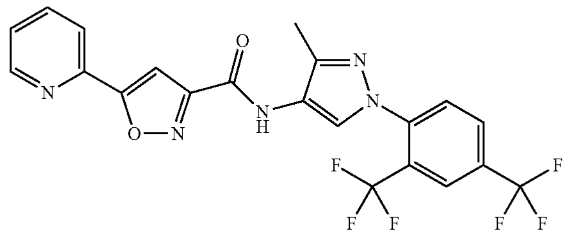 [SMILES: Cc1nn(-c2ccc(C(F)(F)F)cc2C(F)(F)F)cc1NC(=O)c1cc(-c2ccccn2)on1] | N-(1-(2,4-bis(trifluoromethyl)phenyl)-3-methyl-1H-pyrazol-4-yl)-5-(pyridin-2-yl)isoxazole-3-carboxamide |
| 66 | 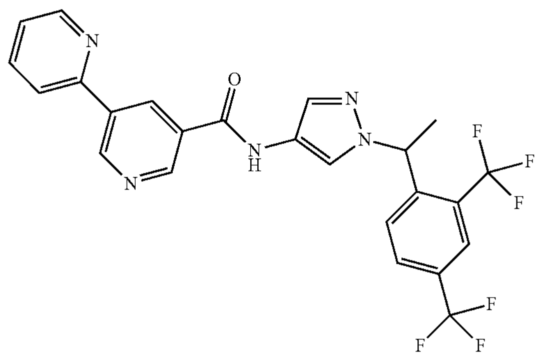 [SMILES: CC(c1ccc(C(F)(F)F)cc1C(F)(F)F)n1cc(NC(=O)c2cncc(-c3ccccn3)c2)cn1] | N-(1-(1-(2,4-bis(trifluoromethyl)phenyl)ethyl)-1H-pyrazol-4-yl)-[2,3'-bipyridine]-5'-carboxamide |
| 67 | 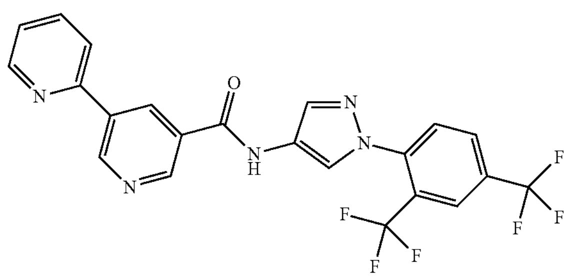 [SMILES: O=C(Nc1cnn(-c2ccc(C(F)(F)F)cc2C(F)(F)F)c1)c1cncc(-c2ccccn2)c1] | N-(1-(2,4-bis(trifluoromethyl)phenyl)-1H-pyrazol-4-yl)-[2,3'-bipyridine]-5'-carboxamide |
| 68 | 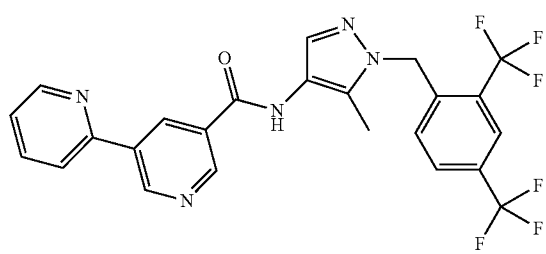 [SMILES: Cc1c(NC(=O)c2cncc(-c3ccccn3)c2)cnn1Cc1ccc(C(F)(F)F)cc1C(F)(F)F] | N-(1-(2,4-bis(trifluoromethyl)benzyl)-5-methyl-1H-pyrazol-4-yl)-[2,3'-bipyridine]-5'-carboxamide |
| 69 | 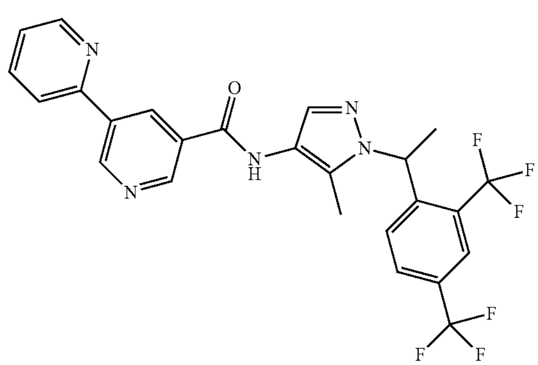 [SMILES: Cc1c(NC(=O)c2cncc(-c3ccccn3)c2)cnn1C(C)c1ccc(C(F)(F)F)cc1C(F)(F)F] | N-(1-(1-(2,4-bis(trifluoromethyl)phenyl)ethyl)-5-methyl-1H-pyrazol-4-yl)-[2,3'-bipyridine]-5'-carboxamide |

TABLE 1-continued

| Cmpd No. | Structure | Chemical Name |
|---|---|---|
| 70 | 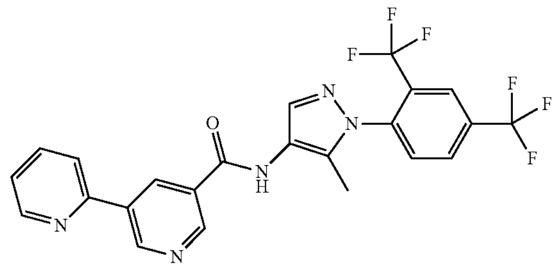 [SMILES: Cc1c(NC(=O)c2cncc(-c3ccccn3)c2)cnn1-c1ccc(C(F)(F)F)cc1C(F)(F)F] | N-(1-(2,4-bis(trifluoromethyl)phenyl)-5-methyl-1H-pyrazol-4-yl)-[2,3'-bipyridine]-5'-carboxamide |
| 71 | 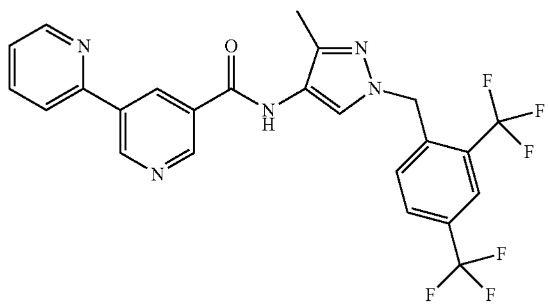 [SMILES: Cc1nn(Cc2ccc(C(F)(F)F)cc2C(F)(F)F)cc1NC(=O)c1cncc(-c2ccccn2)c1] | N-(1-(2,4-bis(trifluoromethyl)benzyl)-3-methyl-1H-pyrazol-4-yl)-[2,3'-bipyridine]-5'-carboxamide |
| 72 | 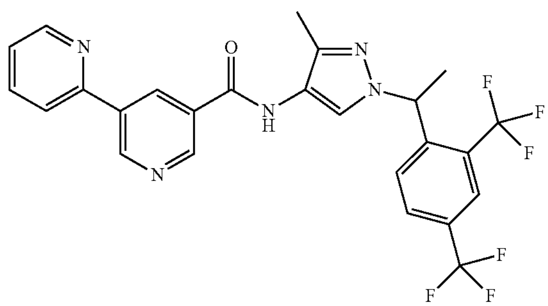 [SMILES: Cc1nn(C(C)c2ccc(C(F)(F)F)cc2C(F)(F)F)cc1NC(=O)c1cncc(-c2ccccn2)c1] | N-(1-(1-(2,4-bis(trifluoromethyl)phenyl)ethyl)-3-methyl-1H-pyrazol-4-yl)-[2,3'-bipyridine]-5'-carboxamide |
| 73 | 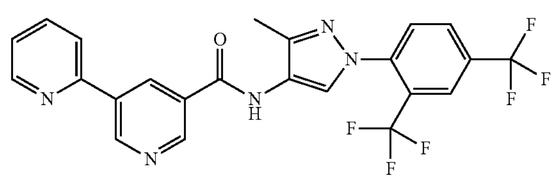 [SMILES: Cc1nn(-c2ccc(C(F)(F)F)cc2C(F)(F)F)cc1NC(=O)c1cncc(-c2ccccn2)c1] | N-(1-(2,4-bis(trifluoromethyl)phenyl)-3-methyl-1H-pyrazol-4-yl)-[2,3'-bipyridine]-5'-carboxamide |
| 74 | 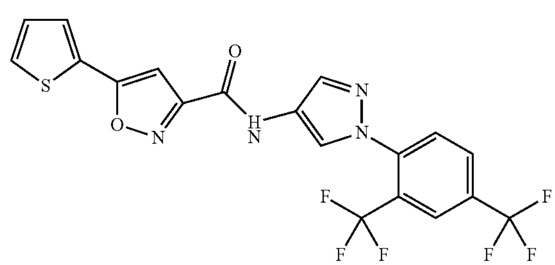 [SMILES: O=C(Nc1cnn(-c2ccc(C(F)(F)F)cc2C(F)(F)F)c1)c1cc(-c2cccs2)on1] | N-(1-(2,4-bis(trifluoromethyl)phenyl)-1H-pyrazol-4-yl)-5-(thiophen-2-yl)isoxazole-3-carboxamide |

TABLE 1-continued

| Cmpd No. | Structure | Chemical Name |
| --- | --- | --- |
| 75 | 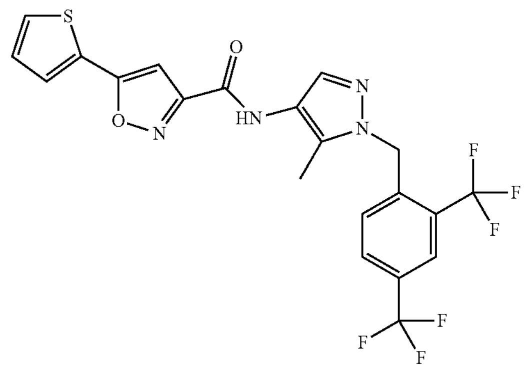 [SMILES: Cc1c(NC(=O)c2cc(-c3cccs3)on2)cnn1Cc1ccc(C(F)(F)F)cc1C(F)(F)F] | N-(1-(2,4-bis(trifluoromethyl)benzyl)-5-methyl-1H-pyrazol-4-yl)-5-(thiophen-2-yl)isoxazole-3-carboxamide |
| 76 | 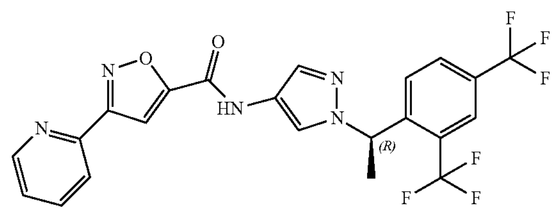 | (R)-N-(1-(1-(2,4-bis(trifluoromethyl)phenyl)ethyl)-1H-pyrazol-4-yl)-3-(pyridin-2-yl)isoxazole-5-carboxamide |
| 77 | 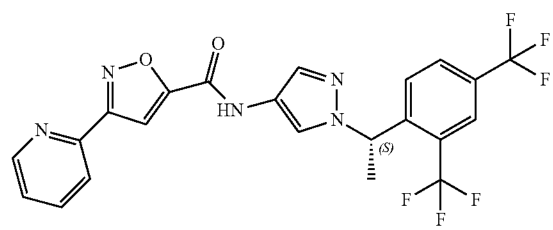 | (S)-N-(1-(1-(2,4-bis(trifluoromethyl)phenyl)ethyl)-1H-pyrazol-4-yl)-3-(pyridin-2-yl)isoxazole-5-carboxamide |
| 78 | 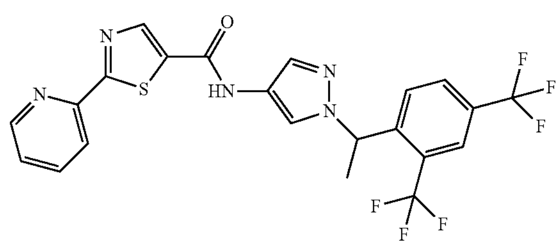 [SMILES: CC(c1ccc(C(F)(F)F)cc1C(F)(F)F)n1cc(NC(=O)c2cnc(-c3ccccn3)s2)cn1] | N-(1-(1-(2,4-bis(trifluoromethyl)phenyl)ethyl)-1H-pyrazol-4-yl)-2-(pridin-2-yl)thiazole-5-carboxamide |
| 79 | 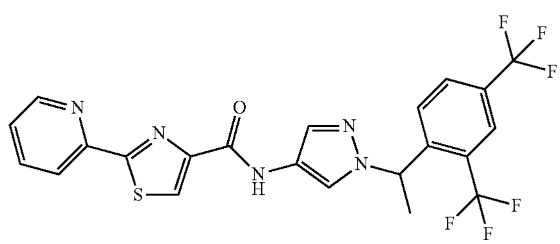 [SMILES: CC(c1ccc(C(F)(F)F)cc1C(F)(F)F)n1cc(NC(=O)c2csc(-c3ccccn3)n2)cn1] | N-(1-(1-(2,4-bis(trifluoromethyl)phenyl)ethyl)-1H-pyrazol-4-yl)-2-(pyridin-2-yl)thiazole-4-carboxamide |

TABLE 1-continued

| Cmpd No. | Structure | Chemical Name |
|---|---|---|
| 80 | 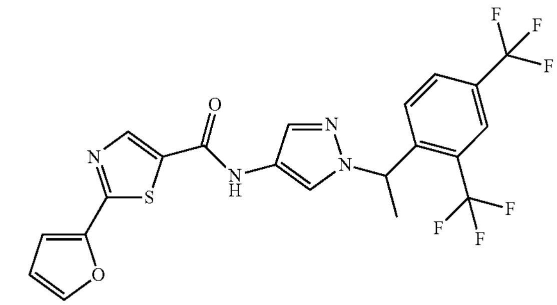 [SMILES: CC(c1ccc(C(F)(F)F)cc1C(F)(F)F)n1cc(NC(=O)c2cnc(-c3ccco3)s2)cn1] | N-(1-(1-(2,4-bis(trifluoromethyl)phenyl)ethyl)-1H-pyrazol-4-yl)-2-(furan-2-yl)thiazole-5-carboxamide |
| 81 | 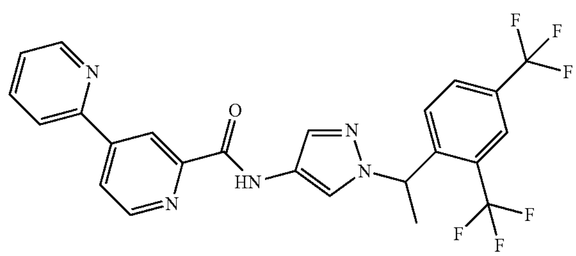 [SMILES: CC(c1ccc(C(F)(F)F)cc1C(F)(F)F)n1cc(NC(=O)c2cc(-c3ccccn3)ccn2)cn1] | N-(1-(1-(2,4-bis(trifluoromethyl)phenyl)ethyl)-1H-pyrazol-4-yl)-[2,4'-bipyridine]-2'-carboxamide |
| 82 | 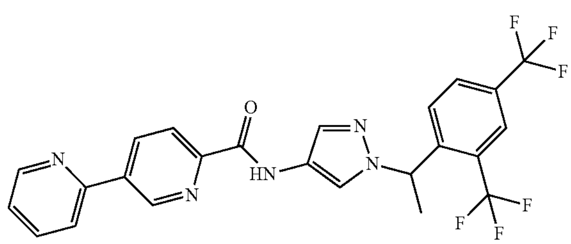 [SMILES: CC(c1ccc(C(F)(F)F)cc1C(F)(F)F)n1cc(NC(=O)c2ccc(-c3ccccn3)cn2)cn1] | N-(1-(1-(2,4-bis(trifluoromethyi)phenyl)ethyl)-1H-pyrazol-4-yl)-[2,3'-bipyridine]-6'-carboxamide |
| 83 | 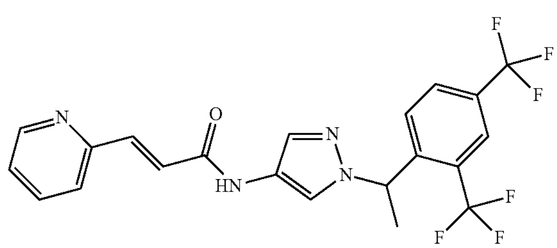 [SMILES: CC(c1ccc(C(F)(F)F)cc1C(F)(F)F)n1cc(NC(=O)/C=C/c2ccccn2)cn1] | (E)-N-(1-(1-(2,4-bis(trifluoromethyl)phenyl)ethyl)-1H-pyrazol-4-yl)-3-(pyridin-2-yl)acrylamide |
| 84 | 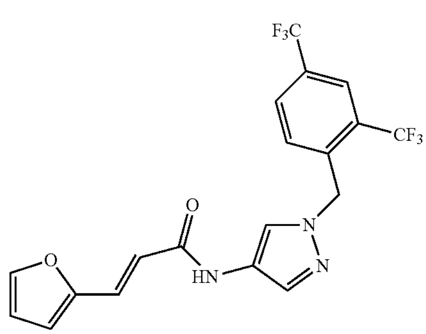 [SMILES: O=C(/C=C/c1ccco1)Nc1cnn(Cc2ccc(C(F)(F)F)cc2C(F)(F)F)c1] | (E)-N-(1-(2,4-bis(trifluoromethyl)benzyl)-1H-pyrazol-4-yl)-3-(furan-2-yl)acrylamide |

TABLE 1-continued

| Cmpd No. | Structure | Chemical Name |
|---|---|---|
| 85 | 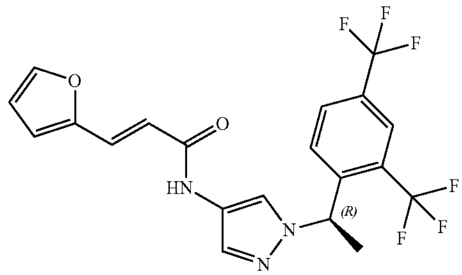 | (R,E)-N-(1-(1-(2,4-bis(trifluoromethyl)phenyl)ethyl)-1H-pyrazol-4-yl)-3-(furan-2-yl)acrylamide |
| 86 | 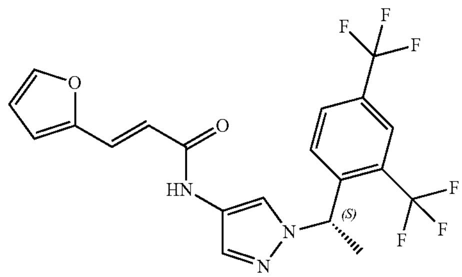 | (S,E)-N-(1-(1-(2,4-bis(trifluoromethyl)phenyl)ethyl)-1H-pyrazol-4-yl)-3-(furan-2-yl)acrylamide |
| 87 | 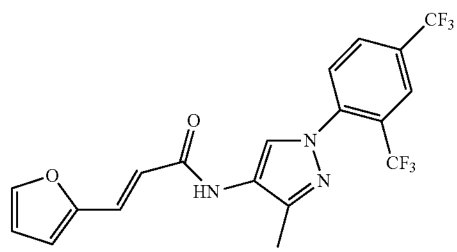 [SMILES: Cc1nn(-c2ccc(C(F)(F)F)cc2C(F)(F)F)cc1NC(=O)/C=C/c1ccco1] | (E)-N-(1-(2,4-bis(trifluoromethyl)phenyl)-3-methyl-1H-pyrazol-4-yl)-3-(furan-2-yl)acrylamide |
| 88 | 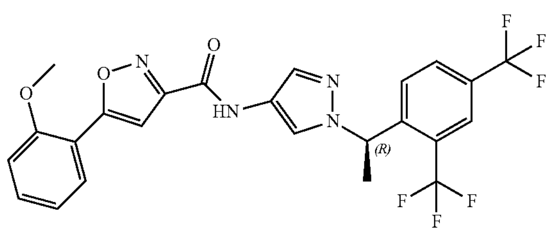 | (R)-N-(1-(1-(2,4-bis(trifluoromethyl)phenyl)ethyl)-1H-pyrazol-4-yl)-5-(2-methoxyphenyl)isoxazole-3-carboxamide |
| 89 | 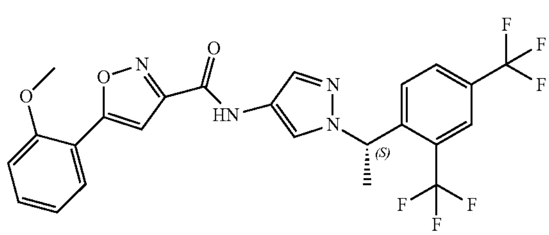 | (S)-N-(1-(1-(2,4-bis(trifluoromethyl)phenyl)ethyl)-1H-pyrazol-4-yl)-5-(2-methoxyphenyl)isoxazole-3-carboxamide |
| 90 | 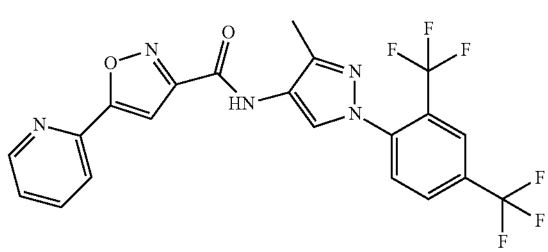 [SMILES: Cc1nn(-c2ccc(C(F)(F)F)cc2C(F)(F)F)cc1NC(=O)c1cc(-c2ccccn2)on1] | N-(1-(2,4-bis(trifluoromethyl)phenyl)-3-methyl-1H-pyrazol-4-yl)-5-(pyridin-2-yl)isoxazole-3-carboxamide |

TABLE 1-continued

| Cmpd No. | Structure | Chemical Name |
|---|---|---|
| 91 | 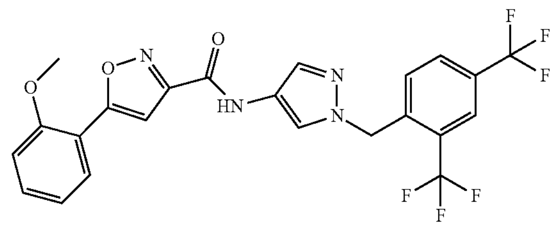 [SMILES: COc1ccccc1-c1cc(C(=O)Nc2cnn(Cc3ccc(C(F)(F)F)cc3C(F)(F)F)c2)no1] | N-(1-(2,4-bis(trifluoromethyl)benzyl-1H-pyrazol-4-yl)-5-(2-methoxyl)henyl)-isoxazole-3-carboxamide |
| 92 | 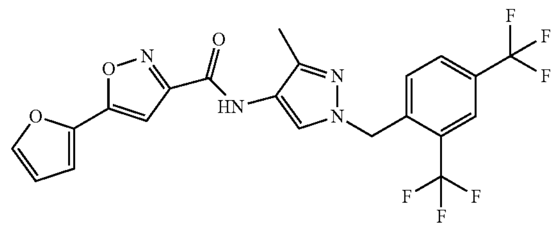 [SMILES: Cc1nn(Cc2ccc(C(F)(F)F)cc2C(F)(F)F)cc1NC(=O)c1cc(-c2ccco2)on1] | N-(1-(2,4-bis(trifluoromethyl)benzyl)-3-methyl-1H-pyrazol-4-yl)-5-(furan-2-yl)isoxazole-3-carboxatnide |
| 93 | 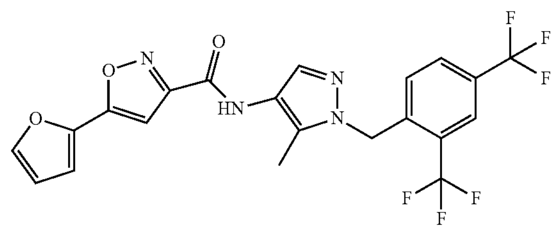 [SMILES: Cc1c(NC(=O)c2cc(-c3ccco3)on2)cnn1Cc1ccc(C(F)(F)F)cc1C(F)(F)F] | N-(1-(2,4-bis(trifluoromethyl)benzyl)-5-methyl-1H-pyrazol-4-yl)-5-(furan-2-yl)isoxazole-3-carboxamide |
| 94 | 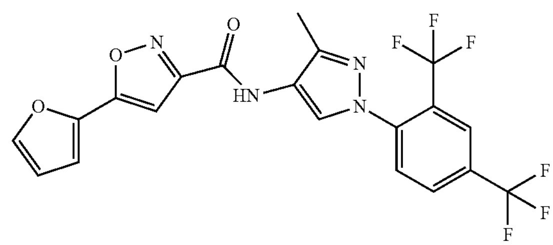 [SMILES: Cc1nn(-c2ccc(C(F)(F)F)cc2C(F)(F)F)cc1NC(=O)c1cc(-c2ccco2)on1] | N-(1-(2,4-bis(trifluoromethyl)phenyl)-3-methyl-1H-pyrazol-4-yl)-5-(furan-2-yl)isoxazole-3-carboxamide |
| 95 | 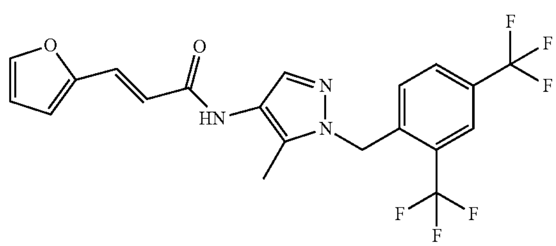 [SMILES: Cc1c(NC(=O)/C=C/c2ccco2)cnn1Cc1ccc(C(F)(F)F)cc1C(F)(F)F] | (E)-N-(1-(2,4-bis(trifluoromethyl)benzyl)-5-methyl-1H-pyrazol-4-yl)-3-(furan-2-yl)acrylamide |
| 96 | 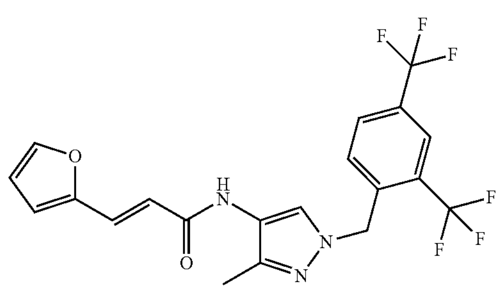 [SMILES: Cc1nn(Cc2ccc(C(F)(F)F)cc2C(F)(F)F)cc1NC(=O)/C=C/c1ccco1] | (E)-N-(1-(2,4-bis(trifluoromethyl)benzyl)-3-methyl-1H-pyrazol-4-yl)-3-(furan-2-yl)acrylamide |

TABLE 1-continued

| Cmpd No. | Structure | Chemical Name |
|---|---|---|
| 97 | 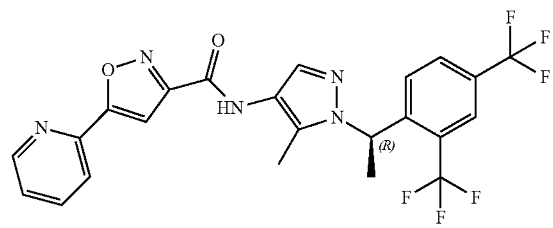 | (R)-N-(1-(1-(2,4-bis(trifluoromethyl)phenyl)ethyl)-5-methyl-1H-pyrazol-4-yl)-5-(pyridin-2-yl)isoxazole-3-carboxamide |
| 98 | 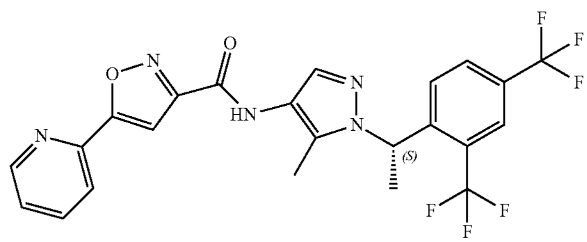 | (S)-N-(1-(1-(2,4-bis(trifluoromethyl)phenyl)ethyl)-5-methyl-1H-pyrazol-4-yl)-5-(pyridin-2-yl)isoxazole-3-carboxamide |
| 99 | 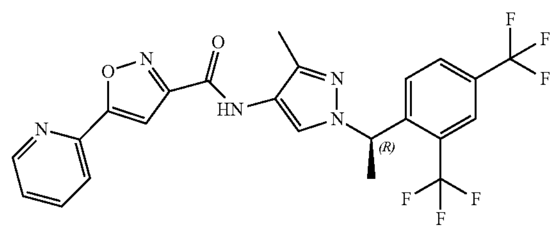 | (R)-N-(1-(1-(2,4-bis(trifluoromethyl)phenyl)ethyl)-3-methyl-1H-pyrazol-4-yl)-5-(pyridin-2-yl)isoxazole-3-carboxamide |
| 100 | 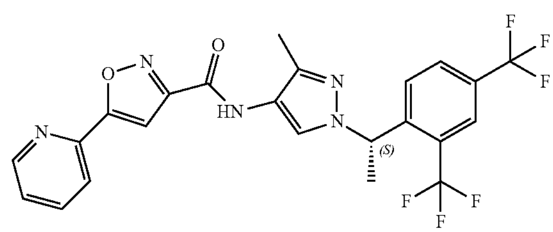 | (S)-N-(1-(1-(2,4-bis(trifluoromethyl)phenyl)ethyl)-3-methyl-1H-pyrazol-4-yl)-5-(pyridin-2-yl)isoxazole-3-carboxamide |
| 101 | 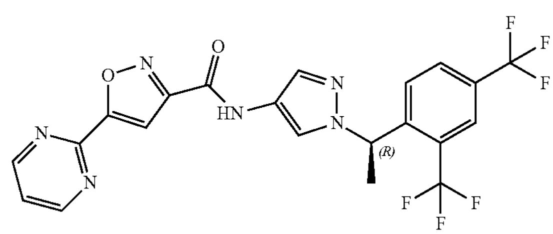 | (R)-N-(1-(1-(2,4-bis(trifluoromethyl)phenyl)ethyl)-1H-pyrazol-4-yl)-5-(pyrimidin-2-yl)isoxazole-3-carboxamide |
| 102 | 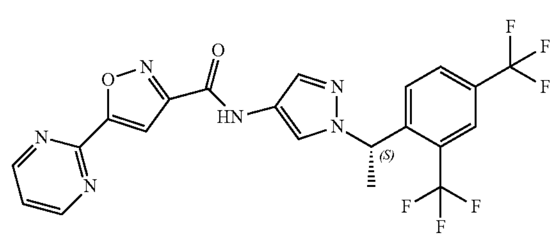 | (S)-N-(1-(1-(2,4-bis(trifluoromethyl)phenyl)ethyl)-1H-pyrazol-4-yl)-5-(primidin-2-yl)isoxazole-3-carboxamide |

TABLE 1-continued

| Cmpd No. | Structure | Chemical Name |
|---|---|---|
| 103 | 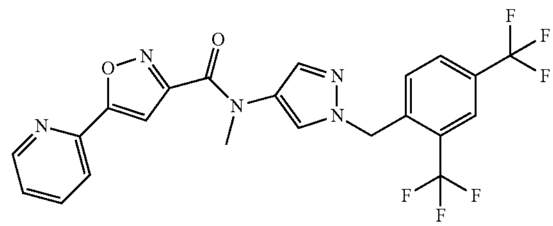 [SMILES: CN(C(=O)c1cc(-c2ccccn2)on1)c1cnn(Cc2ccc(C(F)(F)F)cc2C(F)(F)F)c1] | N-(1-(2,4-bis(trifluoromethyl)benzyl-1H-pyrazol-4-yl)-N-methyl-5-(pyridin-2-yl)isoxazole-3-carboxamide |
| 104 | 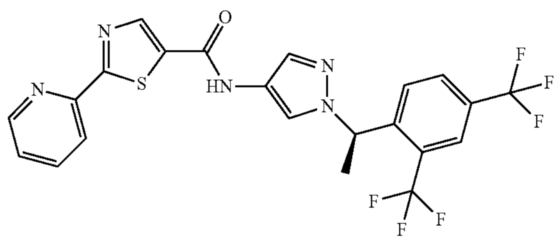 [SMILES: C[C@H](c1ccc(C(F)(F)F)cc1C(F)(F)F)n1cc(NC(=O)c2cnc(-c3ccccn3)s2)cn1] | (R)-N-(1-(1-(2,4-bis(trifluoromethyl)phenyl)ethyl)-1H-pyrazol-4-yl)-2-(pyridin-2-yl)thiazole-5-carboxamide |
| 105 | 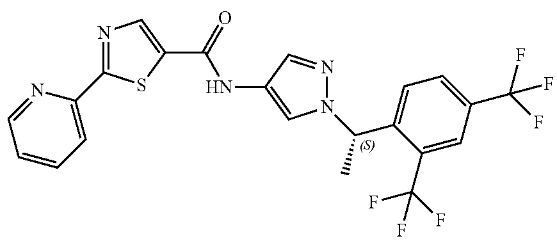 | (S)-N-(1-(1-(2,4-bis(trifluoromethyl)phenyl)ethyl)-1H-pyrazol-4-yl)-2-(pyridin-2-yl)thiazole-5-carboxamide |
| 106 | 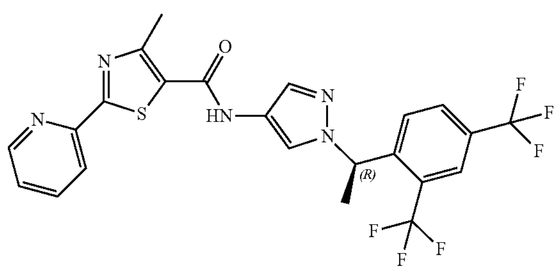 | (R)-N-(1-(1-(2,4-bis(trifluoromethyl)phenyl)ethyl)-1H-pyrazol-4-yl)-4-methyl-2-(pyridin-2-yl)thiazole-5-carboxamide |
| 107 | 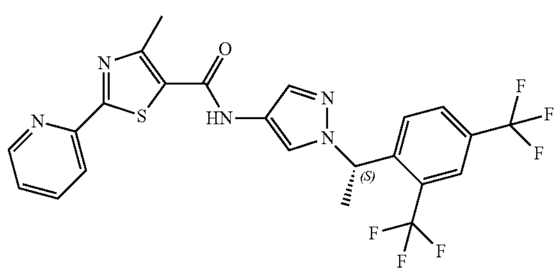 | (S)-N-(1-(1-(2,4-bis(trifluoromethyl)phenyl)ethyl)-1H-pyrazol-4-yl)-4-methyl-2-(pyridin-2-yl)thiazole-5-carboxamide |
| 108 | 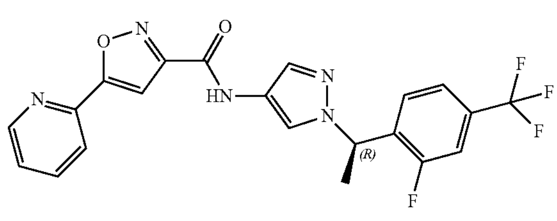 | (R)-N-(1-(1-(2-fluoro-4-(trifluoromethyl)phenyl)ethyl)-1H-pyrazol-4-yl)-5-(pyridin-2-yl)isoxazole-3-carboxamide |

TABLE 1-continued

| Cmpd No. | Structure | Chemical Name |
|---|---|---|
| 109 | 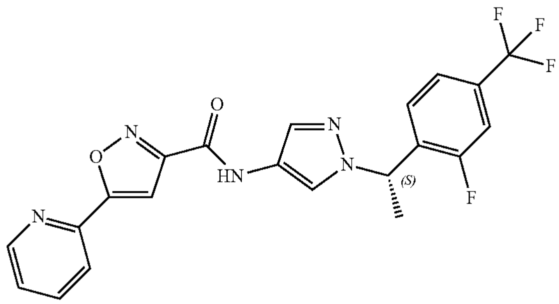 | (S)-N-(1-(1-(2-fluoro-4-(trifluoromethyl)phenyl)ethyl)-1H-pyrazol-4-yl)-5-(pyridin-2-yl)isoxazole-3-carboxamide |
| 110 | 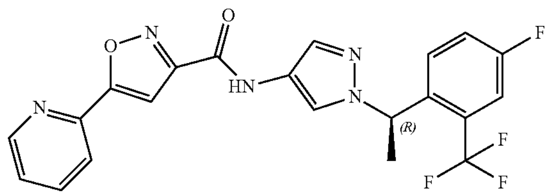 | (R)-N-(1-(1-(4-fluoro-2-(trifluoromethyl)phenyl)ethyl)-1H-pyrazol-4-yl)-5-(pridin-2-yl)isoxazole-3-carboxamide |
| 111 | 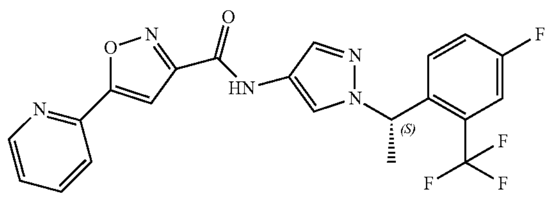 | (S)-N-(1-(1-(4-fluoro-2-(trifluoromethyl)phenyl)ethyl)-1H-pyrazol-4-yl)-5-(pyridin-2-yl)isoxazole-3-carboxamide |
| 112 | 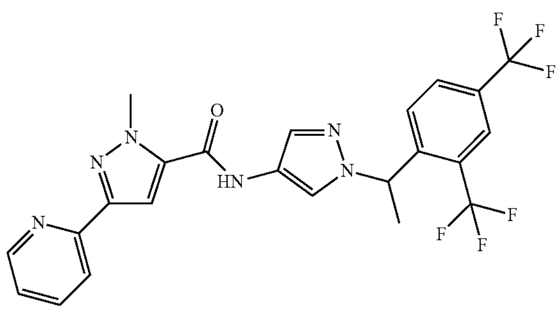 [SMILES: CC(c1ccc(C(F)(F)F)cc1C(F)(F)F)n1cc(NC(=O)c2cc(-c3ccccn3)nn2C)cn1] | N-(1-(1-(2,4-bis(trifluoromethyl)phenyl)ethyl)-1H-pyrazol-4-yl)-1-methyl-3-(pyridin-2-yl)-1H-pyrazole-5-carboxamide |
| 113 | 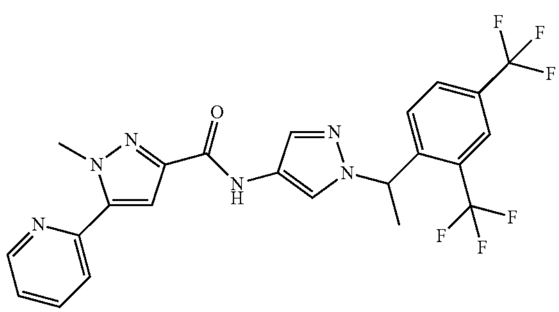 [SMILES: CC(c1ccc(C(F)(F)F)cc1C(F)(F)F)n1cc(NC(=O)c2cc(-c3ccccn3)n(C)n2)cn1] | N-(1-(1-(2,4-bis(trifluoromethyl)phenyl)ethyl)-1H-pyrazol-4-yl)-1-methyl-5-(pyridin-2-yl)-1H-pyrazole-3-carboxamide |

TABLE 1-continued

| Cmpd No. | Structure | Chemical Name |
|---|---|---|
| 114 | 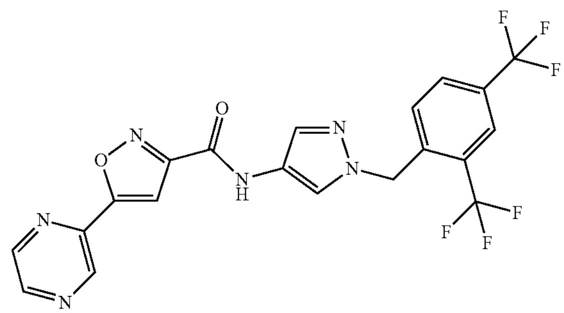 [SMILES: O=C(Nc1cnn(Cc2ccc(C(F)(F)F)cc2C(F)(F)F)c1)c1cc(-c2cnccn2)on1] | N-(1-(2,4-bis(trifluoromethyl)benzyl)-1H-pyrazol-4-yl)-5-(pyrazin-2-yl)isoxazole-3-carboxamide |
| 115 | 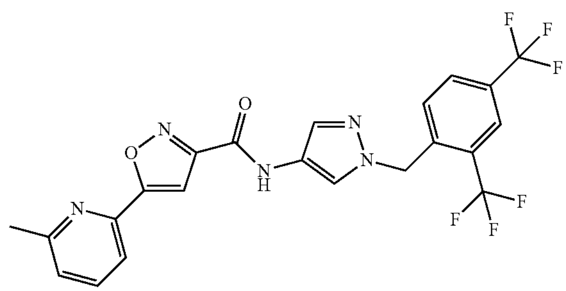 [SMILES: Cc1cccc(-c2cc(C(=O)Nc3cnn(Cc4ccc(C(F)(F)F)cc4C(F)(F)F)c3)no2)n1] | N-(1-(2,4-bis(trifluoromethyl)benzyl)-1H-pyrazol-4-yl)-5-(6-methylpyridin-2-yl)isoxazole-3-carboxamide |
| 116 | 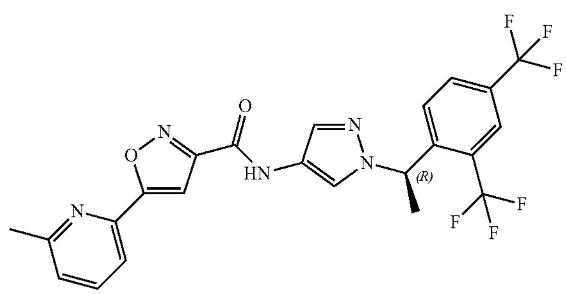 | (R)-N-(1-(1-(2,4-bis(trifluoromethyl)phenyl)ethyl)-1H-pyrazol-4-yl)-5-(6-methylpyridin-2-yl)isoxazole-3-carboxamide |
| 117 | 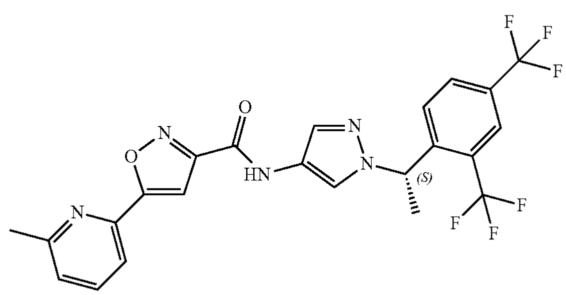 | (S)-N-(1-(1-(2,4-bis(trifluoromethyl)phenyl)ethyl)-1H-pyrazol-4-yl)-5-(6-methylpyridin-2-yl)isoxazole-3-carboxamide |
| 118 | 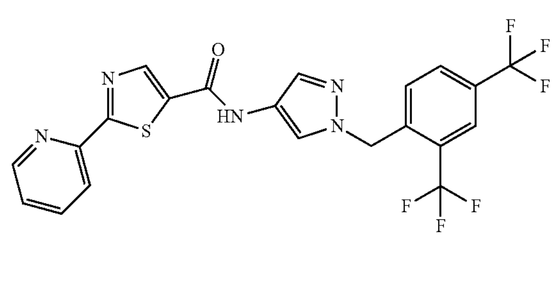 [SMILES: O=C(Nc1cnn(Cc2ccc(C(F)(F)F)cc2C(F)(F)F)c1)c1cnc(-c2ccccn2)s1] | N-(1-(2,4-bis(trifluoromethyl)benzyl)-1H-pyrazol-4-yl)-2-(pyridin-2-yl)thiazole-5-carboxamide |

TABLE 1-continued

| Cmpd No. | Structure | Chemical Name |
|---|---|---|
| 119 | 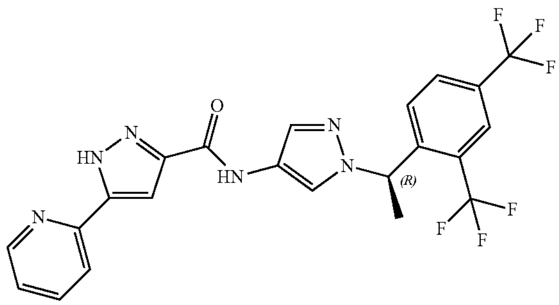 | (R)-N-(1-(1-(2,4-bis(trifluoromethyl)phenyl)ethyl)-1H-pyrazol-4-yl)-5-(pyridin-2-yl)-1H-pyrazole-3-carboxamide |
| 120 | 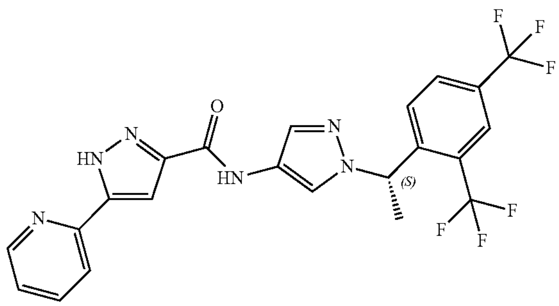 | (S)-N-(1-(1-(2,4-bis(trifluoromethyl)phenyl)ethyl)-1H-pyrazol-4-yl)-5-(pyridin-2-yl)-1H-pyrazole-3-carboxamide |
| 121 | 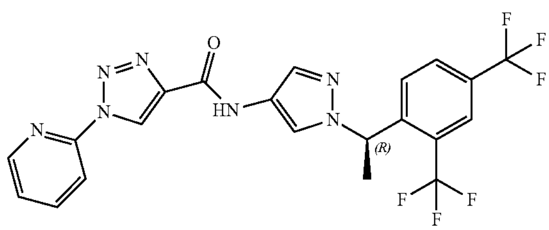 | (R)-N-(1-(1-(2,4-bis(trifluoromethyl)phenyl)ethyl)-1H-pyrazol-4-yl)-1-(pyridin-2-yl)-1H-1,2,3-triazole-4-carboxamide |
| 122 | 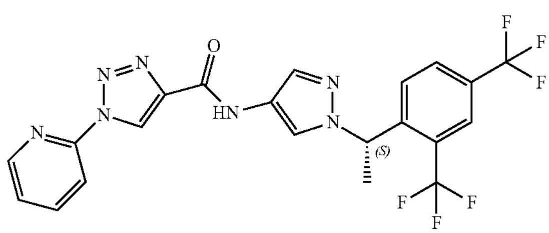 | (S)-N-(1-(1-(2,4-bis(trifluoromethyl)phenyl)ethyl)-1H-pyrazol-4-yl)-1-(pyridin-2-yl)-1H-1,2,3-triazole-4-carboxamide |
| 123 | 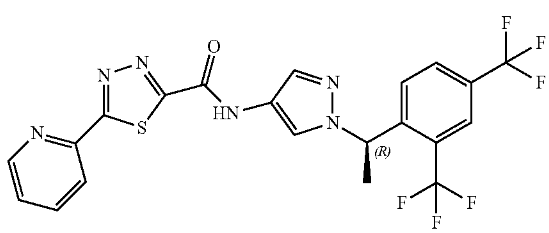 | (R)-N-(1-(1-(2,4-bis(trifluoromethyl)phenyl)ethyl)-1H-pyrazol-4-yl)-5-(pyridin-2-yl)-1,3,4-thiadiazole-2-carboxamide |
| 124 | 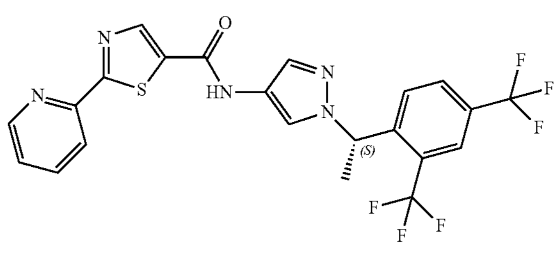 | (S)-N-(1-(1-(2,4-bis(trifluoromethyl)phenyl)ethyl)-1H-pyrazol-4-yl)-5-(pyridin-2-yl)-1,3,4-thiadiazole-2-carboxamide |

TABLE 1-continued

| Cmpd No. | Structure | Chemical Name |
| --- | --- | --- |
| 125 | 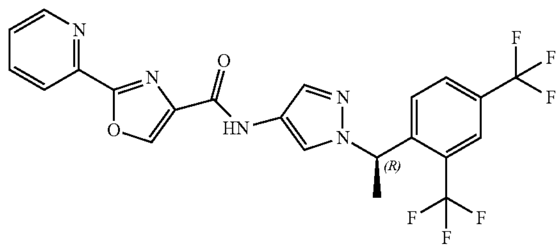 | (R)-N-(1-(1-(2,4-bis(trifluoromethyl)phenyl)ethyl)-1H-pyrazol-4-yl)-2-(pyridin-2-yl)oxazole-4-carboxamide |
| 126 | 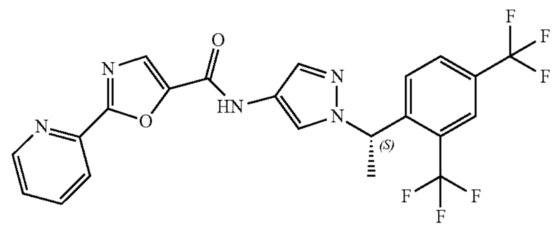 | (S)-N-(1-(1-(2,4-bis(trifluoromethyl)phenyl)ethyl)-1H-pyrazol-4-yl)-2-(pridin-2-yl)oxazole-4-carboxamide |
| 127 | 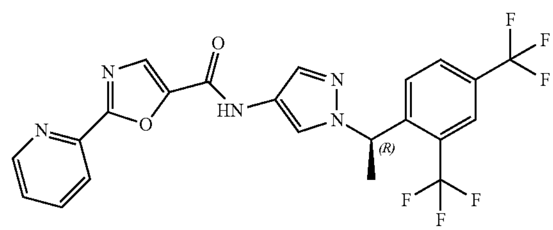 | (R)-N-(1-(1-(2,4-bis(trifluoromethyl)phenyl)ethyl)-1H-pyrazol-4-yl)-2-(pyridin-2-yl)oxazole-5-carboxamide |
| 128 | 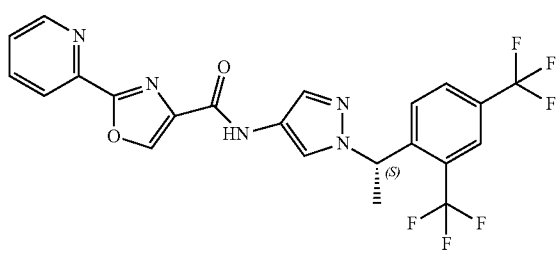 | (S)-N-(1-(1-(2,4-bis(trifluoromethyl)phenyl)-ethyl)-1H-pyrazol-4-yl)-2-(pyridin-2-yl)oxazole-5-carboxamide |
| 129 | 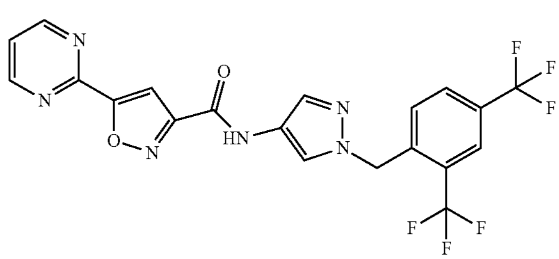 [SMILES: O=C(Nc1cnn(Cc2ccc(C(F)(F)F)cc2C(F)(F)F)c1)c1cc(-c2ncccn2)on1] | N-(1-(2,4-bis(trifluoromethyl)benzyl)-1H-pyrazol-4-yl)-5-(pyrimidin-2-yl)isoxazole-3-carboxamide |
| 130 | 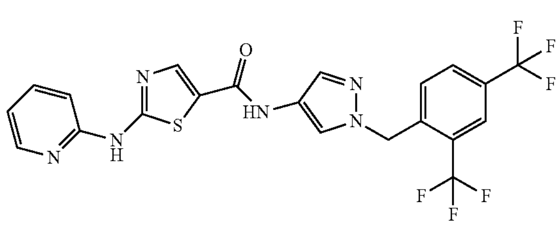 [SMILES: O=C(Nc1cnn(Cc2ccc(C(F)(F)F)cc2C(F)(F)F)c1)c1cnc(Nc2ccccn2)s1] | N-(1-(2,4-bis(trifluoromethyl)benzyl)-1H-pyrazol-4-yl)-2-(pyridin-2-ylamino)thiazole-5-carboxamide |

TABLE 1-continued

| Cmpd No. | Structure | Chemical Name |
|---|---|---|
| 131 | 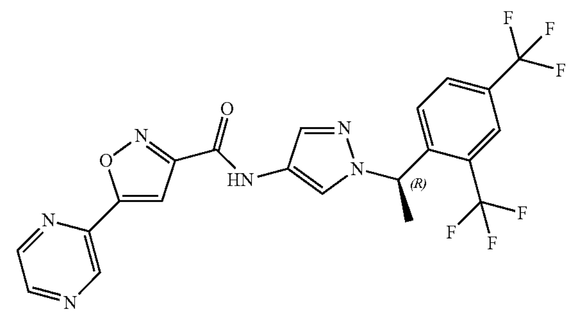 | (R)-N-(1-(1-(2,4-bis(trifluoromethyl)phenyl)ethyl)-1H-pyrazol-4-yl)-5-(pyrazin-2-yl)isoxazole-3-carboxamide |
| 132 | 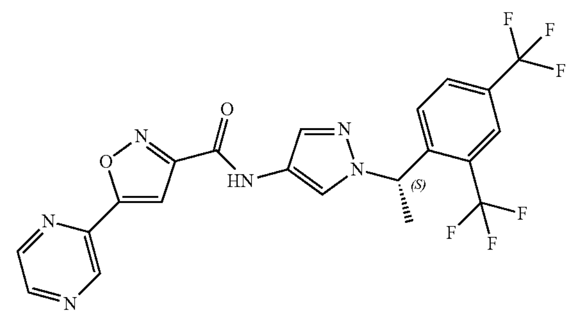 | (S)-N-(1-(1-(2,4-bis(trifluoromethyl)phenyl)ethyl)-1H-pyrazol-4-yl)-5-(pyrazin-2-yl)isoxazole-3-carboxamide |
| 133 | 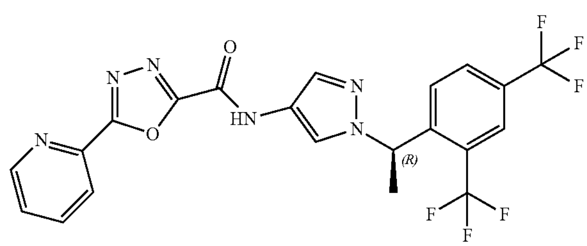 | (R)-N-(1-(1-(2,4-bis(trifluoromethyl)phenyl)ethyl)-1H-pyrazol-4-yl)-5-(pyridin-2-yl)-1,3,4-oxadiazole-2-carboxamide |
| 134 | 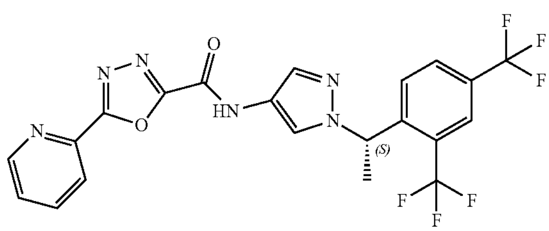 | (S)-N-(1-(1-(2,4-bis(trifluoromethyl)phenyl)ethyl)-1H-pyrazol-4-yl)-5-(pyridin-2-yl)-1,3,4-oxadiazole-2-carboxamide |
| 135 | 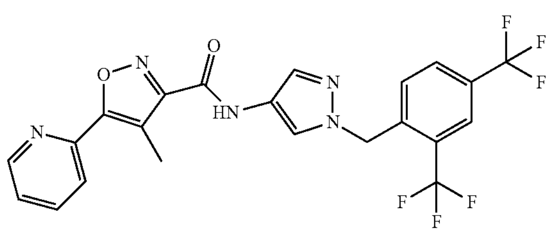 [SMILES: Cc1c(C(=O)Nc2cnn(Cc3ccc(C(F)(F)F)cc3C(F)(F)F)c2)noc1-c1ccccn1] | N-(1-(2,4-bis(trifluoromethyl)benzyl)-1H-pyrazol-4-yl)-4-methyl-5-(pyridin-2-yl)isoxazole-3-carboxamide |
| 136 | 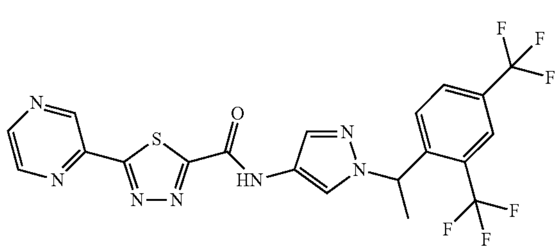 [SMILES: CC(c1ccc(C(F)(F)F)cc1C(F)(F)F)n1cc(NC(=O)c2nnc(-c3cnccn3)s2)cn1] | N-(1-(1-(2,4-bis(trifluoromethyl)phenyl)ethyl)-1H-pyrazol-4-yl)-5-(pyrazin-2-yl)-1,3,4-thiadiazol-2-carboxamide |

TABLE 1-continued

| Cmpd No. | Structure | Chemical Name |
|---|---|---|
| 137 | 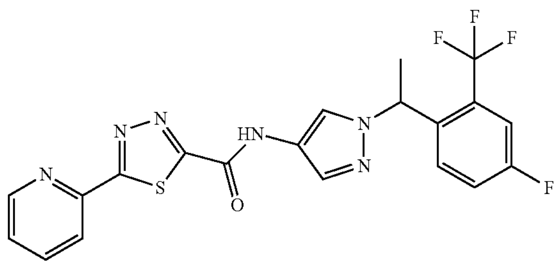 [SMILES: CC(c1ccc(F)cc1C(F)(F)F)n1cc(NC(=O)c2nnc(-c3ccccn3)s2)cn1] | N-(1-(1-(4-fluoro-2-(trifluoromethyl)phenyl)ethyl)-1H-pyrazol-4-yl)-5-(pyridin-2-yl)-1,3,4-thiadiazole-2-carboxamide |
| 138 | 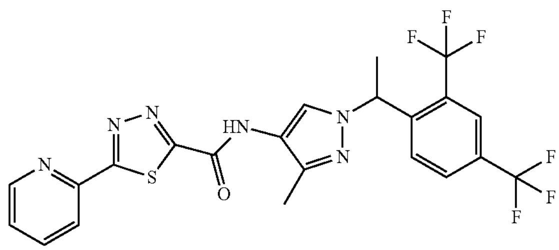 [SMILES: Cc1nn(C(C)c2ccc(C(F)(F)F)cc2C(F)(F)F)cc1NC(=O)c1nnc(-c2ccccn2)s1] | N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide |
| 139 | 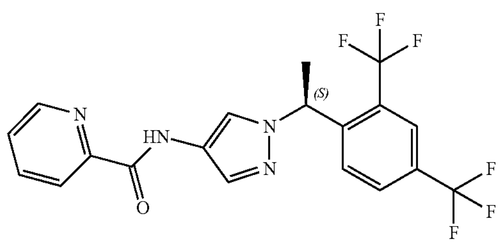 | (S)-N-(1-(1-(2,4-bis(trifluoromethyl)phenyl)ethyl)-1H-pyrazol-4-yl)picolinamide |
| 140 | 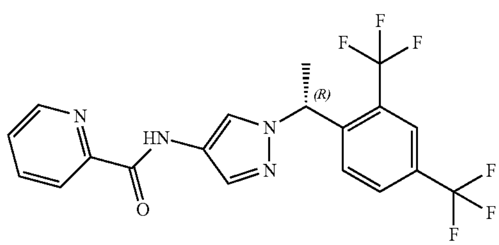 | (R)-N-(1-(1-2,4-bis(trifluoromethyl)phenyl)ethyl)-1H-pyrazol-4-yl)picolinamide |
| 141 | 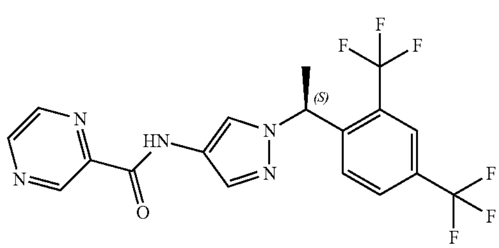 | (S)-N-(1-(1-(2,4-bis(trifluoromethyl)phenyl)ethyl)-1H-pyrazol-4-yl)pyrazine-2-carboxamide |
| 142 | 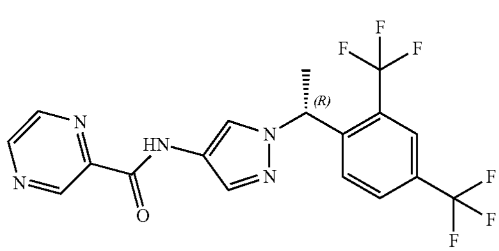 | (R)-N-(1-(1-(2,4-bis(trifluoromethyl)phenyl)ethyl)-1H-pyrazol-4-yl)pyrazine-2-carboxamide |

TABLE 1-continued

| Cmpd No. | Chemical Name |
|---|---|
| 143 | N-(1-(2,3-dihydro-1H-inden-1-yl)-1H-pyrazol-4-yl)-5-(pyridin-2-yl)isoxazole-3-carboxamide |
| 144 | N-(1-(2,3-dihydro-1H-inden-1-yl)-1H-pyrazol-4-yl)-5-(furan-2-yl)-1,3,4-thiadiazole-2-carboxamide |
| 145 | N-(1-(2,6-dichlorobenzyl)-1H-pyrazol-4-yl)-5-(pyridin-2-yl)-1,3,4-thiadiazole-2-carboxamide |
| 146 | N-(1-(2,6-dichlorobenzyl)-1H-pyrazol-4-yl)-5-(pyridin-2-yl)isoxazole-3-carboxamide |
| 147 | N-(1-(2,6-dichlorobenzyl)-1H-pyrazol-4-yl)-2-(furan-2-yl)thiazole-5-carboxamide |
| 148 | N-(1-(2,6-dichlorobenzyl)-1H-pyrazol-4-yl)-5-(furan-2-yl)-1,3,4-thiadiazole-2-carboxamide |
| 149 | (R)-N-(1-(2,3-dihydro-1H-inden-1-yl)-1H-pyrazol-4-yl)-5-(furan-2-yl)isoxazole-3-carboxamide |

TABLE 1-continued

| Cmpd No. | Structure | Chemical Name |
|---|---|---|
| 150 | 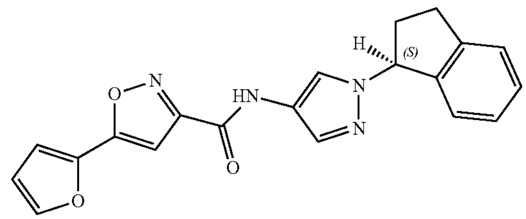 | (S)-N-(1-(2,3-dihydro-1H-inden-1-yl)-1H-pyrazol-4-yl)-5-(furan-2-yl)isoxazole-3-carboxamide |
| 151 | 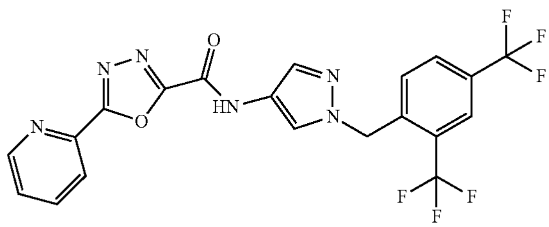 [SMILES: O=C(Nc1cnn(Cc2ccc(C(F)(F)F)cc2C(F)(F)F)c1)c1nnc(-c2ccccn2)o1] | N-(1-(2,4-bis(trifluoromethyl)benzyl)-1H-pyrazol-4-yl)-5-(pyridin-2-yl)-1,3,4-oxadiazole-2-carboxamide |
| 152 | 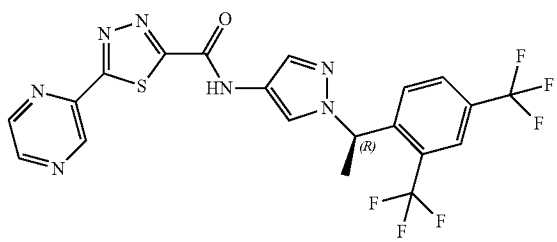 | (R)-N-(1-(1-(2,4-bis(trifluoromethyl)phenyl)ethyl)-1H-pyrazol-4-yl)-5-(pyrazin-2-yl)-1,3,4-thiadiazole-2-carboxamide |
| 153 | 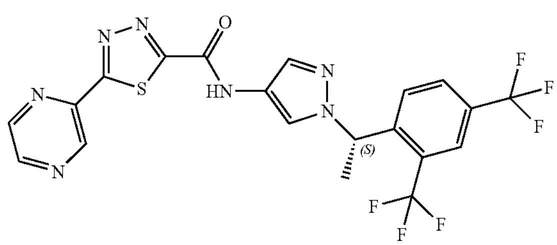 | (S)-N-(1-(1-(2,4-bis(trifluoromethyl)phenyl)ethyl)-1H-pyrazol-4-yl)-5-(pyrazin-2-yl)-1,3,4-thiadiazole-2-carboxamide |
| 154 | 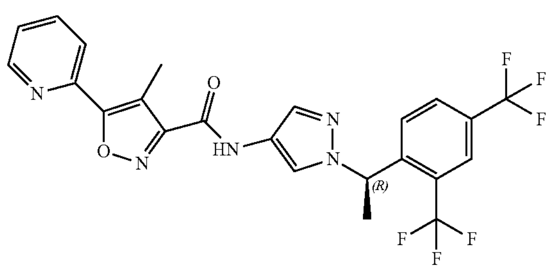 | (R)-N-(1-(1-(2,4-bis(trifluoromethyl)phenyl)ethyl)-1H-pyrazol-4-yl)-4-methyl-5-(pyridin-2-yl)isoxazole-3-carboxamide |
| 155 | 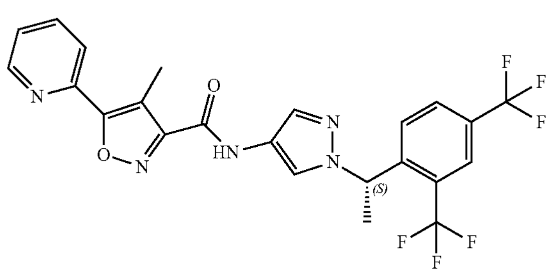 | (S)-N-(1-(1-(2,4-bis(trifluoromethyl)phenyl)ethyl)-1H-pyrazol-4-yl)-4-methyl-5-(pyridin-2-yl)isoxazole-3-carboxamide |

TABLE 1-continued

| Cmpd No. | Structure | Chemical Name |
|---|---|---|
| 156 | 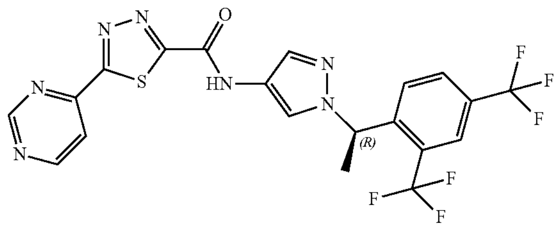 | (R)-N-(1-(1-(2,4-bis(trifluorornethyl)phenyl)ethyl)-1H-pyrazol-4-yl)-5-(pyrimidin-4-yl)-1,3,4-thiadiazol-2-carboxamide |
| 157 | 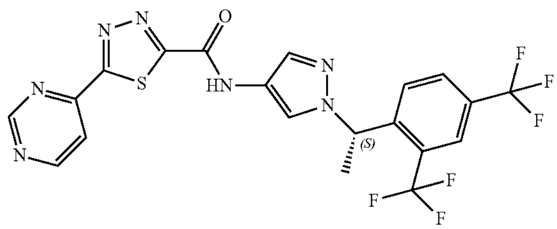 | (S)-N-(1-(1-(2,4-bis(trifluoromethyl)phenyl)ethyl)-1H-pyrazol-4-yl)-5-(pyrimidin-4-yl)-1,3,4-thiadiazole-2-carboxamide |
| 158 | 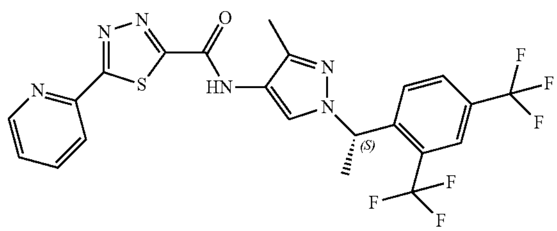 | (S)-N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide |
| 159 | 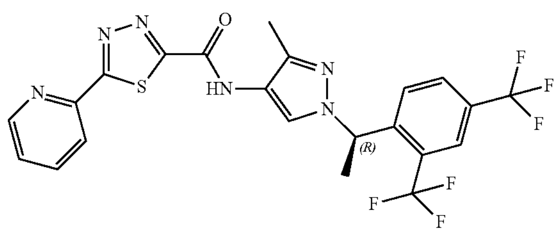 | (R)-N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide |
| 160 | 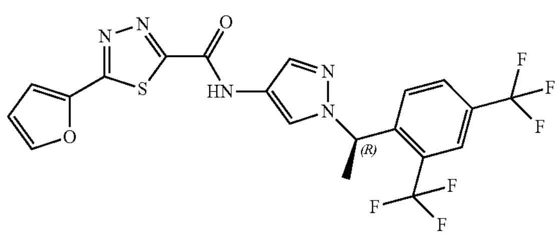 | (R)-N-(1-(1-(2,4-bis(trifluoromethyl)phenyl)ethyl)-1H-pyrazol-4-yl)-5-(furan-2-yl)-1,3,4-thiadiazol-2-carboxamide |
| 161 | 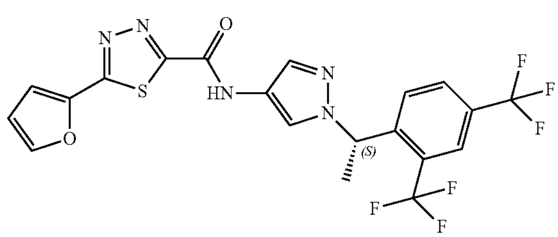 | (S)-N-(1-(1-(2,4-bis(trifluoromethyl)phenyl)ethyl)-1H-pyrazol-4-yl)-5-(furan-2-yl)-1,3,4-thiadiazole-2-carboxamide |

In some embodiments, provided herein are compounds described in Table 1, or a pharmaceutically acceptable salt thereof, and uses thereof.

The embodiments and variations described herein are suitable for compounds of any formulae detailed herein, where applicable.

Provided herein is a compound selected from the group consisting of:

N-(1-(1-(2,4-bis(trifluoromethyl)phenyl)propyl)-1H-pyrazol-4-yl)-5-(pyridin-2-yl)isoxazole-3-carboxamide;

N-(1-(2,4-bis(trifluoromethyl)benzyl)-1H-pyrazol-4-yl)-5-(2-hydroxypropan-2-yl)isoxazole-3-carboxamide;

5-acetyl-N-(1-(2,4-bis(trifluoromethyl)benzyl)-1H-pyrazol-4-yl)isoxazole-3-carboxamide N-(1-(2,4-bis(trifluoromethyl)benzyl)-1H-pyrazol-4-yl)-3-(3-fluorophenyl)-1,2,4-oxadiazole-5-carboxamide;

N-(1-(1-(2,4-bis(trifluoromethyl)phenyl)ethyl)-1H-pyrazol-4-yl)-5-(pyridin-2-yl) isoxazole-3-carboxamide;

N-(1-(1-(2,4-bis(trifluoromethyl)phenyl)ethyl)-1H-pyrazol-4-yl)-5-(furan-2-yl)isoxazole-3-carboxamide;

N-(1-(1-(2,4-bis(trifluoromethyl)phenyl)ethyl)-1H-pyrazol-4-yl)-5-(furan-2-yl)isoxazole-3-carboxamide;

N-(1-(2,4-bis(trifluoromethyl)benzyl)-1H-pyrazol-4-yl)-5-(pyridin-4-yl)isoxazole-3-carboxamide;

N-(1-(2,4-bis(trifluoromethyl)benzyl)-1H-pyrazol-4-yl)-5-(pyridin-2-yl)isoxazole-3-carboxamide;

N-(1-{1-[2,4-bis(trifluoromethyl)phenyl]ethyl}-1H-pyrazol-4-yl)-5-(furan-2-yl) isoxazole-3-carboxamide;

N-{1-[2,4-bis(trifluoromethyl)benzyl]-1H-pyrazol-4-yl}-5-tert-butyl-1,2-oxazole-3-carboxamide;

N-(1-(2,4-bis(trifluoromethyl)benzyl)-1H-pyrazol-4-yl)-5-(thiophen-2-yl)isoxazole-3-carboxamide;

N-(1-(2,4-bis(trifluoromethyl)benzyl)-1H-pyrazol-4-yl)-[3,3'-bipyridine]-5-carboxamide;

N-(1-(2,4-bis(trifluoromethyl)benzyl)-1H-pyrazol-4-yl)-5-(2,4-difluorophenyl)isoxazole-3-carboxamide;

N-(1-(2,4-bis(trifluoromethyl)benzyl)-1H-imidazol-4-yl)-5-(furan-2-yl)isoxazole-3-carboxamide;

N-(1-(2, 3-dihydro-1H-inden-2-yl)-1H-pyrazol-4-yl)-5-(furan-2-yl) isoxazole-3-carboxamide;

N-(1-(2, 3-dihydro-1H-inden-1-yl)-1H-pyrazol-4-yl)-5-(furan-2-yl) isoxazole-3-carboxamide;

N-(1-(2,4-bis(trifluoromethyl)benzyl)-1H-pyrazol-4-yl)-5-(4 fluorophenyl)nicotinamide;

N-(1-(2,4-bis(trifluoromethyl)benzyl)-1H-pyrazol-4-yl)-5-phenylnicotinamide;

N-(1-(2,4-bis(trifluoromethyl)benzyl)-1H-pyrazol-4-yl)-5-(5-methylfuran-2-yl)isoxazole-3-carboxamide;

N-(1-(2,4-bis(trifluoromethyl)benzyl)-1H-pyrazol-4-yl) isoxazole-3-carboxamide;

N-(1-(2, 6-dichlorobenzyl)-1H-pyrazol-4-yl)-5-(furan-2-yl) isoxazole-3-carboxamide; N-(1-(4-cyanobenzyl)-1H-pyrazol-4-yl)-5-(furan-2-yl)isoxazole-3-carboxamide;

N-(1-(4-cyano-3-(trifluoromethyl)benzyl)-1H-pyrazol-4-yl)-5-(furan-2-yl)isoxazole-3-carboxamide;

N-(1-(2,4-bis(trifluoromethyl)phenyl)-1H-pyrazol-4-yl)-5-(furan-2-yl)isoxazole-3-carboxamide;

N-(1-(3,5-bis(trifluoromethyl)benzyl)-1H-pyrazole-4-yl)-5-(furan-2-yl)isoxazole-3-carboxamide;

N-(1-(2,4-bis(trifluoromethyl)benzyl)-3-methyl-1H-pyrazol-4-yl)-5-(pyridin-2-yl)isoxazole-3-carboxamide;

N-(1-(2,4-bis(trifluoromethyl)benzyl)-5-methyl-1H-pyrazol-4-yl)-5-(pyridin-2-yl)isoxazole-3-carboxamide;

N-(1-(2,4-bis(trifluoromethyl)benzyl)-1H-pyrazol-4-yl)-5-(3-chloropyridin-2-yl)isoxazole-3-carboxamide;

N-(1-(1-(2,4-bis(trifluoromethyl)phenyl)ethyl)-1H-pyrazol-4-yl)-5-(3-chloropyridin-2-yl)isoxazole-3-carboxamide;

N-(1-((2,4-bis(trifluoromethyl)phenyl)(cyclopropyl)methyl)-1H-pyrazol-4-yl)-5-(pyridin-2-yl)isoxazole-3-carboxamide;

N-(1-(1-(2,4-bis(trifluoromethyl)phenyl)ethyl)-1H-pyrazol-4-yl)-5-(3-chloropyridin-2-yl)isoxazole-3-carboxamide;

N-(1-(1-(2,4-bis(trifluoromethyl)phenyl)ethyl)-1H-pyrazol-4-yl)-5-(pyridin-3-yl)isoxazole-3-carboxamide;

N-(1-(2,4-bis(trifluoromethyl)benzyl)-5-methyl-1H-pyrazol-4-yl)-5-(furan-2-yl)isoxazole-3-carboxamide;

N-(1-(1-(2,4-bis(trifluoromethyl)phenyl)ethyl)-5-methyl-1H-pyrazol-4-yl)-5-(furan-2-yl)isoxazole-3-carboxamide;

N-(1-(2,4-bis(trifluoromethyl)phenyl)-5-methyl-1H-pyrazol-4-yl)-5-(furan-2-yl)isoxazole-3-carboxamide;

N-(1-(2,4-bis(trifluoromethyl)benzyl)-3-methyl-1H-pyrazol-4-yl)-5-(furan-2-yl)isoxazole-3-carboxamide;

N-(1-(1-(2,4-bis(trifluoromethyl)phenyl)ethyl)-3-methyl-1H-pyrazol-4-yl)-5-(furan-2-yl)isoxazole-3-carboxamide;

N-(1-(2,4-bis(trifluoromethyl)benzyl)-1H-pyrazol-4-yl)-5-(furan-2-yl)nicotinamide;

N-(1-(1-(2,4-bis(trifluoromethyl)phenyl)ethyl)-1H-pyrazol-4-yl)-5-(furan-2-yl)nicotinamide;

N-(1-(2,4-bis(trifluoromethyl)phenyl)-1H-pyrazol-4-yl)-5-(furan-2-yl)nicotinamide;

N-(1-(2,4-bis(trifluoromethyl)benzyl)-5-methyl-1H-pyrazol-4-yl)-5-(furan-2-yl)nicotinamide;

N-(1-(2,4-bis(trifluoromethyl)benzyl)-3-methyl-1H-pyrazol-4-yl)-5-(furan-2-yl)nicotinamide;

N-(1-(2,4-bis(trifluoromethyl)phenyl)-3-methyl-1H-pyrazol-4-yl)-5-(furan-2-yl)isoxazole-3-carboxamide;

N-(1-(2,4-bis(trifluoromethyl)benzyl)-5-methyl-1H-pyrazol-4-yl)-5-(furan-2-yl)nicotinamide;

N-(1-(1-(2,4-bis(trifluoromethyl)phenyl)ethyl)-5-methyl-1H-pyrazol-4-yl)-5-(furan-2-yl)nicotinamide;

N-(1-(1-(2,4-bis(trifluoromethyl)phenyl)ethyl)-3-methyl-1H-pyrazol-4-yl)-5-(furan-2-yl)nicotinamide;

N-(1-(2,4-bis(trifluoromethyl)phenyl)-3-methyl-1H-pyrazol-4-yl)-5-(furan-2-yl)nicotinamide;

N-(1-(1-(2,4-bis(trifluoromethyl)phenyl)ethyl)-1H-pyrazol-4-yl)-3-(furan-2-yl)acrylamide;

N-(1-(2,4-bis(trifluoromethyl)phenyl)-1H-pyrazol-4-yl)-3-(furan-2-yl)acrylamide;

N-(1-(2,4-bis(trifluoromethyl)benzyl)-5-methyl-1H-pyrazol-4-yl)-3-(furan-2-yl)acrylamide;

N-(1-(1-(2,4-bis(trifluoromethyl)phenyl)ethyl)-5-methyl-1H-pyrazol-4-yl)-3-(furan-2-yl)acrylamide;

N-(1-(2,4-bis(trifluoromethyl)phenyl)-5-methyl-1H-pyrazol-4-yl)-3-(furan-2-yl)acrylamide;

N-(1-(2,4-bis(trifluoromethyl)benzyl)-3-methyl-1H-pyrazol-4-yl)-3-(furan-2-yl)acrylamide;

N-(1-(1-(2,4-bis(trifluoromethyl)phenyl)ethyl)-3-methyl-1H-pyrazol-4-yl)-3-(furan-2-yl)acrylamide N-(1-(2,4-bis(trifluoromethyl)phenyl)-3-methyl-1H-pyrazol-4-yl)-3-(furan-2-yl)acrylamide;

N-(1-(2,4-bis(trifluoromethyl)phenyl)-1H-pyrazol-4-yl)-5-(pyridin-2-yl)isoxazole-3-carboxamide;

N-(1-(1-(2,4-bis(trifluoromethyl)phenyl)ethyl)-5-methyl-1H-pyrazol-4-yl)-5-(pyridin-2-yl)isoxazole-3-carboxamide;

N-(1-(2,4-bis(trifluoromethyl)phenyl)-5-methyl-1H-pyrazol-4-yl)-5-(pyridin-2-yl)isoxazole-3-carboxamide;

N-(1-(1-(2,4-bis(trifluoromethyl)phenyl)ethyl)-3-methyl-1H-pyrazol-4-yl)-5-(pyridin-2-yl)isoxazole-3-carboxamide;

N-(1-(2,4-bis(trifluoromethyl)phenyl)-3-methyl-1H-pyrazol-4-yl)-5-(pyridin-2-yl)isoxazole-3-carboxamide;

N-(1-(1-(2,4-bis(trifluoromethyl)phenyl)ethyl)-1H-pyrazol-4-yl)-[2,3'-bipyridine]-5'-carboxamide;

N-(1-(2,4-bis(trifluoromethyl)phenyl)-1H-pyrazol-4-yl)-[2,3'-bipyridine]-5'-carboxamide;

N-(1-(2,4-bis(trifluoromethyl)benzyl)-5-methyl-1H-pyrazol-4-yl)-[2,3'-bipyridine]-5'-carboxamide;

N-(1-(1-(2,4-bis(trifluoromethyl)phenyl)ethyl)-5-methyl-1H-pyrazol-4-yl)-[2,3'-bipyridine]-5'-carboxamide;

N-(1-(2,4-bis(trifluoromethyl)phenyl)-5-methyl-1H-pyrazol-4-yl)-[2,3'-bipyridine]-5'-carboxamide;

N-(1-(2,4-bis(trifluoromethyl)benzyl)-3-methyl-1H-pyrazol-4-yl)-[2,3'-bipyridine]-5'-carboxamide;

N-(1-(1-(2,4-bis(trifluoromethyl)phenyl)ethyl)-3-methyl-1H-pyrazol-4-yl)-[2,3'-bipyridine]-5'-carboxamide;
N-(1-(2,4-bis(trifluoromethyl)phenyl)-3-methyl-1H-pyrazol-4-yl)-[2,3'-bipyridine]-5'-carboxamide;
N-(1-(2,4-bis(trifluoromethyl)phenyl)-1H-pyrazol-4-yl)-5-(thiophen-2-yl)isoxazole-3-carboxamide;
N-(1-(2,4-bis(trifluoromethyl)benzyl)-5-methyl-1H-pyrazol-4-yl)-5-(thiophen-2-yl)isoxazole-3-carboxamide;
N-(1-(1-(2,4-bis(trifluoromethyl)phenyl)ethyl)-1H-pyrazol-4-yl)-3-(pyridin-2-yl)isoxazole-5-carboxamide;
N-(1-(1-(2,4-bis(trifluoromethyl)phenyl)ethyl)-1H-pyrazol-4-yl)-2-(pyridin-2-yl)thiazole-5-carboxamide;
N-(1-(1-(2,4-bis(trifluoromethyl)phenyl)ethyl)-1H-pyrazol-4-yl)-2-(pyridin-2-yl)thiazole-4-carboxamide;
N-(1-(1-(2,4-bis(trifluoromethyl)phenyl)ethyl)-1H-pyrazol-4-yl)-2-(furan-2-yl)thiazole-5-carboxamide;
N-(1-(1-(2,4-bis(trifluoromethyl)phenyl)ethyl)-1H-pyrazol-4-yl)-[2,4'-bipyridine]-2'-carboxamide;
N-(1-(1-(2,4-bis(trifluoromethyl)phenyl)ethyl)-1H-pyrazol-4-yl)-[2,3'-bipyridine]-6'-carboxamide;
N-(1-(1-(2,4-bis(trifluoromethyl)phenyl)ethyl)-1H-pyrazol-4-yl)-3-(pyridin-2-yl)acrylamide;
N-(1-(2,4-bis(trifluoromethyl)benzyl)-1H-pyrazol-4-yl)-3-(furan-2-yl)acrylamide;
N-(1-(1-(2,4-bis(trifluoromethyl)phenyl)ethyl)-1H-pyrazol-4-yl)-3-(furan-2-yl)acrylamide;
N-(1-(2,4-bis(trifluoromethyl)phenyl)-3-methyl-1H-pyrazol-4-yl)-3-(furan-2-yl)acrylamide;
N-(1-(1-(2,4-bis(trifluoromethyl)phenyl)ethyl)-1H-pyrazol-4-yl)-5-(2-methoxyphenyl)isoxazole-3-carboxamide;
N-(1-(2,4-bis(trifluoromethyl)phenyl)-3-methyl-1H-pyrazol-4-yl)-5-(pyridin-2-yl)isoxazole-3-carboxamide;
N-(1-(2,4-bis(trifluoromethyl)benzyl)-1H-pyrazol-4-yl)-5-(2-methoxyphenyl)isoxazole-3-carboxamide;
N-(1-(2,4-bis(trifluoromethyl)benzyl)-3-methyl-1H-pyrazol-4-yl)-5-(furan-2-yl)isoxazole-3-carboxamide;
N-(1-(2,4-bis(trifluoromethyl)benzyl)-5-methyl-1H-pyrazol-4-yl)-5-(furan-2-yl)isoxazole-3-carboxamide;
N-(1-(2,4-bis(trifluoromethyl)phenyl)-3-methyl-1H-pyrazol-4-yl)-5-(furan-2-yl)isoxazole-3-carboxamide;
N-(1-(2,4-bis(trifluoromethyl)benzyl)-5-methyl-1H-pyrazol-4-yl)-3-(furan-2-yl)acrylamide;
N-(1-(2,4-bis(trifluoromethyl)benzyl)-3-methyl-1H-pyrazol-4-yl)-3-(furan-2-yl)acrylamide;
N-(1-(1-(2,4-bis(trifluoromethyl)phenyl)ethyl)-5-methyl-1H-pyrazol-4-yl)-5-(pyridin-2-yl)isoxazole-3-carboxamide;
N-(1-(1-(2,4-bis(trifluoromethyl)phenyl)ethyl)-3-methyl-1H-pyrazol-4-yl)-5-(pyridin-2-yl)isoxazole-3-carboxamide;
N-(1-(1-(2,4-bis(trifluoromethyl)phenyl)ethyl)-1H-pyrazol-4-yl)-5-(pyrimidin-2-yl)isoxazole-3-carboxamide;
N-(1-(2,4-bis(trifluoromethyl)benzyl)-1H-pyrazol-4-yl)-N-methyl-5-(pyridin-2-yl)isoxazole-3-carboxamide;
N-(1-(1-(2,4-bis(trifluoromethyl)phenyl)ethyl)-1H-pyrazol-4-yl)-2-(pyridin-2-yl)thiazole-5-carboxamide;
N-(1-(1-(2,4-bis(trifluoromethyl)phenyl)ethyl)-1H-pyrazol-4-yl)-4-methyl-2-(pyridin-2-yl)thiazole-5-carboxamide;
N-(1-(1-(2-fluoro-4-(trifluoromethyl)phenyl)ethyl)-1H-pyrazol-4-yl)-5-(pyridin-2-yl)isoxazole-3-carboxamide;
N-(1-(1-(4-fluoro-2-(trifluoromethyl)phenyl)ethyl)-1H-pyrazol-4-yl)-5-(pyridin-2-yl)isoxazole-3-carboxamide;
N-(1-(1-(2,4-bis(trifluoromethyl)phenyl)ethyl)-1H-pyrazol-4-yl)-1-methyl-3-(pyridin-2-yl)-1H-pyrazole-5-carboxamide;
N-(1-(1-(2,4-bis(trifluoromethyl)phenyl)ethyl)-1H-pyrazol-4-yl)-1-methyl-5-(pyridin-2-yl)-1H-pyrazole-3-carboxamide;
N-(1-(2,4-bis(trifluoromethyl)benzyl)-1H-pyrazol-4-yl)-5-(pyrazin-2-yl)isoxazole-3-carboxamide;
N-(1-(2,4-bis(trifluoromethyl)benzyl)-1H-pyrazol-4-yl)-5-(6-methylpyridin-2-yl)isoxazole-3-carboxamide;
N-(1-(1-(2,4-bis(trifluoromethyl)phenyl)ethyl)-1H-pyrazol-4-yl)-5-(6-methylpyridin-2-yl)isoxazole-3-carboxamide;
N-(1-(2,4-bis(trifluoromethyl)benzyl)-1H-pyrazol-4-yl)-2-(pyridin-2-yl)thiazole-5-carboxamide;
N-(1-(1-(2,4-bis(trifluoromethyl)phenyl)ethyl)-1H-pyrazol-4-yl)-5-(pyridin-2-yl)-1H-pyrazole-3-carboxamide;
N-(1-(1-(2,4-bis(trifluoromethyl)phenyl)ethyl)-1H-pyrazol-4-yl)-1-(pyridin-2-yl)-1H-1,2,3-triazole-4-carboxamide;
N-(1-(1-(2,4-bis(trifluoromethyl)phenyl)ethyl)-1H-pyrazol-4-yl)-5-(pyridin-2-yl)-1,3,4-thiadiazole-2-carboxamide;
N-(1-(1-(2,4-bis(trifluoromethyl)phenyl)ethyl)-1H-pyrazol-4-yl)-2-(pyridin-2-yl)oxazole-4-carboxamide;
N-(1-(1-(2,4-bis(trifluoromethyl)phenyl)ethyl)-1H-pyrazol-4-yl)-2-(pyridin-2-yl)oxazole-5-carboxamide;
N-(1-(2,4-bis(trifluoromethyl)benzyl)-1H-pyrazol-4-yl)-5-(pyrimidin-2-yl)isoxazole-3-carboxamide;
N-(1-(2,4-bis(trifluoromethyl)benzyl)-1H-pyrazol-4-yl)-2-(pyridin-2-ylamino)thiazole-5-carboxamide;
N-(1-(1-(2,4-bis(trifluoromethyl)phenyl)ethyl)-1H-pyrazol-4-yl)-5-(pyrazin-2-yl)isoxazole-3-carboxamide;
N-(1-(1-(2,4-bis(trifluoromethyl)phenyl)ethyl)-1H-pyrazol-4-yl)-5-(pyridin-2-yl)-1,3,4-oxadiazole-2-carboxamide;
N-(1-(2,4-bis(trifluoromethyl)benzyl)-1H-pyrazol-4-yl)-4-methyl-5-(pyridin-2-yl)isoxazole-3-carboxamide;
N-(1-(1-(2,4-bis(trifluoromethyl)phenyl)ethyl)-1H-pyrazol-4-yl)-5-(pyrazin-2-yl)-1,3,4-thiadiazole-2-carboxamide;
N-(1-(1-(4-fluoro-2-(trifluoromethyl)phenyl)ethyl)-1H-pyrazol-4-yl)-5-(pyridin-2-yl)-1,3,4-thiadiazole-2-carboxamide;
N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide;
N-(1-(1-(2,4-bis(trifluoromethyl)phenyl)ethyl)-1H-pyrazol-4-yl)picolinamide;
N-(1-(1-(2,4-bis(trifluoromethyl)phenyl)ethyl)-1H-pyrazol-4-yl)pyrazine-2-carboxamide;
N-(1-(2,3-dihydro-1H-inden-1-yl)-1H-pyrazol-4-yl)-5-(pyridin-2-yl)isoxazole-3-carboxamide;
N-(1-(2,3-dihydro-1H-inden-1-yl)-1H-pyrazol-4-yl)-5-(furan-2-yl)-1,3,4-thiadiazole-2-carboxamide;
N-(1-(2,6-dichlorobenzyl)-1H-pyrazol-4-yl)-5-(pyridin-2-yl)-1,3,4-thiadiazole-2-carboxamide;
N-(1-(2,6-dichlorobenzyl)-1H-pyrazol-4-yl)-5-(pyridin-2-yl)isoxazole-3-carboxamide;
N-(1-(2,6-dichlorobenzyl)-1H-pyrazol-4-yl)-2-(furan-2-yl)thiazole-5-carboxamide;
N-(1-(2,6-dichlorobenzyl)-1H-pyrazol-4-yl)-5-(furan-2-yl)-1,3,4-thiadiazole-2-carboxamide;
N-(1-(2,3-dihydro-1H-inden-1-yl)-1H-pyrazol-4-yl)-5-(furan-2-yl)isoxazole-3-carboxamide;
N-(1-(2,4-bis(trifluoromethyl)benzyl)-1H-pyrazol-4-yl)-5-(pyridin-2-yl)-1,3,4-oxadiazole-2-carboxamide;
N-(1-(1-(2,4-bis(trifluoromethyl)phenyl)ethyl)-1H-pyrazol-4-yl)-5-(pyrazin-2-yl)-1,3,4-thiadiazole-2-carboxamide;
N-(1-(1-(2,4-bis(trifluoromethyl)phenyl)ethyl)-1H-pyrazol-4-yl)-4-methyl-5-(pyridin-2-yl)isoxazole-3-carboxamide;
N-(1-(1-(2,4-bis(trifluoromethyl)phenyl)ethyl)-1H-pyrazol-4-yl)-5-(pyrimidin-4-yl)-1,3,4-thiadiazole-2-carboxamide;

N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide; and N-(1-(1-(2,4-bis(trifluoromethyl)phenyl)ethyl)-1H-pyrazol-4-yl)-5-(furan-2-yl)-1,3,4-thiadiazole-2-carboxamide, or a pharmaceutically acceptable salt thereof. Also provided herein are, where applicable, any and all stereoisomers of the compounds depicted herein, including geometric isomers (e.g., cis/trans isomers or E/Z isomers), enantiomers, diastereomers, or mixtures thereof in any ratio, including racemic mixtures.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. Compounds of any formula given herein may have asymmetric centers and therefore exist in different enantiomeric or diastereomeric forms. All optical isomers and stereoisomers of the compounds of the general formula, and mixtures thereof in any ratio, are considered within the scope of the formula. Thus, any formula given herein is intended to represent a racemate, one or more enantiomeric forms, one or more diastereomeric forms, one or more atropisomeric forms, and mixtures thereof in any ratio. Where a compound of Table 1 is depicted with a particular stereochemical configuration, also provided herein is any alternative stereochemical configuration of the compound, as well as a mixture of stereoisomers of the compound in any ratio. For example, where a compound of Table 1 has a stereocenter that is in an "S" stereochemical configuration, also provided herein is the enantiomer of the compound wherein that stereocenter is in an "R" stereochemical configuration. Likewise, when a compound of Table 1 has a stereocenter that is in an "R" configuration, also provided herein is enantiomer of the compound in an "S" stereochemical configuration. Also provided are mixtures of the compound with both the "S" and the "R" stereochemical configuration. Furthermore, certain structures may exist as geometric isomers (i.e., cis and trans isomers), as tautomers, or as atropisomers. For example, compounds of any formula given herein may contain bonds with restricted rotation and therefore exist in different geometric configurations. Where a compound of Table 1 is depicted as a particular geometric isomer (e.g., E or Z isomer, or cis or trans isomer), also provided herein is any alternative geometric configuration of the compound, as well as a mixture of geometric isomers of the compound in any ratio. For example, where a compound of Table 1 is depicted as a "Z" isomer, also provided herein is the "E" isomer of the compound. Likewise, where a compound of Table 1 is depicted as an "E" isomer, also provided herein is the "Z" isomer of the compound. Also provided are mixtures of the compound with both the "E" and the "Z" stereochemical configuration, wherein the mixtures are in any ratio. Similarly, where a compound of Table 1 is depicted as a "cis" isomer, also provided herein is the "trans" isomer of the compound; and where a compound is depicted as a "trans" isomer, also provided herein is the "cis" isomer of the compound. Also provided are mixtures of the compound with both the "cis" and the "trans" stereochemical configuration, wherein the mixtures are in any ratio. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$, $^{13}N$, $^{15}O$, $^{17}O$, $^{32}P$, $^{35}S$, $^{36}Cl$. Certain isotope labeled compounds (e.g. $^{3}H$ and $^{14}C$) are useful in compound or substrate tissue distribution study. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, I.V. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate In some embodiments, compounds of the Formula (I) may be synthesized according to Scheme 1.

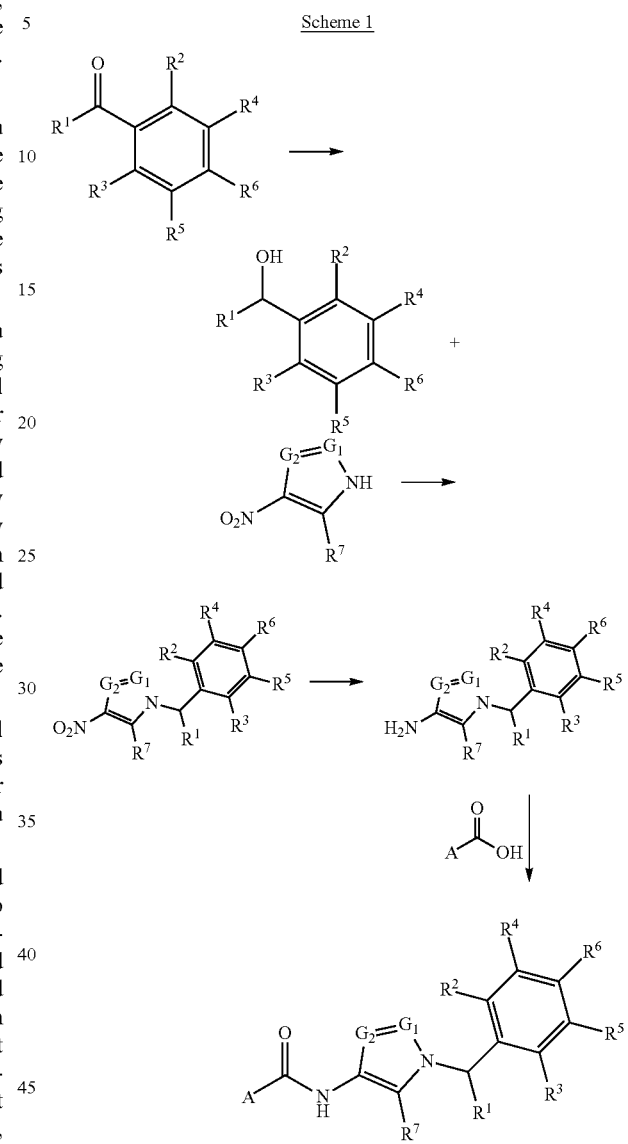

wherein $R^1$, $R^2$, $R^3$, $R^4$, $R^5$, $R^6$, $R^7$, $G_1$, $G_2$, and A are as defined for Formula (A), (I), or any variation thereof detailed herein.

An exemplary embodiment of the preparative method in Scheme 1 is shown in Scheme 1a.

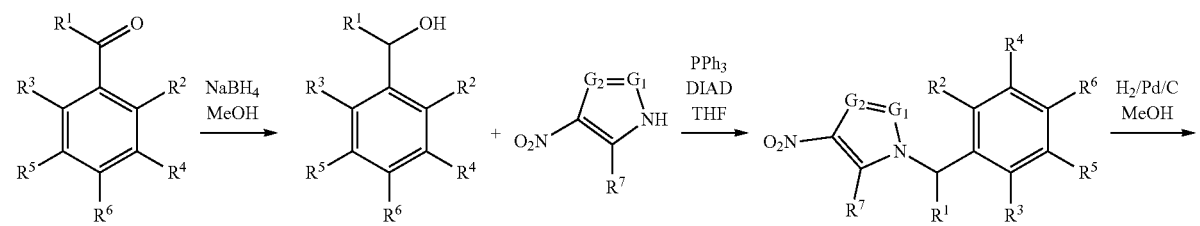

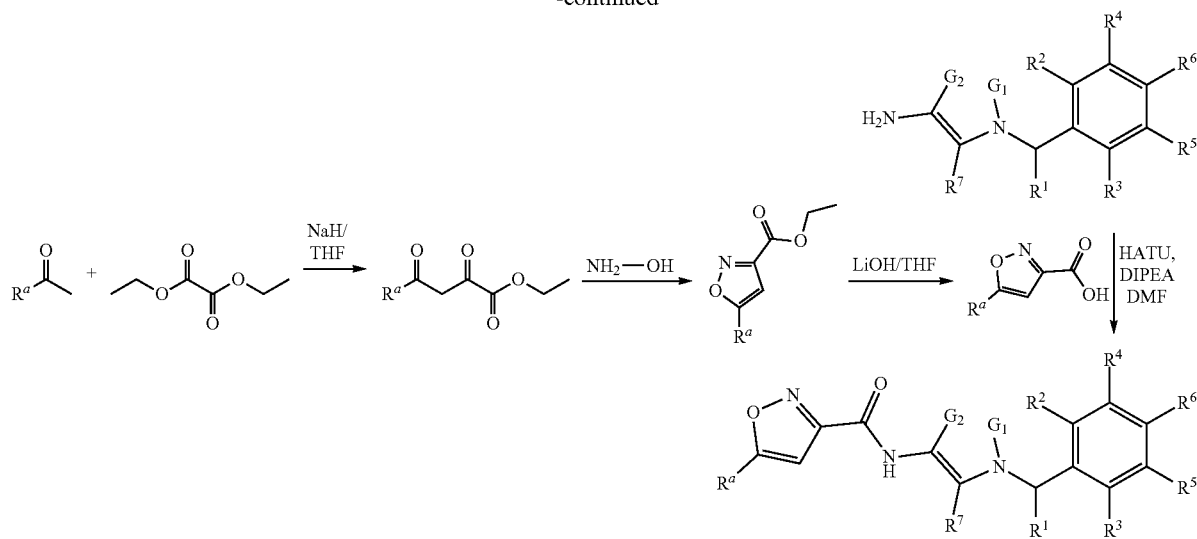
wherein $R^1$, $R^2$, $R^3$, $R^4$, $R^5$, $R^6$, $R^7$, $G_1$, $G_2$, and $R^a$ are as defined for Formula (A), (I), or any variation thereof detailed herein.
In some embodiments, compounds of the Formula (I) may be synthesized according to Scheme 2.
Scheme 2
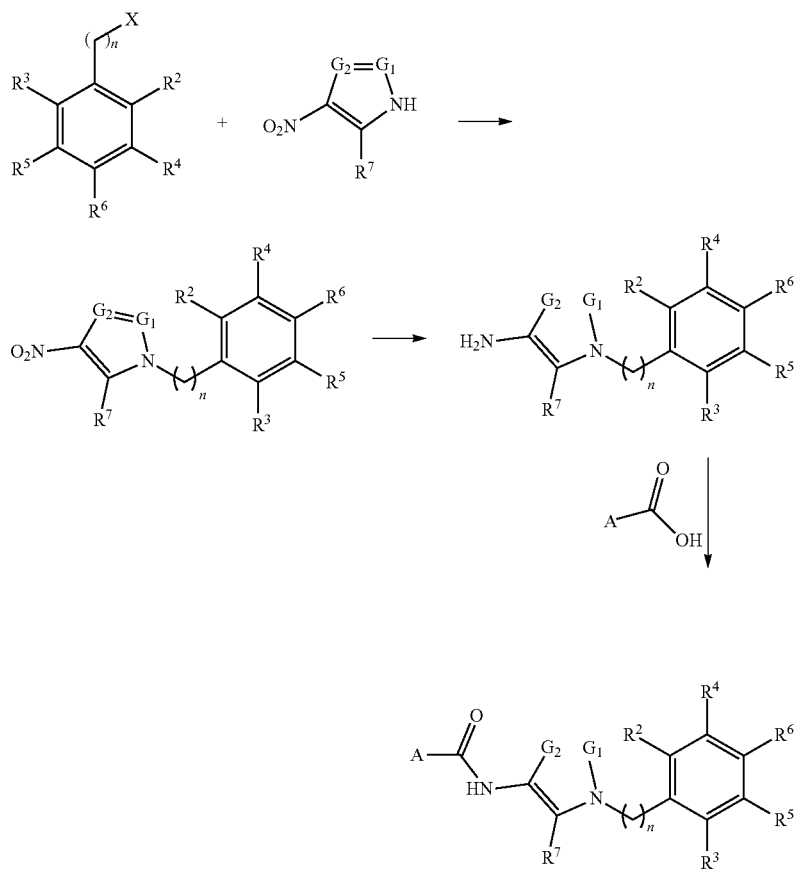

wherein A, $R^2$, $R^3$, $R^4$, $R^5$, $R^6$, $R^7$, $G_1$, $G_2$, and n are as defined for Formula (A), (I), or any variation thereof detailed herein, and X is a halogen.

An exemplary embodiment of the preparative method in Scheme 2 is shown in Scheme 2a.

Scheme 2a

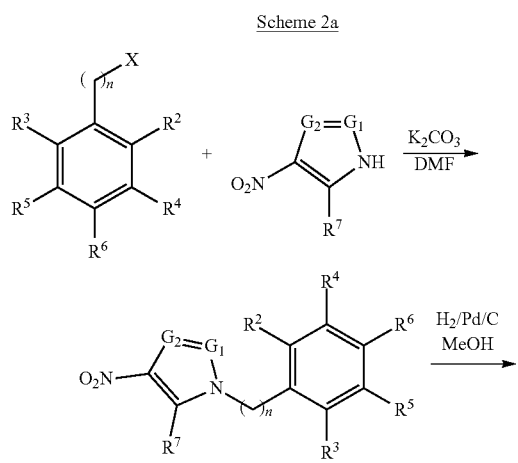

-continued

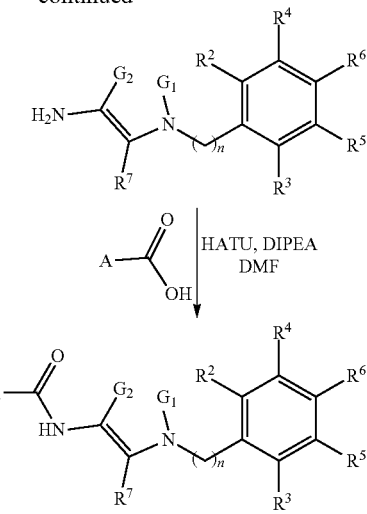

wherein A, $R^2$, $R^3$, $R^4$, $R^5$, $R^6$, $R^7$, $G_1$, $G_2$, and n are as defined for Formula (A), (I), or any variation thereof detailed herein, and X is a halogen.

In some embodiments, compounds of the Formula (I) may be synthesized according to Scheme 3.

Scheme 3

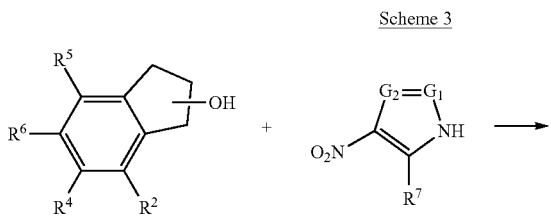

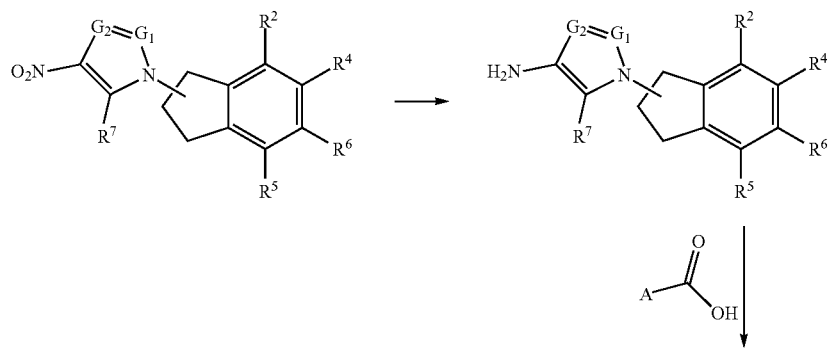

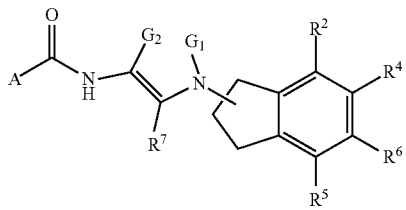

wherein A, $R^2$, $R^4$, $R^5$, $R^6$, $R^7$, $G_1$, and $G_2$ are as defined for Formula (A), (I), or any variation thereof detailed herein.

An exemplary embodiment of the preparative method in Scheme 3 is shown in Scheme 3a.

Scheme 3a

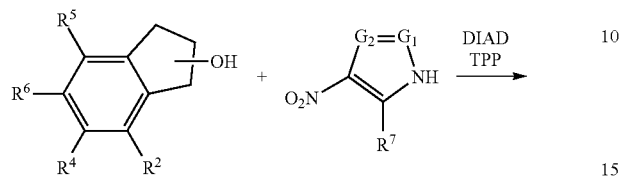

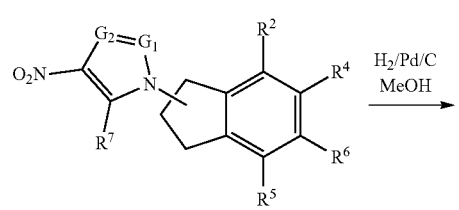

-continued

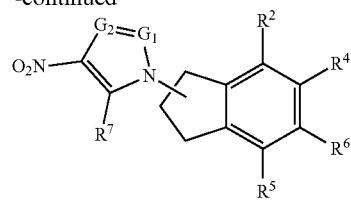

wherein A, $R^2$, $R^4$, $R^5$, $R^6$, $R^7$, $G_1$, and $G_2$ are as defined for Formula (A), (I), or any variation thereof detailed herein.

In some embodiments, compounds of the Formula (I) may be synthesized according to Scheme 4.

Scheme 4

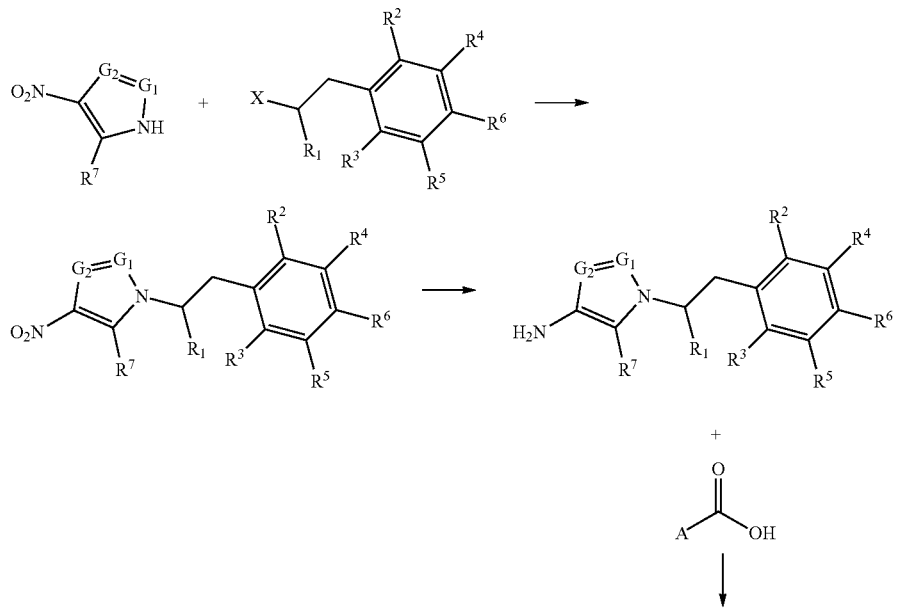

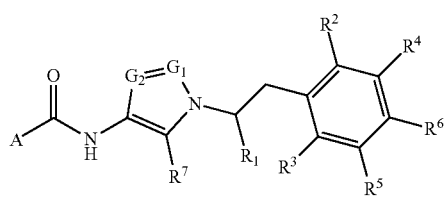

wherein A, $R^1$, $R^2$, $R^3$, $R^4$, $R^5$, $R^6$, $R^7$, $G_1$, and $G_2$ are as defined for Formula (A), (I), or any variation thereof detailed herein, and X is a halogen.

Particular examples are provided in the Example section below. It is understood that the schemes above may be modified to arrive at various compounds of the invention by selection of appropriate reagents and starting materials. For a general description of protecting groups and their use, see P. G. M. Wuts and T. W. Greene, Greene's Protective Groups in Organic Synthesis 4$^{th}$ edition, Wiley-Interscience, New York, 2006.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, PA, 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use and Uses

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In some embodiments, provided herein is a method of inhibiting the ATF6 pathway. In some embodiments, provided herein is a method of inhibiting the ATF6. In some embodiments, the ATF6 is ATF6a. The compounds or salts thereof described herein and compositions described herein are believed to be effective for inhibiting the ATF6 pathway, ATF6, and/or ATF6a.

In some embodiments, the method of inhibiting the ATF6 pathway, ATF6, or ATF6a comprises administering or delivering to a cell comprising ATF6 or ATF6a a compound described herein, or a pharmaceutically acceptable salt thereof, or a pharmaceutical composition described herein. In some embodiments, the cell is a diseased cell, such as a cancer cell. In some embodiments, the cell has an activated ATF6 pathway. In some embodiments, the cell has been exposed to an ER stress-inducing condition. Several ER stress-inducing conditions are known in the art, such as glucose deprivation, aberrant $Ca^{2+}$ regulation, viral infection, hypoxia, and exposure to a ER stress-inducing molecule such as thapsigargin, ionomycin, or tunicamycin.

In some embodiments, the method of inhibiting the ATF6 pathway, ATF6, or ATF6a comprises administering or delivering a compound described herein, or a pharmaceutically acceptable salt thereof, or a pharmaceutical composition described herein to a tumor.

In some embodiments, the inhibition of the ATF6 pathway, ATF6, or ATF6a comprises inhibiting expression of an ATF6 and/or ATF6a target gene. In some embodiments, the inhibition of the ATF6 pathway, ATF6, or ATF6a comprises inhibiting expression of an ATF6a target gene. In some embodiments, the expression of the ATF6 and/or ATF6a target gene is inhibited by at least about 10%, 20%, 30%, 40%, 50%, 60%, 70%, 80%, 90%, 95%, or 98%.

In some embodiments, the ATF6 and/or ATF6a target gene comprises a promoter comprising a ER-stress responsive element (ERSE). In some embodiments, the promoter comprises a sequence that shares at least about 70%, 75%, 80%, 85%, 90%, 95%, 96%, 97%, 98%, or 99% sequence identity with CCAATCGGCGGCGGCCACG (SEQ ID NO. 1). In some embodiments, the promoter comprises SEQ ID NO. 1. In some embodiments, the ATF6 and/or ATF6a target gene is GRP78, HERPUD1, or ERO1B. In some embodiments, the ATF6a target gene is GRP78. Inhibition of expression of an ATF6 and/or ATF6α target gene can be determined by methods known in the art, such as by detection of the mRNA of the target gene using a techniques such as PCR, qPCR, or northern blotting, or by detection of polypeptide gene product, such as by western blotting or mass spectrometry.

In some embodiments, the compound, salt thereof, or composition inhibits the ATF6 pathway, ATF6, or ATF6α with an $IC_{50}$ of less than about 10 µM, such as less than about 5 µM, 2 µM, 1 µM, 900 nM, 800 nM, 700 nM, or 600 nM. In some embodiments, the compound, salt thereof, or composition inhibits the ATF6 pathway, ATF6, or ATF6α with an $IC_{50}$ between about 10 nM and 5 µM, such between about 50 nM and 2 µM, 100 nM and 1 µM, or 20 nM and 1 µM. The half maximal inhibitory concentration ($IC_{50}$) is a measure of the effectiveness of a substance in inhibiting a specific biological or biochemical function. The $IC_{50}$ is a quantitative measure that indicates how much of an inhibitor is needed to inhibit a given biological process or component of a process such as an enzyme, cell, cell receptor or microorganism by half. Methods of determining $IC_{50}$ in vitro and in vivo are known in the art.

In some embodiments, the compounds or salts thereof described herein and compositions described herein are administered in an amount wherein ATF6β activity is not inhibited or is inhibited to a lesser extent. In some embodiments, inhibition of ATF6α is at least or at least about 2 fold greater than inhibition of ATF6β activity, for example at least or at least about 3 fold, 4 fold, 5 fold, 8 fold, 10 fold, 15 fold, 30 fold, 50 fold, 60 fold, 75 fold, or 100 fold greater.

Provided herein is a method of treating a disease in an individual comprising administering an effective amount of a compound of Formula (I) or any embodiment, variation or aspect thereof, including but not limited to a compound of Formula (Ia), (Ib), (Ic), (Id), (Ie), (If), (Ig), (Ih), (Ii), (Ij), or (Ik), or any embodiment or variation or aspect thereof, (collectively, a compound of Formula (I) or the present compounds or the compounds detailed or described herein) or a pharmaceutically acceptable salt thereof, to the individual.

In some embodiments, provided herein is a method of treating a disease mediated by the ATF6 pathway in an individual comprising administering an effective amount of a compound of Formula (A), (I), or a pharmaceutically acceptable salt thereof, to the individual. In some embodiments, provided herein is a method of treating a disease mediated by the activation of the ATF6 pathway in an individual comprising administering an effective amount of a compound of Formula (A), (I), or a pharmaceutically acceptable salt thereof, to the individual. In some embodiments, provided herein is a method of treating a disease mediated by the activation of ATF6 in an individual comprising administering an effective amount of a compound of Formula (A), (I), or a pharmaceutically acceptable salt thereof, to the individual. In some embodiments, provided herein is a method of treating a disease mediated by the activation of ATF6α in an individual comprising administering an effective amount of a compound of Formula (A), (I), or a pharmaceutically acceptable salt thereof, to the individual.

In some embodiments, provided herein is a method of treating a disease characterized by activation of the ATF6 pathway in an individual comprising administering an effective amount of a compound of Formula (A), (I), or a pharmaceutically acceptable salt thereof, to the individual. In some embodiments, provided herein is a method of treating a disease characterized by activation of ATF6 in an individual comprising administering an effective amount of a compound of Formula (A), (I), or a pharmaceutically acceptable salt thereof, to the individual. In some embodiments, provided herein is a method of treating a disease characterized by activation of ATF6α in an individual comprising administering an effective amount of a compound of Formula (A), (I), or a pharmaceutically acceptable salt thereof, to the individual. In some embodiments, provided herein is a method of treating a disease characterized by increased expression of an ATF6 target gene in an individual comprising administering an effective amount of a compound of Formula (A), (I), or a pharmaceutically acceptable salt thereof, to the individual. In some embodiments, provided herein is a method of treating a disease characterized by increased expression of an ATF6α target gene in an individual comprising administering an effective amount of a compound of Formula (A), (I), or a pharmaceutically acceptable salt thereof, to the individual. In some embodiments, the increased expression is in comparison to a non-diseased tissue or cell.

The present compounds or salts thereof are believed to be effective for treating a variety of diseases and disorders, such as diseases wherein ATF6-activated transcription targets play a role in the pathogenesis or development of the disease. For example, in some embodiments, the present compounds and compositions may be used to treat viral infection, cancer, a neurodegenerative disease, or a vascular disease, such as a cardiovascular disease. In some embodiments, the disease is viral infection, hereditary cerebellar atrophy and ataxia, or Alzheimer's disease. In some embodiments, the disease is type 2 diabetes mellitus or diabetic nephropathy. In some embodiments, the disease is myocardial atrophy, heart failure, atherosclerosis, or ischemia, such as ischemic heart disease or cerebral ischemia.

It has been demonstrated that ATF6 branch of the UPR is central for viral infection. For example, ATF6 is important for maintaining cell viability and modulating immune responses during West Nile virus infection (Ambrose R J. Virol. February 2013 vol. 87 no. 4 2206-2214). Also, African swine fever virus activates ATF6 branch to prevent early apoptosis and ensure viral replication (Galindo I, Cell Death Dis 2012 Jul. 5; 3:e341. doi: 10.1038/cddis.2012.81). Accordingly, in some embodiments, a compound or salt thereof described herein or a composition described herein may be used in a method of treating or preventing a viral infection. In some embodiments, the viral infection is an African swine fever virus, a dengue virus, an enterovirus, a hepatitis B virus, a hepatitis C virus, influenza virus, a tick-borne encephalitis virus, or a West Nile virus infection.

In some embodiments, the viral infection is caused by a virus that activates ATF6 in an infected cell.

In some embodiments, a compound or salt thereof described herein or a composition described herein may be used in a method of treating cancer, such as breast cancer, colorectal cancer, ovarian cancer, prostate cancer, pancreatic cancer, kidney cancer, lung cancer, melanoma, fibrosarcoma, bone sarcoma, connective tissue sarcoma, renal cell carcinoma, giant cell carcinoma, squamous cell carcinoma, leukemia, skin cancer, soft tissue cancer, liver cancer, gastrointestinal carcinoma, or adenocarcinoma. In some embodiments, the compound, salt, or composition may be used in a method of treating metastatic kidney cancer, chronic lymphocytary leukemia, pancreatic adenocarcinoma, or non-small cell lung cancer.

ATF6α transcription targets are expressed at high levels in cancer cells. For example, a correlation exists between intracellular GRP78 level and tumor size (Cai, J. W., et al., J Cell Physiol, 1993, 154(2): 229-37). Furthermore, when GRP78/BiP expression was experimentally suppressed in cancer cells that were then injected into mice, the cells were unable to form tumors due to an increased sensitivity to cytotoxic T-cell (CTL) response and tumor necrosis factor (TNF) (Jamora, C., et al., Proc Natl Acad Sci USA, 1996, 93(15): 7690-7694; Sugawara, S., et al., Cancer Res, 1993, 53(24): 6001-6005).

Cancer cells that are cellularly dormant lack proliferative markers and exist in a quiescent state. Cells known to experience cellular dormancy include disseminated tumor cells (DTCs) and tumor cells located within the circulation (termed circulating tumor cells (CTCs)) (Hensel, J. A., et al., Nat Rev Clin Oncol, 2013, 10(1): 41-51). Minimal residual disease caused by solitary DTCs is a well-recognized event associated with unfavorable patient prognosis. DTCs, which usually stain negative for proliferation markers (e.g., Ki67), may be the source of tumor recurrence that can develop up to decades after treatment of the primary tumor (Meng, S., et al., Clin Cancer Res, 2004, 10(24): 8152-8162). ATF6α has been reported to be a transducing survival signal through an ATF6α-Rheb-mTOR pathway for dormant carcinoma cells (Schewe, D. M. et al., Proc Natl Acad Sci USA, 2008, 105(30): 10519-10524). ATF6α signaling is important for protection against ER and low glucose stress, and the interaction between ATF6α and mTOR signaling appears to confer resistance of dormant cancer cells to doxorubicin and to the mTOR inhibitor rapamycin, revealing a potential drug resistance mechanism (Schewe, D. M. et al., Proc Natl Acad Sci USA, 2008, 105(30): 10519-10524).

In addition, a multicancer study showed higher ATF6 expression in metastases vs. primary lesions and colon cancer patients with increased expression of ATF6α in their primary tumors had higher chances of relapse (Ramaswamy, S., et al., Proc Natl Acad Sci USA, 2001, 98(26): 15149-15154).

In some embodiments, a compound or salt thereof described herein or a composition described herein may be used in a method of treating cancer in an individual, wherein one or more cancer cells in the individual are dormant cancer cells. In some embodiments, one or more of the dormant cancer cells are disseminated tumor cells or circulating tumor cells. In some embodiments, one or more of the dormant cancer cells are disseminated tumor cells.

In some embodiments, a compound or salt thereof described herein or a composition described herein may be used in a method of treating cancer in an individual, wherein the individual has had a prior treatment. In some embodiments, the cancer is resistant or refractory to the prior treatment. In some embodiments, the cancer has progressed on the prior treatment. In the embodiments, the cancer is a recurrent cancer. In some embodiments, the prior treatment was treatment with a ubiquitin-proteasome pathway inhibitor (e.g., bortezomib), a taxane (e.g., paclitaxel or docetaxel), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), an mTOR inhibitor (e.g., rapamycin), an immune-check point inhibitor, or an agent that is used in immune oncology. In some embodiments, the cancer is resistant to treatment with a ubiquitin-proteasome pathway inhibitor (e.g., bortezomib), a taxane (e.g., paclitaxel or docetaxel), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), an mTOR inhibitor (e.g., rapamycin), an immune-check point inhibitor, or an agent that is used in immune oncology. In some embodiments, the cancer is resistant to treatment with doxorubicin and/or rapamycin.

In some embodiments, the administration of the compound, salt, or composition reduces tumor growth, tumor proliferation, or tumorigenicity in the individual. In some embodiments, the compound, salt, or composition may be used in a method of reducing tumor growth, tumor proliferation, or tumorigenicity in an individual in need thereof. In some embodiments, tumor growth is slowed or arrested. In some embodiments, tumor growth is reduced at least about 10%, 20%, 30%, 40%, 50%, 60%, 70%, 80%, or 90%. In some embodiments, the tumor is reduced in size. In some embodiments, tumor size is reduced at least about 10%, 20%, 30%, 40%, 50%, 60%, 70%, 80%, or 90%. In some embodiments, tumor metastasis is prevented or slowed. In some embodiments, the tumor growth, tumor proliferation, or tumorigenicity is compared to the tumor growth, tumor proliferation, or tumorigenicity in the individual prior to the administration of the compound, salt, or composition. In some embodiments, the tumor growth, tumor proliferation, or tumorigenicity is compared to the tumor growth, tumor proliferation, or tumorigenicity in a similar individual or group of individuals. Methods of measuring tumor growth, tumor proliferation, and tumorigenicity are known in the art, for example by repeated imaging of the individual.

The present compounds or salts thereof are also believed to be effective at inhibiting angiogenesis. Activation of ATF6 and PERK contributes to the survival effect of vascular endothelial growth factor (VEGF) on endothelial cells (ECs) by positively regulating mTORC2-mediated phosphorylation of AKT on Ser473, which is required for full activity of AKT. Depletion of PLCγ, ATF6, or eIF2a dramatically inhibited VEGF-induced vascularization in vivo in mouse Matrigel plugs, a standard angiogenesis assay (Karali, E. et al, Molecular Cell, 2014, 54:559-572). Accordingly, the present compounds or salts thereof are believed to be effective for treating a variety of diseases and disorders associated with angiogenesis.

Angiogenesis has been implicated in the pathogenesis of a variety of diseases disorders including solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Accordingly, in some embodiments, the present compounds and compositions are used in a method to treat cancer, such as any cancer described herein, undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

A breakdown in gut barrier defenses in conjunction with microbial dysbiosis is emerging as a key contributor to several disorders, including inflammatory bowel disease, type 1 diabetes, Alzheimer's disease, and cancer. Particularly, in patients with colorectal cancer (CRC), high expression levels of ATF6 in tumor tissues were associated with increased tumor size and reduced disease-free survival. On the other hand, an altered microbiota has been associated with CRC. These data suggest a connection between activation of the UPR, the microbiota, and colon tumorigenesis. It has been demonstrated that a novel relationship between UPR activation via ATF6 and microbiota dependent colon tumorigenesis. Goblet cell loss and bacterial infiltration into epithelial crypts occur before tumor formation and antibiotic treatment of nATF6IEC mice significantly decreased tumor burden. In an inducible mouse model of ATF6 activation, there was 100% tumor incidence at 26 weeks. Four days after activated ATF6 induction, there was a notable increase in the proximity of bacteria to the colonic epithelium with increased cell proliferation, suggesting that these alterations are early events downstream of ATF6 activation. Some researchers found that microbial dysbiosis along with decreased microbial diversity was present in the cecal contents of nATF6IEC mice, as assessed by 16S rRNA gene amplicon sequencing at 5 weeks of age, which is before the onset of tumorigenesis. This dysbiotic microbiota enhanced tumor formation upon transfer into germ-free nATF6IEC mice as compared with transfer of control microbiota into nATF6IEC mice. These data suggest that microbial dysbiosis and subsequent STAT3 signaling in the epithelium significantly contribute to tumorigenesis in this model Accordingly, in some embodiments, a compound or salt thereof described herein or a composition described herein may be used in a method for preventing or treating CRC through inhibition of ATF6 preventing goblet cell loss and dysbiosis. In some embodiments, a compound or salt thereof described herein or a composition described herein may be used in a method for blocking ATF6 signaling and reversing dysbiosis to antagonize tumor progression in a subset of CRC patients.

The capacity of the UPR signaling arms to distinctly influence ER proteostasis and function suggests that selective activation of these pathways has significant potential to alleviate pathologic imbalances in ER proteostasis associated with etiologically diverse human diseases. In particular, activation of the ATF6 signaling arm has been shown to be useful for ameliorating disease-associated imbalances in ER proteostasis and function. The stress-independent activation of the ATF6 transcription factor using a chemical genetic approach induces protective remodeling of ER proteostasis pathways to selectively reduce secretion and extracellular aggregation of destabilized, amyloid disease-associated proteins, such as transthyretin and immunoglobulin light chain, without significantly impacting the secretion of the endogenous proteome (Shoulders et al., 2013; Chen et al., 2014; Cooley et al., 2014; Plate et al., 2016). Accordingly, a compound or salt thereof described herein or a composition described herein may be used in a method for correcting pathologic imbalances in ER proteostasis in cellular and animal models of protein misfolding and aggregation diseases.

One aspect of the present invention is based on the unexpected discovery that overexpression of ATF6 in a cell prevents cell death that would otherwise occur when an undesired accumulation of proteins occurs in that cell. Accordingly, in some embodiments, a compound or salt thereof described herein or a composition described herein may be used in a method for treating a condition such as Parkinson's disease (PD) associated with the abnormal accumulation of molecules that interact with parkin and that are not properly disposed of within a cell.

In some embodiments, a compound or salt thereof described herein or a composition described herein may be used in a method for preventing cell death. For example, preventing neuronal cell death is contemplated within the present invention, including preventing the death of nigral neurons in a mammal, including humans.

In some embodiments, a compound or salt thereof described herein or a composition described herein may be used in a method for treating neurodegenerative diseases associated with abnormal precipitation and/or aggregation of proteins. For example, the brains of patients with Alzheimer's disease exhibit neurofibrillary tangles (NFT), senile plaques, and cerebrovascular deposits of amyloid-beta; the brains of patients with prion disorders exhibit plaques comprising prion proteins; the brains of patients with Huntington's disease exhibit huntingtin precipitates; patients with dominantly inherited spinocerebellar ataxias exhibit corresponding ataxin protein precipitates; patients with multiple system atrophy exhibit alpha-synuclein deposits; patients with progressive supranuclear palsy exhibit tau precipitates; and patients with familial amyotrophic lateral sclerosis exhibit SOD1 precipitates (Johnson, W. G., J. Anat. 4:609-616 (2000)). Because these various diseases share common pathological mechanisms, it is likely that they share pathways that lead to aberrant aggregation and/or precipitation of proteins (Hardy, J. and Gwinn-Hardy, K., Science 282(5391):1075-1079 (1998)).

In some embodiments, a compound or salt thereof described herein or a composition described herein may be used in a method as either a stand-alone therapy, or as a conjunctive therapy with other agents that are either palliative (e.g., agents that relieve the symptoms of the disorder to be treated), and/or agents that target the etiology of the disorder. For example, the administration to a subject of a composition that increases the expression of ATF6 may be carried out in conjunction with the administration of L-DOPA, dopamine agonists, monoamine oxidase B inhibitors, or any other composition useful in the treatment of a neurodegenerative disease, such as Parkinson's disease.

Overexpression of the active ATF6 transcription factor in the heart also has been shown to improve cardiac performance in mouse models of ischemic heart disease, through a mechanism involving ATF6-dependent regulation of the antioxidant gene, catalase (Jin et al., 2017). Similarly, overexpression of the active ATF6 transcription factor in the liver improves insulin sensitivity in obese mice (Ozcan et al., 2016). These results indicate that ATF6 activation offers a unique therapeutic opportunity to ameliorate ER proteostasis defects implicated in diverse diseases.

In some embodiments, a compound or salt thereof described herein or a composition described herein may be used in a method for enhancing myocardial recovery from I/R damage, specifically by activating the endogenous adaptive ATF6 gene program in the heart.

The ATF6α pathway also plays a role in stress-induced lipid accumulation. p50ATF6 interacts with the nuclear form of SREBP-2, thereby antagonizing SREBP-2-regulated transcription of lipogenic genes and lipid accumulation in cultured hepatocytes and kidney cells. Moreover, Atf6α-deleted mice displayed hepatic dysfunction and steatosis much longer than wild-type mice in response to pharmacological induction of ER stress. This could be explained by chronic expression of CHOP and sustained suppression of C/EBPα and/or a failure of ATF6α-mediated induction of genes encoding protein chaperone, trafficking, and ERAD functions. When fed a HFD, Atf6α$^{-/-}$ mice developed hepatic steatosis and glucose intolerance in association with increased expression of SREBP-1c. On the other hand, overexpression of a functionally active nuclear fragment of ATF6 in zebrafish caused fatty liver, suggesting that fine-tuning of ATF6α may be important to prevent liver steatosis.

In some embodiments, a compound or salt thereof described herein or a composition described herein may be used in a method of treating metabolic disorders, such as obesity, type I- and type II diabetes, pancreatitis, dyslipidemia, hyperlipidemia conditions, non-alcoholic fatty liver disease (NAFLD), non-alcoholic steatohepatitis (NASH), insulin resistance, hyperinsulinemia, glucose intolerance, hyperglycemia, metabolic syndrome, acute myocardial infarction, hypertension, cardiovascular diseases, atherosclerosis, peripheral arterial disease, apoplexy, heart failure, coronary artery heart disease, renal disease, diabetic complications, neuropathy, gastroparesis, disorder associated with a serious inactivation mutation in insulin receptor, and other metabolic disorders.

In some embodiments, a compound or salt thereof described herein or a composition described herein may be used in a method of treating ischemic heart disease or myocardial recovery from ischemia/reperfusion (I/R).

In accordance with the present disclosure, in some embodiments, the individual is a mammal. In some embodiments, the individual is a primate, bovine, ovine, porcine, equine, canine, feline, rabbit, or rodent. In some embodiments, the individual is a human. In some embodiments, the individual has any of the diseases or disorders disclosed herein. In some embodiments, the individual is a risk for developing any of the diseases or disorders disclosed herein.

Also provided herein are uses of a compound described herein or a pharmaceutically acceptable salt thereof, or a pharmaceutical composition described herein, in the manufacture of a medicament. In some embodiments, the manufacture of a medicament is for the treatment of a disorder or disease described herein. In some embodiments, the manufacture of a medicament is for the prevention and/or treatment of a disorder or disease mediated by the ATF6 pathway, ATF6, or ATF6α.

Combination Therapy

As provided herein, compounds or salts thereof described herein and compositions described herein may be administered with an agent to treat any of the diseases and disorders disclosed herein. In some embodiments, the agent modulates the Unfolded Protein Response or the Integrated Stress Response. In some embodiments, the agent is an anti-angiogenesis agent. In some embodiments, the agent is an anticancer agent. In some embodiments, the agent targets an immune checkpoint protein.

In some embodiments, (a) a compound described herein, or a pharmaceutically acceptable salt thereof, or a pharmaceutical composition described herein and (b) an agent are sequentially administered, concurrently administered or simultaneously administered. In certain embodiments, (a) a compound described herein, or a pharmaceutically acceptable salt thereof, or a pharmaceutical composition described herein and (b) an agent are administered with a time separation of about 15 minutes or less, such as about any of 10, 5, or 1 minutes or less. In certain embodiments, (a) a compound described herein, or a pharmaceutically acceptable salt thereof, or a pharmaceutical composition described herein and (b) an agent are administered with a time separation of about 15 minutes or more, such as about any of 20, 30, 40, 50, 60, or more minutes. Either (a) a compound described herein, or a pharmaceutically acceptable salt thereof, or a pharmaceutical composition described herein and (b) an agent may be administered first. In certain embodiments, (a) a compound described herein, or a pharmaceutically acceptable salt thereof, or a pharmaceutical composition described herein and (b) an agent are administered simultaneously.

In some embodiments, the agent modulates the Unfolded Protein Response or the Integrated Stress Response. In some embodiments, the agent inhibits the Unfolded Protein Response or the Integrated Stress Response. In some embodiments, the agent modulates the PERK pathway. In some embodiments, the agent inhibits the PERK pathway. In some embodiments, the agent inhibits PERK. ATF6 is known to work in partnership with IRE1, as one of the target genes of ATF6 is XBP1, the key substrate of IRE1 (Yoshida, H., et al., Cell, 2001, 107(7): 881-891), for example ATF6 and IRE1 signaling are important for survival of melanoma cells undergoing ER stress, suggesting a potential benefit in the use of ATF6 inhibitors in combination with IRE1 inhibitors (Tay, K. H., et al., Cell Signal, 2014, 26(2): 287-294). Accordingly, in some embodiments, the agent modulates the IRE1/XBP1 pathway. In some embodiments, the agent inhibits the IRE1/XBP1 pathway. In some embodiments, the agent inhibits IRE1 or XBP1.

In some embodiments, the agent is an anti-angiogenesis agent. The present compounds or salts thereof are believed to be effective at inhibiting angiogenesis and for treating diseases and disorders associated with angiogenesis. Accordingly, provided herein is a method of inhibiting angiogenesis comprising administering to an individual (a) a compound described herein, or a pharmaceutically acceptable salt thereof, or a pharmaceutical composition described herein and (b) an anti-angiogenesis agent. Also provided herein is a method of treating a disease or disorder associated with angiogenesis, such as any disease or disorder associated with angiogenesis disclosed herein, comprising administering to an individual (a) a compound described herein, or a pharmaceutically acceptable salt thereof, or a pharmaceutical composition described herein and (b) an anti-angiogenesis agent. In some embodiments, the anti-angiogenesis agent is a VEGF antagonist. In some embodiments, the anti-angiogenesis agent is bevacizumab or ranibizumab.

The role of angiogenesis as a mediator of immune regulation in the tumor microenvironment has recently come into focus. Furthermore, emerging evidence indicates that immunotherapy can lead to immune-mediated vasculopathy in the tumor, suggesting that the tumor vasculature may be an important interface between the tumor-directed immune response and the cancer itself. The introduction of immune checkpoint inhibition as an effective immunotherapeutic strategy for many cancers has led to a better understanding of this interface. Initial studies of the complex relationship between angiogenesis, VEGF signaling and the immune system suggest that the combination of immune checkpoint blockade with angiogenesis inhibition has potential and efforts to enhance immunotherapy will broadly impact the future of oncology. The effect of ATF6 over VEGF signaling reinforces the idea of the use of ATF6 inhibitors as a combination with immune checkpoint inhibitors (Ott, P. A., F. S. Hodi, and E. I. Buchbinder, Inhibition of Immune Checkpoints and Vascular Endothelial Growth Factor as Combination Therapy for Metastatic Melanoma: An Overview of Rationale, Preclinical Evidence, and Initial Clinical Data. Front Oncol, 2015. 5: p. 202).

Accordingly, in some embodiments, the agent targets an immune checkpoint protein. In some embodiments, the agent is an antibody that targets an immune checkpoint protein. In some embodiments, the agent targets PD-1, PD-L1, PD-L2, CTLA4, TIM3, LAG3, CCR4, OX40, OX40L, IDO, and A2AR. In some embodiments, the agent is an anti-PD-1 antibody, an anti-PD-L1 antibody, or an anti-CTLA-4 antibody.

Provided herein is a method of enhancing an immune response in an individual comprising administering to the individual (a) a compound described herein, or a pharmaceutically acceptable salt thereof, or a pharmaceutical composition described herein and (b) an agent that targets an immune checkpoint protein. In some embodiments, the individual has cancer. In some embodiments, the enhanced immune response is directed to a tumor or cancerous cell.

Also provided herein are methods of treating cancer in an individual in need thereof comprising administering to the individual (a) a compound described herein, or a pharmaceutically acceptable salt thereof, or a pharmaceutical composition described herein and (b) an agent that targets an immune checkpoint protein, wherein an immune response of the individual is increased.

In some embodiments, the agent is an anticancer agent. In some embodiments, anticancer agent is an ubiquitin-proteasome pathway inhibitor (e.g., bortezomib), a taxane (e.g., paclitaxel or docetaxil), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), or an agent that modulates the Unfolded Protein Response or the Integrated Stress Response (e.g. an IRE1/XBP1 inhibitor or a PERK inhibitor). In some embodiments, the anticancer agent is oxaliplatin, 5-fluorouracil, or gemcitabine. In some embodiments, the anticancer agent is an immune-check point inhibitor, or an agent that is used in immune oncology.

In some embodiments, an effective amount of a compound described herein, or a pharmaceutically acceptable salt thereof, or a pharmaceutical composition described herein is administered to an individual with cancer to increase sensitivity to one or more anticancer treatments.

Therapeutic resistance is a major barrier to improvement of outcomes for patients with cancer. Radiation can induce ER stress and its downstream signaling and appears to be linked to changes in ROS balance secondary to irradiation. Previously, knockdown of ATF6 was sufficient to enhance radiation induced cell death (Dadey, D. Y., et al., Oncotarget, 2016, 7(2): 2080-2092). This suggests ATF6 as a potential therapeutic target to enhance the efficacy of radiation therapy.

In some embodiments, an effective amount of a compound described herein, or a pharmaceutically acceptable salt thereof, or a pharmaceutical composition described herein is administered to an individual with cancer to increase sensitivity to radiation. In some embodiments, provided herein are methods of treating cancer in an individual in need thereof comprising administering to the individual (a) a compound described herein, or a pharmaceutically acceptable salt thereof, or a pharmaceutical composition described herein and (b) radiation.

In some embodiments, an effective amount of a compound described herein, or a pharmaceutically acceptable salt thereof, or a pharmaceutical composition described herein is administered to an individual with cancer to increase sensitivity to one or more anticancer agents. In some embodiments, the anticancer agent is an ubiquitin-proteasome pathway inhibitor (e.g., bortezomib), a taxane (e.g., paclitaxel or docetaxil), a Cox-2 inhibitor (e.g., celecoxib), a platinum-based antineoplastic drug (e.g., cisplatin or oxaliplatin), an anthracycline (e.g. doxorubicin), a pyrimidine analog (e.g. 5-fluorouracil or gemcitabine), a topoisomerase inhibitor (e.g., etoposide), or an agent that modulates the Unfolded Protein Response or the Integrated Stress Response (e.g. an IRE1/XBP1 inhibitor or a PERK inhibitor). In some embodiments, the anticancer agent is oxaliplatin, 5-fluorouracil, or gemcitabine. In some embodiments, the anticancer agent is an immune-check point inhibitor, or an agent that is used in immune oncology.

Provided herein is a method of treating metabolic and/or fibrotic diseases in an individual comprising administering to the individual (a) a compound described herein, or a pharmaceutically acceptable salt thereof, or a pharmaceutical composition described herein and (b) an agent. In some embodiments, the agent is a proteasome inhibitor, e.g., bortezomib, carfilzomib and ixazomib. In some embodiments, the agent is a monoclonal antibody, e.g., daratumumab and elotuzumab. In some embodiments, the agent is an Inhibitors of Histone deacetylases (HDACs) protein, e.g., panobinostat, romidepsin and vorinostat. In some embodiments, the agent is an Immunomodulatory drug (IMiD). e.g., thalidomide, lenalidomide, and pomalidomide. In some embodiments, the agent is an adrenal corticosteroid, e.g., dexamethasone, prednisone, prednisolone, and methylprednisolone. In some embodiments, the agent is a therapy targeting the IRE1-XBP1.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account factors, e.g., the mode or route of administration or drug delivery, the pharmacokinetics of the agent, the severity and course of the disease to be treated, the subject's health status, condition, and weight. An exemplary dose is in the range of about from about 0.1 mg to 10 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral, and transdermal. In some embodiments, the compound or composition is administered orally. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

Also provided herein are compositions (including pharmaceutical compositions) as described herein for the use in treating, preventing, and/or delaying the onset and/or development of a disease described herein and other methods described herein. In certain embodiments, the composition comprises a pharmaceutical formulation which is present in a unit dosage form.

Articles of Manufacture and Kits

The present disclosure further provides articles of manufacture comprising a compound of the disclosure or a salt thereof, composition, and unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the disclosure, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of disease described herein, such as cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Synthetic Examples

The following examples are offered to illustrate but not to limit the present disclosure. One of skill in the art will recognize that the following synthetic reactions and schemes may be modified by choice of suitable starting materials and reagents in order to access other compounds of Formula (A), (I), (Ia), (Ib), (Ic), (Id), (Ie), (If), (Ig), (Ii), (Ij), or (Ik), or a salt thereof. The compounds are prepared using the general methods described above.

The following abbreviations are used throughout the Examples: DCM (dichloromethane), DIAD (diisopropyl azodicarboxylate), DIPEA or DIEA (N,N-diisopropylethylamine), DMF (N,N-dimethylformamide), DMSO (dimethyl sulfoxide), HATU ((1-[bis(dimethylamino)methylene]-1H-1,2,3-triazolo[4,5-b]pyridinium 3-oxid hexafluorophosphate), HPLC (high-pressure liquid chromatography), IPA (isopropyl alcohol), LCMS (liquid chromatography mass spectrometry), NMR (nuclear magnetic resonance), PPh$_3$ (triphenylphosphane), RT (room temperature), TEA (triethylamine), THF (tetrahydrofuran), and TLC (thin layer chromatography).

Example S1. Synthesis of N-(1-(1-(2,4-bis(trifluoromethyl)phenyl)propyl)-1H-pyrazol-4-yl)-5-(pyridin-2-yl)isoxazole-3-carboxamide (Compound 1)

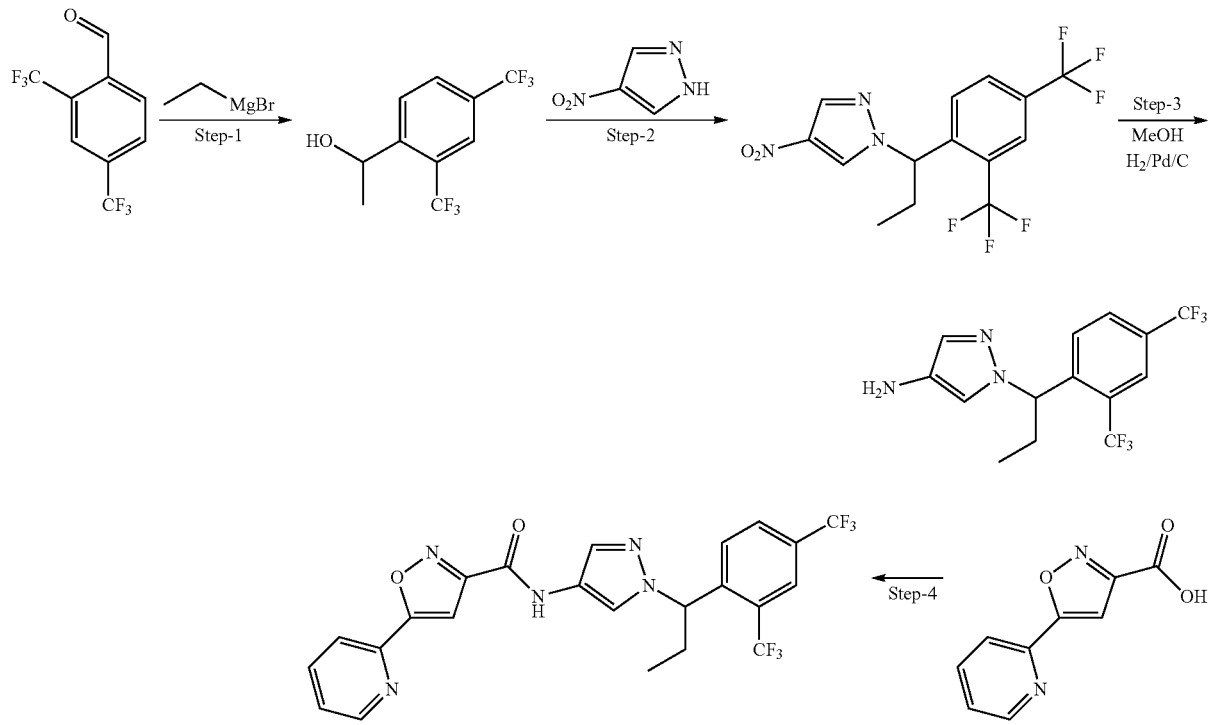

Step 1: Synthesis of 1-(2,4-bis(trifluoromethyl)phenyl)ethan-1-ol. To a stirred solution of 2,4-bis(trifluoromethyl)benzaldehyde (500 mg, 2.06 mmol, 1 equiv) in THF (5 mL) was added ethylmagnesium bromide (412 mg, 3 ml), 3.09 mmol, 1.5 equiv) portion wise at rt, and the reaction was stirred for 10 minutes. The reaction mixture was allowed to stir for 1 hour at RT. Product formation was confirmed by TLC & NMR. After completion of the reaction, the reaction mixture was quenched with water and extracted with ethyl acetate (50 mL×3). The combined organic extracts were washed with water (50 mL×2), dried over anhydrous $Na_2SO_4$ and concentrated under reduced pressure to obtain 1-(2,4-bis(trifluoromethyl)phenyl)ethan-1-ol. (110 gm, 19% as colourless liquid). $^1$H NMR (400 MHz, DMSO-$d_6$) δ=8.13-8.06 (m, 1H), 8.05-7.99 (m, 1H), 7.94 (s, 1H), 4.80 (br. s., 1H), 1.65-1.52 (m, 2H), 0.92 (t, J=7.2 Hz, 3H).

Step 2: Synthesis of 1-(1-(2,4-bis(trifluoromethyl)phenyl)propyl)-4-nitro-1H-pyrazole. To a stirred solution of $PPh_3$ (196 mg, 0.73 mmol, 1.0 equiv) and DIAD (148 mg, 0.73 mmol, 1.0 equiv) in THF (2 mL) was added 1-(2,4-bis(trifluoromethyl)phenyl)ethan-1-ol (200 mg, 0.73 mmol, 1.0 equiv). Followed by drop-wise addition of 4-nitro-1H-pyrazole (66 mg, 0.58 mmol, 0.8 equiv), the reaction mixture was stirred at RT for 1 h. Product formation was confirmed with TLC & LCMS. After completion of reaction mixture were diluted with EtOAc (50 mL) & washed with water (50 mL×3). Organic layer dried over $Na_2SO_4$ & concentrated under reduced pressure to obtain crude which was further purified by flash column chromatography to obtain pure product 1-(1-(2,4-bis(trifluoromethyl)phenyl)propyl)-4-nitro-1H-pyrazole (200 mg, 76% as brown liquid). LCMS: 368 [M+H]$^+$.

Step 3: Synthesis of 1-(1-(2,4-bis(trifluoromethyl)phenyl)propyl)-1H-pyrazol-4-amine. To a stirred solution of 1-(1-(2,4-bis(trifluoromethyl)phenyl)propyl)-4-nitro-1H-pyrazole (200 mg, 0.54 mmol, 1.0 equiv) in methanol (10 mL) under nitrogen palladium on carbon[Pd/C](46 mg, 10% w/w) was added. The reaction mixture was purged with $H_2$ gas for 2 h. Product formation was confirmed by LCMS. After the completion of reaction, reaction mixture was filtered through Celite bed & Filtrate was concentrate under reduced pressure to 1-(1-(2,4-bis(trifluoromethyl)phenyl)propyl)-1H-pyrazol-4-amine (200 mg, 100% as brown colour liquid). LCMS: 338 [M+H]$^+$.

Step 4: Synthesis of N-(1-(1-(2,4-bis(trifluoromethyl)phenyl)propyl)-1H-pyrazol-4-yl)-5-(pyridin-2-yl)isoxazole-3-carboxamide. To a solution of 5-(pyridin-2-yl)isoxazole-3-carboxylic acid (60 mg, 0.31 mmol, 1 equiv) in DMF (1 mL), were added HATU (132 mg, 0.31 mmol, 1.1 equiv). The mixture was treated drop wise with DIPEA (130 mg, 1.01 mmol, 3.2 equiv). After stirring at RT for 15 minutes, the mixture was treated drop wise with a solution of the 1-(1-(2,4-bis(trifluoromethyl)phenyl)propyl)-1H-pyrazol-4-amine (106 mg, 0.31 mmol, 1 equiv) in DMF (1 mL). The reaction mixture was kept under stirring for 24 h. Product formation was confirmed with TLC & LCMS and reaction mixture was diluted EtOAc (50 mL) & washed with water (50 mL×2). Organic layer dried over $Na_2SO_4$ & concentrated under reduced pressure to obtain crude which was further purified by flash column chromatography to obtain pure product N-(1-(1-(2,4-bis(trifluoromethyl)phenyl)propyl)-1H-pyrazol-4-yl)-5-(pyridin-2-yl)isoxazole-3-carboxamide. (10 mg, 6.2% as off white solid). $^1$H NMR (400 MHz, DMSO-$d_6$) δ 11.08 (s, 1H), 8.75 (d, J=5.1 Hz, 1H), 8.19 (s, 1H), 8.06 (dp, J=15.2, 8.1 Hz, 5H), 7.77 (s, 1H), 7.56 (t, J=6.0 Hz, 1H), 7.46 (s, 1H), 5.62 (dd, J=9.1, 5.8 Hz, 1H), 2.44 (dd, J=15.2, 7.9 Hz, OH), 2.12 (dp, J=13.6, 6.7 Hz, 1H), 0.86 (t, J=7.4 Hz, 3H). LCMS: 510 [M+H]$^+$

Example S2. Synthesis of N-(1-(2,4-bis(trifluoromethyl)benzyl)-1H-pyrazol-4-yl)-5-(2-hydroxypropan-2-yl)isoxazole-3-carboxamide (Compound 2)

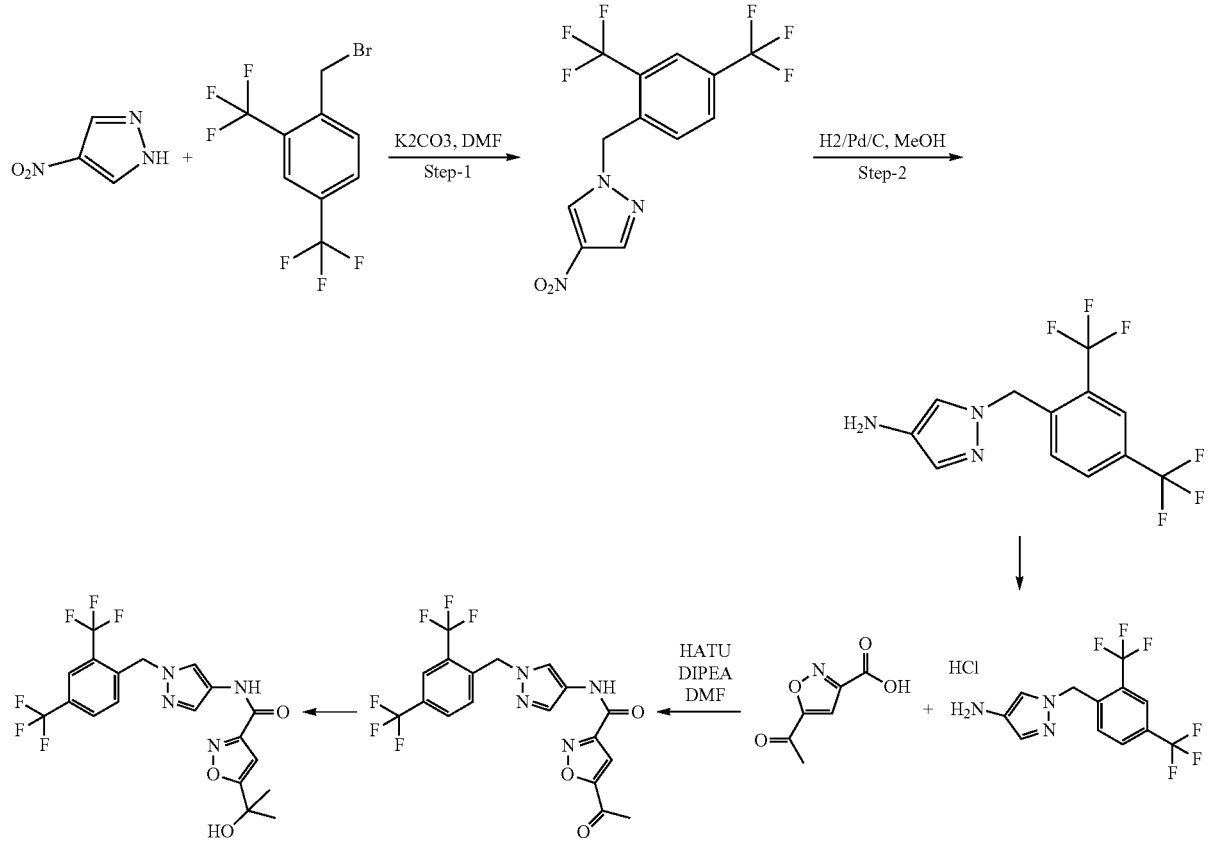

Step 1: Synthesis of 1-(2,4-bis(trifluoromethyl)benzyl)-4-nitro-1H-pyrazole. 4-nitro-1H-pyrazole (0.73 g, 0.006 moles, 1 eq) was taken in DMF (20 mL). Cool this reaction mixture by ice water up to 0° C. add $K_2CO_3$ (1.34 g, 0.009 mole, 1.5 eq) portion wise in it stirred reaction mixture for 10 minute and then add 1-(bromomethyl)-2,4-bis(trifluoromethyl)benzene (2.0 g, 0.006 mole, 1 eq) in it by drop by drop. Stir above reaction mixture for 1 hour (reaction was monitored by TLC & LCMS). After completion of reaction, reaction mixture was diluted with ethyl acetate (50 mL) and extracted with water (50 mL). Collect organic layer and concentrate it to obtain product which further purified by flash chromatography to obtain White color product. LCMS: 339 $[M+H]^+$.

Step 2: Synthesis of 1-(2,4-bis(trifluoromethyl)benzyl)-1H-pyrazol-4-amine. To a stirred solution of 1-(2,4-bis(trifluoromethyl)benzyl)-4-nitro-1H-pyrazole (2 gm, 1 eq) in Methanol (20 mL) under Nitrogen add Palladium on Carbon [Pd/C](10% by weight) in it & purged the reaction mixture by Hydrogen gas for a 2 hour. Reaction was monitored by LCMS. After the completion of reaction, reaction mixture was filtered through Celite bed & Filtered was concentrate to obtained product which is purified by flash chromatography to get Brown Color viscous Liquid. LCMS: 309 $[M+H]^+$.

Step 3: Synthesis of 1-(2,4-bis(trifluoromethyl)benzyl)-1H-pyrazol-4-amine hydrochloride. To 1-(2,4-bis(trifluoromethyl)benzyl)-1H-pyrazol-4-amine (1 gm) was dissolved in ethanol. To it 20 ml HCl in ethanol (15 ml) at 0° C. was added and kept under stirring for half hour at RT Resulting suspension was filtered. And residue obtained was triturated with ether to obtain product 1-(2,4-bis(trifluoromethyl)benzyl)-1H-pyrazol-4-amine hydrochloride. LCMS: 309 $[M+H]^+$.

Step 4: Synthesis of 5-acetyl-N-(1-(2,4-bis(trifluoromethyl)benzyl)-1H-pyrazol-4-yl)isoxazole-3-carboxamide. 5-acetylisoxazole-3-carboxylic acid (500.0 mg, 1 eq, 3.22 m mole) was taken in 5 ml of DMF. To it HATU (1.22 gm., 1 eq, 3.22 m mole)) was added. To it DIPEA (832.25 mg, 2 eq, 6.45 m mole) was added. Reaction mixture was kept under stirring for 20 min. To it 1-(2,4-bis(trifluoromethyl)benzyl)-1H-pyrazol-4-amine hydrochloride (1.112 gm., 1 eq, 3.22 m mole) was added. Resulting reaction mixture was kept under stirring for 24 hr. Work up was done by Adding water and recovered with ethyl acetate. And resulting crude was purified by triturating with IPA. LCMS: 446 $[M+H]^+$.

Step 5: Synthesis of N-(1-(2,4-bis(trifluoromethyl)benzyl)-1H-pyrazol-4-yl)-5-(2-hydroxypropan-2-yl)isoxazole-3-carboxamide. 1-(2,4-bis(trifluoromethyl)benzyl)-1H-pyrazol-4-amine hydrochloride (200.0 mg, 1 eq, 0.447 m mole) was taken in THF at 0° C. To it 3M methyl magnesium bromide (70.99 mg, 4 eq, 1.789 m mole) in diethyl ether was added at 0° C. Reaction mixture was kept on stirring at 0° C. for half an hour. Reaction was quenched with ammonium chloride solution and recovered by ethyl acetate. Obtained residue was sent to prep for purification. $^1$H NMR (400 MHz, DMSO-$d_6$) δ 10.99 (br. S., 1H), 8.27 (s, 1H), 7.99-8.13 (m, 2H), 7.74 (s, 1H), 7.04 (d, J=8.33 Hz, 1H), 6.67 (s, 1H), 5.75 (br. S., 1H), 5.64 (br. S., 2H), 1.50 (s, 6H). LCMS: 462 $[M+H]^+$.

Example S3. Synthesis of 5-acetyl-N-(1-(2,4-bis(trifluoromethyl)benzyl)-1H-pyrazol-4-yl)isoxazole-3-carboxamide (Compound 3)

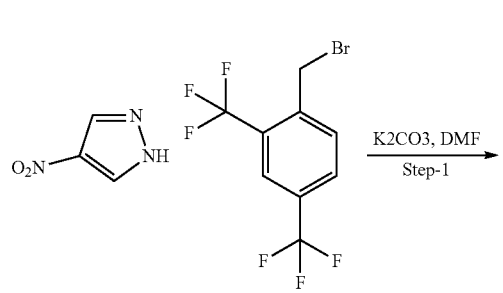

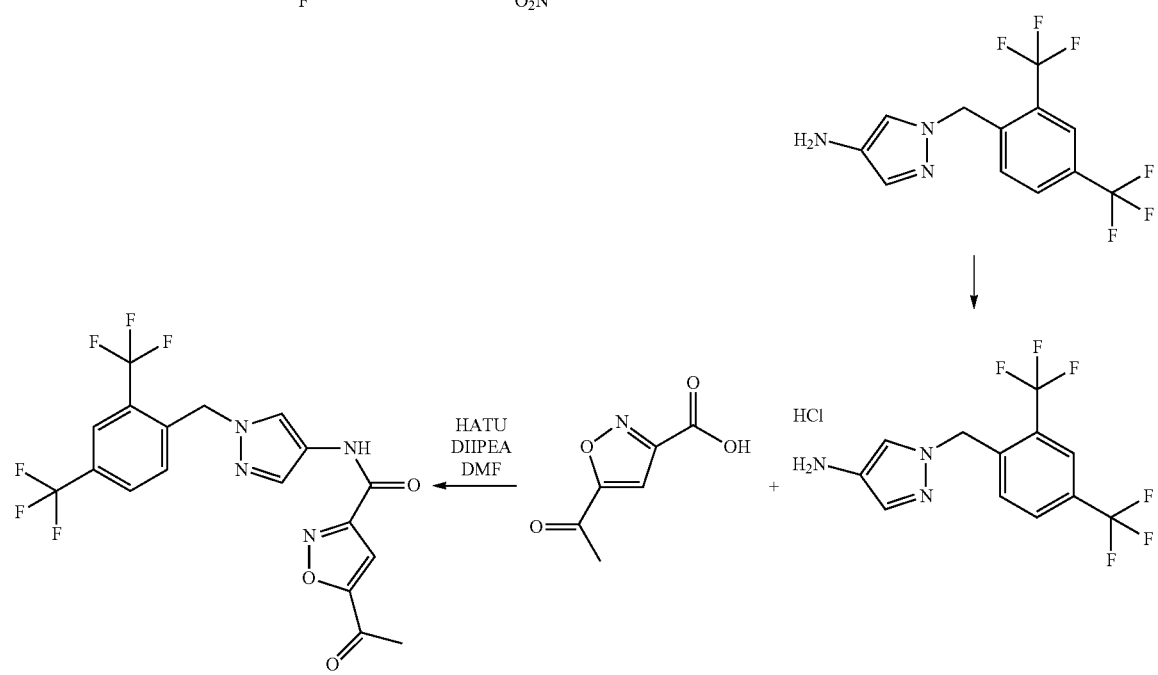

Step 1: Synthesis of 1-(2,4-bis(trifluoromethyl)benzyl)-4-nitro-1H-pyrazole. 4-nitro-1H-pyrazole (0.73 g, 0.006 moles, 1 eq) was taken in DMF (20 mL). Cool this reaction mixture by ice water up to 0° C. add K₂CO₃ (1.34 g, 0.009 mole, 1.5 eq) portion wise in it stirred reaction mixture for 10 minute and then add 1-(bromomethyl)-2,4-bis(trifluoromethyl)benzene (2.0 g, 0.006 mole, 1 eq) in it by drop by drop. Stir above reaction mixture for 1 hour (reaction was monitored by TLC & LCMS). After completion of reaction, reaction mixture was diluted with ethyl acetate (50 mL) and extracted with water (50 mL). Collect organic layer and concentrate it to obtain product which further purified by flash chromatography to obtain White color product. LCMS: 339 [M+H]⁺.

Step 2: Synthesis of 1-(2,4-bis(trifluoromethyl)benzyl)-1H-pyrazol-4-amine. To a stirred solution of 1-(2,4-bis(trifluoromethyl)benzyl)-4-nitro-1H-pyrazole (2 gm, 1 eq) in methanol (20 mL) under Nitrogen add Palladium on Carbon [Pd/C](10% by weight) in it & purged the reaction mixture by Hydrogen gas for a 2 hour. Reaction was monitored by LCMS. After the completion of reaction, reaction mixture was filtered through Celite bed & Filtered was concentrate to obtained product which is purified by flash chromatography to get Brown Color viscous Liquid. LCMS: 309 [M+H]⁺.

Step 3: Synthesis of 1-(2,4-bis(trifluoromethyl)benzyl)-1H-pyrazol-4-amine hydrochloride. To 1-(2,4-bis(trifluoromethyl)benzyl)-1H-pyrazol-4-amine (1 gm) was dissolved in ethanol. To it 20 ml of HCl in ethanol (15 ml) at 0° C. was added and kept under stirring for half hour at RT Resulting suspension was filtered. And residue obtained was triturated with ether to obtain product 1-(2,4-bis(trifluoromethyl)benzyl)-1H-pyrazol-4-amine hydrochloride. LCMS: 309 [M+H]⁺.

Step 4: Synthesis of 5-acetyl-N-(1-(2,4-bis(trifluoromethyl)benzyl)-1H-pyrazol-4-yl)isoxazole-3-carboxamide. 5-acetylisoxazole-3-carboxylic acid (200.0 mg, 1 eq, 1.29 m mole)) was taken in 3 ml of DMF. To it HATU (491.4 mg, 1 eq, 1.29 m mole)) was added. To it DIPEA (332.8 mg, 2 eq, and 2.58 m mole) was added. Reaction mixture was kept under stirring for 20 min. To it 1-(2,4-bis(trifluoromethyl)benzyl)-1H-pyrazol-4-amine hydrochloride (445.1 mg, 1 eq, 1.29 m mole) was added. Resulting reaction mixture was kept under stirring for 24 hr. Work up was done by Adding water and recovered with ethyl acetate. And resulting crude was purified by triturating with IPA. ¹H NMR (400 MHz, DMSO-d₆) δ 11.23 (br. s., 1H), 8.32 (s, 1H), 7.96-8.16 (m, 2H), 7.78 (s, 1H), 7.72 (s, 1H), 7.06 (d, J=7.89 Hz, 1H), 5.67 (br. s., 2H), 2.57-2.67 (m, 3H). LCMS: 446 [M+H]+.

Example S4. Synthesis of N-(1-(2,4-bis(trifluoromethyl)benzyl)-1H-pyrazol-4-yl)-3-(3-fluorophenyl)-1,2,4-oxadiazole-5-carboxamide formate (Compound 4 formate)

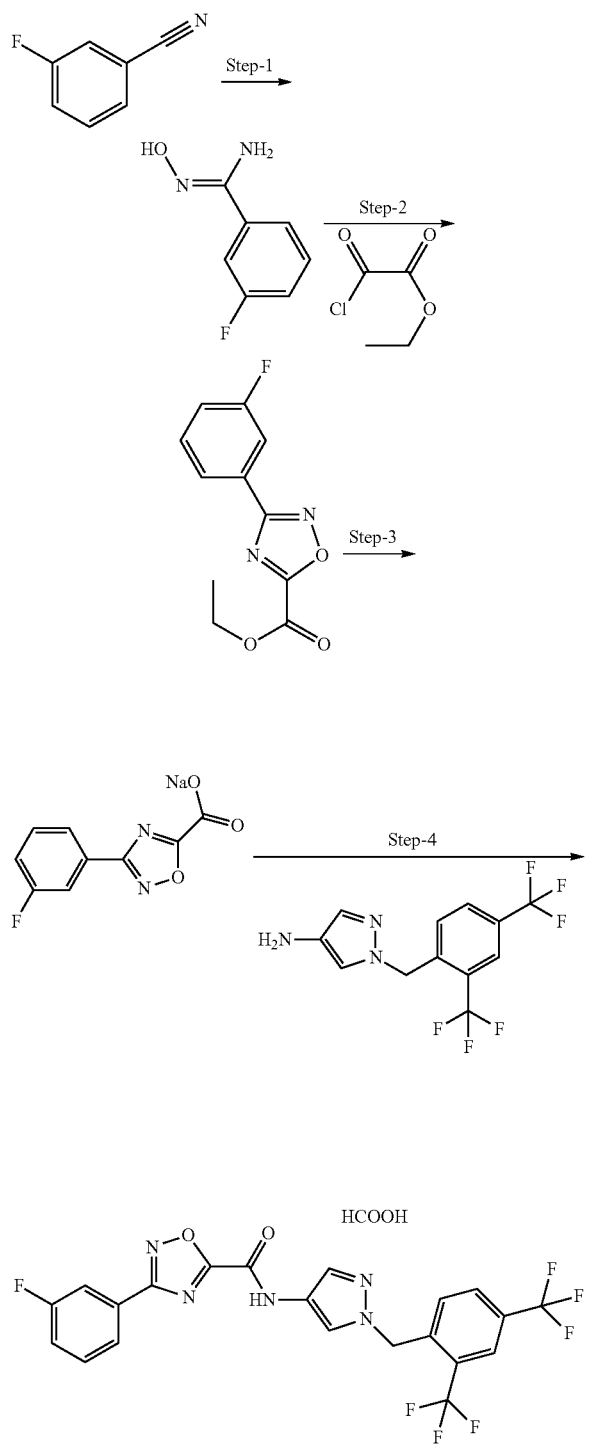

Step 1: Synthesis Of (Z)-3-fluoro-N'-hydroxybenzimidamide. 3-fluorobenzonitrile (3.0 gm, 1 eq, 0.024 moles) was dissolved inn THF:MeOH (1:1). To it NH₂OH·HCl (1.5 eq, 2.60 gm, and 0.037 mole) was added. To it TEA (3.5 eq, 12.08 ml, and 0.086 mole) was added. And reaction mixture kept at RT for 24 hours. Work UP was done by evaporating Reaction mixture up to dryness. And then 20% MeOH/DCM was added and obtained suspension was filtered. Organic layer was dried over Na₂SO₄ and concentrated under reduced pressure to get the product as white solid (Z)-3-fluoro-N'-hydroxybenzimidamide (2.5 g). LCMS: 154 [M+H]+.

Step 2: Synthesis Of ethyl 3-(3-fluorophenyl)-1, 2, 4-oxadiazole-5-carboxylate. (Z)-3-fluoro-N'-hydroxybenzimidamide (2.0 gm., 1 eq, 0.0129 moles) was taken in 15 ml of THF. To it ethyl 2-chloro-2-oxoacetate (3.5 gm., 2 eq, 0.0259 moles) was added at 0° C. reaction mixture was kept stirring for 15 minute at RT. After that Reaction was kept stirring for 30 hrs at 70° C. Work up was done by quenching with water and recovered with ethyl acetate. Organic layer was dried over Na₂SO₄ and concentrated under reduced pressure to get the product as yellow liquid of ethyl 3-(3-fluorophenyl)-1, 2, 4-oxadiazole-5-carboxylate (2.1 g). LCMS: 236 [M+H]+.

Step 3: Synthesis Of sodium 3-(3-fluorophenyl)-1, 2, 4-oxadiazole-5-carboxylate (5). Ethyl 3-(3-fluorophenyl)-1, 2, 4-oxadiazole-5-carboxylate (1 eq, 1 gm, 0.004 moles) was taken in 5 ml of methanol. To it NaOH (1 eq, 169 mg, and 0.004 moles) was added And Kept at RT for 2 hrs. Reaction work up was done by evaporating MeOH. And Obtained crude was triturated with diethyl ether to get product as white crystalline solid of sodium 3-(3-fluorophenyl)-1, 2, 4-oxadiazole-5-carboxylate (600 mg)

Step 4: Synthesis N-(1-(2, 4-bis (trifluoromethyl) benzyl)-1H-pyrazol-4-yl)-3-(3-fluorophenyl)-1, 2, 4-oxadiazole-5-carboxamide formate. Sodium 3-(3-fluorophenyl)-1, 2, 4-oxadiazole-5-carboxylate (100 mg, 1 eq, 0.434 m moles) was taken in DCM (2 ml) To it at 0° C. oxalyl chloride (164.3 mg, 3 eq, 1.30 m moles) was added. To it a drop of DMF was added. After 15 minutes Reaction mixture was kept stirring for 1 hr. at RT. Reaction mixture was taken under vacuum up to dryness to obtain 3-(3-fluorophenyl)-1,2,4-oxadiazole-5-carbonyl chloride. Another side 1-(2, 4-bis (trifluoromethyl) benzyl)-1H-pyrazol-4-amine (147.7 mg, 1.1 eq, 0.478 m moles) in DCM (2 ml) was taken. To it TEA (6 eq, 0.36 ml, and 2.604 m moles) was kept under stirring at RT for half an hour. This Reaction mixture was added to 3-(3-fluorophenyl)-1, 2, 4-oxadiazole-5-carbonyl chloride. Reaction mixture was kept under stirring for 24 hr. at RT. Reaction work up was done by adding water and recovered with ethyl acetate. Organic layer was dried over Na₂SO₄ and concentrated under reduced pressure to get the crude. Obtained crude was sent for purification. Product was obtained N-(1-(2,4-bis(trifluoromethyl)benzyl)-1H-pyrazol-4-yl)-3-(3-fluorophenyl)-1,2,4-oxadiazole-5-carboxamide formate (12 mg). ¹H NMR (400 MHz, DMSO-d₆) δ 8.45 (s, 1H), 8.40 (s, 1H), 8.08 (d, J=7.6 Hz, 2H), 7.96 (d, J=7.7 Hz, 1H), 7.86 (d, J=9.1 Hz, 2H), 7.75-7.65 (m, 1H), 7.53 (td, J=8.7, 2.9 Hz, 1H), 7.06 (d, J=8.2 Hz, 1H), 6.90 (s, 1H), 5.69 (s, 2H), 2.39 (s, 0H), 1.52 (d, J=19.7 Hz, 1H), 1.23 (s, 6H), 1.04 (d, J=5.0 Hz, 0H), 0.84 (q, J=10.8, 8.5 Hz, 1H), 0.07 (s, 0H), −0.07 (s, 1H). LCMS: 499 [M+H]+.

Example S5. Synthesis of (S)- and (R)—N-(1-(1-(2, 4-bis(trifluoromethyl)phenyl)ethyl)-1H-pyrazol-4-yl)-5-(pyridin-2-yl)isoxazole-3-carboxamide (Compounds 5 and 6)

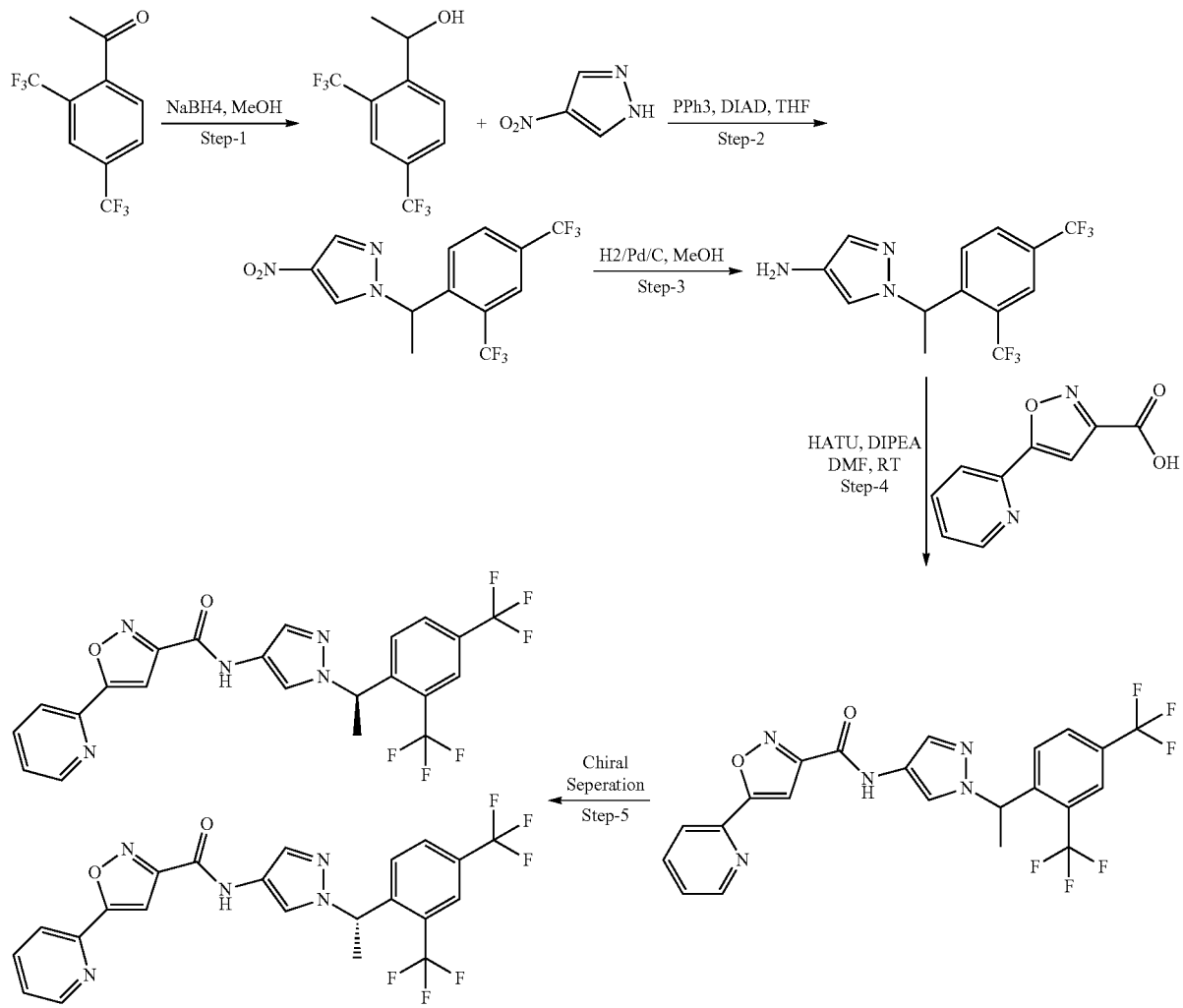

Step 1: Synthesis of 1-[2,4-bis(trifluoromethyl)phenyl] ethanol. To a stirred solution of 1-[2,4-bis(trifluoromethyl) phenyl]ethanone (1 gm, 0.003 mol, 1.0 equiv) in Methanol (5 mL) was added NaBH₄ (0.216 gm, 0.005 mol, 1.2 equiv) portion wise at 0° C. and stirred for 10 minutes. The reaction mixture was allowed to stir for 1 hour at RT. Product formation was confirmed by TLC & LCMS. After completion of reaction, reaction mixture was quenched with water and extracted with ethyl acetate (50 mL×3). Combined organic extracts were washed with water (50 mL×2), dried over anhydrous $Na_2SO_4$ and concentrated under reduced pressure to obtain 1-[2,4-bis (trifluoromethyl) phenyl]ethanol (1 gm, 100% (crude) as colorless liquid). 1H NMR (400 MHz, DMSO-d₆) δ 8.04-8.15 (m, 2H), 7.93 (s, 1H), 5.70 (d, J=3.95 Hz, 1H), 5.09 (br. s., 1H), 1.34 (d, J=6.14 Hz, 3H).

Step 2: Synthesis of 1-{1-[2,4-bis(trifluoromethyl)phenyl]ethyl}-4nitro-1H-pyrazole. To a stirred solution of PPh₃ (517 mg, 1.93 mmol, 1.0 equiv) and DIAD (319 mg, 1.93 mmol, 1.0 equiv) in THF (2 mL), was added 4-nitro-1H-pyrazole (175 mg, 1.55 mmol, 0.8 equiv), and Followed by the addition of 1-[2, 4-bis (trifluoromethyl) phenyl] ethanol (500 mg, 1.93 mmol, 1.0 equiv). The reaction mixture was stirred at RT for 1 h. Product formation was confirmed with TLC & LCMS. After completion of reaction mixture were diluted with EtOAc (50 mL) & washed with water (50 mL×3). Organic layer dried over $Na_2SO_4$ & concentrated under reduced pressure to obtain crude which was further purified by flash column chromatography to obtain pure product 1-{1-[2,4-bis (trifluoromethyl)phenyl]ethyl}-4nitro-1H-pyrazole (550 mg, 84% as brown liquid). LCMS: 354 [M+H]⁺.

Step 3: Synthesis of 1-{1-[2,4-bis(trifluoromethyl)phenyl]ethyl}-1H-pyrazol-4-amine. To a stirred solution of 1-(2,4-bis(trifluoromethyl)benzyl)-4-nitro-1H-pyrazole (500 mg, 1.41 mmol, 1.0 equiv) in Methanol (10 mL) under nitrogen Palladium on Carbon[Pd/C] (75 mg, 10% w/w) was added. Purge the reaction mixture with H₂ gas for 2 h. Product formation was confirmed by LCMS. After the completion of reaction, reaction mixture was filtered through Celite bed & Filtrate was concentrate under reduced pressure to obtain 1-{1-[2, 4-bis (trifluoromethyl) phenyl] ethyl}-1H-pyrazol-4-amine (450 mg, 100% (crude) as brown colour liquid). LCMS: 324 [M+H]⁺.

Step 4: Synthesis of N-(1-(1-(2,4-bis(trifluoromethyl)phenyl)ethyl)-1H-pyrazol-4-yl)-5-(pyridin-2-yl)isoxazole-3-carboxamide. To a solution of 5-(pyridin-2-yl)isoxazole-3-carboxylic acid (200 mg, 1.11 mmol, 1 equiv) in DMF (1 mL), were added HATU (467 mg, 1.22 mmol, 1.1 equiv). The mixture was treated drop wise with DIPEA (461 mg, 3.57 mmol, 3.2 equiv). After stirring at RT for 15 minutes, the mixture was treated drop wise with a solution of the 1-{1-[(2,4bis(trifluoromethyl)phenyl]ethyl}-1H-pyrazol-4-amine (360 mg, 1.11 mmol, 1 equiv) in DMF (1 mL). The reaction mixture was kept under stirring for 24 h. Product formation was confirmed with TLC & LCMS and reaction mixture was diluted EtOAc (50 mL) & washed with water (50 mL×2). Organic layer dried over $Na_2SO_4$ & concentrated under reduced pressure to obtain crude which was further purified by flash column chromatography to obtain pure product N-(1-(1-(2,4-bis(trifluoromethyl)phenyl)ethyl)-1H-pyrazol-4-yl)-5-(pyridin-2-yl)isoxazole-3-carboxamide. (70 mg, 26% as off white solid). LCMS: 496 [M+H]$^+$.

Step 5: (S) & (R)—N-(1-(1-(2,4-bis(trifluoromethyl)phenyl)ethyl)-1H-pyrazol-4-yl)-5-(pyridin-2-yl)isoxazole-3-carboxamide. The racemic mixture of N-(1-(1-(2,4-bis(trifluoromethyl)phenyl)ethyl)-1H-pyrazol-4-yl)-5-(pyridin-2-yl)isoxazole-3-carboxamide (70 mg) was purified by chiral HPLC to obtain the single enantiomers as Enantiomer A (18 mg) and Enantiomer B (20 mg). (Enantiomer A): $^1$H NMR (400 MHz, DMSO-$d_6$) δ 11.09 (s, 1H), 8.76 (d, J=4.7 Hz, 1H), 8.20 (s, 1H), 8.12-7.99 (m, 4H), 7.74 (d, J=8.6 Hz, 1H), 7.56 (dd, J=7.5, 4.8 Hz, 1H), 7.47 (s, 1H), 5.94 (q, J=6.8 Hz, 1H), 1.88 (d, J=6.9 Hz, 3H). (Enantiomer B): $^1$H NMR (400 MHz, DMSO-$d_6$) δ 11.09 (s, 1H), 8.76 (d, J=4.6 Hz, 1H), 8.20 (s, 1H), 8.12-7.96 (m, 4H), 7.74 (d, J=8.9 Hz, 1H), 7.60-7.52 (m, 1H), 7.47 (s, 1H), 5.94 (q, J=6.9 Hz, 1H), 1.88 (d, J=6.8 Hz, 3H).

Example S6. Synthesis of (S)- and (R)—N-(1-(1-(2,4-bis(trifluoromethyl)phenyl)ethyl)-1H-pyrazol-4-yl)-5-(furan-2-yl)isoxazole-3-carboxamide (Compounds 7 and 8)

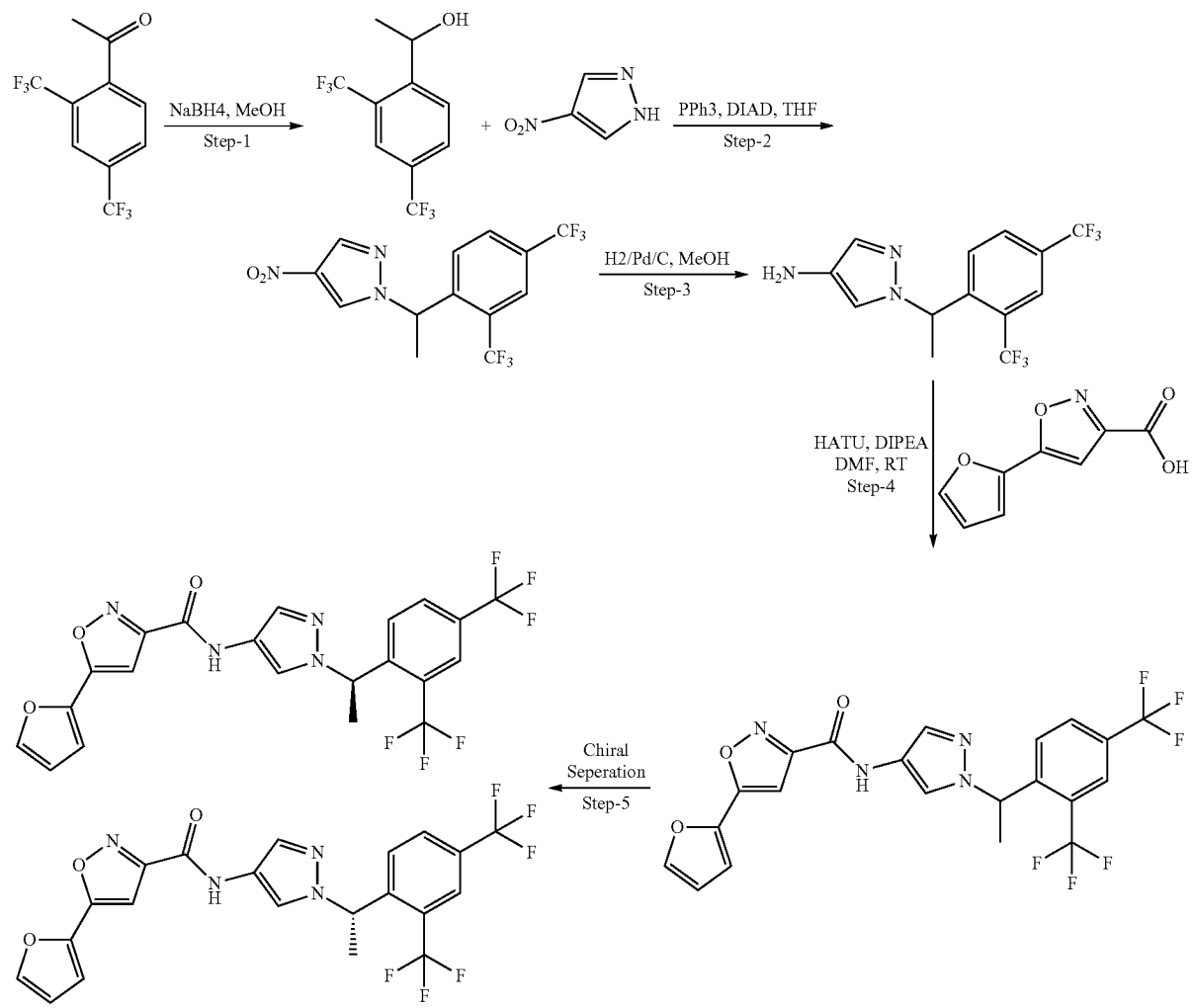

Step 1: Synthesis of 1-(2,4-bis(trifluoromethyl)phenyl)ethan-1-ol. To a stirred solution of 1-(2,4-bis(trifluoromethyl)phenyl)ethan-1-one (1 gm, 0.003 mol, 1.0 eq) in Methanol (5 mL) was added $NaBH_4$ (0.216 gm, 0.005 mol, 1.2 eq) portion wise at 0° C. and stirred for 10 minutes. The reaction mixture was allowed to stir for 1 hour at RT. Product formation was confirmed by TLC & NMR. After completion of reaction, reaction mixture was quenched with water and extracted with ethyl acetate (50 mL×3). Combined organic extracts were washed with water (50 mL×2), dried over anhydrous Na₂SO₄ and concentrated under reduced pressure to obtain 1-(2,4-bis(trifluoromethyl)phenyl)ethan-1-ol (1 gm, 100% as colorless liquid). ¹H NMR (400 MHz, DMSO-d₆) δ 8.04-8.15 (m, 2H), 7.93 (s, 1H), 5.70 (d, J=3.95 Hz, 1H), 5.09 (br. s., 1H), 1.34 (d, J=6.14 Hz, 3H).

Step 2: Synthesis of 1-(1-(2,4-bis(trifluoromethyl)phenyl)ethyl)-4-nitro-1H-pyrazole. To a stirred solution of PPh₃ (517 mg, 1.93 mmol, 1.0 eq) and DIAD (319 mg, 1.93 mmol, 1.0 eq) in THF (2 mL) was added 1-(2,4-bis(trifluoromethyl)phenyl)ethan-1-ol (500 mg, 1.93 mmol, 1.0 eq). Followed by drop wise addition of 4-nitro-1H-pyrazole (175 mg, 1.55 mmol, 0.8 eq), The reaction mixture was stirred at RT for overnight. Product formation was confirmed with TLC & LCMS. After completion of reaction mixture were diluted with EtOAc (50 mL) & washed with water (50 mL×3). Organic layer dried over Na₂SO₄ & concentrated under reduced pressure to obtain crude which was further purified by flash column chromatography to obtain pure product 1-(1-(2,4-bis(trifluoromethyl)phenyl)ethyl)-4-nitro-1H-pyrazole (550 mg, 84% as brown liquid). LCMS: 353 [M+H]⁺.

Step 3: Synthesis of 1-(1-(2,4-bis(trifluoromethyl)phenyl)ethyl)-1H-pyrazol-4-amine. To a stirred solution of 1-(2,4-bis(trifluoromethyl)benzyl)-4-nitro-1H-pyrazole (500 mg, 1.41 mmol, 1.0 eq) in Methanol (10 mL) under nitrogen Palladium on Carbon[Pd/C](75 mg, 10% w/w) was added. Purge the reaction mixture with H₂ gas for 2 h. Product formation was confirmed by LCMS. After the completion of reaction, reaction mixture was filtered through Celite bed & Filtrate was concentrate under reduced pressure to obtain 1-(1-(2,4-bis(trifluoromethyl)phenyl)ethyl)-1H-pyrazol-4-amine (450 mg, 100% as brown colour liquid). LCMS: 323 [M+H]⁺.

Step 4: Synthesis of N-(1-(1-(2,4-bis(trifluoromethyl)phenyl)ethyl)-1H-pyrazol-4-yl)-5-(furan-2-yl)isoxazole-3-carboxamide. To a solution of 5-(furan-2-yl)isoxazole-3-carboxylic acid (200 mg, 1.11 mmol, 1 eq) in DMF (1 mL), were added HATU (467 mg, 1.22 mmol, 1.1 eq). The mixture was treated drop wise with DIPEA (461 mg, 3.57 mmol, 3.2 eq). After stirring at RT for 15 minutes, the mixture was treated drop wise with a solution of the 1-{1 [2,4bis(trifluoromethyl)phenyl]ethyl}-1H-pyrazol-4-amine (360 mg, 1.11 mmol, 1 eq) in DMF (1 mL). The reaction mixture was kept under stirring for 24 h. Product formation was confirmed with TLC & LCMS and reaction mixture was diluted EtOAc (50 mL) & washed with water (50 mL×2). Organic layer dried over Na₂SO₄ & concentrated under reduced pressure to obtain crude which was further purified by flash column chromatography to obtain pure product N-(1-(1-(2,4-bis(trifluoromethyl)phenyl)ethyl)-1H-pyrazol-4-yl)-5-(furan-2-yl)isoxazole-3-carboxamide. (150 mg, 27% as off white solid). LCMS: 484 [M+H]⁺.

Step 5: (S) & (R)—N-(1-(1-(2,4-bis(trifluoromethyl)phenyl)ethyl)-1H-pyrazol-4-yl)-5-(furan-2-yl)isoxazole-3-carboxamide. The racemic mixture of N-(1-(1-(2,4-bis(trifluoromethyl)phenyl)ethyl)-1H-pyrazol-4-yl)-5-(furan-2-yl)isoxazole-3-carboxamide (mg) was purified by chiral HPLC to obtain the single enantiomers as Enantiomer A (45 mg) and Enantiomer B (40 mg). LCMS: 484 [M+H]⁺. (Enantiomer A): ¹H NMR (400 MHz, DMSO-d₆) δ 11.06 (s, 1H), 8.19 (s, 1H), 8.09 (d, J=8.3 Hz, 1H), 8.05 (s, 1H), 8.00 (s, 1H), 7.73 (d, J=6.9 Hz, 1H), 7.28 (d, J=3.6 Hz, 1H), 7.14 (s, 1H), 6.80-6.74 (m, 1H), 5.93 (q, J=6.9 Hz, 1H), 1.87 (d, J=6.9 Hz, 3H). (Enantiomer B): ¹H NMR (400 MHz, DMSO-d₆) δ 11.05 (s, 1H), 8.18 (s, 1H), 8.08 (d, J=8.3 Hz, 1H), 8.04 (s, 1H), 8.00 (d, J=1.9 Hz, 1H), 7.73 (d, J=7.5 Hz, 1H), 7.28 (d, J=3.6 Hz, 1H), 7.14 (s, 1H), 6.80–6.74 (m, 1H), 5.93 (q, J=6.9 Hz, 1H), 1.87 (d, J=6.9 Hz, 3H).

Example S7. Synthesis of N-(1-(1-(2,4-bis(trifluoromethyl)phenyl)-ethyl)-1H-pyrazol-4-yl)-5-(thiophen-2-yl)isoxazole-3-carboxamide (Compound 9)

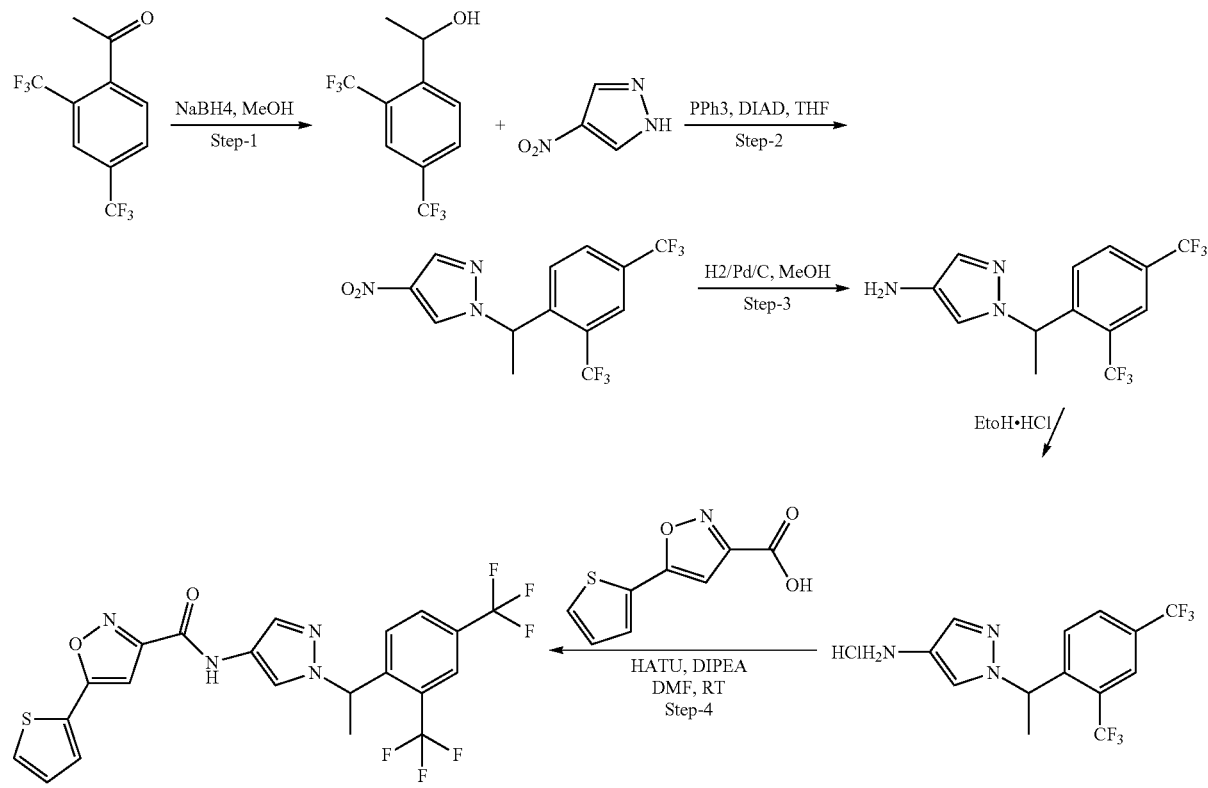

Step 1: Synthesis of 1-[2,4-bis(trifluoromethyl)phenyl] ethanol. To a stirred solution of 1-[2,4-bis(trifluoromethyl)phenyl]ethanone (1 gm, 0.003 mol, 1.0 equiv) in Methanol (5 mL) was added NaBH₄ (0.216 gm, 0.005 mol, 1.2 equiv) portion wise at 0° C. and stirred for 10 minutes. The reaction mixture was allowed to stir for 1 hour at RT. Product formation was confirmed by TLC & LCMS. After completion of reaction, reaction mixture was quenched with water and extracted with ethyl acetate (50 mL×3). Combined organic extracts were washed with water (50 mL×2), dried over anhydrous Na2SO4 and concentrated under reduced pressure to obtain 1-[2,4-bis (trifluoromethyl) phenyl]ethanol (1 gm, 100% (crude) as colorless liquid). ¹H NMR (400 MHz, DMSO-$d_6$) δ 8.04-8.15 (m, 2H), 7.93 (s, 1H), 5.70 (d, J=3.95 Hz, 1H), 5.09 (br. s., 1H), 1.34 (d, J=6.14 Hz, 3H).

Step 2: Synthesis of 1-{1-[2,4-bis(trifluoromethyl)phenyl]ethyl}-4nitro-1H-pyrazole. To a stirred solution of PPh₃ (517 mg, 1.93 mmol, 1.0 equiv) and DIAD (319 mg, 1.93 mmol, 1.0 equiv) in THF (2 mL), was added 4-nitro-1H-pyrazole (175 mg, 1.55 mmol, 0.8 equiv), and Followed by the addition of 1-[2, 4-bis (trifluoromethyl) phenyl]ethanol (500 mg, 1.93 mmol, 1.0 equiv). The reaction mixture was stirred at RT for 1 h. Product formation was confirmed with TLC & LCMS. After completion of reaction mixture were diluted with EtOAc (50 mL) & washed with water (50 mL×3). Organic layer dried over Na₂SO₄ & concentrated under reduced pressure to obtain crude which was further purified by flash column chromatography to obtain pure product 1-{1-[2,4-bis (trifluoromethyl)phenyl]ethyl}-4-nitro-1H-pyrazole (550 mg, 84% as brown liquid). LCMS: 354 [M+H]⁺.

Step 3: Synthesis of 1-{1-[2,4-bis(trifluoromethyl)phenyl]ethyl}-1H-pyrazol-4-amine. To a stirred solution of 1-(2,4-bis(trifluoromethyl)benzyl)-4-nitro-1H-pyrazole (500 mg, 1.41 mmol, 1.0 equiv) in methanol (10 mL) under nitrogen palladium on carbon[Pd/C](75 mg, 10% w/w) was added. Purge the reaction mixture with H₂ gas for 2 h. Product formation was confirmed by LCMS. After the completion of reaction, reaction mixture was filtered through Celite bed & Filtrate was concentrate under reduced pressure to obtain 1-{1-[2, 4-bis (trifluoromethyl) phenyl]ethyl}-1H-pyrazol-4-amine (450 mg, 100% (crude) as brown colour liquid). LCMS: 324 [M+H]⁺.

Step 4: N-(1-(1-(2,4-bis(trifluoromethyl)phenyl)ethyl)-1H-pyrazol-4-yl)-5-(thiophen-2-yl)isoxazole-3-carboxamide. To a solution of 5-furan-2-yl-isoxazole-3-carboxylic acid (200 mg, 1.11 mmol, 1 equiv) in DMF (1 mL), were added HATU (467 mg, 1.22 mmol, 1.1 equiv). The mixture was treated drop wise with DIPEA (461 mg, 3.57 mmol, 3.2 equiv). After stirring at RT for 15 minutes, the mixture was treated drop wise with a solution of the 1-{1[2,4bis(trifluoromethyl)phenyl]ethyl}-1H-pyrazol-4-amine (360 mg, 1.11 mmol, 1 equiv) in DMF (1 mL). The reaction mixture was kept under stirring for 24 h. Product formation was confirmed with TLC & LCMS and reaction mixture was diluted EtOAc (50 mL) & washed with water (50 mL×2). Organic layer dried over Na₂SO₄ & concentrated under reduced pressure to obtain crude which was further purified by flash column chromatography to obtain pure product N-(1-(1-(2, 4-bis(trifluoromethyl)phenyl)ethyl)-1H-pyrazol-4-yl)-5-(thiophen-2-yl)isoxazole-3-carboxamide. (70 mg, 28% as off white solid). ¹H NMR (400 MHz, DMSO-$d_6$) δ 11.04 (s, 1H), 8.19 (s, 1H), 8.09 (d, J=8.3 Hz, 1H), 8.05 (s, 1H), 7.89 (d, J=5.0 Hz, 1H), 7.84 (d, J=3.7 Hz, 1H), 7.73 (d, J=7.6 Hz, 1H), 7.32-7.21 (m, 1H), 5.93 (q, J=6.9 Hz, 1H), 1.87 (d, J=6.9 Hz, 3H). LCMS: 501 [M+H]⁺.

Example S8. Synthesis of N-(1-(2,4-bis(trifluoromethyl)benzyl)-1H-pyrazol-4-yl)-5-(pyridin-4-yl)isoxazole-3-carboxamide (Compound 10)

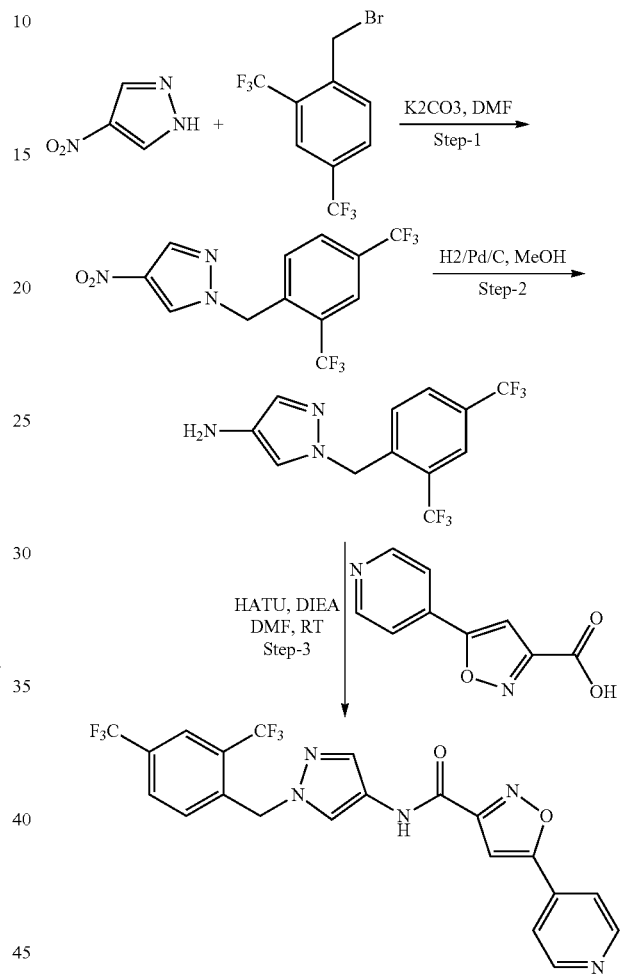

Step 1: Synthesis of 1-(2,4-bis (trifluoromethyl) benzyl)-4-nitro-1H-pyrazole. To a stirred solution of 4-nitro-1H-pyrazole (1.83 g, 16.28 mmol, 1 eq) in DMF (10 ml) was added K₂CO₃ (3.36 gm, 24.42 mmol, 1.5 eq) portion wise at 0° C. and stirred for 10 minutes. 1-(bromomethyl)-2,4-bis (trifluoromethyl)benzene (5.0 gm, 16.28 mmol, 1 eq) was added drop wise 0° C. The reaction mixture was allowed to stir for 1 hour at RT. Product formation was confirmed by LCMS. After completion of reaction, reaction mixture was diluted with water and extracted with ethyl acetate (100 mL×3). Combined organic extracts were washed with water (100 mL×4), dried over anhydrous Na₂SO₄ and concentrated under reduced pressure to obtain 1-(2,4-bis (trifluoromethyl) benzyl)-4-nitro-1H-pyrazole (4.5 g, as white solid). LCMS: 339 [M+H]⁺.

Step 2: Synthesis of 1-(2, 4-bis (trifluoromethyl)-1H-pyrazol-4-amine. To a stirred solution of 1-(2,4-bis(trifluoromethyl)benzyl)-4-nitro-1H-pyrazole (2.5 g, 1 eq) in Methanol (40 mL) under nitrogen Palladium on Carbon[Pd/C](250 mg, 10% w/w) was added. Purge the reaction mixture with H₂ gas for 2 h. Product formation was confirmed by LCMS. After the completion of reaction, reaction mixture was filtered through Celite bed & Filtrate was concentrate under reduced pressure to obtain 1-(2, 4-bis (trifluoromethyl)-1H-pyrazol-4-amine (0.800 g, as brown colour liquid). LCMS: 309 [M+H]⁺.

Step 3: Synthesis of N-(1-(2,4-bis(trifluoromethyl)benzyl)-1H-pyrazol-4-yl)-5-(pyridin-4-yl)isoxazole-3-carboxamide. To a stirred solution of 5-(pyridin-4-yl)-1,2-oxazole-3-carboxylic acid (50 mg, 0.263 mmol, 1 eq) in DMF (5 mL) add HATU (109 mg, 0.289 mmol, 1.1 eq) and stirred resulting reaction mixture for one hour. Then add 1-(2, 4-bis (trifluoromethyl)-1H-pyrazol-4-amine (81 mg, 0.263 mmol, 1 eq) and DIPEA (108 mg, 0.841 mmol, 3.2 eq) and stirred reaction mixture for overnight at RT. The reaction mixture was diluted with Ethyl Acetate (50 mL) and washed with Water (70 mL), collect Organic layer and dried over Anhydrous Sodium Sulphate and concentrate on rota vapour to yield crude product which is further purified by Reversed phase chromatography (10 mg). ¹H NMR (400 MHz, DMSO-d₆) δ ppm 5.66 (br. s., 2H) 7.04 (d, J=7.02 Hz, 1H) 7.77 (d, J=8.33 Hz, 2H) 7.93 (d, J=5.70 Hz, 2H) 8.02-8.12 (m, 1H) 8.32 (s, 1H) 8.51 (br. s., 1H) 8.78 (d, J=4.82 Hz, 2H) 11.19 (br. s., 1H). LCMS: 481 (M+H)⁺.

Example S9. Synthesis of N-(1-(2,4-bis(trifluoromethyl)benzyl)-1H-pyrazol-4-yl)-5-(pyridin-2-yl)isoxazole-3-carboxamide (Compound 11)

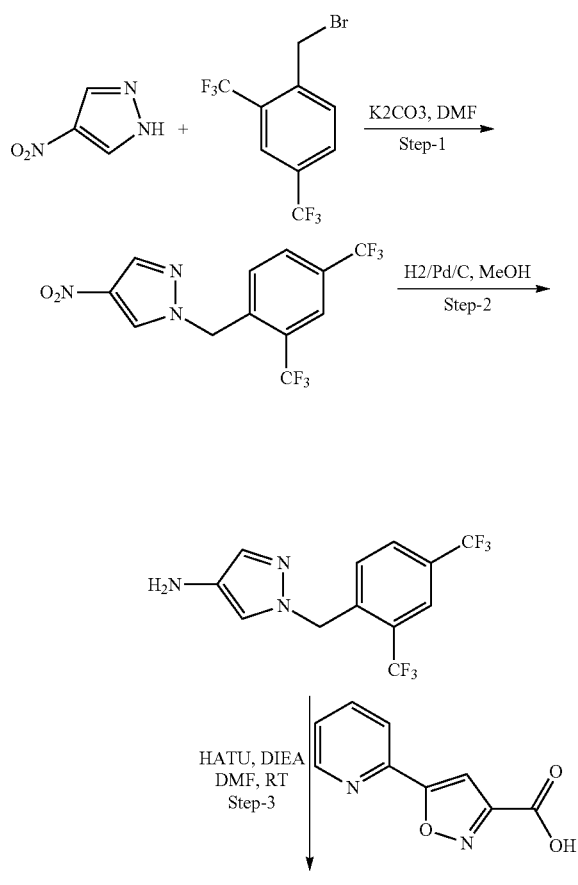

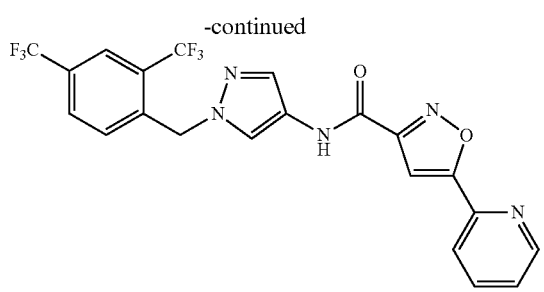

Step 1: Synthesis of 1-(2,4-bis (trifluoromethyl) benzyl)-4-nitro-1H-pyrazole. To a stirred solution of 4-nitro-1H-pyrazole (1.83 g, 16.28 mmol, 1 eq) in DMF (10 ml) was added K₂CO₃ (3.36 gm, 24.42 mmol, 1.5 eq) portion wise at 0° C. and stirred for 10 minutes. 1-(bromomethyl)-2,4-bis (trifluoromethyl)benzene (5.0 gm, 16.28 mmol, 1 eq) was added drop wise 0° C. The reaction mixture was allowed to stir for 1 hour at RT. Product formation was confirmed by LCMS. After completion of reaction, reaction mixture was diluted with water and extracted with ethyl acetate (100 mL×3). Combined organic extracts were washed with water (100 mL×4), dried over anhydrous Na₂SO₄ and concentrated under reduced pressure to obtain 1-(2,4-bis (trifluoromethyl) benzyl)-4-nitro-1H-pyrazole (4.5 g, as white solid). LCMS: 339 [M+H]⁺.

Step 2: Synthesis of 1-(2, 4-bis (trifluoromethyl)-1H-pyrazol-amine. To a stirred solution of 1-(2,4-bis(trifluoromethyl)benzyl)-4-nitro-1H-pyrazole (2.5 g, 1 eq) in Methanol (40 mL) under nitrogen Palladium on Carbon[Pd/C](250 mg, 10% w/w) was added. Purge the reaction mixture with H₂ gas for 2 h. Product formation was confirmed by LCMS. After the completion of reaction, reaction mixture was filtered through Celite bed & Filtrate was concentrate under reduced pressure to obtain 1-(2, 4-bis (trifluoromethyl)-1H-pyrazol-4-amine (0.800 g, as brown colour liquid). LCMS: 309 [M+H]⁺.

Step 3: Synthesis of N-(1-(2,4-bis(trifluoromethyl)benzyl)-1H-pyrazol-4-yl)-5-(pyridin-2-yl)isoxazole-3-carboxamide. To a stirred solution of 5-(pyridin-2-yl)-1,2-oxazole-3-carboxylic acid (50 mg, 0.263 mmol, 1 eq) in DMF (5 mL) add HATU (109 mg, 0.289 mmol, 1.1 eq) and stirred resulting reaction mixture for one hour. Then add 1-(2, 4-bis (trifluoromethyl)-1H-pyrazol-4-amine (81 mg, 0.263 mmol, 1 eq) and DIPEA (108 mg, 0.841 mmol, 3.2 eq) and stirred reaction mixture for overnight at RT. The reaction mixture was diluted with Ethyl Acetate (50 mL) and washed with water (70 mL), collect Organic layer and dried over Anhydrous Sodium Sulphate and concentrate on rota vapor to yield crude product which is further purified by Reversed phase chromatography (5 mg). ¹H NMR (400 MHz, DMSO-d₆) δ ppm 5.67 (br. s., 2H) 7.07 (d, J=8.77 Hz, 1H) 7.50 (s, 3H) 7.57 (d, J=7.02 Hz, 1H) 7.79 (s, 1H) 7.99-8.11 (m, 2H) 8.33 (s, 1H) 8.76 (br. s., 1H) 11.15 (s, 1H). LCMS: 481[M+H]⁺.

Example S10. Synthesis of N-(1-{1-[2,4-bis(trifluoromethyl)phenyl]ethyl}-1H-pyrazol-4-yl)-5-(furan-2-yl) isoxazole-3-carboxamide (Compound 12)

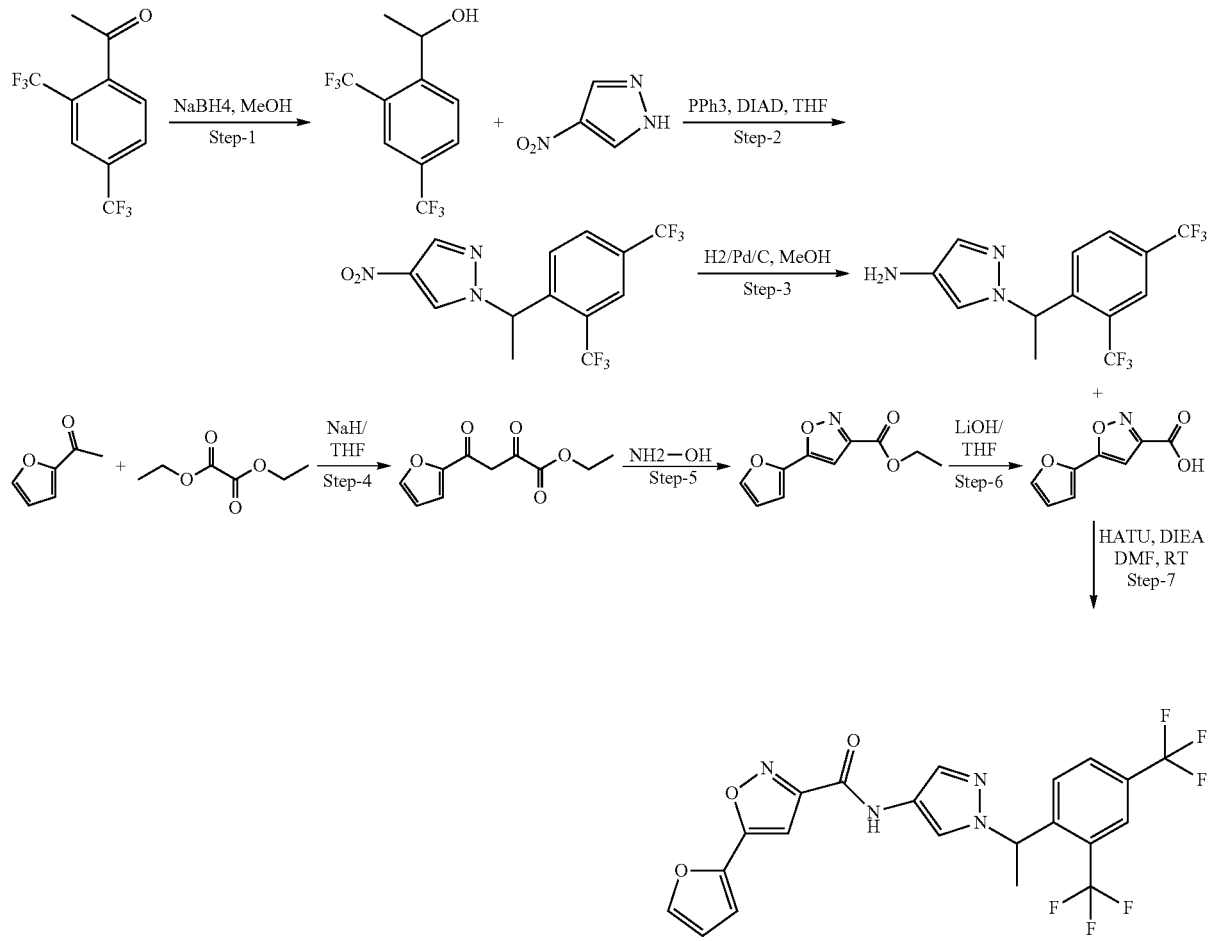

Step 1: Synthesis of 1-[2,4-bis(trifluoromethyl)phenyl] ethanol. To a stirred solution of 1-[2,4-bis(trifluoromethyl) phenyl]ethanone (100 mg, 0.39 mmol, 1.0 equiv) in Methanol (5 mL) was added NaBH₄ (17 mg, 0.46 mmol, 1.2 equiv) portion wise at 0° C. and stirred for 10 minutes. The reaction mixture was allowed to stir for 1 hour at RT. Product formation was confirmed by TLC & LCMS. After completion of reaction, reaction mixture was quenched with water and extracted with ethyl acetate (50 mL×3). Combined organic extracts were washed with water (50 mL×2), dried over anhydrous Na₂SO₄ and concentrated under reduced pressure to obtain 1-[2,4-bis (trifluoromethyl) phenyl]ethanol (100 mg, 100% (crude) as colorless liquid). ¹H NMR (400 MHz, DMSO-d₆) δ 8.04-8.15 (m, 2H), 7.93 (s, 1H), 5.70 (d, J=3.95 Hz, 1H), 5.09 (br. s., 1H), 1.34 (d, J=6.14 Hz, 3H).

Step 2: Synthesis of 1-{1-[2,4-bis(trifluoromethyl)phenyl]ethyl}-4nitro-1H-pyrazole. To a stirred solution of PPh₃ (103 mg, 0.38 mmol, 1.0 equiv) and DIAD (78 mg, 0.38 mmol, 1.0 equiv) in THF (2 mL), was added 4-nitro-1H-pyrazole (35 mg, 0.31 mmol, 0.8 equiv), and Followed by the addition of 1-[2, 4-bis (trifluoromethyl) phenyl]ethanol (100 mg, 1.93 mmol, 1.0 equiv). The Resultant reaction mixture was stirred at RT for 1 h. Product formation was confirmed with TLC & LCMS. After completion of reaction mixture were diluted with EtOAc (50 mL) & washed with water (50 mL×3). Organic layer dried over Na₂SO₄ & concentrated under reduced pressure to obtain crude which was further purified by flash column chromatography to obtain pure product 1-{1-[2,4-bis (trifluoromethyl)phenyl] ethyl}-4nitro-1H-pyrazole (75 mg, 55% as brown liquid). LCMS: 354 [M+H]⁺.

Step 3: Synthesis of 1-{1-[2,4-bis(trifluoromethyl)phenyl]ethyl}-1H-pyrazol-4-amine. To a stirred solution of 1-(2,4-bis(trifluoromethyl)benzyl)-4-nitro-1H-pyrazole (200 mg, 1.0 equiv) in Methanol (10 mL) under nitrogen Palladium on Carbon[Pd/C](20 mg, 10% w/w) was added. Purge the reaction mixture with H₂ gas for 2 h. Product formation was confirmed by LCMS. After the completion of reaction, reaction mixture was filtered through Celite bed & Filtrate was concentrate under reduced pressure to obtain 1-{1-[2, 4-bis (trifluoromethyl) phenyl]ethyl}-1H-pyrazol-4-amine (200 mg, as brown colour liquid). LCMS: 324 [M+H]⁺.

Step 4: Synthesis of ethyl 4-(2-furyl)-2, 4-dioxobutyrate. To a solution of 2-acetylfuran (5.0 g, 45.40 mmol, 1 equiv) in THF was added portion wise 60% Sodium hydride (3.63 g, 90.81 mmol, 2.0 equiv) at 0° C. The resultant reaction mixture was stirred for another 30 minutes at RT, followed by drop wise addition of diethyl oxalate (12.28 ml, 90.81 mmol, 2.0 equiv) at 0° C. and reaction mixture was stir for another 18 hours at RT. Product formation was confirmed by TLC and LCMS. The reaction mixture was quenched with ice water and washed with diethyl ether (2×100 mL). Aqueous layer was separated and neutralized with 1N HCl and extracted with EtOAc (3×100 mL). Combined organic extracts were washed with water (2×100 mL), dried over anhydrous $Na_2SO_4$ and concentrated under reduced pressure to obtain crude which was purified by combi-flash chromatography (15-20% Ethyl acetate in hexane) to obtain Ethyl 4-(2-furyl)-2, 4-dioxobutyrate (3.6 g, 45% as yellow solid). LCMS: 211 $[M+H]^+$.

Step 5: Synthesis of 5-furan-2-yl-isoxazole-3-carboxylic acid ethyl ester. A suspension of 4-furan-2-yl-2, 4-dioxobutyric acid ethyl ester (1.6 g, 7.61 mmol, 1.0 equiv) and hydroxylamine hydrochloride salt (0.528 g, 7.61 mmol, 1.0 equiv) in EtOH was stirred at 85° C. for 2 h. Product formation was confirmed by TLC and LCMS. The resulting mixture was concentrated under reduced pressure, the residue was dissolved in DCM and distilled water. Organic phase was separated, dried over anhydrous $Na_2SO_4$, filtered through silica gel pad, and then concentrated under reduced pressure to give 5-furan-2-yl-isoxazole-3-carboxylic acid ethyl ester. The crude product obtained was used in the next steps without further purification (700 mg, 52% as yellow solid). LCMS: 208 $[M+H]^+$.

Step 6: Synthesis of 5-furan-2-yl-isoxazole-3-carboxylicacid. To a solution of 5-furan-2-yl-isoxazole-3-carboxylic acid ethyl ester (0.5 g, 2.41 mmol) in THF (30 mL) and methanol (6 mL) was slowly added in lithium hydroxide aqueous solution (10 mL). The resulting mixture was stirred for 16 hrs. THF was concentrated under reduced pressure. The resulting residue was acidified with 1N HCl and extracted with ethyl acetate (3×100 mL). Combined organic extracts were washed with distilled water, dried over anhydrous $Na_2SO_4$ and concentrated under reduced pressure to obtain 5-furan-2-yl-isoxazole-3-carboxylic acid (225 mg, 52% as white solid). LCMS: 180 $[M+H]^+$.

Step 7: N-(1-{1-[2,4-bis(trifluoromethyl)phenyl]ethyl}-1H-pyrazol-4-yl)-5-(furan-2-yl) isoxazole-3-carboxamide. To a solution of 5-furan-2-yl-isoxazole-3-carboxylic acid (100 mg, 0.55 mmol, 1 equiv) in DMF (1 mL), were added HATU (233 mg, 0.61 mmol, 1.1 equiv). The mixture was treated drop wise with DIPEA (230 mg, 1.78 mmol, 3.2 equiv). After stirring at RT for 15 minutes, the mixture was treated drop wise with a solution of the 1-{1-[2,4bis(trifluoromethyl)phenyl]ethyl}-1H-pyrazol-4-amine (180 mg, 0.55 mmol, 1 equiv) in DMF (1 mL). The reaction mixture was kept under stirring for 24 h. The reaction mixture was diluted water (50 mL). The resulting precipitate was filtered off and freeze dried on lyophilizer. Crude material obtained was purified by reverse phase HPLC to afford N-(1-{1-[2,4-bis (trifluoromethyl)phenyl]ethyl}-1H-pyrazol-4-yl)-5-(furan-2-yl)isoxazole-3-carboxamide. (7 mg, 3% as an white solid). $^1$H NMR: (400 MHz, DMSO-$d_6$) δ 11.07 (s, 1H), 8.18 (d, J=6.4 Hz, 1H), 8.05 (s, 1H), 8.00 (s, 1H), 7.73 (t, J=4.2 Hz, 2H), 7.28 (d, J=3.6 Hz, 1H), 7.17-7.05 (m, 1H), 6.80-6.67 (m, 1H), 5.93 (q, J=6.9 Hz, 1H), 1.87 (d, J=6.9 Hz, 3H). LCMS: 485 $[M+H]^+$.

Example S11. Synthesis of N-{1-[2,4-bis(trifluoromethyl)benzyl]-1H-pyrazol-4-yl}-5-tert-butyl-1,2-oxazole-3-carboxamide (Compound 13)

Step 1: Synthesis of 1-(2,4-bis (trifluoromethyl) benzyl)-4-nitro-1H-pyrazole. To a stirred solution of 4-nitro-1H-pyrazole (1.83 g, 16.28 mmol, 1 eq) in DMF (10 ml) was added $K_2CO_3$ (3.36 gm, 24.42 mmol, 1.5 eq) portion wise at 0° C. and stirred for 10 minutes. 1-(bromomethyl)-2,4-bis (trifluoromethyl)benzene (5.0 gm, 16.28 mmol, 1 eq) was added drop wise 0° C. The reaction mixture was allowed to stir for 1 hour at RT. Product formation was confirmed by LCMS. After completion of reaction, reaction mixture was diluted with water and extracted with ethyl acetate (100 mL×3). Combined organic extracts were washed with water (100 mL×4), dried over anhydrous $Na_2SO_4$ and concentrated under reduced pressure to obtain 1-(2,4-bis (trifluoromethyl) benzyl)-4-nitro-1H-pyrazole (4.5 g, as white solid). LCMS: 339 $[M+H]^+$.

Step 2: Synthesis of 1-(2, 4-bis (trifluoromethyl)-1H-pyrazol-4-amine. To a stirred solution of 1-(2,4-bis(trifluoromethyl)benzyl)-4-nitro-1H-pyrazole (2.5 g, 1 eq) in Methanol (40 mL) under nitrogen Palladium on Carbon[Pd/C](250 mg, 10% w/w) was added. Purge the reaction mixture with $H_2$ gas for 2 h. Product formation was confirmed by LCMS. After the completion of reaction, reaction mixture was filtered through Celite bed & Filtrate was concentrate under reduced pressure to obtain 1-(2, 4-bis (trifluoromethyl)-1H-pyrazol-4-amine (0.800 g, as brown colour liquid). LCMS: 309 $[M+H]^+$.

Step 3: Synthesis of N-{1-[2,4-bis(trifluoromethyl)benzyl]-1H-pyrazol-4-yl}-5-tert-butyl-1,2-oxazole-3-carboxamide. To a stirred solution of 5-tert-butyl-1,2-oxazole-3-carboxylic acid (100 mg, 0.588 mmol, 1 eq) in DMF (8 mL) add HATU (246 mg, 0646 mmol, 1.1 eq) and stirred the reaction mixture for half hour then add 1-(2, 4-bis (trifluoromethyl)-1H-pyrazol-4-amine (182 mg, 0.588 mmol, 1 eq) and DIPEA (242 mg, 1.881 mmol, 3.2 eq) stirred the resulting reaction mixture for overnight at room temperature. Reaction was monitored with TLC and LCMS. Reaction mixture was diluted with Ethyl acetate and washed with water, collect organic layer dried over sodium sulphate and concentrate over to rota vapour to yield crude product which is further purified by reversed phase chromatography (15 mg). $^1$H NMR (400 MHz, DMSO-$d_6$) δ ppm 1.35 (s, 9H) 5.65 (s, 2H) 6.64 (s, 1H) 7.06 (d, J=7.89 Hz, 1H) 7.75 (s, 1H) 7.99-8.17 (m, 2H) 8.29 (s, 1H) 10.97 (s, 1H). LCMS: 461 (M+H)$^+$.

Example S12. Synthesis of N-(1-(2,4-bis(trifluoromethyl)benzyl)-1H-pyrazol-4-yl)-5-(thiophen-2-yl)isoxazole-3-carboxamide (Compound 14)

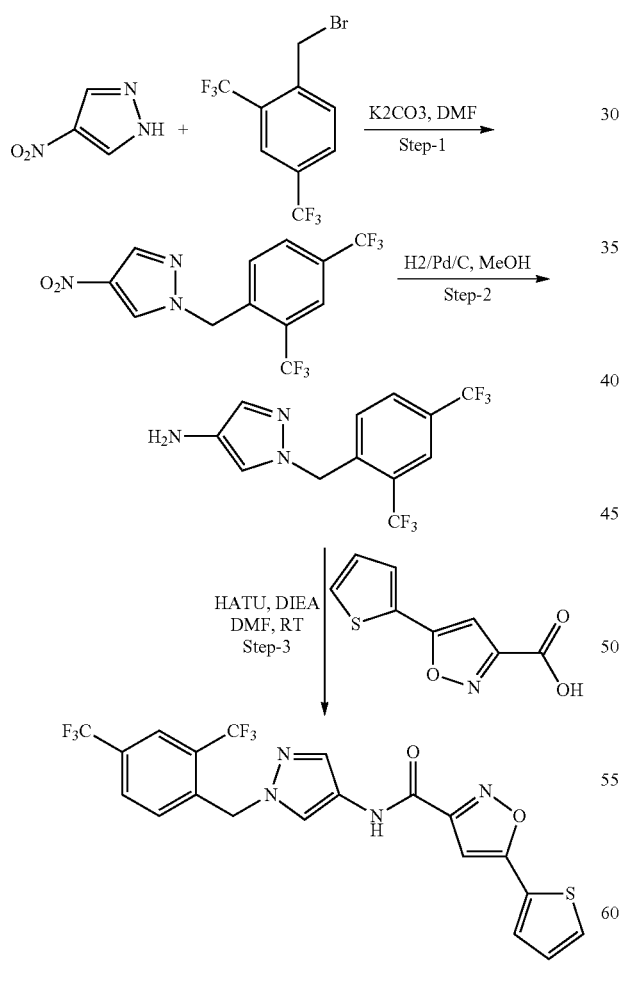

Step 1: Synthesis of 1-(2,4-bis (trifluoromethyl) benzyl)-4-nitro-1H-pyrazole. To a stirred solution of 4-nitro-1H-pyrazole (1.83 gm, 16.28 mmol, 1 eq) in DMF (10 ml) was added $K_2CO_3$ (3.36 gm, 24.42 mmol, 1.5 eq) portion wise at 0° C. and stirred for 10 minutes. 1-(bromomethyl)-2,4-bis (trifluoromethyl)benzene (5.0 gm, 16.28 mmol, 1 eq) was added drop wise 0° C. The reaction mixture was allowed to stir for 1 hour at RT. Product formation was confirmed by LCMS. After completion of reaction, reaction mixture was diluted with water and extracted with ethyl acetate (100 mL×3). Combined organic extracts were washed with water (100 mL×4), dried over anhydrous $Na_2SO_4$ and concentrated under reduced pressure to obtain 1-(2,4-bis (trifluoromethyl) benzyl)-4-nitro-1H-pyrazole (4.5 g, as white solid). LCMS: 339 [M+H]$^+$.

Step 2: Synthesis of 1-(2, 4-bis (trifluoromethyl)-1H-pyrazol-4-amine. To a stirred solution of 1-(2,4-bis(trifluoromethyl)benzyl)-4-nitro-1H-pyrazole (2.5 g, 1 eq) in Methanol (40 mL) under nitrogen Palladium on Carbon[Pd/C](250 mg, 10% w/w) was added. Purge the reaction mixture with $H_2$ gas for 2 h. Product formation was confirmed by LCMS. After the completion of reaction, reaction mixture was filtered through Celite bed & Filtrate was concentrate under reduced pressure to obtain 1-(2, 4-bis (trifluoromethyl)-1H-pyrazol-4-amine (0.800 g, as brown colour liquid). LCMS: 309 [M+H]$^+$.

Step 3: Synthesis of N-(1-(2,4-bis(trifluoromethyl)benzyl)-1H-pyrazol-4-yl)-5-(thiophen-2-yl)isoxazole-3-carboxamide. To a stirred solution of 5-(thiophen-2-yl)-1,2-oxazole-3-carboxylic acid (100 mg, 0.512 mmol, 1 eq) in DMF (5 mL) add HATU (213 mg, 0.0.513 mmol, 1.1 eq) and stirred resulting reaction mixture for one hour. Then add 1-(2, 4-bis (trifluoromethyl)-1H-pyrazol-4-amine (158 mg, 0.0.512 mmol, 1 eq) and DIPEA (210 mg, 1.63 mmol, 3.2 eq) and stirred reaction mixture for overnight at RT. The reaction mixture was diluted with Ethyl Acetate (50 mL) and washed with Water (70 mL), collect Organic layer and dried over Anhydrous Sodium Sulphate and concentrate on rota vapour to yield crude product which is further purified by Reversed phase chromatography (7 mg white solid). 1H NMR (400 MHz, DMSO-$d_6$) δ ppm 5.67 (br. s., 2H) 7.05 (d, J=7.45 Hz, 1H) 7.29 (br. s., 2H) 7.78 (s, 1H) 7.84 (br. s., 1H) 7.90 (d, J=4.38 Hz, 2H) 8.04-8.14 (m, 2H) 8.32 (s, 1H) 11.11 (s, 1H). LCMS: 486 (M+H)$^+$.

Example S13. Synthesis of N-(1-(2,4-bis(trifluoromethyl)benzyl)-1H-pyrazol-4-yl-[3,3'-bipyridine]-5-carboxamide (Compound 15)

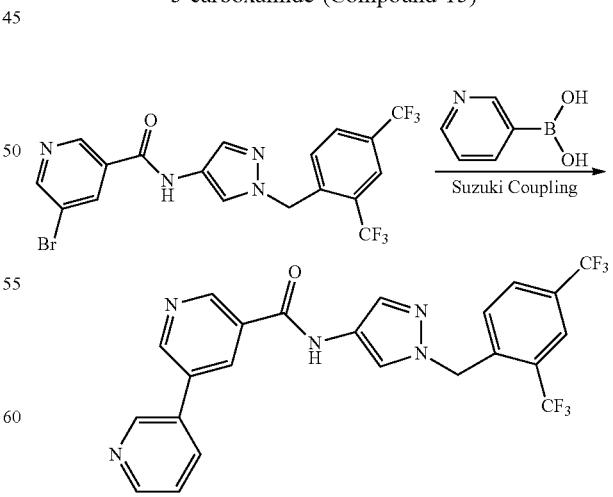

To a stirred solution of N-(1-(2,4-bis(trifluoromethyl)benzyl)-1H-pyrazol-4-yl)-5-bromonicotinamide (100 mg, 0.20 mmol, 1 equiv) and pyridin-3-ylboronic acid (32 mg, 0.26 mmol, 1.3 equiv) in DMF (7 mL), was added Na$_2$CO$_3$ (53 mg, 0.50 mmol, 2.5 equiv), water (1.5 mL) and Tetrakis (23 mg, 0.020 mmol, 0.1 equiv). The resultant reaction mixture was heated at 100° C. for 2 h. Reaction was monitored by TLC and LCMS. After completion of reaction, the reaction mixture cooled to RT and water (20 mL) was added. The resultant solid which was filter out and washed with water dry on vacuum to obtain crude. The crude product which was purified by prep purification to obtain solid N-(1-(2,4-bis(trifluoromethyl)benzyl)-1H-pyrazol-4-yl)-[3,3'-bipyridine]-5-carboxamide (25 mg, 25%) as off white solid. $^1$H NMR (400 MHz, DMSO-d$_6$) δ 10.89 (s, 1H), 9.13 (dd, J=4.7, 2.2 Hz, 2H), 9.06 (d, J=2.5 Hz, 1H), 8.68 (d, J=4.6 Hz, 1H), 8.64 (s, 1H), 8.34 (s, 1H), 8.27 (d, J=8.0 Hz, 1H), 8.08 (d, J=5.4 Hz, 2H), 7.77 (s, 1H), 7.58 (dd, J=7.9, 4.8 Hz, 1H), 7.10 (d, J=8.2 Hz, 1H), 5.68 (s, 2H), 1.62 (s, 2H).

Example S14. Synthesis of N-(1-(2,4-bis(trifluoromethyl)benzyl)-1H-pyrazol-4-yl-5-(2,4-difluorophenyl)isoxazole-3-carboxamide (Compound 16)

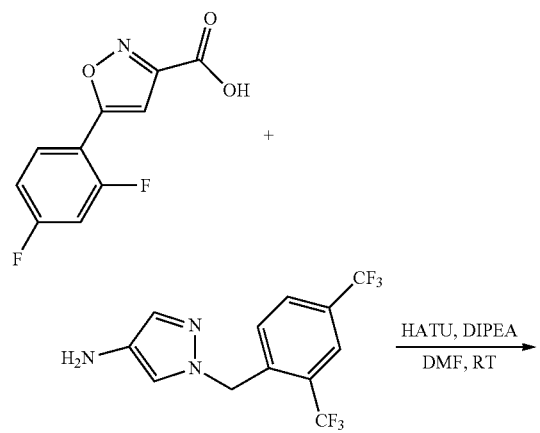

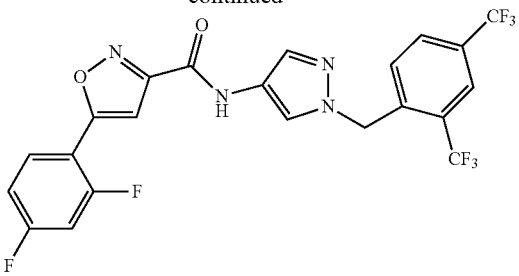

To a solution of 5-(2,4-difluorophenyl)isoxazole-3-carboxylic acid (100 mg, 0.44 mmol, 1 equiv) in DMF (1 mL), were added HATU (185 mg, 0.48 mmol, 1.1 equiv). The mixture was treated drop wise with DIPEA (183 mg, 1.42 mmol, 3.2 equiv). After stirring at RT for 15 minutes, the mixture was treated drop wise with a solution of the 1-(2,4-bis(trifluoromethyl)benzyl)-1H-pyrazol-4-amine (137 mg, 0.44 mmol, 1 equiv) in DMF (1 mL). The reaction mixture was kept under stirring for 24 hrs at RT. Product formation was confirmed with TLC & LCMS and reaction mixture was diluted EtOAc (50 mL) & washed with water (50 mL×2). Organic layer dried over Na$_2$SO$_4$ & concentrated under reduced pressure to obtain crude which was further purified by flash column chromatography to obtain pure product N-(1-(2,4-bis(trifluoromethyl)benzyl)-1H-pyrazol-4-yl)-5-(2,4-difluorophenyl)isoxazole-3-carboxamide. (36 mg, 15.7% as off white solid). $^1$H NMR (400 MHz, DMSO-d$_6$) δ 11.16 (s, 1H), 8.33 (s, 1H), 8.10 (q, J=8.3 Hz, 3H), 7.78 (s, 1H), 7.61 (t, J=10.9 Hz, 1H), 7.35 (dd, J=10.1, 7.7 Hz, 1H), 7.26 (d, J=2.9 Hz, 1H), 7.06 (d, J=8.1 Hz, 1H), 5.67 (s, 2H).

Example S15. Synthesis of N-(1-(2,4-bis(trifluoromethyl)benzyl)-1H-imidazol-4-yl)-5-(furan-2-yl)isoxazole-3-carboxamide (Compound 17)

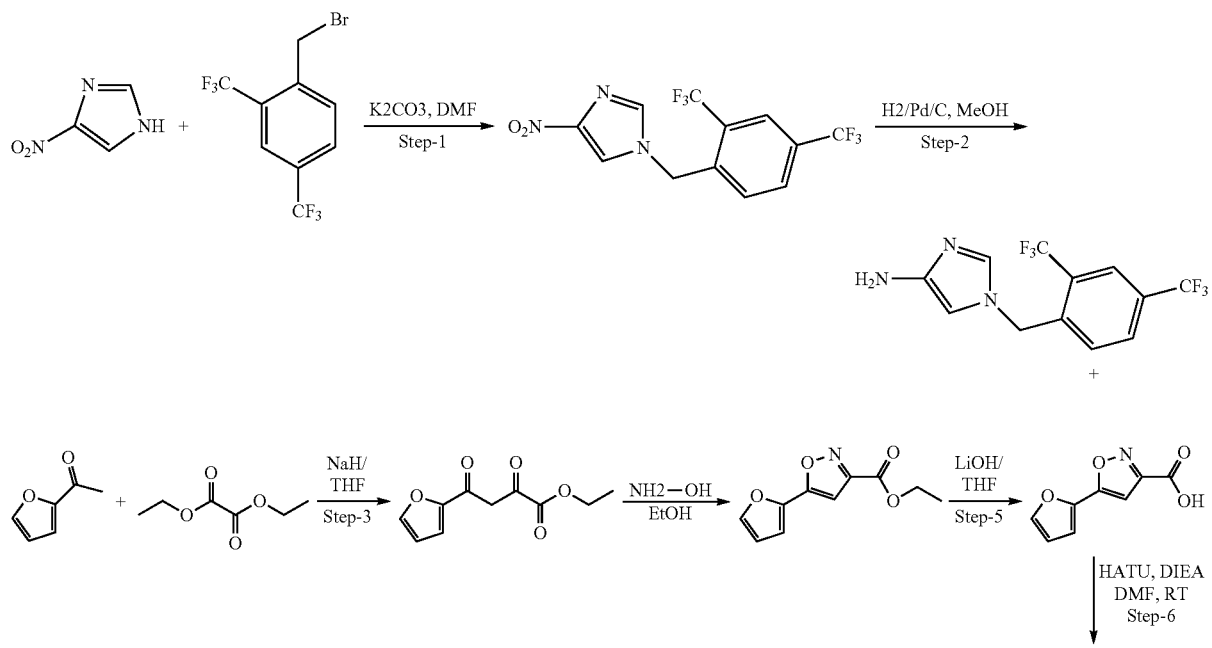

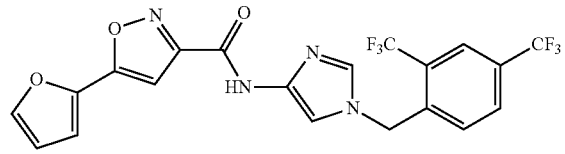

Step 1: Synthesis of 1-(2,4-bis(trifluoromethyl)benzyl)-4-nitro-1H-imidazole. To a stirred solution of 4-nitro-1H-imidazole (0.368 g, 0.003 mol, 1 equiv) in DMF (20 mL). Cool this reaction mixture by ice water up to 0° C. add K$_2$CO$_3$ (0.674 g, 0.004 mol, 1.5 equiv) portion wise in it stirred reaction mixture for 10 minute and then add 1-(bromomethyl)-2,4-bis(trifluoromethyl)benzene (1.0 g, 0.003 mol, 1 equiv) in it by dropwise. The reaction mixture was allowed to stir for 1 hour at RT. Product formation was confirmed by LCMS. After completion of reaction, reaction mixture was diluted with water and extracted with ethyl acetate (100 mL×3). Combined organic extracts were washed with water (100 mL×4), dried over anhydrous Na$_2$SO$_4$ and concentrated under reduced pressure to obtain 1-(2,4-bis(trifluoromethyl)benzyl)-4-nitro-1H-imidazole (1.1 g, 100% crude) as off-white solid. LCMS: 339 [M+H]$^+$.

Step 2: Synthesis of 1-(2,4-bis(trifluoromethyl)benzyl)-1H-imidazol-4-amine. To a stirred solution of 1-(2,4-bis(trifluoromethyl)benzyl)-4-nitro-1H-imidazole (500 mg, 1 equiv) in Methanol (20 mL) under Nitrogen add Palladium on Carbon[Pd/C](100 mg, 10% w/w) in it & purged the reaction mixture by Hydrogen gas for 2 hour. Reaction was monitored by LCMS. After the completion of reaction, reaction mixture was filtered through Celite bed & Filtered was concentrate to obtained product which is purified by flash chromatography to get 1-(2,4-bis(trifluoromethyl)benzyl)-1H-imidazol-4-amine (460 mg, 100% crude) as a brown-colored viscous liquid. LCMS: 309 [M+H]$^+$.

Step 3: Synthesis of ethyl 4-(2-furyl)-2, 4-dioxobutyrate. To a solution of 2-acetylfuran (5.0 g, 45.40 mmol, 1 equiv) in THF was added portion wise 60% Sodium hydride (3.63 g, 90.81 mmol, 2 equiv) at 0° C. The resultant reaction mixture was stirred for another 30 minutes at RT, followed by drop wise addition of diethyl oxalate (12.28 ml, 90.81 mmol, 2 equiv) at 0° C. and reaction mixture was stir for another 18 hours at RT. Product formation was confirmed by TLC and LCMS. The reaction mixture was quenched with ice water and washed with diethyl ether (2×100 mL). Aqueous layer was separated and neutralized with 1N HCl and extracted with EtOAc (3×100 mL). Combined organic extracts were washed with water (2×100 mL), dried over anhydrous Na$_2$SO$_4$ and concentrated under reduced pressure to obtain crude which was purified by combi-flash chromatography (0-20% Ethyl acetate in hexane) to obtain ethyl 4-(furan-2-yl)-2,4-dioxobutanoate (3.6 g, 45% as a yellow solid). LCMS: 210 [M+H]$^+$.

Step 4: Synthesis of ethyl 5-(furan-2-yl)isoxazole-3-carboxylate. A suspension of ethyl 4-(furan-2-yl)-2,4-dioxobutanoate (1.6 g, 7.61 mmol, 1 equiv) and hydroxylamine hydrochloride salt (0.528 g, 7.61 mmol, 1 equiv) in EtOH was stirred at 85° C. for 2 h. Product formation was confirmed by TLC and LCMS. The resulting mixture was concentrated under reduced pressure, the residue was dissolved in DCM and distilled water. Organic phase was separated, dried over anhydrous Na$_2$SO$_4$, filtered through silica gel pad, and then concentrated under reduced pressure to give ethyl 5-(furan-2-yl)isoxazole-3-carboxylate. The crude product obtained was used in the next steps without further purification (700 mg, 52% as yellow solid). LCMS: 207 [M+H]$^+$.

Step 5: Synthesis of 5-(furan-2-yl)isoxazole-3-carboxylicacid. To a solution of 5-furan-2-yl-isoxazole-3-carboxylic acid ethyl ester (0.5 g, 2.41 mmol) in THF (30 mL) and methanol (6 mL) was slowly added in lithium hydroxide aqueous solution (10 mL). The resulting mixture was stirred for 16 hrs. THF was concentrated under reduced pressure. The resulting residue was acidified with 1N HCl and extracted with ethyl acetate (3×100 mL). Combined organic extracts were washed with distilled water, dried over anhydrous Na$_2$SO$_4$ and concentrated under reduced pressure to obtain 5-furan-2-yl-isoxazole-3-carboxylic acid (225 mg, 52% as white solid). LCMS: 179 [M+H]$^+$.

Step 6: Synthesis of N-(1-(2,4-bis(trifluoromethyl)benzyl)-1H-imidazol-4-yl)-5-(furan-2-yl)isoxazole-3-carboxamide. To stirred solution of 5-(furan-2-yl)isoxazole-3-carboxylic acid (200 mg, 0.647 mmol, 1 equiv) in DMF (10 ml) add HATU (270 mg, 0.711 mmol, 1.1 equiv) was added DIPEA (267 mg, 2.07 mmol, 3.2 equiv). After stirring at RT for 15 minutes, then add 1-(2,4-bis(trifluoromethyl)benzyl)-1H-imidazol-4-amine (115 mg, 0.647 mmol, 1 equiv). Stirred reaction mixture for overnight at room temperature. Reaction monitored by LCMS. Reaction mixture was diluted with ethyl acetate (30 mL) and washed with water (50 mL). The organic layer dried over anhydrous sodium sulphate & concentrate to get crude product which is purified by using column chromatography (100 mg, 32% as white solid). $^1$H NMR (400 MHz, DMSO-d$_6$) δ=11.21 (br. s., 1H), 8.17-8.05 (m, 2H), 8.00 (s, 1H), 7.74 (s, 1H), 7.49 (s, 1H), 7.24 (br. s., 3H), 6.76 (br. s., 1H), 5.57 (br. s., 2H). LCMS: 471 [M+H]$^+$.

Example S16. Synthesis of N-(1-(2, 3-dihydro-M-inden-2-yl)-1H-pyrazol-4-yl)-5-(furan-2-yl) isoxazole-3-carboxamide (Compound 18)

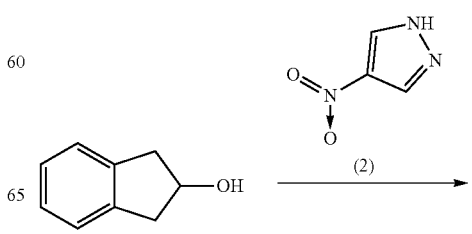

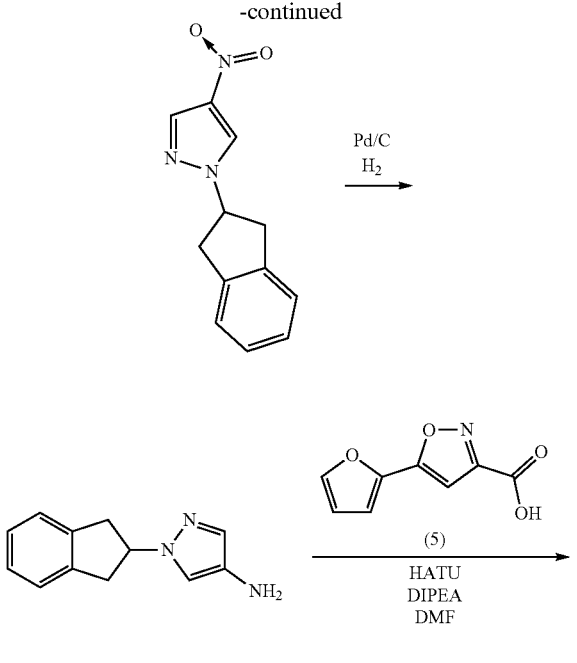

for one hour. Reaction was monitored by TLC and LCMS. Reaction mixture was filtered through Celite bed and washed with Methanol and concentrate on reduced pressure to yield crude product 1-(2, 3-dihydro-1H-inden-2-yl)-1H-pyrazol-4-amine which is used directly for next step. LCMS: 199 [M+H]+.

Step 3: Synthesis of N-(1-(2, 3-dihydro-1H-inden-2-yl)-1H-pyrazol-4-yl)-5-(furan-2-yl) isoxazole-3-carboxamide. 5-(furan-2-yl) isoxazole-3-carboxylic acid (200 mg, 1 eq, 1.117 mmole) was taken in 5 mL of DMF. To it, HATU (424.5 mg, 1.117 mmole, and 1 eq) was added. To it DIPEA (0.288 mg. 2 eq, and 2.234 m mole) was added. Reaction mixture was kept under stirring for 20 min. To it, 1-(2, 3-dihydro-1H-inden-2-yl)-1H-pyrazol-4-amine (222.3, 1 eq, 1.117 mmole) was added. Resulting reaction mixture was kept under stirring for 24 hr. Work up was done by Adding water and recovered with ethyl acetate. Crude was triturated with IPA: Hexane (1:9) kept stirring overnight and filtered. Residue obtained as product N-(1-(2, 3-dihydro-1H-inden-2-yl)-1H-pyrazol-4-yl)-5-(furan-2-yl) isoxazole-3-carboxamide. $^1$H NMR (400 MHz, DMSO-d$_6$) δ 10.98 (s, 1H), 8.01 (d, J=7.5 Hz, 2H), 7.66 (s, 1H), 7.31-7.12 (m, 6H), 6.77 (dd, J=3.4, 1.8 Hz, 1H), 5.29-5.17 (m, 1H), 3.43 (dd, J=16.2, 7.8 Hz, 2H), 3.27 (dd, J=16.1, 5.9 Hz, 2H). LCMS: 360 [M+H]+.

Example S17. Synthesis of N-(1-(2, 3-dihydro-1H-inden-1-yl)-1H-pyrazol-4-yl)-5-(furan-2-yl) isoxazole-3-carboxamide (Compound 19)

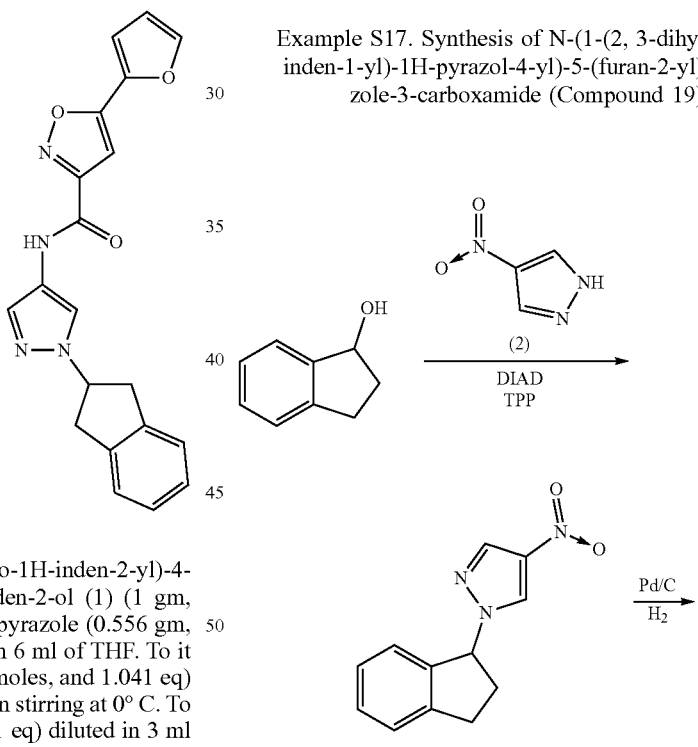

Step 1: Synthesis Of 1-(2, 3-dihydro-1H-inden-2-yl)-4-nitro-1H-pyrazole. 2, 3-dihydro-1H-inden-2-ol (1) (1 gm, 0.007 moles, and 1 eq) and 4-nitro-1H-pyrazole (0.556 gm, 0.0049 moles, and 0.66 eq) was taken in 6 ml of THF. To it Triphenylphosphine (2.035 gm., 0.007 moles, and 1.041 eq) was added. Reaction mixture was kept on stirring at 0° C. To it DIAD (1.569 gm., 0.007 moles, 1.041 eq) diluted in 3 ml of THF was added drop wise. Mixture was kept on stirring for 10 minutes at 0° C. After that reaction was kept in microwave for 15 minutes at 140° C. Reaction mixture was concentrated up to dryness and columned get the product as yellow oil 1-(2,3-dihydro-1H-inden-2-yl)-4-nitro-1H-pyrazole (3). LCMS: 229 [M+H]+.

Step 2: Synthesis Of 1-(2, 3-dihydro-1H-inden-2-yl)-1H-pyrazol-4-amine. To a stirred solution of 1-(2,3-dihydro-1H-inden-2-yl)-4-nitro-1H-pyrazole (250 mg) in MeOH (10 mL) and purged with Nitrogen gas then add Pd/C 10% by wt. of 1-(2,3-dihydro-1H-inden-1-yl)-4-nitro-1H-pyrazole) in it and again purged with nitrogen for further 5 minute then resulting reaction mixture was purged with Hydrogen gas

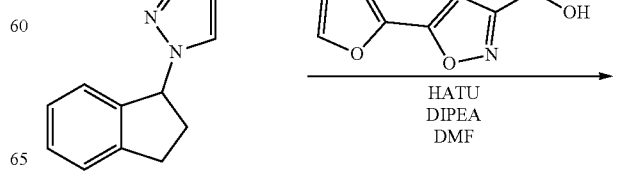

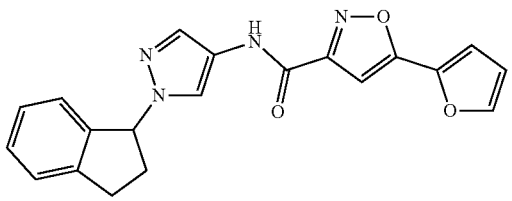

Step 1: Synthesis Of 1-(2, 3-dihydro-1H-inden-1-yl)-4-nitro-1H-pyrazole. 2, 3-dihydro-1H-inden-1-ol (1 gm, 0.007 moles, and 1 eq) and 4-nitro-1H-pyrazole (0.556 gm, 0.0049 moles, and 0.6 eq) was taken in 6 ml of THF. To it Triphenylphosphione (2.035 gm., 0.007 moles, and 1.041 eq) was added. Reaction mixture was kept on stirring at 0° C. To it DIAD (1.56 gm., 0.007 moles, 1.041 eq) diluted in 3 ml of THF was added drop wise. Mixture was kept on stirring for 10 minutes at 0° C. After that reaction was kept in microwave for 15 minutes at 140° C. Reaction mixture was concentrated up to dryness and columned to get the product as yellow oil 1-(2, 3-dihydro-1H-inden-1-yl)-4-nitro-1H-pyrazole.

Step 2: Synthesis Of 1-(2, 3-dihydro-1H-inden-1-yl)-1H-pyrazol-4-amine. To a stirred solution of 1-(2,3-dihydro-1H-inden-1-yl)-4-nitro-1H-pyrazole (200 mg) in MeOH (10 mL) and purged with Nitrogen gas then added Pd/C (20 mg 10% by wt. of 1-(2,3-dihydro-1H-inden-1-yl)-4-nitro-1H-pyrazole) in it and again purged with nitrogen for further 5 minute then resulting reaction mixture was purged with Hydrogen gas for one hour. Reaction was monitored by TLC and LCMS. Reaction mixture was filtered through Celite bed and washed with Methanol and concentrate on reduced pressure to yield crude product 1-(2, 3-dihydro-1H-inden-1-yl)-1H-pyrazol-4-amine, which is used directly for next step. LCMS: 199 [M+H]$^+$.

Step 3: Synthesis of N-(1-(2, 3-dihydro-1H-inden-1-yl)-1H-pyrazol-4-yl)-5-(furan-2-yl) isoxazole-3-carboxamide. 5-(furan-2-yl) isoxazole-3-carboxylic acid (100 mg, 1 eq, 0.502 m mole) was taken in 5 ml of DMF. To it HATU (190.9 mg, 0.502 mmole, and 1 eq) was added. To it DIPEA (0.17 ml, 2 eq, and 1.005 m mole) was added. Reaction mixture was kept under stirring for 20 min. To it 1-(2, 3-dihydro-1H-inden-1-yl)-1H-pyrazol-4-amine (4) (89.9 mg, 1 eq, 0.502 m mole) was added. Resulting reaction mixture was kept under stirring for 24 hr. Work up was done by adding water and recovered with ethyl acetate. Crude was triturated with IPA: Hexane (1:9) kept stirring overnight and filtered. Residue obtained as product N-(1-(2, 3-dihydro-1H-inden-1-yl)-1H-pyrazol-4-yl)-5-(furan-2-yl) isoxazole-3-carboxamide. $^1$H NMR (400 MHz, DMSO-d$_6$) δ 11.01 (s, 1H), 8.01 (d, J=4.3 Hz, 2H), 7.67 (s, 1H), 7.35 (d, J=7.6 Hz, 1H), 7.32-7.24 (m, 2H), 7.19 (t, J=7.4 Hz, 1H), 7.14 (s, 1H), 7.07 (d, J=7.5 Hz, 1H), 6.80-6.74 (m, 1H), 5.92 (t, J=7.1 Hz, 1H), 3.12 (ddd, J=14.6, 8.7, 5.1 Hz, 1H), 2.93 (dt, J=15.7, 7.5 Hz, 1H), 2.61 (dtd, J=13.1, 8.2, 5.1 Hz, 1H), 2.35 (dq, J=13.4, 6.6 Hz, 1H). LCMS: 360 [M+H]$^+$.

Example S18. Synthesis of N-(1-(2,4-bis(trifluoromethyl)benzyl)-1H-pyrazol-4-yl)-5-(4 fluorophenyl)nicotinamide (Compound 20)

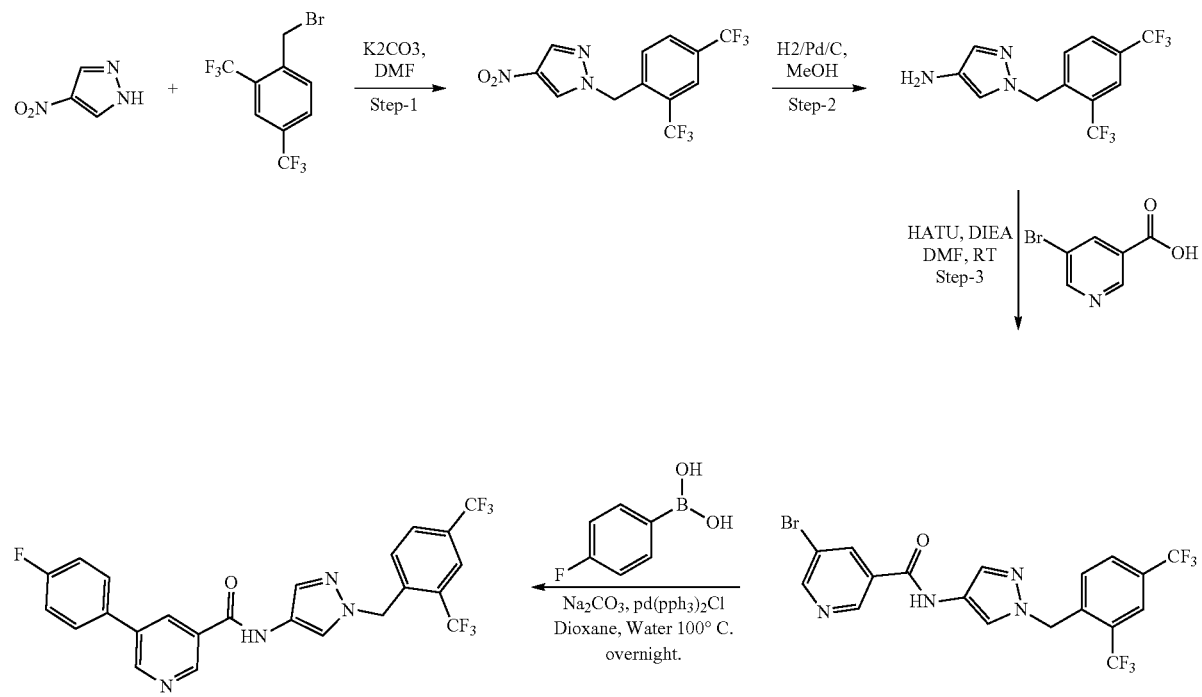

Step 1: Synthesis of 1-(2,4-bis (trifluoromethyl) benzyl)-4-nitro-1H-pyrazole. To a stirred solution of 4-nitro-1H-pyrazole (1.83 g, 16.28 mmol, 1 eq) in DMF (10 ml) was added K$_2$CO$_3$ (3.36 gm, 24.42 mmol, 1.5 eq) portion wise at 0° C. and stirred for 10 minutes. 1-(bromomethyl)-2,4-bis (trifluoromethyl)benzene (5.0 gm, 16.28 mmol, 1 eq) was added drop wise 0° C. The reaction mixture was allowed to stir for 1 hour at RT. Product formation was confirmed by LCMS. After completion of reaction, reaction mixture was diluted with water and extracted with ethyl acetate (100 mL×3). Combined organic extracts were washed with water (100 mL×4), dried over anhydrous Na$_2$SO$_4$ and concentrated under reduced pressure to obtain 1-(2,4-bis (trifluoromethyl) benzyl)-4-nitro-1H-pyrazole (4.5 g, as white solid). LCMS: 339 [M+H]$^+$.

Step 2: Synthesis of 1-(2, 4-bis (trifluoromethyl)-1H-pyrazol-4-amine. To a stirred solution of 1-(2,4-bis(trifluoromethyl)benzyl)-4-nitro-1H-pyrazole (1.0 g, 1 eq) in Methanol (20 mL) under nitrogen Palladium on Carbon[Pd/C](100 mg, 10% w/w) was added. Purge the reaction mixture with H$_2$ gas for 2 h. Product formation was confirmed by LCMS. After the completion of reaction, reaction mixture was filtered through Celite bed & Filtrate was concentrate under reduced pressure to obtain 1-(2, 4-bis (trifluoromethyl)-1H-pyrazol-4-amine (0.800 g, as brown colour liquid). LCMS: 309 [M+H]$^+$.

Step 3: Synthesis of N-(1-(2,4-bis(trifluoromethyl)benzyl)-1H-pyrazol-4-yl)-5-bromonicotinamide. To stirred solution of 5-bromonicotinic acid (200 mg, 1.01 mmol, 1 eq) in DMF (15 mL) add HATU (422 mg, 1.11 mmol, 1.1 eq) and stirred for half hours then add 1-(2,4-bis(trifluoromethyl)benzyl)-1H-pyrazol-4-amine (300 mg, 1.01 mmol, 1 eq) and DIEA (0.550 mL, 3.23 mmol, 3.2 eq) in it. Stirred reaction mixture for overnight at room temperature. Reaction monitored by LCMS. Reaction mixture was diluted with ethyl acetate (150 mL) and washed with water (100 mL). The organic layer dried over anhydrous sodium sulphate & concentrate to get product (450 mg, brown solid). LCMS: 492 [M+H]$^+$.

Step 4: Synthesis of N-(1-(2,4-bis(trifluoromethyl)benzyl)-1H-pyrazol-4-yl)-5-(4 fluorophenyl)nicotinamide. To a solution of N-(1-(2,4-bis(trifluoromethyl)benzyl)-1H-pyrazol-4-yl)-5-bromonicotinamide (150 mg, 0.30 mmol, 1. eq) in Dioxane (05 mL) was added (4 fluorophenyl)boronic acid (46 mg, 0.33 mmol, 1.1 eq), Na$_2$CO$_3$ (60 mg, 0.60 mmol, 2.0 eq) followed by the addition of Pd(PPh3)2Cl2 (10 mg, 0.015 mmol. 0.05 eq). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was triturate in (5 mL) isopropyl alcohol and concentrate under reduce pressure to obtain N-(1-(2,4-bis(trifluoromethyl)benzyl)-1H-pyrazol-4-yl)-5-(4 fluorophenyl)nicotinamide (20 mg, brown solid). $^1$H NMR (400 MHz, DMSO-d$_6$) δ ppm 5.67 (s, 2H) 7.10 (d, J=8.77 Hz, 1H) 7.40 (t, J=8.55 Hz, 2H) 7.76 (s, 1H) 7.89 (dd, J=8.77, 5.26 Hz, 2H) 8.09 (br. s., 2H) 8.34 (s, 1H) 8.53 (br. s., 1H) 9.06 (br. s., 2H) 10.81 (s, 1H). LCMS: 509 [M+H]$^+$.

Example S19. Synthesis of N-(1-(2,4-bis(trifluoromethyl)benzyl)-1H-pyrazol-4-yl)-5-phenylnicotinamide (Compound 21)

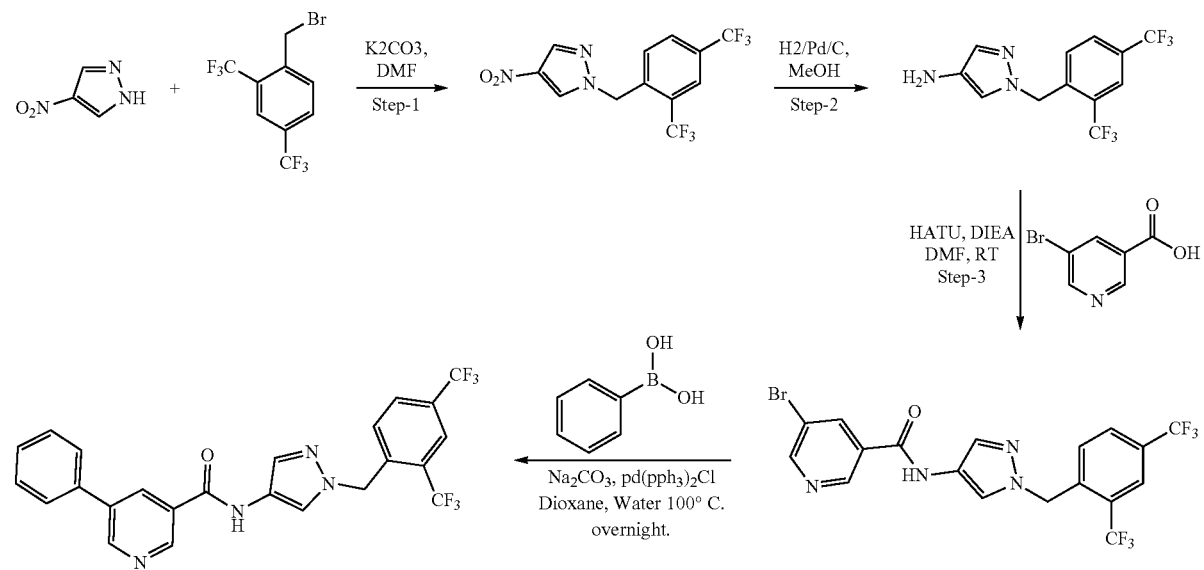

Step 1: Synthesis of 1-(2,4-bis (trifluoromethyl) benzyl)-4-nitro-1H-pyrazole. To a stirred solution of 4-nitro-1H-pyrazole (1.83 g, 16.28 mmol, 1 equiv) in DMF (10 ml) was added K$_2$CO$_3$ (3.36 gm, 24.42 mmol, 1.5 equiv) portion wise at 0° C. and stirred for 10 minutes. 1-(bromomethyl)-2,4-bis(trifluoromethyl)benzene (5.0 gm, 16.28 mmol, 1 equiv) was added drop wise 0° C. The reaction mixture was allowed to stir for 1 hour at RT. Product formation was confirmed by LCMS. After completion of reaction, reaction mixture was diluted with water and extracted with ethyl acetate (100 mL×3). Combined organic extracts were washed with water (100 mL×4), dried over anhydrous Na$_2$SO$_4$ and concentrated under reduced pressure to obtain 1-(2,4-bis (trifluoromethyl) benzyl)-4-nitro-1H-pyrazole (4.5 g, as a white solid). LCMS: 339 [M+H]$^+$.

Step 2: Synthesis of 1-(2, 4-bis (trifluoromethyl)-1H-pyrazol-4-amine. To a stirred solution of 1-(2,4-bis(trifluoromethyl)benzyl)-4-nitro-1H-pyrazole (1.0 g, 1 eq) in Methanol (20 mL) under nitrogen Palladium on Carbon[Pd/C] (100 mg, 10% w/w) was added. Purge the reaction mixture with H$_2$ gas for 2 h. Product formation was confirmed by LCMS. After the completion of reaction, reaction mixture was filtered through Celite bed & Filtrate was concentrate under reduced pressure to obtain 1-(2, 4-bis (trifluoromethyl)-1H-pyrazol-4-amine (0.800 g, as brown color liquid). LCMS: 309 [M+H]$^+$.

Step 3: Synthesis of N-(1-(2,4-bis(trifluoromethyl)benzyl)-1H-pyrazol-4-yl)-5-bromonicotinamide. To stirred solution of 5-bromonicotinic acid (200 mg, 1.01 mmol, 1 eq) in DMF (15 ml) add HATU (422 mg, 1.11 mmol, 1.1 eq) and stirred for half hours then add 1-(2,4-bis(trifluoromethyl)benzyl)-1H-pyrazol-4-amine (300 mg, 1.01 mmol, 1 eq) and DIEA (0.550 mL, 3.23 mmol, 3.2 eq) in it. Stirred reaction mixture for overnight at room temperature. Reaction monitored by LCMS. Reaction mixture was diluted with ethyl acetate (150 mL) and washed with water (100 mL). The organic layer dried over anhydrous sodium sulphate & concentrate to get product (450 mg, brown solid). LCMS: 492 [M+H]$^+$.

Step 4: Synthesis of N-(1-(2,4-bis(trifluoromethyl)benzyl)-1H-pyrazol-4-yl)-5-phenylnicotinamide. To a solution of N-(1-(2,4-bis(trifluoromethyl)benzyl)-1H-pyrazol-4-yl)-5-bromonicotinamide (150 mg, 0.30 mmol, 1. eq) in Dioxane (05 mL) was added phenylboronic acid (39 mg, 0.33 mmol, 1.1 eq), Na$_2$CO$_3$ (60 mg, 0.60 mmol, 2.0 eq) followed by the addition of Pd(PPh3)2Cl2 (10 mg, 0.015 mmol. 0.05 eq). The resulting reaction mixture was heated at 100° C. for overnight. Product formation was confirmed by LCMS. After the completion of reaction, the mixture was filtered through celite bed, washed with ethyl acetate (100 mL). Filtrate was concentrated under reduced pressure. The crude product obtained was triturate in (5 mL) Isopropyl alcohol and concentrate under reduce pressure to obtain N-(1-(2,4-bis(trifluoromethyl)benzyl)-1H-pyrazol-4-yl)-5-phenylnicotinamide. (20 mg, brown solid). 1H NMR (400 MHz, DMSO-d$_6$) δ ppm 5.67 (br. s., 2H) 7.10 (d, J=7.02 Hz, 2H) 7.48 (br. s., 1H) 7.56 (t, J=7.24 Hz, 1H) 7.76 (s, 1H) 7.84 (d, J=7.45 Hz, 3H) 8.09 (br. s., 1H) 8.34 (s, 1H) 8.55 (br. s., 2H) 9.08 (br. s., 1H) 10.81 (s, 1H). LCMS: 491 [M+H]$^+$.

Example S20. Synthesis of N-(1-(2,4-bis(trifluoromethyl)benzyl)-1H-pyrazol-4-yl)-5-(5-methylfuran-2-yl)isoxazole-3-carboxamide (Compound 22)

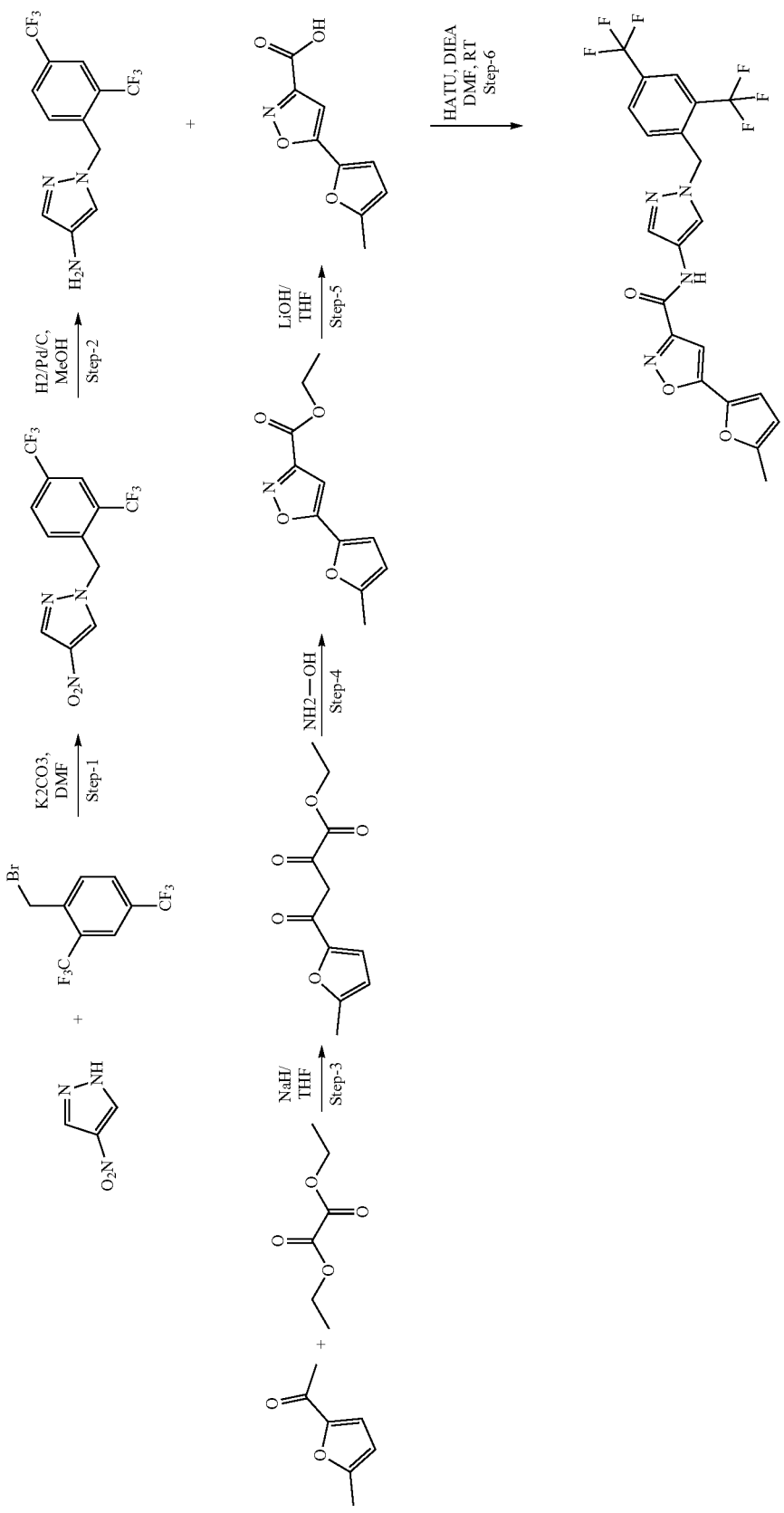

Step 1: Synthesis of 1-(2,4-bis (trifluoromethyl) benzyl)-4-nitro-1H-pyrazole. To a stirred solution of 4-nitro-1H-pyrazole (2.0 g, 6.51 mmol, 1 eq) in DMF (20 ml) was added $K_2CO_3$ portion wise at 0° C. and stirred for 10 minutes. 1-(bromomethyl)-2,4-bis(trifluoromethyl)benzene (0.73 gm, 6.51 mmol, 1 eq) was added drop wise 0° C. The reaction mixture was allowed to stir for 1 hour at RT. Product formation was confirmed by LCMS. After completion of reaction, reaction mixture was diluted with water and extracted with ethyl acetate (100 mL×3). Combined organic extracts were washed with water (100 mL×4), dried over anhydrous $Na_2SO_4$ and concentrated under reduced pressure to obtain 1-(2,4-bis (trifluoromethyl) benzyl)-4-nitro-1H-pyrazole (2.1 g, as white solid). LCMS: 339 $[M+H]^+$.

Step 2: Synthesis of 1-(2, 4-bis (trifluoromethyl)-1H-pyrazol-4-amine. To a stirred solution of 1-(2,4-bis(trifluoromethyl)benzyl)-4-nitro-1H-pyrazole (1.0 g, 1 eq) in Methanol (20 mL) under nitrogen Palladium on Carbon[Pd/C](100 mg, 10% w/w) was added. Purge the reaction mixture with $H_2$ gas for 2 h. Product formation was confirmed by LCMS. After the completion of reaction, reaction mixture was filtered through Celite bed & Filtrate was concentrate under reduced pressure to obtain 1-(2, 4-bis (trifluoromethyl)-1H-pyrazol-4-amine (0.800 g, as brown color liquid). LCMS: 309 $[M+H]^+$.

Step 3: Synthesis of ethyl 4-(5-methylfuran-2-yl)-2,4-dioxobutanoate. To a solution of 2-acetyl-5-methylfuran (1.0 g, 8.05 mmol, 1 eq) in THF was added portion wise 60% Sodium hydride (0.386 g, 16.11 mmol, 2 eq) at 0° C. The resultant reaction mixture was stirred for another 30 minutes at RT, followed by drop wise addition of diethyl oxalate (2.35 ml, 16.11 mmol, 2 eq) at 0° C. and reaction mixture was stir for another 18 hours at RT. Product formation was confirmed by TLC and LCMS. The reaction mixture was quenched with ice water and washed with diethyl ether (2×50 mL). Aqueous layer was separated and neutralized with 1N HCl and extracted with EtOAc (3×50 mL). Combined organic extracts were washed with water (2×50 mL), dried over anhydrous $Na_2SO_4$ and concentrated under reduced pressure to obtain crude which was purified by combi-flash chromatography (0-20% Ethyl acetate in hexane) to obtain ethyl 4-(5-methylfuran-2-yl)-2,4-dioxobutyrate (1.0 g, 55% as yellow solid). LCMS: 224 $[M+H]^+$.

Step 4: Synthesis of ethyl 5-(5-methylfuran-2-yl) isoxazole-3-carboxylate. A suspension of Ethyl 4-(5-methylfuran-2-yl)-2,4-dioxobutyrate (1.0 g, 4.46 mmol, 1 eq) and hydroxylamine hydrochloride salt (0.218 g, 4.46 mmol, 1 eq) in EtOH was stirred at 85° C. for 2 h. Product formation was confirmed by TLC and LCMS. The resulting mixture was concentrated under reduced pressure, the residue was dissolved in DCM and distilled water. Organic phase was separated, dried over anhydrous $Na_2SO_4$, filtered through silica gel pad, and then concentrated under reduced pressure to give ethyl 5-(5-methylfuran-2-yl) isoxazole-3-carboxylate. The crude product obtained was used in the next steps without further purification (600 mg, 52% as a yellow solid). LCMS: 221 $[M+H]^+$.

Step 5: Synthesis of 5-(5-methylfuran-2-yl)isoxazole-3-carboxylicacid. To a solution of ethyl 5-(5-methylfuran-2-yl) isoxazole-3-carboxylate (0.5 g, mmol) in THF (30 mL) and methanol (6 mL) was slowly added in 1N lithium hydroxide aqueous solution (10 mL). The resulting mixture was stirred for 16 hrs. THF was concentrated under reduced pressure. The resulting residue was acidified with 1N HCl and extracted with ethyl acetate (3×100 mL). Combined organic extracts washed with distilled water, dried over anhydrous $Na_2SO_4$ and concentrated under reduced pressure to obtain 5-methylfuran-2-yl-isoxazole-3-carboxylic acid (180 mg, 52% as a white solid). LCMS: 193 $[M+H]^+$.

Step 6: Synthesis of N-(1-(2,4-bis(trifluoromethyl)benzyl)-1H-pyrazol-4-yl)-5-(5-methylfuran-2-yl)isoxazole-3-carboxamide. To a solution of 5-methylfuran-2-yl-isoxazole-3-carboxylic acid (100 mg, 0.518 mmol, 1 eq) in DMF (1 mL), were added HATU (216 mg, 0.569 mmol, 1.1 eq). The mixture was treated drop wise with DIPEA (214 mg, 1.65 mmol, 3.2 eq). After stirring at RT for 15 minutes, the mixture was treated drop wise with a solution of the 1 (2, 4bis (trifluoromethyl) benzyl)-1H-pyrazol-4-amine (176 mg, 0.569 mmol, 1 eq) in DMF (1 mL). The reaction mixture was kept under stirring for 24 h. The reaction mixture was diluted water (25 mL). The resulting precipitate was filtered off and freeze dried on lyophilizer. Crude material obtained was purified by reverse phase HPLC to afford N-(1-(2,4-bis (trifluoromethyl)benzyl)-1H-pyrazol-4-yl)-5-(5-methylfuran-2-yl)isoxazole-3-carboxamide. (55 mg, as an white solid). 1H NMR (400 MHz, DMSO-$d_6$) δ ppm 1.22-1.23 (m, 1H) 2.40 (s, 3H) 5.66 (s, 2H) 6.40 (d, J=3.07 Hz, 1H) 7.01-7.10 (m, 2H) 7.17 (d, J=3.51 Hz, 1H) 7.77 (s, 1H) 8.05-8.11 (m, 1H) 8.31 (s, 1H) 11.10 (s, 1H). LCMS: 484 $[M+H]^+$.

Example S21. Synthesis of N-(1-(2,4-bis(trifluoromethyl)benzyl)-1H-pyrazol-4-yl)isoxazole-3-carboxamide (Compound 23)

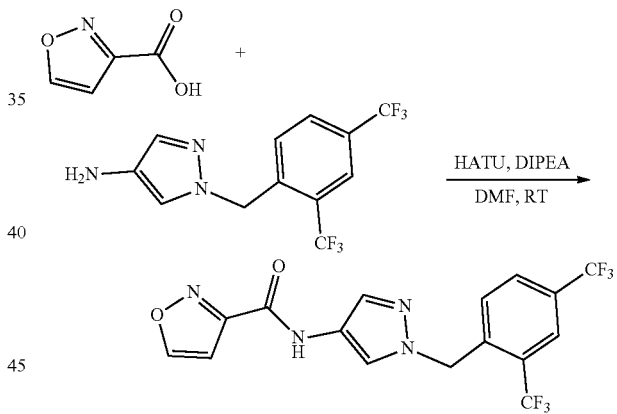

To a solution of isoxazole-3-carboxylic acid (100 mg, 0.88 mmol, 1 equiv) in DMF (1 mL), were added HATU (369 mg, 0.97 mmol, 1.1 equiv). The mixture was treated drop wise with DIPEA (365 mg, 2.83 mmol, 3.2 equiv). After stirring at RT for 15 minutes, the mixture was treated drop wise with a solution of 1-(2,4-bis(trifluoromethyl) benzyl)-1H-pyrazol-4-amine (273 mg, 0.884 mmol, 1 equiv) in DMF (1 mL). The reaction mixture was kept under stirring for 24 h at RT. Product formation was confirmed with TLC & LCMS and reaction mixture was diluted EtOAc (50 mL) & washed with water (50 mL×2). Organic layer dried over $Na_2SO_4$ & concentrated under reduced pressure to obtain crude which was further purified by flash column chromatography to obtain pure product N-(1-(2,4-bis(trifluoromethyl)benzyl)-1H-pyrazol-4-yl)isoxazole-3-carboxamide. (40 mg, 11% as off white solid). $^1$H NMR (400 MHz, DMSO-$d_6$) δ 11.06 (s, 1H), 9.14 (d, J=1.5 Hz, 1H), 8.29 (s, 1H), 8.06 (d, J=8.3 Hz, 2H), 7.76 (s, 1H), 7.05 (d, J=8.1 Hz, 1H), 6.99 (d, J=1.7 Hz, 1H), 5.66 (s, 2H).

Example S22. Synthesis of N-(1-(2, 6-dichlorobenzyl)-1H-pyrazol-4-yl)-5-(furan-2-yl) isoxazole-3-carboxamide (Compound 24)

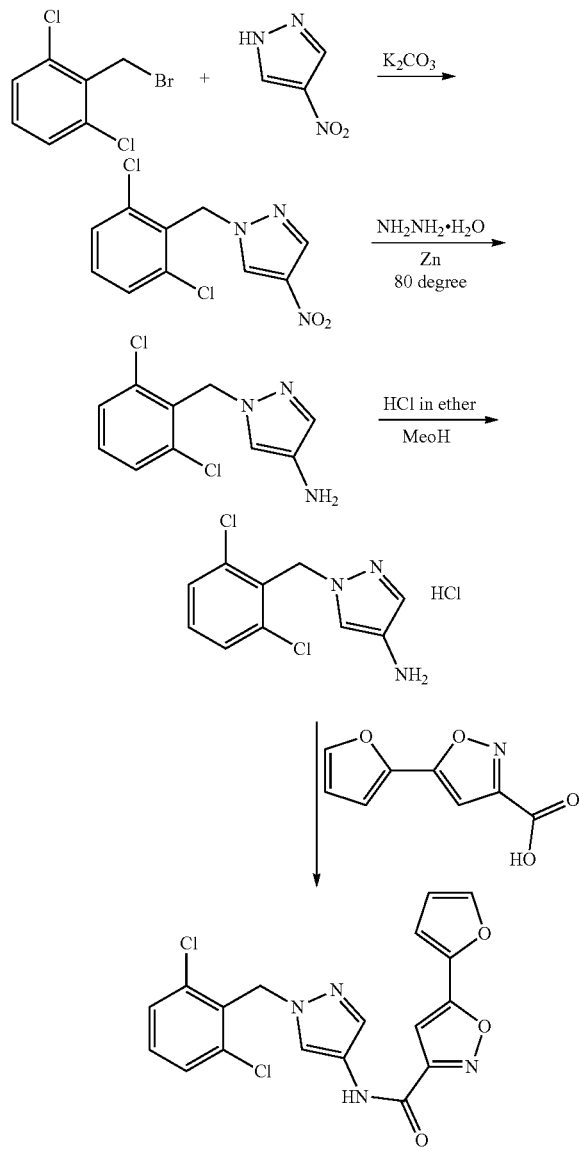

Step 1: Synthesis Of 1-(2, 6-dichlorobenzyl)-4-nitro-1H-pyrazole. 4-nitro-1H-pyrazole (1.177 gm., 1 eq, 0.0104 moles) in 5 ml of DMF was taken. To it, K₂CO₃ (2.15 gm., 0.015 moles, 1.5 eq) was added at 0° C. reaction mixture is kept under stirring for 30 minutes. To it, 2-(bromomethyl)-1,3-dichlorobenzene (2.5 gm, 0.0104 moles, 1 eq) was added and reaction mixture was kept under stirring for 1 hour. work up of reaction was done by adding water and recovered in ethyl acetate. Organic layer was concentrated over reduced pressure to get the desired product 1-(2, 6-dichlorobenzyl)-4-nitro-1H-pyrazole. LCMS: 272 [M+H]⁺.

Step 2: Synthesis of 1-(2, 6-dichlorobenzyl)-1H-pyrazol-4-amine. 1-(2, 6-dichlorobenzyl)-4-nitro-1H-pyrazole (3) (1 gm., 0.003 moles, 1 eq) was taken in methanol. To it zinc (962 mg, 0.014 moles 4 eq) was added. To it Hydrazine monohydrate (6 ml) was added. Reaction mixture was refluxed for 24 hour at 80° C. Reaction was monitored. Work up was done by passing reaction mixture through cellite bed. Obtained organic layer was washed with water to extract out remaining hydrazine hydrate. And then layer was concentrated under reduced pressure to obtained desired product 1-(2, 6-dichlorobenzyl)-1H-pyrazol-4-amine. LCMS: 241 [M+H]⁺.

Step 3: Synthesis Of 1-(2, 6-dichlorobenzyl)-1H-pyrazol-4-amine hydrochloride. To 1-(2, 6-dichlorobenzyl)-1H-pyrazol-4-amine (0.8 gm) was dissolved in methanol. To it 5 ml of HCl in ether was added and kept under stirring for overnight. Resulting suspension was filtered. And residue obtained was dried over by ether wash. Obtained product 1-(2, 6-dichlorobenzyl)-1H-pyrazol-4-amine hydrochloride. LCMS: 241 [M+H]⁺.

Step 4: Synthesis of N-(1-(2, 6-dichlorobenzyl)-1H-pyrazol-4-yl)-5-(furan-2-yl) isoxazole-3-carboxamide. 5-(furan-2-yl) isoxazole-3-carboxylic acid (100 mg, 1 eq, 0.558 m mole) was taken in 3 ml of DMF. To it HATU (212.8 mg, 0.558 m mole, and 1 eq) was added. To it DIPEA (144.13 mg, 2 eq, and 1.117 m mole) was added. Reaction mixture was kept under stirring for 20 min. To it 1-(2, 6-dichlorobenzyl)-1H-pyrazol-4-amine. HCl (186.3 mg, 1.2 eq, 0.670 mmole) was added. Resulting reaction mixture was kept under stirring for 24 hr. Work up was done by adding water and recovered with ethyl acetate. And resulting crude was purified by PREP. Obtained product was N-(1-(2, 6-dichlorobenzyl)-1H-pyrazol-4-yl)-5-(furan-2-yl) isoxazole-3-carboxamide. ¹H NMR (400 MHz, DMSO-d₆) δ 11.00 (s, 1H), 8.06 (s, 1H), 8.00 (s, 1H), 7.63 (s, 1H), 7.56 (d, J=8.1 Hz, 2H), 7.45 (t, J=8.1 Hz, 1H), 7.28 (d, J=3.5 Hz, 1H), 7.13 (s, 1H), 6.77 (dd, J=3.4, 1.8 Hz, 1H), 5.55 (s, 2H), 5.32 (s, OH), 3.97 (s, OH), 1.23 (s, 1H), 0.89-0.81 (m, OH). LCMS: 402 [M+H]⁺.

Example S23. Synthesis of N-(1-(4-cyanobenzyl)-1H-pyrazol-4-yl)-5-(furan-2-yl)isoxazole-3-carboxamide (Compound 25)

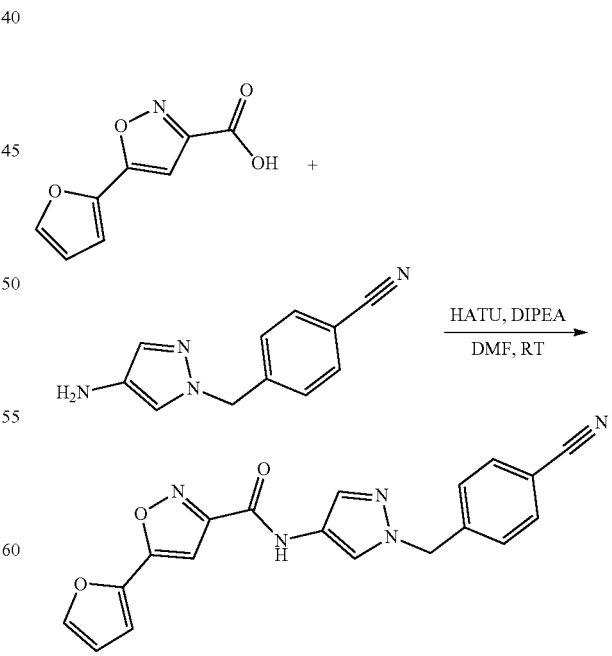

To a solution of 5-(furan-2-yl)isoxazole-3-carboxylic acid (100 mg, 0.55 mmol, 1 equiv) in DMF (1 mL), were added HATU (233 mg, 0.61 mmol, 1.1 equiv). The mixture was treated drop wise with DIPEA (230 mg, 1.78 mmol, 3.2 equiv). After stirring at RT for 15 minutes, the mixture was treated drop wise with a solution of the 4-((4-amino-1H-pyrazol-1-yl)methyl)benzonitrile (110 mg, 0.55 mmol, 1 equiv) in DMF (1 mL). The reaction mixture was kept under stirring for 24 at RT. Product formation was confirmed with TLC & LCMS and reaction mixture was diluted EtOAc (50 mL) & washed with water (50 mL×2). Organic layer dried over $Na_2SO_4$ & concentrated under reduced pressure to obtain crude The crude product which was purified by prep purification to obtain solid N-(1-(4-cyanobenzyl)-1H-pyrazol-4-yl)-5-(furan-2-yl)isoxazole-3-carboxamide. (30 mg, 18% as off white solid). $^1$H NMR (400 MHz, DMSO-$d_6$) δ 11.06 (s, 1H), 8.25 (s, 1H), 8.00 (d, J=1.8 Hz, 1H), 7.82 (d, J=7.9 Hz, 1H), 7.70 (s, 1H), 7.36 (d, J=8.0 Hz, 1H), 7.29 (d, J=3.5 Hz, 1H), 7.16 (s, 1H), 6.77 (dd, J=3.4, 1.8 Hz, 1H), 5.46 (s, 2H), 2.92 (q, J=7.2 Hz, 1H).

Example S24. Synthesis of N-(1-(4-cyano-3-(trifluoromethyl)benzyl)-1H-pyrazol-4-yl)-5-(furan-2-yl) isoxazole-3-carboxamide (Compound 26)

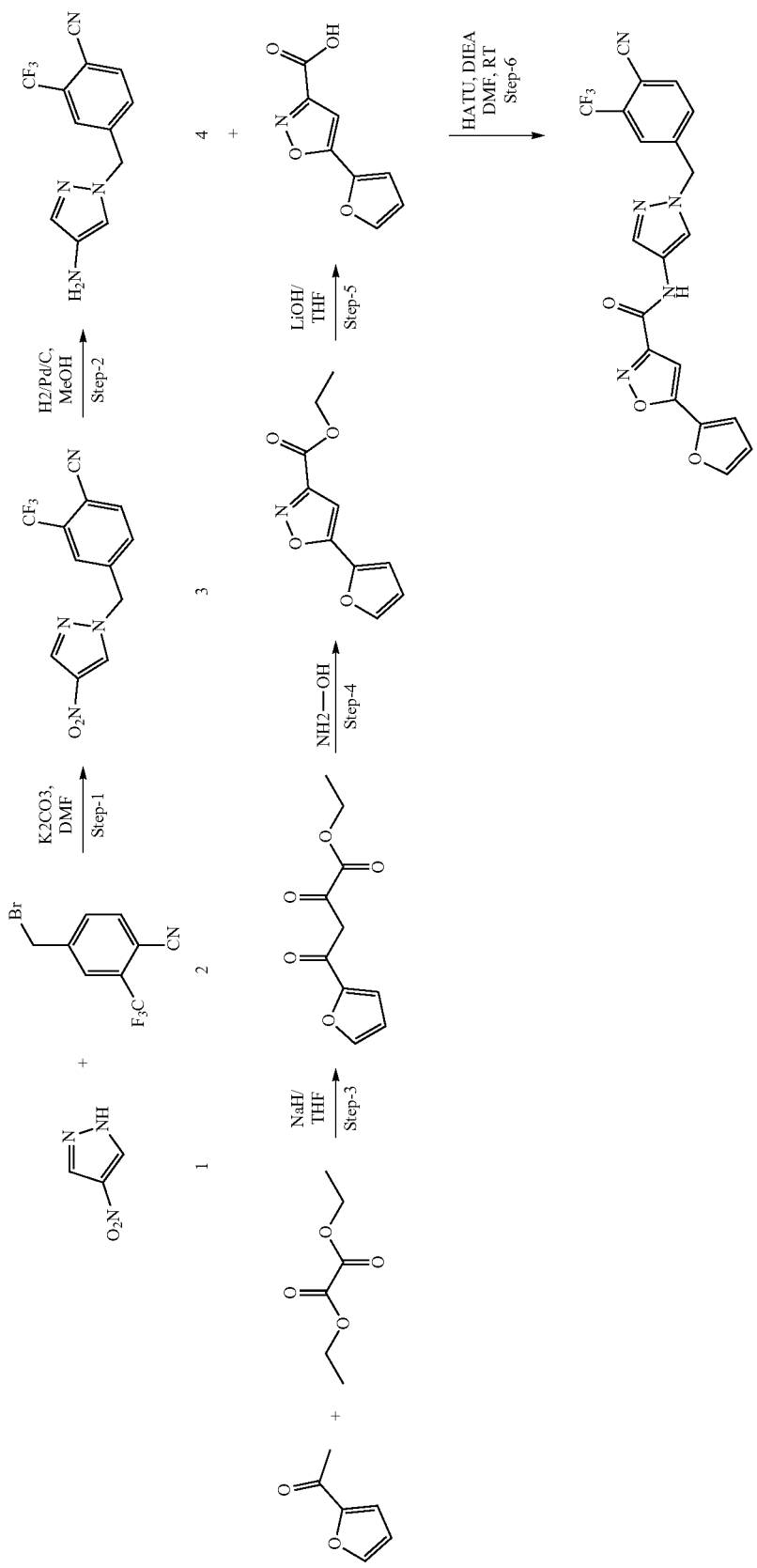

Step 1: Synthesis of 4-((4-nitro-1H-pyrazol-1-yl)methyl)-2-(trifluoromethyl)benzonitrile. To a stirred solution of 4-nitro-1H-pyrazole (0.213 g, 1.893 mmol, 1 eq) in DMF (20 mL). Cool this reaction mixture by ice water up to 0° C. add $K_2CO_3$ (0.39 g, 2.839 mmol, 1.5 eq) portion wise in it stirred reaction mixture for 10 minute and then add 4-(bromomethyl)-2-(trifluoromethyl)benzonitrile (0.500 g, 1.893 mmol, 1 eq) in it by drop by drop. Stir above reaction mixture for 1 hour (reaction was monitored by TLC & LCMS). After completion of reaction, reaction mixture was diluted with ethyl acetate (50 mL) and extracted with water (50 mL). Collect organic layer and concentrate it to obtain product which further purified by flash chromatography to obtain a white-colored product. LCMS: 297 [M+H]$^+$. Step 2: Synthesis of 4-((4-amino-1H-pyrazol-1-yl)methyl)-2-(trifluoromethyl)benzonitrile. To a stirred solution of 44(4-nitro-1H-pyrazol-1-yl)methyl)-2-(trifluoromethyl)benzonitrile (500 mg, 1 eq) in Methanol (20 mL) under Nitrogen add Palladium on Carbon[Pd/C](10% by weight) in it & purged the reaction mixture by Hydrogen gas for a 2 hour. Reaction was monitored by LCMS. After the completion of reaction, reaction mixture was filtered through Celite bed & filtered was concentrate to obtained product which is purified by flash chromatography to get Brown Color viscous Liquid. LCMS: 267 [M+H]$^+$.

Step 3: Synthesis of ethyl 4-(2-furyl)-2, 4-dioxobutyrate. To a solution of 2-acetylfuran (5.0 g, 45.40 mmol, 1 eq) in THF was added portion wise 60% Sodium hydride (3.63 g, 90.81 mmol, 2 eq) at 0° C. The resultant reaction mixture was stirred for another 30 minutes at RT, followed by drop wise addition of diethyl oxalate (12.28 ml, 90.81 mmol, 2 eq) at 0° C. and reaction mixture was stir for another 18 hours at RT. Product formation was confirmed by TLC and LCMS. The reaction mixture was quenched with ice water and washed with diethyl ether (2×100 mL). Aqueous layer was separated and neutralized with 1N HCl and extracted with EtOAc (3×100 mL). Combined organic extracts were washed with water (2×100 mL), dried over anhydrous $Na_2SO_4$ and concentrated under reduced pressure to obtain crude which was purified by combi-flash chromatography (0-20% Ethyl acetate in hexane) to obtain Ethyl 4-(2-furyl)-2, 4-dioxobutyrate (3.6 g, 45% as yellow solid). LCMS: 210 [M+H]$^+$.

Step 4: Synthesis of 5-furan-2-yl-isoxazole-3-carboxylic acid ethyl ester. A suspension of 4-furan-2-yl-2, 4-dioxobutyric acid ethyl ester (1.6 g, 7.61 mmol, 1 eq) and hydroxylamine hydrochloride salt (0.528 g, 7.61 mmol, 1 eq) in EtOH was stirred at 85° C. for 2 h. Product formation was confirmed by TLC and LCMS. The resulting mixture was concentrated under reduced pressure, the residue was dissolved in DCM and distilled water. Organic phase was separated, dried over anhydrous $Na_2SO_4$, filtered through silica gel pad, and then concentrated under reduced pressure to give 5-furan-2-yl-isoxazole-3-carboxylic acid ethyl ester. The crude product obtained was used in the next steps without further purification (700 mg, 52% as a yellow solid). LCMS: 207 [M+H]$^+$.

Step 5: Synthesis of 5-furan-2-yl-isoxazole-3-carboxylicacid. To a solution of 5-furan-2-yl-isoxazole-3-carboxylic acid ethyl ester (0.5 g, 2.41 mmol) in THF (30 mL) and methanol (6 mL) was slowly added in lithium hydroxide aqueous solution (10 mL). The resulting mixture was stirred for 16 hrs. THF was concentrated under reduced pressure. The resulting residue was acidified with 1N HCl and extracted with ethyl acetate (3×100 mL). Combined organic extracts were washed with distilled water, dried over anhydrous $Na_2SO_4$ and concentrated under reduced pressure to obtain 5-furan-2-yl-isoxazole-3-carboxylic acid (225 mg, 52% as white solid). LCMS: 179 [M+H]$^+$.

Step 6: Synthesis of N-(1-(4-cyano-3-(trifluoromethyl)benzyl)-1H-pyrazol-4-yl)-5-(furan-2-yl)isoxazole-3-carboxamide. To stirred solution of 5-(furan-2-yl)isoxazole-3-carboxylic acid (100 mg, 0.563 mmol, 1 eq) in DMF (10 ml) add HATU (235 mg, 0.619 mmol, 1.1 eq) and stirred for half hours then add 4-((4-amino-1H-pyrazol-1-yl)methyl)-2-(trifluoromethyl)benzonitrile (150 mg, 0.563 mmol, 1 eq) and DIEA in it. Stirred reaction mixture for overnight at room temperature. Reaction monitored by LCMS. Reaction mixture was diluted with ethyl acetate (30 mL) and washed with water (50 mL). The organic layer dried over anhydrous sodium sulphate & concentrate to get product which is further purified by reversed phase chromatography. (10 mg white solid). $^1$H NMR (400 MHz, DMSO-d$_6$) δ ppm 5.57 (s, 2H) 6.78 (br. s., 1H) 7.17 (s, 1H) 7.29 (d, J=3.51 Hz, 2H) 7.73 (s, 1H) 7.88 (s, 1H) 8.01 (s, 1H) 8.16 (d, J=7.45 Hz, 1H) 8.31 (s, 1H) 11.09 (s, 1H). LCMS: 428 [M+H]$^+$.

Example S25. Synthesis of N-(1-(2,4-bis(trifluoromethyl)phenyl)-1H-pyrazol-4-yl)-5-(furan-2-yl)isoxazole-3-carboxamide (Compound 27)

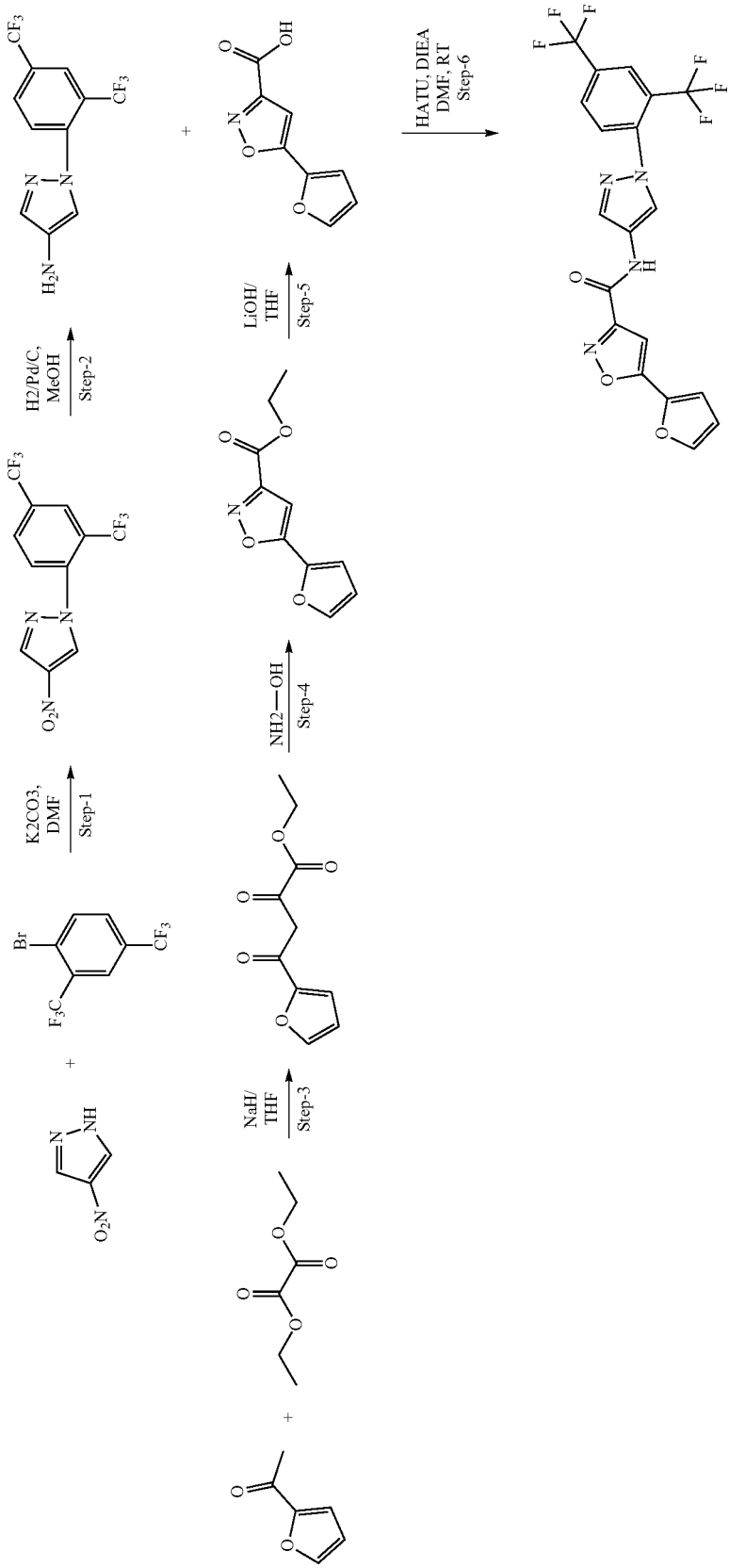

Step 1: Synthesis of 1-(2,4-bis (trifluoromethyl) benzyl)-4-nitro-1H-pyrazole. To a stirred solution of 4-nitro-1H-pyrazole (2.0 g, 6.51 mmol, 1 eq) in DMF (20 ml) was added K$_2$CO$_3$ portion wise at 0° C. and stirred for 10 minutes. 1-(bromomethyl)-2,4-bis(trifluoromethyl)benzene (0.73 gm, 6.51 mmol, 1 eq) was added drop wise 0° C. The reaction mixture was allowed to stir for 1 hour at RT. Product formation was confirmed by LCMS. After completion of reaction, reaction mixture was diluted with water and extracted with ethyl acetate (100 mL×3). Combined organic extracts were washed with water (100 mL×4), dried over anhydrous Na$_2$SO$_4$ and concentrated under reduced pressure to obtain 1-(2,4-bis (trifluoromethyl) benzyl)-4-nitro-1H-pyrazole (2.1 g, as white solid). LCMS: 326 [M+H]$^+$.

Step 2: Synthesis of 1-(2, 4-bis (trifluoromethyl)-1H-pyrazol-4-amine. To a stirred solution of 1-(2,4-bis(trifluoromethyl)benzyl)-4-nitro-1H-pyrazole (1.0 g, 1 eq) in Methanol (20 mL) under nitrogen Palladium on Carbon[Pd/C](100 mg, 10% w/w) was added. Purge the reaction mixture with H$_2$ gas for 2 h. Product formation was confirmed by LCMS. After the completion of reaction, reaction mixture was filtered through Celite bed & Filtrate was concentrate under reduced pressure to obtain 1-(2, 4-bis (trifluoromethyl)-1H-pyrazol-4-amine (0.800 g, as brown colour liquid). LCMS: 296 [M+H]$^+$.

Step 3: Synthesis of ethyl 4-(2-furyl)-2, 4-dioxobutyrate. To a solution of 2-acetylfuran (5.0 g, 45.40 mmol, 1 eq) in THF was added portion wise 60% Sodium hydride (3.63 g, 90.81 mmol, 2 eq) at 0° C. The resultant reaction mixture was stirred for another 30 minutes at RT, followed by drop wise addition of diethyl oxalate (12.28 ml, 90.81 mmol, 2 eq) at 0° C. and reaction mixture was stir for another 18 hours at RT. Product formation was confirmed by TLC and LCMS. The reaction mixture was quenched with ice water and washed with diethyl ether (2×100 mL). Aqueous layer was separated and neutralized with 1N HCl and extracted with EtOAc (3×100 mL). Combined organic extracts were washed with water (2×100 mL), dried over anhydrous Na$_2$SO$_4$ and concentrated under reduced pressure to obtain crude which was purified by combi-flash chromatography (0-20% Ethyl acetate in hexane) to obtain Ethyl 4-(2-furyl)-2, 4-dioxobutyrate (3.6 g, 45% as yellow solid). LCMS: 210 [M+H]$^+$.

Step 4: Synthesis of 5-furan-2-yl-isoxazole-3-carboxylic acid ethyl ester. A suspension of 4-furan-2-yl-2, 4-dioxobutyric acid ethyl ester (1.6 g, 7.61 mmol, 1 eq) and hydroxylamine hydrochloride salt (0.528 g, 7.61 mmol, 1 eq) in EtOH was stirred at 85° C. for 2 h. Product formation was confirmed by TLC and LCMS. The resulting mixture was concentrated under reduced pressure, the residue was dissolved in DCM and distilled water. Organic phase was separated, dried over anhydrous Na$_2$SO$_4$, filtered through silica gel pad, and then concentrated under reduced pressure to give 5-furan-2-yl-isoxazole-3-carboxylic acid ethyl ester. The crude product obtained was used in the next steps without further purification (700 mg, 52% as yellow solid). LCMS: 207 [M+H]$^+$.

Step 5: Synthesis of 5-furan-2-yl-isoxazole-3-carboxylic acid. To a solution of 5-furan-2-yl-isoxazole-3-carboxylic acid ethyl ester (0.5 g, 2.41 mmol) in THF (30 mL) and methanol (6 mL) was slowly added in lithium hydroxide aqueous solution (10 mL). The resulting mixture was stirred for 16 hrs. THF was concentrated under reduced pressure. The resulting residue was acidified with 1N HCl and extracted with ethyl acetate (3×100 mL). Combined organic extracts were washed with distilled water, dried over anhydrous Na$_2$SO$_4$ and concentrated under reduced pressure to obtain 5-furan-2-yl-isoxazole-3-carboxylic acid (225 mg, 52% as white solid). LCMS: 179 [M+H]$^+$.

Step 6: Synthesis of N-(1-(2,4-bis(trifluoromethyl)phenyl)-1H-pyrazol-4-yl)-5-(furan-2-yl)isoxazole-3-carboxamide. To stirred solution of 5-(furan-2-yl)isoxazole-3-carboxylic acid (60 mg, 0.338 mmol, 1 eq) in DMF (10 ml) add HATU (141 mg, 0.0.372 mmol, 1.1 eq) and stirred for half hours then add 1-(2,4-bis(trifluoromethyl)-1H-pyrazol-4-amine (100 mg, 0.338 mmol, 1 eq) and DIEA (0.18 mL, 1.081 mmol, 3.2 eq) in it. Stirred reaction mixture for overnight at room temperature. Reaction monitored by LCMS. Reaction mixture was diluted with ethyl acetate (30 mL) and washed with water (50 mL). The organic layer dried over anhydrous sodium sulphate & concentrate to get product (12 mg). $^1$H NMR (400 MHz, DMSO-d$_6$) δ ppm 6.79 (br. s., 2H) 7.21 (s, 2H) 7.31 (br. s., 1H) 8.06 (s, 1H) 8.02 (s, 1H) 8.27 (br. s., 1H) 8.49 (br. s., 1H) 11.30 (br. s., 1H). LCMS: 457 [M+H]$^+$.

Example S26. Synthesis of N-(1-(3,5-bis(trifluoromethyl)benzyl)-1H-pyrazole-4-yl)-5-(furan-2-yl) isoxazole-3-carboxamide (Compound 28)

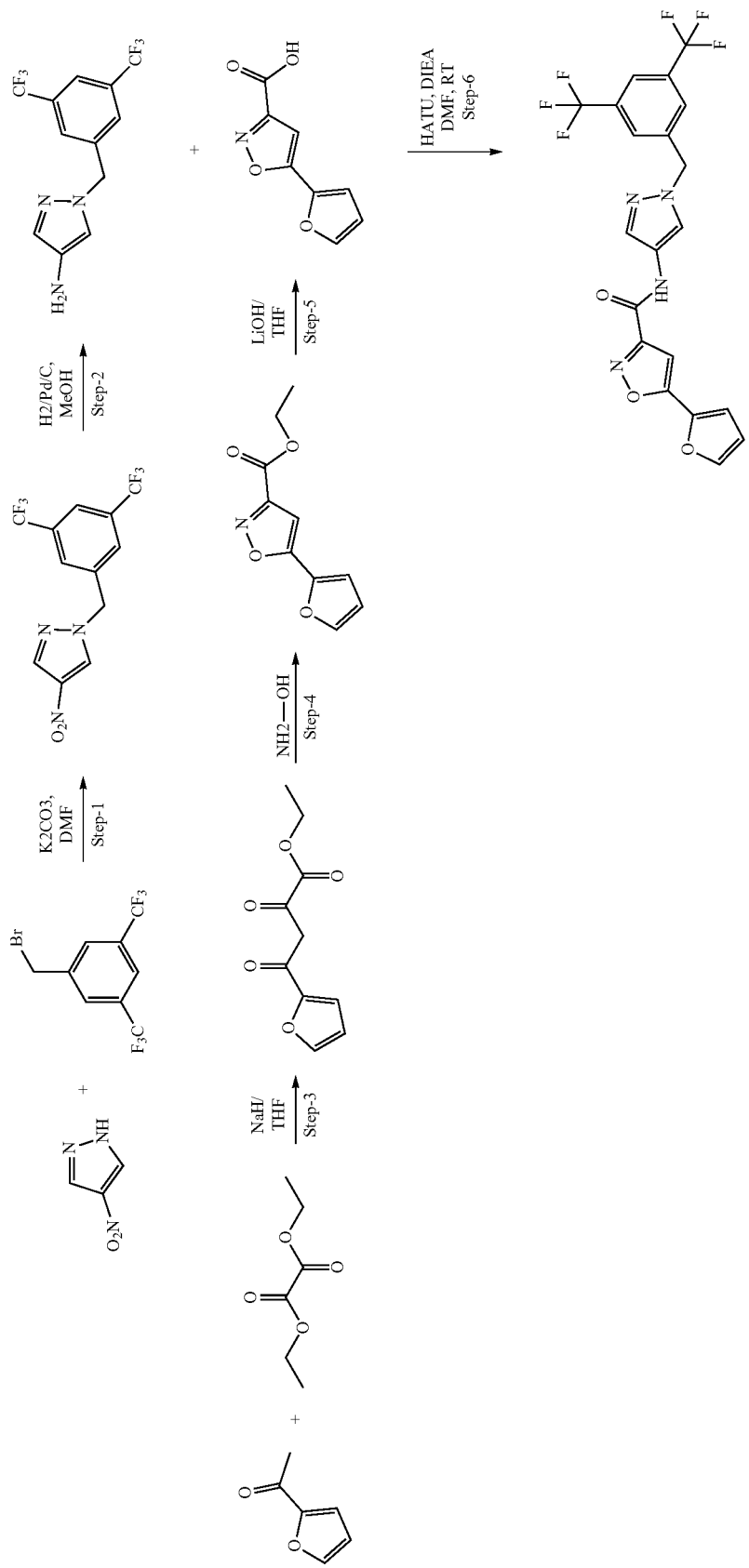

Step 1: Synthesis of 1-(3,5-bis(trifluoromethyl)benzyl)-4-nitro-1H-pyrazole. To a stirred solution of 4-nitro-1H-pyrazole (0.55 g, 4.88 mmol, 1 equiv) in DMF (20 mL). Cool this reaction mixture by ice water up to 0° C. add $K_2CO_3$ (1.01 g, 7.32 mmol, 1.5 equiv) portion wise in it stirred reaction mixture for 10 minute and then add 1-(bromomethyl)-3,5-bis(trifluoromethyl)benzene (1.5 g, 4.88 mmol, 1 equiv) in it by drop by drop. Stir above reaction mixture for 1 hour (reaction was monitored by TLC & LCMS). After completion of reaction, reaction mixture was diluted with ethyl acetate (50 mL) and extracted with water (50 mL). Collect organic layer and concentrate it to obtain product which further purified by flash chromatography to obtain a white-colored product. LCMS: 339 $[M+H]^+$.

Step 2: Synthesis of 1-(3, 5-bis (trifluoromethyl)-1H-pyrazol-4-amine. To a stirred solution of 1-(3,5-bis(trifluoromethyl)benzyl)-4-nitro-1H-pyrazole (500 mg, 1 equiv) in Methanol (20 mL) under Nitrogen add Palladium on Carbon [Pd/C](10% by weight) in it & purged the reaction mixture by Hydrogen gas for a 2 hour. Reaction was monitored by LCMS. After the completion of reaction, reaction mixture was filtered through Celite bed & Filtered was concentrate to obtained product which is purified by flash chromatography to get Brown Color viscous Liquid. LCMS: 309 $[M+H]^+$.

Step 3: Synthesis of ethyl 4-(2-furyl)-2, 4-dioxobutyrate. To a solution of 2-acetylfuran (5.0 g, 45.40 mmol, 1 equiv) in THF was added portion wise 60% Sodium hydride (3.63 g, 90.81 mmol, 2 equiv) at 0° C. The resultant reaction mixture was stirred for another 30 minutes at RT, followed by drop wise addition of diethyl oxalate (12.28 ml, 90.81 mmol, 2 equiv) at 0° C. and reaction mixture was stir for another 18 hours at RT. Product formation was confirmed by TLC and LCMS. The reaction mixture was quenched with ice water and washed with diethyl ether (2×100 mL). Aqueous layer was separated and neutralized with 1N HCl and extracted with EtOAc (3×100 mL). Combined organic extracts were washed with water (2×100 mL), dried over anhydrous $Na_2SO_4$ and concentrated under reduced pressure to obtain crude which was purified by combi-flash chromatography (0-20% Ethyl acetate in hexane) to obtain Ethyl 4-(2-furyl)-2, 4-dioxobutyrate (3.6 g, 45% as yellow solid). LCMS: 210 $[M+H]^+$.

Step 4: Synthesis of 5-furan-2-yl-isoxazole-3-carboxylic acid ethyl ester. A suspension of 4-furan-2-yl-2, 4-dioxobutyric acid ethyl ester (1.6 g, 7.61 mmol, 1 equiv) and hydroxylamine hydrochloride salt (0.528 g, 7.61 mmol, 1 equiv) in EtOH was stirred at 85° C. for 2 h. Product formation was confirmed by TLC and LCMS. The resulting mixture was concentrated under reduced pressure, the residue was dissolved in DCM and distilled water. Organic phase was separated, dried over anhydrous $Na_2SO_4$, filtered through silica gel pad, and then concentrated under reduced pressure to give 5-furan-2-yl-isoxazole-3-carboxylic acid ethyl ester. The crude product obtained was used in the next steps without further purification (700 mg, 52% as a yellow solid). LCMS: 207 $[M+H]^+$.

Step 5: Synthesis of 5-furan-2-yl-isoxazole-3-carboxylicacid. To a solution of 5-furan-2-yl-isoxazole-3-carboxylic acid ethyl ester (0.5 g, 2.41 mmol) in THF (30 mL) and methanol (6 mL) was slowly added in lithium hydroxide aqueous solution (10 mL). The resulting mixture was stirred for 16 hrs. THF was concentrated under reduced pressure. The resulting residue was acidified with 1N HCl and extracted with ethyl acetate (3×100 mL). Combined organic extracts were washed with distilled water, dried over anhydrous $Na_2SO_4$ and concentrated under reduced pressure to obtain 5-furan-2-yl-isoxazole-3-carboxylic acid (225 mg, 52% as a white solid). LCMS: 179 $[M+H]^+$.

Step 6: Synthesis of N-(1-(3,5-bis(trifluoromethyl)benzyl)-1H-pyrazole-4-yl)-5-(furan-2-yl)isoxazole-3-carboxamide. To stirred solution of 5-(furan-2-yl)isoxazole-3-carboxylic acid (100 mg, 0.558 mmol, 1 equiv) in DMF (10 ml) add HATU (233 mg, 0.613 mmol, 1.1 equiv) and stirred for half hours then add 1-(3,5-bis(trifluoromethyl)-1H-pyrazol-4-amine (172 mg, 0.558 mmol, 1 equiv) and DIEA in it. Stirred reaction mixture for overnight at room temperature. Reaction monitored by LCMS. Reaction mixture was diluted with ethyl acetate (30 mL) and washed with water (50 mL). The organic layer dried over anhydrous sodium sulphate & concentrate to get crude product which is purified by stritulation using Isopropyl Alcohol (12 mg white solid). $^1$H NMR (400 MHz, DMSO-$d_6$) δ ppm 5.56 (s, 2H) 7.16 (s, 1H) 7.29 (d, J=3.51 Hz, 1H) 7.72 (s, 2H) 7.95 (s, 2H) 8.01 (s, 1H) 8.08 (br. s., 1H) 8.33 (s, 1H) 11.06 (s, 1H). LCMS: 471 $[M+H]^+$.

Example S27. Synthesis of N-(1-(2,4-bis(trifluoromethyl)benzyl)-3-methyl-1H-pyrazol-4-yl)-5-(pyridin-2-yl)isoxazole-3-carboxamide and N-(1-(2, 4-bis(trifluoromethyl)benzyl)-5-methyl-1H-pyrazol-4-yl)-5-(pyridin-2-yl)isoxazole-3-carboxamide (Compounds 29 and 30)

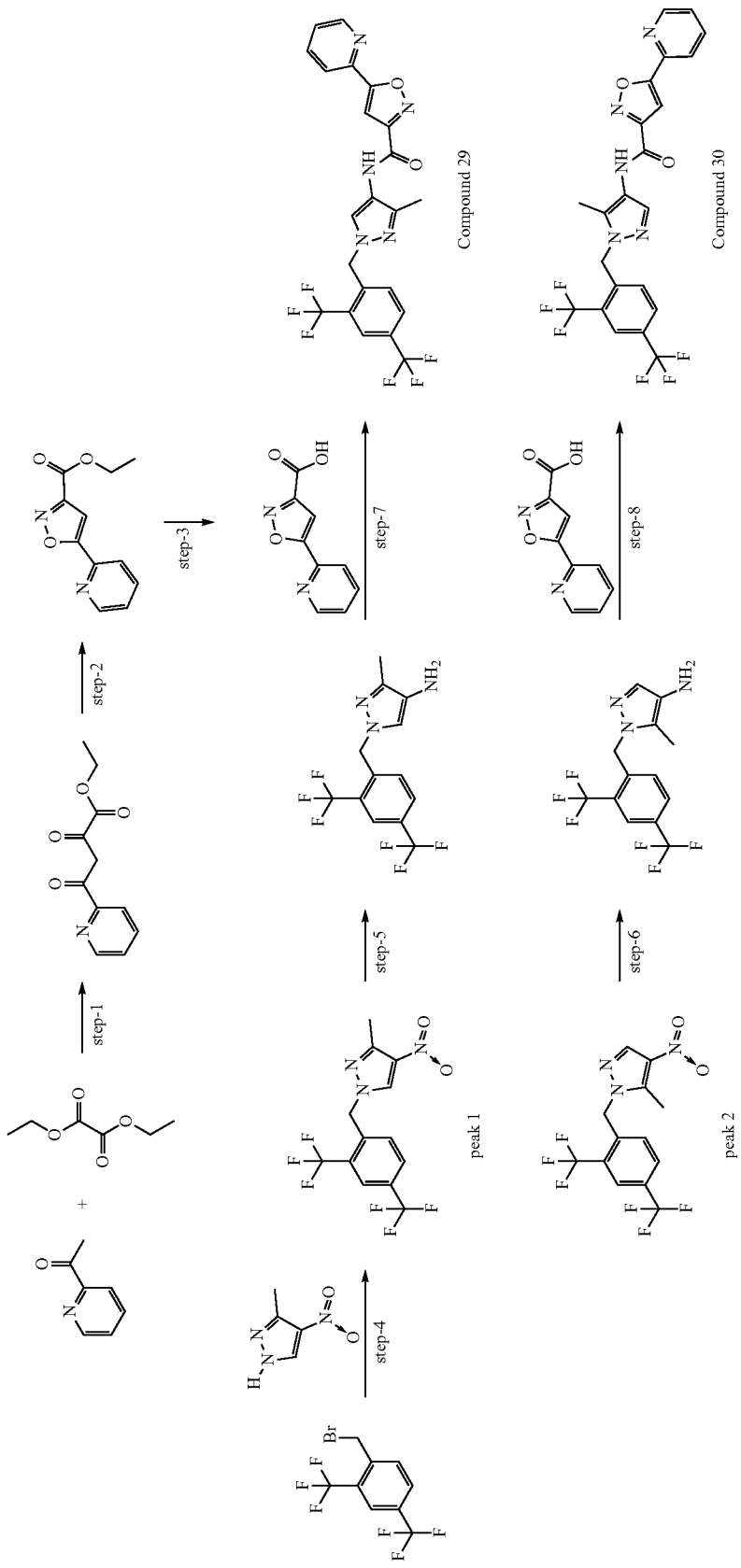

Step 1: Synthesis of ethyl 2,4-dioxo-4-(pyridin-2-yl)butanoate. To a solution of 1-(pyridin-2-yl)ethan-1-one (5.0 g, 0.04 mol, 1 eq) in THF was added portion wise 60% Sodium hydride (3.3 g, 0.08 mol, 2.0 eq) at 0° C. The resultant reaction mixture was stirred for another 30 minutes at RT, followed by drop wise addition of diethyl oxalate (11.2 ml, 0.08 mol, 2.0 eq) at 0° C. and reaction mixture was stir for another 18 hours at RT. Product formation was confirmed by TLC and LCMS. Aqueous layer was separated and neutralized with 1N HCl and extracted with EtOAc (3×100 mL). Combined organic extracts were washed with water (2×100 mL), dried over anhydrous $Na_2SO_4$ and concentrated under reduced pressure to obtain crude which was purified by combi-flash chromatography (0-20% Ethyl acetate in hexane) to obtain ethyl 2,4-dioxo-4-(pyridin-2-yl)butanoate (3 g, yellow solid). LCMS: 221[M+H]$^+$.

Step 2: Synthesis of ethyl 5-(pyridin-2-yl)isoxazole-3-carboxylate. A suspension of ethyl 2,4-dioxo-4-(pyridin-2-yl)butanoate (1.6 g, 7.61 mmol, 1.0 eq) and hydroxylamine hydrochloride salt (0.528 g, 7.61 mmol, 1.0 eq) in EtOH was stirred at 85° C. for 48 h. Product formation was confirmed by TLC and LCMS. The resulting mixture was concentrated under reduced pressure, the residue was dissolved in DCM and distilled water. Organic phase was separated, dried over anhydrous $Na_2SO_4$, filtered through silica gel pad, and then concentrated under reduced pressure to give ethyl 5-(pyridin-2-yl)isoxazole-3-carboxylate. Obtain crude which was purified by combi-flash chromatography (0-20% Ethyl acetate in hexane). LCMS: 218 [M+H]$^+$.

Step 3: Synthesis of 5-(pyridin-2-yl)isoxazole-3-carboxylic acid. To a solution of ethyl 5-(pyridin-2-yl)isoxazole-3-carboxylate (0.5 g, 2.41 mmol) in THF (30 mL) and methanol (6 mL) was slowly added in lithium hydroxide aqueous solution (10 mL). The resulting mixture was stirred for 16 hrs. THF was concentrated under reduced pressure. The resulting residue was acidified with 1N HCl and extracted with ethyl acetate (3×100 mL). Combined organic extracts were washed with distilled water, dried over anhydrous $Na_2SO_4$ and concentrated under reduced pressure to obtain 5-(pyridin-2-yl)isoxazole-3-carboxylic acid (225 mg, 52% as white solid). LCMS: 190 [M+H]$^+$.

Step 4: Synthesis of 1-(2,4-bis(trifluoromethyl)benzyl)-3-methyl-4-nitro-1H-pyrazole (peak 1) and 1-(2,4-bis(trifluoromethyl)benzyl)-5-methyl-4-nitro-1H-pyrazole (peak 2). To a stirred solution of 3-methyl-4-nitro-1H-pyrazole (1.24 g, 0.009 mol, 1 equiv) in DMF (20 mL) was added $K_2CO_3$ (1.86 g, 0.013 mol, 1 equiv) portion wise at 0° C. and stirred for 10 minutes. 1-(bromomethyl)-2,4-bis(trifluoromethyl)benzene (3 gm, 0.009 mol, 1 equiv) was added drop wise 0° C. The reaction mixture was allowed to stir for 1 hour at RT. Product formation was confirmed by LCMS. After completion of reaction, reaction mixture was diluted with water and extracted with ethyl acetate (100 mL×3). Combined organic extracts were washed with water (100 mL×4), dried over anhydrous $Na_2SO_4$ and concentrated under reduced pressure to obtain mixture of 1-(2,4-bis (trifluoromethyl)benzyl)-3-methyl-4-nitro-1H-pyrazole (peak 1) and 1-(2,4-bis(trifluoromethyl)benzyl)-5-methyl-4-nitro-1H-pyrazole (peak 2). obtained crude was sent for separation in prep. LCMS: 353 [M+H]$^+$.

Step 5: Synthesis of 1-(2,4-bis(trifluoromethyl)benzyl)-3-methyl-1H-pyrazol-4-amine (peak 1). To a stirred solution of 1-(2,4-bis(trifluoromethyl)benzyl)-3-methyl-4-nitro-1H-pyrazole (peak 1) (150 mg, 1 equiv) in Methanol (10 mL) under nitrogen Palladium on Carbon[Pd/C] (10% w/w) was added. Purge the reaction mixture with $H_2$ gas for 6 h. Product formation was confirmed by LCMS. After the completion of reaction, reaction mixture was filtered through Celite bed & Filtrate was concentrate under reduced pressure to obtain 1-(2,4-bis(trifluoromethyl)benzyl)-3-methyl-1H-pyrazol-4-amine (peak 1). LCMS: 323 [M+H]$^+$.

Step 6: Synthesis of 1-(2,4-bis(trifluoromethyl)benzyl)-5-methyl-1H-pyrazol-4-amine (peak 2). To a stirred solution of 1-(2,4-bis(trifluoromethyl)benzyl)-5-methyl-4-nitro-1H-pyrazole (peak 2) (500 mg, 1 equiv) in Methanol (10 mL) under nitrogen Palladium on Carbon[Pd/C] (10% w/w) was added. Purge the reaction mixture with $H_2$ gas for 6 h. Product formation was confirmed by LCMS. After the completion of reaction, reaction mixture was filtered through Celite bed & Filtrate was concentrate under reduced pressure to obtain 1-(2,4-bis(trifluoromethyl)benzyl)-5-methyl-1H-pyrazol-4-amine (peak 2). LCMS: 323 [M+H]$^+$.

Step 7: Synthesis of N-(1-(2,4-bis(trifluoromethyl)benzyl)-3-methyl-1H-pyrazol-4-yl)-5-(pyridin-2-yl)isoxazole-3-carboxamide (Compound 29). To a solution of 5-(pyridin-2-yl)isoxazole-3-carboxylic acid (50 mg, 0.263 mmol, 1 equiv) in DMF (1 mL), were added HATU (100 mg, 0.263 mmol, 1 equiv). After stirring at RT for 15 minutes, the mixture was treated drop wise with DIPEA (0.13 ml, 0.775 mmol, 2 equiv). After stirring at RT for 15 minutes, the mixture was treated drop wise with a solution of the 1-(2,4-bis(trifluoromethyl)benzyl)-3-methyl-1H-pyrazol-4-amine (peak 1) (85 mg, 0.263 mmol, 1 equiv) in DMF (1 mL). The reaction mixture was kept under stirring for 24 h. The reaction mixture was diluted water (50 mL). The resulting precipitate was filtered off. Crude material obtained was purified by trituration with hexane. $^1$H NMR (400 MHz, DMSO-d$_6$) δ 10.40 (s, 1H), 8.77 (d, J=4.82 Hz, 1H), 8.02-8.11 (m, 4H), 7.76 (s, 1H), 7.54-7.58 (m, 1H), 7.50 (s, 1H), 6.85 (d, J=7.89 Hz, 2H), 5.59 (s, 2H), 2.19 (s, 3H). LCMS: 495 [M+H]$^+$.

Step 8: Synthesis of N-(1-(2,4-bis(trifluoromethyl)benzyl)-5-methyl-1H-pyrazol-4-yl)-5-(pyridin-2-yl)isoxazole-3-carboxamide (Compound 30). To a solution of 5-(pyridin-2-yl)isoxazole-3-carboxylic acid (100 mg, 0.52 mmol, 1 equiv) in DMF (1 mL), were added HATU (200 mg, 0.52 mmol, 1 equiv). After stirring at RT for 15 minutes, the mixture was treated drop wise with DIPEA (135.7 mg, 1.05 mmol, 2 equiv). After stirring at RT for 15 minutes, the mixture was treated drop wise with a solution of the 1-(2,4-bis(trifluoromethyl)benzyl)-5-methyl-1H-pyrazol-4-amine (peak 2) (170 mg, 0.52 mmol, 1 equiv) in DMF (1 mL). The reaction mixture was kept under stirring for 24 h. The reaction mixture was diluted water (50 mL). The resulting precipitate was filtered off. Crude material obtained was purified by trituration with IPA. $^1$H NMR (400 MHz, DMSO-d$_6$) δ 10.39 (s, 1H), 8.76 (br. s., 1H), 8.23 (s, 1H), 8.00-8.12 (m, 4H), 7.55-7.58 (m, 1H), 7.51 (s, 1H), 7.12 (d, J=8.33 Hz, 1H), 5.58 (s, 2H), 2.21 (s, 3H). LCMS: 495 [M+H]$^+$.

Example S28. Synthesis of N-(1-(2,4-bis(trifluoromethyl)benzyl)-1H-pyrazol-4-yl-5-(3-chloropyridin-2-yl)isoxazole-3-carboxamide (Compound 31)

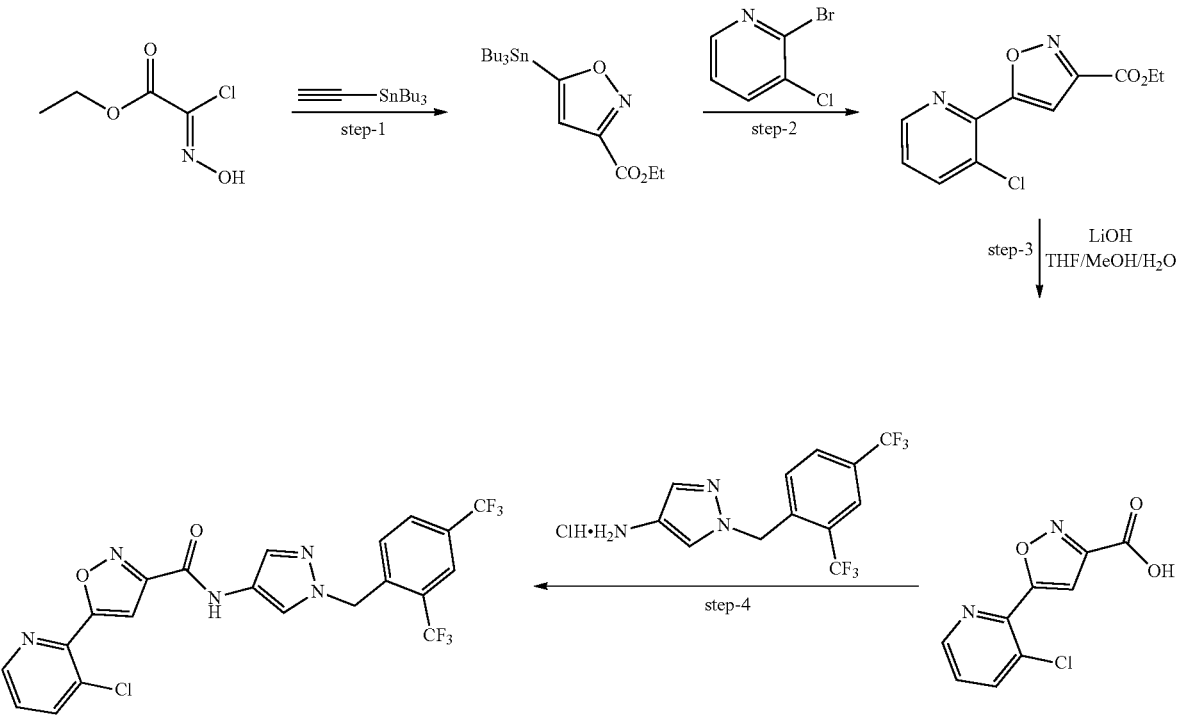

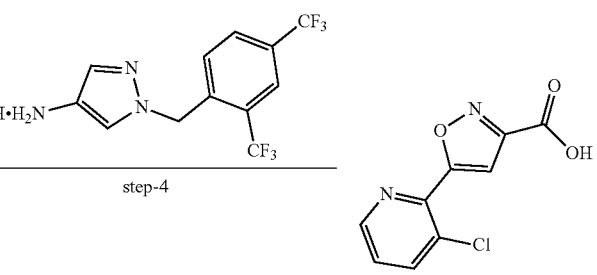

Step 1: Synthesis of ethyl 5-(tributylstannyl)isoxazole-3-carboxylate. To a solution of ethyl (Z)-2-chloro-2-(hydroxyimino)acetate (2.0 gm, 0.013 mol, 1 equiv) in DCM (20 ml) was added K$_2$CO$_3$ (2.01 gm, 0.014 mol, 2 equiv) at RT. The resultant reaction mixture was stirred for another 30 minutes at RT, followed by drop wise addition of tributyl(ethynyl)stannane (4.01 gm, 0.013 mol, 1 equiv) at RT and reaction mixture was stir for another 18 hours at RT. Product formation was confirmed by TLC and LCMS. The reaction mixture was quenched with ice water and extracted with DCM (2×100 mL). Combined organic extracts were washed with water (2×100 mL), dried over anhydrous Na$_2$SO$_4$ and concentrated under reduced pressure to obtain crude which was further purified by combi-flash chromatography (5-10% ethyl acetate in hexane) to obtain ethyl 5-(tributylstannyl)isoxazole-3-carboxylate (2.1 gm, 35% as brown liquid). LCMS: 432 [M+H]$^+$.

Step 2: Synthesis of ethyl 5-(3-chloropyridin-2-yl)isoxazole-3-carboxylate. A suspension of ethyl 5-(tributylstannyl)isoxazole-3-carboxylate (600 mg, 1.39 mmol, 1.0 equiv) and 2-bromo-3-chloropyridine (267 mg, 1.39 mmol, 1.0 equiv) in Toulene (2 ml) was degassed using nitrogen for 5 minutes. Tetrakis (161 mg, 0.13 mmol, 1.0 equiv) was added to reaction mixture. The resultant reaction mixture was heated at 100° C. for 16 h. Product formation was confirmed by TLC and LCMS. The resulting mixture was diluted with water extracted with ethyl acetate (2×100 mL). The organic phase was separated, dried over anhydrous Na$_2$SO$_4$, concentrated under reduced pressure to obtain crude which was further purified by combi-flash chromatography (10-15% Ethyl acetate in hexane) to obtain ethyl 5-(3-chloropyridin-2-yl)isoxazole-3-carboxylate (200 mg, 56% as off white solid). LCMS: 253[M+H]$^+$.

Step 3: Synthesis of 5-(3-chloropyridin-2-yl)isoxazole-3-carboxylic acid. To a solution of ethyl 5-(3-chloropyridin-2-yl)isoxazole-3-carboxylate (200 mg, 0.79 mmol, 1.0 equiv) in THF (5 mL), methanol (3 mL) and water (2 mL) was added in lithium hydroxide (66 mg, 1.58 mmol, 2.0 equiv) The resulting mixture was stirred for 16 hrs. THF was concentrated under reduced pressure. The resulting residue was acidified with 1N HCl and extracted with ethyl acetate (3×100 mL). Combined organic extracts were washed with distilled water, dried over anhydrous Na$_2$SO$_4$ and concentrated under reduced pressure to obtain 5-(3-chloropyridin-2-yl)isoxazole-3-carboxylic acid (200 mg, 88% as white solid). LCMS: 225 [M+H]$^+$.

Step 4: Synthesis of N-(1-(2,4-bis(trifluoromethyl)benzyl)-1H-pyrazol-4-yl)-5-(3-chloropyridin-2-yl)isoxazole-3-carboxamide. To a solution of 5-(3-chloropyridin-2-yl)isoxazole-3-carboxylic acid (50 mg, 0.22 mmol, 1 equiv) in DMF (1 mL), were added HATU (93 mg, 0.24 mmol, 1.1 equiv). The mixture was treated drop wise with DIPEA (92 mg, 0.71 mmol, 3.2 equiv). After stirring at RT for 15 minutes, the mixture was treated drop wise with a solution of the 1-(2,4-bis(trifluoromethyl)benzyl)-1H-pyrazol-4-amine hydrochloride (68 mg, 0.22 mmol, 1 equiv) in DMF (1 mL). The reaction mixture was kept under stirring for 24 h. Product formation was confirmed with TLC & LCMS and reaction mixture was diluted EtOAc (50 mL) & washed with water (50 mL×2). Organic layer dried over Na$_2$SO$_4$ & concentrated under reduced pressure to obtain crude which was further purified by flash column chromatography to obtain pure product N-(1-(2,4-bis(trifluoromethyl)benzyl)-1H-pyrazol-4-yl)-5-(3-chloropyridin-2-yl)isoxazole-3-carboxamide. (8 mg, 7% as off white solid). $^1$H NMR (400 MHz, DMSO-d$_6$) δ 11.20 (s, 1H), 8.76 (d, J=4.5 Hz, 1H), 8.33 (s, 1H), 8.21 (d, J=8.3 Hz, 1H), 8.07 (d, J=7.2 Hz, 2H), 7.79 (s, 1H), 7.64 (dd, J=8.2, 4.6 Hz, 1H), 7.57 (s, 1H), 7.07 (d, J=8.1 Hz, 1H), 5.67 (s, 2H). LCMS: 516 [M+H]$^+$.

Example S29. Synthesis of N-(1-(1-(2,4-bis(trifluoromethyl)phenyl)ethyl)-1H-pyrazol-4-yl)-5-(3-chloropyridin-2-yl)isoxazole-3-carboxamide (Compound 32)

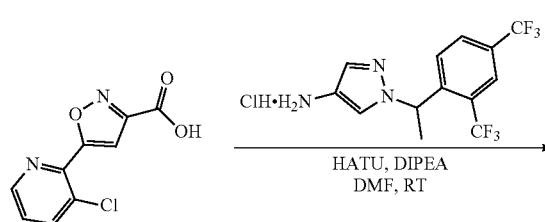

To a solution of 5-(pyridin-2-yl)isoxazole-3-carboxylic acid (50 mg, 0.22 mmol, 1 equiv) and HATU (72 mg, 0.22 mmol, 1 equiv) in DMF (1 mL). The mixture was allow to stir for 30 mins followed by the addition of DIPEA (92 mg, 0.71 mmol, 3.2 equiv) and a solution of the 1-{1[2,4bis(trifluoromethyl)phenyl]ethyl}-1H-pyrazol-4-amineHydrochloride (72 mg, 0.22 mmol, 1 equiv) in DMF (1 mL) was added. The reaction mixture was kept under stirring for 24 h at RT. Product formation was confirmed with TLC & LCMS and reaction mixture was diluted EtOAc (50 mL) & washed with water (50 mL×2). Organic layer dried over $Na_2SO_4$ & concentrated under reduced pressure to obtain crude which was further purified by flash column chromatography to obtain pure product N-(1-(1-(2,4-bis(trifluoromethyl)phenyl)ethyl)-1H-pyrazol-4-yl)-5-(3-chloropyridin-2-yl)isoxazole-3-carboxamide. (20 mg, 17% as off white solid). $^1$H NMR (400 MHz, DMSO-$d_6$) δ 11.14 (s, 1H), 8.76 (d, J=4.6 Hz, 1H), 8.21 (d, J=8.7 Hz, 2H), 8.13-8.03 (m, 2H), 7.74 (d, J=7.5 Hz, 2H), 7.64 (dd, J=8.3, 4.6 Hz, 1H), 7.54 (s, 1H), 5.94 (q, J=6.5 Hz, 1H), 1.88 (d, J=6.9 Hz, 3H). LCMS: 522 [M+H]$^+$.

Example S30. Synthesis of N-(1-((2,4-bis(trifluoromethyl)phenyl)(cyclopropyl)methyl)-1H-pyrazol-4-yl)-5-(pyridin-2-yl)isoxazole-3-carboxamide (Compound 33)

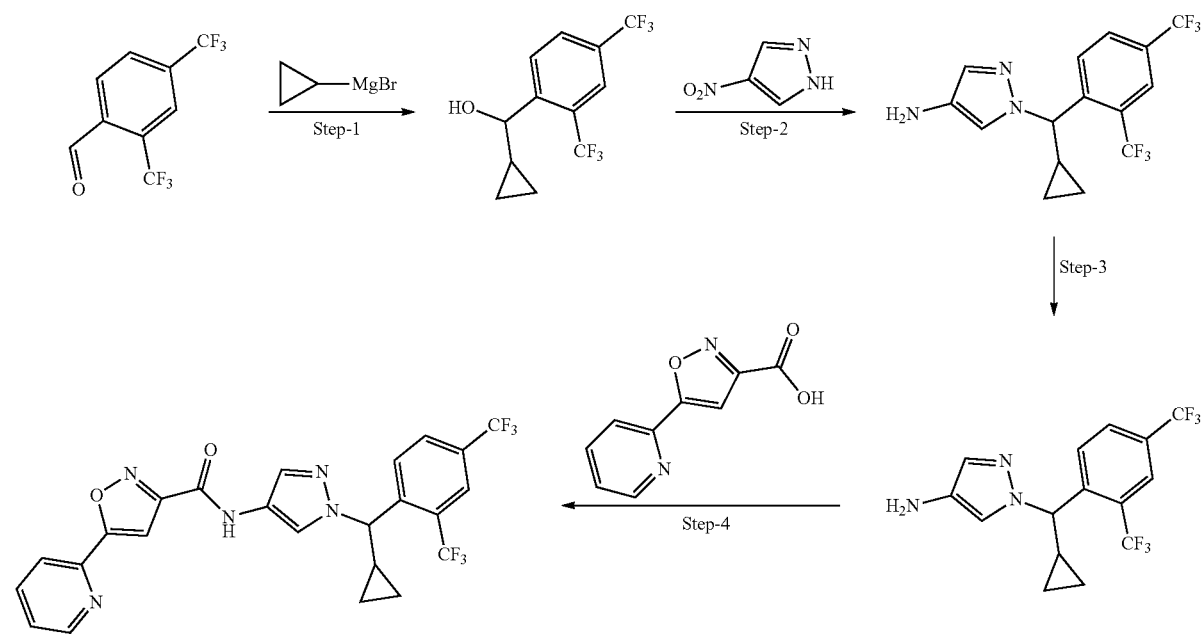

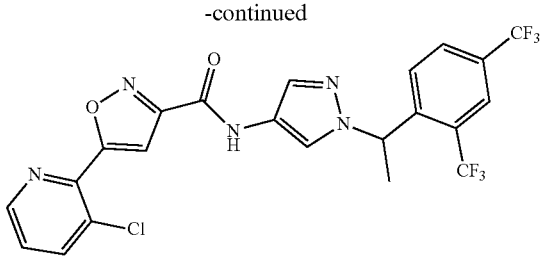

Step 1: Synthesis of (2,4-bis(trifluoromethyl)phenyl)(cyclopropyl)methanol. To a stirred solution of 2,4-bis(trifluoromethyl)benzaldehyde (300 mg, 1.23 mmol, 1.0 equivuiv) in THF (5 mL) was added Cyclopropyl magnesium Bromide (0.269 gm, 1.85 mol, 1.5 equiv) portion wise at rt and stirred for 10 minutes. The reaction mixture was allowed to stir for 1 hour at RT. Product formation was confirmed by TLC & NMR. After completion of the reaction, the reaction mixture was quenched with water and extracted with ethyl acetate (50 mL×3). Combined organic extracts were washed with water (50 mL×2), dried over anhydrous $Na_2SO_4$ and concentrated under reduced pressure to obtain (2,4bis(trifluoromethyl)phenyl)(cyclopropyl) methanol (350 gm, 100% crude as colorless liquid). $^1$H NMR (400 MHz, DMSO-$d_6$) δ 8.15-8.02 (m, 2H), 7.94 (s, 1H), 5.67 (d, J=4.8 Hz, 1H), 4.61 (br. s., 1H), 1.14-1.06 (m, 1H), 0.58-0.49 (m, 1H), 0.46-0.28 (m, 3H).

Step 2: Synthesis of 1-((2,4-bis(trifluoromethyl)phenyl)(cyclopropyl)methyl)-4-nitro-1H-pyrazole. To a stirred solution of $PPh_3$ (329 mg, 1.23 mmol, 1.0 equiv) and DIAD (248 mg, 1.23 mmol, 1.0 equiv) in THF (2 mL) was added (2,4bis(trifluoromethyl)phenyl)(cyclopropyl)methanol (350 mg, 1.23 mmol, 1.0 equiv). Followed by drop wise addition of 4-nitro-1H-pyrazole (111 mg 0.98 mmol, 0.8 equiv), The reaction mixture was stirred at RT for 1 h. Product formation was confirmed with TLC & LCMS. After completion of reaction mixture were diluted with EtOAc (50 mL) & washed with water (50 mL×3). Organic layer dried over $Na_2SO_4$ & concentrated under reduced pressure to obtain crude which was further purified by flash column chromatography to obtain pure product 1-(1-(2,4-bis(trifluoromethyl)phenyl)ethyl)-4-nitro-1H-pyrazole (130 mg, 30% as brown liquid). 1H NMR (400 MHz, DMSO-$d_6$) δ 9.21 (s, 1H), 8.29-8.20 (m, 2H), 8.17 (d, J=8.3 Hz, 1H), 8.05 (s, 1H), 5.03 (d, J=10.1 Hz, 1H), 1.22 (br. s., 1H), 0.76 (br. s., 2H), 0.69 (br. s., 1H), 0.37 (br. s., 1H).

Step 3: Synthesis of 1-((2,4-bis(trifluoromethyl)phenyl)(cyclopropyl)methyl)-1H-pyrazol-4-amine. To a stirred solution of 1-(2,4-bis(trifluoromethyl)benzyl)-4-nitro-1H-pyrazole (220 mg, 0.58 mmol, 1.0 equiv) in Methanol (10 mL) under nitrogen Palladium on Carbon[Pd/C] (49 mg, 10% w/w) was added. Purge the reaction mixture with $H_2$ gas for 2 h. Product formation was confirmed by LCMS. After the completion of reaction, reaction mixture was filtered through Celite bed & Filtrate was concentrate under reduced pressure to 1-((2,4-bis(trifluoromethyl)phenyl)(cyclopropyl)methyl)-1H-pyrazol-4-amine (120 mg, 58% crude as brown colour liquid). LCMS: 350 [M+H]$^+$.

Step 4: Synthesis of N-(1-((2,4-bis(trifluoromethyl)phenyl)(cyclopropyl)methyl)-1H-pyrazol-4-yl)-5-(pyridin-2-yl)isoxazole-3-carboxamide. To a solution of 5-(pyridin-2-yl)isoxazole-3-carboxylic acid (60 mg, 0.31 mmol, 1 equiv) in DMF (1 mL), were added HATU (132 mg, 0.34 mmol, 1.1 equiv). The mixture was treated drop wise with DIPEA (130 mg, 1.01 mmol, 3.2 equiv). After stirring at RT for 15 minutes, the mixture was treated drop wise with a solution of the 1-((2,4-bis(trifluoromethyl)phenyl)(cyclopropyl)methyl)-1H-pyrazol-4-amine (110 mg, 0.31 mmol, 1 equiv) in DMF (1 mL). The reaction mixture was kept under stirring for 24 h. Product formation was confirmed with TLC & LCMS and reaction mixture was diluted EtOAc (50 mL) & washed with water (50 mL×2). Organic layer dried over $Na_2SO_4$ & concentrated under reduced pressure to obtain crude which was further purified by flash column chromatography to obtain pure product N-(1-(1-(2,4-bis(trifluoromethyl)phenyl)ethyl)-1H-pyrazol-4-yl)-5-(furan-2-yl)isoxazole-3-carboxamide. (65 mg, 40% as off white solid). $^1$H NMR (400 MHz, DMSO-$d_6$) δ 11.06 (s, 1H), 8.76 (d, J=4.7 Hz, 1H), 8.36 (s, 1H), 8.20 (d, J=8.5 Hz, 1H), 8.14 (d, J=8.5 Hz, 1H), 8.12-7.98 (m, 3H), 7.70 (s, 1H), 7.56 (t, J=6.1 Hz, 1H), 7.47 (s, 1H), 4.96 (d, J=9.6 Hz, 1H), 1.94 (qd, J=9.0, 8.6, 4.3 Hz, 1H), 0.70 (dddd, J=28.2, 18.9, 9.1, 4.8 Hz, 3H), 0.35 (dq, J=10.4, 5.4, 4.9 Hz, 1H). LCMS: 530 [M+H]$^+$.

Example S31. Synthesis of (R)- and (S)—N-(1-(1-(2,4-bis(trifluoromethyl)phenyl)ethyl)-1H-pyrazol-4-yl)-5-(3-chloropyridin-2-yl)isoxazole-3-carboxamide (Compounds 34 and 35)

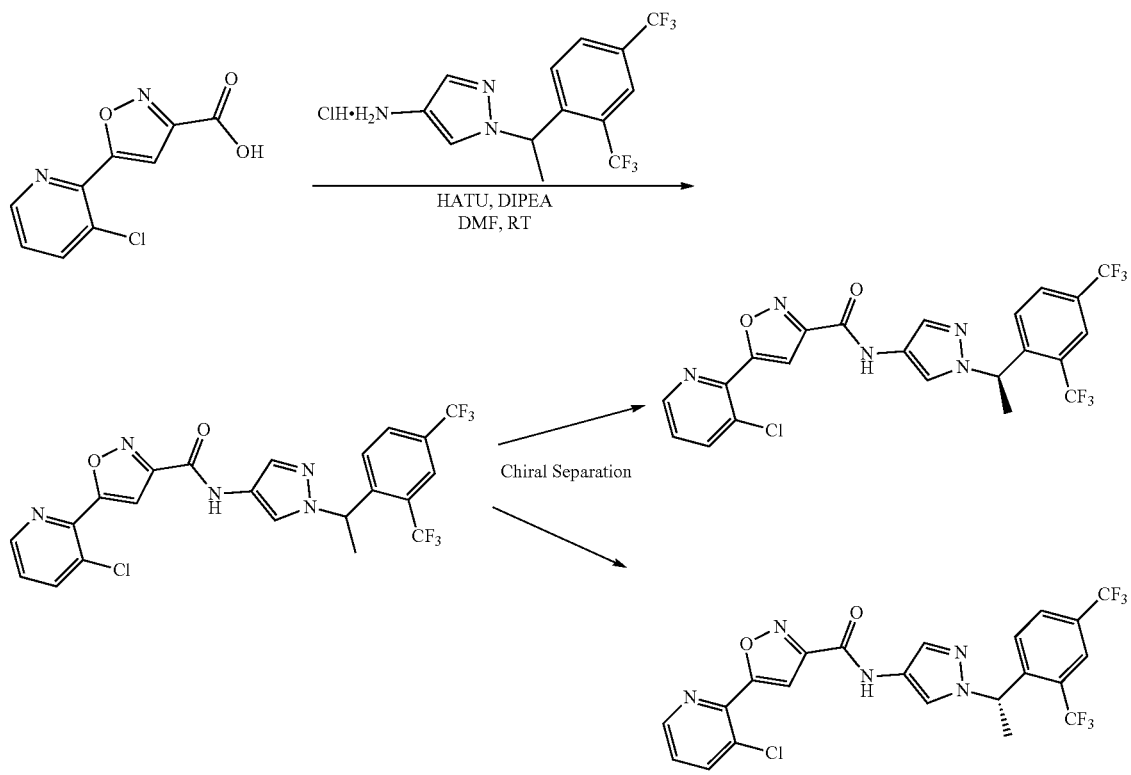

Step 1: Synthesis of N-(1-(1-(2,4-bis(trifluoromethyl)phenyl)ethyl)-1H-pyrazol-4-yl)-5-(3-chloropyridin-2-yl) isoxazole-3-carboxamide. To a solution of 5-(pyridin-2-yl) isoxazole-3-carboxylic acid (95 mg, 0.42 mmol, 1 equiv) and HATU (177 mg, 0.46 mmol, 1 equiv) in DMF (1 mL). The mixture was allow to stir for 30 mins followed by the addition of DIPEA (175 mg, 1.35 mmol, 3.2 equiv) and a solution of the 1-{1[2,4bis(trifluoromethyl)phenyl]ethyl}-

1H-pyrazol-4-amineHydrochloride (131 mg, 0.42 mmol, 1 equiv) in DMF (1 mL) was added. The reaction mixture was kept under stirring for 24 h at RT. Product formation was confirmed with TLC & LCMS and reaction mixture was diluted EtOAc (50 mL) & washed with water (50 mL×2). Organic layer dried over Na$_2$SO$_4$ & concentrated under reduced pressure to obtain crude which was further purified by flash column chromatography to obtain pure product N-(1-(1-(2,4-bis(trifluoromethyl)phenyl)ethyl)-1H-pyrazol-4-yl)-5-(3-chloropyridin-2-yl)isoxazole-3-carboxamide (95 mg, 42% as off white solid). $^1$H NMR (400 MHz, DMSO-d$_6$) δ 11.14 (s, 1H), 8.76 (d, J=4.6 Hz, 1H), 8.21 (d, J=8.7 Hz, 2H), 8.13-8.03 (m, 2H), 7.74 (d, J=7.5 Hz, 2H), 7.64 (dd, J=8.3, 4.6 Hz, 1H), 7.54 (s, 1H), 5.94 (q, J=6.5 Hz, 1H), 1.88 (d, J=6.9 Hz, 3H). LCMS: 522 [M+H]$^+$.

Step 2: (R) & (S)—N-(1-(1-(2,4-bis(trifluoromethyl)phenyl)ethyl)-1H-pyrazol-4-yl)-5-(3-chloropyridin-2-yl)isoxazole-3-carboxamide. The racemic mixture of N-(1-(1-(2,4-bis(trifluoromethyl)phenyl)ethyl)-1H-pyrazol-4-yl)-5-(3-chloropyridin-2-yl)isoxazole-3-carboxamide (90 mg) was purified by chiral HPLC to obtain the single enantiomers as Enantiomer A (12 mg) and Enantiomer B (11 mg). (Enantiomer A): $^1$H NMR (400 MHz, DMSO-d$_6$) δ 11.14 (s, 1H), 8.76 (d, J=4.6 Hz, 1H), 8.21 (d, J=8.7 Hz, 2H), 8.13-8.03 (m, 2H), 7.74 (d, J=7.5 Hz, 2H), 7.64 (dd, J=8.3, 4.6 Hz, 1H), 7.54 (s, 1H), 5.94 (q, J=6.5 Hz, 1H), 1.88 (d, J=6.9 Hz, 3H). (Enantiomer B): $^1$H NMR (400 MHz, DMSO-d$_6$) δ 11.14 (s, 1H), 8.76 (d, J=4.6 Hz, 1H), 8.21 (d, J=8.7 Hz, 2H), 8.13-8.03 (m, 2H), 7.74 (d, J=7.5 Hz, 2H), 7.64 (dd, J=8.3, 4.6 Hz, 1H), 7.54 (s, 1H), 5.94 (q, J=6.5 Hz, 1H), 1.88 (d, J=6.9 Hz, 3H).

Example S32. Synthesis of (R)- and (S)—N-(1-(1-(2,4-bis(trifluoromethyl)phenyl)ethyl)-1H-pyrazol-4-yl)-5-(pyridin-3-yl)isoxazole-3-carboxamide (Compounds 36 and 37)

Step 1: Synthesis of N-(1-(1-(2,4-bis(trifluoromethyl)phenyl)ethyl)-1H-pyrazol-4-yl)-5-(pyridin-3-yl)isoxazole-3-carboxamide. To a solution of 5-(pyridin-3-yl)isoxazole-3-carboxylic acid (50 mg, 0.263 mmol, 1 equiv) and HATU (100.2 mg, 0.263 mmol, 1 equiv) in DMF (1 mL). The mixture was allow to stir for 30 mins followed by the addition of DIPEA (101.8 mg, 0.789 mmol, 3 equiv) and a solution of the 1-{1[2,4bis(trifluoromethyl)phenyl]ethyl}-1H-pyrazol-4-amineHydrochloride (94.73 mg, 0.263 mmol, 1 equiv) in DMF (1 mL) was added. The reaction mixture was kept under stirring for 24 h at RT. Product formation was confirmed with TLC & LCMS and reaction mixture was diluted EtOAc (50 mL) & washed with water (50 mL×2). Organic layer dried over Na$_2$SO$_4$ & concentrated under reduced pressure to obtain crude which was further purified by flash column chromatography to obtain pure product N-(1-(1-(2,4-bis(trifluoromethyl)phenyl)ethyl)-1H-pyrazol-4-yl)-5-(pyridin-3-yl)isoxazole-3-carboxamide LCMS: 495 [M+H]$^+$.

Step 2: (R) & (S)—N-(1-(1-(2,4-bis(trifluoromethyl)phenyl)ethyl)-1H-pyrazol-4-yl)-5-(pyridin-3-yl)isoxazole-3-carboxamide. The racemic mixture of N-(1-(1-(2,4-bis(trifluoromethyl)phenyl)ethyl)-1H-pyrazol-4-yl)-5-(pyridin-3-yl)isoxazole-3-carboxamide (60 mg) was purified by chiral HPLC to obtain the single enantiomers as Enantiomer A (12 mg) and Enantiomer B (15 mg). (Enantiomer A): $^1$H NMR (400 MHz, DMSO-d$_6$) δ 11.09 (s, 1H), 9.20 (s, 1H), 8.74 (d, J=3.51 Hz, 1H), 8.38 (d, J=7.89 Hz, 1H), 8.20 (s, 1H), 8.02-8.14 (m, 2H), 7.70-7.80 (m, 2H), 7.57-7.65 (m, 2H), 5.94 (d, J=6.58 Hz, 1H), 1.88 (d, J=6.58 Hz, 3H). (Enantiomer B): $^1$H NMR (400 MHz, DMSO-d$_6$) δ 11.09 (s, 1H), 9.20 (s, 1H), 8.74 (d, J=3.51 Hz, 1H), 8.38 (d, J=8.33 Hz, 1H), 8.20 (s, 1H), 8.04-8.11 (m, 2H), 7.70-7.77 (m, 2H), 7.59-7.63 (m, 2H), 5.94 (d, J=6.58 Hz, 1H), 1.88 (d, J=6.58 Hz, 3H).

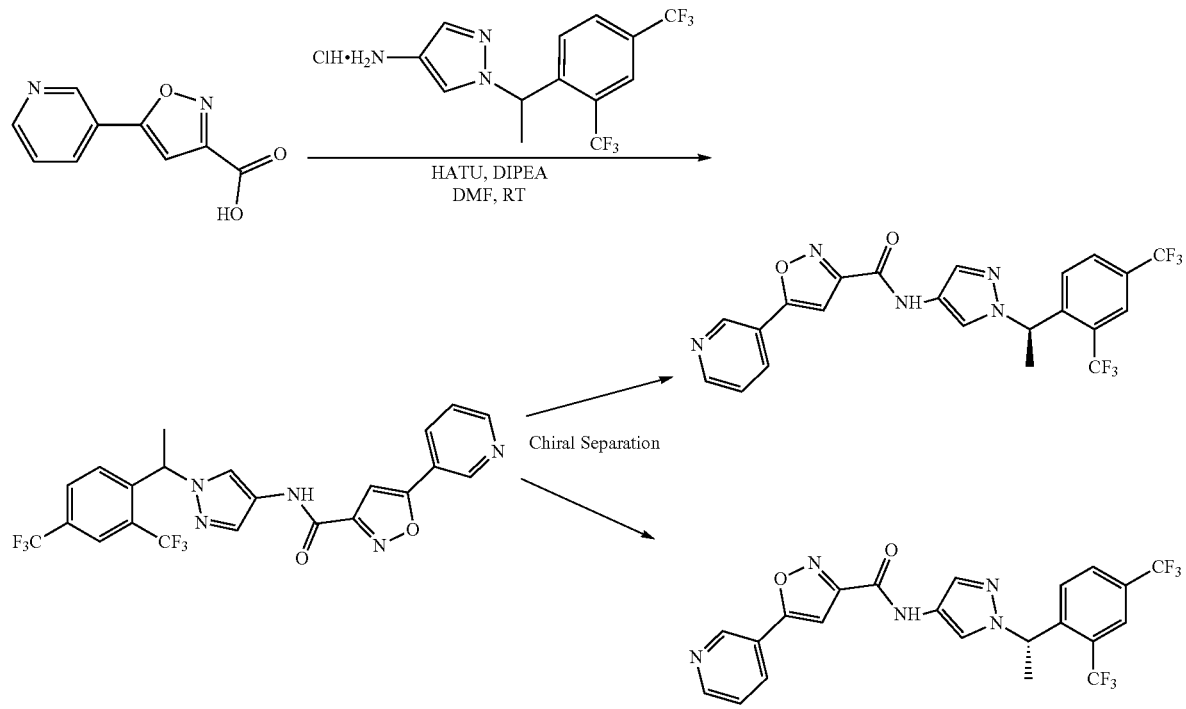

Example S34. Synthesis of (R) & (S) N-(1-(1-(2,4-bis(trifluoromethyl)phenyl)ethyl)-1H-pyrazol-4-yl)-3-(pyridin-2-yl)isoazole-5-carboxamide (Compounds 76 and 77)

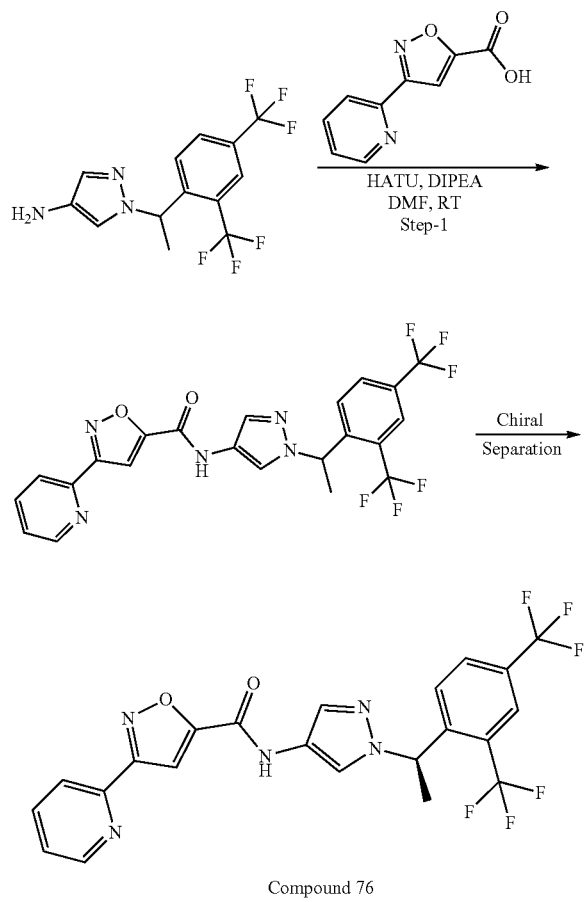

Compound 76

Compound 77

Step 1: Synthesis of N-(1-(1-(2,4-bis(trifluoromethyl)phenyl)ethyl)-1H-pyrazol-4-yl)-3-(pyridin-2-yl)isoxazole-5-carboxamide. To a solution of 3-(pyridin-2-yl)isoxazole-5-carboxylic acid (100 mg, 0.44 mmol, 1 equiv) and HATU (168 mg, 0.44 mmol, 1 equiv) in DMF (1 mL). The mixture was allow to stirring for 30 mins followed by the addition of DIPEA (185 mg, 1.41 mmol, 3.2 equiv) and a solution of the 1-{1[2,4bis(trifluoromethyl)phenyl]ethyl}-1H-pyrazol-4-amineHydrochloride (142 mg, 0.44 mmol, 1 equiv) in DMF (1 mL) was added. The reaction mixture was kept under stirring for 24 h at RT. Product formation was confirmed with TLC and LCMS and reaction mixture was diluted EtOAc (50 mL) and washed with water (2×50 mL). Organic layer dried over $Na_2SO_4$ and concentrated under reduced pressure to obtain crude which was further purified by flash column chromatography to obtain pure product N-(1-(1-(2,4-bis(trifluoromethyl)phenyl)ethyl)-1H-pyrazol-4-yl)-3-(pyridin-2-yl)isoxazole-5-carboxamide (150 mg, as off white solid). LCMS: 496 $[M+H]^+$. $^1H$ NMR (400 MHz, DMSO-$d_6$) δ 11.18 (s, 1H), 8.76 (d, J=4.8 Hz, 1H), 8.21 (s, 1H), 8.10 (dd, J=8.5, 4.2 Hz, 2H), 8.05 (s, 1H), 8.01 (td, J=7.7, 1.8 Hz, 1H), 7.79-7.69 (m, 2H), 7.68 (s, 1H), 7.58 (dd, J=7.5, 4.8 Hz, 1H), 5.95 (q, J=7.0 Hz, 1H), 1.88 (d, J=6.9 Hz, 3H).

Step 2: Synthesis of (R) and (S)—N-(1-(1-(2,4-bis(trifluoromethyl)phenyl)ethyl)-1H-pyrazol-4-yl)-3-(pyridin-2-yl)isoxazole-5-carboxamide. The enantiomers of N-(1-(1-(2,4-bis(trifluoromethyl)phenyl)ethyl)-1H-pyrazol-4-yl)-3-(pyridin-2-yl)isoxazole-5-carboxamide (90 mg, elution time: 3.69 min & 4.78 min), were separated by chiral SFC (Daicel Chiralcel® OD-H, 250×20 mm, 5 μm. Isocratic program with analytical grade liquid carbon dioxide and HPLC grade Isopropanol, Total flow: 51 g/min, Co-Solvent Percentage: 20% to obtain Compound 40 (R)—N-(1-(1-(2,4-bis(trifluoromethyl)phenyl)ethyl)-1H-pyrazol-4-yl)-3-(pyridin-2-yl)isoxazole-5-carboxamide (22 mg) and Compound 41 (S)—N-(1-(1-(2,4-bis(trifluoromethyl)phenyl)ethyl)-1H-pyrazol-4-yl)-3-(pyridin-2-yl)isoxazole-5-carboxamide (23 mg). (Compound 76) LCMS: 496 $[M+H]^+$. $^1H$ NMR (400 MHz, DMSO-$d_6$) δ 11.18 (s, 1H), 8.76 (d, J=4.8 Hz, 1H), 8.21 (s, 1H), 8.10 (dd, J=8.5, 4.2 Hz, 2H), 8.05 (s, 1H), 8.01 (td, J=7.7, 1.8 Hz, 1H), 7.79-7.69 (m, 2H), 7.68 (s, 1H), 7.58 (dd, J=7.5, 4.8 Hz, 1H), 5.95 (q, J=7.0 Hz, 1H), 1.88 (d, J=6.9 Hz, 3H). (Compound 77) LCMS: 496 $[M+H]^+$. $^1H$ NMR (400 MHz, DMSO-$d_6$) δ 11.18 (s, 1H), 8.76 (d, J=4.8 Hz, 1H), 8.21 (s, 1H), 8.10 (dd, J=8.5, 4.2 Hz, 2H), 8.05 (s, 1H), 8.01 (td, J=7.7, 1.8 Hz, 1H), 7.79-7.69 (m, 2H), 7.68 (s, 1H), 7.58 (dd, J 0.5, 4.8 Hz, 1H), 5.95 (q, J=7.0 Hz, 1H), 1.88 (d, J=6.9 Hz, 3H).

Example S35. Synthesis of N-(1-(1-(2,4-bis(trifluoromethyl)phenyl)ethyl)-1H-pyrazol-4-yl)-2-(pyridin-2-vi)thiazole-5-carboxamide (Compound 78)

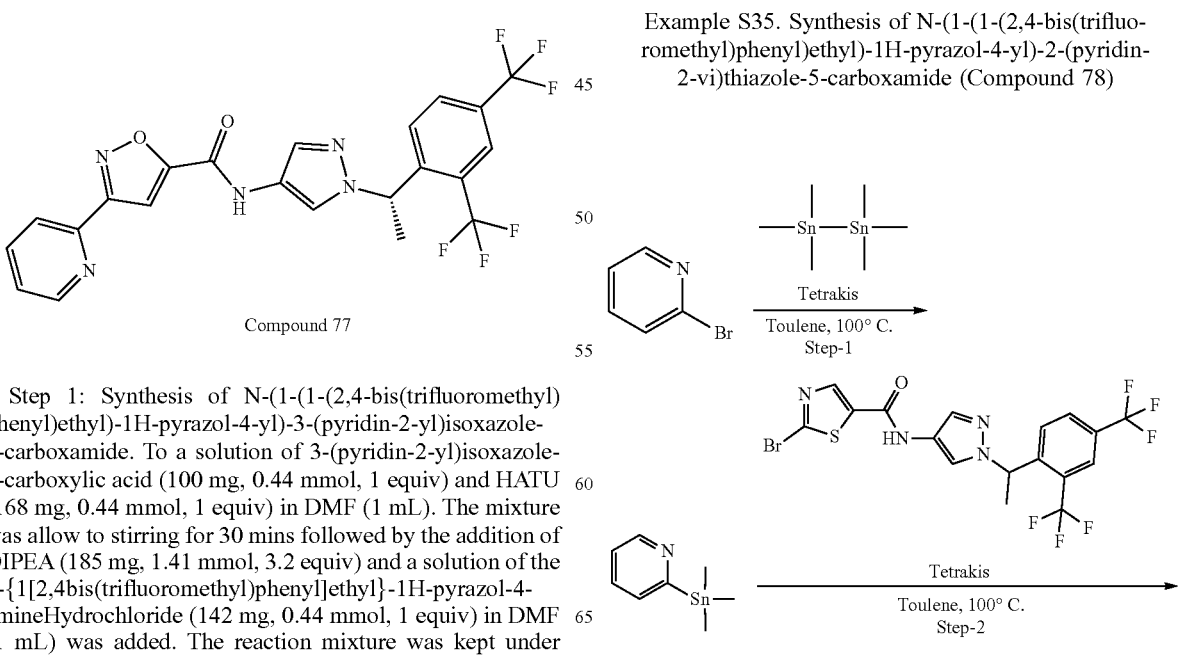

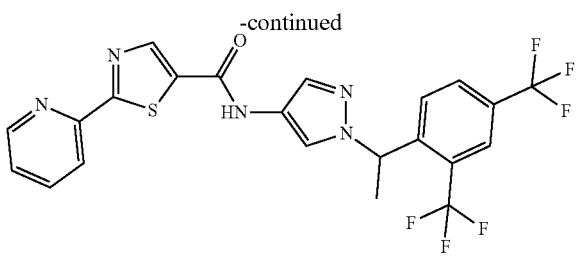

Step 1: Synthesis of 2-(trimethylstannyl)pyridine. To a solution of 2-bromopyridine (100 mg, 0.63 mmol, 1 equiv) in dry toluene (30 mL) was added the 1,1,1,2,2,2-hexamethyldistannane (227.0 mg, 0.69 mmol, 1.1 equiv), and the mixture was degassed for 10 min. To this mixture was added Pd(PPh$_3$)$_4$ (73 mg, 0.063 mmol, 0.1 equiv), and the mixture was again degassed for 5 min. The reaction mixture was stirred at 150° C. for 20 mins under microwave, after which time TLC indicated complete consumption of the SM. The mixture was concentrated in vacuo to provide the crude product 2-(trimethylstannyl)pyridine (150 mg, crude) which was taken forward without further purification. LCMS: 244 [M+H]$^+$.

Step 2: Synthesis of N-(1-(1-(2,4-bis(trifluoromethyl)phenyl)ethyl)-1H-pyrazol-4-yl)-2-(pyridin-2-yl)thiazole-5-carboxamide. To a solution of N-(1-(1-(2,4-bis(trifluoromethyl)phenyl)ethyl)-1H-pyrazol-4-yl)-2-bromothiazole-5-carboxamide (50 mg, 0.20 mmol, 1 equiv) in dry toluene (30 mL) was added the 2-(trimethylstannyl)pyridine (105 mg, 0.206 mmol, 1 equiv), and the mixture was degassed for 10 min. To this mixture was added Pd(PPh$_3$)$_4$ (23 mg, 0.20 mmol, 1 equiv), and the mixture was again degassed for 5 min. The reaction mixture was stirred at 80° C. for 8 h, after which time TLC indicated complete consumption of the SM. The mixture was quenched with H$_2$O, extracted with EtOAc, dried over anhydrous Na$_2$SO$_4$, and concentrated under reduced pressure to provide the product. which was further purified by flash column chromatography and reverse phase HPLC to obtain pure product N-(1-(1-(2,4-bis(trifluoromethyl)phenyl)ethyl)-1H-pyrazol-4-yl)-2-(pyridin-2-yl) thiazole-5-carboxamide (5 mg, as off white solid). LCMS: 512 [M+H]$^+$. $^1$H NMR (400 MHz, CDCl$_3$) δ 8.64 (d, J=4.8 Hz, 1H), 8.33 (s, 1H), 8.20 (d, J=8.0 Hz, 1H), 8.15 (s, 1H), 7.92 (s, 1H), 7.89-7.81 (m, 1H), 7.79 (s, 1H), 7.75 (d, J=8.3 Hz, 1H), 7.65-7.56 (m, 2H), 7.39 (dd, J=7.5, 4.8 Hz, 1H), 5.92 (q, J=6.9 Hz, 1H), 1.95 (d, J=6.9 Hz, 3H).

Example S36. Synthesis of N-(1-(1-(2,4-bis(trifluoromethyl)phenyl)ethyl)-1H-pyrazol-4-yl)-2-(pyridin-2-yl)thiazole-4-carboxamide (Compound 79)

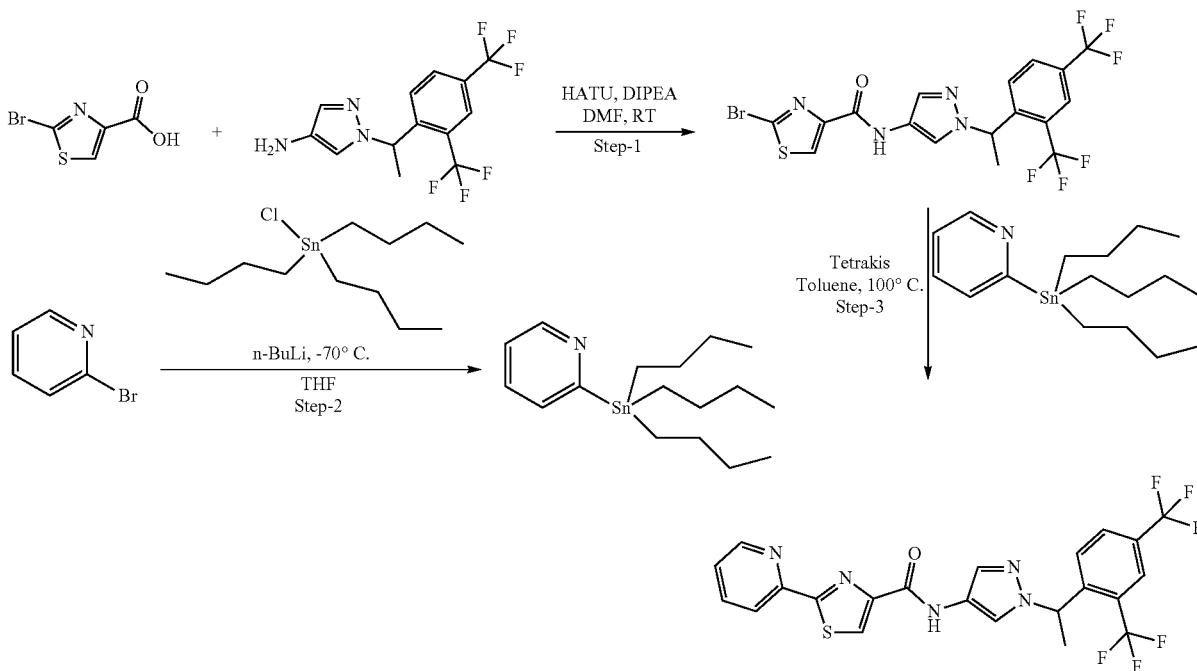

Step 1: Synthesis of N-(1-(1-(2,4-bis(trifluoromethyl)phenyl)ethyl)-1H-pyrazol-4-yl)-2-bromothiazole-4-carboxamide. To a solution of 2-bromothiazole-4-carboxylic acid (200 mg, 0.96 mmol, 1 equiv) and HATU (401 mg, 1.05 mmol, 1.1 equiv) in DMF (1 mL). The mixture was allow to stir for 30 mins followed by the addition of DIPEA (396 mg, 3.07 mmol, 3.2 equiv) and a solution of the 1-{1[2,4bis(trifluoromethyl)phenyl]ethyl}-1H-pyrazol-4-amineHydrochloride (344 mg, 0.96 mmol, 1 equiv) in DMF (1 mL) was added. The reaction mixture was kept under stirring for 24 h at RT. Product formation was confirmed with TLC and LCMS and reaction mixture was diluted EtOAc (50 mL) and washed with water (2×50 mL). Organic layer dried over Na$_2$SO$_4$ and concentrated under reduced pressure to obtain crude which was further purified by flash column chromatography (EtOAc/Hexane) to obtain title compound N-(1-(1-(2,4-bis (trifluoromethyl)phenyl)ethyl)-1H-pyrazol-4-yl)-2-bromothiazole-4-carboxamide as off white solid0(360 mg). LCMS: 515 [M+H]$^+$.

Step 2: Synthesis of 2-(tributylstannyl)pyridine. To a solution of 2-bromopyridine (1 g, 0.006 mol, 1 equiv) in THF (20 mL) at −70° C. was n-BuLi (2.5 M in hexane, 3.0 mL, 0.007 mol) at −70° C. The mixture was stirred to −50° C. and stirred for 1 hour. Tributylchlorostannane (Bu₃SnCl) (2.2 gm, 0.0069 mol 1.1 equiv) were dissolved in THF (50 mL) and added to the reaction mixture dropwise at 0° C. The resulting orange mixture was allow to stirred to 0° C. over 2 hrs. The mixture was quenched with saturated NaOH and extracted with EtOAc and washed with NH₄Cl solution. The combined organics were dried and concentrated to obtain crude product 2-(tributylstannyl)pyridine crude as yellow liquid (1.2 g). LCMS: 370 [M+H]⁺.

Step 3: Synthesis of N-(1-(1-(2,4-bis(trifluoromethyl)phenyl)ethyl)-1H-pyrazol-4-yl)-2-(pyridin-2-yl)thiazole-4-carboxamide. To a solution of the N-(1-(1-(2,4-bis(trifluoromethyl)phenyl)ethyl)-1H-pyrazol-4-yl)-2-bromothiazole-4-carboxamide (100 mg, 0.27 mmol, 1 equiv) in dry toluene (2 mL) was added the 2-(tributylstannyl)pyridine (139 mg, 0.27 mmol, 1 equiv) and the mixture was degassed for 10 min. To this mixture was added Pd(PPh3)4 (31 mg, 0.027 mmol, 0.1 equiv) and the mixture was again degassed for 5 min. The reaction mixture was stirred at 100 deg C. for 12 h, after completion of reaction. The reaction mixture was quenched with H2O, extracted with EtOAc, dried (Na₂SO₄), and concentrated under reduced pressure to obtain crude product which was further purified by flash column chromatography and reverse phase HPLC to obtained N-(1-(1-(2,4-bis(trifluoromethyl)phenyl)ethyl)-1H-pyrazol-4-yl)-2-(pyridin-2-yl) thiazole-4-carboxamide (20 mg, as white solid). LCMS: 512 [M+H]⁺. ¹H NMR (400 MHz, DMSO-d₆) δ 10.58 (s, 1H), 8.68 (d, J=4.8 Hz, 1H), 8.46 (s, 1H), 8.37 (d, J=7.9 Hz, 1H), 8.22 (s, 1H), 8.13-8.01 (m, 3H), 7.84 (s, 1H), 7.75 (d, J=8.3 Hz, 1H), 7.61-7.52 (m, 1H), 5.93 (q, J=6.9 Hz, 1H), 1.88 (d, J=6.8 Hz, 3H).

Example S37. Synthesis of N-(1-(1-(2,4-bis(trifluoromethyl)phenyl)ethyl)-1H-pyrazol-4-yl)-2-(furan-2-yl)thiazole-5-carboxamide (Compound 80)

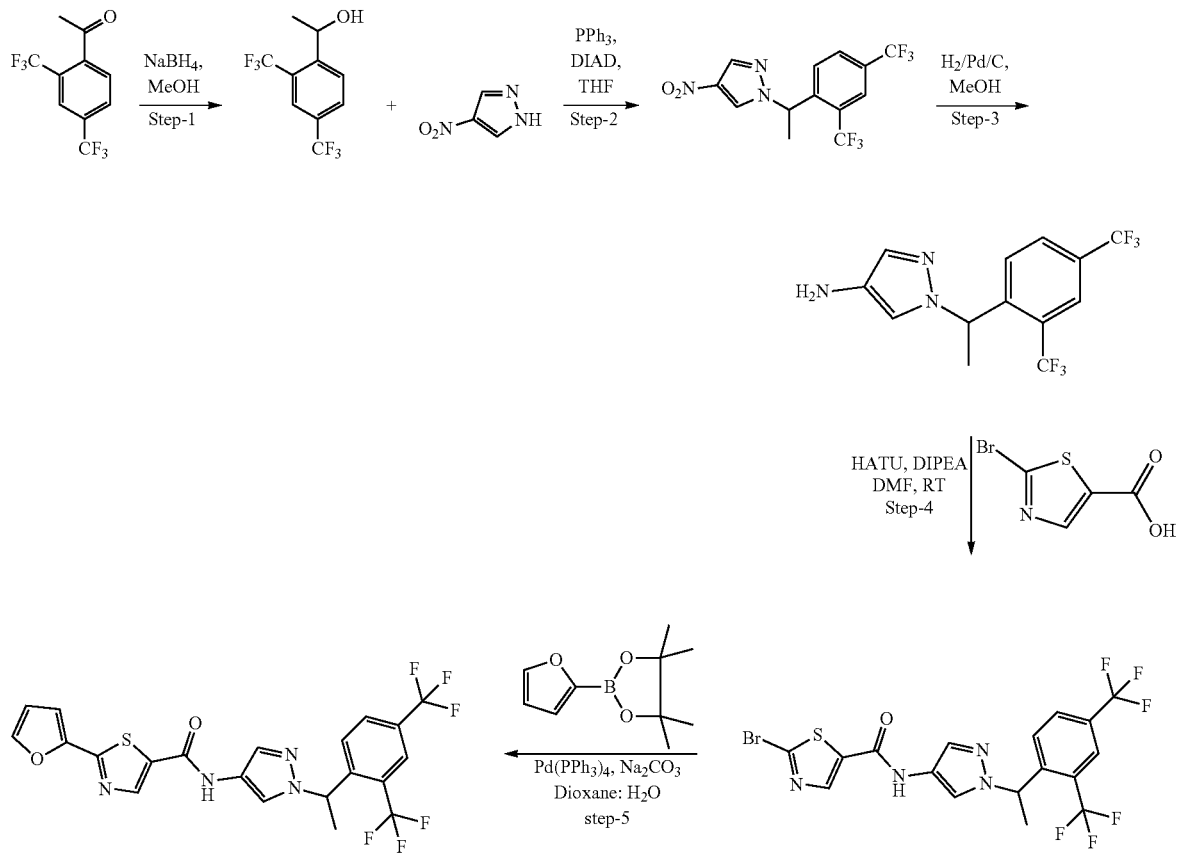

Step 1: Synthesis of 1-(2,4-bis(trifluoromethyl)phenyl) ethan-1-ol. To a stirred solution of 1-(2,4-bis(trifluoromethyl)phenyl)ethan-1-one (1 g, 0.003 mol, 1.0 eq) in methanol (5 mL) was added NaBH₄ (0.216 g, 0.005 mol, 1.2 eq) portion wise at 0° C. and stirred for 10 minutes. The reaction mixture was allowed to stir for 1 hour at RT. Product formation was confirmed by TLC and NMR. After completion of reaction, reaction mixture was quenched with water and extracted with ethyl acetate (3×50 mL), Combined organic extracts were washed with water (2×50 mL), dried over anhydrous Na₂SO₄ and concentrated under reduced pressure to obtain 1-(2,4-bis(trifluoromethyl)phenyl)ethan-1-ol (1 g, as colourless liquid). ¹H NMR (400 MHz, DMSO-d₆) δ 8.04-8.15 (m, 2H), 7.93 (s, 1H), 5.70 (d, J=3.95 Hz, 1H), 5.09 (br. s., 1H), 1.34 (d, J=6.14 Hz, 3H).

Step 2: Synthesis of 1-(1-(2,4-bis(trifluoromethyl)phenyl) ethyl)-4-nitro-1H-pyrazole. To a stirred solution of PPh₃ (517 mg, 1.93 mmol, 1.0 eq) and DIAD (319 mg, 1.93 mmol, 1.0 eq) in THF (2 mL) was added 1-(2,4-bis(trifluoromethyl)phenyl)ethan-1-ol (500 mg, 1.93 mmol, 1.0 eq). The reaction mixture was added 4-nitro-1H-pyrazole (175 mg, 1.55 mmol, 0.8 eq). The reaction mixture was stirred at RT for overnight. Product formation was confirmed with TLC and LCMS. After completion of reaction mixture were diluted with EtOAc (50 mL) and washed with water (50 mL×3). Organic layer dried over Na$_2$SO$_4$ and concentrated under reduced pressure to obtain crude which was further purified by flash column chromatography to obtain pure product 1-(1-(2,4-bis(trifluoromethyl)phenyl)ethyl)-4-nitro-1H-pyrazole (550 mg, as brown liquid). LCMS: 353 [M+H]$^+$.

Step 3: Synthesis of 1-(1-(2,4-bis(trifluoromethyl)phenyl)ethyl)-1H-pyrazol-4-amine. To a stirred solution of 1-(2,4-bis(trifluoromethyl)benzyl)-4-nitro-1H-pyrazole (500 mg, 1.41 mmol, 1.0 eq) in Methanol (10 mL) under nitrogen Palladium on Carbon (75 mg, 10% w/w) was added. Purge the reaction mixture with H$_2$ gas for 2 h. Product formation was confirmed by LCMS. After the completion of reaction, reaction mixture was filtered through Celite bed and Filtrate was concentrate under reduced pressure to obtain 1-(1-(2,4-bis(trifluoromethyl)phenyl)ethyl)-1H-pyrazol-4-amine (450 mg, as brown colour liquid). LCMS: 323 [M+H]$^+$.

Step 4: Synthesis of N-(1-(1-(2,4-bis(trifluorometh7yl)phenyl)ethyl)-1H-pyrazol-4-yl)-2-bromothiazole-5-carboxamide. To a solution of 2-bromothiazole-5-carboxylic acid (200 mg, 0.96 mmol, 1 eq) in DMF (1 mL), were added HATU (438.28 mg, 1.152 mmol, 1.2 eq). The mixture was treated drop wise with DIPEA (396 mg mg, 3.072 mmol, 3.2 eq). After stirring at RT for 15 minutes, the mixture was treated drop wise with a solution of the 1-{1[2,4-bis(trifluoromethyl)phenyl]ethyl}-1H-pyrazol-4-amine (345 mg, 0.96 mmol, 1 eq) in DMF (1 mL). The reaction mixture was kept under stirring for 24 h. Product formation was confirmed with TLC and LCMS and reaction mixture was diluted EtOAc (50 mL) and washed with water (2×50 mL). Organic layer dried over Na$_2$SO$_4$ and concentrated under reduced pressure to obtain crude which was further purified by flash column chromatography to obtain pure product N-(1-(1-(2,4-bis(trifluorometh7yl)phenyl)ethyl)-1H-pyrazol-4-yl)-2-bromothiazole-5-carboxamide (150 mg, as white solid). LCMS: 511 [M+H]$^+$.

Step 5: Synthesis of N-(1-(1-(2,4-bis(trifluoromethyl)phenyl)ethyl)-1H-pyrazol-4-yl)2-(furan-2-yl)thiazole-5-carboxamide. To a stirred solution of N-(1-(1-(2,4-bis(trifluorometh7yl)phenyl)ethyl)-1H-pyrazol-4-yl)-2-bromothiazole-5-carboxamide (100 mg, 0.19 mmol 1 eq), 2-(furan-2-yl)-4,4,5,5-tetramethyl-1,3,2-dioxaborolane (36 mg, 0.19 mmol, 1 eq), Na$_2$CO$_3$ (40 mg, 0.38 mmol, 2 eq) in dioxane, H$_2$O was added catalyst (22 mg, 0.019 mmol, 0.1 eq) under anhydrous condition. The reaction mixture was kept under stirring for 24 h. Product formation was confirmed with TLC and LCMS and reaction mixture was diluted EtOAc (50 mL) and washed with water (2×50 mL). Organic layer dried over Na$_2$SO$_4$ and concentrated under reduced pressure to obtain crude which was further purified by flash column chromatography to obtain pure product N-(1-(1-(2,4-bis(trifluoromethyl)phenyl)ethyl)-1H-pyrazol-4-yl)2-(furan-2-yl)thiazole-5-carboxamide (50 mg). LCMS: 500 [M+H]$^+$. $^1$H NMR (400 MHz, DMSO-d$_6$) δ 10.77 (s, 1H), 8.51 (s, 1H), 8.14 (s, 1H), 8.09 (d, J=8.4 Hz, 1H), 8.05 (s, 1H), 7.97 (s, 1H), 7.73 (d, J=8.3 Hz, 1H), 7.66 (s, 1H), 7.25 (d, J=3.5 Hz, 1H), 6.79-6.72 (m, 1H), 5.93 (q, J=6.9 Hz, 1H), 1.87 (d, J=6.9 Hz, 3H).

Example S38. Synthesis of N-(1-(1-(2,4-bis(trifluoromethyl)phenyl)ethyl)-1H-pyrazol-[2,4'-bipyridine]-2'-carboxamide (Compound 81)

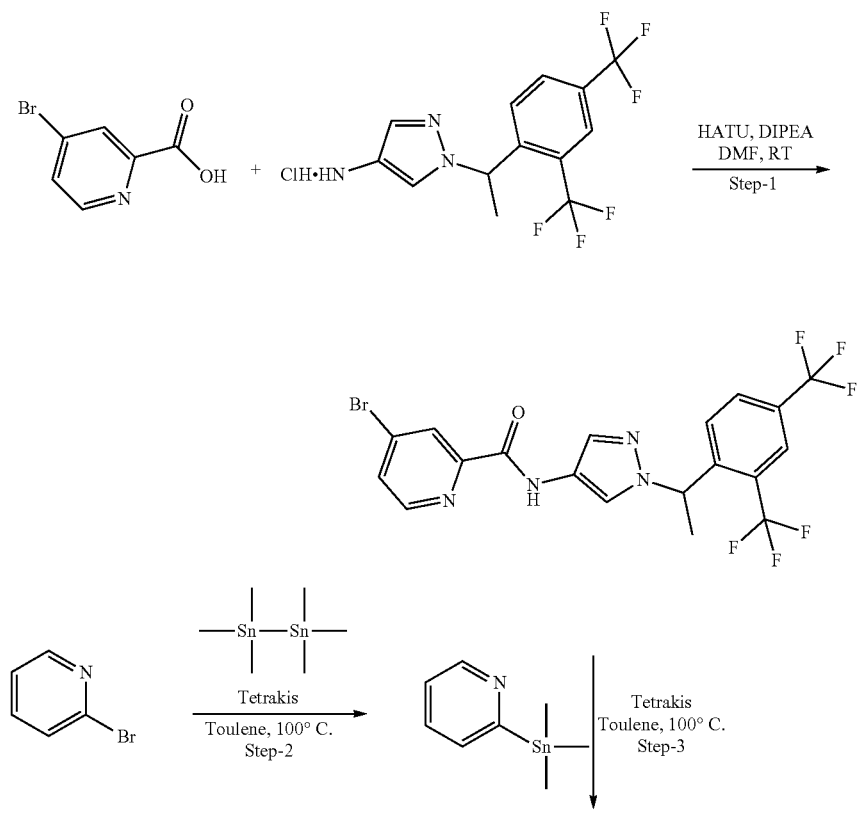

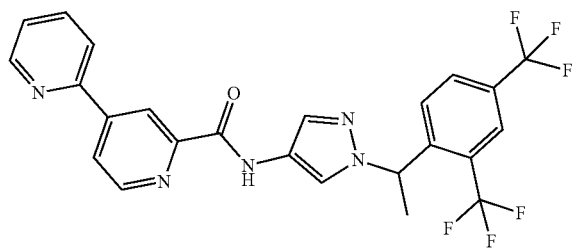

Step 1: Synthesis of N-(1-(1-(2,4-bis(trifluoromethyl)phenyl)ethyl)-1H-pyrazol-4-yl)-4-bromopicolinamide. To a solution of 2-bromothiazole-4-carboxylic acid (200 mg, 0.96 mmol, 1 equiv) in DMF (1 mL) was added HATU (401 mg, 1.05 mmol, 1.1 equiv). The mixture was allow to stir for 30 mins followed by the addition of DIPEA (396 mg, 3.07 mmol, 3.2 equiv) and a solution of the 1-{1[2,4bis(trifluoromethyl)phenyl]ethyl}-1H-pyrazol-4-amineHydrochloride (344 mg, 0.96 mmol, 1 equiv) in DMF (1 mL). The reaction mixture was kept under stirring for 24 h at RT. Product formation was confirmed with TLC and LCMS and reaction mixture was diluted EtOAc (50 mL) and washed with water (2×50 mL). Organic layer dried over $Na_2SO_4$ and concentrated under reduced pressure to obtain crude which was further purified by flash column chromatography to obtain pure product N-(1-(1-(2,4-bis(trifluoromethyl)phenyl)ethyl)-1H-pyrazol-4-yl)-2-bromothiazole-4-carboxamide (360 mg, crude as off white solid). LCMS: 507 [M+H]$^+$.

Step 2: Synthesis of 2-(trimethylstannyl)pyridine. To a solution of 2-bromopyridine (100 mg, 0.63 mmol, 1 equiv) in dry toluene (30 mL) was added the 1,1,1,2,2,2-hexamethyldistannane (227.0 mg, 0.6p mmol, 1.1 equiv), and the mixture was degassed for 10 min. To this mixture was added Pd(PPh$_3$)$_4$ (73 mg, 0.063 mmol, 0.1 equiv), and the mixture was again degassed for 5 min. The reaction mixture was stirred at 150 C for 20 mins under microwave, after which time TLC indicated complete consumption of the SM. The mixture was concentrated in vacuo to provide the crude product 2-(trimethylstannyl)pyridine (360 mg, 72% crude) which was taken forward without further purification.

Step 3: Synthesis of N-(1-(1-(2,4-bis(trifluoromethyl)phenyl)ethyl)-1H-pyrazol-4-yl)-[2,4'-bipyridine]-2'-carboxamide. To a solution of N-(1-(1-(2,4-bis(trifluoromethyl)phenyl)ethyl)-1H-pyrazol-4-yl)-4-bromopicolinamide (50 mg, 0.20 mmol, 1 equiv) in dry toluene (30 mL) was added the 2-(trimethylstannyl)pyridine (105 mg, 0.206 mmol, 1 equiv), and the mixture was degassed for 10 min. To this mixture was added Pd(PPh$_3$)$_4$ (23 mg, 0.20 mmol, 1 equiv), and the mixture was again degassed for 5 min. The reaction mixture was stirred at 80 C for 8 h, after which time TLC indicated complete consumption of the starting material. The mixture was quenched with H$_2$O, extracted with EtOAc, dried over anhydrous Na$_2$SO$_4$, and concentrated in vacuo to provide the product, which was further purified by flash column chromatography and reverse phase HPLC to obtain title compound N-(1-(1-(2,4-bis(trifluoromethyl)phenyl)ethyl)-1H-pyrazol-4-yl)-2-(pyridin-2-yl)thiazole-5-carboxamide (5 mg, as off white solid). LCMS: 506 [M+H]$^+$. $^1$H NMR (400 MHz, CDCl$_3$) δ 8.64 (d, J=4.8 Hz, 1H), 8.33 (s, 1H), 8.20 (d, J=8.0 Hz, 1H), 8.15 (s, 1H), 7.92 (s, 1H), 7.89-7.81 (m, 1H), 7.79 (s, 1H), 7.75 (d, J=8.3 Hz, 1H), 7.65-7.56 (m, 3H), 7.39 (dd, J=7.5, 4.8 Hz, 1H), 5.92 (q, J=6.9 Hz, 1H), 1.95 (d, J=6.9 Hz, 3H).

Example S39. Synthesis of N-(1-(1-(2,4-bis(trifluoromethyl)phenyl)ethyl)-1H-pyrazol-4-yl)-[2,3'-bipyridine]-6'-carboxamide (Compound 82)

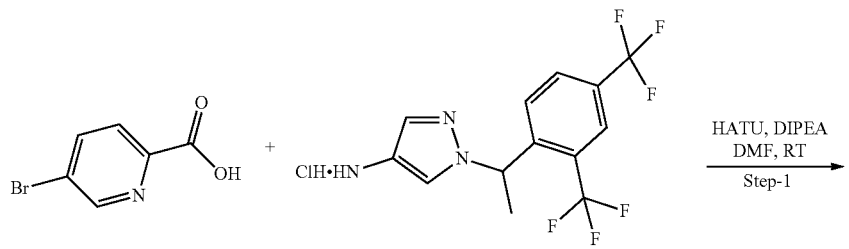

-continued

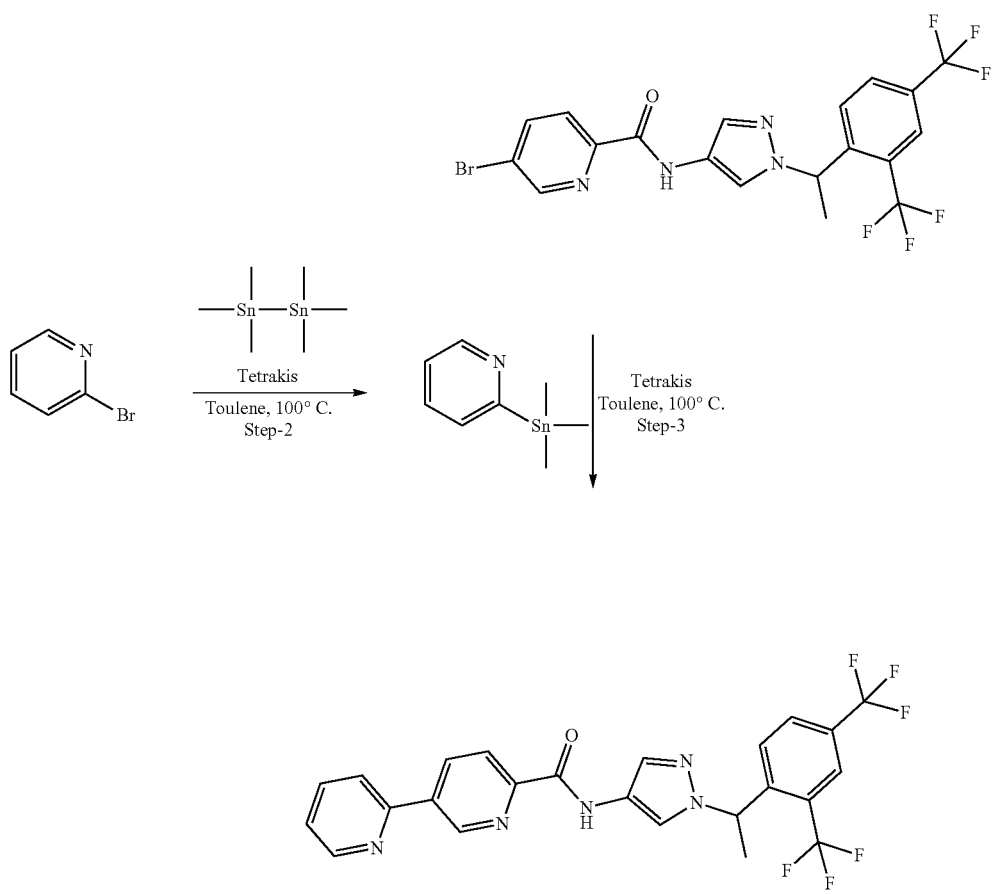

Step 1: Synthesis of N-(1-(1-(2,4-bis(trifluoromethyl)phenyl)ethyl)-1H-pyrazol-4-yl)-5-bromopicolinamide. To a solution of 5-bromopicolinic acid (200 mg, 0.82 mmol, 1 equiv) and HATU (345 mg, 0.090 mmol, 1.1 equiv) in DMF (2 mL). The mixture was allow to stir for 30 mins followed by the addition of DIPEA (341 mg, 2.64 mmol, 3.2 equiv) and a solution of the 1-{1-[2,4bis(trifluoromethyl)phenyl]ethyl}-1H-pyrazol-4-amineHydrochloride (266 mg, 0.82 mmol, 1 equiv) in DMF (1 mL). The reaction mixture was kept under stirring for 24 h at room temperature. Product formation was confirmed with TLC and LCMS and reaction mixture was diluted EtOAc (50 mL) and washed with water (2×50 mL). Organic layer dried over anhydrous $Na_2SO_4$ and concentrated under reduced pressure to obtain crude which was further purified by flash column chromatography (EtoAC/hexane) to obtain pure product N-(1-(1-(2,4-bis(trifluoromethyl)phenyl)ethyl)-1H-pyrazol-4-yl)-5-bromopicolinamide. (250 mg, as off white solid). LCMS: 507 [M+H]$^+$.

Step 2: Synthesis of 2-(trimethylstannyl)pyridine. To a solution of 2-bromopyridine (150 mg, 0.94 mmol, 1 equiv) in dry toluene (2 mL) was added the 1,1,1,2,2,2-hexamethyldistannane (341 mg, 1.04 mmol, 1.1 equiv), and the mixture was degassed for 10 min. The reaction mixture was added Pd(PPh$_3$)$_4$ (109 mg, 0.094 mmol, 0.1 equiv), and the mixture was again degassed for 5 min. The reaction mixture was stirred at 150° C. for 20 mins under microwave, after which time TLC indicated complete consumption of the starting material. The mixture was concentrated under reduced pressure to provide the crude product 2-(trimethylstannyl)pyridine (230 mg, crude) which was taken forward without further purification. LCMS: 244 [M+H]$^+$.

Step 3: Synthesis of N-(1-(1-(2,4-bis(trifluoromethyl)phenyl)ethyl)-1H-pyrazol-4-yl)-[2,3'-bipyridine]-6'-carboxamide. To a solution of N-(1-(1-(2,4-bis(trifluoromethyl)phenyl)ethyl)-1H-pyrazol-4-yl)-5-bromopicolinamide (200 mg, 0.39 mmol, 1 equiv) in dry toluene (5 mL) was added the 2-(trimethylstannyl)pyridine (143 mg, 0.59 mmol, 1 equiv), and the mixture was degassed for 10 min. To this mixture was added Pd(PPh$_3$)$_4$ (45 mg, 0.039 mmol, 1 equiv), and the mixture was again degassed for 5 min. The reaction mixture was stirred at 80° C. for overnight, after which time TLC indicated complete consumption of the starting material. The mixture was quenched with H$_2$O, extracted with EtOAc, dried over anhydrous Na$_2$SO$_4$, and concentrated in vacuo to provide the product. which was further purified by flash column chromatography (AtOAc/hexane) and reverse phase HPLC to obtain pure product N-(1-(1-(2,4-bis(trifluoromethyl)phenyl)ethyl)-1H-pyrazol-4-yl)-[2,3'-bipyridine]-6'-carboxamide (25 mg, as off white solid). LCMS: 506 [M+H]$^+$. $^1$H NMR (400 MHz, DMSO-d$_6$) δ 10.84 (s, 1H), 9.41 (d, J=2.1 Hz, 1H), 9.13 (d, J=2.0 Hz, 1H), 8.93 (s, 1H), 8.76 (d, J=4.7 Hz, 1H), 8.23 (s, 1H), 8.16 (d, J=8.0 Hz, 1H), 8.10 (d, J=8.4 Hz, 1H), 8.06 (s, 1H), 7.99 (t, J=7.5 Hz, 1H), 7.79-7.69 (m, 2H), 7.48 (dd, J=7.7, 4.8 Hz, 1H), 5.94 (q, J=6.8 Hz, 1H), 1.89 (d, J=6.9 Hz, 3H).

Example S40. Synthesis of (E)-N-(1-(1-(2,4-bis(trifluoromethyl)phenyl)ethyl)-1H-1-pyrazol-4-yl)-3-(pyridin-2-yl)acrylamide (Compound 83)

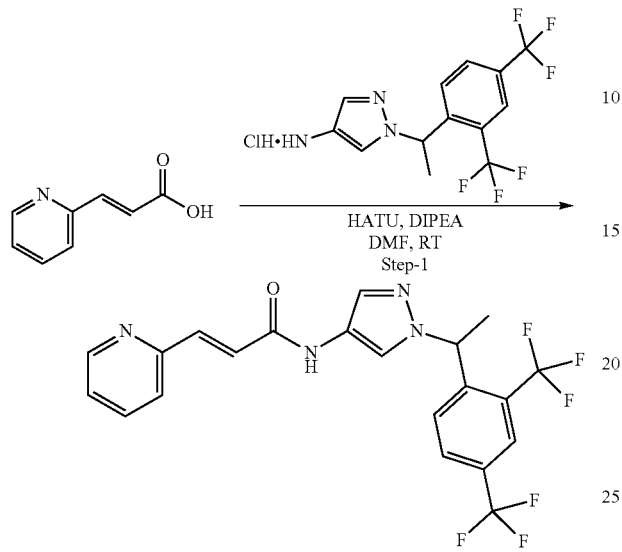

Step 1: Synthesis of (E)-N-(1-(1-(2,4-bis(trifluoromethyl)phenyl)ethyl)-1H-pyrazol-4-yl)-3-(pyridin-2-yl)acrylamide. To a solution of (E)-3-(pyridin-2-yl)acrylic acid (100 mg, 0.67 mmol, 1 equiv) in DMF (1 mL) was added HATU (280 mg, 0.73 mmol, 1 equiv). The mixture was allow to stir for 30 mins followed by the addition of DIPEA (277 mg, 2.4 mmol, 3.2 equiv) and a solution of the 1-{1[2,4bis(trifluoromethyl)phenyl]ethyl}-1H-pyrazol-4-amineHydrochloride (240 mg, 0.67 mmol, 1 equiv) in DMF (1 mL). The reaction mixture was kept under stirring for 24 h at room temperature. Product formation was confirmed with TLC and LCMS and reaction mixture was diluted EtOAc (50 mL) and washed with water (2×50 mL). Organic layer dried over anhydrous $Na_2SO_4$ and concentrated under reduced pressure to obtain crude which was further purified by flash column chromatography (EtOAc/Hexane) and reverse phase HPLC to obtain title compound (E)-N-(1-(1-(2,4-bis(trifluoromethyl)phenyl)ethyl)-1H-pyrazol-4-yl)-3-(pyridin-2-yl)acrylamide as free base (35 mg, 11% as off white solid). LCMS: 455 $[M+H]^+$. $^1$H NMR (400 MHz, DMSO-$d_6$) δ 10.50 (s, 1H), 8.66-8.59 (m, 1H), 8.14 (s, 1H), 8.08 (d, J=8.4 Hz, 1H), 8.05 (s, 1H), 7.85 (td, J=7.6, 1.9 Hz, 1H), 7.72 (d, J=8.4 Hz, 1H), 7.65-7.57 (m, 2H), 7.53 (d, J=15.3 Hz, 1H), 7.38 (dd, J=7.6, 4.8 Hz, 1H), 7.18 (d, J=15.3 Hz, 1H), 5.91 (q, J=6.8 Hz, 1H), 1.86 (d, J=6.9 Hz, 3H).

Example S41. Synthesis of (E)-N-(1-(2,4-bis(trifluoromethyl)benzyl)-1H-pyrazol-4-yl)-3-(furan-2-yl)acrylamide (Compound 84)

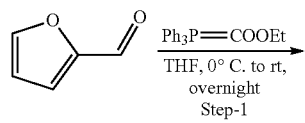

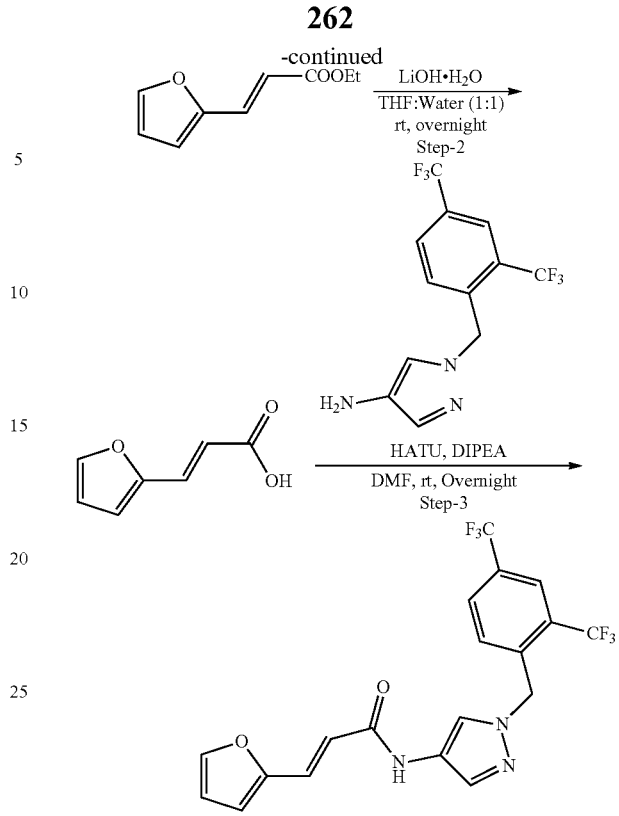

Step 1: Synthesis of ethyl (E)-3-(furan-2-yl)acrylate. To the stirred solution of triphenylphosphene ethyl ester Wittig salt (507 mg, 1.46 mmol, 1.4 equiv) in THF (10 ml) at 0° C. was added furfural aldehyde (100 mg, 1.04 mmol, 1.0 equiv). The resulting reaction mixture was stirred overnight at room temperature. The progress of reaction was monitored through TLC. After completion of the reaction, the reaction mixture was evaporated to obtain crude residue which was purified by flash column chromatography to obtain ethyl (E)-3-(furan-2-yl)acrylate as liquid (300 mg). LCMS: 167 $[M+H]^+$.

Step 2: Synthesis of (E)-3-(furan-2-yl)acrylic acid. To the stirred solution of (E)-3-(furan-2-yl)acrylate (380 mg, 2.29 mmol, 1.0 equiv) in THF:Water (1:1) (10 ml) at 0° C. was added LiOH·$H_2O$ (288 mg, 6.87 mmol, 3.0 equiv). The resulting reaction mixture was stirred overnight at room temperature. The progress of reaction was monitored through TLC. After completion of the reaction, the reaction mixture neutralized with 10% HCl, extracted with DCM (2×50 mL). The organic layers were combined, dried over anhydrous $Na_2SO_4$ and evaporated to obtain crude residue which was purified by flash column chromatography using DCM/MeOH as eluent to obtain as (E)-3-(furan-2-yl)acrylic acid as white solid (330 mg). LCMS: 139 $[M+H]^+$.

Step 3: Synthesis of (E)-N-(1-(2,4-bis(trifluoromethyl)benzyl)-1H-pyrazol-4-yl)-3-(furan-2-yl)acrylamide. To a solution of (E)-3-(furan-2-yl)acrylic acid (60 mg, 0.435 mmol, 1 equiv) in DMF (3 mL), was added HATU (182 mg, 0.478 mmol, 1.1 equiv). After stirring at RT for 15 minutes, the reaction mixture was added DIPEA (0.23 mL, 1.304 mmol, 3 equiv) and 1-(2,4-bis(trifluoromethyl)benzyl)-1H-pyrazol-4-amine hydrochloride (150 mg, 0.435 mmol, 1 equiv). The reaction mixture was stirred overnight at the room temperature. The progress of reaction was monitored through TLC and LCMS. After completion of the reaction, the reaction mixture was diluted ice-water (30 mL) and was extracted with EtOAc (2×30 mL). The combined organic layers were washed with ice-cold water, dried over anhdrous Na$_2$SO$_4$ and evaporated to obtain crude residue which was purified by column chromatography to obtain (E)-N-(1-(2,4-bis(trifluoromethyl)benzyl)-1H-pyrazol-4-yl)-3-(furan-2-yl)acrylamide as white solid (100 mg). LCMS: 446 [M+H]$^+$. $^1$H NMR (400 MHz, DMSO-d$_6$) δ 10.38 (s, 1H), 8.23 (s, 1H), 8.06 (d, J=8.3 Hz, 2H), 7.84-7.78 (m, 1H), 7.61 (s, 1H), 7.34 (d, J=15.5 Hz, 1H), 7.03 (d, J=8.3 Hz, 1H), 6.84 (d, J=3.4 Hz, 1H), 6.65-6.58 (m, 1H), 6.53 (d, J=15.5 Hz, 1H), 5.63 (s, 2H).

Example S42. Synthesis of (E)-N-(1-(1-(2,4-bis(trifluoromethyl)phenyl)ethyl-1H-pyrazol-4-yl)-3-(furan-2-yl)acrylamide (Compounds 85 & 86)

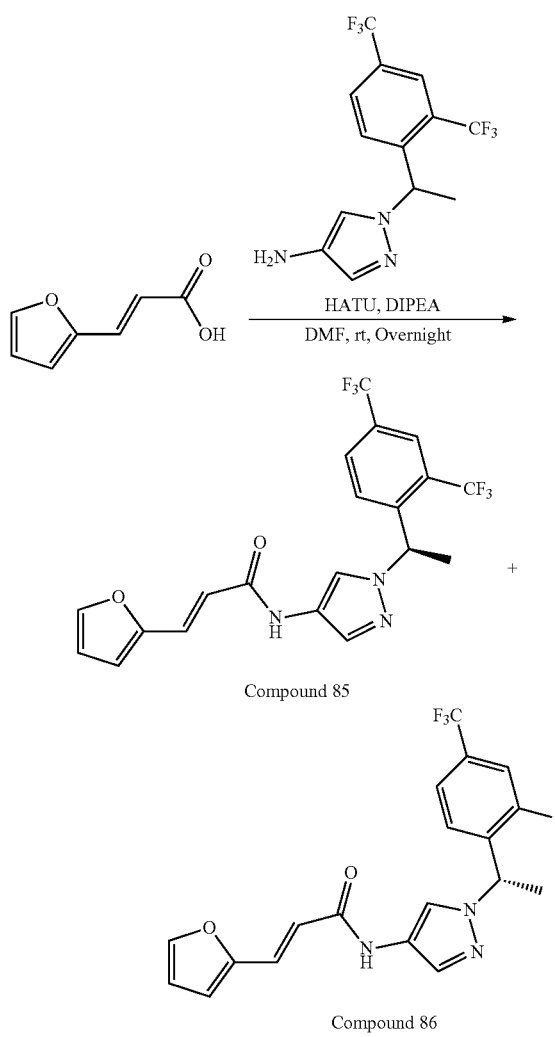

Compound 85

Compound 86

Step 1: Synthesis of (E)-N-(1-(1-(2,4-bis(trifluoromethyl)phenyl)ethyl)-1H-pyrazol-4-yl)-3-(furan-2-yl)acrylamide. To a solution of (E)-3-(furan-2-yl)acrylic acid (60 mg, 0.435 mmol, 1 equiv) in DMF (3 mL), was added HATU (182 mg, 0.478 mmol, 1.1 equiv). After stirring at RT for 15 minutes, the mixture was added DIPEA (0.25 mL, 1.304 mmol, 3 equiv) and 1-(1-(2,4-bis(trifluoromethyl)phenyl)ethyl)-1H-pyrazol-4-amine (156 mg, 0.435 mmol, 1 equiv). The reaction mixture was stirred overnight at the room temperature. The progress of reaction was monitored through TLC and LCMS. After completion of the reaction, the reaction mixture was diluted ice-water (30 mL) and was extracted with EtOAc (2×30 mL). The combined organic layers were washed with ice-cold water, dried over anhdrous Na$_2$SO$_4$ and evaporated to obtain crude residue which was purified by column chromatography to obtain (E)-N-(1-(1-(2,4-bis(trifluoromethyl)phenyl)ethyl)-1H-pyrazol-4-yl)-3-(furan-2-yl)acrylamide as white solid (100 mg). The enantiomers (elution time: 4.47 min & 4.68), were separated by chiral SFC (Daicel Chiralcel®-ODH, 250×20 mm, 5 μm). Isocratic program with analytical grade liquid carbon dioxide and HPLC grade Ethanol (0.1% TFA), Total flow: 56 g/min, Co-Solvent Percentage: 12% to obtain (R,E)-N-(1-(1-(2,4-bis(trifluoromethyl)phenyl)ethyl)-1H-pyrazol-4-yl)-3-(furan-2-yl)acrylamide (10 mg) and (S,E)-N-(1-(1-(2,4-bis(trifluoromethyl)phenyl)ethyl)-1H-pyrazol-4-yl)-3-(furan-2-yl)acrylamide (20 mg). LCMS: 444 [M+H]$^+$. $^1$H NMR (400 MHz, DMSO-d$_6$) δ ppm 10.33 (s, 1H) 8.12 (s, 1H) 8.08 (d, J=8.33 Hz, 1H) 8.04 (s, 1H) 7.80 (s, 1H) 7.71 (d, J=8.33 Hz, 1H) 7.56 (s, 1H) 7.31 (d, J=15.35 Hz, 1H) 6.83 (d, J=3.51 Hz, 1H) 6.61 (d, J=3.07 Hz, 1H) 6.50 (d, J=15.35 Hz, 1H) 5.90 (d, J=7.02 Hz, 1H) 1.85 (d, J=7.02 Hz, 2H).

Example S43. Synthesis of (E)-N-(1-(1-(2,4-bis(trifluoromethyl)phenyl)ethyl)-1H-pyrazol-4-yl)-3-(furan-2-yl)acrylamide (Compound 87)

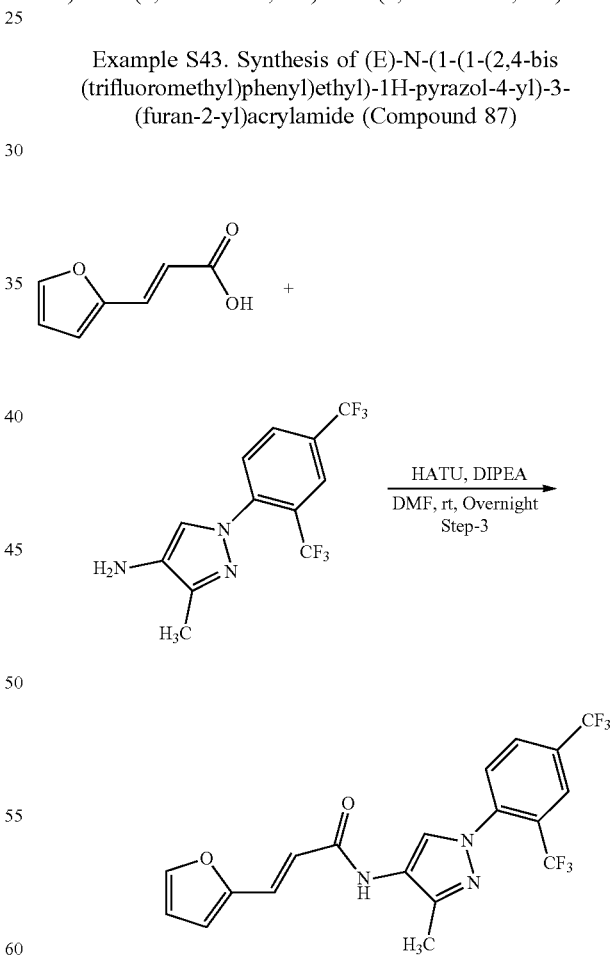

Step 3: Synthesis of (E)-N-(1-(2,4-bis(trifluoromethyl)phenyl)-3-methyl-1H-pyrazol-4-yl)-3-(furan-2-yl)acrylamide. To a solution of (E)-3-(furan-2-yl)acrylic acid (40 mg, 0.290 mmol, 1 equiv) in DMF (3 mL), was added HATU (121 mg, 0.319 mmol, 1.1 equiv). After stirring at RT for 15 minutes, the mixture was added DIPEA (0.16 mL, 0.870 mmol, 3 equiv) and 1-(2,4-bis(trifluoromethyl)phenyl)-3-methyl-1H-pyrazol-4-amine (100 mg, 0.290 mmol, 1 equiv). The reaction mixture was stirred overnight at the room temperature. The progress of reaction was monitored through TLC and LCMS. After completion of the reaction, the reaction mixture was diluted ice-water (30 mL) and was extracted with EtOAc (2×30 mL). The combined organic layers were washed with ice-cold water, dried over anhydrous Na$_2$SO$_4$ and evaporated to obtain crude residue which was purified by column chromatography to obtain (E)-N-(1-(2,4-bis(trifluoromethyl)phenyl)-3-methyl-1H-pyrazol-4-yl)-3-(furan-2-yl)acrylamide as white solid (40 mg). LCMS: 430 [M+H]$^+$. $^1$H NMR (400 MHz, DMSO-d$_6$) δ 9.93 (s, 1H), 8.49 (s, 1H), 8.25-8.17 (m, 2H), 7.89 (d, J=8.4 Hz, 1H), 7.83 (s, 1H), 7.37 (d, J=15.5 Hz, 1H), 6.85 (d, J=3.4 Hz, 1H), 6.79 (d, J=15.5 Hz, 1H), 6.63 (t, J=2.6 Hz, 1H), 2.31 (s, 3H).

Example S44. Synthesis of (R)- and (S)—N-(1-(1-(2,4-bis(trifluoromethyl)phenyl)ethyl)-1H-pyrazol-4-yl)-5-(2-methoxyphenyl)isoxazole-3-carboxamide (Compounds 88 & 89)

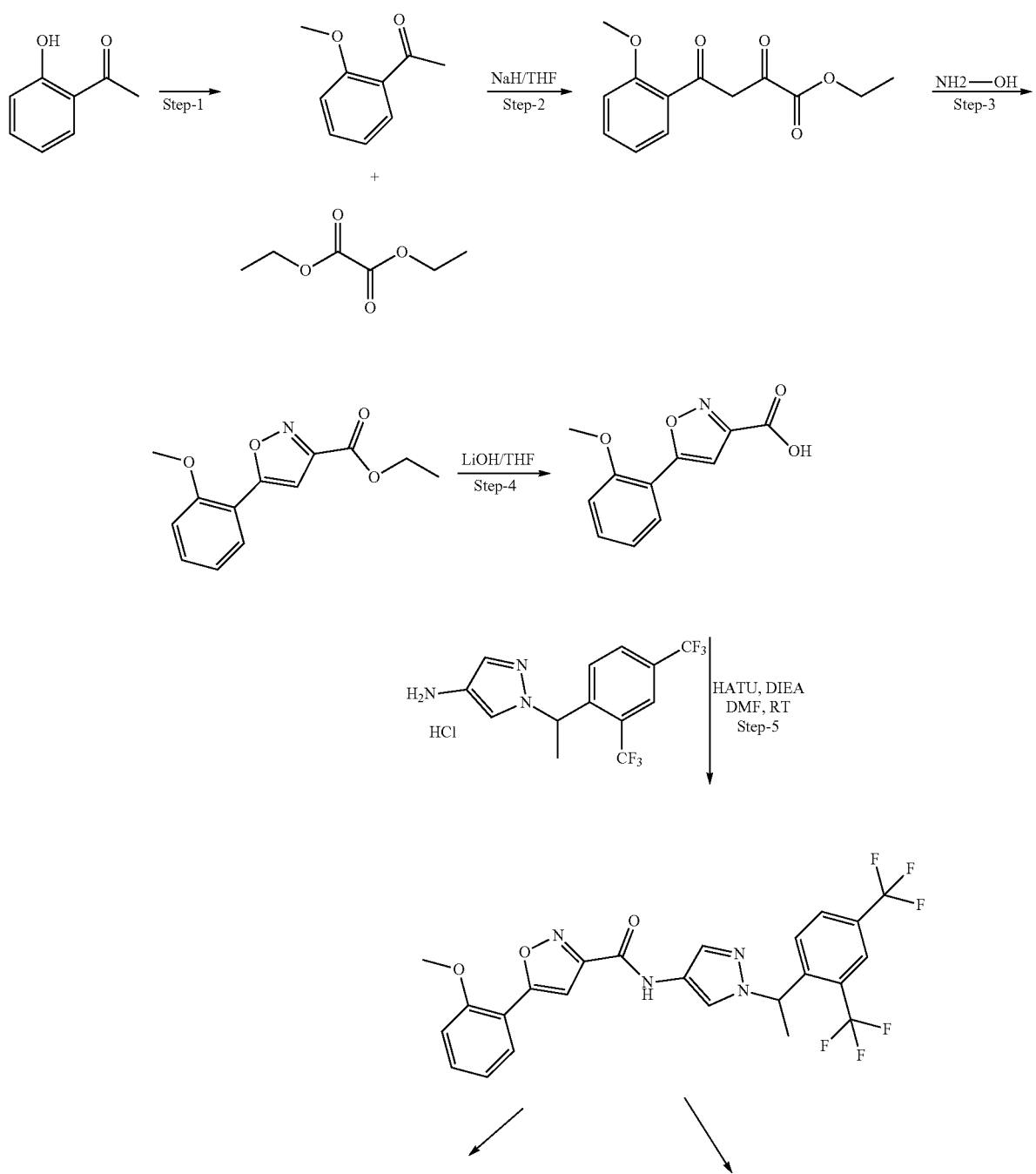

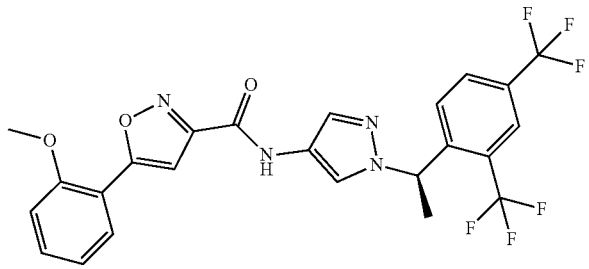

Compound 88

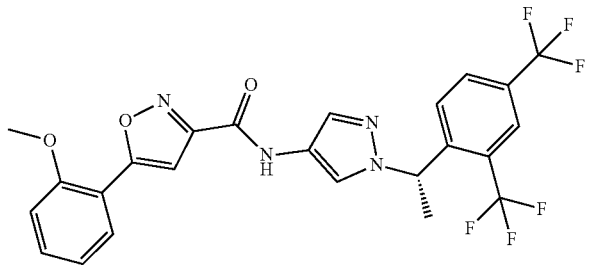

Compound 89

Step 1: Synthesis of 1-(2-methoxyphenyl)ethan-1-one. To a solution of 1-(2-hydroxyphenyl)ethan-1-one (2 g, 0.014 moles, 1 eq) in DMF (20 mL) at 0° C. was added $K_2CO_3$ (4.05 gm, 0.029 moles, 2 eq). The reaction mixture was stirred for 30 minutes followed by addition of methyl iodide (4.17 g, 2 eq, 0.029 moles). The reaction mixture was stirred for another for 24 hour at RT. The reaction mixture quenched with water and extracted with EtOAc (3×100 mL). The organic layers were collected and were washed with water (2×100 mL), dried over anhydrous $Na_2SO_4$ and concentrated under reduced pressure to obtain crude which was purified by combi-flash chromatography using EtOAc/hexane as eluent to obtain the title compound as free base (1.2 gm). LCMS: 151 [M+H]$^+$.

Step 2: Synthesis of ethyl 4-(2-methoxyphenyl)-2,4-dioxobutanoate. To a solution of 1-(2-methoxyphenyl)ethan-1-one (500 mg, 3.33 mmol, 1 equiv) in THF was added NaH (60%, 159.84 mg, 3.996 mmol, 1.2 equiv) in portion wise at 0° C. The resultant reaction mixture was stirred for another 30 minutes at RT, followed by drop wise addition of diethyl oxalate (972.36 mg, 6.66 mmol, 2 equiv) at 0° C. and reaction mixture was stir for another 18 hours at room temperature. Product formation was confirmed by TLC and LCMS. The reaction mixture neutralized with 1N HCl and extracted with EtOAc (3×100 mL). Combined organic extracts were washed with water (2×100 mL), dried over anhydrous $Na_2SO_4$ and concentrated under reduced pressure to obtain crude which was purified by combi-flash chromatography (0-20% Ethyl acetate in hexane) to obtain ethyl 4-(2-methoxyphenyl)-2,4-dioxobutanoate (0.6 g). LCMS: 251 [M+H]$^+$.

Step 3: Synthesis of ethyl 5-(2-methoxyphenyl)isoxazole-3-carboxylate. A suspension of ethyl 4-(2-methoxyphenyl)-2,4-dioxobutanoate (500 mg, 2 mmol, 1 eq) and hydroxylamine hydrochloride (210 mg, 3 mmol, 1 eq) in EtOH was stirred at 85° C. for 24 h. Product formation was confirmed by TLC and LCMS. The resulting mixture was concentrated under reduced pressure; the residue was dissolved in DCM and water. Organic phase was separated, dried over anhydrous $Na_2SO_4$, filtered through silica gel pad, and then concentrated under reduced pressure to give crude which was purified by flash chromatography to obtain title compound ethyl 5-(2-methoxyphenyl)isoxazole-3-carboxylate (0.2 g). LCMS: 248 [M+H]$^+$.

Step 4: Synthesis of 5-(2-methoxyphenyl)isoxazole-3-carboxylic acid. To a solution of ethyl 5-(2-methoxyphenyl)isoxazole-3-carboxylate (120 mg, 0.54 mmol) in THF (30 mL) and methanol (6 mL) was slowly added in lithium hydroxide aqueous solution (10 mL). The resulting mixture was stirred for 16 hrs. Reaction mixture was concentrated under reduced pressure to obtain crude which was acidified with 1N HCl and obtained precipitates were filtered and dried obtain the title compound as free base (0.1 gm). LCMS: 220 [M+H]$^+$.

Step 5: Synthesis of N-(1-(1-(2,4-bis(trifluoromethyl)phenyl)ethyl)-1H-pyrazol-4-yl)-5-(2-methoxyphenyl)isoxazole-3-carboxamide. To a solution of 5-(2-methoxyphenyl)isoxazole-3-carboxylic acid acid (60 mg, 0.273 mmol, 1 equiv) in DMF (1 mL), was added HATU (104 mg, 0.273 mmol, 1 equiv). The mixture was treated drop wise with DIPEA (106.6 g, 0.821 mmol, 3 equiv). After stirring at RT for 15 minutes, the mixture was added a solution of the 1-(1-(2,4-bis(trifluoromethyl)phenyl)ethyl)-1H-pyrazol-4-amine (98.3 mg, 0.273 mmol, 1 equiv) in DMF (1 mL). The reaction mixture was kept under stirring for 24 h. The reaction mixture was diluted water (50 mL). The precipitated solid was filtered, dried under vacuum and was purified by triturations with hexane to obtained N-(1-(1-(2,4-bis(trifluoromethyl)phenyl)ethyl)-1H-pyrazol-4-yl)-5-(2-methoxyphenyl)isoxazole-3-carboxamide (50 mg). The enantiomers (elution time: 2.3 min & 3.4 min), were separated by chiral SFC (Daicel Chiralpak®-IC, 250×20 mm, 5 μm). Isocratic program with analytical grade liquid carbon dioxide and HPLC grade Ethanol (0.1% TFA), Total flow: 56 g/min, Co-Solvent Percentage: 25% After to obtained (R) N-(1-(1-(2,4-bis(trifluoromethyl)phenyl)ethyl)-1H-pyrazol-4-yl)-5-(2-methoxyphenyl)isoxazole-3-carboxamide (14 mg) and (S)N-(1-(1-(2,4-bis(trifluoromethyl)phenyl)ethyl)-1H-pyrazol-4-yl)-5-(2-methoxyphenyl)isoxazole-3-carboxamide (13 mg). (Compound 88) $^1$H NMR (400 MHz, DMSO-$d_6$) δ 11.03 (s, 1H), 8.18 (s, 1H), 8.09 (d, J=8.5 Hz, 1H), 8.05 (s, 1H), 7.96-7.88 (m, 1H), 7.74 (d, J=8.4 Hz, 2H), 7.60-7.51 (m, 1H), 7.27 (d, J=8.4 Hz, 1H), 7.19 (s, 1H), 7.15 (t, J=7.6 Hz, 1H), 5.93 (q, J=6.9 Hz, 1H), 3.98 (s, 3H), 1.87 (d, J=6.9 Hz, 3H). (Compound 89) $^1$H NMR (400 MHz, DMSO-$d_6$) δ 11.03 (s, 1H), 8.18 (s, 1H), 8.09 (d, J=8.3 Hz, 1H), 8.05 (s, 1H), 7.92 (d, J=7.8 Hz, 1H), 7.74 (d, J=8.5 Hz, 2H), 7.55 (t, J=7.9 Hz, 1H), 7.27 (d, J=8.4 Hz, 1H), 7.19 (s, 1H), 7.15 (t, J=7.6 Hz, 1H), 5.93 (q, J=7.0 Hz, 1H), 3.98 (s, 3H), 1.87 (d, J=6.9 Hz, 3H).

Example S45. Synthesis of N-(1-(2,4-bis(trifluoromethyl)phenyl)-3-methyl-1H-pyrazol-4-yl)-5-(pyridin-2-yl)isoxazole-3-carboxamide (Compound 90)

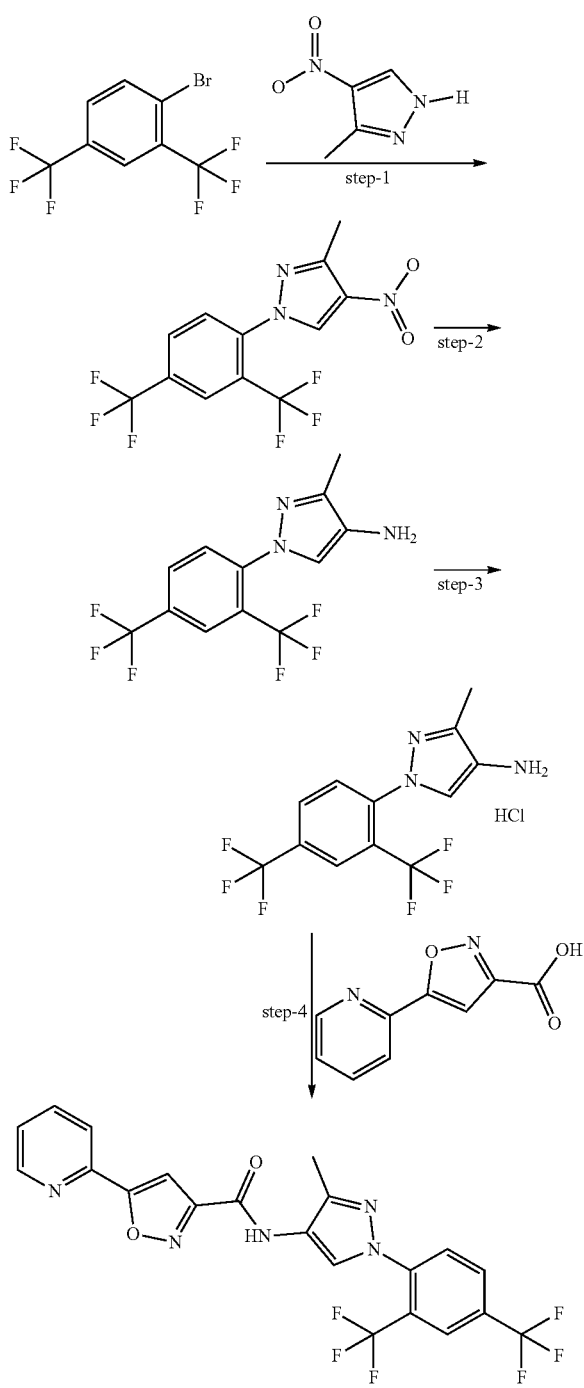

Step 1: Synthesis of 1-(2,4-bis(trifluoromethyl)phenyl)-3-methyl-4-nitro-1H-pyrazole. To a stirred solution of 3-methyl-4-nitro-1H-pyrazole (869 mg, 0.068 mmol, 1 equiv) 1-bromo-2,4-bis(trifluoromethyl)benzene (2 g, 0.068 mmoles, 1 eq) in DMF (20 mL) was added $K_2CO_3$ (1.89 g, 0.0136 mmol, 2 equiv) and the reaction mixture was stirred for 15 minutes. CuI (0.026 g, 0.2 eq, 0.001 moles) and L-proline (0.317 g, 0.02 mmol, 0.4 equiv) were added to the reaction mixture. The reaction mixture was allowed to stir for 24 hour at 100° C. Product formation was confirmed by LCMS. After completion of reaction, reaction mixture was diluted with water and extracted with ethyl acetate (3×100 mL). Combined organic extracts were washed with water (4×100 mL), dried over anhydrous $Na_2SO_4$ and concentrated under reduced pressure to obtain which was purified by flash chromatography (EtOAc/Hexane) to obtain title compound 1-(2,4-bis(trifluoromethyl)phenyl)-3-methyl-4-nitro-1H-pyrazole (1.0 g). LCMS 339 $[M+H]^+$.

Step 2: Synthesis of 1-(2,4-bis(trifluoromethyl)phenyl)-3-methyl-1H-pyrazol-4-amine. To a stirred solution of 1-(2,4-bis(trifluoromethyl)phenyl)-3-methyl-4-nitro-1H-pyrazole of (500 mg, 1 equiv) in methanol (10 mL) under nitrogen was added Palladium on Carbon (10% w/w, 50 mg) was added. Purged reaction mixture with $H_2$ gas for 6 hrs. Product formation was confirmed by LCMS. After the completion of reaction, reaction mixture was filtered through Celite bed and filtrate was concentrate under reduced pressure to obtain 1-(2,4-bis(trifluoromethyl)phenyl)-3-methyl-1H-pyrazol-4-amine (5.0 g). LCMS: 310 $[M+H]^+$.

Step 3: Synthesis of 1-(2,4-bis(trifluoromethyl)phenyl)-3-methyl-1H-pyrazol-4-amine hydrochloride. To 1-(2,4-bis(trifluoromethyl)phenyl)-3-methyl-1H-pyrazol-4-amine (500 mg) in ethanol was added 1.25 M HCl in ethanol (15 mL) at 0° C. was added and kept under stirring for half hour at RT. Resulting suspension was filtered and residue obtained was triturated with ether to obtain product 1-(2,4-bis(trifluoromethyl)phenyl)-3-methyl-1H-pyrazol-4-amine hydrochloride (0.5 g). LCMS: 310 $[M+H]^+$.

Step 4: Synthesis N-(1-(2,4-bis(trifluoromethyl)phenyl)-3-methyl-1H-pyrazol-4-yl)-5-(pyridin-2-yl)isoxazole-3-carboxamide. To a solution of 5-(pyridin-2-yl)isoxazole-3-carboxylic acid (55 mg, 0.289 mmol, 1 equiv) in DMF (1 mL), was added HATU (110 mg, 0.289 mmol, 1 equiv). After stirring at RT for 15 minutes, the mixture was treated drop wise with DIPEA (112.1 mg, 0.869 mmol, 3 equiv). After stirring at RT for 15 minutes, the mixture was added a solution of the 1-(2,4-bis(trifluoromethyl)phenyl)-3-methyl-1H-pyrazol-4-amine hydrochloride (110.4 mg, 0.289 mmol, 1 equiv) in DMF (1 mL). The reaction mixture was kept under stirring for 24 hrs. The reaction mixture was diluted water (50 mL). The resulting precipitates were filtered under vacuum, dried and triturated with trituration with hexane to yield the title compound as free base (45 mg). LCMS: 482 $[M+H]^+$. $^1$H NMR (400 MHz, DMSO-$d_6$) δ 10.59 (br. s., 1H), 8.77 (br. s., 1H), 8.42 (br. s., 1H), 8.23 (br. s., 2H), 8.03 (br. s., 2H), 7.93 (br. s., 1H), 7.54 (s, 2H), 2.33 (s, 3H).

Example S46. Synthesis of N-(1-(2,4-bis(trifluoromethyl)benzyl)-1H-pyrazol-4-yl)-5-(2-methoxyphenyl)isoxazole-3-carboxamide (Compound 91)

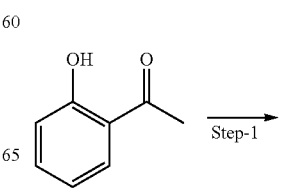

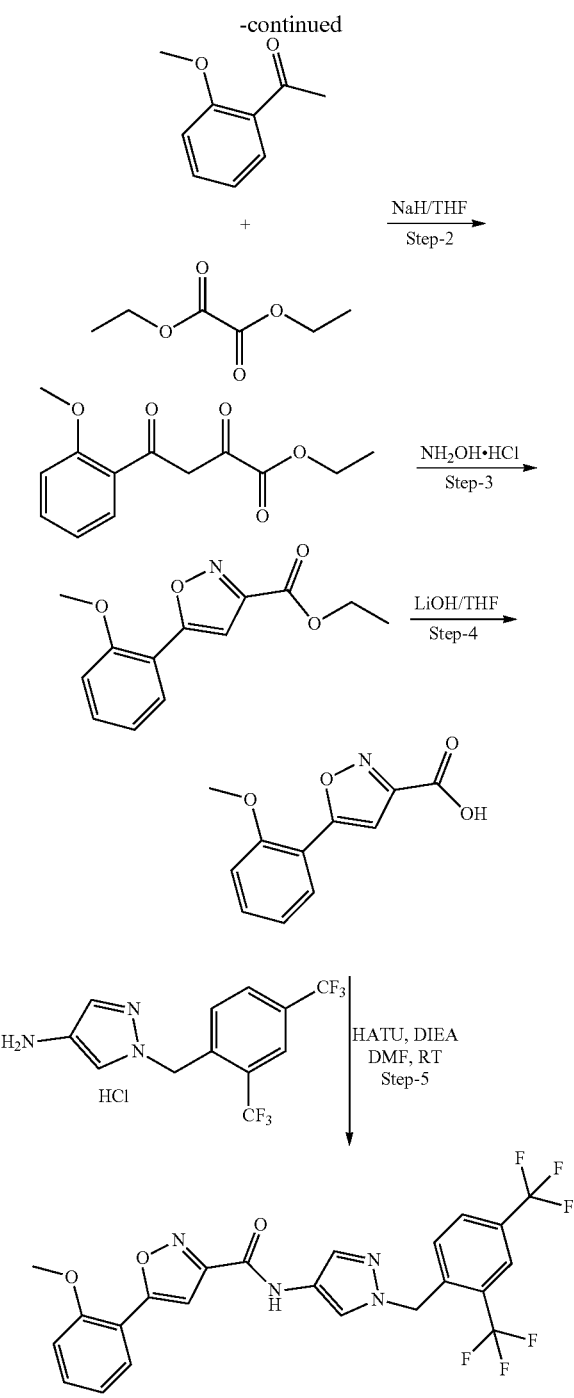

Step 1: Synthesis of 1-(2-methoxyphenyl)ethan-1-one. To a solution of 1-(2-hydroxyphenyl)ethan-1-one (2 g, 0.014 moles, 1 eq) in DMF (20 mL) at 0° C. was added $K_2CO_3$ (4.05 gm, 0.029 moles, 2 eq). The reaction mixture was stirred for 30 minutes followed by addition of methyl iodide (4.17 g, 2 eq, 0.029 moles). The reaction mixture was stirred for another for 24 hour at RT. The reaction mixture quenched with water and extracted with EtOAc (3×100 mL). The organic layers were collected and were washed with water (2×100 mL), dried over anhydrous $Na_2SO_4$ and concentrated under reduced pressure to obtain crude which was purified by combi-flash chromatography using EtOAc/hexane as eluent to obtain the title compound as free base (1.2 g). LCMS: 150 [M+H]⁺.

Step 2: Synthesis of ethyl 4-(2-methoxyphenyl)-2,4-dioxobutanoate. To a solution of 1-(2-methoxyphenyl)ethan-1-one (500 mg, 3.33 mmol, 1 equiv) in THF was added portion wise 60% Sodium hydride (159.84 mg, 3.996 mmol, 1.2 equiv) at 0° C. The resultant reaction mixture was stirred for another 30 minutes at RT, followed by drop wise addition of diethyl oxalate (972.36 mg, 6.66 mmol, 2 equiv) at 0° C. and reaction mixture was stir for another 18 hours at room temperature. Product formation was confirmed by TLC and LCMS. The reaction mixture neutralized with 1N HCl and extracted with EtOAc (3×100 mL). Combined organic extracts were washed with water (2×100 mL), dried over anhydrous $Na_2SO_4$ and concentrated under reduced pressure to obtain crude which was purified by flash chromatography (0-20% Ethyl acetate in hexane) to obtain ethyl 4-(2-methoxyphenyl)-2,4-dioxobutanoate (0.6 g). LCMS: 251 [M+H]⁺.

Step 3: Synthesis of ethyl 5-(2-methoxyphenyl)isoxazole-3-carboxylate. A suspension of ethyl 4-(2-methoxyphenyl)-2,4-dioxobutanoate (500 mg, 2 mmol, 1 eq) and hydroxylamine hydrochloride (210 mg, 3 mmol, 1 eq) in EtOH was stirred at 85° C. for 24 h. Product formation was confirmed by TLC and LCMS. The resulting mixture was concentrated under reduced pressure; the residue was dissolved in DCM and water. The organic phase was separated, dried over anhydrous $Na_2SO_4$, filtered through silica gel pad, and then concentrated under reduced pressure to give ethyl 5-(2-methoxyphenyl)isoxazole-3-carboxylate as crude compound as free base (0.5 g crude). LCMS: 248 [M+H]⁺.

Step 4: Synthesis of 5-(2-methoxyphenyl)isoxazole-3-carboxylic acid. To a solution of ethyl 5-(2-methoxyphenyl)isoxazole-3-carboxylate (500 mg, 0.54 mmol, 1 equiv) in THF (30 mL) and methanol (6 mL) was slowly added in lithium hydroxide aqueous solution (10 mL). The resulting mixture was stirred for 16 hrs. Reaction mixture was concentrated under reduced pressure to obtain crude which was acidified with 1N HCl and obtained suspension was filtered and dried under vacuum to obtain title compound as free base (0.5 g). LCMS: 220 [M+H]⁺.

Step 5: Synthesis of N-(1-(2,4-bis(trifluoromethyl)benzyl)-1H-pyrazol-4-yl)-5-(2-methoxyphenyl)isoxazole-3-carboxamide. To a solution of 5-(2-methoxyphenyl)isoxazole-3-carboxylic acid acid (66 mg, 0.289 mmol, 1 equiv) in DMF (1 mL), were added HATU (110 mg, 0.289 mmol, 1 equiv). The mixture was treated drop wise with DIPEA (112.7 mg, 0.869 mmol, 3 equiv). After stirring at RT for 15 minutes, the mixture was treated added a solution of the 1-(2,4-bis(trifluoromethyl)benzyl)-1H-pyrazol-4-amine 5-(2-methoxyphenyl)isoxazole-3-carboxylate hydrochloride (100 mg, 0.289 mmol, 1 equiv) in DMF (1 mL). The reaction mixture was kept under stirring for 24 hrs. The reaction mixture was diluted water (50 mL). The resulting precipitate was filtered and dried under vacuum. The solid was purified by trituration with hexane to yield the title compound as free base (65 mg). LCMS: 511 [M+H]⁺. ¹H NMR (400 MHz, DMSO-$d_6$) δ 11.10 (s, 1H), 8.32 (s, 1H), 8.07 (d, J=7.8 Hz, 2H), 7.97-7.89 (m, 1H), 7.79 (s, 1H), 7.56 (t, J=7.7 Hz, 1H), 7.28 (d, J=8.5 Hz, 1H), 7.21 (s, 1H), 7.15 (t, J=7.6 Hz, 1H), 7.06 (d, J=8.3 Hz, 1H), 5.67 (s, 2H), 3.99 (s, 3H).

Example S47. Synthesis of N-(1-(2,4-bis(trifluoromethyl)benzyl)-3-methyl-1H-pyrazol-4-yl)-5-(furan-2-yl)isoxazole-3-carboxamide and N-(1-(2,4-bis(trifluoromethyl)benzyl)-5-methyl-1H-pyrazol-4-yl)-5-(furan-2-yl)isoxazole-3-carboxamide (Compounds 92 & 93)

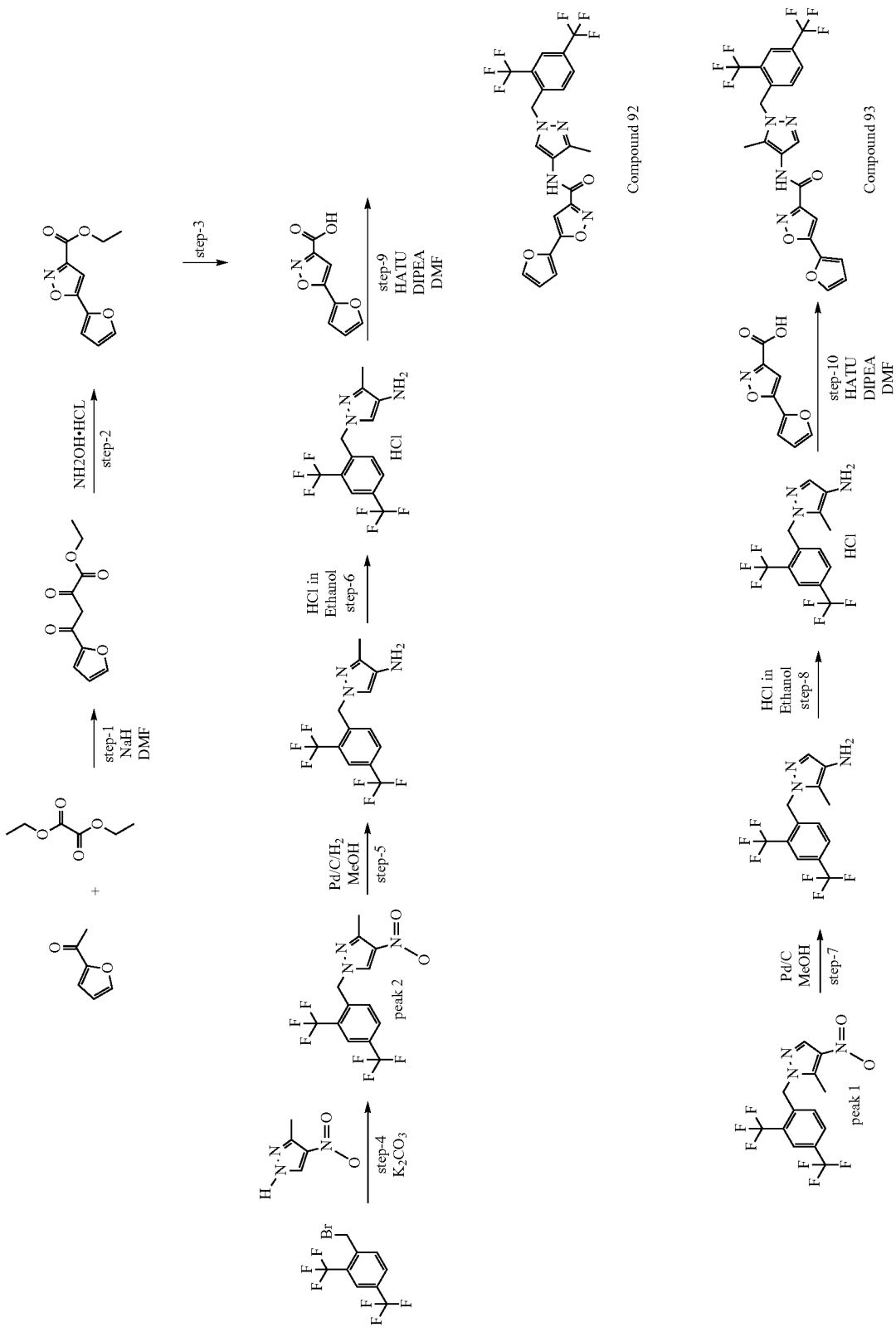

Step 1: Synthesis of ethyl 4-(2-furyl)-2, 4-dioxobutyrate. To a solution of 2-acetylfuran (5.0 g, 45.40 mmol, 1 equiv) in THF was added portion wise NaH (60% 3.63 g, 90.81 mmol, 2 equiv) at 0° C. The resultant reaction mixture was stirred for another 30 minutes at room temperature, followed by drop wise addition of diethyl oxalate (12.28 ml, 90.81 mmol, 2 equiv) at 0° C. and reaction mixture was stir for another 18 hrs at RT. Product formation was confirmed by TLC and LCMS. The reaction mixture was quenched with ice water and washed with diethyl ether (2×100 mL). Aqueous layer was separated and neutralized with 1N HCl and extracted with EtOAc (3×100 mL). Combined organic extracts were washed with water (2×100 mL), dried over anhydrous $Na_2SO_4$ and concentrated under reduced pressure to obtain crude which was purified by combi-flash chromatography (0-20% Ethyl acetate in hexane) to obtain Ethyl 4-(2-furyl)-2, 4-dioxobutyrate (3.6 g) as yellow solid. LCMS: 211 $[M+H]^+$.

Step 2: Synthesis of 5-furan-2-yl-isoxazole-3-carboxylic acid ethyl ester. A suspension of 4-furan-2-yl-2, 4-dioxobutyric acid ethyl ester (1.6 g, 7.61 mmol, 1 eq) and hydroxylamine hydrochloride (0.528 g, 7.61 mmol, 1 eq) in EtOH was stirred at 85° C. for 2 h. Product formation was confirmed by TLC and LCMS. The resulting mixture was concentrated under reduced pressure, the residue was dissolved in DCM and water. Organic phase was separated, dried over anhydrous $Na_2SO_4$, filtered through silica gel pad, and then concentrated under reduced pressure to give 5-furan-2-yl-isoxazole-3-carboxylic acid ethyl ester. The crude product was used in the next steps without any purification (700 mg) as yellow solid. LCMS: 208 $[M+H]^+$.

Step 3: Synthesis of 5-furan-2-yl-isoxazole-3-carboxylicacid. To a solution of 5-furan-2-yl-isoxazole-3-carboxylic acid ethyl ester (0.5 g, 2.41 mmol) in THF (30 mL) and methanol (6 mL) was slowly added in lithium hydroxide aqueous solution (10 mL). The resulting mixture was stirred for 16 hrs. Reaction mixture was concentrated under reduced pressure to obtain crude which was acidified with 1N HCl and extracted with ethyl acetate (3×100 mL). Combined organic extracts were washed with distilled water, dried over anhydrous $Na_2SO_4$ and concentrated under reduced pressure to obtain 5-furan-2-yl-isoxazole-3-carboxylic acid (225 mg) as white solid. LCMS: 180 $[M+H]^+$.

Step 4: Synthesis of 1-(2,4-bis(trifluoromethyl)benzyl)-3-methyl-4-nitro-1H-pyrazole (Compound 58) and 1-(2,4-bis(trifluoromethyl)benzyl)-5-methyl-4-nitro-1H-pyrazole (Compound 59). To a stirred solution of 3-methyl-4-nitro-1H-pyrazole (1.48 g, 0.01 mol, 1 equiv) in DMF (20 mL) was added $K_2CO_3$ (2.71 g, 0.019 mol, 1.5 equiv) portion wise at 0° C. and stirred for 10 minutes. 1-(bromomethyl)-2,4-bis(trifluoromethyl)benzene (4 gm, 0.01 mol, 1 equiv) was added drop wise 0° C. The reaction mixture was allowed to stir for 1 hour at room temperature. Product formation was confirmed by LCMS. After completion of reaction, reaction mixture was diluted with water and extracted with ethyl acetate (3×100 mL). Combined organic extracts were washed with water (4×100 mL), dried over anhydrous $Na_2SO_4$ and concentrated under reduced pressure to obtain residue which was purified by flash column chromatography (EtOAc/Hexane) to obtain the title compound as 1-(2,4-bis(trifluoromethyl)benzyl)-3-methyl-4-nitro-1H-pyrazole (0.6 g) and 1-(2,4-bis(trifluoromethyl)benzyl)-5-methyl-4-nitro-1H-pyrazole (1.4 g). LCMS: 354 $[M+H]^+$.

Step 5: Synthesis of 1-(2,4-bis(trifluoromethyl)benzyl)-3-methyl-1H-pyrazol-4-amine (Compound 58). To a stirred solution of 1-(2,4-bis(trifluoromethyl)benzyl)-3-methyl-4-nitro-1H-pyrazole (500 mg, 1 equiv) in methanol (10 mL) under nitrogen Palladium on Carbon [Pd/C] (10% w/w, 50 mg) was added. Purge the reaction mixture with $H_2$ gas for 6 hrs. Product formation was confirmed by LCMS. After the completion of reaction, reaction mixture was filtered through Celite bed and filtrate was concentrate under reduced pressure to obtain 1-(2,4-bis(trifluoromethyl)benzyl)-3-methyl-1H-pyrazol-4-amine (0.5 g crude). LCMS: 324 $[M+H]^+$.

Step 6: Synthesis of 1-(2,4-bis(trifluoromethyl)benzyl)-3-methyl-1H-pyrazol-4-amine hydrochloride (Compound 58). To 1-(2,4-bis (trifluoromethyl)benzyl)-3-methyl-1H-pyrazol-4-amine (500 mg) in ethanol was added 1.25 M HCl in ethanol (15 mL) at 0° C. and kept under stirring for half hour at RT. Resulting suspension was filtered, dried under vacuum residue was triturated with ether to obtain title compound 1-(2,4-bis(trifluoromethyl)benzyl)-3-methyl-1H-pyrazol-4-amine hydrochloride (0.5 g). LCMS: 324 $[M+H]^+$.

Step 7: Synthesis of 1-(2,4-bis(trifluoromethyl)benzyl)-5-methyl-1H-pyrazol-4-amine (Compound 59). To a stirred solution of 1-(2,4-bis(trifluoromethyl)benzyl)-5-methyl-4-nitro-1H-pyrazole (1 g, 1 equiv) in Methanol (10 mL) under nitrogen was added Palladium on Carbon [Pd/C] (10% w/w, 100 mg) was added. The reaction mixture was purged with $H_2$ gas for 6 hrs. The product formation was confirmed by LCMS. After the completion of reaction, reaction mixture was filtered through Celite bed and Filtrate was concentrate under reduced pressure to obtain 1-(2,4-bis(trifluoromethyl)benzyl)-5-methyl-1H-pyrazol-4-amine (1 g crude). LCMS: 324 $[M+H]^+$.

Step 8: Synthesis of 1-(2,4-bis(trifluoromethyl)benzyl)-5-methyl-1H-pyrazol-4-amine hydrochloride (Compound 59). 1-(2,4-bis (trifluoromethyl)benzyl)-5-methyl-1H-pyrazol-4-amine (500 mg) in ethanol was added 1.25 M HCl in ethanol (15 mL) at 0° C. and kept under stirring for half hour at RT. Resulting suspension was filtered, dried under vacuum residue was triturated with ether to obtain title compound 1-(2,4-bis(trifluoromethyl)benzyl)-5-methyl-1H-pyrazol-4-amine hydrochloride (0.5 g). LCMS: 324 $[M+H]^+$.

Step 9: Synthesis of N-(1-(2,4-bis(trifluoromethyl)benzyl)-3-methyl-1H-pyrazol-4-yl)-5-(furan-2-yl)isoxazole-3-carboxamide (Compound 96). To a solution of 5-(furan-2-yl)isoxazole-3-carboxylic acid (49.8 mg, 0.278 mmol, 1 equiv) in DMF (1 mL), were added HATU (106 mg, 0.278 mmol, 1 equiv). After stirring at RT for 15 minutes, the mixture was treated drop wise with DIPEA (107.7 mg, 0.835 mmol, 3 equiv). After stirring at RT for 15 minutes, the mixture was treated drop wise with a solution of the 1-(2, 4-bis(trifluoromethyl)benzyl)-3-methyl-1H-pyrazol-4-amine hydrochloride (100 mg, 0.278 mmol, 1 equiv) in DMF (1 mL). The reaction mixture was kept under stirring for 24 hrs. The reaction mixture was diluted water (50 mL). The resulting precipitate was filtered off and the solid was purified by trituration with hexane to yield the title compound as free base (30 mg). LCMS: 485 $[M+H]^+$. $^1H$ NMR (400 MHz, DMSO-$d_6$) δ 10.36 (s, 1H), 8.12-8.04 (m, 2H), 8.01 (d, J=1.6 Hz, 1H), 7.74 (s, 1H), 7.28 (d, J=3.6 Hz, 1H), 7.17 (s, 1H), 6.84 (d, J=8.2 Hz, 1H), 6.78 (dd, J=3.5, 1.8 Hz, 1H), 5.58 (s, 2H), 2.18 (s, 3H).

Step 10: Synthesis of N-(1-(2,4-bis(trifluoromethyl)benzyl)-5-methyl-1H-pyrazol-4-yl)-5-(furan-2-yl)isoxazole-3-carboxamide (Compound 97). To a solution of 5-(furan-2-yl)isoxazole-3-carboxylic acid (49.8 mg, 0.278 mmol, 1 equiv) in DMF (1 mL), were added HATU (106 mg, 0.278 mmol, 1 equiv). After stirring at RT for 15 minutes, the mixture was treated drop wise with DIPEA (107.7 mg, 0.835 mmol, 3 equiv). After stirring at RT for 15 minutes, the mixture was treated drop wise with a solution of the 1-(2,4-bis(trifluoromethyl)benzyl)-5-methyl-1H-pyrazol-4-amine hydrochloride (100 mg, 0.278 mmol, 1 equiv) in DMF (1 mL). The reaction mixture was kept under stirring for 24 h. The reaction mixture was diluted water (50 mL). The reaction mixture was kept under stirring for 24 hrs. The reaction mixture was diluted water (50 mL). The resulting precipitate was filtered off and the solid was purified by trituration with isopropyl alcohol to yield the title compound as free base (20 mg). LCMS: 485 [M+H]+. $^1$H NMR (400 MHz, DMSO-d$_6$) δ 10.37 (s, 1H), 8.21 (s, 1H), 8.09 (d, J=9.5 Hz, 2H), 8.01 (s, 1H), 7.28 (d, J=3.6 Hz, 1H), 7.18 (s, 1H), 7.11 (d, J=8.2 Hz, 1H), 6.83-6.74 (m, 1H), 5.57 (s, 2H), 2.19 (s, 3H).

Example S48. Synthesis of N-(1-(2,4-bis(trifluoromethyl)phenyl)-3-methyl-1H-pyrazol-4-yl)-5-(furan-2-yl)isoxazole-3-carboxamide (Compound 94)

equiv) and 1-bromo-2,4-bis(trifluoromethyl)benzene (2 g, 0.068 mmoles, 1 eq) in DMF (20 mL) was added K$_2$CO$_3$ (1.89 g, 0.0136 mmol, 2 equiv). The reaction mixture was stirred for 15 minutes followed by the addition of CuI (0.026 g, 0.2 eq, 0.001 moles) and L-Proline (0.317 g, 0.4 eq, 0.02 mmol) was added The reaction mixture was allowed to stir for 24 hour at 100° C. Product formation was confirmed by LCMS. After completion of reaction, reaction mixture was diluted with water and extracted with ethyl acetate (3×100 mL). Combined organic extracts were washed with water (4×100 mL), dried over anhydrous Na$_2$SO$_4$ and concentrated under reduced pressure to obtain crude which was purified by flash Chromatography to yield title compound as 1-(2,4-bis(trifluoromethyl)phenyl)-3-methyl-4-nitro-1H-pyrazole (1 g). LCMS: 341 [M+H]+.

Step 2: Synthesis of 1-(2,4-bis(trifluoromethyl)phenyl)-3-methyl-1H-pyrazol-4-amine. To a stirred solution of 1-(2,4-bis(trifluoromethyl)phenyl)-3-methyl-4-nitro-1H-pyrazole of (500 mg, 1 equiv) in methanol (10 mL) under nitrogen was added Palladium on Carbon [Pd/C] (10% w/w,

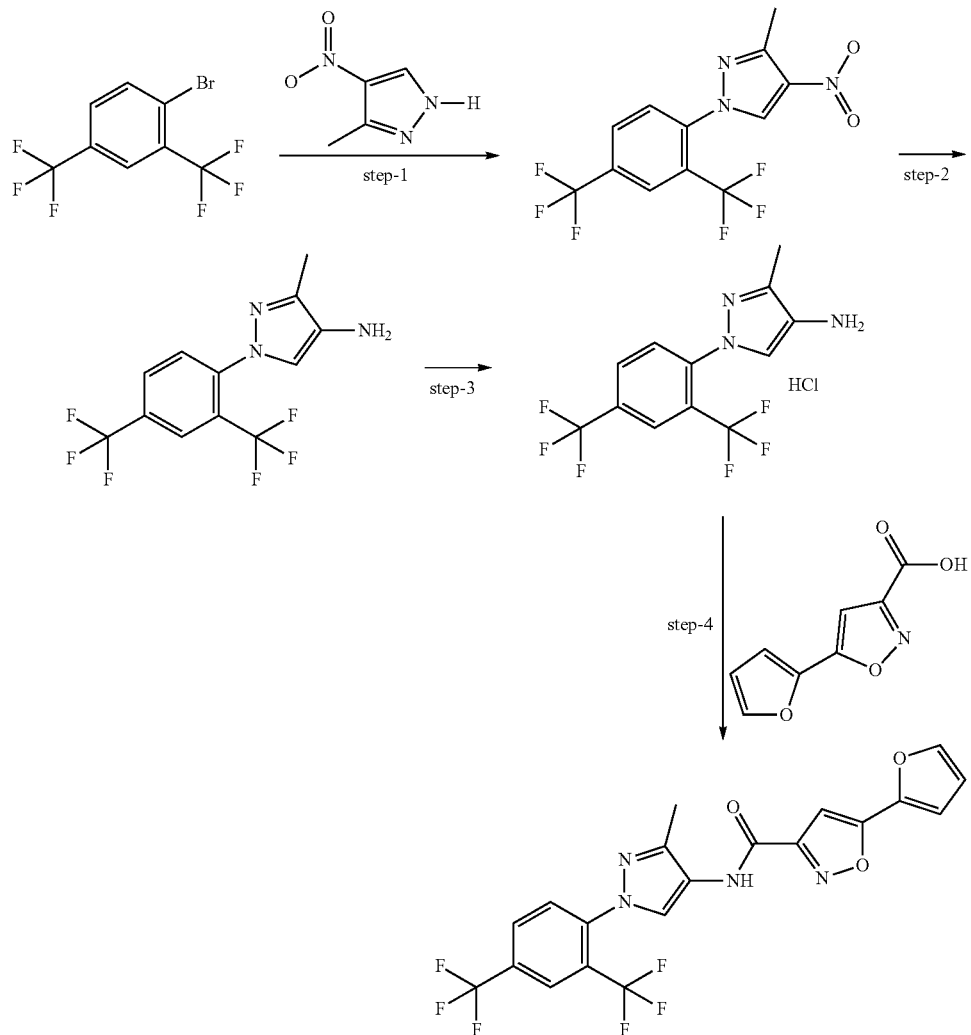

Step 1: Synthesis of 1-(2,4-bis(trifluoromethyl)phenyl)-3-methyl-4-nitro-1H-pyrazole. To a stirred solution of 3-methyl-4-nitro-1H-pyrazole (869 mg, 0.068 mmol, 1 50 mg) was added. The reaction mixture was purged with hydrogen for 6 hrs. Product formation was confirmed by LCMS. After the completion of reaction, reaction mixture was filtered through celite bed and filtrate was concentrated under reduced pressure to obtain 1-(2,4-bis(trifluoromethyl)phenyl)-3-methyl-1H-pyrazol-4-amine (0.5 g crude). LCMS: 310 [M+H]$^+$.

Step 3: Synthesis of 1-(2,4-bis(trifluoromethyl)phenyl)-3-methyl-1H-pyrazol-4-amine hydrochloride. To 1-(2,4-bis(trifluoromethyl)phenyl)-3-methyl-1H-pyrazol-4-amine (500 mg) in ethanol was added 1.25 M HCl in ethanol (15 mL) at 0° C. and kept under stirring for half hour at RT. Resulting suspension was filtered, dried under vacuum residue was triturated with ether to obtain title compound 1-(2,4-bis(trifluoromethyl)phenyl)-3-methyl-1H-pyrazol-4-amine hydrochloride (0.5 g). LCMS: 310 [M+H]$^+$.

Step 4: Synthesis N-(1-(2,4-bis(trifluoromethyl)phenyl)-3-methyl-1H-pyrazol-4-yl)-5-(furan-2-yl)isoxazole-3-carboxamide. To a solution 5-(furan-2-yl)isoxazole-3-carboxylic acid (100 mg, 0.558 mmol, 1 equiv) in DMF (1 mL), were added HATU (212.8 mg, 0.558 mmol, 1 equiv). After stirring at RT for 15 minutes, the mixture was treated drop wise with DIPEA (216.2 mg, 1.67 mmol, 3 equiv). After stirring at RT for 15 minutes, the mixture was treated drop wise with a solution of the 1-(2,4-bis(trifluoromethyl)phenyl)-3-methyl-1H-pyrazol-4-amine hydrochloride (192.7 mg, 0.558 mmol, 1 equiv) in DMF (1 mL). The reaction mixture was kept under stirring for 24 h. The reaction mixture was diluted water (50 mL). The resulting precipitate was filtered off. The crude material was purified by trituration with hexane (15 mg). LCMS: 471 [M+H]$^+$. $^1$H NMR (400 MHz, DMSO-d$_6$) δ 10.56 (s, 1H), 8.42 (s, 1H), 8.28-8.20 (m, 2H), 8.01 (d, J=1.8 Hz, 1H), 7.91 (d, J=8.3 Hz, 1H), 7.29 (d, J=3.6 Hz, 1H), 7.21 (s, 1H), 6.78 (dd, J=3.5, 1.8 Hz, 1H), 2.31 (s, 3H).

Example S49. Synthesis of (E)-N-(1-(2,4-bis(trifluoromethyl)benzyl)-5-methyl-1H-pyrazol-4-yl)-3-(furan-2-yl)acrylamide (Compound 95)

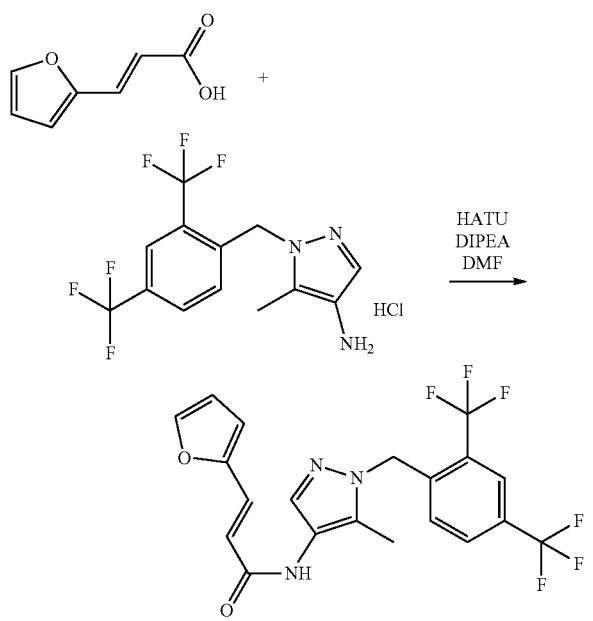

Step 1: Synthesis of (E)-N-(1-(2,4-bis(trifluoromethyl) benzyl)-5-methyl-1H-pyrazol-4-yl)-3-(furan-2-yl)acrylamide. To a solution of (E)-3-(furan-2-yl)acrylic acid (100 mg, 0.724 mmol, 1 equiv) in DMF (1 mL), was added HATU (276.08 mg, 0.724 mmol, 1 equiv). After stirring at RT for 15 minutes, the mixture was treated drop wise with DIPEA (280.4 mg, 21.73 mmol, 3 equiv). After stirring at RT for 15 minutes, the mixture was added drop wise with a solution of the 1-(2,4-bis(trifluoromethyl)benzyl)-5-methyl-1H-pyrazol-4-amine hydrochloride (250 mg, 0.724 mmol, 1 equiv) in DMF (1 mL). The reaction mixture was kept under stirring for 24 h. The reaction mixture was diluted water (50 mL). The resulting precipitate was filtered off and the crude material obtained was purified by flash chromatography using EtOAc hexane as eluent to obtain title compound as free base (37 mg). LCMS: 444 [M+H]$^+$. $^1$H NMR (400 MHz, DMSO-d$_6$) δ 9.70 (s, 1H), 8.08 (s, 1H), 8.06-8.01 (m, 1H), 7.90 (s, 1H), 7.81 (d, J=1.8 Hz, 1H), 7.34 (d, J=15.5 Hz, 1H), 6.83 (d, J=3.4 Hz, 1H), 6.78 (d, J=8.2 Hz, 1H), 6.69 (d, J=15.5 Hz, 1H), 6.61 (dd, J=3.4, 1.8 Hz, 1H), 5.55 (s, 2H), 2.18 (s, 3H).

Example S50. Synthesis of (E)-N-(1-(2,4-bis(trifluoromethyl)benzyl)-3-methyl-1H-pyrazol-4-yl)-3-(furan-2-yl)acrylamide (Compound 96)

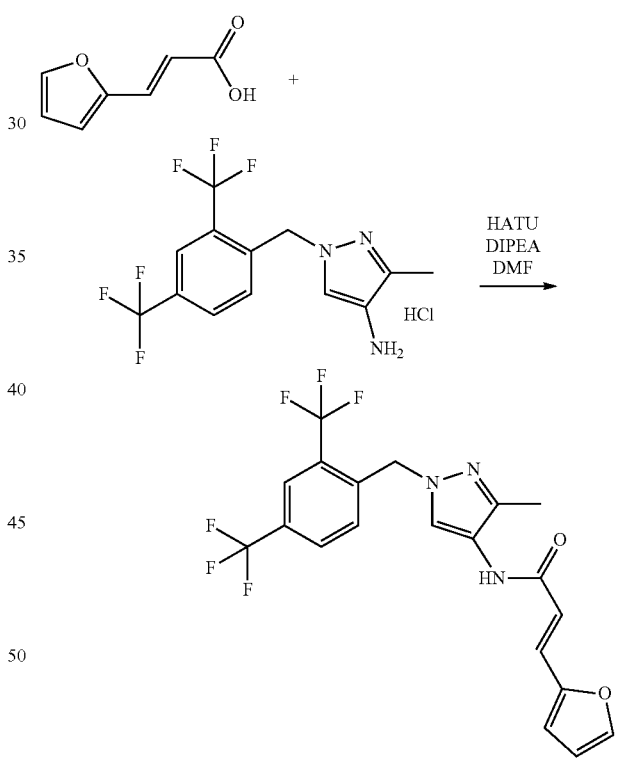

Step 1: Synthesis of (E)-N-(1-(2,4-bis(trifluoromethyl) benzyl)-3-methyl-1H-pyrazol-4-yl)-3-(furan-2-yl)acrylamide. To a solution of (E)-3-(furan-2-yl)acrylic acid (100 mg, 0.724 mmol, 1 equiv) in DMF (1 mL), were added HATU (276.08 mg, 0.724 mmol, 1 equiv). After stirring at RT for 15 minutes, the mixture was treated drop wise with DIPEA (280.4 mg, 21.73 mmol, 3 equiv). After stirring at RT for 15 minutes, the mixture was treated drop wise with a solution of the 1-(2,4-bis(trifluoromethyl)benzyl)-3-methyl-1H-pyrazol-4-amine hydrochloride (250 mg, 0.724 mmol, 1 equiv) in DMF (1 mL). The reaction mixture was kept under stirring for 24 hrs. The reaction mixture was diluted water (50 mL). The resulting precipitate was filtered off and the crude material obtained was purified by flash chromatography using EtOAc hexane as eluent to obtain title compound as free base (21 mg). LCMS: 444 [M+H]$^+$. $^1$H NMR (400 MHz, DMSO-d$_6$) δ 9.75 (s, 1H), 8.28 (s, 1H), 8.06 (d, J=4.2 Hz, 2H), 7.81 (d, J=1.9 Hz, 1H), 7.33 (d, J=15.5 Hz, 1H), 7.05 (d, J=8.5 Hz, 1H), 6.82 (d, J=3.4 Hz, 1H), 6.76 (d, J=15.5 Hz, 1H), 6.61 (dd, J=3.4, 1.8 Hz, 1H), 5.54 (s, 2H), 2.19 (s, 3H).

Example S51. Synthesis of (R)—N-(1-(1-(2,4-bis(trifluoromethyl)phenyl)ethyl)-5-methyl-1H-pyrazol-4-yl)-5-(pyridin-2-yl)isoxazole-3-carboxamide (Compound 97), (S)—N-(1-(1-(2,4-bis(trifluoromethyl)phenyl)ethyl)-5-methyl-1H-pyrazol-4-yl)-5-(pyridin-2-yl)isoxazole-3-carboxamide (Compound 98), (R)—N-(1-(1-(2,4-1bis(trifluoromethyl)phenyl)ethyl)-3-methyl-1H-pyrazol-4-yl)-5-(pyridin-2-yl)isoxazole-3-carboxamide (Compound 99), z (S)—N-(1-(1-(2,4-bis(trifluoromethyl)phenyl)ethyl)-3-methyl-1H-pyrazol-4-yl)-5-(pyridin-2-yl)isoxazole-3-carboxamide (Compound 100)

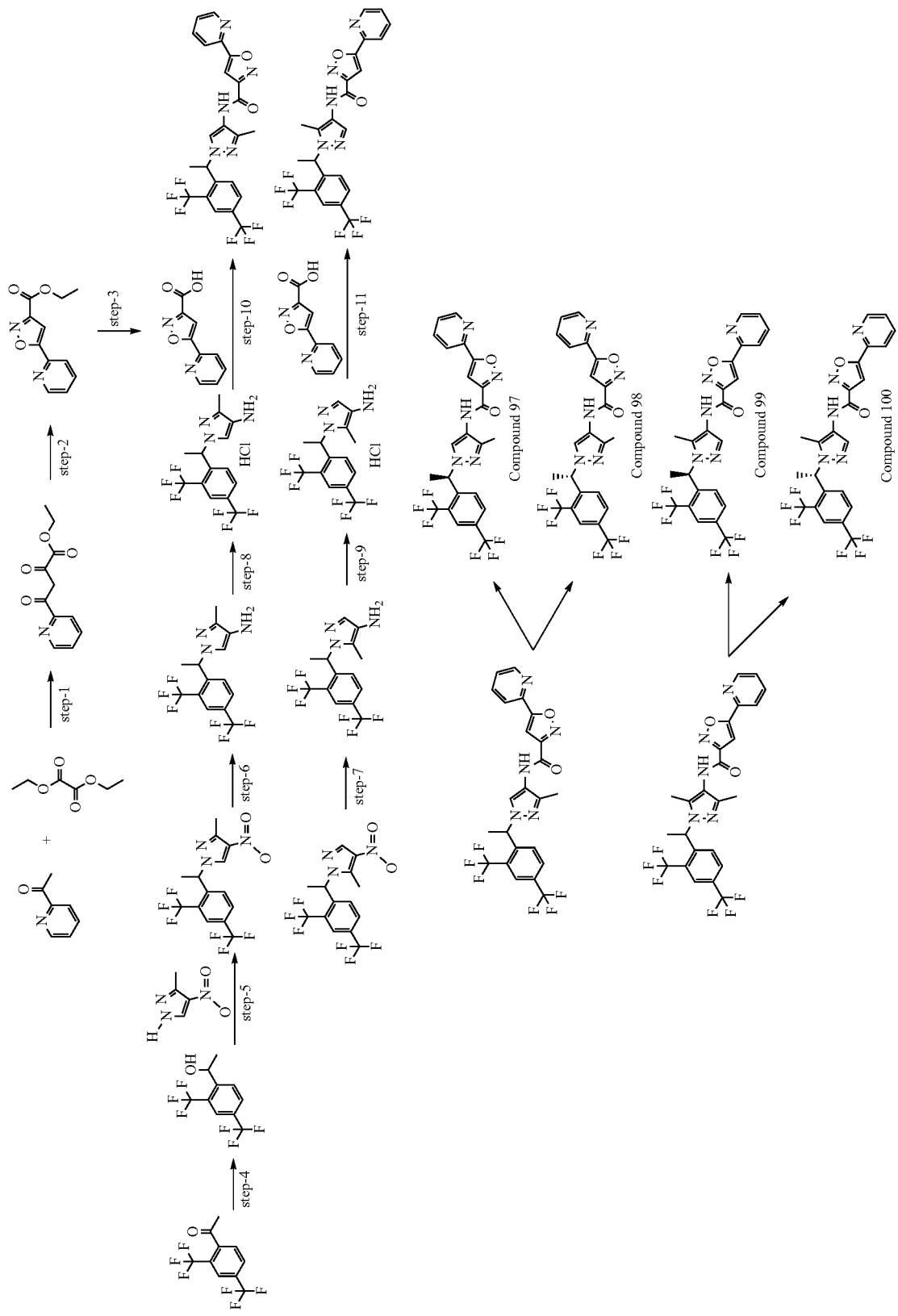

Step 1: Synthesis of ethyl 2,4-dioxo-4-(pyridin-2-yl)butanoate. To a solution of 1-(pyridin-2-yl)ethan-1-one (5.0 g, 0.04 mol, 1 eq) in THF was added portion wise NaH (60%, 3.3 g, 0.08 mol, 2.0 eq) at 0° C. The resultant reaction mixture was stirred for another 30 minutes at room temperature followed by drop wise addition of diethyl oxalate (11.2 ml, 0.08 mol, 2.0 eq) at 0° C. and reaction mixture was stir for another 18 hrs at room temperature. Product formation was confirmed by TLC and LCMS. The reaction mixture was neutralized with 1N HCl and extracted with EtOAc (3×100 mL). Combined organic extracts were washed with water (2×100 mL), dried over anhydrous $Na_2SO_4$ and concentrated under reduced pressure to obtain crude which was purified by flash chromatography (0-20% Ethyl acetate in hexane) to obtain ethyl 2,4-dioxo-4-(pyridin-2-yl)butanoate (3 g, yellow solid). LCMS: 221 $[M+H]^+$.

Step 2: Synthesis of ethyl 5-(pyridin-2-yl)isoxazole-3-carboxylate. A suspension of ethyl 2,4-dioxo-4-(pyridin-2-yl)butanoate (1.6 g, 7.61 mmol, 1.0 eq) and hydroxylamine hydrochloride (0.528 g, 7.61 mmol, 1.0 eq) in EtOH was stirred at 85° C. for 48 hrs. Product formation was confirmed by TLC and LCMS. The resulting mixture was concentrated under reduced pressure, the residue was dissolved in DCM and distilled water. The organic phase was separated, dried over anhydrous $Na_2SO_4$, filtered through silica gel pad, and then concentrated under reduced pressure to give residue which was purified by flash chromatography (0-20% Ethyl acetate in hexane) to obtain ethyl 5-(pyridin-2-yl)isoxazole-3-carboxylate. LCMS: 218 $[M+H]^+$.

Step 3: Synthesis of 5-(pyridin-2-yl)isoxazole-3-carboxylic acid. To a solution of ethyl 5-(pyridin-2-yl)isoxazole-3-carboxylate (0.5 g, 2.41 mmol) in THF (30 mL) and methanol (6 mL) was slowly added in lithium hydroxide aqueous solution (10 mL). The resulting mixture was stirred for 16 hrs. THF was concentrated under reduced pressure. The resulting residue was acidified with 1N HCl and extracted with ethyl acetate (3×100 mL). Combined organic extracts were washed with distilled water, dried over anhydrous $Na_2SO_4$ and concentrated under reduced pressure to obtain 5-(pyridin-2-yl)isoxazole-3-carboxylic acid (225 mg, as white solid). LCMS: 190 $[M+H]^+$.

Step 4: Synthesis of 1-[2,4-bis(trifluoromethyl)phenyl]ethanol. To a stirred solution of 1-[2,4-bis(trifluoromethyl)phenyl]ethanone (4 g, 0.008 mol, 1.0 equiv) in Methanol (5 mL) was added $NaBH_4$ (0.572 g, 0.008 mol, 1 equiv) portion wise at 0° C. and stirred for 10 minutes. The reaction mixture was allowed to stir for 1 hour at room temperature. Product formation was confirmed by TLC and LCMS. After completion of reaction, reaction mixture was quenched with water and extracted with ethyl acetate (3×50 mL). Combined organic extracts were washed with water (2×50 mL), dried over anhydrous $Na_2SO_4$ and concentrated under reduced pressure to obtain 1[2,4-bis (trifluoromethyl) phenyl]ethanol as colourless liquid (4 g). $^1H$ NMR (400 MHz, DMSO-$d_6$): δ 8.04-8.15 (m, 2H), 7.93 (s, 1H), 5.70 (d, J=3.95 Hz, 1H), 5.09 (br. s., 1H), 1.34 (d, J=6.14 Hz, 3H).

Step 5: Synthesis of 1-(1-(2,4-bis(trifluoromethyl)phenyl)ethyl)-5-methyl-4-nitro-1H-pyrazole and 1-(1-(2,4-bis(trifluoromethyl)phenyl)ethyl)-3-methyl-4-nitro-1H-pyrazole. To a stirred solution of $PPh_3$ (4.28 g, 0.016 mole, 1.1 equiv) and DIAD (3.33 gm, 0.016 mole, 1.1 equiv) in THF (2 mL), was added 4-nitro-1H-pyrazole (1.96 g, 0.004 mmol, 1.0 equiv) The reaction mixture was added 1-[2, 4-bis (trifluoromethyl) phenyl] ethanol (4 g, 0.004 mmol, 1.0 equiv). The reaction mixture was stirred at room temperature for 1 hrs. Product formation was confirmed with TLC and LCMS. After completion of reaction mixture were diluted with EtOAc (50 mL) and washed with water (3×50 mL). Organic layer dried over anhydrous $Na_2SO_4$ and concentrated under reduced pressure to obtain crude which was further purified by flash column chromatography to obtain pure product 1-(1-(2,4-bis(trifluoromethyl)phenyl)ethyl)-5-methyl-4-nitro-1H-pyrazole (0.5 gm) and 1-(1-(2,4-bis(trifluoromethyl)phenyl)ethyl)-3-methyl-4-nitro-1H-pyrazole (1.5 gm). LCMS: 368 $[M+H]^+$.

Step 6: Synthesis of 1-(1-(2,4-bis(trifluoromethyl)phenyl)ethyl)-3-methyl-1H-pyrazol-4-amine. To a stirred solution of 1-(1-(2,4-bis(trifluoromethyl)phenyl)ethyl)-3-methyl-4-nitro-1H-pyrazole (1 g, 1 equiv) in Methanol (10 mL) under nitrogen Palladium on Carbon[Pd/C] (10% w/w) was added. Purge the reaction mixture with $H_2$ gas for 6 h. Product formation was confirmed by LCMS. After the completion of reaction, reaction mixture was filtered through Celite bed and Filtrate was concentrate under reduced pressure to obtain 1-(1-(2,4-bis(trifluoromethyl)phenyl)ethyl)-3-methyl-1H-pyrazol-4-amine (0.9 gm). LCMS: 338 $[M+H]^+$.

Step 7: Synthesis of 1-(1-(2,4-bis(trifluoromethyl)phenyl)ethyl)-5-methyl-1H-pyrazol-4-amine. To a stirred solution of 1-(1-(2,4-bis(trifluoromethyl)phenyl)ethyl)-5-methyl-4-nitro-1H-pyrazole (400 mg, 1 equiv) in methanol (10 mL) under nitrogen Palladium on Carbon [Pd/C] (10% w/w, 40 mg) was added. The reaction mixture was purged with hydrogen for 6 hrs. Product formation was confirmed by LCMS. After the completion of reaction, reaction mixture was filtered through celite bed and filtrate was concentrated under reduced pressure to obtain 1-(1-(2,4-bis(trifluoromethyl)phenyl)ethyl)-5-methyl-1H-pyrazol-4-amine (0.3 gm). LCMS: 338 $[M+H]^+$.

Step 8: Synthesis of 1-(1-(2,4-bis(trifluoromethyl)phenyl)ethyl)-3-methyl-1H-pyrazol-4-amine hydrochloride. To 1-(1-(2,4-bis(trifluoromethyl)phenyl)ethyl)-3-methyl-1H-pyrazol-4-amine (800 mg) in ethanol was added 1.25 M HCl in ethanol (15 mL) at 0° C. and kept under stirring for half hour at RT. Resulting suspension was filtered, dried under vacuum residue was triturated with ether to obtain title compound 1-(1-(2,4-bis(trifluoromethyl)phenyl)ethyl)-3-methyl-1H-pyrazol-4-amine hydrochloride (0.8 g). LCMS: 338 $[M+H]^+$.

Step 9: Synthesis of 1-(1-(2,4-bis(trifluoromethyl)phenyl)ethyl)-5-methyl-1H-pyrazol-4-amine hydrochloride. To 1-(1-(2,4-bis(trifluoromethyl)phenyl)ethyl)-5-methyl-1H-pyrazol-4-amine (350 mg) in ethanol was added 1.25 M HCl in ethanol (15 mL) at 0° C. and kept under stirring for half hour at RT. Resulting suspension was filtered, dried under vacuum residue was triturated with ether to obtain title compound 1-(1-(2,4-bis(trifluoromethyl)phenyl)ethyl)-5-methyl-1H-pyrazol-4-amine hydrochloride (0.3 gm). LCMS: 338 $[M+H]^+$.

Step 10: Synthesis of (R)—N-(1-(1-(2,4-bis(trifluoromethyl)phenyl)ethyl)-3-methyl-1H-pyrazol-4-yl)-5-(pyridin-2-yl)isoxazole-3-carboxamide (Compound 99) and (S)—N-(1-(1-(2,4-bis(trifluoromethyl)phenyl)ethyl)-3-methyl-1H-pyrazol-4-yl)-5-(pyridin-2-yl)isoxazole-3-carboxamide (Compound 100). To a solution of 5-(pyridin-2-yl)isoxazole-3-carboxylic acid (100 mg, 0.526 mmol, 1 equiv) in DMF (1 mL), was added HATU (200 mg, 0.526 mmol, 1 equiv). After stirring at RT for 15 minutes, the mixture was treated drop wise with DIPEA (207.6 mg, 1.57 mmol, 1 equiv). After stirring at RT for 15 minutes, the mixture was treated drop wise with a solution of the 1-(1-(2,4-bis(trifluoromethyl)phenyl)ethyl)-3-methyl-1H-pyrazol-4-amine (196.3 mg, 0.526 mmol, 1 equiv) in DMF (1 mL). The reaction mixture was kept under stirring for 24 h. The reaction mixture was diluted water (50 mL). The resulting precipitate was filtered off and the solid was triturated to obtain title compound. The enantiomers (elution time: 4.07 min & 4.7 min), were separated by chiral SFC (Daicel Chiralpak®-IC, 250×20 mm, 5 μm). Isocratic program with analytical grade liquid carbon dioxide and HPLC grade Isopropanol, Total flow: 56 g/min, Co-Solvent Percentage: 25% to obtained (R)—N-(1-(1-(2,4-bis(trifluoromethyl)phenyl)ethyl)-3-methyl-1H-pyrazol-4-yl)-5-(pyridin-2-yl)isoxazole-3-carboxamide (9 mg) and (S)—N-(1-(1-(2,4-bis(trifluoromethyl)phenyl)ethyl)-3-methyl-1H-pyrazol-4-yl)-5-(pyridin-2-yl)isoxazole-3-carboxamide (10 mg). LCMS: 511 [M+H]$^+$.

Step 11: Synthesis of (R)—N-(1-(1-(2,4-bis(trifluoromethyl)phenyl)ethyl)-5-methyl-1H-pyrazol-4-yl)-5-(pyridin-2-yl)isoxazole-3-carboxamide (Compound 97) and (S)—N-(1-(1-(2,4-bis(trifluoromethyl)phenyl)ethyl)-5-methyl-1H-pyrazol-4-yl)-5-(pyridin-2-yl)isoxazole-3-carboxamide (Compound 98). To a solution of 5-(pyridin-2-yl)isoxazole-3-carboxylic acid (100 mg, 0.526 mmol, 1 equiv) in DMF (1 mL), were added HATU (200 mg, 0.526 mmol, 1 equiv). After stirring at RT for 15 minutes, the mixture was treated drop wise with DIPEA (207.6 mg, 1.57 mmol, 1 equiv). After stirring at RT for 15 minutes, the mixture was treated drop wise with a solution of the 1-(1-(2,4-bis(trifluoromethyl)phenyl)ethyl)-5-methyl-1H-pyrazol-4-amine (196.3 mg, 0.526 mmol, 1 equiv) in DMF (1 mL). The reaction mixture was kept under stirring for 24 h. The reaction mixture was diluted water (50 mL). The resulting precipitate was filtered off and the solid was triturated with hexane to obtain title compound. The enantiomers (elution time: 4.57 min & 5.27 min), were separated by chiral SFC (Daicel Chiralpak®-IC, 250×20 mm, 5 μm. Isocratic program with analytical grade liquid carbon dioxide and HPLC grade Isopropanol, Total flow: 56 g/min, Co-Solvent Percentage: 17% to obtained (R)—N-(1-(1-(2,4-bis(trifluoromethyl)phenyl)ethyl)-5-methyl-1H-pyrazol-4-yl)-5-(pyridin-2-yl)isoxazole-3-carboxamide (10 mg) and (S)—N-(1-(1-(2,4-bis(trifluoromethyl)phenyl)ethyl)-5-methyl-1H-pyrazol-4-yl)-5-(pyridin-2-yl)isoxazole-3-carboxamide (9 mg). LCMS: 511 [M+H]$^+$. $^1$H NMR (Compound 99) (400 MHz, DMSO-d$_6$) δ 10.29 (s, 1H), 8.75 (d, J=4.8 Hz, 1H), 8.06 (dq, J=15.0, 8.3 Hz, 4H), 7.79 (s, 1H), 7.56 (d, J=7.7 Hz, 2H), 7.47 (s, 1H), 5.93 (q, J=6.9 Hz, 1H), 2.06 (s, 3H), 1.85 (d, J=6.8 Hz, 3H). 1H NMR (Compound 100) (400 MHz, DMSO-d$_6$) δ 10.29 (s, 1H), 8.75 (d, J=4.8 Hz, 1H), 8.13-7.98 (m, 4H), 7.79 (s, 1H), 7.56 (t, J=5.9 Hz, 2H), 7.47 (s, 1H), 5.93 (q, J=7.0 Hz, 1H), 2.06 (s, 3H), 1.85 (d, J=6.8 Hz, 3H). $^1$H NMR (Compound 97) (400 MHz, DMSO-d$_6$) δ 10.34 (s, 1H), 8.76 (d, J=5.0 Hz, 1H), 8.16 (s, 1H), 8.14-7.99 (m, 4H), 7.74 (d, J=8.2 Hz, 1H), 7.56 (t, J=6.2 Hz, 1H), 7.48 (s, 1H), 5.84 (q, J=7.1 Hz, 1H), 2.18 (s, 3H), 1.84 (d, J=6.9 Hz, 3H). 1H NMR (Compound 98) (400 MHz, DMSO-d$_6$) δ 10.34 (s, 1H), 8.76 (d, J=4.9 Hz, 1H), 8.15 (s, 1H), 8.14-7.99 (m, 4H), 7.74 (d, J=8.3 Hz, 1H), 7.56 (t, J=6.4 Hz, 1H), 7.48 (s, 1H), 5.84 (q, J=6.9 Hz, 1H), 2.18 (s, 3H), 1.84 (d, J=6.9 Hz, 3H), 1.24 (d, J=6.7 Hz, 1H).

Example S52. Synthesis of (R)—N-(1-(1(2,4-bis(trifluoromethyl)phenyl)ethyl)-1H-pyrazol-4-yl)-5-(pyrimidin-2-yl)isoxazole-3-carboxamide and (S)—N-(1(1-(2,4-bis(trifluoromethyl)phenyl)ethyl)-1H-pyrazol-4-yl)-5-(pyrimidin-2-yl)isoxazole-3-carboxamide (Compounds 101 & 102)

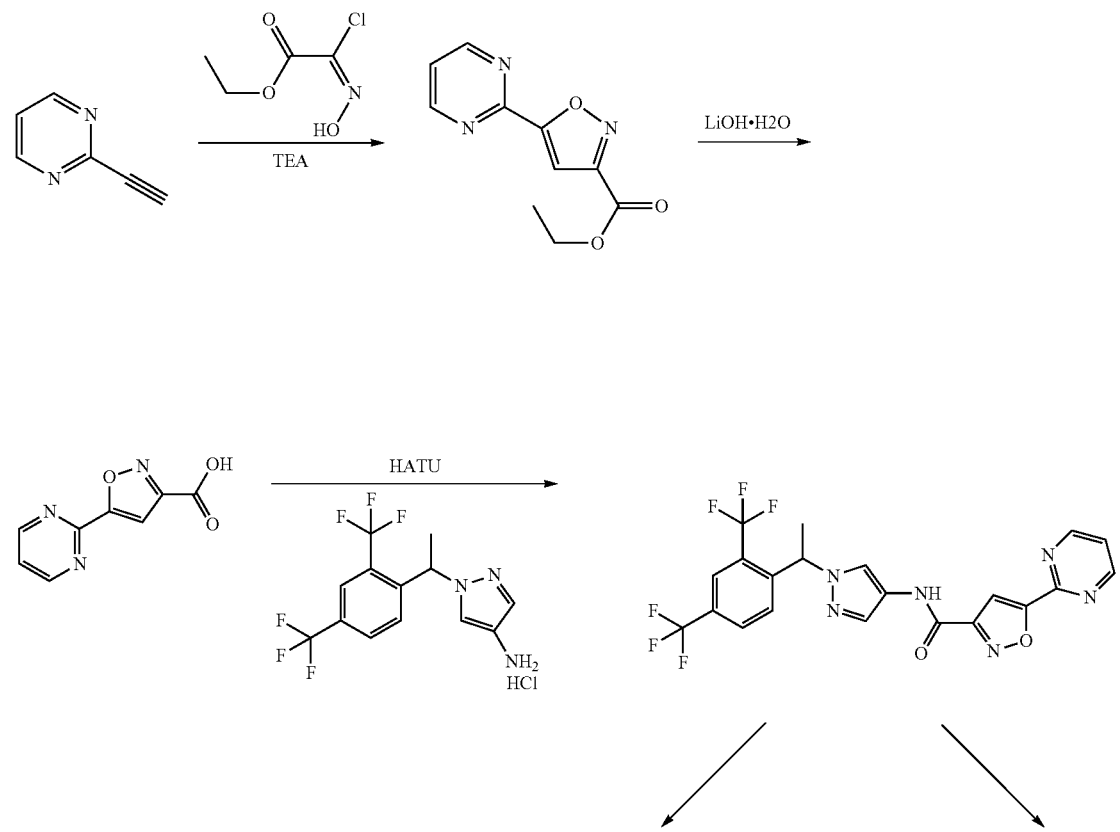

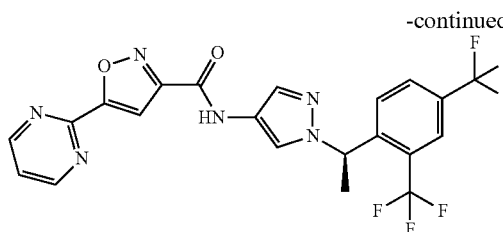

Compound 101

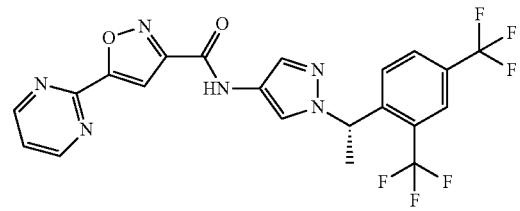

Compound 102

Step 1: Synthesis of ethyl 5-(pyrimidin-2-yl) isoxazole-3-carboxylate. To a mixture of (Z)-ethyl 2-chloro-2-(hydroxyimino) acetate (200 mg, 1.21 m mole, 1 eq) and 2-ethynylpyrimidine (252.1 mg, 1.21 mmol, 1 equiv) in ether (80 mL) at room temperature was added a solution of TEA (0.337 mL, 2.42 mmol, 2.0 equiv) in ether (20 mL) drop wise over 60 minutes. The reaction mixture was stirred for 2 h at room temperature. The reaction mixture was filtered, and the filtrate was concentrated to yellow oil which was purified by flash silica gel chromatography using a mixture of ethyl acetate in hexane to afford ethyl 5-(pyrimidin-2-yl) isoxazole-3-carboxylate as a white solid (0.07 g). LCMS: 220 [M+H]$^+$.

Step 2: Synthesis of 5-(pyrimidin-2-yl) isoxazole-3-carboxylic acid. To a solution of ethyl 5-(pyrimidin-2-yl) isoxazole-3-carboxylate (60 mg, 0.273 mmol, 1 eq) in THF (2 mL) and water (2 mL) was added lithium hydroxide (10.95 mg, 0.0.328 mmol, 1.2 eq). The resulting mixture was stirred for 16 hrs. Reaction mixture was concentrated under reduced pressure to obtain crude which was acidified with 1N HCl and obtained suspension was lypolised. Obtained crude was triturated with ether to obtain title product as 5-(pyrimidin-2-yl) isoxazole-3-carboxylic acid (52.2 mg). LCMS: 191 [M+H]$^+$.

Step 3: Synthesis of (R)—N-(1-(1-(2,4-bis(trifluoromethyl)phenyl)ethyl)-1H-pyrazol-4-yl)-5-(pyrimidin-2-yl) isoxazole-3-carboxamide and (S)—N-(1-(1-(2,4-bis(trifluoromethyl)phenyl)ethyl)-1H-pyrazol-4-yl)-5-(pyrimidin-2-yl)isoxazole-3-carboxamide. To a solution of 5-(pyrimidin-2-yl)isoxazole-3-carboxylic acid (40 mg, 0.209 mmol, 1 equiv) in DMF (2 mL), were added HATU (79.7 mg, 0.209 mmol, 1 equiv). The mixture was treated drop wise with DIPEA (81.04 mg, 0.628 mmol, 3 equiv). After stirring at RT for 15 minutes, the mixture was treated drop wise with a solution of the 1-(1-(2,4-bis(trifluoromethyl)phenyl)ethyl)-1H-pyrazol-4-amine hydrochloride (75.18 mg, 0.0.209 mmol, 1 equiv) in DMF (1 mL). The reaction mixture was kept under stirring for 24 hrs. The reaction mixture was diluted water (50 mL). The resulting precipitate was filtered off and the solid was triturated with DCM: hexane (2:8) to obtained N-(1-(1-(2,4-bis(trifluoromethyl)phenyl)ethyl)-1H-pyrazol-4-yl)-5-(pyrimidin-2-yl)isoxazole-3-carboxamide. The enantiomers (elution time: 8.8 min & 15.15 min), were separated by chiral HPLC (Daicel Chiralpak®-IC, 250×20 mm, 5 μm). Isocratic program with HPLC grade n-Hexane and HPLC grade Ethanol, Total flow: 18 ml/min, Ethanol Percentage: 40% to obtained (R)—N-(1-(1-(2,4-bis(trifluoromethyl)phenyl)ethyl)-1H-pyrazol-4-yl)-5-(pyrimidin-2-yl)isoxazole-3-carboxamide (9 mg) and (S)—N-(1-(1-(2,4-bis(trifluoromethyl)phenyl)ethyl)-1H-pyrazol-4-yl)-5-(pyrimidin-2-yl)isoxazole-3-carboxamide (8 mg). LCMS: 482 [M+H]$^+$. (Compound 101) $^1$H NMR (400 MHz, DMSO-d$_6$) δ 11.15 (s, 1H), 9.03 (d, J=5.26 Hz, 2H), 8.21 (s, 1H), 7.99-8.13 (m, 3H), 7.69-7.79 (m, 3H), 7.66 (t, J=4.82 Hz, 1H), 7.54 (s, 1H), 5.94 (d, J=7.89 Hz, 1H), 1.87 (d, J=6.58 Hz, 3H). (Compound 102) $^1$H NMR (400 MHz, DMSO-d$_6$) δ 11.15 (s, 1H), 9.03 (d, J=5.26 Hz, 2H), 8.21 (s, 1H), 7.99-8.13 (m, 3H), 7.69-7.79 (m, 3H), 7.66 (t, J=4.82 Hz, 1H), 7.54 (s, 1H), 5.94 (d, J=7.89 Hz, 1H), 1.87 (d, J=6.58 Hz, 3H).

Example S53. Synthesis of N-(1-(2,4-bis(trifluoromethyl)benzyl)-1H-pyrazol-4-yl)-N-methy-5-(pyridin-2-yl)isoxazole-3-carboxamide (Compound 103)

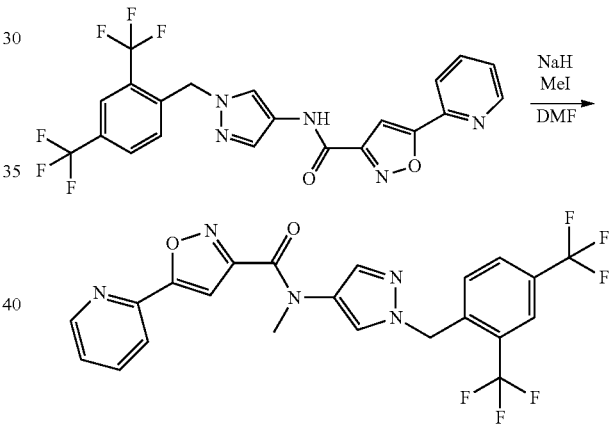

Step 1: Synthesis of N-(1-(2,4-bis(trifluoromethyl)benzyl)-1H-pyrazol-4-yl)-N-methyl-5-(pyridin-2-yl)isoxazole-3-carboxamide. To a solution of 1 N-(1-(2,4-bis(trifluoromethyl)benzyl)-1H-pyrazol-4-yl)-5-(pyridin-2-yl)isoxazole-3-carboxamide (50 mg, 0.103 mmoles, 1 eq) in DMF (2 mL) at 0° C. was added NaH (4.15 mg, 0.103 mmol, 1 eq) was added. After stirring the reaction for 30 min at same temperature was added methyl iodide (14.75 mg, 0.103 mmoles, 1 eq). The resulting reaction mixture was stirring for 2 hour at 0° C. The reaction mixture quenched with water (10 mL) and extracted with EtOAc (3×20 mL). The organic layers were collected and were washed with water (2×10 mL), dried over anhydrous Na$_2$SO$_4$ and concentrated under reduced pressure to obtain crude which was purified by reverse phase purification to obtain title compound as free base. LCMS: 496 [M+H]$^+$. $^1$H NMR (400 MHz, DMSO-d$_6$) δ 8.69 (d, J=4.8 Hz, 1H), 8.11-7.92 (m, 6H), 7.66 (s, 1H), 7.56 (dt, J=11.9, 5.5 Hz, 1H), 7.50-7.39 (m, 1H), 7.11 (d, J=16.1 Hz, 1H), 6.52 (d, J=8.2 Hz, 1H), 5.69 (s, 1H), 5.53 (s, 2H), 3.47 (s, 1H), 3.36 (s, 2H).

Example S54. Synthesis of (R)—N-(1-(1-(2,4-bis(trifluoromethyl)phenyl)ethyl)-1H-pyrazol-4-yl)-2-(pyridin-2-yl)thiazole-5-carboxamide and (S)—N-(1-(1-(2,4-bis(trifluoromethyl)phenyl)ethyl)-1H-pyrazol-4-yl)-2-(pyridin-2-yl)thiazole-5-carboxamide (Compounds 104 & 105)

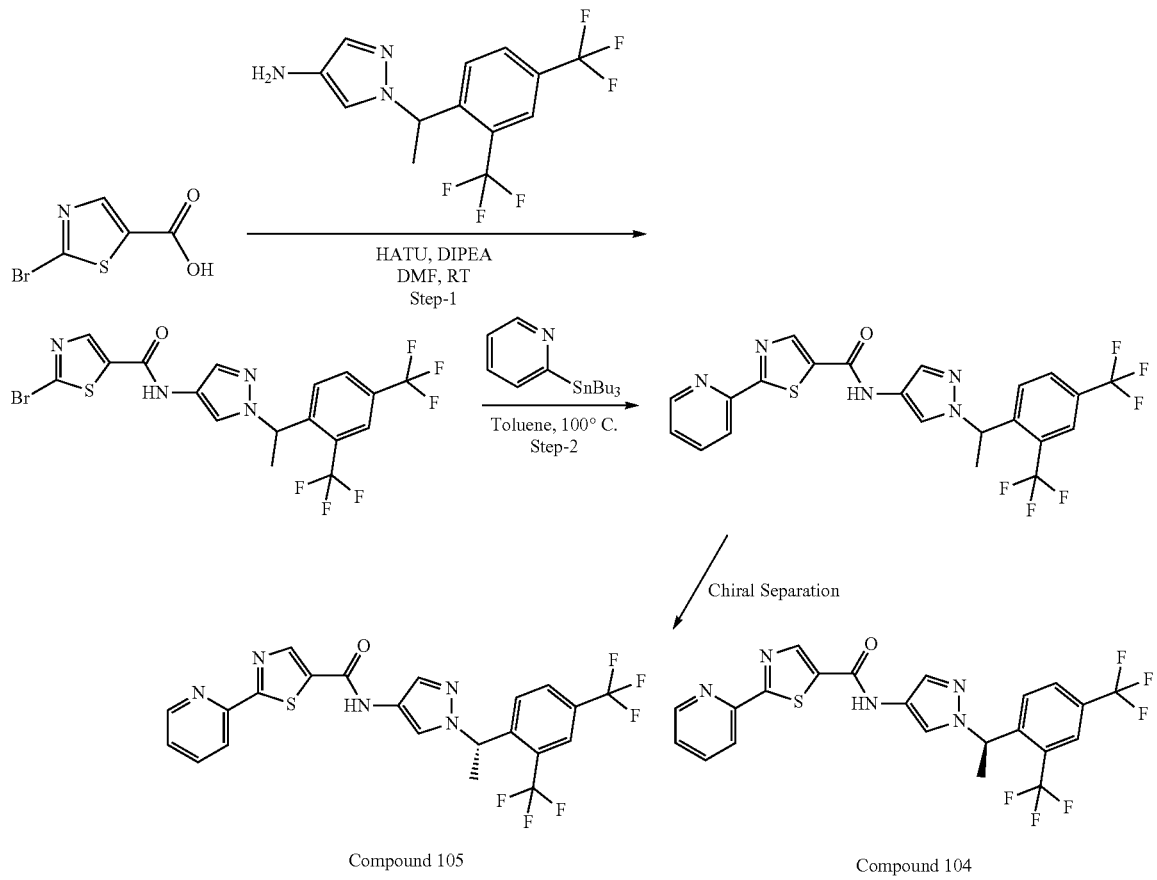

Compound 105    Compound 104

Step 1: Synthesis of N-(1-(1-(2,4-bis(trifluoromethyl)phenyl)ethyl)-1H-pyrazol-4-yl)-2-bromothiazole-5-carboxamide. To a solution of 2-bromothiazole-5-carboxylic acid (800 mg, 3.84 mmol, 1 equiv) in DMF (5 mL) was added HATU (1376 mg, 4.23 mmol, 1.1 equiv). The mixture was allow to stir for 30 mins followed by the addition of DIPEA (1587 mg, 12.3 mmol, 3.2 equiv) and a solution of the 1-{1[2,4bis(trifluoromethyl)phenyl]ethyl}-1H-pyrazol-4-amineHydrochloride (1376 mg, 3.84 mmol, 1 equiv) in DMF (1 mL). The reaction mixture was kept under stirring for 24 hrs at room temperature. The product formation was confirmed with TLC and LCMS. The reaction mixture was diluted EtOAc (50 mL) and washed with water (2×50 mL). The organic layers were collected and dried over $Na_2SO_4$ and concentrated under reduced pressure to obtain crude which was further purified by flash column chromatography (EtOAc/hexane) to obtain pure product N-(1-(1-(2,4-bis(trifluoromethyl)phenyl)ethyl)-1H-pyrazol-4-yl)-2-bromothiazole-5-carboxamide as off white solid (800 mg). LCMS: 514 [M+H]+.

Step 2: N-(1-(1-(2,4-bis(trifluoromethyl)phenyl)ethyl)-1H-pyrazol-4-yl)-2-(pyridin-2-yl)thiazole-5-carboxamide. To a solution of N-(1-(1-(2,4-bis(trifluoromethyl)phenyl) ethyl)-1H-pyrazol-4-yl)-2-bromothiazole-5-carboxamide (400 mg, 0.77 mmol, 1 equiv) in dry toluene (5 mL) was added the 2-(trimethylstannyl)pyridine (287 mg, 0.77 mmol, 1 equiv), and the mixture was degassed for 10 minutes. To this mixture was added $Pd(PPh_3)_4$ (90 mg, 0.077 mmol, 1 equiv), and the mixture was again degassed for 5 minutes. The reaction mixture was stirred at 80° C. for overnight, after which time TLC indicated complete consumption of the starting material. The mixture was quenched with $H_2O$, extracted with EtOAc (2×100 mL), dried over anhydrous $Na_2SO_4$, and concentrated in vacuo to provide the crude product which was further purified by flash column chromatography (EtOAc/hexane) to obtain title compound N-(1-(1-(2,4-bis(trifluoromethyl)phenyl)ethyl)-1H-pyrazol-4-yl)-2-(pyridin-2-yl)thiazole-5-carboxamide as off white solid (150 mg). LCMS: 512 [M+H]+. 1 H NMR (400 MHz, DMSO-$d_6$) δ 10.80 (s, 1H), 8.68 (d, J=4.8 Hz, 1H), 8.59 (s, 1H), 8.18 (d, J=9.0 Hz, 2H), 8.13-7.97 (m, 3H), 7.73 (d, J=8.3 Hz, 1H), 7.68 (s, 1H), 7.56 (dd, J=7.5, 4.8 Hz, 1H), 5.93 (q, J=6.9 Hz, 1H), 1.88 (d, J=6.9 Hz, 3H).

Step 3: Synthesis of (R) and (S)—N-(1-(1-(2,4-bis(trifluoromethyl)phenyl)ethyl)-1H-pyrazol-4-yl)-2-(pyridin-2-yl)thiazole-5-carboxamide. The enantiomers of N-(1-(1-(2,4-bis(trifluoromethyl)phenyl)ethyl)-1H-pyrazol-4-yl)-2-(pyridin-2-yl)thiazole-5-carboxamide (150 mg, elution time: 5.5 min & 7.47 min), were separated by chiral SFC (Daicel Chiralcel®-ODH, 250×20 mm, 5 µm). Isocratic program with analytical grade liquid carbon dioxide and HPLC grade Isopropanol, Total flow: 56 g/min, Co-Solvent Percentage: 22% to obtain (R)—N-(1-(1-(2,4-bis(trifluoromethyl)phenyl)ethyl)-1H-pyrazol-4-yl)-2-(pyridin-2-yl)thiazole-5-carboxamide (45 mg) and (S)—N-(1-(1-(2,4-bis(trifluoromethyl)phenyl)ethyl)-1H-pyrazol-4-yl)-2-(pyridin-2-yl)thiazole-5-carboxamide (43 mg). (Compound 104) LCMS: 512 [M+H]$^+$. $^1$H NMR (400 MHz, DMSO-d$_6$) δ 10.80 (s, 1H), 8.68 (d, J=4.8 Hz, 1H), 8.59 (s, 1H), 8.18 (d, J=9.0 Hz, 2H), 8.13-7.97 (m, 3H), 7.73 (d, J=8.3 Hz, 1H), 7.68 (s, 1H), 7.56 (dd, J=7.5, 4.8 Hz, 1H), 5.93 (q, J=6.9 Hz, 1H), 1.88 (d, J=6.9 Hz, 3H). (Compound 105) LCMS: 512 [M+H]$^+$. $^1$H NMR (400 MHz, DMSO-d$_6$) δ 10.80 (s, 1H), 8.68 (d, J=4.8 Hz, 1H), 8.59 (s, 1H), 8.18 (d, J=9.0 Hz, 2H), 8.13-7.97 (m, 3H), 7.73 (d, J=8.3 Hz, 1H), 7.68 (s, 1H), 7.56 (dd, J=7.5, 4.8 Hz, 1H), 5.93 (q, J=6.9 Hz, 1H), 1.88 (d, J=6.9 Hz, 3H).

Example S55. Synthesis of (R)—N-(1-(1-(2,4-bis(trifluoromethyl)phenyl)ethyl)-1H-pyrazol-4-yl)-4-methyl-2-(pyridin-2-yl)thiazole-5-carboxamide and (S)—N-(1-(1-(2,4-bis(trifluoromethyl)phenyl)ethyl)-1H-pyrazol-4-yl)-4-methyl-2-(pyridin-2-yl)thiazole-5-carboxamide (Compounds 106 & 107)

1H-pyrazol-4-amine hydrochloride (483 mg, 1.35 mmol, 1 equiv) in DMF (1 mL) was added. The reaction mixture was kept under stirring for 24 hrs at room temperature.) Product formation was confirmed with TLC and LCMS and reaction mixture was diluted EtOAc (50 mL) and washed with water (2×50 mL). The organic layer dried over anhydrous Na$_2$SO$_4$ and concentrated under reduced pressure to obtain crude which was further purified by flash column chromatography (EtOAc/Hexane) to obtain pure product N-(1-(1-(2,4-bis(trifluoromethyl)phenyl)ethyl)-1H-pyrazol-4-yl)-2-bromo-4-methylthiazole-5-carboxamide as off white solid (200 mg). LCMS: 526 [M+H]$^+$.

Step 2: Synthesis N-(1-(1-(2,4-bis(trifluoromethyl)phenyl)ethyl)-1H-pyrazol-4-yl)-4-methyl-2-(pyridin-2-yl)thiazole-5-carboxamide. To a solution of N-(1-(1-(2,4-bis(trifluoromethyl)phenyl)ethyl)-1H-pyrazol-4-yl)-2-bromo-4-methylthiazole-5-carboxamide (100 mg, 0.18 mmol, 1 equiv) in dry toluene (5 mL) was added the 2-(tributylstannyl)pyridine (69 mg, 0.18 mmol, 1 equiv), and the mixture was degassed for 10 min. To this mixture was added

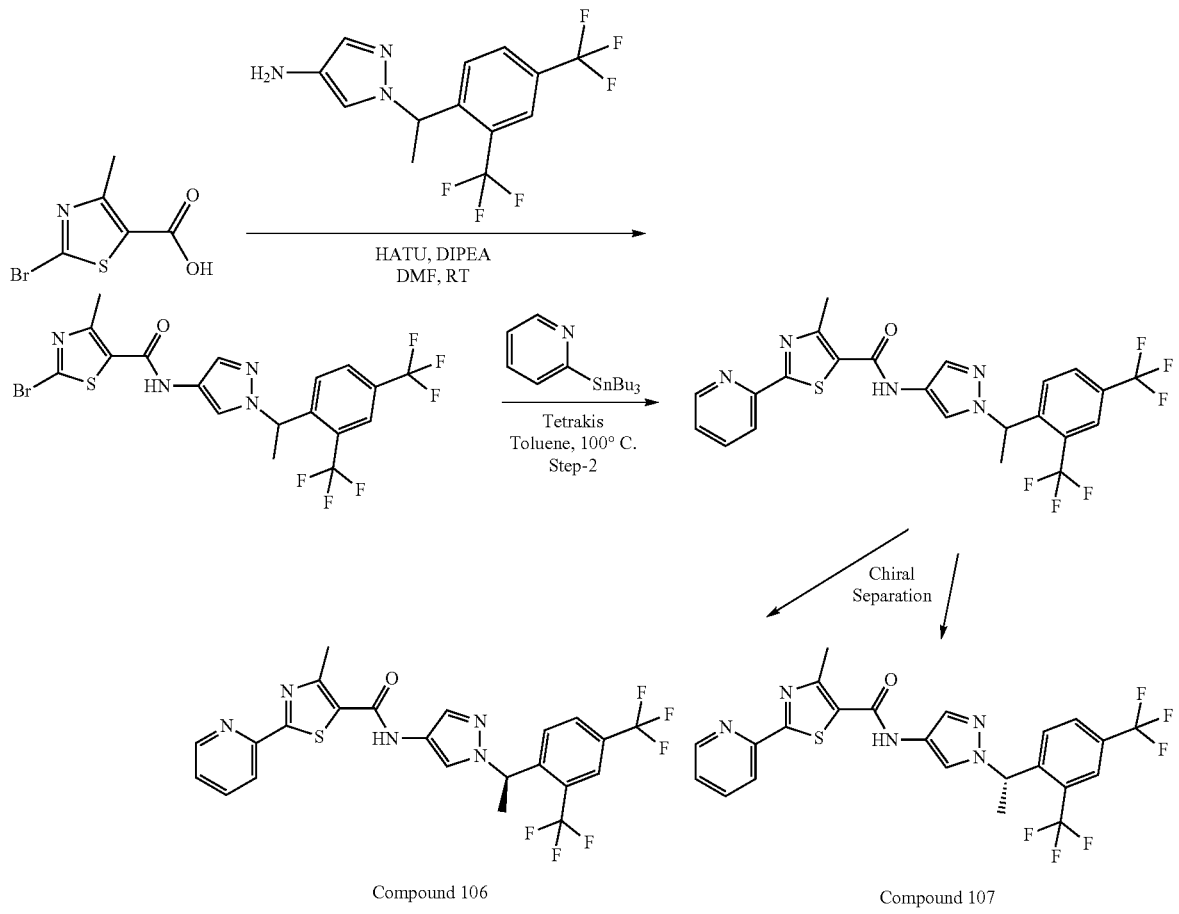

Compound 106      Compound 107

Step 1: Synthesis of N-(1-(1-(2,4-bis(trifluoromethyl)phenyl)ethyl)-1H-pyrazol-4-yl)-2-bromo-4-methylthiazole-5-carboxamide. To a solution of 2-bromo-4-methylthiazole-5-carboxylic acid (300 mg, 1.35 mmol, 1 equiv) in DMF (1 mL) was added HATU (564 mg, 1.48 mmol, 1.1 equiv). The mixture was allow to stir for 30 mins followed by the addition of DIPEA (557 mg, 4.32 mmol, 3.2 equiv) and a solution of the 1-(1-(2,4-bis(trifluoromethyl)phenyl)ethyl)-

Pd(Pppf)Cl$_2$ (15 mg, 0.018 mmol, 1 equiv), and the mixture was again degassed for 5 min. The reaction mixture was stirred at 80 C for overnight, after which time TLC indicated complete consumption of the SM. The mixture was quenched with H2O, extracted with EtOAc, dried (Na2SO4), and concentrated in vacuo to provide the product which was further purified by flash column chromatography and reverse phase HPLC to obtain pure product N-(1-(1-(2, 4-bis(trifluoromethyl)phenyl)ethyl)-1H-pyrazol-4-yl)-4-methyl-2-(pyridin-2-yl)thiazole-5-carboxamide (80 mg, as off white solid). LCMS: 526 [M+H]⁺. ¹H NMR (400 MHz, DMSO-d₆) δ 10.47 (s, 1H), 8.66 (d, J=4.7 Hz, 1H), 8.20-7.95 (m, 5H), 7.73 (d, J=8.3 Hz, 1H), 7.67 (s, 1H), 7.55 (dd, J=7.6, 4.8 Hz, 1H), 5.92 (q, J=6.8 Hz, 1H), 2.67 (s, 3H), 1.87 (d, J=6.9 Hz, 3H).

Step 3: Synthesis of (R) and (S)—N-(1-(1-(2,4-bis(trifluoromethyl)phenyl)ethyl)-1H-pyrazol-4-yl)-4-methyl-2-(pyridin-2-yl)thiazole-5-carboxamide. The enantiomers of N-(1-(1-(2,4-bis(trifluoromethyl)phenyl)ethyl)-1H-pyrazol-4-yl)-5-(3-chloropyridin-2-yl)isoxazole-3-carboxamide (90 mg, elution time: 6.28 min & 9.54), were separated by chiral SFC (Daicel Chiralpak®-IC, 250×20 mm, 5 µm). Isocratic program with analytical grade liquid carbon dioxide and HPLC grade Isopropanol, Total flow: 56 g/min, Co-Solvent Percentage: 22% to obtained (R)—N-(1-(1-(2,4-bis(trifluoromethyl)phenyl)ethyl)-1H-pyrazol-4-yl)-4-methyl-2-(pyridin-2-yl)thiazole-5-carboxamide (12 mg) and (S)—(S)—N-(1-(1-(2,4-bis(trifluoromethyl)phenyl)ethyl)-1H-pyrazol-4-yl)-4-methyl-2-(pyridin-2-yl)thiazole-5-carboxamide (11 mg). (Compound 106) ¹H NMR (400 MHz, DMSO-d₆) δ 10.47 (s, 1H), 8.66 (d, J=4.7 Hz, 1H), 8.20-7.95 (m, 5H), 7.73 (d, J=8.3 Hz, 1H), 7.67 (s, 1H), 7.55 (dd, J=7.6, 4.8 Hz, 1H), 5.92 (q, J=6.8 Hz, 1H), 2.67 (s, 3H), 1.87 (d, J=6.9 Hz, 3H). (Compound 107) ¹H NMR (400 MHz, DMSO-d₆) δ 10.47 (s, 1H), 8.66 (d, J=4.7 Hz, 1H), 8.20-7.95 (m, 5H), 7.73 (d, J=8.3 Hz, 1H), 7.67 (s, 1H), 7.55 (dd, J=7.6, 4.8 Hz, 1H), 5.92 (q, J=6.8 Hz, 1H), 2.67 (s, 3H), 1.87 (d, J=6.9 Hz, 3H).

Example S56. Synthesis of (R)—N-(1-(1-(2-fluoro-4-(trifluoromethyl)phenyl)ethyl-1H-pyrazol-4-yl)-5-(pyridin-2-yl)isoxazole-3-carboxamide and (S)—N-(1-(1-(2-fluoro-4-(trifluoromethyl)phenyl)ethyl)-1H-pyrazol-4-yl)-5-yl)isoxazole-3-carboxamide (Compounds 108 & 109)

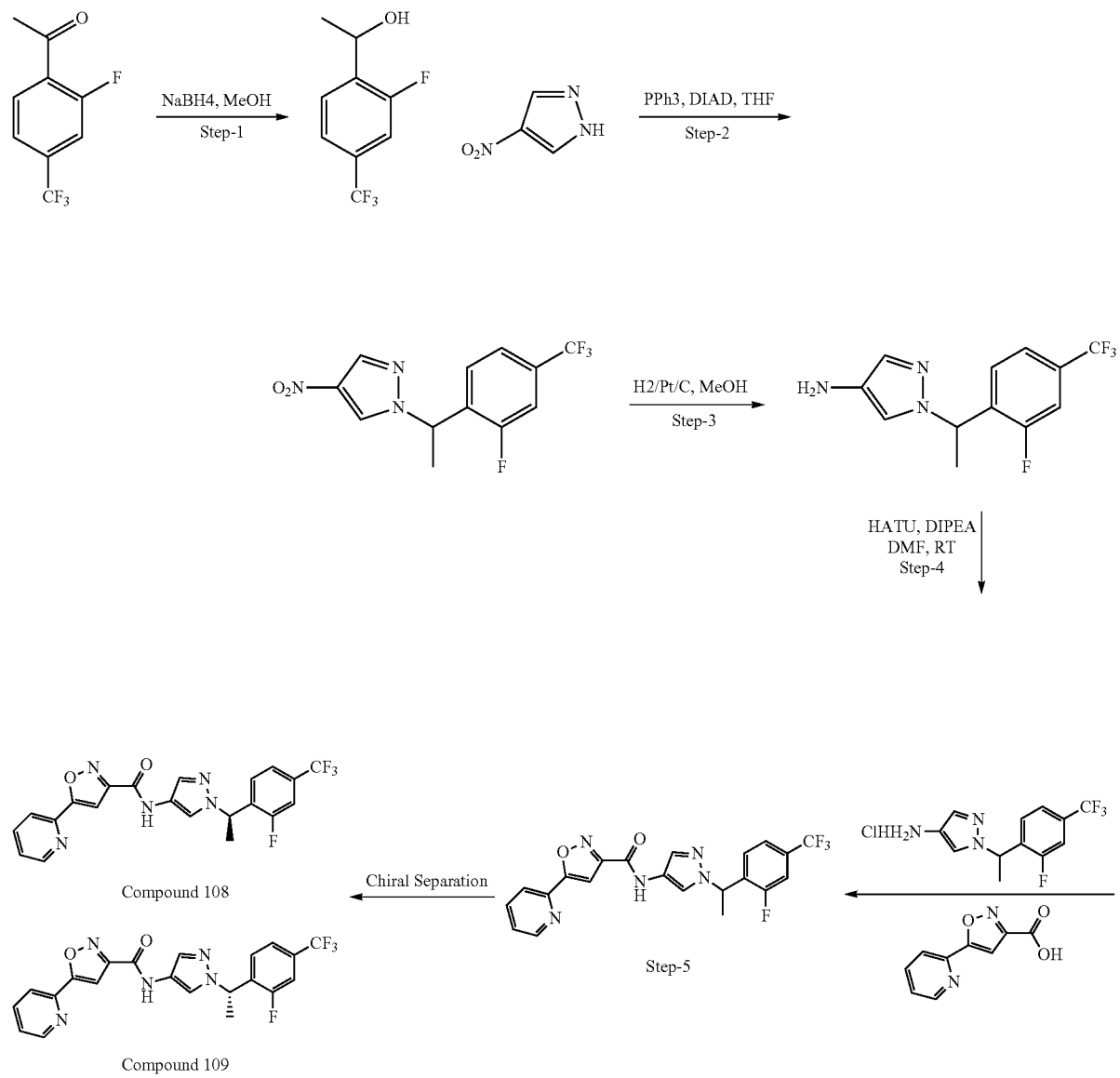

Step 1: Synthesis of 1-(2-fluoro-4-(trifluoromethyl)phenyl)ethan-1-ol. To a stirred solution of 1-(2-fluoro-4-(trifluoromethyl)phenyl)ethan-1-one (0.5 gm, 2.40 mmol, 1.0 eq) in Methanol (5 mL) was added NaBH₄ (0.133 gm, 3.60 mmol, 1.5 eq) portion wise at 0° C. and stirred for 10 minutes. The reaction mixture was allowed to stir for 1 hour at RT. Product formation was confirmed by TLC and NMR. After completion of reaction, reaction mixture was quenched with water and extracted with ethyl acetate (50 mL×3). Combined organic extracts were washed with water (2×50 mL), dried over anhydrous Na₂SO₄ and concentrated under reduced pressure to obtain 1-(2-fluoro-4-(trifluoromethyl)phenyl)ethan-1-ol (0.5 gm, 100% as colourless liquid).

Step 2: Synthesis of 1-(1-(2-fluoro-4-(trifluoromethyl)phenyl)ethyl)-4-nitro-1H-pyrazole. To a stirred solution of PPh₃ (640 mg, 2.40 mmol, 1.0 eq) and DIAD (480 mg, 2.40 mmol, 1.0 eq) in THF (2 mL) was added 1-(2-fluoro-4-(trifluoromethyl)phenyl)ethan-1-ol (500 mg, 2.40 mmol, 1.0 eq) Followed by drop wise addition of 4-nitro-1H-pyrazole (217.2 mg, 1.92 mmol, 0.8 eq), The reaction mixture was stirred at RT for overnight. Product formation was confirmed with TLC AND LCMS. After completion of reaction mixture were diluted with EtOAc (50 mL) and washed with water (50 mL×3). Organic layer dried over Na₂SO₄ and concentrated under reduced pressure to obtain crude which was further purified by flash column chromatography to obtain pure product 1-(1-(2-fluoro-4-(trifluoromethyl)phenyl)ethyl)-4-nitro-1H-pyrazole (450 mg, as brown liquid). LCMS: 304 [M+H]⁺.

Step 3: Synthesis of 1-(1-(2-fluoro-4-(trifluoromethyl)phenyl)ethyl)-1H-pyrazol-4-amine. To a stirred solution of 1-(1-(2-fluoro-4-(trifluoromethyl)phenyl)ethyl)-4-nitro-1H-pyrazole (450 mg, 1.41 mmol, 1.0 eq) in Methanol (10 mL) under nitrogen Palladium on Carbon (45.7 mg, 10% w/w) was added. Purge the reaction mixture with H₂ gas for 2 h. Product formation was confirmed by LCMS. After the completion of reaction, reaction mixture was filtered through Celite bed and Filtrate was concentrate under reduced pressure to obtain 1-(1-(2-fluoro-4-(trifluoromethyl)phenyl)ethyl)-1H-pyrazol-4-amine (0.4 gm, crude as brown colour liquid). LCMS: 274 [M+H]⁺.

Step 4: Synthesis of 1-(1-(2-fluoro-4-(trifluoromethyl)phenyl)ethyl)-1H-pyrazol-4-amine hydrochloride. To a stirred solution of 1-(1-(2-fluoro-4-(trifluoromethyl)phenyl)ethyl)-1H-pyrazol-4-amine (0.4 gm) in 2.5 M Ethanolic. HCl (10 mL). The reaction mixture was stirred at RT for overnight. Product formation was confirmed with TLC AND LCMS. After the completion of reaction, reaction mixture was triturate with Diethyl ether to obtain white colour product (0.4 gm mg). LCMS: 274 [M+H]⁺.

Step 5: Synthesis of N-(1-(1-(2-fluoro-4-(trifluoromethyl)phenyl)ethyl)-1H-pyrazol-4-yl)-5-(pyridine-2-yl)isoxazole-3-carboxamide. To a solution of 5-pyridine-yl-isoxazole-3-carboxylic acid (100 mg, 0.52 mmol, 1 equiv) in DMF (1 mL), were added HATU (197 mg, 0.52 mmol, 1 equiv). The mixture was treated drop wise with DIPEA (201 mg, 1.56 mmol, 3 equiv). After stirring at RT for 15 minutes, the mixture was treated drop wise with a solution of the 1-(1-(2-fluoro-4-(trifluoromethyl)phenyl)ethyl)-1H-pyrazol-4-amine (142 mg, 0.52 mmol, 1 equiv) in DMF (2 mL). The reaction mixture was kept under stirring for 24 h. Product formation was confirmed with TLC AND LCMS and reaction mixture was diluted EtOAc (50 mL) and washed with water (2×50 mL). Organic layer dried over Na₂SO₄ and concentrated under reduced pressure to obtain crude which was further purified by flash column chromatography to obtain pure product N-(1-(1-(2-fluoro-4-(trifluoromethyl)phenyl)ethyl)-1H-pyrazol-4-yl)-5-(pyridine-2-yl)isoxazole-3-carboxamide. (140 mg, as off white solid). LCMS: 446 [M+H]⁺. ¹H NMR (400 MHz, DMSO-d₆) δ 11.08 (s, 1H), 8.76 (d, J=4.8 Hz, 1H), 8.65 (s, OH), 8.23 (s, 1H), 8.09 (d, J=7.9 Hz, 1H), 8.03 (t, J=7.8 Hz, 1H), 7.76-7.68 (m, 2H), 7.63-7.53 (m, 2H), 7.48 (s, 1H), 7.37 (t, J=7.8 Hz, 1H), 5.98 (q, J=7.0 Hz, 1H), 1.84 (d, J=7.0 Hz, 3H).

Synthesis of N-(1-(1-(2-fluoro-4-(trifluoromethyl)phenyl)ethyl)-1H-pyrazol-4-yl)-5-(pyridine-2-yl)isoxazole-3-carboxamide. The enantiomers of N-(1-(1-(2-fluoro-4-(trifluoromethyl)phenyl)ethyl)-1H-pyrazol-4-yl)-5-(pyridine-2-yl)isoxazole-3-carboxamide (100 mg, elution time: 6.28 min & 9.28 min), were separated by chiral SFC (Daicel Chiralcel®-ODH, 250×20 mm, 5 μm. Isocratic program with analytical grade liquid carbon dioxide and HPLC grade Isopropanol, Total flow: 56 g/min, Co-Solvent Percentage: 20% to obtained (R)—N-(1-(1-(2-fluoro-4-(trifluoromethyl)phenyl)ethyl)-1H-pyrazol-4-yl)-5-(pyridine-2-yl)isoxazole-3-carboxamide (45 mg) and (S)—N-(1-(1-(2-fluoro-4-(trifluoromethyl)phenyl)ethyl)-1H-pyrazol-4-yl)-5-(pyridine-2-yl)isoxazole-3-carboxamide. (40 mg). LCMS: 446 [M+H]⁺. (Compound 108) ¹H NMR (400 MHz, DMSO-d₆) δ 11.08 (s, 1H), 8.76 (d, J=4.8 Hz, 1H), 8.65 (s, OH), 8.23 (s, 1H), 8.09 (d, J=7.9 Hz, 1H), 8.03 (t, J=7.8 Hz, 1H), 7.76-7.68 (m, 2H), 7.63-7.53 (m, 2H), 7.48 (s, 1H), 7.37 (t, J=7.8 Hz, 1H), 5.98 (q, J=7.0 Hz, 1H), 1.84 (d, J=7.0 Hz, 3H). (Compound 109) ¹H NMR (400 MHz, DMSO-d₆) δ 11.08 (s, 1H), 8.76 (d, J=4.8 Hz, 1H), 8.23 (s, 1H), 8.06 (dt, J=15.6, 7.9 Hz, 2H), 7.76-7.68 (m, 2H), 7.63-7.53 (m, 2H), 7.48 (s, 1H), 7.37 (t, J=7.7 Hz, 1H), 5.98 (q, J=6.9 Hz, 1H), 1.84 (d, J=7.1 Hz, 3H).

Example S57. Synthesis of (R)—N-(1-(1-(4-fluoro-2-(trifluoromethyl)phenyl)ethyl)-1H-pyrazol-4-yl)-5-(pyridin-2-yl)isoxazole-3-carboxamide and (S)—N-(1-(1-(4-fluoro-2-(trifluoromethyl)phenyl)ethyl)-1H-pyrazol-4-yl)-5-(pyridin-2-yl)isoxazole-3-carboxamide (Compounds 110 & 111)

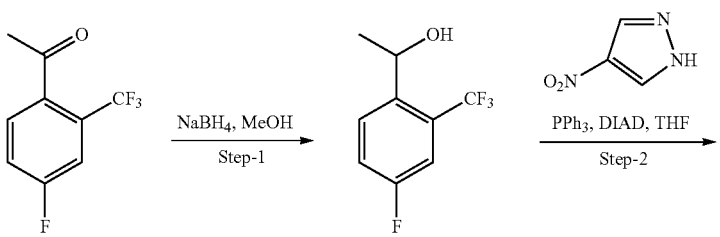

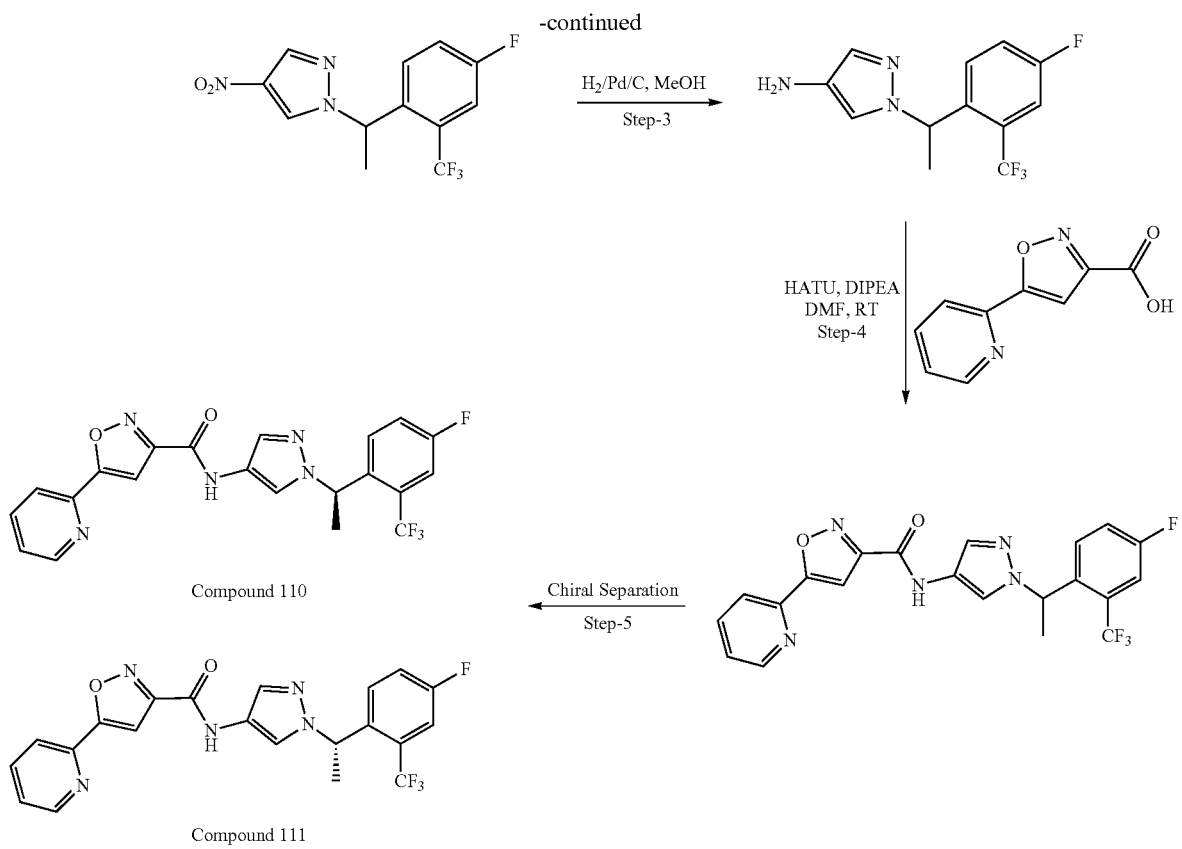

Compound 110

Compound 111

Step 1: Synthesis of 1-(4-fluoro-2-(trifluoromethyl)phenyl)ethan-1-ol. To a stirred solution of 1-(4-fluoro-2-(trifluoromethyl)phenyl)ethan-1-one (0.5 g 2.4 mmol, 1.0 equiv) in methanol (5 mL) was added NaBH$_4$ (0.133 g, 3.60 mmol, 1.5 eq) portion wise at 0° C. and stirred for 10 minutes. The reaction mixture was allowed to stir for 1 hour at RT. Product formation was confirmed by TLC and NMR. After completion of reaction, reaction mixture was quenched with water (50 mL) and extracted with ethyl acetate (3×50 mL). They combined organic layers were washed with water (2×50 mL), dried over anhydrous Na$_2$SO$_4$ and concentrated under reduced pressure to obtain 1-(4-fluoro-2-(trifluoromethyl)phenyl)ethan-1-ol as colourless liquid (0.5 gm).

Step 2: Synthesis of 1-(1-(4-fluoro-2-(trifluoromethyl)phenyl)ethyl)-4-nitro-1H-pyrazole. To a stirred solution of PPh$_3$ (640 mg, 2.40 mmol, 1.0 eq) and DIAD (484.8 mg, 2.40 mmol, 1.0 eq) in THF (2 mL) was added 1-(4-fluoro-2-(trifluoromethyl)phenyl)ethan-1-ol (500 mg, 2.40 mmol, 1.0 eq). Followed by drop wise addition of 4-nitro-1H-pyrazole (217.2 mg, 1.92 mmol, 0.8 eq), The reaction mixture was stirred at RT for overnight. Product formation was confirmed with TLC and LCMS. After completion of reaction mixture were diluted with EtOAc (50 mL) and washed with water (3×50 mL). Organic layer dried over Na$_2$SO$_4$ and concentrated under reduced pressure to obtain crude which was further purified by flash column chromatography (EtOAc/hexane) to obtain pure product 1-(1-(4-fluoro-2-(trifluoromethyl)phenyl)ethyl)-4-nitro-1H-pyrazole as brown liquid (340 mg). LCMS: 304 [M+H]$^+$.

Step 3: Synthesis of 1-(1-(4-fluoro-2-(trifluoromethyl)phenyl)ethyl)-1H-pyrazol-4-amine. To a stirred solution of 1-(1-(4-fluoro-2-(trifluoromethyl)phenyl)ethyl)-4-nitro-1H-pyrazole (0.3 gm) in methanol (10 mL) under nitrogen was added palladium on carbon [Pd/C] (10% w/w, 75 mg). the reaction mixture was purged with hydrogen gas for 2 hrs. Product formation was confirmed by LCMS. After the completion of reaction, reaction mixture was filtered through celite bed and filtrate was concentrate under reduced pressure to obtain 1-(1-(4-fluoro-2-(trifluoromethyl)phenyl)ethyl)-1H-pyrazol-4-amine as brown colour liquid (0.3 g). LCMS: 274 [M+H]$^+$.

Step 4: Synthesis of N-(1-(1-(4-fluoro-2-(trifluoromethyl)phenyl)ethyl)-1H-pyrazol-4-3/1)-5-(pyridine-2-yl)isoxazole-3-carboxamide. To a solution of 5-pyridine-yl-isoxazole-3-carboxylic acid (100 mg, 0.52 mmol, 1 equiv) in DMF (1 mL), was added HATU (197 mg, 0.52 mmol, 1 equiv). The mixture was treated drop wise with DIPEA (201 mg, 1.56 mmol, 3.0 eq). After stirring at RT for 15 minutes, the mixture was treated drop wise with a solution of the 1-(1-(4-fluoro-2-(trifluoromethyl)phenyl)ethyl)-1H-pyrazol-4-amine (142 mg, 0.52 mmol, 1 equiv) in DMF (1 mL). The reaction mixture was kept under stirring for 24 hrs. Product formation was confirmed with TLC and LCMS and reaction mixture was diluted EtOAc (50 mL) and washed with water (2×50 mL). Organic layer dried over anhydrous Na$_2$SO$_4$ and concentrated under reduced pressure to obtain crude which was further purified by flash column chromatography to obtain title compound N-(1-(1-(4-fluoro-2-(trifluoromethyl)phenyl)ethyl)-1H-pyrazol-4-yl)-5-(pyridine-2-yl)isoxazole-3-carboxamide as free base (120 mg). LCMS: 446 [M+H]$^+$. $^1$H NMR (400 MHz, DMSO-d$_6$) δ 11.06 (s, 1H), 8.76 (d, J=4.8 Hz, 1H), 8.13 (s, 1H), 8.08 (d, J=7.9 Hz, 1H), 8.04 (dt, J=9.6, 4.8 Hz, 1H), 7.73 (s, 1H), 7.69-7.60 (m, 2H), 7.57 (dt, J=7.3, 3.7 Hz, 2H), 7.46 (s, 1H), 5.83 (q, J=6.9 Hz, 1H), 1.83 (d, J=6.9 Hz, 3H).

Step 5: Enantiomer separation of N-(1-(1-(4-fluoro-2-(trifluoromethyl)phenyl)ethyl)-1H-pyrazol-4-yl)-5-(pyridine-2-yl)isoxazole-3-carboxamide. The enantiomers of N-(1-(1-(4-fluoro-2-(trifluoromethyl)phenyl)ethyl)-1H-pyrazol-4-yl)-5-(pyridine-2-yl)isoxazole-3-carboxamide (100 mg, elution time: 5.85 min & 7.65 min), were separated by chiral SFC (Daicel Chiralcel®-ODH, 250×20 mm, 5 μm). Isocratic program with analytical grade liquid carbon dioxide and HPLC grade Isopropanol, Total flow: 56 g/min, Co-Solvent Percentage: 25% to obtained (R)—N-(1-(1-(4-fluoro-2-(trifluoromethyl)phenyl)ethyl)-1H-pyrazol-4-yl)-5-(pyridine-2-yl)isoxazole-3-carboxamide (45 mg) and (S)—N-(1-(1-(4-fluoro-2-(trifluoromethyl)phenyl)ethyl)-1H-pyrazol-4-yl)-5-(pyridine-2-yl)isoxazole-3-carboxamide (40 mg). LCMS: 446 [M+H]⁺. (Compound 110) ¹H NMR (400 MHz, DMSO-$d_6$) δ 11.07 (s, 1H), 8.76 (d, J=4.7 Hz, 1H), 8.13 (s, 1H), 8.08 (d, J=7.8 Hz, 1H), 8.03 (dd, J=8.2, 6.4 Hz, 1H), 7.73 (s, 1H), 7.69-7.60 (m, 2H), 7.57 (dt, J=7.3, 3.9 Hz, 2H), 7.46 (s, 1H), 5.83 (q, J=7.0 Hz, 1H), 1.83 (d, J=6.9 Hz, 3H). (Compound 111) ¹H NMR (400 MHz, DMSO-$d_6$) δ 11.06 (s, 1H), 8.76 (d, J=4.8 Hz, 1H), 8.13 (s, 1H), 8.08 (d, J=7.9 Hz, 1H), 8.04 (dt, J=9.6, 4.8 Hz, 1H), 7.73 (s, 1H), 7.69-7.60 (m, 2H), 7.57 (dt, J=7.3, 3.7 Hz, 2H), 7.46 (s, 1H), 5.83 (q, J=6.9 Hz, 1H), 1.83 (d, J=6.9 Hz, 3H).

Example S58. Synthesis of N-(1-(1-(2,4-bis(trifluoromethyl)phenyl)ethyl)-1H-pyrazol-4-yl)-1-methyl-3-(pyridin-2-yl)-1H-pyrazole-5-carboxamide (Compound 112)

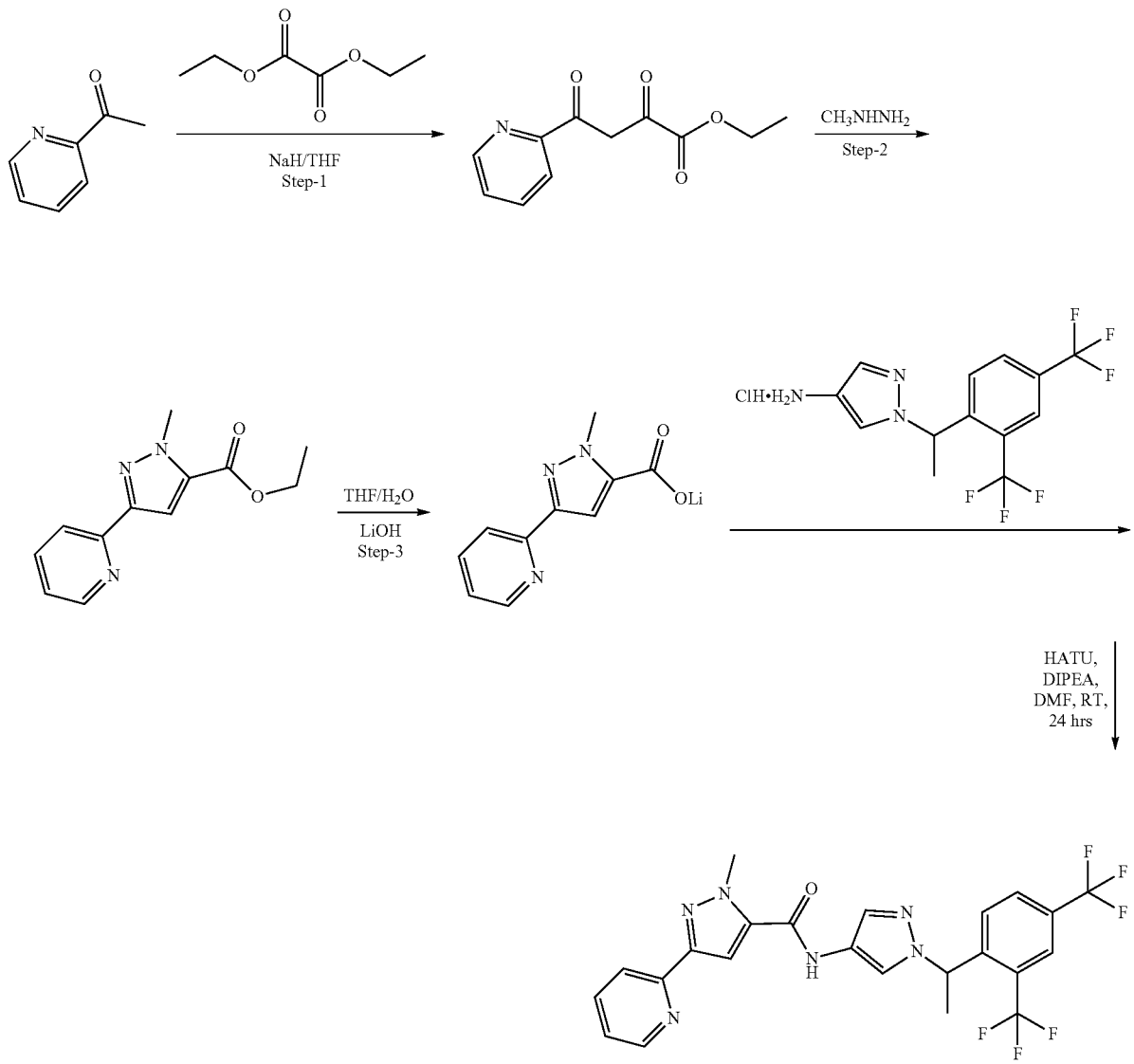

Step 1: Synthesis of ethyl 4-ethyl 2,4-dioxo-4-(pyridin-2-yl)butanoate. To a solution of 60% Sodium hydride (1.48 g, 0.061 mol, 1.5 equiv) in toluene (20 ml) at 0° C., was added 1-(pyridin-2-yl)ethan-1-one (5.0 g, 0.041 mol, 1 equiv) was added drop wise to the reaction mixture at 0° C. The resultant reaction mixture was stirred for another 30 minutes at RT, followed by drop wise addition of diethyl oxalate (9.04 g, 0.061 mol, 1 equiv) at 0° C. and reaction mixture was stirred for another 2 hours at room temperature. Product formation was confirmed by TLC and LCMS. The reaction mixture was quenched with ice water and neutralized with 1N HCl and extracted with EtOAc (3×100 mL).

Combined organic extracts were washed with water (2×100 mL), dried over anhydrous $Na_2SO_4$ and concentrated under reduced pressure to obtain crude which was purified by combi-flash chromatography (10-20% Ethyl acetate in hexane) to obtain ethyl 2,4-dioxo-4-(pyridin-2-yl)butanoate as yellow solid (6 g). LCMS: 222 [M+H]$^+$.

Step 2: Synthesis of ethyl 1-methyl-3-(pyridin-2-yl)-1H-pyrazole-5-carboxylate. A suspension of ethyl 2,4-dioxo-4-(pyridin-2-yl)butanoate (1.0 g, 0.004 mol, 1 equiv) and methylhydrazine (0.208 g, 0.004 mmol, 1.0 equiv) in EtOH (20 ml) was stirred at 85° C. for overnight. Product formation was confirmed by TLC and LCMS. The resulting mixture was concentrated under reduced pressure, the residue was dissolved in ethyl acetate and distilled water. Organic phase was separated, dried over anhydrous $Na_2SO_4$ and it was concentrated under reduced pressure to give crude. The crude product was purified using flash column chromatography using solvent system (10-20% Ethyl acetate in hexane) to obtain ethyl 1-methyl-5-(pyridin-2-yl)-1H-pyrazole-3-carboxylate as pale yellow solid (200 mg). LCMS: 231 [M+H]$^+$.

Step 3: Synthesis of Lithium 1-methyl-3-(pyridin-2-yl)-1H-pyrazole-5-carboxylic acid. To a solution of ethyl 1-methyl-5-(pyridin-2-yl)-1H-pyrazole-3-carboxylate (200 mg, 0.86 mmol, 1.0 equivuiv) in THF (5 mL), and water (2 mL) was added in lithium hydroxide (54 mg, 1.29 mmol, 1.5 equiv). The resulting mixture was stirred for 16 hours. Reaction mixture was concentrated under reduced pressure. The resulting residue was washed with ethyl acetate (2×30 mL). Aqueous layer lyophilised to obtain lithium salt of 1-methyl-3-(pyridin-2-yl)-1H-pyrazole-5-carboxylic acid s off white solid (180 mg crude). LCMS: 204 [M+H]$^+$.

Step 4: Synthesis of N-(1-(1-(2,4-bis(trifluoromethyl)phenyl)ethyl)-1H-pyrazol-4-yl)-1-methyl-3-(pyridin-2-yl)-1H-pyrazole-5-carboxamide. To a solution of 1-methyl-5-(pyridin-2-yl)-1H-pyrazole-3-carboxylic acid (200 mg, 0.95 mmol, 1 equiv) in DMF (3 mL) was added HATU (400 mg, 1.05 mmol, 1.1 equiv). The mixture was allow to stir for 30 mins followed by the addition of DIPEA (395 mg, 3.06 mmol, 3.2 equiv) and a solution of the 1-(1-(2,4-bis(trifluoromethyl)phenyl)ethyl)-1H-pyrazol-4-amine Hydrochloride (342 mg, 0.95 mmol, 1 equiv) in DMF (2 mL) was added. The reaction mixture was kept under stirring for 24 hrs at RT. Product formation was confirmed with TLC and LCMS and reaction mixture was diluted EtOAc (50 mL) and washed with water (2×50 mL). Organic layer dried over anhydrous $Na_2SO_4$ and concentrated under reduced pressure to obtain crude which was further purified by flash column chromatography and reverse HPLC to obtain pure product N-(1-(1-(2,4-bis(trifluoromethyl)phenyl)ethyl)-1H-pyrazol-4-yl)-1-methyl-5-(pyridin-2-yl)-1H-pyrazole-3-carboxamide as off white solid (150 mg). LCMS: 509 [M+H]$^+$. $^1$H NMR (400 MHz, DMSO-d$_6$) δ 10.45 (s, 1H), 8.71 (d, J=4.7 Hz, 1H), 8.16 (s, 1H), 8.08 (d, J=8.4 Hz, 1H), 8.05 (s, 1H), 7.92 (dt, J=12.7, 4.8 Hz, 2H), 7.76 (s, 1H), 7.73 (d, J=8.4 Hz, 1H), 7.43 (td, J=5.2, 4.7, 2.6 Hz, 1H), 7.24 (s, 1H), 5.90 (q, J=6.9 Hz, 1H), 4.24 (s, 3H), 1.86 (d, J=6.9 Hz, 3H).

Example S59. Synthesis of N-(1-(1-(2,4-bis(trifluoromethyl)phenyl)ethyl)-1H-pyrazol-4-yl)-1-methyl-5-(pyridin-2-yl)-1H-pyrazole-3-carboxamide (Compound 113)

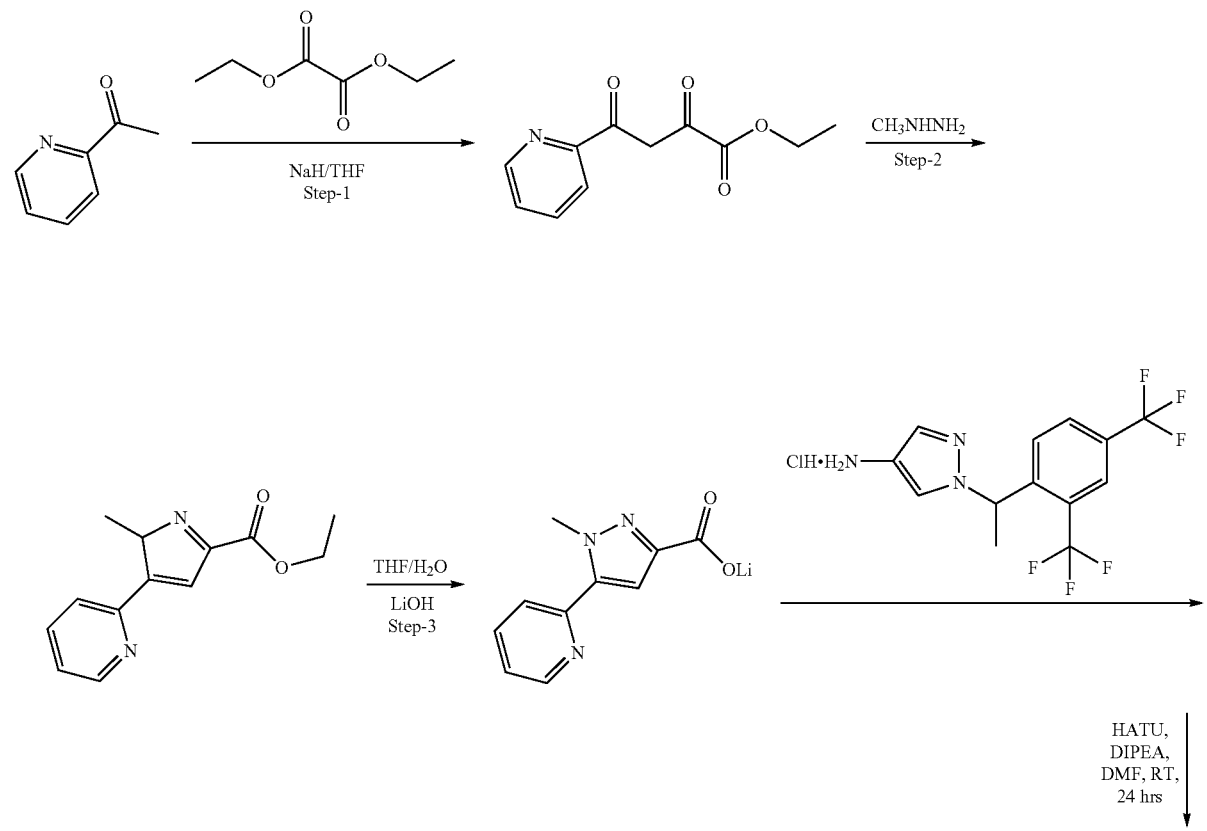

-continued

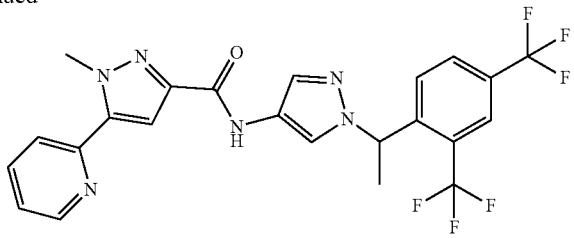

Step 1: Synthesis of ethyl 2,4-dioxo-4-(pyridin-2-yl)butanoate. To a solution of sodium hydride (60%, 1.48 g, 0.061 mol, 1.5 equiv) in toluene (20 mL) at 0° C., was added 1-(pyridin-2-yl)ethan-1-one (5.0 g, 0.041 mol, 1 equiv). The resultant reaction mixture was stirred for another 30 minutes at room temperature, followed by drop wise addition of diethyl oxalate (9.04 g, 0.061 mol, 1 equiv) at 0° C. and reaction mixture was stir for another 2 hours at room temperature. Product formation was confirmed by TLC and LCMS. The reaction mixture was quenched with ice water and neutralized with 1N HCl and extracted with EtOAc (3×100 mL). Combined organic extracts were washed with water (2×100 mL), dried over anhydrous Na$_2$SO$_4$ and concentrated under reduced pressure to obtain crude which was purified by combi-flash chromatography (10-20% EtOAc/hexane) to obtain ethyl 2,4-dioxo-4-(pyridin-2-yl)butanoate as yellow solid (6 g crude). LCMS: 222 [M+H]$^+$.

Step 2: Synthesis of ethyl 1-methyl-5-(pyridin-2-yl)-1H-pyrazole-3-carboxylate. A suspension of ethyl 2,4-dioxo-4-(pyridin-2-yl)butanoate (1.0 g, 0.004 mol, 1 equiv) and methylhydrazine (0.208 g, 0.004 mmol, 1.0 equiv) in EtOH (20 ml) was stirred at 85° C. for overnight. Product formation was confirmed by TLC and LCMS. The resulting mixture was concentrated under reduced pressure, the residue was dissolved in ethyl acetate and distilled water. Organic phase was separated, dried over anhydrous Na$_2$SO$_4$ and it was concentrated under reduced pressure to give crude. The crude product was purified using flash column chromatography using solvent system (10-20% Ethyl acetate in hexane) to obtain ethyl 1-methyl-5-(pyridin-2-yl)-1H-pyrazole-3-carboxylate (300 mg, as off white solid). LCMS: 232 [M+H]$^+$.

Step 3: Synthesis of Lithium-1-methyl-5-(pyridin-2-yl)-1H-pyrazole-3-carboxylic acid. To a solution of 1-methyl-5-(pyridin-2-yl)-1H-pyrazole-3-carboxylic acid (500 mg, 2.28 mmol, 1.0 equivuiv) in THF (5 mL), methanol (3 mL) and water (2 mL) was added in lithium hydroxide (191 mg, 4.56 mmol, 2.0 equiv). The resulting mixture was stirred for 16 hours. Reaction mass was concentrated under reduced pressure. The resulting residue was acidified with 1N HCl and extracted with ethyl acetate (3×100 mL). Combined organic layer were washed with distilled water, dried over anhydrous Na$_2$SO$_4$ and concentrated under reduced pressure to obtain Lithium salt of 1-methyl-5-(pyridin-2-yl)-1H-pyrazole-3-carboxylic acid as pale yellow solid (250 mg). LCMS: 204 [M+H]$^+$.

Synthesis of N-(1-(1-(2,4-bis(trifluoromethyl)phenyl)ethyl)-1H-pyrazol-4-yl)-1-methyl-5-(pyridin-2-yl)-1H-pyrazole-3-carboxamide. To a solution of 1-methyl-5-(pyridin-2-yl)-1H-pyrazole-3-carboxylic acid (200 mg, 0.95 mmol, 1 equiv) and HATU (400 mg, 1.05 mmol, 1.1 equiv) in DMF (1 mL). The mixture was allow to stir for 30 mins followed by the addition of DIPEA (395 mg, 3.06 mmol, 3.2 equiv) and a solution of the 1-(1-(2,4-bis(trifluoromethyl)phenyl)ethyl)-1H-pyrazol-4-amine Hydrochloride (342 mg, 0.95 mmol, 1 equiv) in DMF (1 mL) was added. The reaction mixture was kept under stirring for 24 h at RT. Product formation was confirmed with TLC AND LCMS and reaction mixture was diluted EtOAc (50 mL) and washed with water (2×50 mL). Organic layer dried over Na$_2$SO$_4$ and concentrated under reduced pressure to obtain crude which was further purified by flash column chromatography and reverse HPLC to obtain pure product N-(1-(1-(2,4-bis(trifluoromethyl)phenyl)ethyl)-1H-pyrazol-4-yl)-1-methyl-5-(pyridin-2-yl)-1H-pyrazole-3-carboxamide (35 mg, as white solid). LCMS: 509 [M+H]$^+$. $^1$H NMR (400 MHz, DMSO-d$_6$) δ 10.66 (s, 1H), 8.60 (d, J=4.9 Hz, 1H), 8.18 (s, 1H), 8.12-8.02 (m, 2H), 7.94 (d, J=7.9 Hz, 1H), 7.90-7.81 (m, 1H), 7.77-7.64 (m, 2H), 7.63 (s, 1H), 7.38-7.30 (m, 1H), 5.92 (q, J=6.9 Hz, 1H), 4.18 (s, 3H), 1.87 (d, J=6.9 Hz, 3H).

Example S60. Synthesis of N-(1-(2,4-bis(trifluoromethyl)benzyl)-1H-pyrazol-4-yl)-5-(pyrazin-2-yl)isoxazole-3-carboxamide (Compound 114)

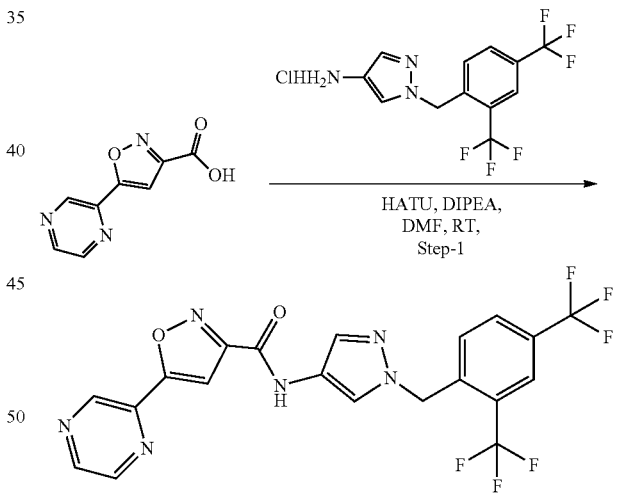

Step 1: Synthesis of N-(1-(2,4-bis(trifluoromethyl)benzyl)-1H-pyrazol-4-yl)-5-(pyrazin-2-yl)isoxazole-3-carboxamide. To a solution of 5-(pyrazin-2-yl)isoxazole-3-carboxylic acid (100 mg, 0.52 mmol, 1 equiv) and HATU (218 mg, 0.57 mmol, 1.1 equiv) in DMF (2 mL). The mixture was allow to stir for 30 mins followed by the addition of DIPEA (216 mg, 1.67 mmol, 3.2 equiv) and a solution of the 1-(2,4-bis(trifluoromethyl)benzyl)-1H-pyrazol-4-amine Hydrochloride (180 mg, 0.52 mmol, 1 equiv) in DMF (1 mL) was added. The reaction mixture was kept under stirring for overnight at RT. Product formation was confirmed with TLC and LCMS and reaction mixture was diluted EtOAc (50 mL) and washed with water (2×50 mL).

Organic layer dried over anhydrous Na₂SO₄ and concentrated under reduced pressure to obtain crude which was further purified by flash column chromatography to obtain title compound N-(1-(2,4-bis(trifluoromethyl)benzyl)-1H-pyrazol-4-yl)-5-(pyrazin-2-yl)isoxazole-3-carboxamide as off white solid (150 mg). LCMS: 483[M+H]⁺. ¹H NMR (400 MHz, DMSO-d₆) δ 11.22 (s, 1H), 9.36 (d, J=1.8 Hz, 1H), 8.88-8.83 (m, 1H), 8.82 (d, J=2.6 Hz, 1H), 8.34 (s, 1H), 8.07 (d, J=7.9 Hz, 2H), 7.75 (d, J=35.8 Hz, 2H), 7.06 (d, J=8.0 Hz, 1H), 5.67 (s, 2H).

Example S61. Synthesis of N-(1-(2,4-bis(trifluoromethyl)benzyl)-1H-pyrazol-4-yl)-5-(6-methylpyridin-2-yl)isoxazole-3-carboxamide (Compound 115)

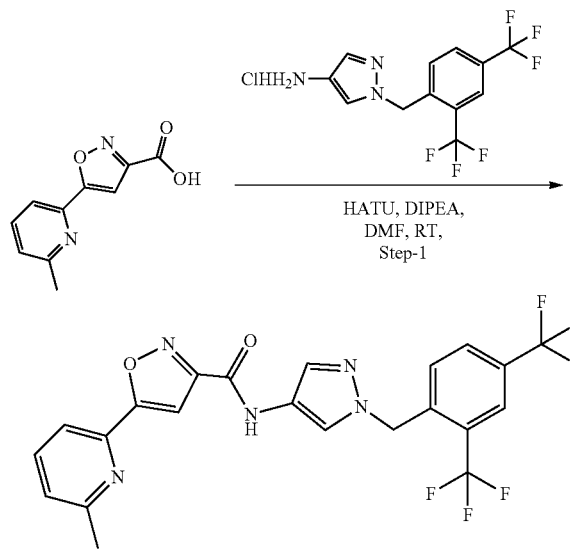

Step 1: Synthesis of N-(1-(2,4-bis(trifluoromethyl)benzyl)-1H-pyrazol-4-yl)-5-(6-methylpyridin-2-yl)isoxazole-3-carboxamide. To a solution of 5-(6-methylpyridin-2-yl)isoxazole-3-carboxylic acid (100 mg, 0.49 mmol, 1 equiv) and HATU (204 mg, 0.53 mmol, 1.1 equiv) in DMF (1 mL). The mixture was allow to stir for 30 mins followed by the addition of DIPEA (202 mg, 1.56 mmol, 3.2 equiv) and a solution of the 1-(2,4-bis(trifluoromethyl)benzyl)-1H-pyrazol-4-amine hydrochloride (168 mg, 0.49 mmol, 1 equiv) in DMF (1 mL) was added. The reaction mixture was kept under stirring for 24 hrs at RT. Product formation was confirmed with TLC and LCMS and reaction mixture was diluted EtOAc (50 mL) and washed with water (2×50 mL). Organic layer dried over anhydrous Na₂SO₄ and concentrated under reduced pressure to obtain crude which was further purified by flash column chromatography to obtain title compound N-(1-(2,4-bis(trifluoromethyl)benzyl)-1H-pyrazol-4-yl)-5-(6-methylpyridin-2-yl)isoxazole-3-carboxamide as off white solid (45 mg). LCMS: 496 [M+H]⁺. ¹H NMR (400 MHz, DMSO-d₆) δ 11.14 (s, 1H), 8.34 (s, 1H), 8.07 (d, J=7.9 Hz, 2H), 7.96-7.85 (m, 2H), 7.79 (s, 1H), 7.47 (s, 1H), 7.43 (d, J=7.2 Hz, 1H), 7.06 (d, J=8.2 Hz, 1H), 5.67 (s, 2H), 2.57 (s, 3H).

Example S62. Synthesis of (R)—N-(1-(1-(2,4-bis(trifluoromethyl)phenyl)ethyl)-1H-pyrazol-4-yl)-5-(6-methylpyridin-2-yl)isoxazole-3-carboxamide and (S)—N-(1-(1-(2,4-bis(trifluoromethyl)phenyl)ethyl-1H-pyrazol-4-yl)-5-(6-methylpyridin-2-yl)isoxazole-3-carboxamide (Compounds 116 & 117)

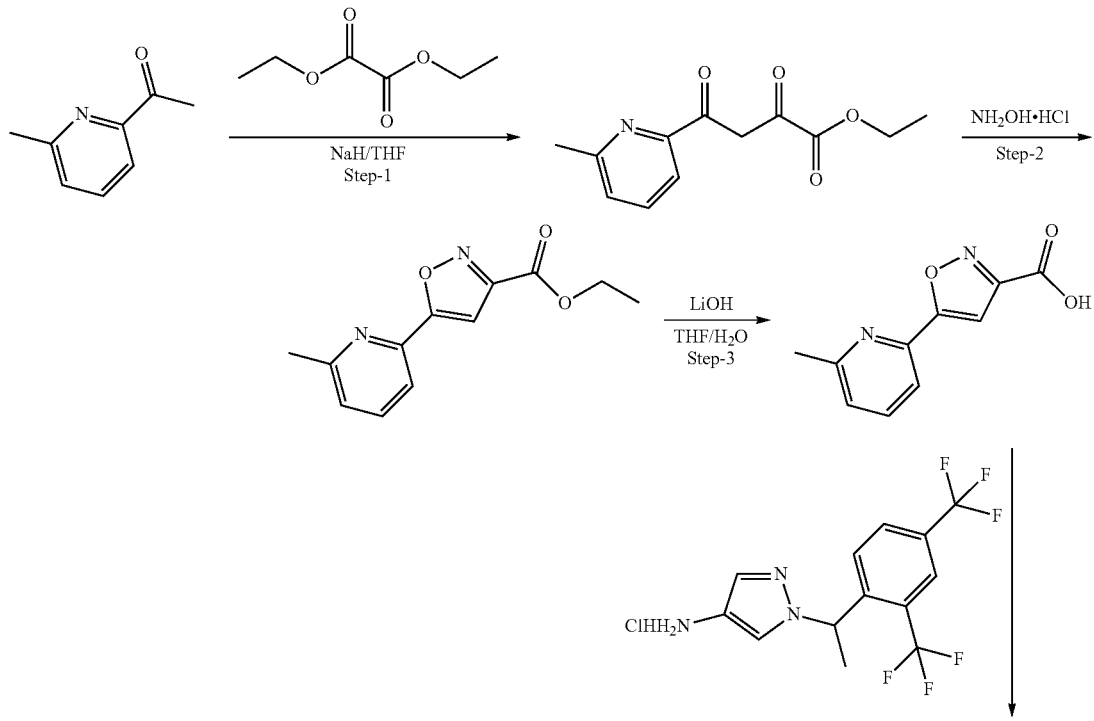

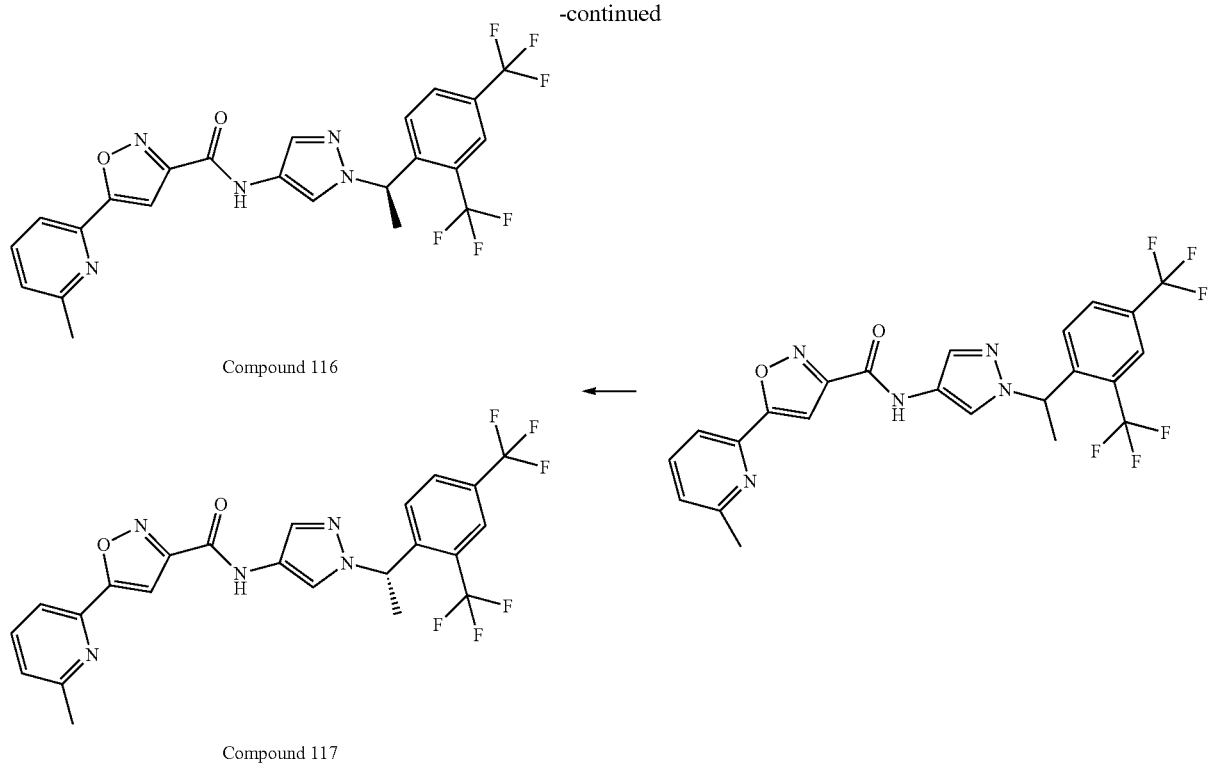

Compound 116

Compound 117

Step 1: Synthesis of ethyl 4-(6-methylpyridin-2-yl)-2,4-dioxobutanoate. To a solution of Sodium hydride (60%, 133 mg, 5.55 mmol, 1.5 equiv) in THF (10 mL) at 0° C., was added 1-(6-methylpyridin-2-yl)ethan-1-one (500 mg, 3.70 mmol, 1 equiv) drop wise. The resultant reaction mixture was stirred for another 30 minutes at RT, followed by drop wise addition of diethyl oxalate (811 mg, 5.55 mmol, 1.5 equiv) at 0° C. and reaction mixture was stir for another 5 hours at rook temperature. Product formation was confirmed by TLC and LCMS. The reaction mixture was quenched with ice water and neutralized with 1N HCl and the yellow precipitate was filtered and dried under reduced pressure to obtain ethyl 4-(6-methylpyridin-2-yl)-2,4-dioxobutanoate as yellow solid (350 mg). LCMS: 236[M+H]$^+$.

Step 2: Synthesis of ethyl 5-(6-methylpyridin-2-yl)isoxazole-3-carboxylate. A suspension of ethyl 4-(6-methylpyridin-2-yl)-2,4-dioxobutanoate (500 mg, 2.12 mmol, 1 equiv) and hydroxylamine hydrochloride (146 mg, 2.12 mmol, 1 equiv) in EtOH (10 ml) was stirred at 85° C. for overnight. Product formation was confirmed by TLC and LCMS. The resulting mixture was concentrated under reduced pressure, the residue was dissolved in ethyl acetate and distilled water. Organic phase was separated, dried over anhydrous Na$_2$SO$_4$ and it was concentrated under reduced pressure to give ethyl 5-(6-methylpyridin-2-yl)isoxazole-3-carboxylate. The crude product was purified using flash column chromatography using solvent system (10-20% Ethyl acetate in hexane) to obtain the title compound as off white solid (300 mg). LCMS: 233 [M+H]$^+$.

Step 3: Synthesis of 5-(6-methylpyridin-2-yl)isoxazole-3-carboxylic acid. To a solution of ethyl 5-(6-methylpyridin-2-yl)isoxazole-3-carboxylate (350 mg, 1.50 mmol, 1.0 equivuiv) in THF (5 mL) and water (2 mL) was added in lithium hydroxide (95 mg, 2.26 mmol, 1.5 equiv). The resulting mixture was stirred for overnight. Reaction mass was concentrated under reduced pressure. The resulting residue was acidified with 1N HCl and the precipitate was filtered and dried under reduced pressure to obtain 5-(6-methylpyridin-2-yl)isoxazole-3-carboxylic acid as white solid (250 mg). LCMS: 205 [M+H]$^+$.

Synthesis of N-(1-(1-(2,4-bis(trifluoromethyl)phenyl)ethyl)-1H-pyrazol-4-yl)-5-(6-methylpyridin-2-yl)isoxazole-3-carboxamide. To a solution of 5-(pyrazin-2-yl)isoxazole-3-carboxylic acid (200 mg, 0.98 mmol, 1 equiv) and HATU (350 mg, 0.96 mmol, 1.0 equiv) in DMF (3 mL). The mixture was allow to stir for 30 mins followed by the addition of DIPEA (404 mg, 1.07 mmol, 3.13 equiv) and a solution of the 1-(1-(2,4-bis(trifluoromethyl)phenyl)ethyl)-1H-pyrazol-4-amine Hydrochloride (350 mg, 0.98 mmol, 1 equiv) in DMF (2 mL) was added. The reaction mixture was kept under stirring for 24 h at RT. Product formation was confirmed with TLC AND LCMS and reaction mixture was diluted EtOAc (100 mL) and washed with water (2×50 mL). Organic layer dried over Na$_2$SO$_4$ and concentrated under reduced pressure to obtain crude which was further purified by flash column chromatography to obtain pure product of N-(1-(1-(2,4-bis(trifluoromethyl)phenyl)ethyl)-1H-pyrazol-4-yl)-5-(6-methylpyridin-2-yl)isoxazole-3-carboxamide (150 mg, 30% as off white solid). LCMS: 509 [M+H]$^+$. $^1$H NMR (400 MHz, DMSO-d$_6$) δ 11.04 (s, 1H), 8.17 (s, 1H), 8.06 (d, J=8.3 Hz, 1H), 8.02 (s, 1H), 7.92-7.81 (m, 2H), 7.70 (d, J=7.7 Hz, 2H), 7.39 (d, J=7.0 Hz, 2H), 5.90 (q, J=6.9 Hz, 1H), 2.53 (s, 3H), 1.84 (d, J=6.9 Hz, 3H), 1.20 (s, 1H).

Synthesis of (R) and (S) of N-(1-(1-(2,4-bis(trifluoromethyl)phenyl)ethyl)-1H-pyrazol-4-yl)-5-(6-methylpyridin-2-yl)isoxazole-3-carboxamide. The enantiomers of N-(1-(1-(2,4-bis(trifluoromethyl)phenyl)ethyl)-1H-pyrazol-4-yl)-5-(6-methylpyridin-2-yl)isoxazole-3-carboxamide (120 mg) (elution time: 3.78 min & 4.86 min), were separated by chiral SFC (Daicel Chiralcel®-ODH, 250×20 mm, 5 µm).

Isocratic program with analytical grade liquid carbon dioxide and HPLC grade Isopropanol, Total flow: 56 g/min, Co-Solvent Percentage: 20% to obtained Peak-1 (R) N-(1-(1-(2,4-bis(trifluoromethyl)phenyl)ethyl)-1H-pyrazol-4-yl)-5-(6-methylpyridin-2-yl)isoxazole-3-carboxamide (40 mg) and Peak-2 (S)- of N-(1-(1-(2,4-bis(trifluoromethyl)phenyl)ethyl)-1H-pyrazol-4-yl)-5-(6-methylpyridin-2-yl)isoxazole-3-carboxamide (40 mg). (Compound 116) LCMS: 509 [M+H]$^+$. $^1$H NMR (400 MHz, DMSO-d$_6$) δ 11.04 (s, 1H), 8.17 (s, 1H), 8.06 (d, J=8.3 Hz, 1H), 8.02 (s, 1H), 7.92-7.81 (m, 2H), 7.70 (d, J=7.7 Hz, 2H), 7.39 (d, J=7.0 Hz, 2H), 5.90 (q, J=6.9 Hz, 1H), 2.53 (s, 3H), 1.84 (d, J=6.9 Hz, 3H), 1.20 (s, 1H). (Compound 117) LCMS: 509 [M+H]$^+$. $^1$H NMR (400 MHz, DMSO-d$_6$) δ 11.04 (s, 1H), 8.17 (s, 1H), 8.06 (d, J=8.3 Hz, 1H), 8.02 (s, 1H), 7.92-7.81 (m, 2H), 7.70 (d, J=7.7 Hz, 2H), 7.39 (d, J=7.0 Hz, 2H), 5.90 (q, J=6.9 Hz, 1H), 2.53 (s, 3H), 1.84 (d, J=6.9 Hz, 3H), 1.20 (s, 1H).

Example S63. Synthesis of N-(1-(2,4-bis(trifluoromethyl)benzyl)-1H-pyrazol-4-yl)-2-(pyridin-2-yl)thiazole-5-carboxamide (Compound 118)

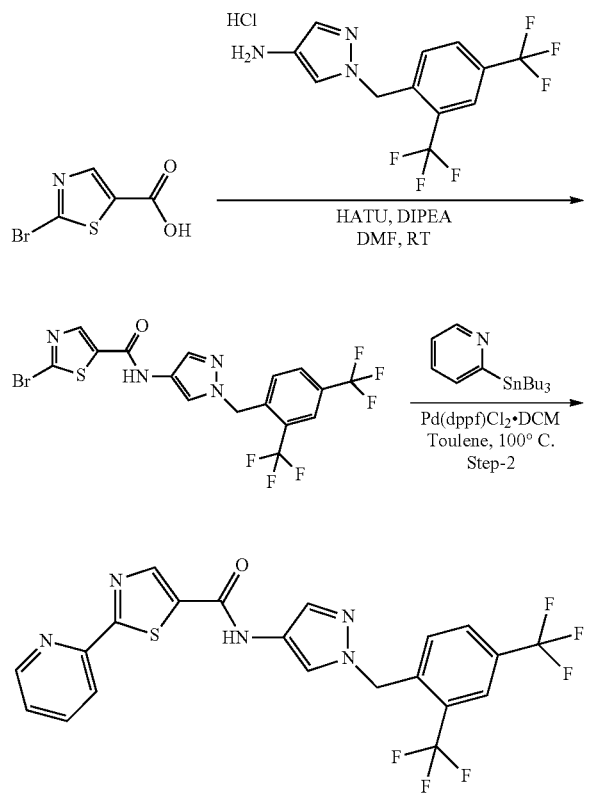

Step 1: Synthesis of N-(1-(2,4-bis(trifluoromethyl)benzyl)-1H-pyrazol-4-yl)-2-bromothiazole-5-carboxamide. To a solution of 2-bromothiazole-5-carboxylic acid (200 mg, 0.96 mmol, 1 equiv) and HATU (401 mg, 1.05 mmol, 1.1 equiv) in DMF (1 mL). The mixture was allow to stir for 30 mins followed by the addition of DIPEA (396 mg, 3.07 mmol, 3.2 equiv) and a solution of the 1-(2,4-bis(trifluoromethyl)benzyl)-1H-pyrazol-4-amine hydrochloride (330 mg, 0.96 mmol, 1 equiv) in DMF (5 mL) was added. The reaction mixture was kept under stirring for 24 hrs at RT. Product formation was confirmed with TLC and LCMS and reaction mixture was diluted EtOAc (50 mL) and washed with water (2×50 mL). Organic layer dried over anhydrous Na$_2$SO$_4$ and concentrated under reduced pressure to obtain crude which was further purified by flash column chromatography to obtain pure product N-(1-(2,4-bis(trifluoromethyl)benzyl)-1H-pyrazol-4-yl)-2-bromothiazole-5-carboxamide as off white solid) (250 mg). LCMS: 500 [M+H]$^+$.

Step 2: N-(1-(2,4-bis(trifluoromethyl)benzyl)-1H-pyrazol-4-yl)-2-(pyridin-2-yl)thiazole-5-carboxamide. To a solution of N-(1-(2,4-bis(trifluoromethyl)benzyl)-1H-pyrazol-4-yl)-2-bromothiazole-5-carboxamide (200 mg, 0.40 mmol, 1 equiv) in dry toluene (5 mL) was added the 2-(tributylstannyl)pyridine (147 mg, 0.40 mmol, 1 equiv), and the mixture was degassed for 10 min. To this mixture was added Pd(Pppf)Cl$_2$·DCM (32 mg, 0.040 mmol, 0.1 equiv), and the mixture was again degassed for 5 min. The reaction mixture was stirred at 100° C. for overnight, after which time TLC indicated complete consumption of the starting material. The mixture was quenched with H$_2$O (mL), extracted with EtOAc (2×50 mL), dried over anhydrous Na$_2$SO$_4$), and concentrated in vacuo to provide the product which was further purified by flash column chromatography (EtOAc/Hexane) and reverse phase HPLC to obtain pure product N-(1-(2,4-bis(trifluoromethyl)benzyl)-1H-pyrazol-4-yl)-2-(pyridin-2-yl)thiazole-5-carboxamide as off white solid (20 mg). LCMS: 497 [M+H]$^+$. $^1$H NMR (400 MHz, DMSO-d$_6$) δ=10.85 (s, 1H), 8.69 (d, J=4.8 Hz, 1H), 8.62 (s, 1H), 8.27 (s, 1H), 8.19 (d, J=7.9 Hz, 1H), 8.11-8.05 (m, 2H), 8.02 (t, J=7.9 Hz, 1H), 7.73 (s, 1H), 7.60-7.54 (m, 1H), 7.09 (d, J=8.3 Hz, 1H), 5.66 (s, 2H).

Example S64. Synthesis of (R)—N-(1-(1-(2,4-bis(trifluoromethyl)phenyl)ethyl)-1H-pyrazol-4-yl)-5-(6-methylpyridin-2-yl)isoxazole-3-carboxamide and (S)—N-(1-(1-(2,4-bis(trifluoromethyl)phenyl)ethyl)-1H-pyrazol-4-yl)-5-(6-methylpyridin-2-yl)isoxazole-3-carboxamide (Compounds 119 & 120)

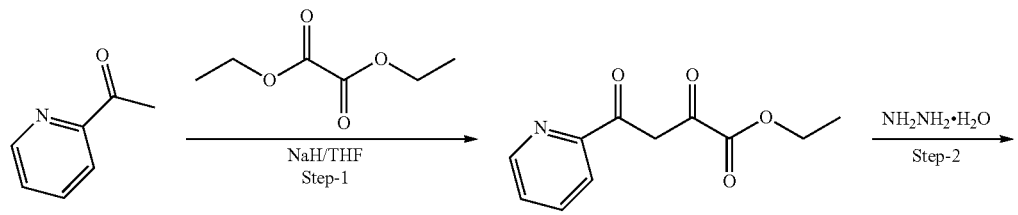

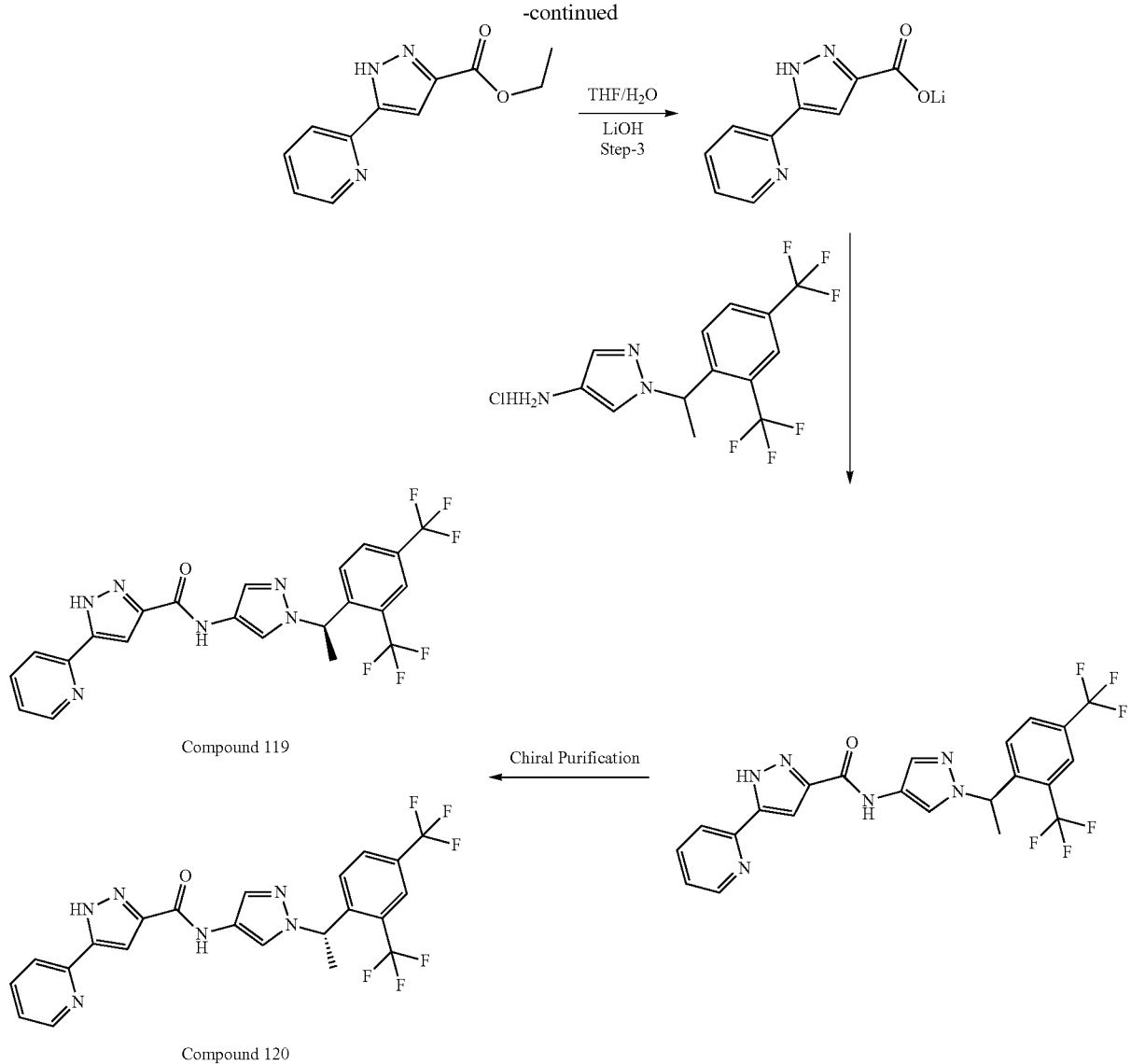

Step-1: Synthesis of ethyl 2,4-dioxo-4-(pyridin-2-yl)butanoate. To a solution of Sodium hydride (60%, 1.48 g, 0.061 mol, 1.5 equiv) in Toluene (20 ml) at 0° C., was added 1-(pyridin-2-yl)ethan-1-one (5.0 g, 0.041 mol, 1 equiv) was added drop wise to the reaction mixture at 0° C. The resultant reaction mixture was stirred for another 30 minutes at room temperature, followed by drop wise addition of diethyl oxalate (9.04 g, 0.061 mol, 1 equiv) at 0° C. and reaction mixture was stir for another 2 hours at room temperature. Product formation was confirmed by TLC and LCMS. The reaction mixture was quenched with ice water and neutralized with 1N HCl and extracted with EtOAc (3×100 mL). Combined organic layers were washed with water (2×100 mL), dried over anhydrous $Na_2SO_4$ and concentrated under reduced pressure to obtain crude which was purified by combi-flash chromatography (10-20% Ethyl acetate in hexane) to obtain ethyl 2,4-dioxo-4-(pyridin-2-yl)butanoate as yellow solid (4.2 g). LCMS: 222 [M+H]$^+$.

Step 2: Synthesis of ethyl 5-(pyridin-2-yl)-1H-pyrazole-3-carboxylate. A suspension of ethyl 2,4-dioxo-4-(pyridin-2-yl)butanoate (1.5 g, 0.006 mol, 1 equiv) and hydrazine hydrate (0.339 g, 0.006 mmol, 1.0 equiv) in EtOH (20 ml) was stirred at 85° C. for overnight. Product formation was confirmed by TLC and LCMS. The resulting mixture was concentrated under reduced pressure, the residue was dissolved in ethyl acetate and distilled water. Organic phase was separated, dried over anhydrous $Na_2SO_4$ and it was concentrated under reduced pressure to give crude. The crude product was purified using flash column chromatography using solvent system (10-20% Ethyl acetate in hexane) to obtain ethyl 5-(pyridin-2-yl)-1H-pyrazole-3-carboxylate (650 mg, 44% as off white solid). LCMS: 218 [M+H]$^+$.

Step 3: Synthesis of lithium 5-(pyridin-2-yl)-1H-pyrazole-3-carboxylate. To a solution of ethyl 5-(pyridin-2-yl)-1H-pyrazole-3-carboxylate (500 mg, 2.30 mmol, 1.0 equiv) in THF (5 mL) and water (2 mL) was added in lithium hydroxide (145 mg, 3.45 mmol, 1.5 equiv). The resulting mixture was stirred for 16 hours. Reaction mass was concentrated under reduced pressure. The resulting residue was acidified with 1N HCl and extracted with ethyl acetate (3×100 mL). Combined organic layer were washed with distilled water, dried over anhydrous Na₂SO₄ and concentrated under reduced pressure to obtain lithium 5-(pyridin-2-yl)-1H-pyrazole-3-carboxylate as white solid (510 mg). LCMS: 190 [M+H]⁺.

Step 4: Synthesis of N-(1-(1-(2,4-bis(trifluoromethyl)phenyl)ethyl)-1H-pyrazol-4-yl)-5-(pyridin-2-yl)-1H-pyrazole-3-carboxamide. To a solution of lithium 5-(pyridin-2-yl)-1H-pyrazole-3-carboxylate (200 mg, 1.025 mmol, 1 equiv) and HATU (428 mg, 1.12 mmol, 1 equiv) in DMF (1 mL). The mixture was allow to stir for 30 mins followed by the addition of DIPEA (423 mg, 3.28 mmol, 3.2 equiv) and a solution of the 1-(1-(2,4-bis(trifluoromethyl)phenyl)ethyl)-1H-pyrazol-4-amine Hydrochloride (367 mg, 1.025 mmol, 1 equiv) in DMF (1 mL) was added. The reaction mixture was kept under stirring for 24 h at RT. Product formation was confirmed with TLC AND LCMS and reaction mixture was diluted EtOAc (50 mL) and washed with water (2×50 mL). Organic layer dried over Na₂SO₄ and concentrated under reduced pressure to obtain crude which was further purified by flash column chromatography to obtain pure product N-(1-(1-(2,4-bis(trifluoromethyl)phenyl)ethyl)-1H-pyrazol-4-yl)-5-(pyridin-2-yl)-1H-pyrazole-3-carboxamide as off white solid (120 mg). LCMS: 495 [M+H]⁺. ¹H NMR (400 MHz, DMSO-d₆) δ 10.46 (s, 1H), 8.63 (dd, J=21.4, 4.9 Hz, 1H), 8.16 (d, J=8.2 Hz, 1H), 8.08 (d, J=8.3 Hz, 1H), 8.05 (s, 1H), 7.95 (dq, J=15.5, 8.2 Hz, 2H), 7.77 (s, 1H), 7.72 (q, J=5.4 Hz, 1H), 7.40 (t, J=6.2 Hz, 1H), 7.33 (s, 1H), 5.91 (p, J=7.5 Hz, 1H), 1.86 (d, J=6.7 Hz, 3H).

Step 5: Synthesis of (R) and (S) N-(1-(1-(2,4-bis(trifluoromethyl)phenyl)ethyl)-1H-pyrazol-4-yl)-5-(pyridin-2-yl)-1H-pyrazole-3-carboxamide. The enantiomers of N-(1-(1-(2,4-bis(trifluoromethyl)phenyl)ethyl)-1H-pyrazol-4-yl)-5-(pyridin-2-yl)-1H-pyrazole-3-carboxamide (110 mg, elution time: 4.86 min & 3.3 min), were separated by chiral SFC (Daicel Chiralcel®-ODH, 250×20 mm, 5 µm). Isocratic program with analytical grade liquid carbon dioxide and HPLC grade Isopropanol, Total flow: 56 g/min, Co-Solvent Percentage: 20% to obtained Peak-1 as (R)—N-(1-(1-(2,4-bis(trifluoromethyl)phenyl)ethyl)-1H-pyrazol-4-yl)-5-(pyridin-2-yl)-1H-pyrazole-3-carboxamide (35 mg) and Peak-2 as (S)—N-(1-(1-(2,4-bis(trifluoromethyl)phenyl)ethyl)-1H-pyrazol-4-yl)-5-(pyridin-2-yl)-1H-pyrazole-3-carboxamide (36 mg). (Compound 119) LCMS: 495 [M+H]⁺. ¹H NMR (400 MHz, DMSO-d₆) δ 10.46 (s, 1H), 8.63 (dd, J=21.4, 4.9 Hz, 1H), 8.16 (d, J=8.2 Hz, 1H), 8.08 (d, J=8.3 Hz, 1H), 8.05 (s, 1H), 7.95 (dq, J=15.5, 8.2 Hz, 2H), 7.77 (s, 1H), 7.72 (q, J=5.4 Hz, 1H), 7.40 (t, J=6.2 Hz, 1H), 7.33 (s, 1H), 5.91 (p, J=7.5 Hz, 1H), 1.86 (d, J=6.7 Hz, 3H). (Compound 120) LCMS: 495 [M+H]⁺. ¹H NMR (400 MHz, DMSO-d₆) δ 10.46 (s, 1H), 8.63 (dd, J=21.4, 4.9 Hz, 1H), 8.16 (d, J=8.2 Hz, 1H), 8.08 (d, J=8.3 Hz, 1H), 8.05 (s, 1H), 7.95 (dq, J=15.5, 8.2 Hz, 2H), 7.77 (s, 1H), 7.72 (q, J=5.4 Hz, 1H), 7.40 (t, J=6.2 Hz, 1H), 7.33 (s, 1H), 5.91 (p, J=7.5 Hz, 1H), 1.86 (d, J=6.7 Hz, 3H).

Example S65. Synthesis of (R)—N-(1-(1-(2,4-bis(trifluoromethyl)phenyl)ethyl-1H-pyrazol-4-yl)-1-(pyridin-2-yl)-1H-1,2,3-triazole-4-carboxamide and (S)—N-(1-(1-(2,4-bis(trifluoromethyl)phenyl)ethyl)-1H-pyrazol-4-yl)-1-(pyridin-2-yl)-1H-1,2,3-triazole-4-carboxamide (Compounds 121 & 122)

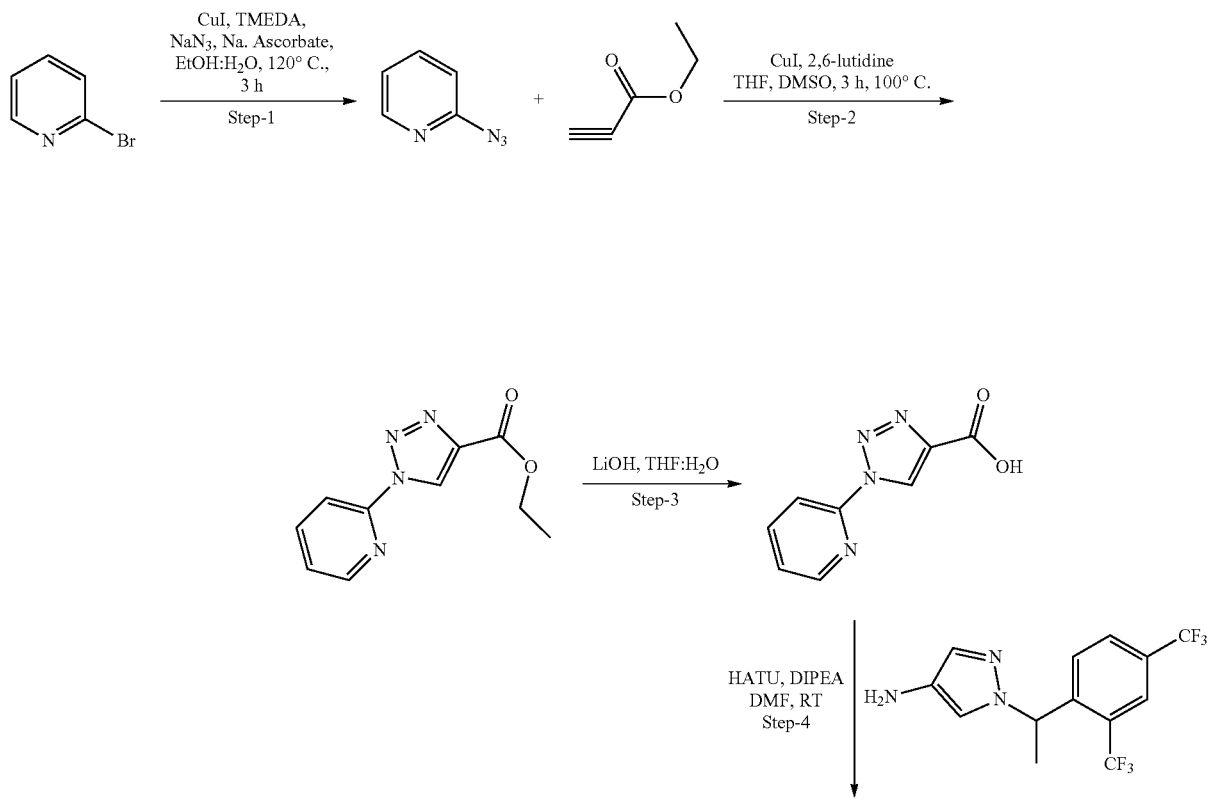

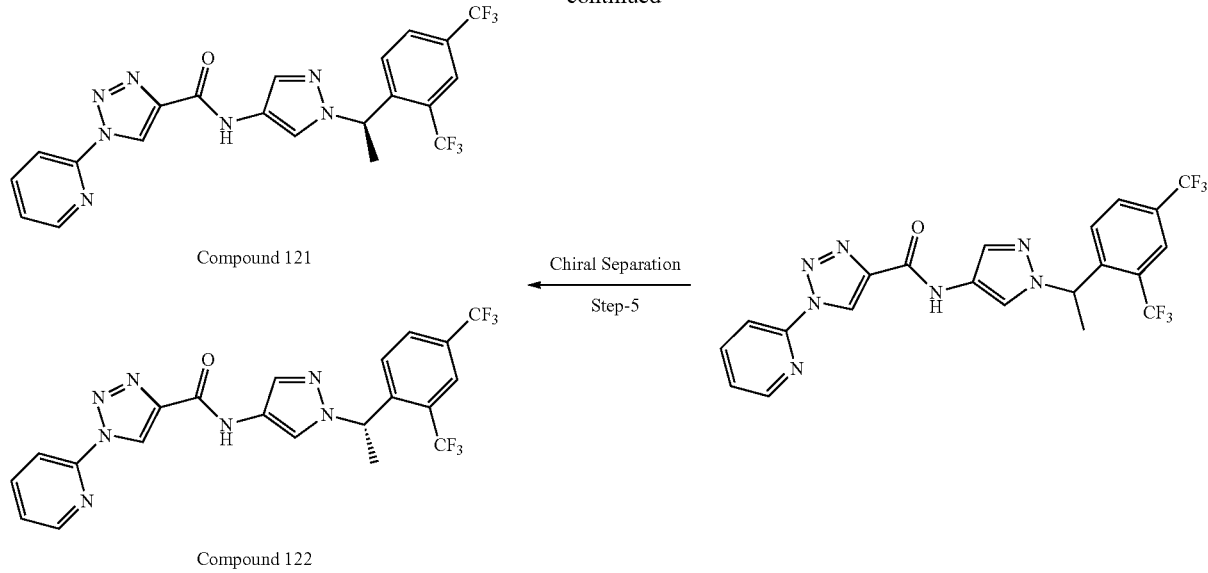

Compound 121

Chiral Separation
Step-5

Compound 122

Step 1: Synthesis of 2-azidopyridine. To a stirred solution of 2-bromopyridine (500 mg, 3.184 mmol, 1.0 eq), Sodium azide (227.7 mg, 3.5 mmol, 1.1 eq.), Sodium ascorbate (315.2 mg, 1.5 mmol, 0.5 eq), TMEDA (0.195 ml, 1.227 mmol, 0.4 eq) in EtOH: $H_2O$ was added CuI (121 mg, 0.636 mmol, 0.2 eq) and stirred for 10 minutes under $N_2$. The reaction mixture was allowed to stir for 3 h at 120° C. Product formation was confirmed by TLC and NMR. After completion of reaction, reaction mixture was dried to evaporate ethanol, extracted with DCM (3×10 mL), dried over anhydrous $Na_2SO_4$ and concentrated under reduced pressure to obtain crude which was purified by flash chromatography (EtOAc/Hexane) to obtain 2-azidopyridine as green solid (200 mg). LCMS: 121 $[M+H]^+$.

Step 2: Synthesis of Ethyl 1-(pyridine-2-yl)-1H-1,2,3-triazole-4-carboxylate. To a stirred solution of 2-azidopyridine (100 mg, 0.83 mmol, 1 eq), ethyl propiolate (2,6-lutidine (17.8 mg, 0.166 mmol, 0.2 equiv) in THF: DMSO (2 mL) was added CuI (31.5 mg, 0.166 mmol, equiv) under $N_2$. The reaction mixture was stirred at 100° C. for 3 hrs. Product formation was confirmed with TLC and LCMS. After completion of reaction mixture were diluted with EtOAc (50 mL) and washed with water (3×10 mL). Organic layer dried over $Na_2SO_4$ and concentrated under reduced pressure to obtain crude which was further purified by flash column chromatography (EtOAc/Hexane) to obtain pure product ethyl 1-(pyridine-2-yl)-1H-1,2,3-triazole-4-carboxylate as green solid (50 mg). LCMS: 219 $[M+H]^+$.

Step 3: Synthesis of 1-(pyridine-2-yl)-1H-1,2,3-triazole-4-carboxylic acid. To a stirred solution of Ethyl 1-(pyridine-2-yl)-1H-1,2,3-triazole-4-carboxylate (50 mg, 1.41 mmol, 1.0 eq) in THF: $H_2O$ (2 mL) was added LiOH (1.5 eq). The reaction mixture was then allowed to stir for 1 hrs at room temperature. Product formation was confirmed by LCMS. After the completion of reaction, reaction mixture was concentrated to evaporate $H_2O$, and acidified with HCl, filtered and dried under vacuum to obtain 1-(pyridine-2-yl)-1H-1,2,3-triazole-4-carboxylic acid as off white solid (40 mg). LCMS: 191 $[M+H]^+$.

Step 4: Synthesis of N-(1-(1-(2,4-bis(trifluoromethyl) phenyl)ethyl)-1H-pyrazol-4-yl)-1-(pyridine-2-yl)-1H-1,2,3-triazole-4-carboxamide. To a solution of 1-(pyridine-2-yl)-1H-1,2,3-triazole-4-carboxylic acid (25 mg, 0.13 mmol, 1 eq) in DMF (1 mL), were added HATU (49.5 mg, 0.13 mmol, 1 eq). The mixture was treated drop wise with DIPEA (50 mg, 0.39 mmol, 3 eq). After stirring at RT for 15 minutes, the mixture was treated drop wise with a solution of 1-(1-(2,4-bis(trifluoromethyl)phenyl)ethyl)-1H-pyrazol-4-amine (42.63 mg, 1.13 mmol, 1 eq) in DMF (1 mL). The reaction mixture was kept under stirring for 24 hrs. Product formation was confirmed with TLC and LCMS and reaction mixture was diluted EtOAc (10 mL) and washed with water (2×10 mL). Organic layer dried over anhydrous $Na_2SO_4$ and concentrated under reduced pressure to obtain crude which was further purified by flash column chromatography to obtain title compound N-(1-(1-(2,4-bis(trifluoromethyl) phenyl)ethyl)-1H-pyrazol-4-yl)-1-(pyridine-2-yl)-1H-1,2,3-triazole-4-carboxamide as grey solid (45 mg). LCMS: 496 $[M+H]^+$. $^1$H NMR (400 MHz, DMSO-$d_6$) δ 11.06 (s, 1H), 8.76 (d, J=4.8 Hz, 1H), 8.13 (s, 1H), 8.08 (d, J=7.9 Hz, 1H), 8.04 (dt, J=9.6, 4.8 Hz, 1H), 7.73 (s, 1H), 7.69-7.60 (m, 2H), 7.57 (dt, J=7.3, 3.7 Hz, 2H), 7.46 (s, 1H), 5.83 (q, J=6.9 Hz, 1H), 1.83 (d, J=6.9 Hz, 3H).

Step 5: Synthesis of R and S—N-(1-(1-(2,4-bis(trifluoromethyl) phenyl)ethyl)-1H-pyrazol-4-yl)-1-(pyridine-2-yl)-1H-1,2,3-triazole-4-carboxamide. The enantiomers of N-(1-(1-(2,4-bis (trifluoromethyl) phenyl)ethyl)-1H-pyrazol-4-yl)-1-(pyridine-2-yl)-1H-1,2,3-triazole-4-carboxamide (40 mg) (elution time: 12.6 min & 19.7 min), were separated by chiral SFC (Daicel Chiralpak®-IC, 250×20 mm, 5 μm). Isocratic program with analytical grade liquid carbon dioxide and HPLC grade Isopropanol, Total flow: 51 g/min, Co-Solvent Percentage: 18% to obtained Peak-1 as (R)—N-(1-(1-(2,4-bis(trifluoromethyl) phenyl)ethyl)-1H-pyrazol-4-yl)-1-(pyridine-2-yl)-1H-1,2,3-triazole-4-carboxamide (10 mg) and Peak-2 as (S)—N-(1-(1-(2,4-bis(trifluoromethyl) phenyl)ethyl)-1H-pyrazol-4-yl)-1-(pyridine-2-yl)-1H-1,2,3-triazole-4-carboxamide (12 mg). LCMS: 496 $[M+H]^+$. (Compound 125) $^1$H NMR (400 MHz, DMSO-$d_6$) δ 11.07 (s, 1H), 8.76 (d, J=4.7 Hz, 1H), 8.13 (s, 1H), 8.08 (d, J=7.8 Hz, 1H), 8.03 (dd, J=8.2, 6.4 Hz, 1H), 7.73 (s, 1H), 7.69-7.60 (m, 2H), 7.57 (dt, J=7.3, 3.9 Hz, 2H), 7.46 (s, 1H), 5.83 (q, J=7.0 Hz, 1H), 1.83 (d, J=6.9 Hz, 3H). (Compound 126) $^1$H NMR (400 MHz, DMSO-$d_6$) δ 11.06 (s, 1H), 8.76

(d, J=4.8 Hz, 1H), 8.13 (s, 1H), 8.08 (d, J=7.9 Hz, 1H), 8.04 (dt, J=9.6, 4.8 Hz, 1H), 7.73 (s, 1H), 7.69-7.60 (m, 2H), 7.57 (dt, J=7.3, 3.7 Hz, 2H), 7.46 (s, 1H), 5.83 (q, J=6.9 Hz, 1H), 1.83 (d, J=6.9 Hz, 3H).

Example S66. Synthesis of (R)—N-(1-(1-(2,4-bis(trifluoromethyl)phenyl)ethyl)-1H-pyrazol-4-yl)-5-(pyridin-2-yl)-1,3,4-thiadiazole-2-carboxamide and (S)—N-(1-(1-(2,4-bis(trifluoromethyl)phenyl)ethyl)-1H-pyrazol-4-yl)-5-(pyridin-2-yl)-1,3,4-thiadiazole-2-carboxamide (Compounds 123 & 124)

were triturated with hexane to obtain picolinohydrazide as white Solid (1.5 g). $^1$H NMR (400 MHz, DMSO-d$_6$) δ 9.86 (br. s., 1H), 8.61 (d, J=4.82 Hz, 1H), 7.91-8.02 (m, 2H), 7.53-7.60 (m, 1H), 4.56 (br. s., 2H)

Synthesis of ethyl 2-oxo-2-(2-picolinoylhydrazinyl)acetate. To the stirred solution Picolinohydrazide (1.5 g, 0.0109 mole, 1 equiv) in DCM at 0° C. was added TEA (1.32 gm, 0.0131 mole, 1 equiv). Reaction mixture was kept on stirring at 0° C. for 30 minutes. The reaction mixture was added Ethyl 2-chloro-2-oxoacetate (1.5 gm, 0.0109 mole, 1 equiv) at the same temperature. The Reaction mixture was stirred at 0° C. for an hour. Reaction was monitored by

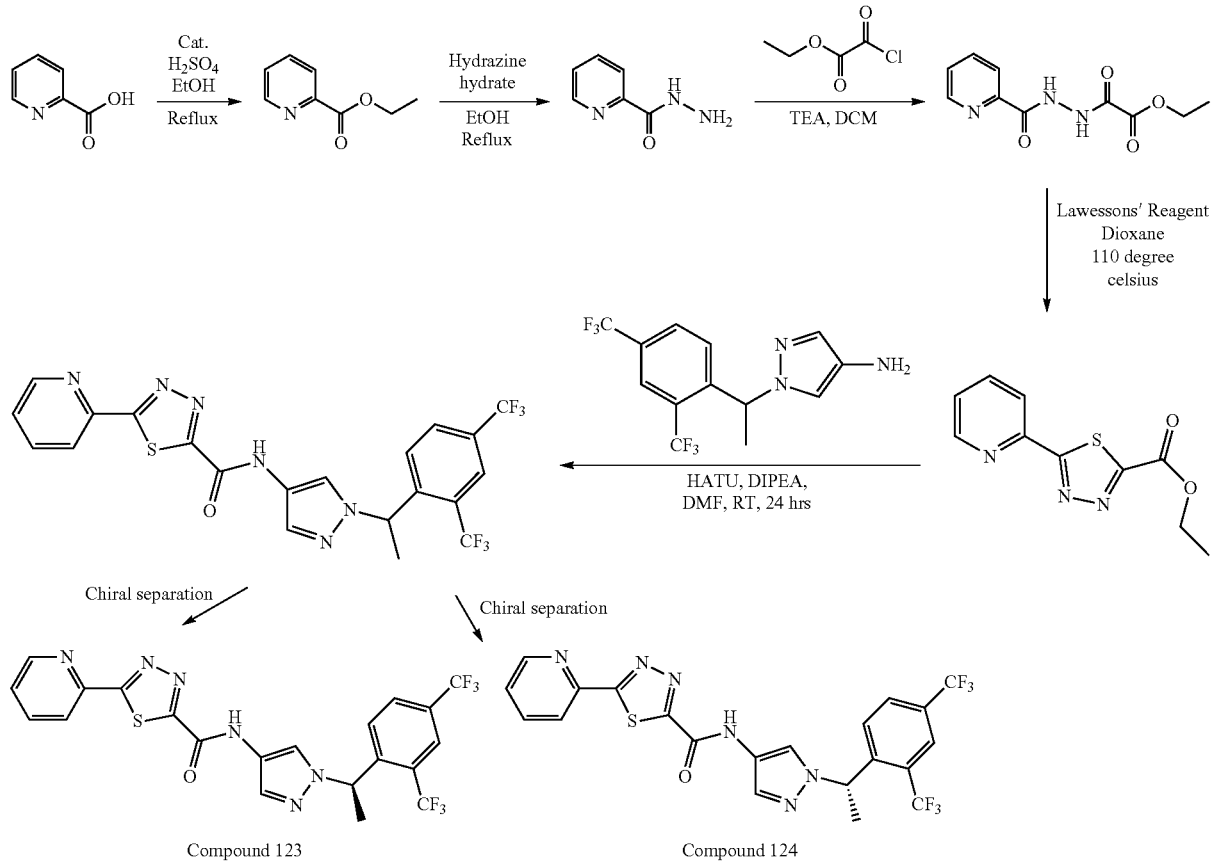

Compound 123

Compound 124

Synthesis of ethyl picolinate. To the stirred solution of picolinic acid (2 g) Ethanol (30 ml) was added conc H$_2$SO$_4$ (1 mL) and the reaction mixture was refluxed 2 days AT 100° C. Reaction was monitored by TLC and LCMS. The solvent was evaporated and crude reaction mixture was neutralized with aqueous NaHCO$_3$. Extraction was done with DCM (3×150 mL). The organic layers were collected, dried over anhydrous Na$_2$SO$_4$ and evaporated to obtain title compound ethyl picolinate transparent oil (1.8 g). $^1$H NMR (400 MHz, DMSO-d$_6$) δ ppm 8.72 (d, J=4.38 Hz, 1H), 8.01-8.09 (m, 1H), 7.96-8.01 (m, 1H), 7.60-7.68 (m, 1H), 4.35 (q, J=7.02 Hz, 2H), 1.33 (t, J=7.24 Hz, 3H).

Synthesis of picolinohydrazide. To the stirred solution of Ethyl picolinate (1.8 gm, 0.0119 moles, 1 equiv) in ethanol (20 mL) was added hydrazine Hydrate (0.715 g, 0.0143 mole, 1.2 equiv) was added. The reaction mixture was refluxed for 3 hour. Reaction was monitored by TLC and LCMS. The solvent was evaporated to obtain product which LCMS. Reaction was quenched by ice-water (30 mL). The product was extracted with DCM (2×100 ml). The organic layers were collected, dried over anhydrous Na$_2$SO$_4$ and evaporated under reduced pressure to obtain crude which was triturated with hexane to obtain title compound as free base (2.2 g). $^1$H NMR (400 MHz, DMSO-d$_6$) δ 10.94 (br. s., 1H), 10.75 (s, 1H), 8.69 (d, J=4.38 Hz, 1H), 8.04 (d, J=3.95 Hz, 2H), 7.62-7.72 (m, 1H), 4.30 (q, J=7.02 Hz, 2H), 1.31 (t, J=7.24 Hz, 3H).

Synthesis of ethyl 5-(pyridin-2-yl)-1,3,4-thiadiazole-2-carboxylate. To stirred solution of Ethyl 2-oxo-2-(2-picolinoylhydrazinyl) acetate (100 mg, 1 eq, and 0.421 mmoles) in Dioxane (4 ml) was added Lawessons' reagent (426.16 mg, 2.5 eq, and 1.05 mmoles). Reaction Mixture was kept on Stirring at 110° C. for 24 hour. Reaction was monitored by LCMS. The reaction mixture was quenched with aq. NaHCoO$_3$ (30 mL). Product was extraction with diethyl ether (3×75 mL). The organic layers were collected, dried over anhydrous Na$_2$SO$_4$ and evaporated under reduced pressure to obtain crude which was purified by Flash Chromatography to obtain title compound ethyl 5-(pyridin-2-yl)-1, 3, 4-thiadiazole-2-carboxylate pale yellow solid (60 mg). $^1$H NMR (400 MHz, DMSO-d$_6$) δ 8.76 (d, J=4.89 Hz, 1H), 8.37 (d, J=8.31 Hz, 1H), 8.10 (dt, J=1.71, 7.70 Hz, 1H), 7.63-7.69 (m, 1H), 4.46 (q, J=7.34 Hz, 2H), 1.32-1.40 (m, 3H).

Synthesis of N-(1-(1-(2,4-bis(trifluoromethyl)phenyl)ethyl)-1H-pyrazol-4-yl)-5-(pyridin-2-yl)-1,3,4-thiadiazole-2-carboxamide. To a solution of ethyl 5-(pyridin-2-yl)-1,3,4-thiadiazole-2-carboxylate (50 mg, 0.212 mmol, 1 equiv) in Toluene (1 mL), was added 1-(1-(2,4-bis(trifluoromethyl)phenyl)ethyl)-1H-pyrazol-4-amine (68.7 mg, 0.212 mmol, 1 equiv) in toluene (1 mL). The mixture was treated drop wise with 2 M Trimethyl Aluminium in toluene (61.056 mg, 0.848 mmol, 4 equiv). The reaction mixture was kept under stirring for 24 h. The reaction mixture was diluted water (50 mL). The resulting suspension was filtered off and extracted with ethyl Acetate (2×50 ml). Obtained organic layer was concentrated was concentrated to obtain crude which was purified by Combi-Flash Chromatography (EtOAc/Hexane0 to obtain title product as free base. LCMS: 501 [M+H]$^+$.

Enatiomer separations of N-(1-(1-(2,4-bis(trifluoromethyl)phenyl)ethyl)-1H-pyrazol-4-yl)-5-(pyridin-2-yl)-1,3,4-thiadiazole-2-carboxamide. The enantiomers of N-(1-(1-(2,4-bis(trifluoromethyl)phenyl)ethyl)-1H-pyrazol-4-yl)-5-(pyridin-2-yl)-1,3,4-thiadiazole-2-carboxamide (elution time: 5.47 min & 6.75 min), were separated by chiral SFC (Daicel Chiralcel®-ODH, 250×20 mm, 5 µm). Isocratic program with analytical grade liquid carbon dioxide and HPLC grade Isopropanol, Total flow: 56 g/min, Co-Solvent Percentage: 18% to obtained Peak-1 as (R)—N-(1-(1-(2,4-bis(trifluoromethyl)phenyl)ethyl)-1H-pyrazol-4-yl)-5-(pyridin-2-yl)-1,3,4-thiadiazole-2-carboxamide (8 mg) Peak-2 as (S)—N-(1-(1-(2,4-bis(trifluoromethyl)phenyl)ethyl)-1H-pyrazol-4-yl)-5-(pyridin-2-yl)-1,3,4-thiadiazole-2-carboxamide (6 mg). (Compound 123) $^1$H NMR (400 MHz, DMSO-d$_6$) δ 11.59 (s, 1H), 8.76 (d, J=4.40 Hz, 1H), 8.35 (d, J=7.83 Hz, 1H), 8.23 (s, 1H), 8.03-8.12 (m, 4H), 7.82 (s, 1H), 7.74 (d, J=8.31 Hz, 1H), 7.66 (d, J=6.36 Hz, 1H), 5.93 (s, 1H), 1.88 (d, J=6.85 Hz, 3H). (Compound 124) $^1$H NMR (400 MHz, DMSO-d$_6$) δ 11.59 (s, 1H), 8.76 (d, J=4.89 Hz, 1H), 8.35 (d, J=8.31 Hz, 1H), 8.23 (s, 1H), 8.03-8.12 (m, 3H), 7.82 (s, 1H), 7.74 (d, J=8.31 Hz, 1H), 7.62-7.68 (m, 1H), 5.94 (d, J=7.34 Hz, 1H), 1.88 (d, J=6.85 Hz, 3H).

Example S67. Synthesis of (R)—N-(1-(1-(2,4-bis(trifluoromethyl)phenyl)ethyl)-1H-pyrazol-4-yl)-2-(pyridin-2-yl)oxazole-4-carboxamide and (S)—N-(1-(1-(2,4-bis(trifluoromethyl)phenyl)ethyl)-1H-pyrazol-4-yl)-2-(pyridin-2-yl)oxazole-4-carboxamide (Compounds 125 & 126)

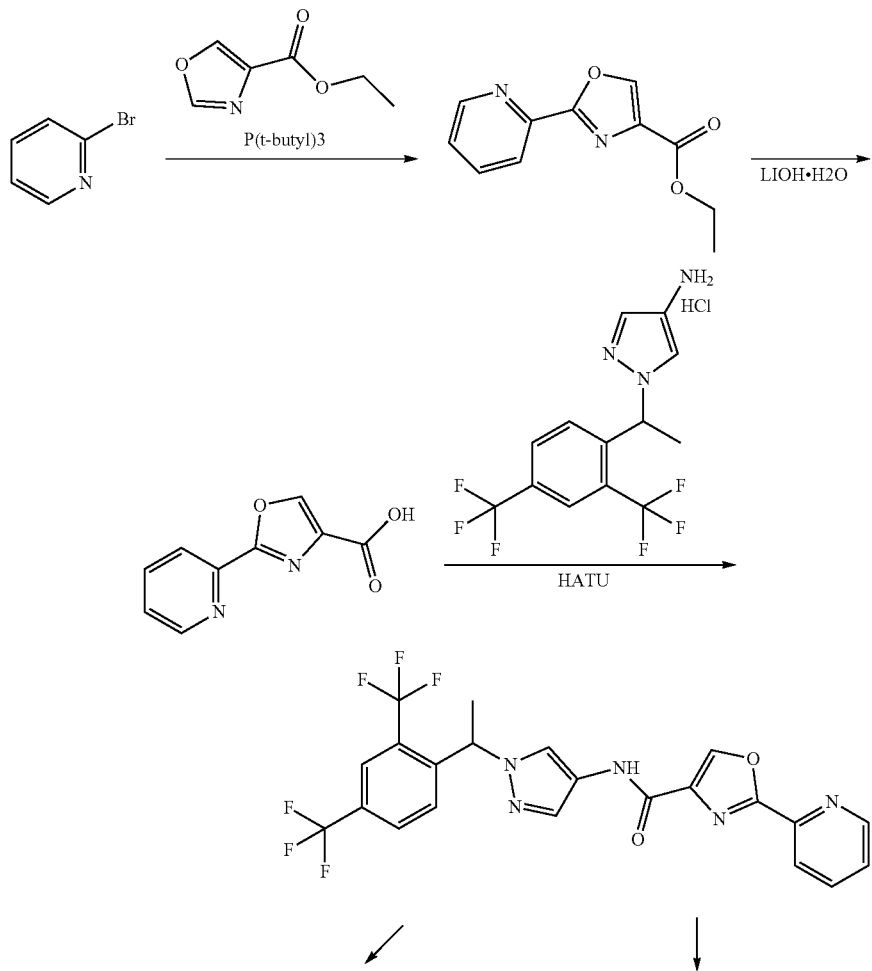

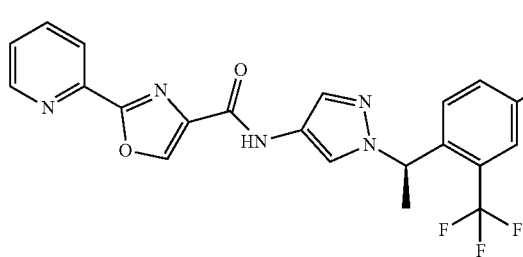

Compound 125

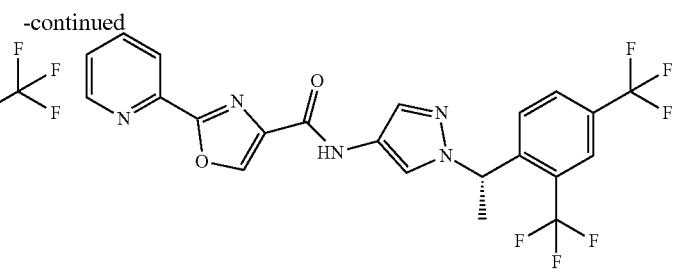

Compound 126

Step 1: Synthesis of ethyl 2-(pyridin-2-yl)oxazole-4-carboxylate. To a stirred suspension of 2-bromopyridine (500 mg, 3.1847 mol, 1 eq), ethyl oxazole-4-carboxylate (500 mg, 3.184 mmol, 1 eq), Cs₂CO₃ (2.5 eq, 2.59 gm, 7.96 mmol) in dioxane (10 mL) and water (2 mL) was purged with nitrogen for 5 minutes. P(o-tolyl)3 (193.6 mg, 0.63 mmol, 0.2 eq) was added to the reaction mixture, which was heated to 80° C. for 2 hours. The cooled reaction mixture was diluted with water, and then extracted with EtOAc. The combined EtOAc extracts was washed with water, dried over Na₂SO₄, filtered through pad of silica gel and concentrated. The residue was purified by using silica gel (eluting with 5-40% EtOAc/hexanes) to give ethyl 2-(pyridin-2-yl)oxazole-4-carboxylate (0.3 g). LCMS: 220 [M+H]⁺.

Step 2: Synthesis of 2-(pyridin-2-yl)oxazole-4-carboxylic acid. To a solution of ethyl 2-(pyridin-2-yl)oxazole-4-carboxylate (250 mg, 1.141 mmol, 1 eq) in THF (2 mL) and water (2 mL) was slowly added lithium hydroxide (54.79 mg, 1.369 mmol, 1.2 eq) The resulting mixture was stirred for 16 hrs. Reaction mixture was concentrated under reduced pressure to obtain crude which was acidified with 1N HCl and obtained suspension was lypolised. Obtained crude was triturated with ether. Obtained ppt. was our product (220 mg) 2-(pyridin-2-yl)oxazole-4-carboxylic acid (0.2 gm). LCMS: 191 [M+H]⁺.

Step 3: Synthesis of N-(1-(1-(2,4-bis(trifluoromethyl)phenyl)ethyl)-1H-pyrazol-4-yl)-2-(pyridin-2-yl)oxazole-4-carboxamide. To a solution of 2-(pyridin-2-yl)oxazole-4-carboxylic acid (100 mg, 0.526 mmol, 1 equiv) in DMF (2 mL), were added HATU (200.5 mg, 0.526 mmol, 1 equiv). The mixture was treated drop wise with DIPEA (203.6 mg, 1.57 mmol, 3 equiv). After stirring at RT for 15 minutes, the mixture was treated drop wise with a solution of the 1-(1-(2,4-bis(trifluoromethyl)phenyl)ethyl)-1H-pyrazol-4-amine hydrochloride (188.9 mg, 0.526 mmol, 1 equiv) in DMF (1 mL). The reaction mixture was kept under stirring for 24 h. The reaction mixture was diluted water (50 mL). The resulting precipitate was filtered off. Crude material obtained was purified by trituration with DCM:hexanes (2:8) to obtain N-(1-(1-(2,4-bis(trifluoromethyl)phenyl)ethyl)-1H-pyrazol-4-yl)-2-(pyridin-2-yl)oxazole-4-carboxamide. The enantiomers (elution time: 8.8 min and 11.5 min), were separated by chiral HPLC (Daicel Chiralpak®-ADH, 250× 20 mm, 5 µm). Isocratic program with HPLC grade n-Hexane and HPLC grade Isopropanol, Total flow: 18 ml/min, Isopropanol Percentage: 15% to obtained (R)N-(1-(1-(2,4-bis(trifluoromethyl)phenyl)ethyl)-1H-pyrazol-4-yl)-2-(pyridin-2-yl)oxazole-4-carboxamide (7 mg) and (S)N-(1-(1-(2,4-bis(trifluoromethyl)phenyl)ethyl)-1H-pyrazol-4-yl)-2-(pyridin-2-yl)oxazole-4-carboxamide (6 mg). LCMS: 497 [M+H]⁺. (Compound 125) ¹H NMR (400 MHz, DMSO-d₆) δ 10.61 (s, 1H), 8.87 (s, 1H), 8.75 (d, J=3.95 Hz, 1H), 8.17-8.24 (m, 2H), 7.98-8.12 (m, 3H), 7.81 (s, 1H), 7.74 (d, J=8.33 Hz, 1H), 7.51-7.63 (m, 1H), 5.92 (d, J=6.58 Hz, 1H), 1.87 (d, J=7.02 Hz, 3H). (Compound 126) ¹H NMR (400 MHz, DMSO-d₆) 1H NMR (400 MHz, DMSO-d₆) δ 10.61 (s, 1H), 8.87 (s, 1H), 8.76 (d, J=4.38 Hz, 1H), 8.14-8.23 (m, 2H), 7.98-8.14 (m, 3H), 7.81 (s, 1H), 7.74 (d, J=8.33 Hz, 1H), 7.55-7.64 (m, 1H), 5.92 (d, J=6.58 Hz, 1H), 1.87 (d, J=7.02 Hz, 3H).

Example S68. Synthesis of (R)—N-(1-(1-(2,4-bis(trifluoromethyl)phenyl)ethyl)-1H-pyrazol-4-yl)-2-(pyridin-2-yl)oxazole-5-carboxamide and (S)—N-(1-(1-(2,4-bis(trifluoromethyl)phenyl)ethyl)-1H-pyrazol-4-yl)-2-(pyridin-2-yl)oxazole-5-carboxamide (Compounds 127 & 128)

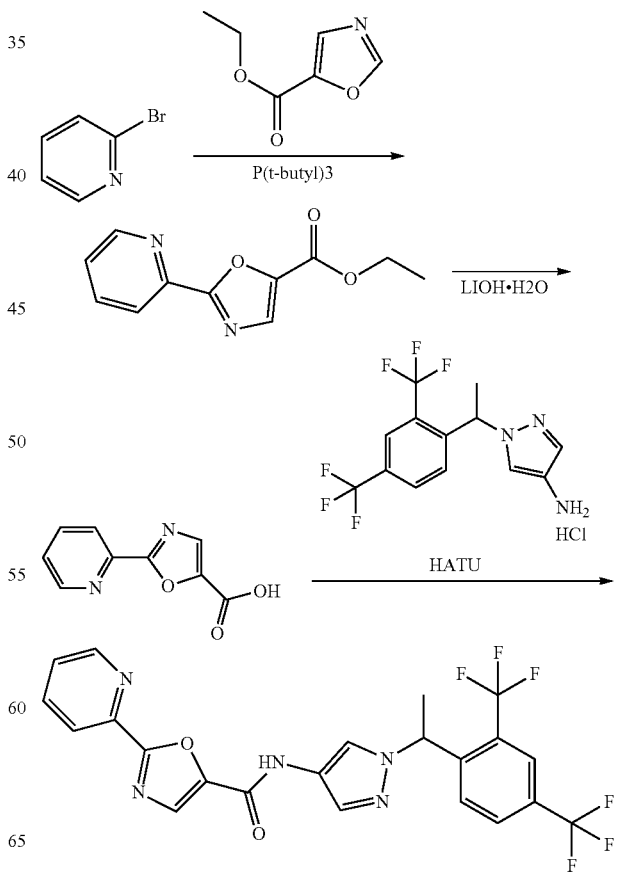

Compound 127

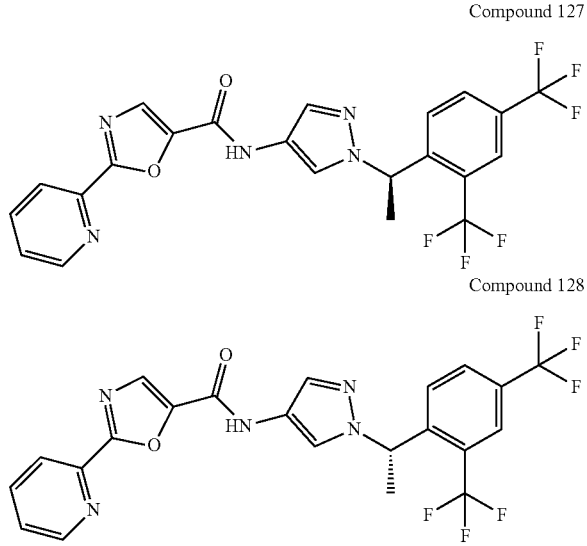

Compound 128

Step 1: Synthesis of ethyl 2-(pyridin-2-yl) oxazole-5-carboxylate. To a stirred suspension of 2-bromopyridine (450 mg, 0.005 mol, 1 eq) ethyl oxazole-5-carboxylate (450 mg, 2.86 mmol, 1 eq), $Cs_2CO_3$ (2.82 gm, 8.59 mmol, 3 eq), dioxane (10 mL) and water (2 mL) was purged with nitrogen for 5 minutes. P(t-Bu)3 (12.87 mg, 0.057. mmol, 0.2 eq) and $Pd(OAc)_2$ (12.873 mg, 0.057 mmol, 0.2 eq) was added to the reaction mixture, which was heated to 80° C. for 2 hours. The cooled reaction mixture was diluted with water, Extracted with EtOAc. The combined EtOAc extracts was washed with water, dried over $Na_2SO_4$, filtered through pad of silica gel and concentrated. The residue was chromatographed on silica gel plug eluting with 5-40% EtOAc/hexanes to give tert-butyl 3-(2-chloropyrimidin-4-yl)-2-methyl-1H-indole-1-carboxylate (0.2 gm). LCMS: 220 $[M+H]^+$.

Step 2: Synthesis of 2-(pyridin-2-yl)oxazole-5-carboxylic acid. To a solution of ethyl 2-(pyridin-2-yl)oxazole-5-carboxylate (200 mg, 0.913 mmol, 1 eq) in THF (2 mL) and water (2 mL) was slowly added lithium hydroxide (43.83 mg, 1.095 mmol, 1.2 eq) The resulting mixture was stirred for 16 hrs. Reaction mixture was concentrated under reduced pressure to obtain crude which was acidified with 1N HCl and obtained suspension was lypolised. Obtained crude was triturated with ether to obtained 2-(pyridin-2-yl)oxazole-5-carboxylic acid. (52 mg). LCMS: 191 $[M+H]^+$.

Step 3: Synthesis of N-(1-(1-(2,4-bis(trifluoromethyl) phenyl)ethyl)-1H-pyrazol-4-yl)-2-(pyridin-2-yl)oxazole-5-carboxamide. To a solution of 2-(pyridin-2-yl)oxazole-5-carboxylic acid (100 mg, 0.526 mmol, 1 equiv) in DMF (2 mL), were added HATU (200.5 mg, 0.526 mmol, 1 equiv). The mixture was treated drop wise with DIPEA (203.6 mg, 1.57 mmol, 3 equiv). After stirring at RT for 15 minutes, the mixture was treated drop wise with a solution of the 1-(1-(2,4-bis(trifluoromethyl)phenyl)ethyl)-1H-pyrazol-4-amine hydrochloride (188.9 mg, 0.526 mmol, 1 equiv) in DMF (1 mL). The reaction mixture was kept under stirring for 24 h. The reaction mixture was diluted water (50 mL). The resulting precipitate was filtered off, to obtain Crude material obtained was triturated with DCM:hexanes (2:8) to give N-(1-(1-(2,4-bis(trifluoromethyl)phenyl)ethyl)-1H-pyrazol-4-yl)-2-(pyridin-2-yl)oxazole-5-carboxamide. The enantiomers (elution time: 7.0 min and 8.8 min), were separated by chiral HPLC (Daicel Chiralpak®-ADH, 250×20 mm, 5 µm. Isocratic program with HPLC grade n-Hexane and HPLC grade Isopropanol, Total flow: 18 ml/min, Isopropanol Percentage: 15% to obtained (8 mg). (R)N-(1-(1-(2,4-bis(trifluoromethyl)phenyl)ethyl)-1H-pyrazol-4-yl)-2-(pyridin-2-yl)oxazole-5-carboxamide 6 mg (S)N-(1-(1-(2,4-bis(trifluoromethyl)phenyl)ethyl)-1H-pyrazol-4-yl)-2-(pyridin-2-yl)oxazole-5-carboxamide). LCMS: 497 $[M+H]^+$. (Compound 127) $^1H$ NMR (400 MHz, DMSO-$d_6$) δ10.84 (s, 1H), 8.77 (d, J=4.38 Hz, 1H), 8.22 (d, J=7.89 Hz, 1H), 8.17 (s, 1H), 7.97-8.11 (m, 4H), 7.70-7.78 (m, 2H), 7.60 (dd, J=5.26, 7.02 Hz, 1H), 5.86-5.97 (m, 1H), 1.87 (d, J=7.02 Hz, 3H). (Compound 128) $^1H$ NMR (400 MHz, DMSO-$d_6$) δ 10.84 (s, 1H), 8.77 (d, J=4.38 Hz, 1H), 8.23 (d, J=7.89 Hz, 1H), 8.18 (s, 1H), 7.97-8.13 (m, 4H), 7.70-7.79 (m, 2H), 7.61 (dd, J=5.26, 7.02 Hz, 1H), 5.88-5.98 (m, 1H), 1.88 (d, J=7.02 Hz, 3H).

Example S69. Synthesis of N-(1-(2,4-bis(trifluoromethyl)benzyl)-1H-pyrazol-4-yl)-5-(pyrimidin-2-yl)isoxazole-3-carboxamide (Compound 129)

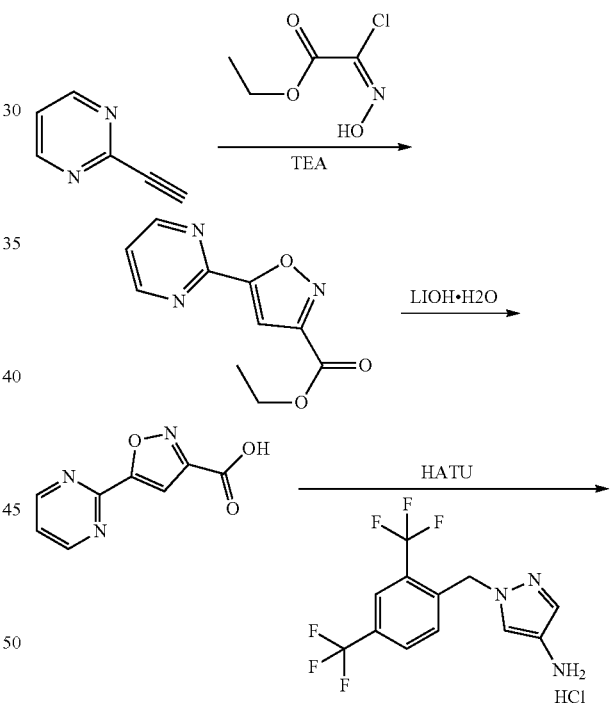

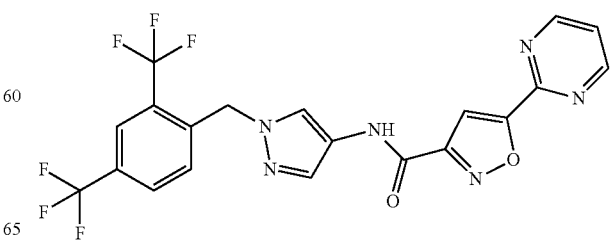

Step 1: Synthesis of ethyl 5-(pyrimidin-2-yl) isoxazole-3-carboxylate. To a stirred mixture of (Z)-ethyl 2-chloro-2-(hydroxyimino) acetate (200 mg, 1.21 mmole, 1 eq) and 2-ethynylpyrimidine (252.1 mg, 1.21 m mole, 1 eq) in ether (80 mL) at room temperature was added a solution of tri ethyl amine (0.337 mL, 2.42 m mole, 2 eq) in ether (20 mL) drop wise over 60 minutes. The reaction mixture was stirred for 2 h at room temperature. The reaction mixture was filtered, and the filtrate was concentrated to yellow oil which was purified by flash silica gel chromatography using a mixture of ethyl acetate in hexane to afford Ethyl 5-(pyrimidin-2-yl) isoxazole-3-carboxylate as a white solid (40 mg). LCMS: 220 [M+H]$^+$.

Step 2: Synthesis of 5-(pyrimidin-2-yl) isoxazole-3-carboxylic acid. To a solution of ethyl 5-(pyrimidin-2-yl) isoxazole-3-carboxylate (35 mg, 0.159 mmol, 1 eq) in THF (2 mL) and water (2 mL) was slowly added lithium hydroxide (7.631 mg, 0.190 mmol, 1.2 eq). The resulting mixture was stirred for 16 hrs. Reaction mixture was concentrated under reduced pressure to obtain crude which was acidified with 1N HCl and lypolised. After lypholisation obtained crude which was triturated with ether to obtained 5-(pyrimidin-2-yl) isoxazole-3-carboxylic acid (0.03 gm). LCMS: 191 [M+H]$^+$.

Step 3: Synthesis of N-(1-(1-(2,4-bis(trifluoromethyl)phenyl)ethyl)-1H-pyrazol-4-yl)-5-(pyrimidin-2-yl)isoxazole-3-carboxamide. To a stirred solution of 5-(pyrimidin-2-yl)isoxazole-3-carboxylic acid (30 mg, 0.157 mmol, 1 equiv) in DMF (2 mL), were added HATU (59.84 mg, 0.157 mmol, 1 equiv) and DIPEA (60.78 mg, 0.471 mmol, 3 equiv). After stirring at RT for 15 minutes, the mixture was added drop wise a solution of the 1-(2,4-bis(trifluoromethyl)benzyl)-1H-pyrazol-4-amine hydrochloride (54.18 mg, 0.157 mmol, 1 equiv) in DMF (1 mL). The reaction mixture was stirred for 24 h. The reaction mixture was diluted water (50 mL). The resulting precipitate was filtered off. Crude material obtained was purified by trituration with DCM: hexane (2:8) to Obtained N-(1-(1-(2,4-bis(trifluoromethyl)phenyl)ethyl)-1H-pyrazol-4-yl)-5-(pyrimidin-2-yl)isoxazole-3-carboxamide (6 mg). LCMS: 483 [M+H]$^+$. 1 H NMR (400 MHz, DMSO-d$_6$) δ 11.21 (s, 1H), 9.04 (d, J=4.89 Hz, 2H), 8.33 (s, 1H), 8.04-8.13 (m, 2H), 7.79 (s, 1H), 7.67 (t, J=4.89 Hz, 1H), 7.57 (s, 1H), 7.07 (d, J=8.31 Hz, 1H), 5.67 (s, 2H).

Example S70. Synthesis of N-(1-(2,4-bis(trifluoromethyl)benzyl)-1H-pyrazol-4-yl)-2-(pyridin-2-ylamino)thiazole-5-carboxamide (Compound 130)

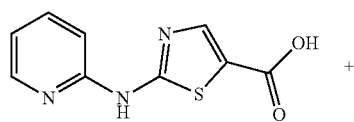

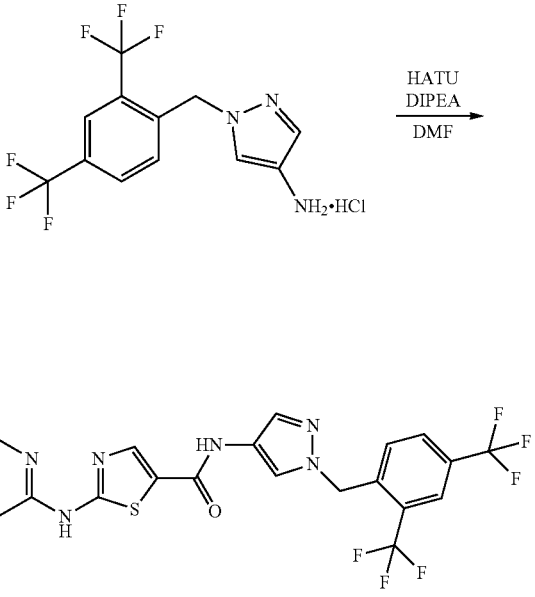

To a solution of 2-(pyridin-2-ylamino)thiazole-5-carboxylic acid (25 mg, 0.113 mmol, 1 equiv) in DMF (1 mL), were added HATU (42.96 mg, 0.113 mmol, 1 equiv). After stirring at RT for 15 minutes, was added DIPEA (43.81 mg, 0.339 mmol, 3 equiv) drop wise. After stirring at RT for 15 minutes, the mixture was added a solution of the 1-(2,4-bis(trifluoromethyl)benzyl)-1H-pyrazol-4-amine hydrochloride (38.98 mg, 0.113 mmol, 1 equiv) in DMF (1 mL). The reaction mixture was stirred at RT for 24 h. The reaction mixture was diluted with water (50 mL). The resulting precipitate was filtered off. Crude material obtained was purified by combi flash chromatography give product which was further triturated by using isopropyl alcohol and hexane to give N-(1-(2,4-bis(trifluoromethyl)benzyl)-1H-pyrazol-4-yl)-2-(pyridin-2-ylamino)thiazole-5-carboxamide (10 mg white solid). LCMS: 513 [M+H]$^+$. $^1$H NMR (400 MHz, DMSO-d$_6$) δ ppm 11.65 (s, 1H) 10.37 (s, 1H) 8.38 (br. s., 1H) 8.20 (s, 1H) 8.14 (s, 1H) 8.08 (br. s., 2H) 7.76 (br. s., 1H) 7.68 (s, 1H) 6.98-7.16 (m, 3H) 5.64 (s, 2H)

Example S71. Synthesis of (R)—N-(1-(1-(2,4-bis(trifluoromethyl)phenyl)ethyl)-1H-pyrazol-4-yl)-5-(pyrazin-2-yl)isoxazole-3-carboxamide and (S)—N-(1-(1-(2,4-bis(trifluoromethyl)phenyl)ethyl)-1H-pyrazol-4-yl)-5-(pyrazin-2-yl)isoazole-3-carboxamide (Compounds 131 & 132)

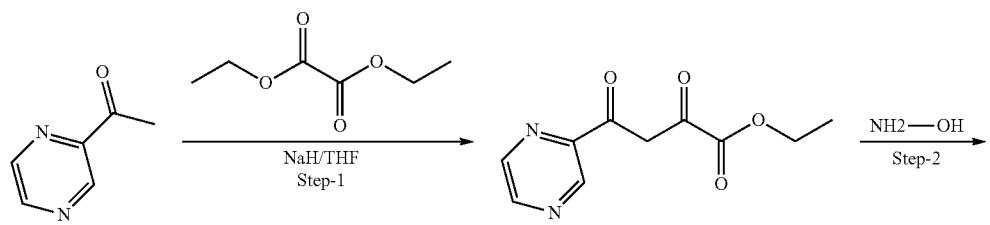

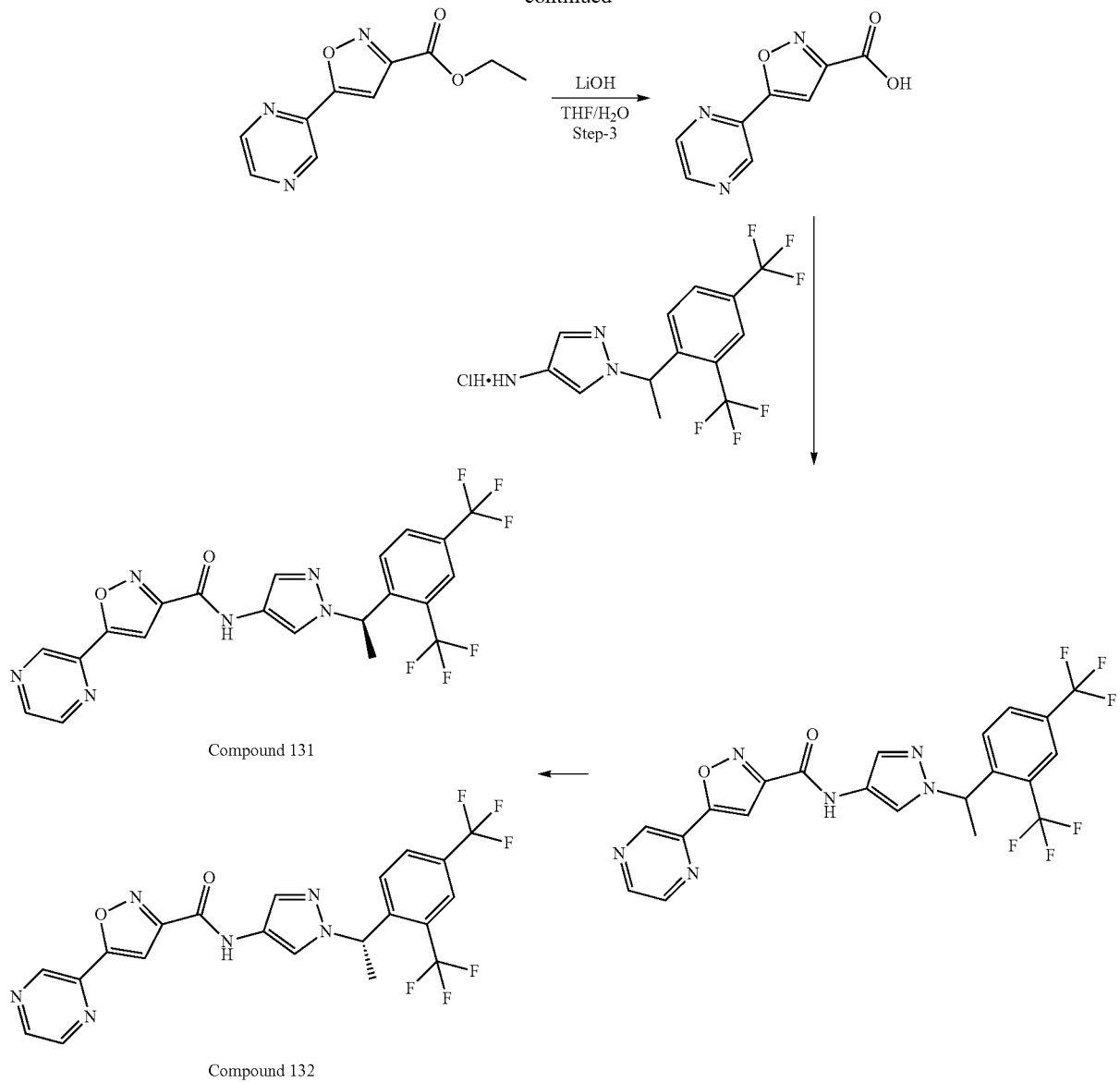

Compound 131

Compound 132

Step 1: Synthesis of ethyl 2,4-dioxo-4-(pyrazin-2-yl)butanoate. To a solution of 60% Sodium hydride (0.590 g, 0.590 mol, 1.5 equiv) in THF (10 ml) at 0° C., was added 1-(pyrazin-2-yl)ethan-1-one (2.0 g, 0.013 mol, 1 equiv) was added drop wise to the reaction mixture at 0° C. The resultant reaction mixture was stirred for another 30 minutes at RT, followed by drop wise addition of diethyl oxalate (2.99 g, 0.024 mol, 1.5 equiv) at 0° C. and reaction mixture was stir for another 18 hours at RT. Product formation was confirmed by TLC and LCMS. The reaction mixture was quenched with ice water and neutralized with 1N HCl and the yellow precipitate was filtered and dried under reduced pressure to obtain ethyl 2,4-dioxo-4-(pyrazin-2-yl)butanoate (3 g, crude as yellow solid). LCMS: 222 [M+H]$^+$.

Step 2: Synthesis of ethyl 5-(pyrazin-2-yl)isoxazole-3-carboxylate. A suspension of ethyl 2,4-dioxo-4-(pyridin-2-yl)butanoate (2.0 g, 0.009 mol, 1 equiv) and hydroxylamine hydrochloride salt (0.621 g, 0.009 mmol, 1.0 equiv) in EtOH (20 ml) was stirred at 85° C. for overnight. Product formation was confirmed by TLC and LCMS. The resulting mixture was concentrated under reduced pressure, the residue was dissolved in ethyl acetate and distilled water. Organic phase was separated, dried over anhydrous Na$_2$SO$_4$ and it was concentrated under reduced pressure to give ethyl 5-(pyrazin-2-yl)isoxazole-3-carboxylate. The crude product was purified using flash column chromatography using solvent system (10-20% Ethyl acetate in hexane) to obtain ethyl 5-(pyrazin-2-yl)isoxazole-3-carboxylate (300 mg, as off white solid). LCMS: 220 [M+H]$^+$.

Step 3: Synthesis of 5-(pyrazin-2-yl)isoxazole-3-carboxylic acid. To a solution of ethyl 5-(pyrazin-2-yl)isoxazole-3-carboxylate (400 mg, 1.82 mmol, 1.0 equivuiv) in THF (5 mL) and water (2 mL) was added in lithium hydroxide (115 mg, 2.73 mmol, 1.5 equiv). The resulting mixture was stirred for overnight. Reaction mass was concentrated under reduced pressure. The resulting residue was acidified with 1N HCl and the precipitate was filtered and dried under reduced pressure to obtain 5-(pyrazin-2-yl)isoxazole-3-carboxylic acid (250 mg, as white solid). LCMS: 191 [M+H]$^+$.

Step 4: Synthesis of N-(1-(1-(2,4-bis(trifluoromethyl)phenyl)ethyl)-1H-pyrazol-4-yl)-5-(pyrazin-2-yl)-1H-pyrazole-3-carboxamide. To a solution of 5-(pyrazin-2-yl)isoxazole-3-carboxylic acid (150 mg, 0.78 mmol, 1 equiv) and HATU (328 mg, 0.86 mmol, 1.1 equiv) in DMF (1 mL). The mixture was allow to stir for 30 mins followed by the addition of DIPEA (324 mg, 2.51 mmol, 3.2 equiv) and a solution of the 1-(1-(2,4-bis(trifluoromethyl)phenyl)ethyl)-1H-pyrazol-4-amine Hydrochloride (281 mg, 0.78 mmol, 1 equiv) in DMF (1 mL) was added.

The reaction mixture was kept under stirring for 24 h at RT. Product formation was confirmed with TLC AND LCMS and reaction mixture was diluted EtOAc (100 mL) and washed with water (2×50 mL). Organic layer dried over $Na_2SO_4$ and concentrated under reduced pressure to obtain crude which was further purified by flash column chromatography to obtain pure product of N-(1-(1-(2,4-bis(trifluoromethyl)phenyl)ethyl)-1H-pyrazol-4-yl)-5-(pyrazin-2-yl)-1H-pyrazole-3-carboxamide (250 mg, as off white solid). $^1$H NMR (400 MHz, DMSO-$d_6$) δ 11.15 (s, 1H), 9.35 (d, J=1.6 Hz, 1H), 8.87-8.82 (m, 1H), 8.81 (d, J=2.5 Hz, 1H), 8.21 (s, 1H), 8.09 (d, J=8.3 Hz, 1H), 8.05 (s, 1H), 7.74 (d, J=10.0 Hz, 2H), 7.67 (s, 1H), 5.94 (q, J=6.8 Hz, 1H), 1.87 (d, J=6.8 Hz, 3H). LCMS: 497 [M+H]$^+$.

Step 5: Synthesis of (R) and (S) of N-(1-(1-(2,4-bis(trifluoromethyl)phenyl)ethyl)-1H-pyrazol-4-yl)-5-(pyrazin-2-yl)-1H-pyrazole-3-carboxamide. The enantiomers of N-(1-(1-(2,4-bis(trifluoromethyl)phenyl)ethyl)-1H-pyrazol-4-yl)-5-(pyrazin-2-yl)-1H-pyrazole-3-carboxamide (220 mg, elution time: 5.6 min and 6.8 min), were separated by chiral SFC (Daicel Chiralpak®-IA, 250×20 mm, 5 μm. Isocratic program with analytical grade liquid carbon dioxide and HPLC grade Isopropanol (0.2% DEA), Total flow: 56 g/min, Co-Solvent Percentage: 20% to obtained (R)- of N-(1-(1-(2,4-bis(trifluoromethyl)phenyl)ethyl)-1H-pyrazol-4-yl)-5-(pyrazin-2-yl)-1H-pyrazole-3-carboxamide (40 mg) and (S)- of N-(1-(1-(2,4-bis(trifluoromethyl)phenyl)ethyl)-1H-pyrazol-4-yl)-5-(pyrazin-2-yl)-1H-pyrazole-3-carboxamide (40 mg). (Compound 131) $^1$H NMR (400 MHz, DMSO-$d_6$) δ 11.15 (s, 1H), 9.35 (d, J=1.6 Hz, 1H), 8.87-8.82 (m, 1H), 8.81 (d, J=2.5 Hz, 1H), 8.21 (s, 1H), 8.09 (d, J=8.3 Hz, 1H), 8.05 (s, 1H), 7.74 (d, J=10.0 Hz, 2H), 7.67 (s, 1H), 5.94 (q, J=6.8 Hz, 1H), 1.87 (d, J=6.8 Hz, 3H). LCMS: 497 [M+H]$^+$. (Compound 132) $^1$H NMR (400 MHz, DMSO-$d_6$) δ 11.15 (s, 1H), 9.35 (d, J=1.6 Hz, 1H), 8.87-8.82 (m, 1H), 8.81 (d, J=2.5 Hz, 1H), 8.21 (s, 1H), 8.09 (d, J=8.3 Hz, 1H), 8.05 (s, 1H), 7.74 (d, J=10.0 Hz, 2H), 7.67 (s, 1H), 5.94 (q, J=6.8 Hz, 1H), 1.87 (d, J=6.8 Hz, 3H). LCMS: 497 [M+H]$^+$.

Example S72. Synthesis of (R)—N-(1-(1-(2,4-bis(trifluoromethyl)phenyl)ethyl)-1H-pyrazol-4-yl)-5-(pyridin-2-yl)-1,3,4-oxadiazole-2-carboxamide and (S)—N-(1-(1-(2,4 bis(trifluoromethyl)phenyl)ethyl)-1H-pyrazol-4-yl)-54 pyridin-2-yl)-1,3,4-oxadiazole-2-carboxamide (Compounds 133 & 134)

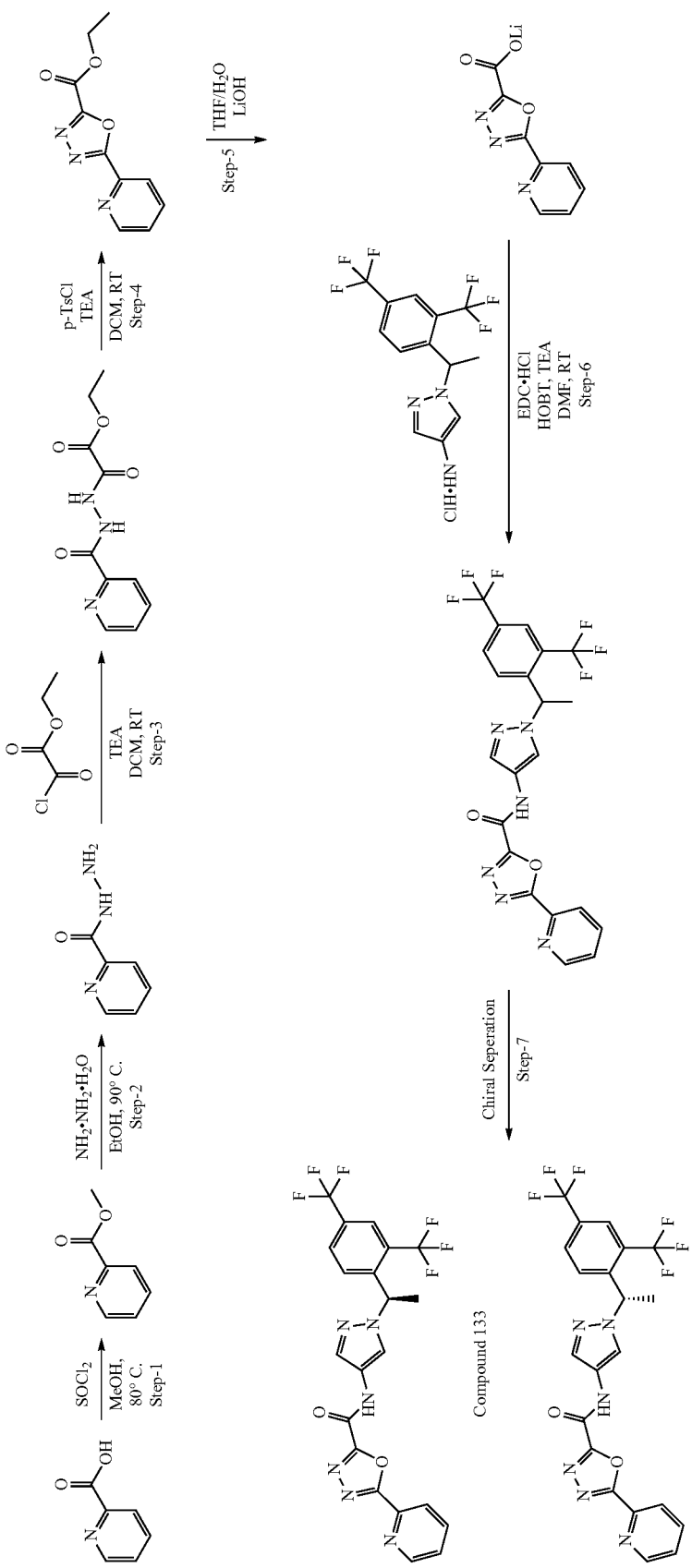

Step 1: Synthesis of methyl picolinate. To a solution of the picolinic acid (6.0 gm, 0.04 mol) in MeOH (60 mL) at 00 C was added dropwise SOCl2 (8.8 gm, 0.073 mol) (5.3 mL). The resulting mixture was refluxed for 12 h, after which time it was concentrated in vacuo. The resulting material was diluted with H$_2$O (150 mL) and extracted with EtOAc. The organic layer was washed with aq NaHCO$_3$ (50 mL), brine (50 mL), dried over Na$_2$SO$_4$, and concentrated in vacuo to provide the pure product methyl picolinate 6.1 gm as transparent liquid. $^1$H NMR (400 MHz, DMSO-d$_6$) d=8.72 (d, J=3.9 Hz, 2H), 8.08-8.04 (m, 2H), 8.03-7.97 (m, 2H), 7.65 (dd, J=5.5, 6.8 Hz, 2H).

Step 2: Synthesis of picolinohydrazide. A suspension of methyl picolinate (6 g, 0.043 mol, 1 equiv) and hydrazine hydrate (4.3 g, 0.08 mol, 2.0 equiv) in EtOH (50 ml) was stirred at 90° C. for overnight. Product formation was confirmed by TLC and LCMS. The resulting mixture was concentrated under reduced pressure, the residue was dissolved in ethyl acetate and distilled water. Organic phase was separated, dried over anhydrous Na$_2$SO$_4$ and it was concentrated under reduced pressure to give crude. The crude product was washed with diethyl ether to obtain picolinohydrazide (5.2 gm, as off white solid). $^1$H NMR (400 MHz, DMSO-d$_6$) d=9.87 (br. s., 1H), 8.61 (d, J=4.8 Hz, 1H), 8.03-7.90 (m, 2H), 7.57 (dt, J=3.3, 5.2 Hz, 1H), 4.62 (br. s., 2H).

Step 3: Synthesis of ethyl 2-oxo-2-(2-picolinoylhydrazinyl)acetate. To a stirred solution of picolinohydrazide (2.0 g, 0.01 mol, 1 equiv) in DCM (20 mL) was added triethylamine (2.2 gm, 0.02 mol, 1.5 equiv) at 0° C. followed by the addition ethyl 2-chloro-2-oxoacetate (2.9 g, 0.02 mmol, 1.5 equiv). After stirring for overnight, reaction mixture was diluted with DCM (30 mL). DCM layer was washed with water (50 mL), brine (50 mL), dried over anhydrous sodium sulfate filtered, concentrated to get crude. The crude was washed with diethyl ether to give 2.2 gm of ethyl 2-oxo-2-(2-picolinoylhydrazinyl)acetate (2.2 gm). LCMS: 239 [M+H]$^+$.

Step 4: Synthesis of ethyl 5-(pyridin-2-yl)-1,3,4-oxadiazole-2-carboxylate. To a mixture of ethyl 2-oxo-2-(2-picolinoylhydrazinyl)acetate (2.0 g, 0.008 mol, 1 equiv) in DCM (10 mL) was added triethylamine (1.28 gm, 0.012 mol, 1.5 equiv) followed by p-tosylchloride (2.41 gm, 0.012 mol, 1.5 equiv) over the period of 10 min. and stirred for overnight at ambient temperature. Reaction mixture was diluted with DCM (20 mL), washed with water (20 mL), brine (20 mL), dried over anhydrous sodium sulfate, filtered, concentrated and purified by column chromatography to give ethyl 5-(pyridin-2-yl)-1,3,4-oxadiazole-2-carboxylate (1.4 gm). LCMS: 220[M+H]$^+$.

Step 5: Synthesis of lithium 5-(pyridin-2-yl)-1,3,4-oxadiazole-2-carboxylate. To a stirred solution of ethyl 5-(pyridin-2-yl)-1,3,4-oxadiazole-2-carboxylate (140 mg, 0.63 mmol, 1 equiv) in THF:water (1:1, 10 mL) was added LiOH (40 mg, 0.95 mmol, 0.95 equiv) and stirred for overnight at room temperature. After completion of the reaction, reaction was concentrated under reduced pressure to get crude lithium salt product 100 mg of lithium 5-(pyridin-2-yl)-1,3,4-oxadiazole-2-carboxylate (0.2 gm). LCMS: 192 [M+H]$^+$.

Step 6: Synthesis of N-(1-(1-(2,4-bis(trifluoromethyl)phenyl)ethyl)-1H-pyrazol-4-yl)-5-(pyridin-2-yl)-1,3,4-oxadiazole-2-carboxamide. To a solution of quinoline-2-carboxylic acid (200 mg, 1.01 mmol, 1 equiv), EDC·HCl (292 mg, 1.52 mmol, 1.5 equiv), HOBT (205 mg, 1.52 mmol, 1.5 equiv) and TEA (328 mg, 3.24 mmol, 3.2 equiv) in DMF (1 mL). The mixture was allow to stir for 5 mins followed by the addition of 1-{1-[2,4bis(trifluoromethyl)phenyl]ethyl}-1H-pyrazol-4-amineHydrochloride (327 mg, 1.01 mmol, 1 equiv) in DMF (2 mL) was added. The reaction mixture was kept under stirring for 1 h at RT. Product formation was confirmed with TLC AND LCMS and reaction mixture was diluted water (30 mL) and extracted with EtOAc (100 mL) and again washed with water (30 mL×4). Organic layer dried over Na$_2$SO$_4$ and concentrated under reduced pressure to obtain crude which was further purified by flash column chromatography to obtain pure 2 N-(1-(1-(2,4-bis(trifluoromethyl)phenyl)ethyl)-1H-pyrazol-4-yl)-5-(pyridin-2-yl)-1,3,4-oxadiazole-2-carboxamide (60 mg, as white solid). $^1$H NMR (400 MHz, DMSO-d$_6$) δ 11.60 (s, 1H), 8.87-8.80 (m, 1H), 8.28 (d, J=7.9 Hz, 1H), 8.23 (s, 1H), 8.15-8.07 (m, 2H), 8.05 (s, 1H), 7.80 (s, 1H), 7.75 (d, J=8.3 Hz, 1H), 7.70 (ddd, J=7.7, 4.8, 1.2 Hz, 1H), 5.96 (q, J=6.9 Hz, 1H), 1.88 (d, J=6.8 Hz, 3H). LCMS: 497 [M+H]$^+$.

Step 7: Synthesis of (R) and (S) N-(1-(1-(2,4-bis(trifluoromethyl)phenyl)ethyl)-1H-pyrazol-4-yl)-5-(pyridin-2-yl)-1,3,4-oxadiazole-2-carboxamide. The enantiomers of (R)—N-(1-(1-(2,4-bis(trifluoromethyl)phenyl)ethyl)-1H-pyrazol-4-yl)-5-(pyridin-2-yl)-1,3,4-oxadiazole-2-carboxamide (80 mg, elution time: 4.77 min and 5.77 min), were separated by chiral SFC (Daicel Chiralpak®-IB, 250×20 mm, 5 μm. Isocratic program with analytical grade liquid carbon dioxide and HPLC grade Isopropanol, Total flow: 56 g/min, Co-Solvent Percentage: 20% to obtained Peak-1(R)—(R)—N-(1-(1-(2,4-bis(trifluoromethyl)phenyl)ethyl)-1H-pyrazol-4-yl)-5-(pyridin-2-yl)-1,3,4-oxadiazole-2-carboxamide (20 mg) and Peak-2 (S)—(R)—N-(1-(1-(2,4-bis(trifluoromethyl)phenyl)ethyl)-1H-pyrazol-4-yl)-5-(pyridin-2-yl)-1,3,4-oxadiazole-2-carboxamide (20 mg). (Compound 133) $^1$H NMR (400 MHz, DMSO-d$_6$) δ 11.60 (s, 1H), 8.87-8.80 (m, 1H), 8.28 (d, J=7.9 Hz, 1H), 8.23 (s, 1H), 8.15-8.07 (m, 2H), 8.05 (s, 1H), 7.80 (s, 1H), 7.75 (d, J=8.3 Hz, 1H), 7.70 (ddd, J=7.7, 4.8, 1.2 Hz, 1H), 5.96 (q, J=6.9 Hz, 1H), 1.88 (d, J=6.8 Hz, 3H). LCMS: 497 [M+H]$^+$. (Compound 134) $^1$H NMR (400 MHz, DMSO-d$_6$) δ 11.60 (s, 1H), 8.87-8.80 (m, 1H), 8.28 (d, J=7.9 Hz, 1H), 8.23 (s, 1H), 8.15-8.07 (m, 2H), 8.05 (s, 1H), 7.80 (s, 1H), 7.75 (d, J=8.3 Hz, 1H), 7.70 (ddd, J=7.7, 4.8, 1.2 Hz, 1H), 5.96 (q, J=6.9 Hz, 1H), 1.88 (d, J=6.8 Hz, 3H). LCMS: 497 [M+H]$^+$.

Example S73. Synthesis of N-(1-(2,4-bis(trifluoromethyl)benzyl)-1H-pyrazol-4-yl)-4-methyl-5-(pyridin-2-yl)isoxazole-3-carboxamide (Compound 135)

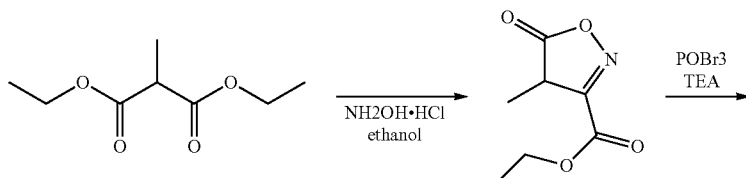

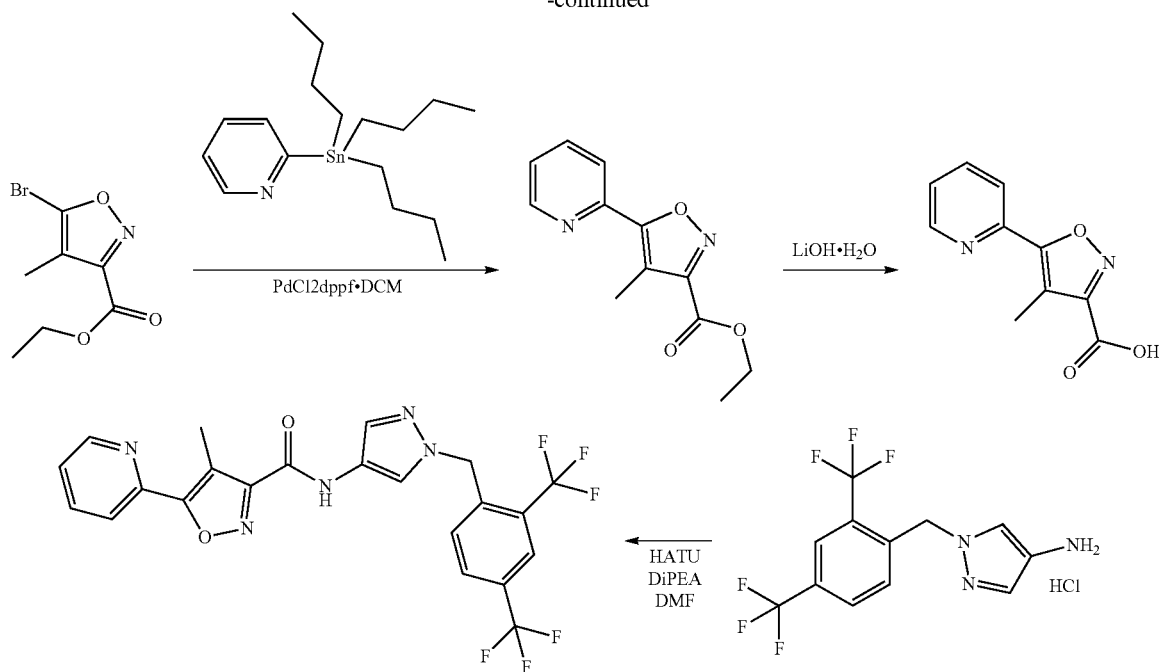

Step 1: Synthesis of ethyl 4-methyl-5-oxo-4,5-dihydroisoxazole-3-carboxylate. A solution of diethyl 2-methylmalonate (2 g, 0.011 mol, 1 eq) and hydroxylamine hydrochloride (0.965 g, 0.013 mol, 1.2 eq) in EtOH (20 mL) was heated to reflux for 12 hours. The reaction mixture was concentrated in vacuo and The reaction mixture water poured into The reaction mixture and extracted with EtOAc (600 mL×5). The combined organic layers were washed with brine, dried over anhydrous $Na_2SO_4$ and concentrated in vacuo the residue obtained was triturated with petroleum ether (100 mL) to provide compound ethyl 4-methyl-5-oxo-4,5-dihydroisoxazole-3-carboxylate (yield 1.2 gm). $^1$H NMR (400 MHz, CHLOROFORM-d) δ ppm 4.42 (q, J=7.02 Hz, 2H), 2.12 (s, 3H), 1.32-1.46 (m, 3H).

Step 2: Synthesis of ethyl 4-methyl-5-oxo-4,5-dihydroisoxazole-3-carboxylate. To mixture of ethyl 4-methyl-5-oxo-4,5-dihydroisoxazole-3-carboxylate (1 g, 0.058 mol, 1 eq) and phosphorous oxybromide (8.39 g, 0.0292 mol, 5 eq) was added dropwise TEA (1.181 gm, 0.0116 mol, 2 eq). The resulting reaction was heated to 80° C. and allowed to stir at this temperature 12 hours. The reaction mixture was then poured into ice water and extracted with EtOAc (600 mL×5). The combined organic layers were washed with brine, dried over anhydrous $Na_2SO_4$ and concentrated in vacuo. The resulting residue was purified using flash column chromatography on silica gel (810 mg). $^1$H NMR (400 MHz, DMSO-$d_6$) δ 4.37 (q, J=7.16 Hz, 2H), 2.10 (s, 3H), 1.32 (t, J=7.02 Hz, 3H).

Step 3: Synthesis of ethyl 4-methyl-5-(pyridin-2-yl)isoxazole-3-carboxylate. To a solution of ethyl 5-bromo-4-methylisoxazole-3-carboxylate (500 mg, 2.127 mmol, 1 eq) in anhydrous Toluene (10 ml) were added 2-(tributylstannyl) pyridine (834 mg, 2.553 mmol, 1 eq), under nitrogen atmosphere at room temperature, nitrogen was purged for 15 minutes and then Pd(dppf)$Cl_2$·$CH_2Cl_2$ (173.8 mg, 0.212 mmol, 0.1 eq) added. the reaction mixture was stirred at 110° C. for 16 hrs. To the reaction solution was added water, and then the reaction solution was extracted with ethyl acetate. The extraction was washed with brine and dried over sodium sulfate. The solvent was removed under reduced pressure. The obtained residue was purified by column chromatography to give ethyl 4-methyl-5-(pyridin-2-yl)isoxazole-3-carboxylate (150 mg). LCMS: 233 [M+H]$^+$.

Step 4: Synthesis of 4-methyl-5-(pyridin-2-yl)isoxazole-3-carboxylic acid. To a solution of ethyl 4-methyl-5-(pyridin-2-yl)isoxazole-3-carboxylate (25 mg, 0.084 mmol, 1 eq) in THF (2 mL) and water (2 mL) was slowly added lithium hydroxide (4.08 mg, 0.102 mmol, 1.2 eq) The resulting mixture was stirred for 16 hrs. Reaction mixture was concentrated under reduced pressure to obtain crude which was acidified with 1N HCl and obtained suspension was lypolised. Obtained crude was triturated with ether to obtained 4-methyl-5-(pyridin-2-yl)isoxazole-3-carboxylic acid (0.03 gm). LCMS: 205 [M+H]$^+$.

Step 5: Synthesis of N-(1-(2,4-bis(trifluoromethyl)benzyl)-1H-pyrazol-4-yl)-4-methyl-5-(pyridin-2-yl)isoxazole-3-carboxamide. To a solution of 4-methyl-5-(pyridin-2-yl)isoxazole-3-carboxylic acid (20 mg, 0.0980 mmol, 1 eq) in DMF (2 mL), were added HATU (30.14 mg, 0.0980 mmol, 1 equiv). The mixture was treated drop wise with DIPEA (37.75 mg, 0.292 mmol, 3 equiv). After stirring at RT for 15 minutes, the mixture was treated drop wise with a solution of the 1-(2,4-bis(trifluoromethyl)benzyl)-1H-pyrazol-4-amine hydrochloride (30.14 mg, 0.0975 mmol, 1 equiv) in DMF (1 mL). The reaction mixture was kept under stirring for 24 h. The reaction mixture was diluted water (50 mL). The resulting precipitate was filtered off. Crude material obtained was purified by trituration with DCM: hexane (2:8) ml N-(1-(2,4-bis(trifluoromethyl)benzyl)-1H-pyrazol-4-yl)-4-methyl-5-(pyridin-2-yl)isoxazole-3-carboxamide (20 mg). LCMS: 496 [M+H]$^+$. $^1$H NMR (400 MHz, DMSO-$d_6$) δ 11.13 (s, 1H), 8.78 (d, J=4.40 Hz, 1H), 8.33 (s, 1H), 8.05-8.09 (m, 2H), 8.00-8.04 (m, 1H), 7.93-7.99 (m, 1H), 7.78 (s, 1H), 7.54 (dd, J=5.14, 6.60 Hz, 1H), 7.07 (d, J=8.31 Hz, 1H), 5.66 (s, 2H), 2.56 (s, 3H).

Example S74. Synthesis of N-(1-(1-(2,4-bis(trifluoromethyl)phenyl)ethyl)-1H-pyrazol-4-yl)-5-(pyrazin-2-yl)-1,3,4-thiadiazole-2-carboxamide (Compound 136)

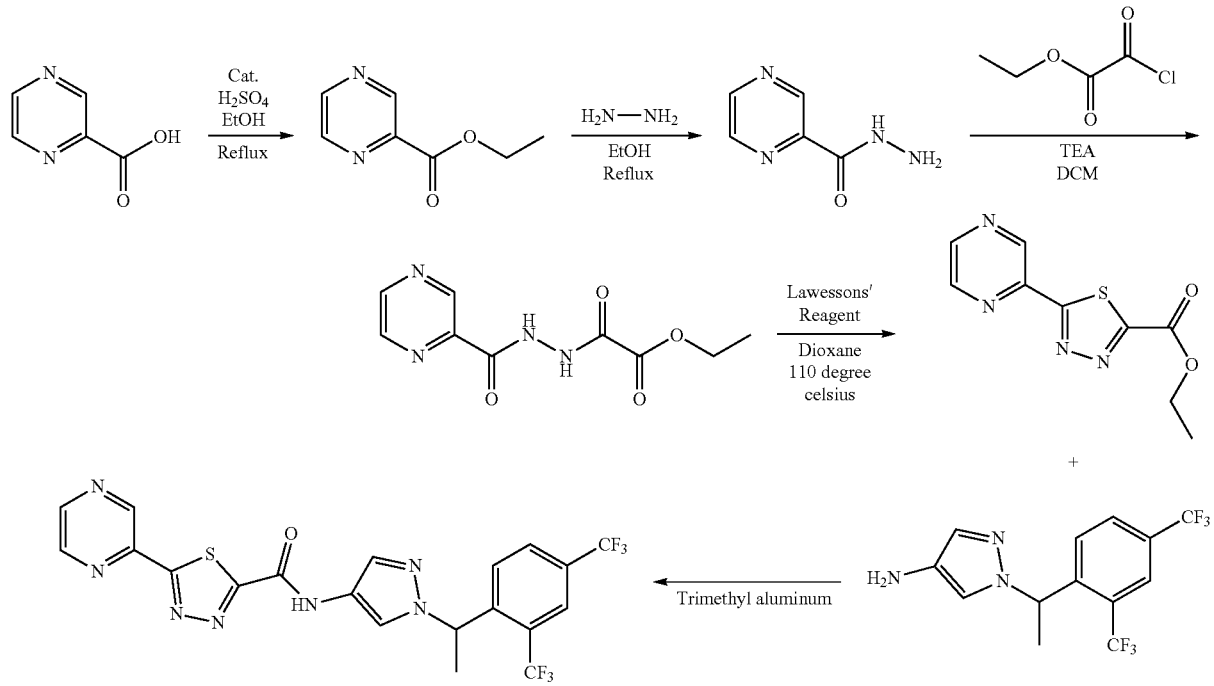

Step 1: Synthesis of ethyl pyrazine-2-carboxylate. To a stirred solution of Pyrazine-2-carboxylic acid (500 mg) in Ethanol (30 ml) was added Conc H2SO4 (1 ml) drop wise and refluxed for 2 days at 100 degree Celsius. Reaction was monitored by NMR. The reaction mixture was concentrated under reduced pressure to obtain crude which was treated with Saturated Sodium Bicarbonate Solution, Extracted with DCM (3×150 ml), Organic Layer dried over anhydrous sodium sulphate and Concentrated under vacuum to obtain Product ethyl pyrazine-2-carboxylate (496 mg, Brown Solid). $^1$H NMR (400 MHz, DMSO-$d_6$) δ 9.16-9.26 (m, 1H), 8.90 (d, J=2.19 Hz, 1H), 8.82 (s, 1H), 4.39 (q, J=7.16 Hz, 2H), 1.35 (t, J=7.24 Hz, 3H).

Step 2: Synthesis of pyrazine-2-carbohydrazide. To as stirred solution of Ethyl pyrazine-2-carboxylate (450 mg, 1 eq, 0.986 mmoles) in ethanol (20 ml) was added hydrazine Hydrate (65.13 mg, 1.2 eq, and 1.184 m moles). Reaction mixture was refluxed for 3 hour. Reaction was monitored by NMR. Reaction Mixture was concentrated under reduced pressure to obtained ppt. was triturated with hexane to obtained pyrazine-2-carbohydrazide (340 mg, Brown Solid). $^1$H NMR (400 MHz, DMSO-$d_6$) δ 10.13 (br. s., 1H), 9.13 (d, J=1.32 Hz, 1H), 8.83 (d, J=2.19 Hz, 1H), 8.59-8.78 (m, 1H), 4.65 (br. s., 2H).

Step 3: Synthesis of ethyl 2-oxo-2-(2-(pyrazine-2-carbonyl)hydrazinyl)acetate. Pyrazine-2-carbohydrazide (400 mg, 1 eq, 2.89 mmoles) was taken in DCM at zero degrees Celsius. TEA (351.3 mg, 1.2 eq, 3.66 m moles) was added. Reaction mixture was kept on stirring at zero degrees Celsius for half an hour. Ethyl 2-chloro-2-oxoacetate (397 mg, 1 eq, 2.89 m moles) was added at zero degree Celsius. Reaction mixture was kept on stirring at zero degrees Celsius for an hour. Reaction was monitored by LCMS. Reaction was quenched by ice. Extraction was done with DCM (2*100 ml). Obtained DCM layer Was Concentrated to Obtain Crude which was triturated with hexane to obtain desired product (2.2 gm Pale yellow Solid). 1H NMR (400 MHz, DMSO-$d_6$) δ 11.03 (br. s., 1H), 10.91-10.98 (m, 1H), 9.08-9.26 (m, 1H), 8.93 (d, J=2.19 Hz, 1H), 8.75-8.85 (m, 1H), 4.31 (q, J=7.02 Hz, 2H), 1.31 (t, J=7.02 Hz, 3H).

Step 4: Synthesis of ethyl 5-(pyrazin-2-yl)-1,3,4-thiadiazole-2-carboxylate. To a stirred solution Ethyl 2-oxo-2-(2-(pyrazine-2-carbonyl)hydrazinyl)acetate (100 mg, 1 eq, and 0.421 mmoles) in Dioxane (4 ml) was added Lawessons' reagent (426.16 mg, 2.5 eq, and 1.05 m moles) at room temperature. Reaction Mixture was heated at 110 degree Celsius for 24 hour. Reaction was monitored by LCMS. Work up was done by Quenching with Saturated Bicarbonate solution (30 ml). Extraction was done by diethyl ether (75 ml×3), Obtained organic layer was concentrated under reduced pressure to obtain crude which was purified by Combi-Flash Chromatography to obtain ethyl 5-(pyrazin-2-yl)-1,3,4-thiadiazole-2-carboxylate (80 mg, Pale yellow) was triturated with DCM: Hexane (2:8) to obtained ethyl 5-(pyrazin-2-yl)-1,3,4-thiadiazole-2-carboxylate (56 mg, pale yellow solid). $^1$H NMR (400 MHz, DMSO-$d_6$) δ 9.55 (s, 1H), 8.90-8.94 (m, 1H), 8.84-8.90 (m, 1H), 4.48 (q, J=7.02 Hz, 2H), 1.38 (t, J=7.02 Hz, 3H).

Step 5: Synthesis of N-(1-(1-(2,4-bis(trifluoromethyl)phenyl)ethyl)-1H-pyrazol-4-yl)-5-(pyrazin-2-yl)-1,3,4-thiadiazole-2-carboxamide. To a solution of ethyl 5-(pyrazin-2-yl)-1,3,4-thiadiazole-2-carboxylate (50 mg, 0.210 mmol, 1 equiv) in Toluene (1 mL), were added 1-(1-(2,4-bis(trifluoromethyl)phenyl)ethyl)-1H-pyrazol-4-amine (68.06 mg, 0.210 mmol, 1 equiv) in Toluene (1 mL). The mixture was added Trimethyl Aluminium (30.25 mg, 0.840 mmol, 4 equiv) drop wise. The reaction mixture was kept under stirring for 24 h at rom temperature. The reaction mixture was diluted water (50 mL). The resulting suspension was filtered off and obtained filtrate was extracted with ethyl Acetate (2×50 ml), Organic layer was concentrated under vacuum to obtained crude which was purified by Combi-Flash Chromatography, Obtained crude product was triturated with DCM: Hexane (2:8) ml to Obtained desired product (3 mg, Pale yellow Sold). LCMS: 513 [M+H]⁺. ¹H NMR (500 MHz, DMSO-d₆) δ 11.67 (s, 1H), 9.53 (s, 1H), 8.91 (d, J=2.6 Hz, 1H), 8.89-8.84 (m, 1H), 8.24 (s, 1H), 8.09 (d, J=8.4 Hz, 1H), 8.06 (s, 1H), 7.82 (s, 1H), 7.74 (d, J=8.3 Hz, 1H), 5.95 (q, J=6.9 Hz, 1H), 1.88 (d, J=6.8 Hz, 3H).

Example S75. Synthesis of N-(1-(1-(2,4-bis(trifluoromethyl)phenyl)ethyl)-1H-pyrazol-4-yl)-5-(pyrazin-2-yl)-1,3,4-thiadiazole-2-carboxamide (Compound 137)

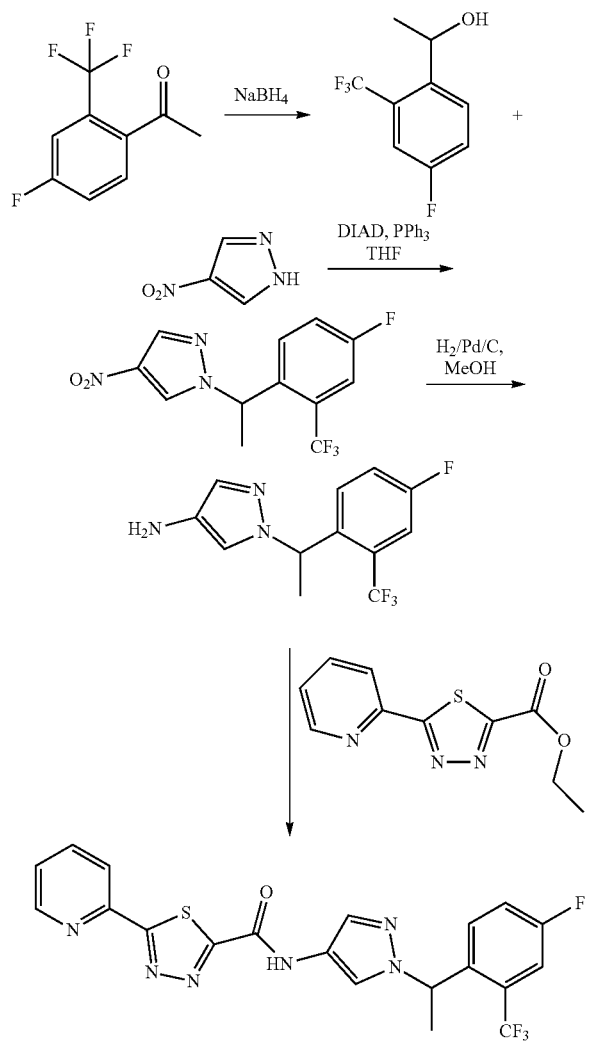

Step 1: Synthesis of 1-(4-fluoro-2-(trifluoromethyl)phenyl)ethan-1-ol. To a stirred solution of 1-(4-fluoro-2-(trifluoromethyl)phenyl)ethan-1-one (500 mg, 0.002 mol, 1.0 equiv) in Methanol (5 mL) was added NaBH₄ (97 mg, 0.003 mol, 1.2 equiv) portion wise at 0° C. and stirred for 10 minutes. The reaction mixture was allowed to stir for 1 hour at RT. Product formation was confirmed by TLC AND LCMS. After completion of reaction, reaction mixture was quenched with water and extracted with ethyl acetate (50 mL×3). Combined organic layer were washed with water (2×50 mL), dried over anhydrous Na₂SO₄ and concentrated under reduced pressure to obtain 1-(4-fluoro-2-(trifluoromethyl)phenyl)ethan-1-ol (468 mg, as colourless liquid). ¹H NMR (400 MHz, DMSO-d₆) δ 8.01-8.16 (m, 2H), 7.93 (s, 1H), 5.70 (d, J=4.40 Hz, 1H), 5.09 (br. s., 1H), 1.34 (d, J=6.36 Hz, 3H).

Step 2: Synthesis of 1-(1-(4-fluoro-2-(trifluoromethyl)phenyl)ethyl)-4-nitro-1H-pyrazole. To a stirred solution of PPh₃ (503 mg, 1.92 mmol, 1.0 equiv) and DIAD (388 mg, 1.92 mmol, 1.0 equiv) in THF (2 mL), was added 4-nitro-1H-pyrazole (217 mg, 1.92 mmol, 1 equiv), and Followed by the addition of 1-(4-fluoro-2-(trifluoromethyl)phenyl)ethan-1-ol (400 mg, 1.92 mmol, 1.0 equiv). The reaction mixture was stirred at RT for 1 h. Product formation was confirmed with TLC AND LCMS. After completion of reaction mixture were diluted with EtOAc (50 mL) and washed with water (50 mL×3). Organic layer dried over Na₂SO₄ and concentrated under reduced pressure to obtain crude which was further purified by flash column chromatography to obtain pure product 1-(1-(4-fluoro-2-(trifluoromethyl)phenyl)ethyl)-4-nitro-1H-pyrazole (250 mg). ¹H NMR (400 MHz, DMSO-d₆) δ 9.11 (s, 1H), 8.29 (s, 1H), 7.65-7.74 (m, 2H), 7.54-7.65 (m, 1H), 5.91 (q, J=6.85 Hz, 1H), 1.87 (d, J=6.85 Hz, 3H).

Step 3: Synthesis of 1-(1-(4-fluoro-2-(trifluoromethyl)phenyl)ethyl)-1H-pyrazol-4-amine. To a stirred solution of 1-(1-(4-fluoro-2-(trifluoromethyl)phenyl)ethyl)-4-nitro-1H-pyrazole (200 mg) in Methanol (10 mL) under nitrogen Palladium on Carbon (40 mg, 10% w/w) was added. Purged reaction mixture with H₂ gas for 2 h. Product formation was confirmed by LCMS. After the completion of reaction, reaction mixture was filtered through Celite bed and Filtrate was concentrate under reduced pressure to obtain 1-(1-(4-fluoro-2-(trifluoromethyl)phenyl)ethyl)-1H-pyrazol-4-amine (160 mg). LCMS: 273 [M+H]⁺. ¹H NMR (400 MHz, DMSO-d₆) δ 7.59 (d, J=9.29 Hz, 1H), 7.47-7.54 (m, 2H), 7.06 (s, 1H), 6.98 (s, 1H), 5.60 (d, J=6.85 Hz, 1H), 3.86 (br. s., 2H), 1.73 (d, J=6.85 Hz, 3H).

Step 4: Synthesis of N-(1-(1-(4-fluoro-2-(trifluoromethyl)phenyl)ethyl)-1H-pyrazol-4-yl)-5-(pyridin-2-yl)-1,3,4-thiadiazole-2-carboxamide. To a solution of ethyl 5-(pyridin-2-yl)-1,3,4-thiadiazole-2-carboxylate (50 mg, 0.212 mmol, 1 equiv) in Toluene (1 mL), were added 1-(1-(4-fluoro-2-(trifluoromethyl)phenyl)ethyl)-1H-pyrazol-4-amine (58.05 mg, 0.212 mmol, 1 equiv) in Toluene (1 mL). The mixture was treated drop wise with Trimethyl Aluminium (49.14 mg, 0.063 mmol, 3 equiv). After stirring at RT for 15 minutes, the mixture was treated drop wise with a solution of the reaction mixture was kept under stirring for 24 h. The reaction mixture was diluted with water (50 mL). The resulting suspension was filtered off and obtained filtrate was extracted with ethyl Acetate (2×50 ml). Obtained organic layer was concentrated under vacuum to obtain crude which was purified by Combi-Flash Chromatography, Obtained Crude product was triturated with DCM: Hexane (2:8) to obtained N-(1-(1-(4-fluoro-2-(trifluoromethyl)phenyl)ethyl)-1H-pyrazol-4-yl)-5-(pyridin-2-yl)-1,3,4-thiadiazole-2-carboxamide (6 mg, off white Solid). LCMS: 462 [M+H]⁺. ¹H NMR (500 MHz, DMSO-d₆) δ 11.58 (s, 1H), 8.76 (d, J=4.7 Hz, 1H), 8.35 (d, J=7.9 Hz, 1H), 8.16 (s, 1H), 8.12-8.05 (m, 1H), 7.79 (s, 1H), 7.69-7.53 (m, 4H), 5.84 (q, J=6.9 Hz, 1H), 1.84 (d, J=6.8 Hz, 3H).

Example S76. Synthesis of N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide (Compound 138)

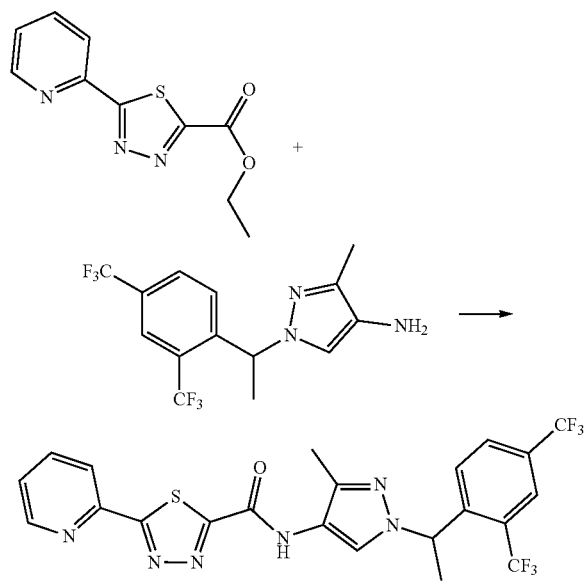

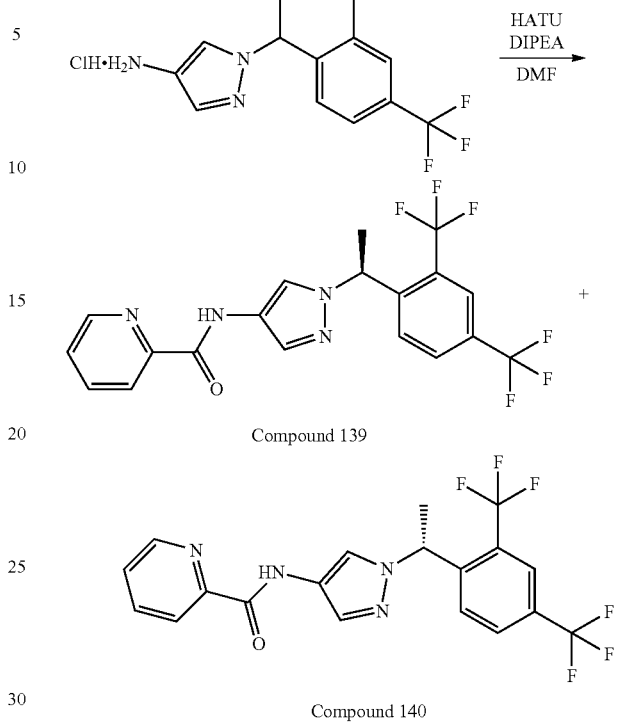

Step 1: Synthesis of N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide. To a stirred solution of ethyl 5-(pyrazin-2-yl)-1,3,4-thiadiazole-2-carboxylate (50 mg, 0.210 mmol, 1 equiv) in Toluene (1 mL), 1-(1-(2,4-bis(trifluoromethyl)phenyl)ethyl)-3-methyl-1H-pyrazol-4-amine (71.7 mg, 0.210 mmol, 1 equiv) in Toluene (1 mL) was added 2M Trimethyl Aluminium in Toluene (49.14 mg, 0.638 mmol, 3 equiv) drop wise. The reaction mixture was stirred at room temperature for 24 h. The reaction mixture was diluted water (50 mL). The resulting suspension was filtered, filtrate was extracted with ethyl Acetate (2×50 ml), Obtained organic layer was concentrated under reduced pressure to obtain crude which was purified by Combi-Flash Chromatography, Obtained Crude product was triturated with DCM:Hexane (2:8) to obtain desired product (8 mg, Pale yellow Solid). LCMS: 526 [M+H]⁺. ¹H NMR (500 MHz, DMSO-d₆) δ 10.79 (s, 1H), 8.76 (d, J=4.7 Hz, 1H), 8.35 (d, J=7.9 Hz, 1H), 8.16 (s, 1H), 8.10 (q, J=7.8 Hz, 2H), 8.05 (s, 1H), 7.75 (d, J=8.3 Hz, 1H), 7.66 (dd, J=7.6, 4.9 Hz, 1H), 5.84 (q, J=7.1 Hz, 1H), 2.20 (s, 3H), 1.84 (d, J=6.9 Hz, 3H).

Example S77. Synthesis of (S)—N-(1-(1-(2,4-bis(trifluoromethyl)phenyl)ethyl)-1H-pyrazol-4-yl)picolinamide and (R)—N-(1-(1-(2,4-bis(trifluoromethyl)phenyl)ethyl)-1H-pyrazol-4-yl)picolinamide (Compounds 139 & 140)

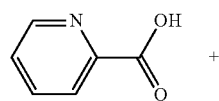

Synthesis of (S)—N-(1-(1-(2,4-bis(trifluoromethyl)phenyl)ethyl)-1H-pyrazol-4-yl)picolinamide and (R)—N-(1-(1-(2,4-bis(trifluoromethyl)phenyl)ethyl)-1H-pyrazol-4-yl)picolinamide. To a solution of Picolinic acid (50 mg, 0.406 mmol, 1 equiv) in DMF (1 mL), were added HATU (154.47 mg, 0.406 mmol, 1 equiv). After stirring at RT for 15 minutes, the mixture was added DIPEA (157.62 mg, 1.218 mmol, 3 equiv). After stirring at RT for 15 minutes, the mixture was added a solution of the 1-(1-(2,4-bis(trifluoromethyl)phenyl)ethyl)-1H-pyrazol-4-amine hydrochloride (145.93 mg, 0.406 mmol, 1 equiv) in DMF (1 mL). The reaction mixture was stirred at RT for 24 h. The reaction mixture was diluted with water (50 mL). The resulting precipitate was filtered off. Crude material was purified by combi flash chromatography to give N-(1-(1-(2,4-bis(trifluoromethyl)phenyl)ethyl)-1H-pyrazol-4-yl)picolinamide. The enantiomers (elution time: 10.2 min & 19.2 min), were separated by chiral HPLC (Daicel Chiralpak®-IC, 250×20 mm, 5 µm. Isocratic program with HPLC grade n-Hexane (0.2% DEA) and HPLC grade Isopropanol, Total flow: 18 ml/min, Isopropanol Percentage: 10% to obtained (S)—N-(1-(1-(2,4-bis(trifluoromethyl)phenyl)ethyl)-1H-pyrazol-4-yl)picolinamide (6 mg white solid) and (R)—N-(1-(1-(2,4-bis(trifluoromethyl)phenyl)ethyl)-1H-pyrazol-4-yl)picolinamide (10 mg white solid). LCMS: 429 [M+H]⁺. (Compound 139) 1H NMR (400 MHz, DMSO-d₆) δ ppm 10.99 (s, 1H) 8.71 (d, J=4.89 Hz, 1H) 8.26 (s, 1H) 8.00-8.13 (m, 4H) 7.86 (s, 1H) 7.73 (d, J=8.31 Hz, 1H) 7.58-7.68 (m, 1H) 5.91 (d, J=6.36 Hz, 1H) 1.87 (d, J=6.85 Hz, 3H). (Compound 140) ¹H NMR (400 MHz, DMSO-d₆) δ ppm 10.98 (s, 1H) 8.71 (d, J=3.91 Hz, 1H) 8.26 (s, 1H) 7.99-8.12 (m, 4H) 7.86 (s, 1H) 7.73 (d, J=8.31 Hz, 1H) 7.61-7.67 (m, 1H) 5.91 (d, J=6.85 Hz, 1H) 1.87 (d, J=6.85 Hz, 3H).

Example S78. Synthesis of (S)—N-(1-(1-(2,4-bis(trifluoromethyl)phenyl)ethyl)-1H-pyrazol-4-yl)pyrazine-2-carboxamide and (R)—N-(1-(1-(2,4-bis(trifluoromethyl)phenyl)ethyl)-1H-pyrazol-4-yl)pyrazine-2-carboxamide (Compounds 141 & 142)

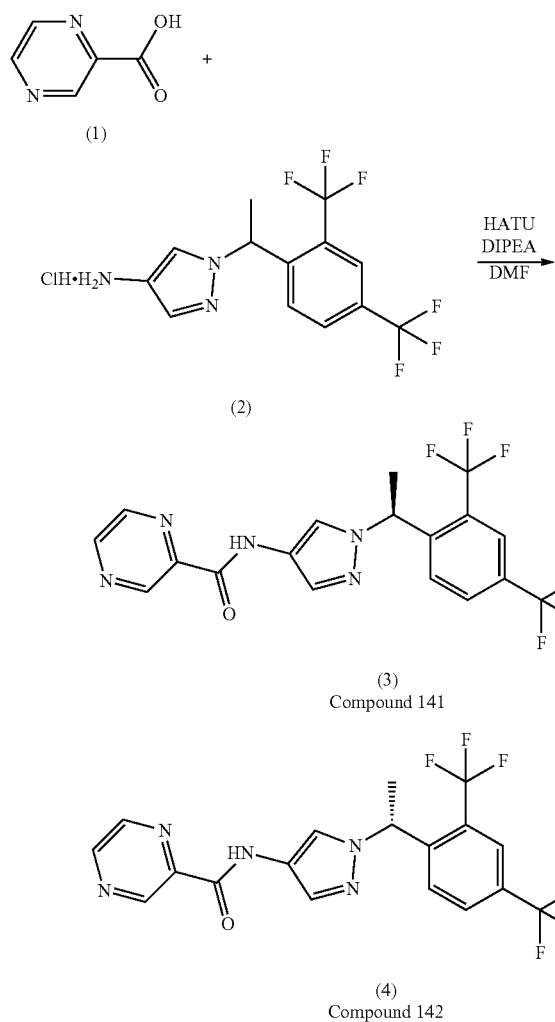

Synthesis of (S)—N-(1-(1-(2,4-bis(trifluoromethyl)phenyl)ethyl)-1H-pyrazol-4-yl)pyrazine-2-carboxamide and (R)—N-(1-(1-(2,4-bis(trifluoromethyl)phenyl)ethyl)-1H-pyrazol-4-yl)pyrazine-2-carboxamide. To a solution of pyrazine-2-carboxylic acid (50 mg, 0.403 mmol, 1 equiv) in DMF (1 mL), were added HATU (153.21 mg, 0.403 mmol, 1 equiv). After stirring at RT for 15 minutes, the mixture was added DIPEA (156.34 mg, 1.209 mmol, and 3 equiv) drop wise. After stirring at RT for 15 minutes, the mixture added a solution of the 1-(1-(2,4-bis(trifluoromethyl)phenyl)ethyl)-1H-pyrazol-4-amine hydrochloride (144.75 mg, 0.403 mmol, 1 equiv) in DMF (1 mL). The reaction mixture was stirred at RT for 24 h. The reaction mixture was diluted with water (50 mL). The resulting precipitate was filtered off. Crude material which was purified by combi flash chromatography to give N-(1-(1-(2,4-bis(trifluoromethyl)phenyl)ethyl)-1H-pyrazol-4-yl)pyrazine-2-carboxamide. The enantiomers (elution time: 20.1 min & 27.3 min), were separated by chiral HPLC (Daicel Chiralpak®-IC, 250×20 mm, 5 μm. Isocratic program with HPLC grade n-Hexane (0.2% DEA) and HPLC grade Isopropanol, Total flow: 18 ml/min, Isopropanol Percentage: 10% to obtained (S)—N-(1-(1-(2,4-bis(trifluoromethyl)phenyl)ethyl)-1H-pyrazol-4-yl)pyrazine-2-carboxamide (15 mg white solid) and (R)—N-(1-(1-(2,4-bis(trifluoromethyl)phenyl)ethyl)-1H-pyrazol-4-yl)pyrazine-2-carboxamide (20 mg white solid). LCMS: 430 [M+H]$^+$. (Compound 141) $^1$H NMR (400 MHz, DMSO-d$_6$) δ ppm 11.14 (s, 1H) 9.25 (s, 1H) 8.91 (d, J=2.45 Hz, 1H) 8.79 (s, 1H) 8.27 (s, 1H) 8.03-8.11 (m, 2H) 7.85 (s, 1H) 7.73 (d, J=8.31 Hz, 1H) 5.92 (d, J=6.85 Hz, 1H) 1.87 (d, J=6.85 Hz, 3H). (Compound 142) $^1$H NMR (400 MHz, DMSO-d$_6$) δ ppm 11.14 (s, 1H) 9.25 (s, 1H) 8.91 (d, J=2.45 Hz, 1H) 8.79 (s, 1H) 8.27 (s, 1H) 8.00-8.13 (m, 2H) 7.85 (s, 1H) 7.73 (d, J=8.80 Hz, 1H) 5.92 (d, J=7.34 Hz, 1H) 1.87 (d, J=6.85 Hz, 3H).

Example S79. Synthesis of N-(1-(2,3-dihydro-1H-inden-1-yl)-1H-pyrazol-4-yl)-5-(pyridin-2-yl)isoxazole-3-carboxamide (Compound 143)

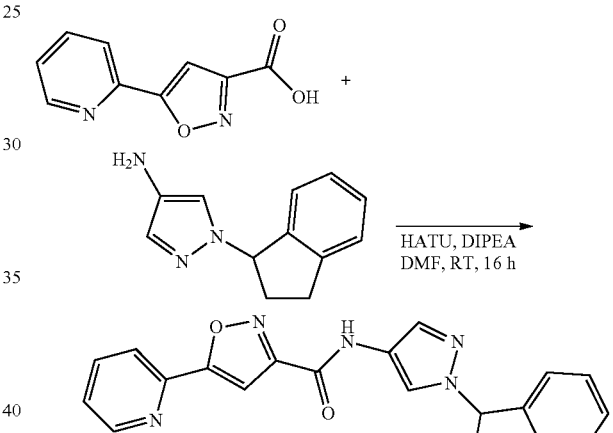

Step 1: Synthesis of N-(1-(2,3-dihydro-1H-inden-1-yl)-1H-pyrazol-4-yl)-5-(pyridin-2-yl)isoxazole-3-carboxamide. To a solution of 5-(pyridin-2-yl)isoxazole-3-carboxylic acid (50 mg, 0.239 mmol, 1 eq) in DMF (2 mL), were added HATU (47.60 mg, 0.239 mmol, 1 equiv). The mixture was added DIPEA (92.5 mg, 0.717 mmol, 2 equiv) drop wise. After stirring at RT for 15 minutes, the mixture was added a solution of 1-(2,3-dihydro-1H-inden-1-yl)-1H-pyrazol-4-amine (47.60 mg, 0.239 mmol, 1 equiv) in DMF (1 mL). The reaction mixture was stirred at RT for 24 h. The reaction mixture was diluted water (50 mL). The resulting precipitate was filtered off. Crude material which was purified by trituration with DCM:hexane (2:8) to obtained N-(1-(2,3-dihydro-1H-inden-1-yl)-1H-pyrazol-4-yl)-5-(pyridin-2-yl)isoxazole-3-carboxamide (30 mg). LCMS: 371 [M+H]$^+$. $^1$H NMR (500 MHz, DMSO-d$_6$) δ 11.05 (s, 1H), 8.76 (d, J=4.7 Hz, 1H), 8.09 (d, J=7.9 Hz, 1H), 8.04 (d, J=9.5 Hz, 2H), 7.68 (s, 1H), 7.57 (dd, J=7.4, 4.8 Hz, 1H), 7.47 (s, 1H), 7.36 (d, J=7.7 Hz, 1H), 7.29 (t, J=7.5 Hz, 1H), 7.20 (t, J=7.5 Hz, 1H), 7.08 (d, J=7.5 Hz, 1H), 5.92 (t, J=7.1 Hz, 1H), 3.12 (ddd, J=14.7, 8.7, 5.2 Hz, 1H), 2.94 (dt, J=15.7, 7.6 Hz, 1H), 2.60 (td, J=8.4, 4.9 Hz, 1H), 2.36 (h, J=6.5 Hz, 1H).

Example S80. Synthesis of N-(1-(2,3-dihydro-1H-inden-1-yl)-1H-pyrazol-4-yl)-5-(pyridin-2-yl)isoxazole-3-carboxamide (Compound 144)

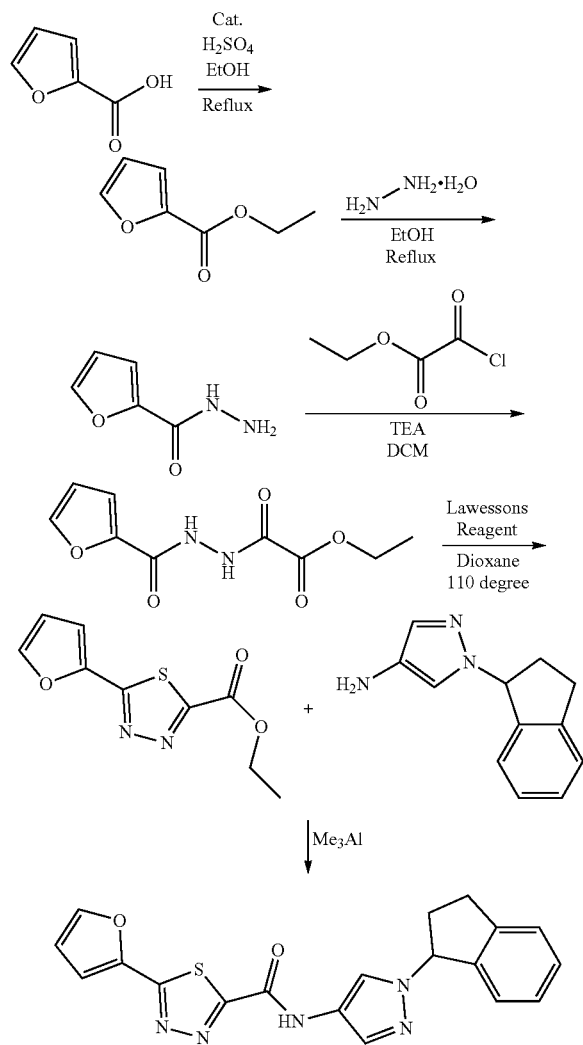

Step 1: Synthesis of ethyl furan-2-carboxylate. To a stirred solution of furan-2-carboxylic acid (500 mg) in Ethanol (30 ml) was added Conc $H_2SO_4$ (1 ml) drop wise and refluxed for 2 days AT 100 degree Celsius. Reaction was monitored by NMR. The reaction mixture was concentrated under vacuum to obtain crude was diluted with Saturated Sodium Bicarbonate Solution and Extracted with DCM (3×150 ml), organic layer dried over anhydrous sodium sulphate, Concentrated under reduced pressure to obtain ethyl pyrazine-2-carboxylate (420 mg). $^1$H NMR (400 MHz, DMSO-$d_6$) δ 7.88-8.04 (m, 1H), 7.29 (d, J=3.42 Hz, 1H), 6.63-6.72 (m, 1H), 4.27 (q, J=7.17 Hz, 2H), 1.28 (t, J=7.09 Hz, 3H).

Step 2: Synthesis of furan-2-carbohydrazide. To a stirred solution of Ethyl furan-2-carboxylate (400 mg, 1 eq, 2.85 mmoles) in ethanol (20 ml) was added hydrazine Hydrate (171.4 mg, 1.2 eq, and 3.42 m moles). Reaction mixture was refluxed for 3 hour. Reaction was monitored by NMR. Reaction Mixture was concentrated under vacuum to obtain crude which was triturated by using hexanes to obtained furan-2-carbohydrazide (310 mg, Brown Solid). 1H NMR (400 MHz, DMSO-$d_6$) δ 9.62 (br. s., 1H), 7.80 (d, J=0.98 Hz, 1H), 7.07 (d, J=3.42 Hz, 1H), 6.59 (dd, J=1.47, 3.42 Hz, 1H), 4.41 (br. s., 2H).

Step 3: Synthesis of ethyl 5-(furan-2-yl)-1,3,4-thiadiazole-2-carboxylate. To a stirred solution of Furan-2-carbohydrazide (200 mg, 1 eq, 21.587 mmoles) and TEA (192.38 mg, 1.2 eq, 1.904 m moles) in DCM at 0 degree temperature was added Ethyl 2-chloro-2-oxoacetate (260.9 mg, 1 eq, 1.904 mmoles) drop wise. Reaction mixture was stirred at 0 degree Temperature an hour. Reaction was monitored by LCMS. Reaction was quenched with ice water and Extracted with DCM (2×100 ml), organic layer dried over anhydrous sodium sulphate, concentrated under reduced pressure to obtain crude which was triturated with hexane to obtain desired product. To a stirred solution ethyl 2-(2-(furan-2-carbonyl)hydrazinyl)-2-oxoacetate (300 mg, 1 eq, and 1.327 mmoles) in Dioxane (4 ml) was added Lawessons' reagent (1.6 gm, 3 eq, and 3.98 mmoles) at RT. Reaction Mixture was heated at 110 degree Celsius for 24 hour. Reaction was monitored by LCMS. Work up was done by Quenching with Saturated Bicarbonate solution (30 ml), Extracted with diethyl ether (76 ml×3), Organic layer dried over anhydrous sodium sulphate, concentrated under vacuum to obtain crude which was purified by Combi-Flash Chromatography to obtain Crude product was triturated with DCM Hexane (2:8) to obtained ethyl 5-(furan-2-yl)-1,3,4-thiadiazole-2-carboxylate (260 mg, pale yellow solid). LCMS: 224 [M+H]$^+$. $^1$H NMR (400 MHz, DMSO-$d_6$) δ 8.11 (d, J=0.98 Hz, 1H), 7.53 (d, J=3.42 Hz, 1H), 6.84 (dd, J=1.71, 3.67 Hz, 1H), 4.39-4.50 (m, 2H), 1.36 (t, J=7.09 Hz, 3H).

Step 4: Synthesis of N-(1-(2, 3-dihydro-1H-inden-1-yl)-1H-pyrazol-4-yl)-5-(furan-2-yl)-1,3,4-thiadiazole-2-carboxamide. To a stirred mixture of ethyl 5-(furan-2-yl)-1,3,4-thiadiazole-2-carboxylate (50 mg, 0.221 mmol, 1 equiv) and 1-(2,3-dihydro-1H-inden-1-yl)-1H-pyrazol-4-amine (44.02 mg, 0.221 mmol, 1 equiv) in Toluene (2 mL) was added Trimethyl Aluminium (510 mg, 0.663 mmol, 3 equiv) at RT. Reaction mixture was stirred at RT for 24 h. The reaction mixture was diluted water (50 mL), The resulting suspension was filtered off and filtered was extracted with ethyl Acetate (50 ml×2), Organic layer dried over anhydrous sodium sulphate, concentrated under vacuum to obtained crude which was purified by Combi-Flash Chromatography to obtain crude product which was triturated with DCM: Hexane (2:8) to obtain desired product (15 mg, Pale yellow Solid). LCMS: 377 [M+H]$^+$. $^1$H NMR (500 MHz, DMSO-$d_6$) δ 11.54 (s, 1H), 8.09 (s, 1H), 8.04 (s, 1H), 7.73 (s, 1H), 7.49 (d, J=3.5 Hz, 1H), 7.36 (d, J=7.6 Hz, 1H), 7.29 (t, J=7.4 Hz, 1H), 7.20 (t, J=7.5 Hz, 1H), 7.07 (d, J=7.6 Hz, 1H), 6.85-6.80 (m, 1H), 5.92 (t, J=7.0 Hz, 1H), 3.12 (ddd, J=14.8, 8.7, 5.1 Hz, 1H), 2.94 (dt, J=15.6, 7.5 Hz, 1H), 2.66-2.56 (m, 1H), 2.35 (q, J=7.0 Hz, 1H).

Example S81. Synthesis of N-(1-(2,6-dichlorobenzyl)-1H-pyrazol-4-yl)-5-(pyridin-2-yl)-1,3,4-thiadiazole-2-carboxamide (Compound 145)

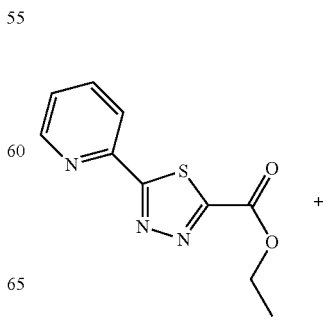

-continued

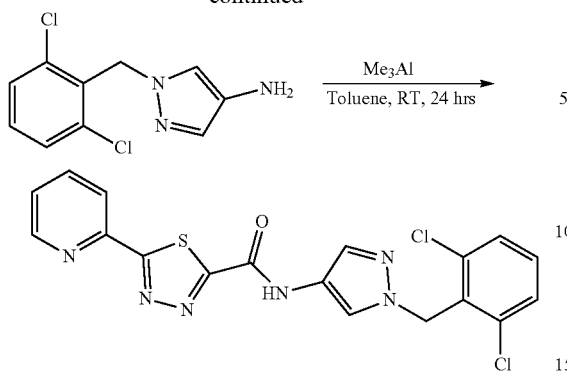

Step 1: Synthesis of N-(1-(2,6-dichlorobenzyl)-1H-pyrazol-4-yl)-5-(pyridin-2-yl)-1,3,4-thiadiazole-2-carboxamide. To a stirred mixture of ethyl 5-(pyridin-2-yl)-1,3,4-thiadiazole-2-carboxylate (50 mg, 0.210 mmol, 1 equiv) and 1-(2,6-dichlorobenzyl)-1H-pyrazol-4-amine (50.84 mg, 0.210 mmol, 1 equiv) in Toluene (2 mL) at RT was added Trimethyl Aluminium (30.37 mg, 0.843 mmol, 4 equiv). Reaction mixture was stirred at RT for 24 h. The reaction mixture was diluted water (50 mL), The resulting suspension was filtered off, Filtrate was extracted with ethyl Acetate (50 ml×2), Organic layer dried over anhydrous sodium sulphate, concentrated under vacuum to obtain crude which was purified by Combi-Flash Chromatography to obtain crude product was triturated with DCM: Hexane (2:8) to obtain desired product (3 mg, Pale yellow Solid). LCMS: 430 [M+H]$^+$. $^1$H NMR (500 MHz, DMSO-d$_6$) δ 11.55 (s, 1H), 8.76 (d, J=4.7 Hz, 1H), 8.35 (d, J=7.9 Hz, 1H), 8.12-8.05 (m, 2H), 7.71 (s, 1H), 7.65 (dd, J=7.6, 4.9 Hz, 1H), 7.57 (d, J=8.1 Hz, 2H), 7.46 (t, J=8.1 Hz, 1H), 5.56 (s, 2H).

Example S82. Synthesis of N-(1-(2,6-dichlorobenzyl)-1H-pyrazol-4-yl)-5-(pyridin-2-yl)isoxazole-3-carboxamide (Compound 146)

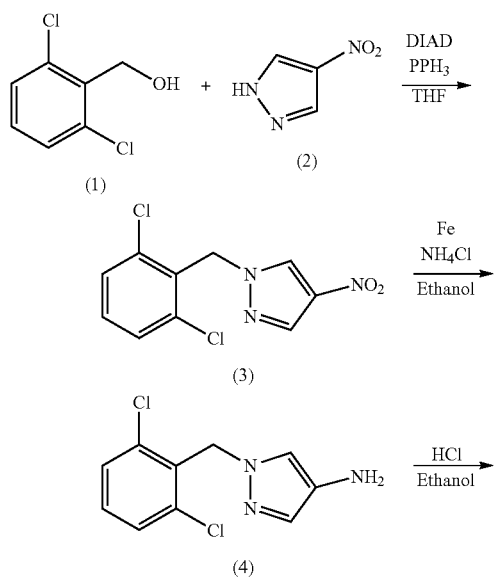

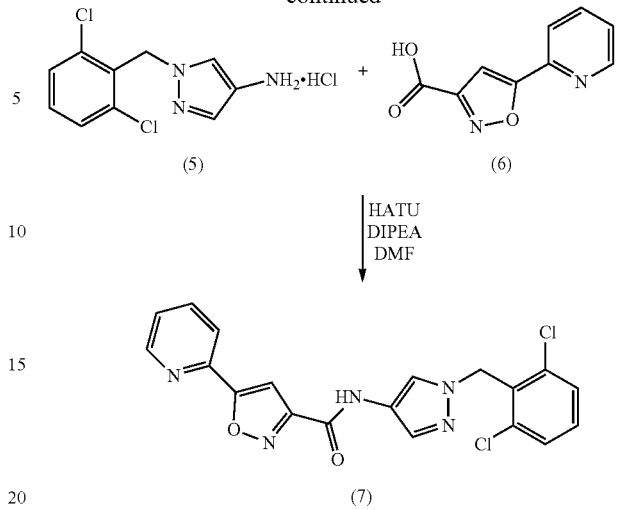

Step 1: Synthesis of 1-(2, 6-dichlorobenzyl)-4-nitro-1H-pyrazole (3). To the stirred solution of Triphenylphosphine (4.44 gm, 0.0168 moles, 1.5 equiv) and DIAD (3.42 gm, 0.0168 moles, 1.5 equiv) THF (20 mL) was added (2,6-dichlorophenyl)methanol (2 gm, 0.0112 moles, 1 equiv) and 4-nitro-1H-pyrazole (1.27 gm, 0.0112 moles, 1 equiv) at RT. Reaction mixture was stirred at RT for 16 H. After completion of the reaction, reaction mixture was extracted with ethylacetate and water twice. The organic layer was collected and evaporated under reduced pressure to give crude material which was purified by using combi flash chromatography to obtain desired product. LCMS: 272 [M+H]$^+$. $^1$H NMR (400 MHz, DMSO-d$_6$) δ ppm 9.04 (s, 1H) 8.23 (s, 1H) 7.49-7.60 (m, 2H) 7.34-7.49 (m, 1H) 5.64 (s, 2H).

Step 2: Synthesis of 1-(2, 6-dichlorobenzyl)-1H-pyrazol-4-amine (4). To a stirred solution pf 1-(2, 6-dichlorobenzyl)-4-nitro-1H-pyrazole (3) (1 gm, 0.003 moles, 1 eq) in 15 mL ethanol-water (1:1) was added Iron (1.03 gm, 0.0185 moles, 5 equiv) and ammonium chloride (0.98 gm, 0.0185 moles, 5 equiv) at RT. Reaction mixture was refluxed for 24 hour at 80 degree Celsius. Reaction mixture was filtered through celite bed. Obtained filtrate was extracted with DCM and water twice. Organic layer was collected and evaporated under reduced pressure to obtain desired product 1-(2, 6-dichlorobenzyl)-1H-pyrazol-4-amine (4). LCMS: 241 [M+H]$^+$.

Step 3: Synthesis of 1-(2, 6-dichlorobenzyl)-1H-pyrazol-4-amine hydrochloride (5). To a stirred solution of 1-(2, 6-dichlorobenzyl)-1H-pyrazol-4-amine (4) (1 gm) in ethanol was added 5 ml of HCl in ethanol (3M) was added and kept under stirring for overnight. Resulting reaction mixture was concentrated to give desired product 1-(2, 6-dichlorobenzyl)-1H-pyrazol-4-amine hydrochloride (5). LCMS: 241 [M+H]$^+$. $^1$H NMR (400 MHz, DMSO-d$_6$) δ ppm 9.98 (br. s., 3H) 7.98 (s, 1H) 7.49-7.57 (m, 2H) 7.45 (d, J=7.83 Hz, 2H) 5.56 (s, 2H).

Step 4: Synthesis of N-(1-(2,6-dichlorobenzyl)-1H-pyrazol-4-yl)-5-(pyridin-2-yl)isoxazole-3-carboxamide. To a stirred solution of 5-(pyridin-2-yl)isoxazole-3-carboxylic acid (34.35 mg, 0.179 mmol, 1 equiv) in DMF (1 mL) was added HATU (68.32 mg, 0.197 mmol, 1 equiv). After stirring at RT for 15 minutes, the mixture was added DIPEA (93.95 mg, 0.537 mmol, 3 equiv). After stirring at RT for 15 minutes, was added a solution of the 1-(2,6-dichlorobenzyl)-1H-pyrazol-4-amine hydrochloride (50 mg, 0.179 mmol, 1 equiv) in DMF (1 mL). The reaction mixture was stirred at RT for 24 h. The reaction mixture was diluted with water (50 mL). The resulting precipitate was filtered off. Crude material obtained was purified by combi flash chromatography to obtained N-(1-(2,6-dichlorobenzyl)-1H-pyrazol-4-yl)-5-(pyridin-2-yl)isoxazole-3-carboxamide (4 mg white solid). LCMS: 414 [M+H]$^+$. $^1$H NMR (400 MHz, DMSO-d$_6$) δ ppm 11.04 (s, 1H) 8.76 (d, J=3.91 Hz, 1H) 7.98-8.12 (m, 3H) 7.64 (s, 1H) 7.57 (d, J=8.31 Hz, 2H) 7.39-7.49 (m, 3H) 5.56 (s, 2H).

Example S83. Synthesis of N-(1-(2,6-dichlorobenzyl)-1H-pyrazol-4-yl)-2-(furan-2-yl)thiazole-5-carboxamide (Compound 147)

equiv) at RT. Reaction mixture was refluxed for 24 hour at 80 degree Celsius. Reaction mixture was filtered through celite bed. Obtained filtrate was extracted with DCM and water twice. Organic layer was collected and evaporated under reduced pressure to obtain desired product 1-(2, 6-dichlorobenzyl)-1H-pyrazol-4-amine (4). LCMS: 242 [M+H]$^+$.

Step 3: Synthesis of 1-(2, 6-dichlorobenzyl)-1H-pyrazol-4-amine hydrochloride (5). To a stirred solution of 1-(2, 6-dichlorobenzyl)-1H-pyrazol-4-amine (4) (1 gm) in ethanol was added 5 ml of HCl in ethanol (3M) was added and kept under stirring for overnight. Resulting reaction mixture was concentrated to give desired product 1-(2, 6-dichlorobenzyl)-1H-pyrazol-4-amine hydrochloride (5). $^1$H NMR (400

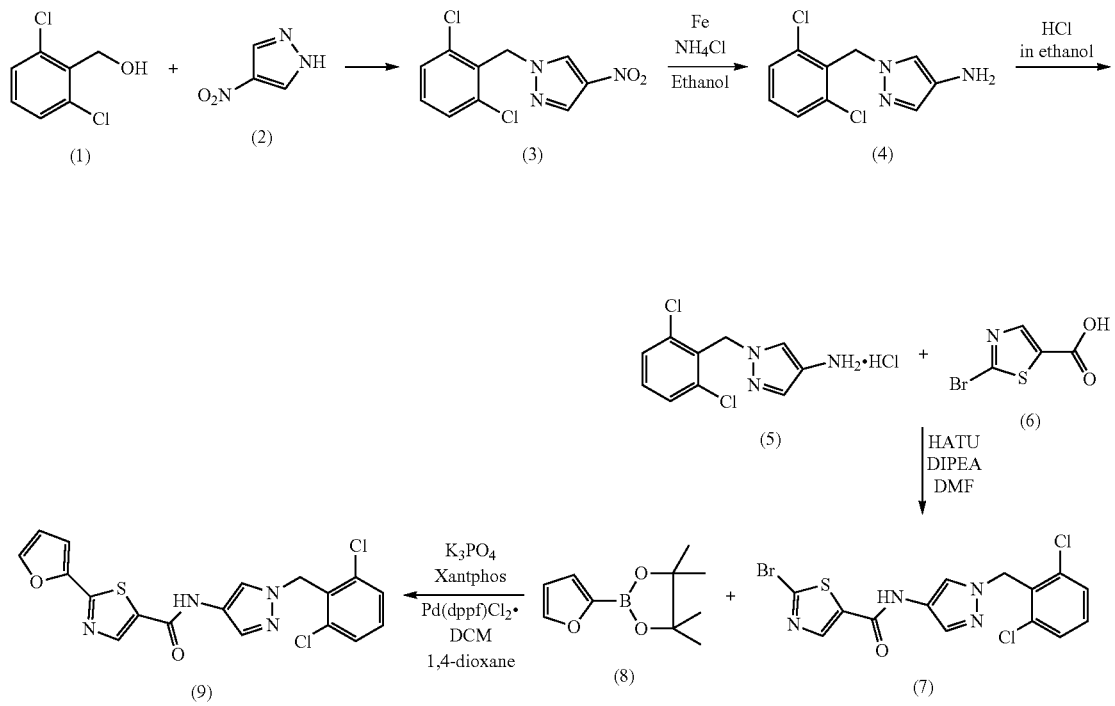

MHz, DMSO-d$_6$) δ ppm 9.98 (br. s., 3H) 7.98 (s, 1H) 7.49-7.57 (m, 2H) 7.45 (d, J=7.83 Hz, 2H) 5.56 (s, 2H).

Step 1: Synthesis Of 1-(2, 6-dichlorobenzyl)-4-nitro-1H-pyrazole (3). To the stirred solution of Triphenylphosphine (4.44 gm, 0.0168 moles, 1.5 equiv) and DIAD (3.42 gm, 0.0168 moles, 1.5 equiv) THF (20 mL) was added (2,6-dichlorophenyl)methanol (2 gm, 0.0112 moles, 1 equiv) and 4-nitro-1H-pyrazole (1.27 gm, 0.0112 moles, 1 equiv) at RT. Reaction mixture was stirred at RT for 16 H. After completion of the reaction, reaction mixture was extracted with ethylacetate and water twice. The organic layer was collected and evaporated under reduced pressure to give crude material which was purified by using combi flash chromatography to obtain desired product. LCMS: 272 [M+H]$^+$. $^1$H NMR (400 MHz, DMSO-d$_6$) d ppm 9.04 (s, 1H) 8.23 (s, 1H) 7.49-7.60 (m, 2H) 7.34-7.49 (m, 1H) 5.64 (s, 2H).

Step 2: Synthesis of 1-(2, 6-dichlorobenzyl)-1H-pyrazol-4-amine (4). To a stirred solution pf 1-(2, 6-dichlorobenzyl)-4-nitro-1H-pyrazole (3) (1 gm, 0.003 moles, 1 eq) in 15 mL ethanol-water (1:1) was added Iron (1.03 gm, 0.0185 moles, 5 equiv) and ammonium chloride (0.98 gm, 0.0185 moles, 5

Step 4: Synthesis of 2-bromo-N-(1-(2,6-dichlorobenzyl)-1H-pyrazol-4-yl)thiazole-5-carboxamide. To a stirred solution of 2-bromothiazole-5-carboxylic acid (500 mg, 2.403 mmol, 1 equiv), HATU (913.14 mg, 2.403 mmol, 1 equiv), DIPEA (929.96 mg, 7.209 mmol, 3 equiv) in DMF (1 mL) was added a solution of 1-(2,6-dichlorobenzyl)-1H-pyrazol-4-amine hydrochloride (668.26 mg, 2.403 mmol, 1 equiv) in DMF (1 mL). The reaction mixture was stirred at RT for 24 h. The reaction mixture was diluted with water (50 mL). The resulting precipitate was filtered off. Crude material was purified by combi flash chromatography to give product which was further triturated with acetone and hexane to give pure product. LCMS: 431 [M+H]$^+$.

Step 5: Synthesis of N-(1-(2,6-dichlorobenzyl)-1H-pyrazol-4-yl)-2-(furan-2-yl)thiazole-5-carboxamide. To a stirred solution of 2-bromo-N-(1-(2,6-dichlorobenzyl)-1H-pyrazol-4-yl)thiazole-5-carboxamide (100 mg, 0.231 mmol, 1 equiv), 2-(furan-2-yl)-4,4,5,5-tetramethyl-1,3,2-dioxaborolane (44.90 mg, 0.231 mmol, 1 equiv), potassium phosphate (97.94 mg, 0.462 mmol, 2 equiv) and xantphos (13.35 mg, 0.0231, 0.1 equiv) in 3 mL 1,4-dioxane at RT and purged with nitrogen for 30 min. After purging, Pd(dppf)Cl$_2$·DCM (18.84 mg, 0.0231 mmol, 0.1 equiv) was added and allowed to heat at 110° C. for 20 hr. After completion of the reaction, reaction mixture was extracted with ethylacetate and water twice. Organic layer was collected and evaporated under reduced pressure to give crude product which was purified by using combi flash chromatography to give N-(1-(2,6-dichlorobenzyl)-1H-pyrazol-4-yl)-2-(furan-2-yl)thiazole-5-carboxamide (25 mg pale yellow solid). LCMS: 419 [M+H]$^+$. $^1$H NMR (400 MHz, DMSO-d$_6$) δ ppm 10.72 (s, 1H) 8.50 (s, 1H) 7.92-8.02 (m, 2H) 7.51-7.62 (m, 3H) 7.41-7.48 (m, 1H) 7.24 (d, J=3.42 Hz, 1H) 6.72-6.78 (m, 1H) 5.55 (s, 2H).

Example S84. Synthesis of N-(1-(2,6-dichlorobenzyl)-1H-pyrazol-4-yl)-5-(furan-2-yl)-1,3,4-thiadiazole-2-carboxamide (Compound 148)

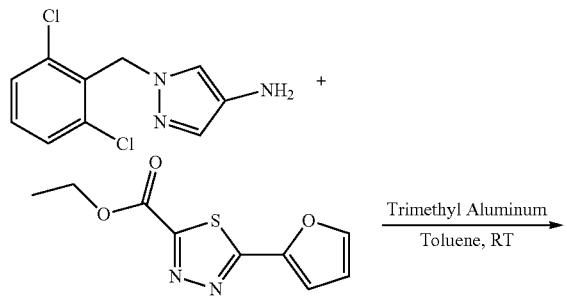

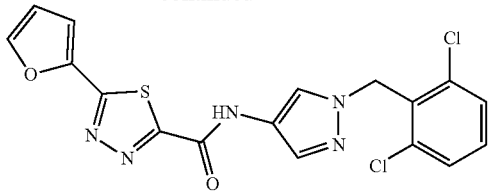

Synthesis of N-(1-(2,6-dichlorobenzyl)-1H-pyrazol-4-yl)-5-(furan-2-yl)-1,3,4-thiadiazole-2-carboxamide. To a stirred solution of (2,6-dichlorobenzyl)-1H-pyrazol-4-amine (54.01 mg, 0.223 mmol, 1 equiv) and ethyl 5-(furan-2-yl)-1,3,4-thiadiazole-2-carboxylate (50 mg, 0.223 mmol, 1 equiv) in Toluene (10 mL) was added Trimethyl Aluminium (0.17 mL, 0.892 mmol, 4 equiv). Reaction mixture was stirred at RT for 24 hr. The reaction mixture was diluted with water and extracted with Ethyl acetate; organic layer was collected and evaporated under reduced pressure to give crude material which was purified by using combi flash chromatography to give N-(1-(2,6-dichlorobenzyl)-1H-pyrazol-4-yl)-5-(furan-2-yl)-1,3,4-thiadiazole-2-carboxamide (8 mg pale yellow solid). LCMS: 420 [M+H]$^+$. $^1$H NMR (400 MHz, DMSO-d$_6$) δ ppm 11.52 (br. s., 1H) 8.08 (s, 2H) 7.70 (s, 1H) 7.51-7.62 (m, 2H) 7.27-7.51 (m, 3H) 6.82 (d, J=3.91 Hz, 1H) 5.56 (s, 2H).

Example S85. Synthesis of (R)—N-(1-(2,3-dihydro-1H-inden-1-yl)-1H-pyrazol-4-yl)-5-(furan-2-yl)isoxazole-3-carboxamide and (S)—N-(1-(2,3-dihydro-1H-inden-1-yl)-1H-pyrazol-4-yl)-5-(furan-2-yl)isoxazole-3-carboxamide (Compounds 149 & 150)

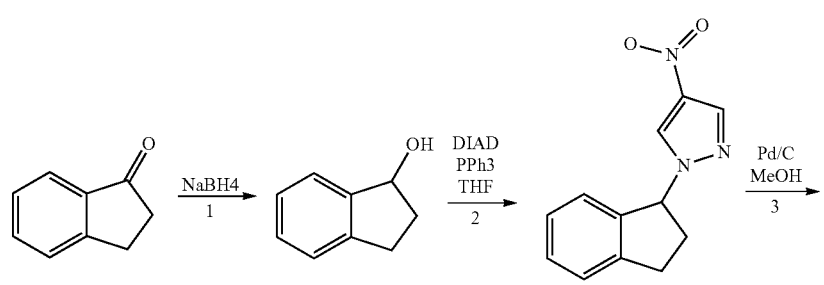

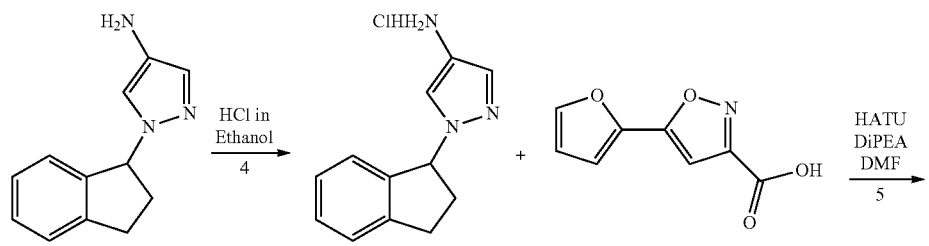

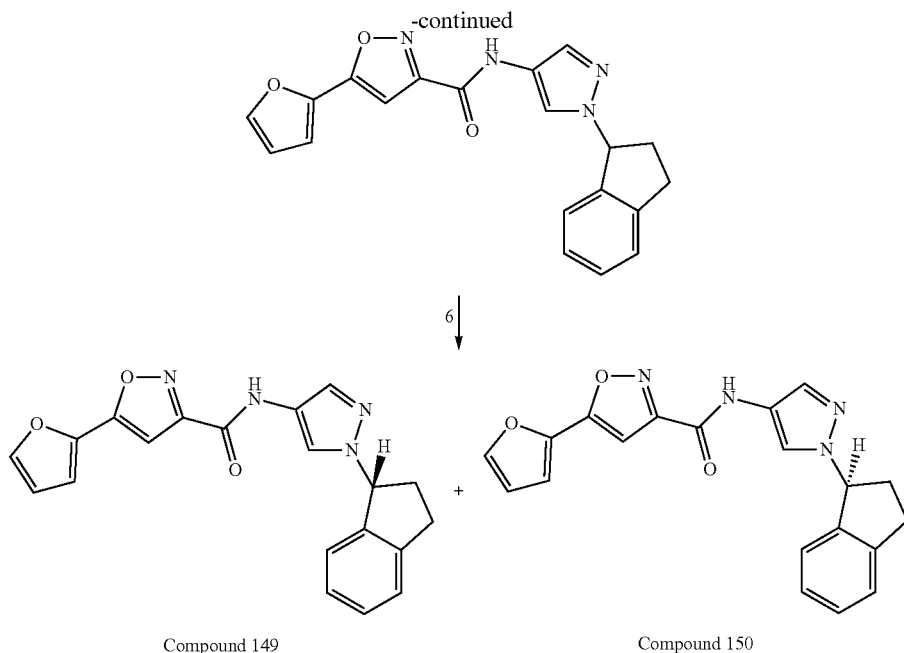

Compound 149  Compound 150

Step 1: Synthesis of 2,3-dihydro-1H-inden-1-ol. To a stirred solution of 2,3-dihydro-1H-inden-1-one (500 mg, 3.78 mmol, 1.0 equiv) in Methanol (5 mL) was added $NaBH_4$ (228 mg, 5.68 mmol, 1.5 equiv) portion wise at 0° C. and stirred for 10 minutes. The reaction mixture was allowed to stir for 1 hour at RT. Product formation was confirmed by TLC AND LCMS. After completion of reaction, reaction mixture was quenched with water and extracted with ethyl acetate (50 mL×3). Combined organic extracts were washed with water (2×50 mL), dried over anhydrous $Na_2SO_4$ and concentrated under reduced pressure to obtain 2,3-dihydro-1H-inden-1-ol (500 mg). $^1H$ NMR (400 MHz, CHLOROFORM-d) δ 7.43 (d, J=5.38 Hz, 1H), 7.19-7.28 (m, 4H), 5.20-5.35 (m, 1H), 3.07 (ddd, J=4.89, 8.56, 15.90 Hz, 1H), 2.83 (td, J=7.70, 15.90 Hz, 1H), 2.43-2.55 (m, 1H), 1.88-2.02 (m, 1H), 1.70 (d, J=6.85 Hz, 1H).

Step 2: Synthesis of 1-(2, 3-dihydro-1H-inden-1-yl)-4-nitro-1H-pyrazole (3). To a stirred solution of 2, 3-dihydro-1H-inden-1-ol (1) (300 mg, 2.238 moles, and 1 eq), 4-nitro-1H-pyrazole (2) (252.9 mg, 2.238 moles, and 1 eq) and Triphenylphosphione (538.66 mg, 2.666 moles, and 1.2 eq) in THF (6 ml) at 0 degree Celsius was added solution of DIAD (266.44 gm, 2.666 moles, 1.2 eq) diluted in THF (3 ml) drop wise. Reaction mixture was heated in microwave for 15 minutes at 140 degree Celsius. Reaction mixture was concentrated under vacuum to obtain crude which was purified by column chromatography to obtain desired product of 1-(2, 3-dihydro-1H-inden-1-yl)-4-nitro-1H-pyrazole (351 mg). $^1H$ NMR (400 MHz, DMSO-$d_6$) δ 8.97 (s, 1H), 8.26 (s, 1H), 7.26-7.39 (m, 2H), 7.10-7.23 (m, 2H), 5.93-6.03 (m, 1H), 3.16-3.24 (m, 1H), 2.88-2.98 (m, 1H), 2.57-2.75 (m, 2H).

Step 3: Synthesis of 1-(2, 3-dihydro-1H-inden-1-yl)-1H-pyrazol-4-amine. To a stirred solution of 1-(2,3-dihydro-1H-inden-1-yl)-4-nitro-1H-pyrazole (3) (350 mg) in MeOH (10 mL) and purged with Nitrogen gas then added 10% Pd/C (70 mg) and again purged with nitrogen for further 5 minute then resulting reaction mixture was purged with Hydrogen gas for one hour. Reaction was monitored by TLC and LCMS. Reaction mixture was filtered through Celite bed and washed with Methanol and concentrate on reduced pressure to yield crude product 1-(2, 3-dihydro-1H-inden-1-yl)-1H-pyrazol-4-amine (310 mg) which is used directly for next step. LCMS: 199 [M+H]$^+$.

Step 4: Synthesis of 1-(2,3-dihydro-1H-inden-1-yl)-1H-pyrazol-4-amine hydrochloride hydrochloride. To a stirred solution of 1-(2, 3-dihydro-1H-inden-1-yl)-1H-pyrazol-4-amine (350 mg) was dissolved in ethanol was added 20 ml HCl in ethanol (15 ml) at zero degree celcius and stirred at RT for half an hour. Resulting suspension was filtered and filtrate was evaporated under vacuum to obtain crude which was triturated with ether to obtain product 1-(2,3-dihydro-1H-inden-1-yl)-1H-pyrazol-4-amine hydrochloride (320 mg). LCMS: 199 [M+H]$^+$.

Step 5: Synthesis of N-(1-(2, 3-dihydro-1H-inden-1-yl)-1H-pyrazol-4-yl)-5-(furan-2-yl) isoxazole-3-carboxamide (6). To a stirred solution of 5-(furan-2-yl) isoxazole-3-carboxylic acid (200 mg, 1 eq, 1.111 mmole), HATU (423.33 mg, 1.111 mmole, and 1 eq) and DIPEA (430 mg, 3 eq, and 3.33 mmole) in 5 ml of DMF at RT was added 1-(2,3-dihydro-1H-inden-1-yl)-1H-pyrazol-4-amine hydrochloride (393.33 mg, 1 eq, 1.111 mmole). Resulting reaction mixture was stirred at RT for 24 hr. Reaction mixture was diluted with water and extracted with ethyl acetate, organic layer dried over anhydrous sodium sulphate, concentrated under vacuum to obtain crude which was triturated with IPA: Hexane (1:9) to obtain N-(1-(2, 3-dihydro-1H-inden-1-yl)-1H-pyrazol-4-yl)-5-(furan-2-yl) isoxazole-3-carboxamide. LCMS: 360 [M+H]$^+$.

Step 6: Synthesis of (R) and (S)—N-(1-(2, 3-dihydro-1H-inden-1-yl)-1H-pyrazol-4-yl)-5-(furan-2-yl) isoxazole-3-carboxamide. The enantiomers of N-(1-(1-(2,4-bis(trifluoromethyl)phenyl)ethyl)-1H-pyrazol-4-yl)-5-(pyridin-3-yl) isoxazole-3-carboxamide (elution time: 16.4 min & 19.7 min), were separated by chiral HPLC (Daicel Chiralpak®-IC, 250×20 mm, 5 μm). Isocratic program with HPLC grade n-Hexane (0.2% DEA) and HPLC grade Isopropanol, Total flow: 18 ml/min, Isopropanol Percentage: 30% to obtain ((R N-(1-(2,3-dihydro-1H-inden-1-yl)-1H-pyrazol-4-yl)-5-(furan-2-yl) isoxazole-3-carboxamide (12 mg) (S)N-(1-(2,3-dihydro-1H-inden-1-yl)-1H-pyrazol-4-yl)-5-(furan-2-yl) isoxazole-3-carboxamide (15 mg). (Compound 149) $^1$H NMR (400 MHz, DMSO-$d_6$) δ 10.99 (s, 1H), 7.99-8.03 (m, 2H), 7.67 (s, 1H), 7.34-7.38 (m, 1H), 7.26-7.32 (m, 2H), 7.20 (t, J=7.09 Hz, 1H), 7.13 (s, 1H), 7.07 (d, J=7.34 Hz, 1H), 6.77 (dd, J=1.96, 3.42 Hz, 1H), 5.87-5.94 (m, 1H), 3.07-3.18 (m, 1H), 2.94 (td, J=7.58, 15.16 Hz, 1H), 2.56-2.68 (m, 1H), 2.31-2.41 (m, 1H). (Compound 150) $^1$H NMR (400 MHz, DMSO-$d_6$) δ 10.99 (s, 1H), 8.01 (d, J=2.93 Hz, 2H), 7.67 (s, 1H), 7.33-7.38 (m, 1H), 7.27-7.32 (m, 2H), 7.20 (t, J=7.34 Hz, 1H), 7.13 (s, 1H), 7.07 (d, J=7.34 Hz, 1H), 6.77 (d, J=1.47 Hz, 1H), 5.91 (t, J=6.85 Hz, 1H), 3.05-3.19 (m, 1H), 2.89-3.00 (m, 1H), 2.57-2.69 (m, 1H), 2.31-2.40 (m, 1H).

Example S86. Synthesis of N-(1-(2,4-bis(trifluoromethyl)benzyl)-1H-pyrazol-4-yl)-5-(pyridin-2-yl)-1,3,4-oxadiazole-2-carboxamide (Compound 151)

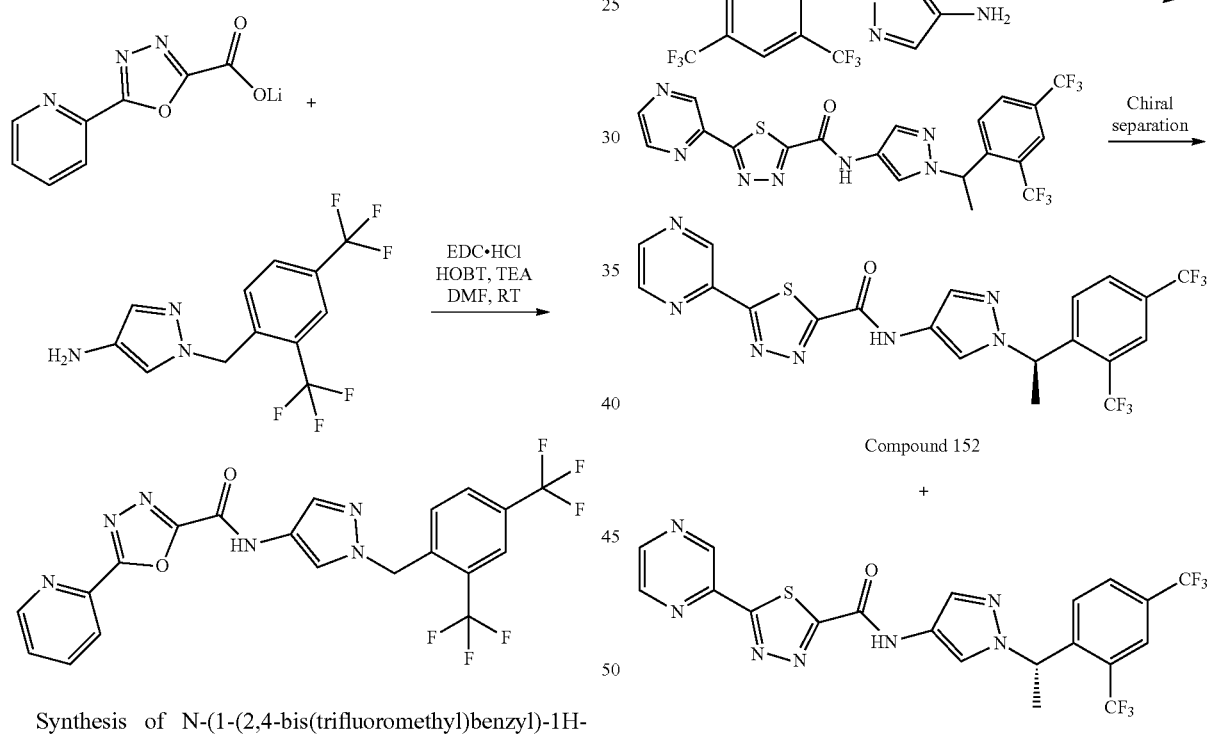

Synthesis of N-(1-(2,4-bis(trifluoromethyl)benzyl)-1H-pyrazol-4-yl)-5-(pyridin-2-yl)-1,3,4-oxadiazole-2-carboxamide. To a stirred solution of lithium 5-(pyridin-2-yl)-1,3,4-oxadiazole-2-carboxylate (120 mg, 0.61, 1 equiv), 1-(2,4-bis(trifluoromethyl)benzyl)-1H-pyrazol-4-amine hydrochloride salt (210 mg, 0.61 mmol, 1 equiv), EDC·HCl (175 mg, 0.91, 1.5 equiv), HoBt (124 mg, 0.91 mmol, 1.5 equiv) and TEA (0.3 mL, 1.827 mmol, 3.0 equiv) in DMF (2 mL) at RT for overnight. Reaction mixture was added ice-water (50 mL), s extracted with EtOAc (2×40 mL), Organic layer was dried over anhydrous sodium sulfate, concentrated under vacuum to obtain crude which was purified by flash chromatography using EtOAc/Hexane system as eluent to afford free base of title compound (5 mg). LCMS: 483 [M+H]$^+$. $^1$H NMR (400 MHz, DMSO-$d_6$) δ ppm 11.72 (s, 1H) 8.84 (d, J=4.89 Hz, 1H) 8.39 (s, 1H) 8.30 (d, J=7.83 Hz, 1H) 8.03-8.16 (m, 3H) 7.84 (s, 1H) 7.63-7.75 (m, 1H) 7.06 (d, J=8.80 Hz, 1H) 5.69 (s, 2H).

Example S87. Synthesis of (R)—N-(1-(1-(2,4-bis(trifluoromethyl)phenyl)ethyl)-1H-pyrazol-4-yl)-5-(pyrazin-2-yl)-1,3,4-thiadiazole-2-carboxamide and (S)—N-(1-(1-(2,4-bis(trifluoromethyl)phenyl)ethyl)-1H-pyrazol-4-yl-5-(pyrazin-2-yl)-1,3,4-thiadiazole-2-carboxamide (Compounds 152 & 153)

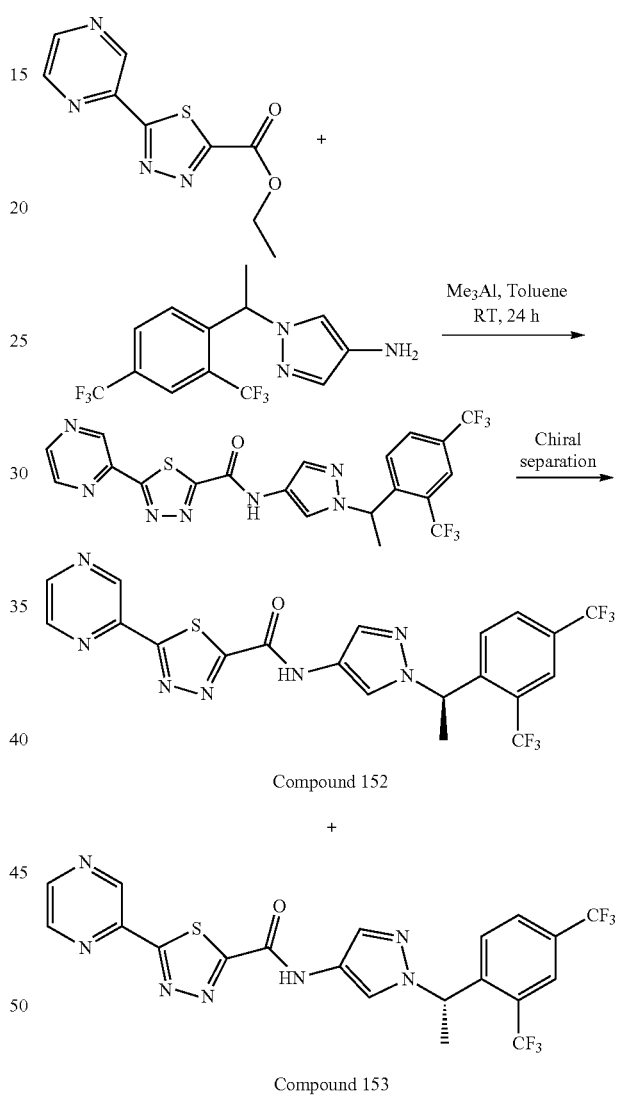

Compound 152

Compound 153

Synthesis of N-(1-(1-(2,4-bis(trifluoromethyl)phenyl) ethyl)-1H-pyrazol-4-yl)-5-(pyrazin-2-yl)-1,3,4-thiadiazole-2-carboxamide. To a stirred solution of ethyl 5-(pyrazin-2-yl)-1,3,4-thiadiazole-2-carboxylate (100 mg, 0.421 mmol, 1 equiv), 1-(1-(2,4-bis(trifluoromethyl)phenyl)ethyl)-1H-pyrazol-4-amine (136.7 mg, 0.421 mmol, 1 equiv) in Toluene (2 mL) was added 2M Trimethyl Aluminium in Toluene (118.14 mg, 0.105 mmol, 4 equiv) at RT. The reaction mixture was stirred at RT for 24 h. The reaction mixture was diluted water (50 mL). The resulting suspension was filtered off, filtrate was extracted with ethyl Acetate (50 ml×2), Organic layer dried over anhydrous sodium sulphate, concentrated under vacuum to obtained crude which was purified by Combi-Flash Chromatography to obtained Crude product was triturated with DCM: Hexane (2:8) to obtain desired product. LCMS: 513 [M+H]⁺.

Synthesis of (R) and (S)—N-(1-(1-(2,4-bis(trifluoromethyl)phenyl)ethyl)-1H-pyrazol-4-yl)-5-(pyrazin-2-yl)-1,3,4-thiadiazole-2-carboxamide. The enantiomers of N-(1-(1-(2,4-bis(trifluoromethyl)phenyl)ethyl)-1H-pyrazol-4-yl)-5-(pyrazin-2-yl)-1,3,4-thiadiazole-2-carboxamide (elution time: 5.3 min & 5.8 min), were separated by chiral SFC (Daicel Chiralcel®-ODH, 250×20 mm, 5 µm). Isocratic program with analytical grade liquid carbon dioxide and HPLC grade Isopropanol, Total flow: 56 g/min, Co-Solvent Percentage: 20% to obtained Peak-1 ((S) N-(1-(1-(2,4-bis(trifluoromethyl)phenyl)ethyl)-1H-pyrazol-4-yl)-5-(pyrazin-2-yl)-1,3,4-thiadiazole-2-carboxamide (20 mg) Peak-2(R) N-(1-(1-(2,4-bis(trifluoromethyl)phenyl)ethyl)-1H-pyrazol-4-yl)-5-(pyrazin-2-yl)-1,3,4-thiadiazole-2-carboxamide (15 mg). (Compound 152) ¹H NMR (400 MHz, DMSO-d₆) δ 11.65 (s, 1H), 9.53 (d, J=1.32 Hz, 1H), 8.91 (d, J=2.63 Hz, 1H), 8.86-8.89 (m, 1H), 8.24 (s, 1H), 8.09 (d, J=8.33 Hz, 1H), 8.06 (s, 1H), 7.83 (s, 1H), 7.75 (d, J=8.33 Hz, 1H), 5.95 (d, J=7.02 Hz, 1H), 1.88 (d, J=6.58 Hz, 3H). (Compound 153) ¹H NMR (400 MHz, DMSO-d₆) δ 11.65 (br. s., 1H), 9.53 (d, J=1.32 Hz, 1H), 8.91 (d, J=2.63 Hz, 1H), 8.85-8.88 (m, 1H), 8.24 (s, 1H), 8.09 (d, J=8.33 Hz, 1H), 8.06 (s, 1H), 7.83 (s, 1H), 7.75 (d, J=8.33 Hz, 1H), 5.91-5.98 (m, 1H), 1.88 (d, J=7.02 Hz, 3H).

Example S88. Synthesis of (R)—N-(1-(1-(2,4-bis(trifluoromethyl)phenyl)ethyl)-1H-pyrazol-4-yl)-4-methyl-5-(pyridin-2-yl)isoxazole-3-carboxamide and (S)—N-(1-(1-(2,4-bis(trifluoromethyl)phenyl)ethyl)-1H-pyrazol-4-yl)-4-methyl-5-(pyridin-2-yl)isoxazole-3-carboxamide (Compounds 154 & 155)

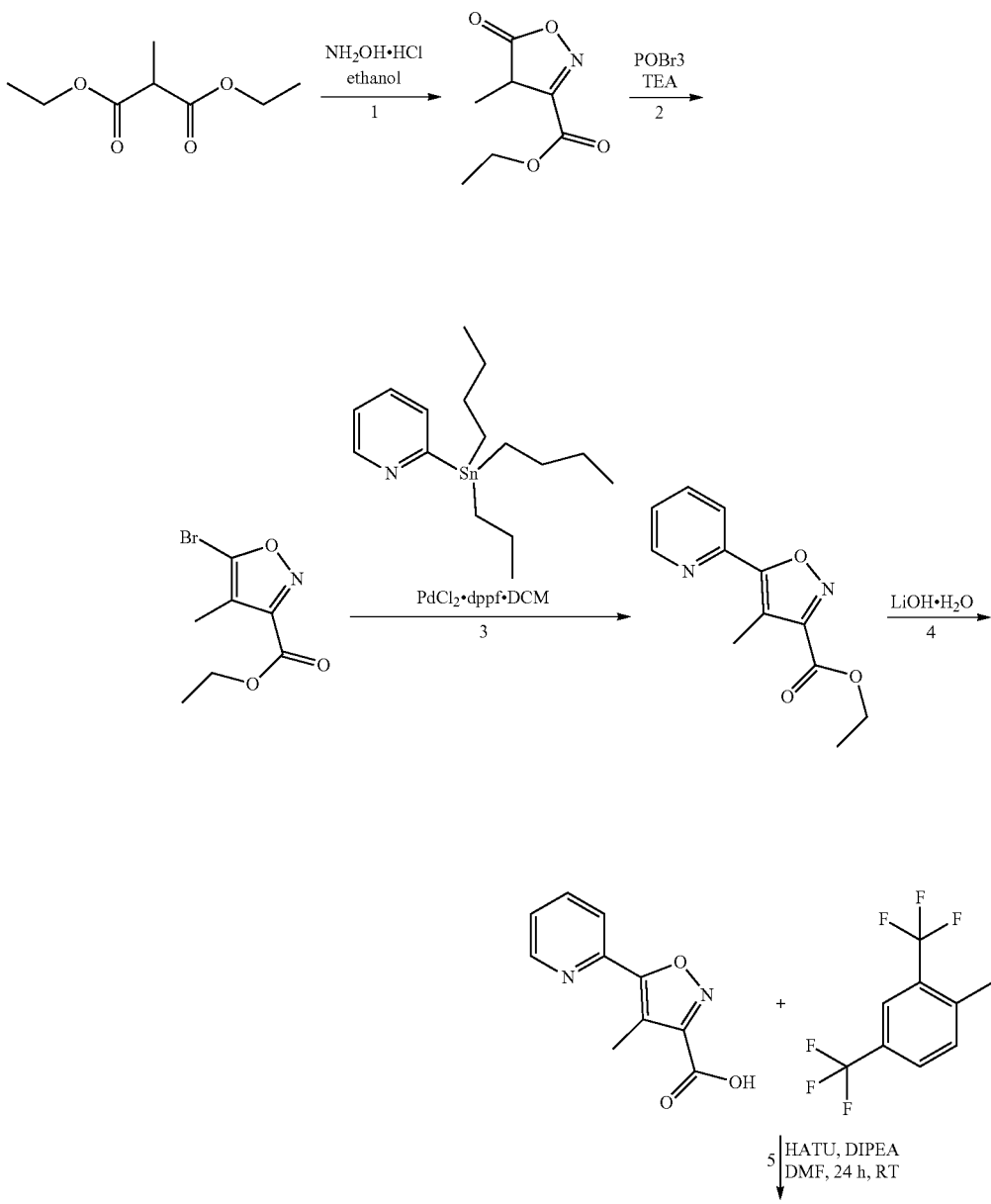

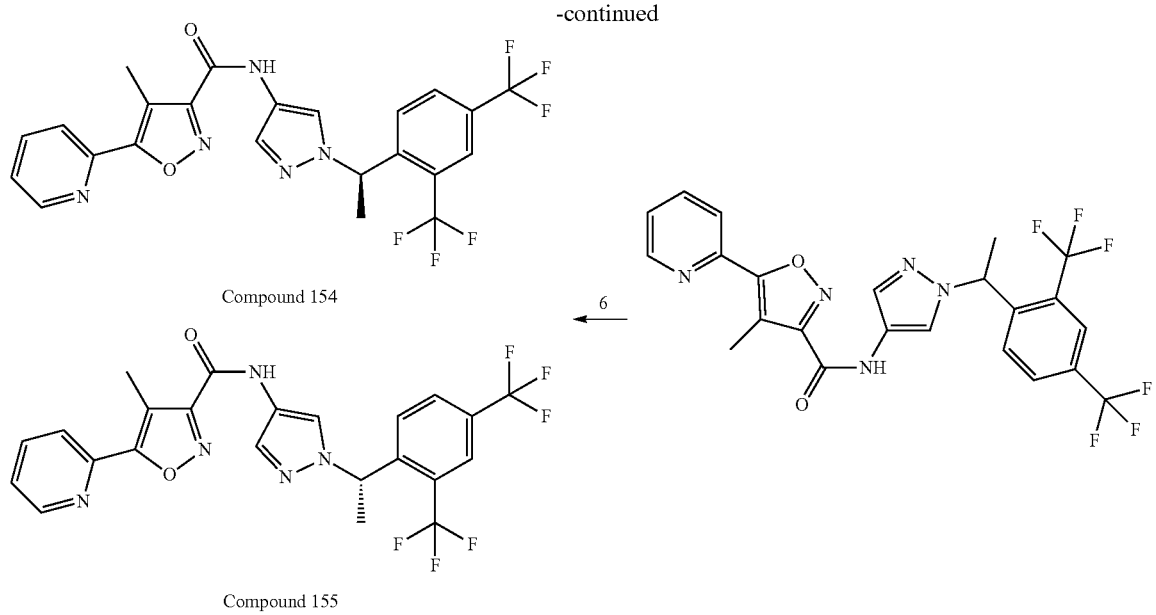

Compound 154

Compound 155

Step 1: Synthesis of ethyl 4-methyl-5-oxo-4,5-dihydroisoxazole-3-carboxylate. A stirred solution of Diethyl 2-methylmalonate (2 g, 0.011 mol, 1 eq), hydroxylamine hydrochloride (0.965 g, 0.013 mol, 1.2 eq) in EtOH (20 mL) at 80 deg C. for 12 hours. Reaction mixture was concentrated under vacuum to obtain crude which was diluted with water and extracted with EtOAc (600 mL×5), Organic layer washed with saturated brine, dried over anhydrous $Na_2SO_4$ and concentrated under vacuum to obtained crude which was triturated with petroleum ether (100 mL) to provide ethyl 4-methyl-5-oxo-4,5-dihydroisoxazole-3-carboxylate (Wt: 1.2 gm). $^1$H NMR (400 MHz, CHLOROFORM-d) δ 4.42 (q, J=7.02 Hz, 2H), 2.12 (s, 3H), 1.32-1.46 (m, 3H).

Step 2: Synthesis of ethyl 4-methyl-5-oxo-4,5-dihydroisoxazole-3-carboxylate. To a stirred mixture of ethyl 4-methyl-5-oxo-4,5-dihydroisoxazole-3-carboxylate (1 g, 0.058 mol, 1.0 eq) and phosphorous oxybromide (8.39 g, 0.0292 mol, 5 eq) was added dropwise TEA (1.181 gm, 0.0116 mol, 2 eq). The resulting reaction mixture was heated to 80° C. and stirred at Room temperature for 12 hours. The reaction mixture was poured into ice water and extracted with EtOAc (600 ml×5), Organic layers washed with brine, dried over anhydrous $Na_2SO_4$ and concentrated under vacuum to obtain crude which was purified by using flash column chromatography on silica gel to obtain desired product (810 mg). $^1$H NMR (400 MHz, DMSO-$d_6$) δ 4.37 (q, J=7.16 Hz, 2H), 2.10 (s, 3H), 1.32 (t, J=7.02 Hz, 3H).

Step 3: Synthesis of ethyl 4-methyl-5-(pyridin-2-yl)isoxazole-3-carboxylate. To a mixture of ethyl 5-bromo-4-methylisoxazole-3-carboxylate (500 mg, 2.127 mmol, 1 eq), 2-(tributylstannyl)pyridine (834 mg, 2.553 mmol, 1 eq) in anhydrous Toluene (10 ml), Nitrogen was purged for 15 minutes was added Pd(dppf)$Cl_2$·$CH_2Cl_2$ (173.8 mg, 0.212 mmol, 0.1 eq). The reaction mixture was stirred at 110° C. for 16 hr. Reaction mixture was added water, extracted with ethyl acetate, Organic layer washed with saturated brine, dried over sodium sulfate and concentrated under vacuum to obtain crude was purified by column chromatography to give ethyl 4-methyl-5-(pyridin-2-yl)isoxazole-3-carboxylate (150 mg). LCMS: 232 [M+H]$^+$.

Step 4: Synthesis of 4-methyl-5-(pyridin-2-yl)isoxazole-3-carboxylic acid. To a stirred solution of ethyl 4-methyl-5-(pyridin-2-yl)isoxazole-3-carboxylate (40 mg, 0.169 mmol, 1 eq) in THF (2 mL) and water (2 mL) was slowly added lithium hydroxide (8.1 mg, 0.203 mmol, 1.2 eq). The resulting mixture was stirred for 16 hrs. Reaction mixture was concentrated under reduced pressure to obtain crude which was acidified with 1N HCl and obtained suspension was lypolised and crude was triturated with ether to obtained 4-methyl-5-(pyridin-2-yl)isoxazole-3-carboxylic acid (30 mg). LCMS: 204 [M+H]$^+$.

Step 5: Synthesis of N-(1-(1-(2,4-bis(trifluoromethyl)phenyl)ethyl)-1H-pyrazol-4-yl)-4-methyl-5-(pyridin-2-yl)isoxazole-3-carboxamide. To a stirred solution of 4-methyl-5-(pyridin-2-yl)isoxazole-3-carboxylic acid (25 mg, 0.121 mmol, 1 eq), HATU (46.01 mg, 0.121 mmol, 1 equiv) and DIPEA (47.195 mg, 0.365 mmol, 3 equiv) in DMF (2 mL) was added solution of 1-(1-(2,4-bis(trifluoromethyl)phenyl)ethyl)-1H-pyrazol-4-amine hydrochloride (43.43 mg, 0.0.121 mmol, 1 equiv) in DMF (1 mL). The reaction mixture was stirred at RT for 24 h. The reaction mixture was diluted water (50 mL). The resulting precipitate was filtered off to obtain crude material which was triturated with DCM: hexane (2:8) to obtained N-(1-(1-(2,4-bis(trifluoromethyl)phenyl)ethyl)-1H-pyrazol-4-yl)-4-methyl-5-(pyridin-2-yl)isoxazole-3-carboxamide. LCMS: 509 [M+H]$^+$.

Step 6: Synthesis of (R) and (S) N N-(1-(1-(2,4-bis(trifluoromethyl)phenyl)ethyl)-1H-pyrazol-4-yl)-4-methyl-5-(pyridin-2-yl)isoxazole-3-carboxamide. The enantiomers of N-(1-(1-(2,4-bis(trifluoromethyl)phenyl)ethyl)-1H-pyrazol-4-yl)-4-methyl-5-(pyridin-2-yl)isoxazole-3-carboxamide (elution time: 12.6 min & 19.2 min) were separated by chiral SFC (Daicel Chiralpak®-IC, 250×20 mm, 5 µm). Isocratic program with analytical grade liquid carbon dioxide and HPLC grade Isopropanol, Total flow: 51 g/min, Co-Solvent Percentage: 18% to obtain ml (R) N-(1-(1-(2,4-bis(trifluoromethyl)phenyl)ethyl)-1H-pyrazol-4-yl)-4-methyl-5-(pyridin-2-yl)isoxazole-3-carboxamide (3 mg) (S) N-(1-(1-(2,4-bis(trifluoromethyl)phenyl)ethyl)-1H-pyrazol-4-yl)-4-methyl-5-(pyridin-2-yl)isoxazole-3-carboxamide (6 mg). LCMS: 509 [M+H]$^+$. (Compound 154) $^1$H NMR (400

MHz, DMSO-d$_6$) δ 11.60 (s, 1H), 8.21 (s, 1H), 8.05 (s, 2H), 8.09 (s, 2H), 7.80 (s, 1H), 7.73 (d, J=8.33 Hz, 1H), 7.50 (d, J=3.95 Hz, 1H), 6.83 (br. s., 1H), 5.94 (d, J=6.58 Hz, 1H), 2.54 (s, 3H) 1.87 (d, J=6.58 Hz, 3H). (Compound 155) $^1$H NMR (400 MHz, DMSO-d$_6$) δ 11.60 (s, 1H), 8.21 (s, 1H), 8.05 (s, 2H), 8.09 (s, 2H), 7.80 (s, 1H), 7.73 (d, J=8.33 Hz, 1H), 7.50 (d, J=3.95 Hz, 1H), 6.83 (br. s., 1H), 5.94 (d, J=6.58 Hz, 1H), 2.54 (s, 3H) 1.87 (d, J=6.58 Hz, 3H).

Example S89. Synthesis of (R)—N-(1-(1-(2,4-bis(trifluoromethyl)phenyl)ethyl)-1H-pyrazol-4-yl)-5-(pyrimidin-4-yl)-1,3,4-thiadiazole-2-carboxamide and (S)—N-(1-(1-(2,4-bis(trifluoromethyl)phenyl)ethyl)-1H-pyrazol-4-yl)-5-(pyrimidin-4-yl)-1,3,4-thiadiazole-2-carboxamide (Compounds 156 & 157)

was taken in ethanol (20 mL). To it hydrazine Hydrate (195.6 mg, 3.913 mmol, 1.2 equiv) was added. Reaction mixture was refluxed for 3 hour. The reaction mixture was concentrated up to dryness. The precipitate were triturated with hexane. Product obtained pyrimidine-4-carbohydrazide (327 mg, Brown Solid). $^1$H NMR (400 MHz, DMSO-d$_6$) δ 10.30 (br. s., 1H), 9.28 (d, J=1.32 Hz, 1H), 9.04 (d, J=4.82 Hz, 1H), 7.97 (dd, J=1.32, 4.82 Hz, 1H), 4.70 (br. s., 2H)

Step 3: Synthesis of ethyl 2-oxo-2-(2-(pyrimidine-4-carbonyl)hydrazinyl)acetate. To stirred solution of Pyrimidine-4-carbohydrazide (250 mg, 1.811 mmol 1 equiv.) in DCM at 0° C. was added TEA (219.5 mg. 1.2 equiv., 2.17 m moles). Reaction mixture was kept on stirring at 0° C. Celsius for 30 minutes. Ethyl 2-chloro-2-oxoacetate (248.1 mg, 1 eq, 1.811 m moles) was added at 0° C. Reaction mixture was kept on stirring at 0° C. for an hour. Reaction was monitored by

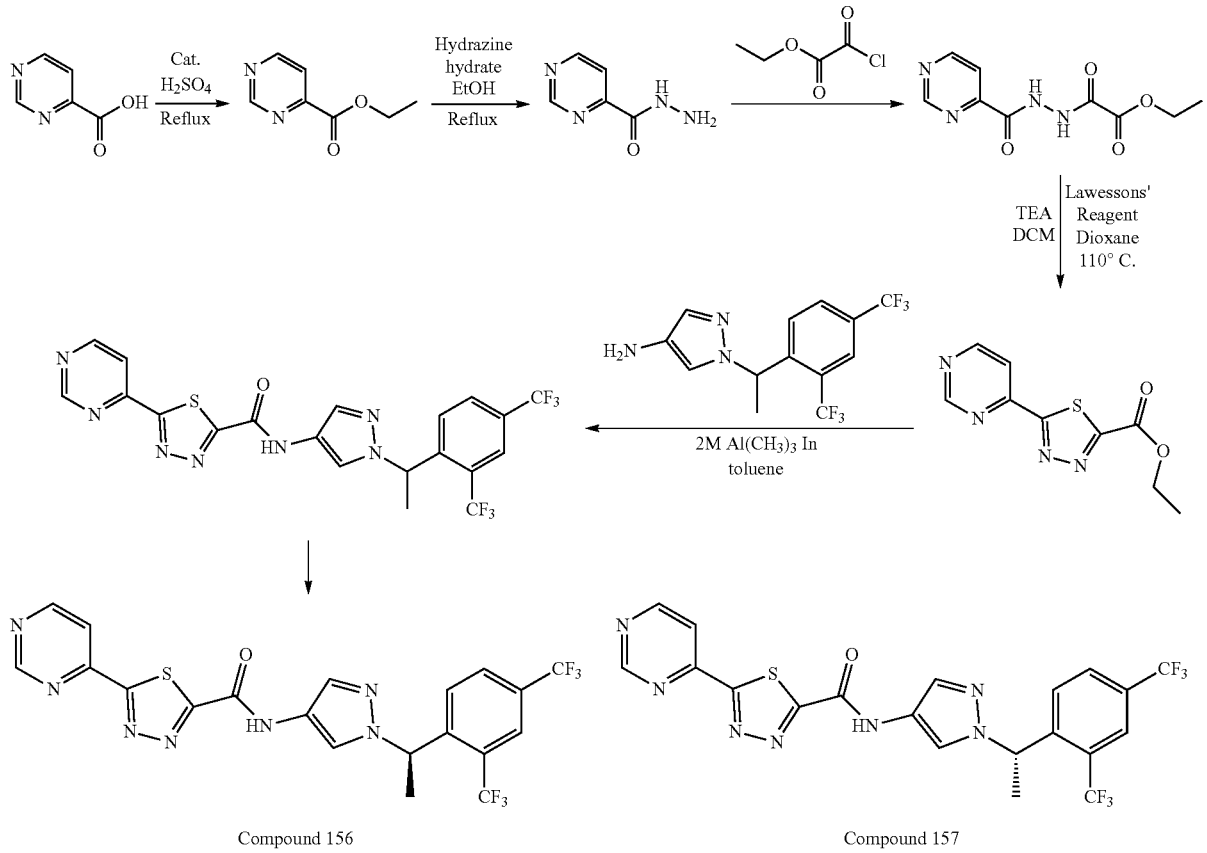

Compound 156

Compound 157

Step 1: Synthesis of ethyl pyrimidine-4-carboxylate. To stirred solution of Pyrimidine-4-carboxylic acid (500 mg) in EtOH (30 mL) was added conc. H$_2$SO$_4$ (1 mL) and refluxed the reaction mixture for 2 days at 100° C. The reaction mixture was concentrated up to dryness and was treated with saturated Sodium Bicarbonate solution to pH 7. Product was extracted with DCM (3×150 ml). The organic layers were collected, dried over anhyd. Na$_2$SO$_4$ and concentrated under reduced pressure to obtain Product ethyl pyrimidine-4-carboxylate brown Solid (450 mg). $^1$H NMR (400 MHz, DMSO-d$_6$) δ 9.39 (s, 1H), 9.09 (d, J=4.82 Hz, 1H), 8.04 (dd, J=1.53, 5.04 Hz, 1H), 4.39 (q, J=7.31 Hz, 2H), 1.34 (t, J=7.24 Hz, 3H).

Step 2: Synthesis of pyrimidine-4-carbohydrazide. Ethyl pyrimidine-4-carboxylate (450 mg, 3.260 mmol, 1 equiv)

LCMS. Reaction was quenched by ice. Extraction was done with DCM (2×100 ml). Obtained DCM layer Was Concentrated to Obtain Crude. Obtain Crude was triturated with hexane to obtain title product as Pale yellow solid (310 mg). $^1$H NMR (400 MHz, DMSO-d$_6$) δ 11.00 (br. s., 1H), 9.31-9.44 (m, 1H), 9.08-9.18 (m, 1H), 7.99-8.13 (m, 1H), 4.20-4.39 (m, 2H), 1.07-1.24 (m, 3H).

Step 4: Synthesis of ethyl 5-(pyrimidin-4-yl)-1,3,4-thiadiazole-2-carboxylate. Ethyl 2-oxo-2-(2-(pyrimidine-4-carbonyl)hydrazinyl)acetate (200 mg, 0.843 mmol, 1 equiv) was taken in Dioxane (4 mL). To the reaction mixture was added Lawessons' reagent (1.356 gm, 3.375 mmoles, 4 equiv). Reaction Mixture was kept on Stirring at 110 0° C. for 24 hour. Reaction was monitored by LCMS. Work up was done by Quenching with Saturated Bicarbonate solution (30 mL). Extraction was done by diethyl ether (3×75 mL) ml. Obtained organic layer was concentrated was concentrated under reduced pressure to obtain crude was purified by Combi-Flash Chromatography (EtOAc/Hexane) to obtain ethyl 5-(pyrimidin-4-yl)-1,3,4-thiadiazole-2-carboxylate pale Brown solid (130 mg). $^1$H NMR (400 MHz, DMSO-$d_6$) δ 9.55 (s, 1H), 8.75-8.97 (m, 2H), 4.48 (q, J=7.02 Hz, 2H), 1.38 (t, J=7.02 Hz, 3H).

Step 5: Synthesis N-(1-(1-(2,4-bis(trifluoromethyl)phenyl)ethyl)-1H-pyrazol-4-yl)-5-(pyrimidin-4-yl)-1,3,4-thiadiazole-2-carboxamide. To a solution of ethyl 5-(pyrimidin-4-yl)-1,3,4-thiadiazole-2-carboxylate (100 mg, 0.421 mmol, 1 equiv) in Toluene (1 mL), were added 1-(1-(2,4-bis(trifluoromethyl)phenyl)ethyl)-1H-pyrazol-4-amine (136.7 mg, 0.421 mmol, 1 equiv) in Toluene (1 mL). The mixture was treated drop wise with trimethyl aluminium (86.60 mg, 1.26 mmol, 4 equiv). The reaction mixture was kept under stirring for 24 h. The reaction mixture was diluted water (50 mL). The resulting suspension was filtered off and followed by, extraction with ethyl Acetate (2×50 ml). T organic layer was concentrated was concentrated under reduced pressure to obtained crude which was purified by Flash Chromatography (EtOAc/Hexane) to obtain the title compound as free base. LCMS: 513 [M+H]$^+$.

Step 6: Synthesis of (R) & (S)—N-(1-(1-(2,4-bis(trifluoromethyl)phenyl)ethyl)-1H-pyrazol-4-yl)-5-(pyrimidin-4-yl)-1,3,4-thiadiazole-2-carboxamide. The enantiomers of N-(1-(1-(2,4-bis(trifluoromethyl)phenyl)ethyl)-1H-pyrazol-4-yl)-5-(pyrimidin-4-yl)-1,3,4-thiadiazole-2-carboxamide carboxamide (elution time: 15.4 min & 11.4 min), were separated by chiral SFC (Daicel Chiralpak®-IC, 250×20 mm, 5 μm. Isocratic program with analytical grade liquid carbon dioxide and HPLC grade[Isopropanol:Acetonitrile (1:1)], Total flow: 51 g/min, Co-Solvent Percentage: 15% to obtain Peak-1 (S)—N-(1-(1-(2,4-bis(trifluoromethyl)phenyl)ethyl)-1H-pyrazol-4-yl)-5-(pyrimidin-4-yl)-1,3,4-thiadiazole-2-carboxamide (20 mg) and Peak-2 (R)—N-(1-(1-(2,4-bis(trifluoromethyl)phenyl)ethyl)-1H-pyrazol-4-yl)-5-(pyrimidin-4-yl)-1,3,4-thiadiazole-2-carboxamide (18 mg). LCMS: 513 [M+H]$^+$. (Compound 156) $^1$H NMR (400 MHz, DMSO-$d_6$) δ 11.69 (s, 1H), 9.41 (s, 1H), 9.12 (d, J=5.26 Hz, 1H), 8.36 (d, J=4.82 Hz, 1H), 7.96-8.17 (m, 2H), 7.83 (s, 1H), 7.74 (d, J=8.33 Hz, 1H), 5.95 (d, J=6.14 Hz, 1H), 1.88 (d, J=6.58 Hz, 3H). (Compound 157) $^1$H NMR (400 MHz, DMSO-$d_6$) δ 11.61 (s, 1H), 9.42 (s, 1H), 9.12 (d, J=5.26 Hz, 1H), 8.36 (d, J=4.82 Hz, 1H), 7.96-8.17 (m, 2H), 7.83 (s, 1H), 7.75 (d, J=8.33 Hz, 1H), 5.95 (d, J=6.14 Hz, 1H), 1.89 (d, J=6.58 Hz, 3H).

Example S90. Synthesis of (R)—N-(1-(1-(2,4-bis(trifluoromethyl)phenyl)ethyl)-1H-pyrazol-4-yl)-5-(pyrimidin-4-yl)-1,3,4-thiadiazole-2-carboxamide and (S)—N-(1-(1-(2,4-bis(trifluoromethyl)phenyl)ethyl)-1H-pyrazol-4-yl)-5-(pyrimidin-4-yl)-1,3,4-thiadiazole-2-carboxamide (Compounds 158 & 159)

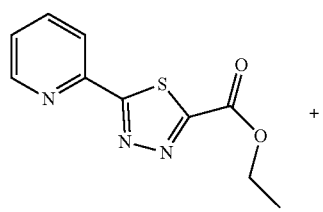

+

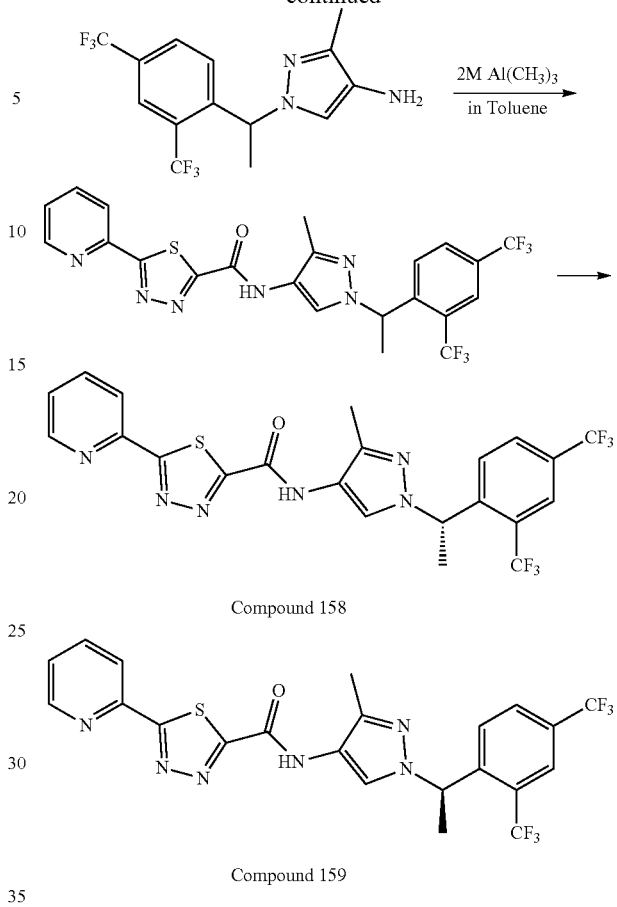

Compound 158

Compound 159

Step 1: Synthesis of N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide. To a solution of ethyl 5-(pyrazin-2-yl)-1,3,4-thiadiazole-2-carboxylate (100 mg, 0.423 mmol, 1 equiv) in Toluene (1 mL), were added 1-(1-(2,4-bis(trifluoromethyl)phenyl)ethyl)-3-methyl-1H-pyrazol-4-amine (142.79 mg, 0.423 mmol, 1 equiv) in Toluene (1 mL). The mixture was treated drop wise with 2M Trimethyl Aluminium in Toluene (59.29 mg, 1.694 mmol, 4 eq). The reaction mixture was kept under stirring for 24 h. The reaction mixture was kept under stirring for 24 h. The reaction mixture was diluted water (50 mL). The resulting suspension was filtered off and followed by extraction with ethyl Acetate (2×50 ml). T organic layer was concentrated was concentrated under reduced pressure to obtained crude which was purified by Flash Chromatography (EtOAc/Hexane) to obtain the title compound as free base. LCMS: 526 [M+H]$^+$. $^1$H NMR (500 MHz, DMSO-$d_6$) δ 10.79 (s, 1H), 8.76 (d, J=4.7 Hz, 1H), 8.35 (d, J=7.9 Hz, 1H), 8.16 (s, 1H), 8.10 (q, J=7.8 Hz, 2H), 8.05 (s, 1H), 7.75 (d, J=8.3 Hz, 1H), 7.66 (dd, J=7.6, 4.9 Hz, 1H), 5.84 (q, J=7.1 Hz, 1H), 2.20 (s, 3H), 1.84 (d, J=6.9 Hz, 3H).

Step 2: Synthesis of (R) & (S)—N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide. The enantiomers N-(1-(1-(2,4-bis(trifluoromethyl)phenyl)ethyl)-3-meth-1-1H-pyrazol-4-yl)-5-(pyridin-2-yl)-1,3,4-thiadiazole-2-carboxamide (elution time: 4.4 min & 6.4 min), were separated by chiral SFC (Daicel Chiralpak®-IA, 250×20 mm, 5 μm. Isocratic program with analytical grade liquid carbon dioxide and HPLC grade Methanol (0.2% DEA), Total flow: 56 g/min, Co-Solvent Percentage: 25% to obtain (S) N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide (12 mg) and (R) N-(1-(1-(2,4-bis(trifluoromethyl)phenyl)ethyl)-3-methyl-1H-pyrazol-4-yl)-5-(pyridin-2-yl)-1,3,4-thiadiazole-2-carboxamide (13 mg). (Compound 158) $^1$H NMR (400 MHz, DMSO-d$_6$) δ 11.69 (s, 1H), 9.41 (s, 1H), 9.12 (d, J=5.26 Hz, 1H), 8.36 (d, J=4.82 Hz, 1H), 8.24 (s, 1H), 8.03-8.14 (m, 2H), 7.83 (s, 1H), 7.74 (d, J=8.33 Hz, 1H), 5.95 (d, J=6.14 Hz, 1H), 1.88 (d, J=6.58 Hz, 3H) (Compound 159) $^1$H NMR (400 MHz, DMSO-d$_6$) δ 11.69 (s, 1H), 9.41 (s, 1H), 9.12 (d, J=5.26 Hz, 1H), 8.36 (d, J=4.82 Hz, 1H), 8.24 (s, 1H), 8.03-8.14 (m, 2H), 7.83 (s, 1H), 7.74 (d, J=8.33 Hz, 1H), 5.95 (d, J=6.14 Hz, 1H), 1.88 (d, J=6.58 Hz, 3H).

Example S91. Synthesis of (R)—N-(1-(1-(2,4-bis(trifluoromethyl)phenyl)ethyl)-1H-pyrazol-4-yl)-5-(furan-2-yl)-1,3,4-thiadiazole-2-carboxamide and (S)—N-(1-(1-(2,4-bis(trifluoromethyl)phenyl)ethyl)-1H-pyrazol-4-yl)-5-(furan-2-yl)-1,3,4-thiadiazole-2-carboxamide (Compounds 160 & 161)

Flash Chromatography (EtOAc/Hexane) to obtain the title compound as free base. LCMS: 502 [M+H]$^+$.

Step 2: Synthesis of (R) & (S)—N-(1-(1-(2,4-bis(trifluoromethyl)phenyl)ethyl)-1H-pyrazol-4-yl)-5-(furan-2-yl)-1,3,4-thiadiazole-2-carboxamide. The enantiomers N-(1-(1-(2,4-bis(trifluoromethyl)phenyl)ethyl)-1H-pyrazol-4-yl)-5-(furan-2-yl)-1,3,4-thiadiazole-2-carboxamide (elution time: 4.28 min & 8.03 min), were separated by chiral SFC (Daicel Chiralpak®-IC, 250×20 mm, 5 μm). Isocratic program with analytical grade liquid carbon dioxide and HPLC grade Methanol, Total flow: 56 g/min, Co-Solvent Percentage: 40% to obtained Peak-1 (R)—N-(1-(1-(2,4-bis(trifluoromethyl)phenyl)ethyl)-1H-pyrazol-4-yl)-5-(furan-2-yl)-1,3,4-thiadiazole-2-carboxamide (5 mg) and Peak-2 (S)—N-(1-(1-(2,4-bis(trifluoromethyl)phenyl)ethyl)-1H-pyrazol-4-yl)-5-(furan-2-yl)-1,3,4-thiadiazole-2-carboxamide (5 mg). (Compound 160) $^1$H NMR (400 MHz, DMSO-d$_6$) δ 11.58 (br. s., 1H), 8.21 (s, 1H), 8.05 (s, 1H), 8.09 (s, 1H), 7.80 (s, 1H), 7.73 (d, J=8.33 Hz, 1H), 7.50 (d, J=3.07 Hz, 1H), 6.83 (br. s., 1H), 5.94 (d, J=6.14 Hz, 1H), 1.87 (d, J=7.02 Hz, 3H). (Compound 161) NMR (400 MHz, DMSO-d$_6$) δ 11.58 (br. s., 1H), 8.21 (s, 1H), 8.05 (s, 1H), 8.09 (s, 1H), 7.80 (s, 1H),

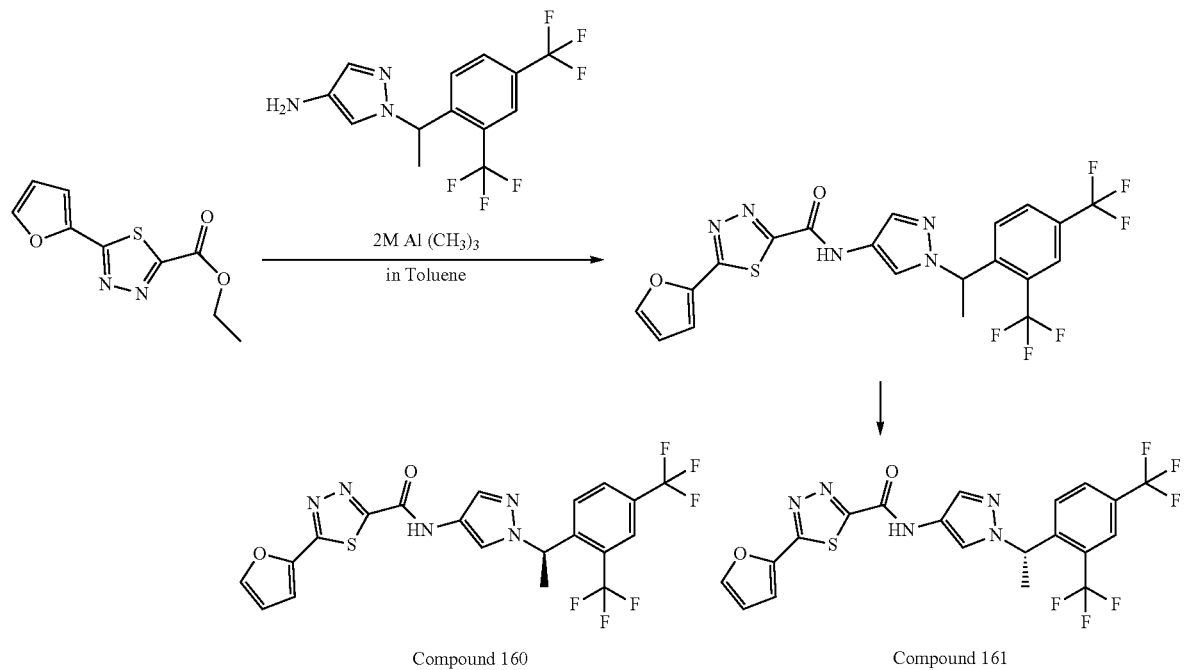

Compound 160

Compound 161

Step 1: Synthesis of N-(1-(1-(2,4-bis(trifluoromethyl)phenyl)ethyl)-1H-pyrazol-4-yl)-5-(furan-2-yl)-1,3,4-thiadiazole-2-carboxamide. To a solution of ethyl 5-(furan-2-yl)-1,3,4-thiadiazole-2-carboxylate (50 mg, 0.223 mmol, 1 equiv) in Toluene (1 mL), were added 1-(1-(2,4-bis(trifluoromethyl)phenyl)ethyl)-1H-pyrazol-4-amine (72.32 mg, 0.223 mmol, 1 equiv) in Toluene (1 mL). The mixture was treated drop wise with 2M Trimethyl Aluminum in Toluene (32.14 mg, 0.892 mmol, 4 equiv). The reaction mixture was kept under stirring for 24 h. The reaction mixture was diluted water (50 mL). The resulting suspension was filtered off and followed by extraction with ethyl Acetate (2×50 ml). T organic layer was concentrated was concentrated under reduced pressure to obtained crude which was purified by 7.73 (d, J=8.33 Hz, 1H), 7.50 (d, J=3.07 Hz, 1H), 6.83 (br. s., 1H), 5.94 (d, J=6.14 Hz, 1H), 1.87 (d, J=7.02 Hz, 3H).

BIOLOGICAL EXAMPLES

Example B1: ERSE ATF6-Luciferase Assays

Human bone osteosarcoma (U2-OS) cells were obtained from the American Type Culture Collection (ATCC HTB-96, ATCC Manassas, VA) and were cultured with growing medium containing Dulbecco's Modified Eagle's Medium (DMEM) (Cat. No.: SH30023.02, HyClone) supplemented with fetal bovine serum (FBS) 10% (Cat. No.: 16000044, Gibco) and 1% penicillin-streptomycin antibiotic cocktail (Cat. No.: SV30010, Hyclone).

Cignal Lenti ATF6 luc reporter (Qiagen #CLS-6031L) was used to produce a stable cell line in U2-OS cells. The lenti ATF6 reporter is a preparation of replication incompetent, VSV-g pseudotyped lentivirus particles expressing the firefly luciferase gene under the control of a minimal (m)CMV promoter and tandem repeats of the ATF6 transcriptional response element (TRE). The number of response elements as well as the intervening sequence between response elements has been experimentally optimized to maximize the signal to noise ratio.

Compounds were prepared as 10 mM stock solutions and stored at −80° C.

U2-OS ATF6 luc reporter cells were thawed 3-4 days and split once prior to assays. For the primary screening, 40,000 U2-OS ATF6 luc cells were plated in 100 µL per well in white 96 well plates (Thermo Scientific Nunc #136101) pre-coated with poly-D-lysine (Cat. No.: P2636, Sigma) and incubated in humidified chambers for 24 hr. At the day of experiment, cells were pre-treated for 30 min with 50 µL growing medium containing either vehicle (dimethyl sulfoxide (DMSO)) (Cat. No.: D2650, Sigma-Aldrich) or 1 µM test compound. After the pre-incubation time, 50 µL of a solution containing 0.2 µM thapsigargin (Tg) (an ER stress inducer) was added to respective wells. This Tg solution also contained vehicle or test compounds at 1 µM. The final concentration of DMSO in each well was kept at 0.3%. Plates were incubated for 8 hr in humidified chambers.

Finally, after 8 hr, plates were cooled to room temperature for 10 min prior to luciferase assays. Luciferase reactions were performed using Luciferase Assay System (Cat. No.: E4550, Promega). Briefly, each well was washed with 100 µl of PBS1× and then 20 µl of lysis reagent were added into each well. Plates were shaken for 10 min, then 50 µl of Luciferase Assay Reagent were added to each well and luminescence was read with an integration time of 1 s and a gain of 110 in a Synergy 4 Microplate reader.

For comparison between days each plate was normalized using unstressed (DMSO, 100% inhibition) and ER stressed (thapsigargin, 0% inhibition) controls and the percent inhibition of ER stress induced luciferase for each compound was calculated.

Percent inhibition of thapsigargin-induced ER stress in ATF6-luc cell reporter at 1 µM was determined for compounds 1-37, and ceapin-A4, ceapin-A7, and ceapin-A8, and is shown in Table 2.

TABLE 2

Inhibition of thapsigargin-induced ER stress in ATF6-luc cell reporter

| Compound No. | Inh. ATF6-Luc @ 1 µM [%] | IC$_{50}$ ATF6-Luc reporter [µM] |
| --- | --- | --- |
| Ceapin-A4 | + | + |
| Ceapin-A7 | +++ | +++ |
| Ceapin-A8 | + | + |
| 1 | ++ | +++ |
| 2 | + | + |
| 3 | + | + |
| 4 | + | + |
| "Enantiomer B" of Example S5 | + | + |
| "Enantiomer A" of Example S5 | +++ | +++ |
| "Enantiomer B" of Example S6 | + | + |
| "Enantiomer A" of Example S6 | +++ | +++ |
| 9 | + | ++ |
| 10 | + | ++ |
| 11 | +++ | +++ |
| 12 | +++ | +++ |
| 13 | + | + |
| 14 | ++ | +++ |
| 15 | + | + |
| 16 | + | + |
| 17 | + | + |
| 18 | + | + |
| 19 | + | + |
| 20 | + | + |
| 21 | + | + |
| 22 | + | ++ |
| 23 | + | + |
| 24 | + | + |
| 25 | + | + |
| 26 | + | + |
| 27 | + | + |
| 28 | + | + |
| 29 | + | + |
| 30 | ++ | ++ |
| 31 | + | + |
| 32 | + | + |
| 33 | + | + |
| 34 | + | + |
| 35 | + | + |
| 36 | + | + |
| 37 | + | + |
| 76 | +++ | +++ |
| 77 | + | + |
| 78 | + | ++ |
| 79 | + | + |
| 80 | + | + |
| 81 | + | + |
| 82 | + | + |
| 83 | + | + |
| 84 | + | + |
| 85 | + | + |
| 86 | + | + |
| 87 | + | + |
| 88 | + | + |
| 89 | + | + |
| 90 | + | + |
| 91 | + | + |
| 92 | + | + |
| 93 | +++ | +++ |
| 94 | + | + |
| 95 | + | + |
| 96 | + | + |
| 97 | ++ | ++ |
| 98 | + | + |
| 99 | ++ | ++ |
| 100 | +++ | +++ |
| 101 | +++ | +++ |
| 102 | + | + |
| 103 | ++ | ++ |
| 104 | ++ | ++ |
| 105 | + | + |
| 106 | + | + |
| 107 | + | + |
| 108 | + | + |
| 109 | + | + |
| 110 | ++ | ++ |
| 111 | + | + |
| 112 | ++ | + |
| 113 | + | + |
| 114 | +++ | +++ |
| 115 | ++ | + |
| 116 | ++ | + |
| 117 | + | + |
| 118 | + | ++ |
| 119 | + | + |
| 120 | + | + |
| 121 | ++ | +++ |

TABLE 2-continued

Inhibition of thapsigargin-induced ER stress in ATF6-luc cell reporter

| Compound No. | Inh. ATF6-Luc @ 1 µM [%] | $IC_{50}$ ATF6-Luc reporter [µM] |
|---|---|---|
| 122 | + | + |
| 123 | +++ | +++ |
| 124 | + | ++ |
| 125 | + | + |
| 126 | + | + |
| 127 | + | + |
| 128 | + | + |
| 129 | +++ | +++ |
| 130 | + | + |
| 131 | +++ | +++ |
| 132 | + | + |
| 133 | + | + |
| 134 | + | + |
| 135 | ++ | + |
| 136 | +++ | +++ |
| 137 | + | + |
| 138 | +++ | +++ |
| 139 | + | + |
| 140 | + | + |
| 141 | + | + |
| 142 | + | + |
| 143 | + | + |
| 144 | + | + |
| 145 | + | + |
| 146 | + | + |
| 147 | + | + |
| 148 | + | + |
| 149 | + | + |
| 150 | + | + |
| 151 | + | + |
| 152 | +++ | +++ |
| 153 | + | + |
| 154 | + | + |
| 155 | + | + |
| 156 | ++ | +++ |
| 157 | + | + |
| 158 | + | + |
| 159 | +++ | +++ |
| 160 | + | + |
| 161 | ++ | +++ |

Ceapin-A4, Ceapin-A7, and Ceapin-A8 refers to compounds described in Gallagher et al. eLife 2016; 5: e11878;
for % of inhibition:
+++ refers to >50% inhibition at 1 µM test compound;
++ refers to 25% < % inhibition < 50% at 1 µM test compound;
+ refers to <25% inhibition at 1 µM;
inh: inhibition.
For $IC_{50}$:
+++ refers to $IC_{50}$ < 1 µM;
++ refers to 1 µM < $IC_{50}$ < 10 µM;
+ refers to $IC_{50}$ > 10 µM.

For the assessment of the half-maximal inhibitory concentration ($IC_{50}$) for selected compounds, dose-response assays were performed. Compounds were serially diluted using DMSO starting at 30 µM until 1 nM. The assays were run as described above. $IC_{50}$ values inhibitory activity compounds 1-37, and Ceapin-A4, Ceapin-A7, and Ceapin-A8 are also shown in Table 2.

Example B2: Oral Bioavailability and PK Parameters

Tested compounds were formulated at 1 mg/mL as a dosing solution for oral administration in vehicle A: 10% dimethylacetamide (DMAC), 20% propylene glycol, and 40% PEG-400 or vehicle B: 10% Kolliphor® EL and 10% ethanol (EtOH).

Balb/c mice approximately 9-10 weeks old were obtained from the vivarium Fundación Ciencia & Vida Chile (Santiago, Chile) and were maintained in a temperature-controlled room with 12/12 hr light/dark schedule with food and water ad libitum. Animals were acclimated for a minimum period of 4 days upon arrival at the testing facility.

At the day of study, mice were weighed, identified by marking the tail with numbers using a non-toxic permanent marker, and designated into ten experimental groups (n=3 per group). Each mouse from all experimental groups received a single oral dose at 10 mg/kg tested compounds by oral gavage using feeding tubes 20 G (Cat. No.: FTP-2038; Instech Salomon Inc.).

Experimental groups were sacrificed by $CO_2$— asphyxiation at different time points (0.083, 0.167, 0.25, 0.5, 1, 2, 4, 6, 8 and 24 hr after dosing) and blood samples were harvested by terminal cardiac puncture. Non-dosed mice were used to collect samples of zero time points. Whole blood was collected into microtainer tubes with ($K_2$) EDTA (Cat. No.: #365974; Becton Dickinson & Co.). Blood samples were centrifuged immediately at 9,000 g at 4° C. for 5 minutes and then plasmas were separated. Plasma samples were placed into individually labeled cryovials and stored in a −80° C. freezer until LC/MS/MS bioanalysis.

The bioanalysis of plasma samples was conducted with a QTRAP 4500 triple quadrupole mass spectrometer (Applied Biosystems SCIEX) in the positive ion mode and interfaced with an Ekspert Ultra LC100 UPLC System (Eksigent). Calibration standards (0.01 to 10 µM) and QCs (0.02, 0.2 and 2.0 µM) were prepared from naïve mouse plasma in parallel with mouse plasma study samples (60 µL) by precipitation with three volumes of ice cold internal standard solution (acetonitrile containing 20 µM of theophylline). The precipitated samples were centrifuged at 6,100 g for 30 min. Following centrifugation, an aliquot of each supernatant was transferred to an autosampler plate and diluted with two volumes of aqueous mobile phase (0.1% formic acid in water). Samples were injected onto a reverse phase analytical column (YMC Triart C18; 2.0×50 mm; 1.9 µm; YMC CO) and eluted with a gradient of 0.1% formic acid in Acetonitrile. Assayed test compound and internal standards were monitored by a multiple reaction monitoring (MRM) experiment using an Analyst software (v1.6.2, Applied Biosystems SCIEX). Quantitation was conducted using a MultiQuant software (v2.1, Applied Biosystems SCIEX) and the resulting calibration curve was fitted with a linear regression and 1/x weighting. The lower limits of quantitation were 1<LLQ<5 ng/mL.

Oral PK parameters were calculated for compounds from the concentration-time data using Phoenix WinNonlin software (v6.4, Certara, Princeton, NJ) by noncompartmental analysis in the sparse sampling mode, as shown in Table 3.

TABLE 3

Pharmacokinetic parameters

| PK Parameters | Ceapin-A7 | 11 | "Enantiomer A" of Example S5 | "Enantiomer A" of Example S6 | 76 | 114 | 123 | 131 |
|---|---|---|---|---|---|---|---|---|
| Compound No. | | | | | | | | |
| Dose [mg/Kg] | 10 | 10 | 10 | 10 | 10 | 10 | 10 | 10 |
| N/time point | 3 | 3 | 3 | 3 | 3 | 3 | 3 | 3 |
| $C_{max}$ [ng/mL] | 68.7 | 2270 | 4590 | 579 | 5180 | 899 | 4560 | 7030 |
| $T_{max}$ [hr] | 0.25 | 0.25 | 1 | 0.5 | 1 | 0.5 | 1 | 6 |
| $AUC_{last}$ [hr * ng/mL] | 39.1 | 9780 | 18500 | 615 | 44100 | 10300 | 38800 | 98700 |
| $AUC_{inf}$ [hr * ng/mL] | 43.3 | 10300 | 32400 | 626 | 45300 | 11900 | 62200 | 107000 |
| $AUC_{Extr}$ [%] | 9.56 | 5.07 | 43 | 1.73 | 2.55 | 14 | 37.7 | 7.75 |
| Vz [L/Kg] | 831 | 8.74 | 3.07 | 36.9 | 1.45 | 10.5 | 4.43 | 0.831 |
| CL [L/hr/Kg] | 231 | 0.971 | 0.31 | 16 | 0.221 | 0.838 | 0.161 | 0.0934 |
| Last time point for $AUC_{last}$ [hr] | 6 | 24 | 8 | 8 | 24 | 24 | 24 | 24 |
| $t_{1/2}$ [hr] | 2.49 | 6.24 | 6.88 | 1.60 | 4.54 | 8.66 | 19.10 | 6.16 |
| Rsq | 0.902 | 0.997 | 0.756 | 0.953 | 0.919 | 0.990 | 0.958 | 1.000 |
| F [%] | 1.04 | 48.6 | 66.3 | 9.6 | 50.6 | 43.3 | 64.1 | 85.9 |

Ceapin-A7 refers to compound described in Gallagher et al. eLife 2016; 5: e11878;
PK: pharmacokinetic;
N: number;
Cmax: Maximum concentration;
Tmax: Maximum time;
AUC: Area under curve;
inf: infinite;
extr: extrapolated;
Vz: Volume of distribution;
Cl: clearance;
MRT: Mean residence time;
$t_{1/2}$: Half-life;
Rsq: coefficient of determination for calculation of λz
F: Bioavailability.

Example B3: In Vitro Microsomal Stability Assay in Human, Rat, and Mouse

Compounds were incubated at a final concentration of 1 µM with 0.5 mg/mL human liver microsomes (hLM) (#HMMCPL; Thermo), mouse liver microsomes (mLM) (#MSMCPL; Thermo) or rat liver microsomes (rLM) (#RTMCPL; Thermo) and 1 mM reduced dihydronicotinamide-adenine dinucleotide phosphate (NADPH) (#N1630; Sigma) in 100 mM phosphate buffer (pH 7.4) at 37° C. The reactions were terminated at 0, 5, 15 and 30 min by the addition of cold acetonitrile containing 50 ng/mL propranolol as an internal standard. The reaction mixtures were partitioned by centrifugation at 15,000 rpm for 15 min and the resulting supernatants were analyzed for percent remaining, Half-life (ti/2, min) and clearance at infinity or intrinsic clearance ($CL_{int}$) by LC-MS/MS (Shimadzu Nexera UPLC with an AB Sciex 4500 detector). Verapamil hydrochloride (#V4369 Aldrich) was used as a positive control in all studies.

Remaining fraction after 30 min of reaction and in vitro PK parameters were calculated for specific compounds as shown in Table 4.

TABLE 4

In Vitro Microsomal Stability Assay

| Compound No. | Rem. @ hLM (%) | Rem. @ mLM (%) | Rem. @ rLM (%) | $T_{1/2}$ @ hLM (min) | $T_{1/2}$ @ mLM (min) | $T_{1/2}$ @ rLM (min) | $Cl_{int}$ @ hLM (µl/min/mg) | $Cl_{int}$ @ mLM (µl/min/mg) | $Cl_{int}$ @ rLM (µl/min/mg) |
|---|---|---|---|---|---|---|---|---|---|
| Ceapin-A7 | 35.4 | 12 | 14.5 | 21.6 | 9.84 | 11.4 | 64.2 | 141 | 121 |
| 1 | 71.4 | 54.8 | 51.8 | 67.7 | 35.1 | 32.4 | 20.5 | 39.5 | 42.7 |
| "Enantiomer A" of Example S5 | 81.9 | 53.8 | 80 | 99.8 | 34.9 | 121 | 13.9 | 39.7 | 11.5 |

TABLE 4-continued

In Vitro Microsomal Stability Assay

| Compound No. | Rem. @ hLM (%) | Rem. @ mLM (%) | Rem. @ rLM (%) | $T_{1/2}$ @ hLM (min) | $T_{1/2}$ @ mLM (min) | $T_{1/2}$ @ rLM (min) | $Cl_{int}$ @ hLM (µL/min/mg) | $Cl_{int}$ @ mLM (µL/min/mg) | $Cl_{int}$ @ rLM (µL/min/mg) |
|---|---|---|---|---|---|---|---|---|---|
| "Enantiomer A" of Example S6 | 41.8 | 3.05 | 1.4 | 24 | 5.97 | 4.89 | 57.8 | 232 | 283 |
| 11 | 73.5 | 40.8 | 44.8 | 67.5 | 25.3 | 31.3 | 21 | 55 | 44 |
| 12 | 46.1 | 1.02 | 0.77 | 29.9 | 4.6 | 4.8 | 46 | 302 | 291 |
| 14 | 50.1 | 5.62 | 0.85 | 32.1 | 7.4 | 4.4 | 43 | 187 | 314 |
| 22 | 3.7 | 3.3 | 4.5 | 6.5 | 6.1 | 6.8 | 211.9 | 227.9 | 203.5 |
| 76 | 69.7 | 74.9 | 59.4 | 57.6 | 71.9 | 39.9 | 24.1 | 19.3 | 34.7 |
| 78 | 80.4 | 76.8 | 71.6 | 95.6 | 78.7 | 62.2 | 14.5 | 17.6 | 22.3 |
| 93 | 74.1 | 51.1 | 69.8 | 76.2 | 40 | 68.7 | 18.2 | 34.7 | 20.2 |
| 97 | 59.3 | 44.5 | 64.4 | 53.6 | 26.6 | 58.7 | 25.9 | 52.2 | 23.6 |
| 99 | 49.2 | 29.2 | 60.9 | 35.4 | 16.3 | 49 | 39.2 | 85.2 | 28.3 |
| 100 | 53.3 | 34.3 | 51.4 | 38.2 | 19.1 | 41.5 | 36.2 | 72.6 | 33.4 |
| 101 | 52.49 | 51.17 | 60.62 | 36.03 | 36.73 | 49.12 | 38.47 | 37.74 | 28.22 |
| 103 | 2.1 | 0.94 | 5.24 | 5.38 | 5.12 | 7.24 | 257.71 | 270.66 | 191.35 |
| 104 | 76.44 | 83.18 | 92.9 | 73.25 | 107.63 | 418.09 | 18.92 | 12.88 | 3.32 |
| 110 | 39.72 | 20.03 | 60.99 | 27.03 | 14.18 | 48.26 | 51.28 | 97.73 | 28.72 |
| 114 | 90.4 | 86.8 | 69.7 | 213 | 164.9 | 55.4 | 6.5 | 8.4 | 25 |
| 121 | 84.4 | 62.5 | 64.5 | 133.4 | 52.4 | 58.1 | 10.4 | 26.4 | 23.9 |
| 123 | 95.5 | 89.7 | 81.5 | 460.3 | 193.2 | 130.1 | 3.0 | 7.2 | 10.7 |
| 129 | 68.0 | 67.9 | 84.5 | 63.2 | 62.6 | 113.7 | 22.0 | 22.0 | 12.0 |
| 136 | 77.8 | 78.7 | 43.9 | 93.9 | 106.2 | 31.7 | 15.0 | 13.0 | 44.0 |
| 138 | 44.8 | 67.0 | 64.9 | 32.2 | 50.9 | 58.9 | 43.0 | 27.0 | 24.0 |
| 152 | 84.4 | 82.6 | 86.4 | 139.0 | 126.9 | 192.2 | 10.0 | 10.9 | 7.2 |

Ceapin-A7 refers to compound described in Gallagher et al. eLife 2016; 5: e11878; for microsomal stability
hLM: human liver microsomes;
mLM: mouse liver microsomes;
rLM: rat liver microsomes;
Rem.: Remaining fraction;
$Cl_{int}$: Intrinsic clearance;
$T_{1/2}$: Half-life;
F.

Example B4: Kinetic Solubility

Compounds were serially diluted in DMSO from a concentration range of 10 mM to 0.78 mM in 96 well V bottom dilution plate (#3363costar). 1 µL of compound from each well was transferred to 96 well Flat bottom clear plates (#655101Greiner) containing 99 µL of PBS at pH-7.4 so that the DMSO concentration should not exceed >1%. Samples were incubated for one hour at 37° C. followed by measurement of light scattering at 625 nm with a laser based microplate nephelometer. Concentration (µM) was then calculated by segmental regression. Amiodarone (#A8423 Aldrich) was used as positive control. Parameters were calculated for specific compounds as shown in Table 5.

TABLE 5

| Kinetic solubility | |
|---|---|
| Compound No. | Kinetic Solubility (µM) |
| Ceapin-A7 | 27.7 |
| 1 | 2.70 |
| "Enantiomer A" of Example S5 | 4.68 |
| "Enantiomer A" of Example S6 | 27.00 |
| 9 | 8.90 |
| 11 | 9.41 |
| 12 | 37.2 |
| 14 | 35.2 |
| 19 | 9.37 |
| 22 | 2.30 |
| 114 | 1.17 |
| 123 | 1.17 |
| 99 | 2.34 |
| 101 | 2.34 |
| 104 | 2.34 |
| 136 | 2.34 |
| 93 | 2.92 |
| 97 | 2.92 |
| 121 | 3.51 |
| 100 | 4.68 |
| 110 | 4.68 |
| 76 | 7.03 |
| 103 | 9.37 |
| 152 | 28.13 |
| 154 | 37.50 |

Ceapin-A7 refers to compound described in Gallagher et al. eLife 2016; 5: e11878

Example B5: Plasma Stability Assay

Compounds are incubated at a final concentration of 1 µM with human, rat and mouse neat plasma at 37° C. The reactions are terminated at 0, 1, 2, 3, 4 and 5 hours post initiation by the addition of cold acetonitrile containing propranolol (50 ng/mL) as an internal standard. The reaction mixtures are partitioned by centrifugation at 15,000 rpm for 15 min and the resulting supernatants are analyzed for remaining compound by LC-MS/MS (Shimadzu Nexera UPLC with an AB Sciex 4500 detector). Procaine hydrochloride (#46608 Aldrich) is used as control for human plasma, Enalpril (#E6888 Aldrich) for rat plasma and Propentheline (#P8891 Aldrich) for mouse plasma.

Example B6: Plasma Protein Binding

The plasma protein binding (PPB) of the compounds in mouse and human plasma is determined using equilibrium dialysis. Plasma containing 2 μm of a compound is aliquoted in one of the chambers of a dialyzer insert (#89809 Thermo). The dialyzer insert contains two chambers of 250 μL volume each, separated by a semi permeable membrane. The second chamber is filled with phosphate buffer saline (PBS) pH 7.4. The assembly is incubated for 4 hours at 37° C. in a water bath. At the end of incubation, an aliquot of plasma and PBS are precipitated using chilled acetonitrile. The samples are vortexed for 30 min, centrifuged for 20 min at 3500 rpm at 4° C. The supernatant is analyzed by LC/MS/MS (Shimadzu Nexera UPLC with an AB Sciex 4500 detector). The % PPB is determined using the following equation % PPB=% total drug-% free drug. Miconazole (#M3512 Aldrich) is used as positive control.

Example B7: CYPz1.50 Inhibition

CYP inhibition by test compounds in human liver microsomes (HLM) for seven major CYP450 isoforms CYP1A2, CYP2C9, CYP2D6, CYP2B6, CYP2C8, CYP2C19 and CYP3A4 were assessed. Reactions were performed by incubating a test compound at concentrations of 0.02, 0.070, 0.21, 0.62, 1.85, 5.56, 16.67 and 50 μM in <1% DMSO with HLM (0.2 mg/mL for CYP1A2 and 0.03 mg/ml for CYP3A4, 0.2 mg/mL for CYP2C19, CYP2D6, and CYP2C9) in 0.1M phosphate buffer, 1 mM NADPH and selective probe substrates of individual isoforms at 37° C. 50 μM phenacetin, 2 μM midazolam, 5 μM diclofenac, 50 μM mephenytoin, 80 μM bupropion, and 5 μM dextromethorphan were used as probe substrates of CYP1A2, CYP3A4, CYP2C9, CYP2C19, CYP2B6, and CYP2D6, respectively. The incubation times were 20 min for CYP1A1, CYP2D6, CYP2C9, CYP2B6, and CYP2C8; 40 min for CYP2C19; and 10 min for CYP 3A4. Following incubations, the reactions were terminated with acetonitrile containing internal standard. The samples were centrifuged and the supernatants were analyzed for the formation of metabolites (1-hydroxymidazolam (CYP3A4), 4-hydroxydiclofenac (CYP2C9), 4-hydroxymephenytoin (CYP2C19) and dextrorphan (CYP2D6), hydroxybupropion (CYP2B6), acetaminophen (CYP1A2), desethylamodiaquine (CYP2C8)) by LC/MS/MS. Selective inhibitors for all isoforms were screened alongside as positive controls. A decrease in the formation of metabolites compared to vehicle control (100%) was used to estimate % inhibition, and the $IC_{50}$ was estimated from concentration-response curves. Parameters were calculated for specific compounds as shown in Table 6.

TABLE 6

| | CYP inhibition | | | | | | |
|---|---|---|---|---|---|---|---|
| Compound No. | CYP-1A2 (μM) | CYP-2C9 (μM) | CYP-2D6 (μM) | CYP-2B6 (μM) | CYP-2C8 (μM) | CYP-2C19 (μM | CYP-3A4 (μM) |
| Ceapin-A7 | >50 | >45.3 | >50 | 7.48 | 0.96 | 5077 | >50 |
| "Enantiomer A" of Example S5 | >50 | 3.07 | 2.30 | 2.49 | 0.86 | 2.31 | >50 |
| "Enantiomer A" of Example S6 | 15.26 | 7.88 | 23.67 | 4.18 | 1.35 | 3.54 | >50 |
| 11 | >50 | 7.77 | >50 | 16.86 | 1.09 | 9.85 | >50 |
| 154 | 10.69 | 14.81 | 22.57 | 15.37 | 10.75 | 6.44 | 15.83 |
| 78 | 22.40 | 5.48 | 2.78 | 4.97 | 1.80 | 5.27 | >50.0 |
| 131 | 30.88 | >50 | >50 | 44.45 | 43.27 | 16.39 | >50 |
| 76 | >50.0 | 6.00 | 7.54 | 6.45 | 1.14 | 3.60 | >50 |
| 114 | >50 | >50 | >50 | >50 | >50 | >50 | >50 |
| 121 | >50 | >45.9 | 35.50 | 23.60 | 30.50 | 2.90 | >50 |
| 123 | >50 | 31.90 | >50 | 42.90 | 33.30 | >50 | >50 |
| 129 | >50 | >50 | >50 | >50 | >50 | >50 | >50 |
| 136 | >50 | >50 | >50 | >50 | >50 | >50 | >50 |
| 152 | >50 | >50 | >50 | >50 | >50 | >50 | >50 |
| 93 | >50 | >50 | >50 | >50 | >50 | >50 | >50 |
| 99 | 41.0 | 2.5 | 32.0 | 4.8 | 1.0 | 8.8 | >50 |
| 138 | >50 | 12.1 | >50 | 5.0 | >50 | 15.0 | 2.4 |

Ceapin-A7 refers to compound described in Gallagher et al. eLife 2016; 5: e11878

Example B8: Cell Proliferation Assays

Pancreatic and colon cancer cell lines are maintained in growing medium containing DMEM supplemented with 10% FBS and 1% penicillin-streptomycin antibiotic cocktail. The chemotherapeutic agents oxaliplatin, 5-fluorouracil and gemcitabine will be obtained from Sigma-Aldrich.

Cell proliferation is measured by both CellTiter-Glo® and MTT assays. Briefly, 2,000 cells will be seeded in a 96 well plate overnight. Cells are treated with either single chemotherapeutic agents oxaliplatin, 5-fluorouracil, and gemcitabine or with the combination of a test compound and oxaliplatin, 5-fluorouracil, or gemcitabine. At 72 hours post-treatment, luminescent-based cell viability is determined using Cell-Titer Glo (CTG) assay according to the manufacturer's instructions (Cat. No.: G7573, Promega).

Percent of cell viability/proliferation is determined by normalizing luminescence signal to untreated control well. All treatments are done in triplicate and reported as % Viability±SD and % Proliferation±SD. Dose response curves are generated to calculate the half-maximal growth inhibition concentration ($GI_{50}$) in GraphPad Prism version 6.07.

Example B9: Genomics of Drug Sensitivity in Cancer (GDSC) Cell Line Screening

A panel of cancer cell lines from different malignancies is used to test the effect of selected compounds by cell viability assay, 72 hours post-treatment, as described in Yang et al. Nucleic Acids Research, 2013, 41(D1): D955-D961. Dose response curves are used to calculate $IC_{50}$ in GraphPad Prism version 6.07.

Example B10: In Vitro Tube Formation Assay

HUVEC cells are pretreated with 100 ng/ml VEGF for 2 h and then incubated for 24 h with test compounds at different concentrations. Cells without VEGF or treated with vehicle plus VEGF are used as controls. Cells are detached and seeded (between $5\times10^3$-$1\times10^4$) in a 96 well plate covered with EC-Matrix™ using the in vitro Angiogenesis assay Kit (Merck) according the manufacturer's instructions and cultured overnight. Tube formation is evaluated by light microscopy. Pattern recognition is evaluated and a numerical value will be associated with a degree of angiogenesis progression (Table 7), several random view-fields (3-10) per well are examined and the values are averaged.

TABLE 7

Assessment of degree of angiogenesis progression

| Pattern | Value |
|---|---|
| Individual cells, well separated | 0 |
| Cells begin to migrate and align themselves | 1 |
| Capillary tubes visible. No sprouting. | 2 |
| Sprouting of new capillary tubes visible. | 3 |
| Closed polygons begin to form. | 4 |
| Complex mesh like structures develop | 5 |

Counting of capillary tubes branch points (Branch Point Counting) formed after a set amount of time (end-point assay) is evaluated. The length of the newly formed capillary tubes is also determined. Branch points in several random view-fields (3-10) per well are counted and the values are averaged. Total Capillary Tube Length is measured in several random view-fields (3-10) per well and the values are averaged. In addition, a visualization of cell-tubes is performed by staining of the tubes with Masson's trichrome.

Example B11: In-Vivo PANC-1 Tumor Model

Six- to seven-week-old female athymic nu/nu mice are purchased from Taconic (Hudson, NY) are acclimated for 1 week on arrival to the animal facility before in-vivo study is initiated. To ensure high tumor take in mice, all cells are grown at exponential growth rates. The PANC-1 cells are collected via trypsin-EDTA, and viability is determined by trypan blue exclusion. Then, the concentration of the cell suspension is adjusted to the required density for injection. One million cells (containing matrigel plus PANC-1 cells in a vol=100 μL) are injected subcutaneously into 6-7 week old athymic BALB/C nude mice. The injection site is continually monitored to determine tumor establishment. Tumors are measured using a digital caliper. When tumor volume reaches an average of 100-150 $cm^3$, mice are randomly assigned to a single agent chemotherapeutic agent control group, a single agent compound group, or a combination groups. Compounds are delivered in a solution of 10% Kolliphor® EL and 10% Ethanol by oral gavage. Chemotherapeutic agents are administered by intra-peritoneal injection. The length (L) and width (W) of the tumors are measured 1-2 times a week using a digital caliper, and the volume of the tumor is calculated using the formula: $0.5*L*W^2$. Mice are also weighed once a week to monitor signs of drug toxicity. After final dose, the mice are humanely euthanized and whole blood samples are collected by cardiac puncture and tissues are excised for further analysis. Tumor tissue is removed and weighed. All other tissues of interest are snap frozen, and are immersed in RNAlater or placed in 10% NBF for histology.

Example B12: Matrigel Plug Angiogenesis Assay

Four- to six-week-old male C57 BL/6 mice are used to assay angiogenesis using the Matrigel Plug assay (Birdsey et al., Blood, 2008, 111:3498-3506). Cold Matrigel (BD) supplemented with VEGF (250 ng/ml) and heparin (50 U/ml) are mixed with different concentration of test compound. In each experimental group, five mice are lightly anesthetized using isoflurane, and cold Matrigel (0.5 ml) containing the above-mentioned additions are injected into the abdominal subcutaneous tissue along the peritoneal midline. After 7 days, mice are euthanized, and Matrigel plugs are removed and fixed in 4% paraformaldehyde, embedded in paraffin, sectioned, and hematoxylin and eosin (H&E) stained. Staining with CD31 is used for the qualitative identification of endothelial cells in histological tissue sections.

Example B13: Xenograft Studies

Cells are grown on chorioallantoic membranes (CAMs) as described (Schewe, D. M. et al., Proc Natl Acad Sci USA, 2008, 105(30): 10519-10524). For nude mice experiments, $0.5\times10^6$ cells are inoculated subcutaneously (s.c.) in the interscapular region of 2- to 3-month-old female BALB/c nude mice. Tumor growth is measured daily by using a caliper.

Example B14: Modulation of ER Proteostasis Network in MM Cell Lines

Because MM cells, similar to their normal counterparts, produce significant amounts of ER-processed proteins, it has been proposed that these cells may be sensitive to perturbations in protein degradation, which would result in the activation of the UPR. One of the hallmarks of UPR induction is the increased transcription and translation of ER molecular chaperones. These genes are induced by the UPR transcription factors XBP1 and ATF6. Although XBP1 splicing and its resulting activation have been shown to be inhibited in PI-treated MM cells, it has been demonstrated that the high constitutive expression of 2 XBP1 target genes products, GRP78 and GRP94, is not reduced by PI treatment and the observation that the XBP1-dependent UPR target gene ERdj4 was normally induced by PIs suggest that the UPR remains functional in PI-treated MM cells. Because both XBP1 and ATF6 can bind to ER stress response elements in the promoters of UPR target genes, it has been suggested that ATF6 may compensate for decreased XBP1 activity in PI-treated MM cells. Consistent with this, it has been shown that the induction of GRP78 and GRP94 is only slightly impaired in XBP1$^{-/-}$ B cells and that the expression of GRP94 requires either, but not both, ATF6 or XBP1.

To determine if exemplary compounds of the invention can modulate of ER proteostasis network, ATF6—dependent molecular components including GRP78/BiP, GRP94 and others were investigated in MM cell lines in absence or presence of Tg-induced ER stress.

U-266, OPM-2, and JJN-3 cells were obtained from Leibniz-Institut DSMZ (Germany). U-266 and OPM-2 cell lines were cultured in RPMI-1640 media supplemented with 10% (v/v) FBS (Cat. No.: 16000044, Gibco) and 1% penicillin-streptomycin antibiotic cocktail. JJN-3 cell line was cultured in 45% (v/v) DME/F-12 media and 45% (v/v) Iscove's Modified Dulbecco's Medium (IMDM) (Cat. No.: 12440046, Thermo Fisher Scientific) supplemented with 10% (v/v) FBS and 1% penicillin-streptomycin antibiotic cocktail.

At the day of experiment, U-266, OPM-2, and JJN-3 cells ($1.5 \times 10^6$ per well) were seeded in 750 µL growing medium in 6-well plate and pre-treated for 30 min adding 750 µL growing medium containing either vehicle (dimethyl sulfoxide (DMSO)) (Cat. No.: D2650, Sigma-Aldrich) or an exemplary compound of the invention at 10 µM. After the pre-incubation time, 500 µL of growing medium containing 0.2 µM Tg were added to respective wells. This Tg solution also contained vehicle or testing compound at 10 µM. The final concentration of DMSO in each well was kept at 0.3%. Plates were incubated for 16 hr in humidified chambers. After incubation, cells were mechanically lysed using 29 G syringes (Cat. No.: 326770, BD Ultra-Fine) in 1× cell lysis buffer (Cat. No.: 9803S, Cell Signaling Technology) containing protease (Cat. No.: 4693159001, Roche) and phosphatase inhibitors (Cat. No.: 4906837001, Roche). Cell lysates were disrupted by sonication in a water bath and then cleared by centrifugation at 13,500 rpm for 15 min. Supernatants containing protein samples were harvested and then quantified using the BCA protein assay kit (Cat. No.: 23225, Thermofisher Scientific). Equal amounts of total proteins (15 µg) were loaded and separated by SDS-PAGE, electrotransferred to PVDF membranes (Cat. No.: 162-0177, Bio-Rad) and blocked in 3% BSA solution for 1 hour. Membranes were probed with the following antibodies: BiP ($C_{50}$B12) (Cat. No.: 3177S, Cell Signaling Technology), HERPUD1 (Cat. No.: 26730S, Cell Signaling Technology), HYOU1 (Cat. No.: 13452S, Cell Signaling Technology), p58$^{IPK}$((Cat. No.: 2940S, Cell Signaling Technology), ERdj3 (Cat. No.: SC-271240, Santa Cruz Biotechnology), GRP94 (Cat. No.: PA5-27866, Thermofisher Scientific), β-actin (Cat. No.: A5441, Sigma-Aldrich). Primary antibodies were detected using appropriate horseradish peroxidase (HRP)-conjugated secondary antibodies, Rabbit IgG HPR-conjugated Antibody (Cat. No.: 611-1322, Rockland Immunochemicals Inc.) or Mouse IgG HRP-conjugated Antibody (Cat. No.: 610-1302, Rockland Immunochemicals Inc.). BiP, ERdj3, HERPUD1, HYOU1 and p58$^{IPK}$ antibodies were used at 1:1,000 dilution, while GRP94 antibody was used at 1:2,000 dilution for overnight hybridization at 4° C. β-actin was used 1:10,000 for 24 hr hybridization at 4° C. Incubations with horseradish peroxidase (HRP)-conjugated secondary antibodies were performed using 1:10,000 dilution for 2 hours at room temperature. Finally, blots were revealed using the Pierce ECL Western Blotting Substrate (Cat. No.: 32106, Thermo Fisher Scientific) under conditions recommended by the manufacturer. Images were captured using the ChemiDoc-MP Imaging System (Bio-Rad) and analyzed with Image Lab Software (Bio-Rad).

Comparison of efficacy between an exemplary compound of the invention and Val-boroPro at 100 and 1000 nM for inhibiting the proteolytic processing of rhFGF21 by rhFAP in vitro is showed in FIG. 1. As shown by the immunoblotting image and densitometry analysis, the intact form of rhFGF21 is preserved in presence of one exemplary compound of the invention even at low concentration.

Example B15: Cytoxicity Assays in MM Cell Lines

The effect of the remodeling of ER proteostasis network mediated by exemplary compounds of the invention on the cell viability of MM cell lines in absence ER stress was investigated.

Figure 2A:
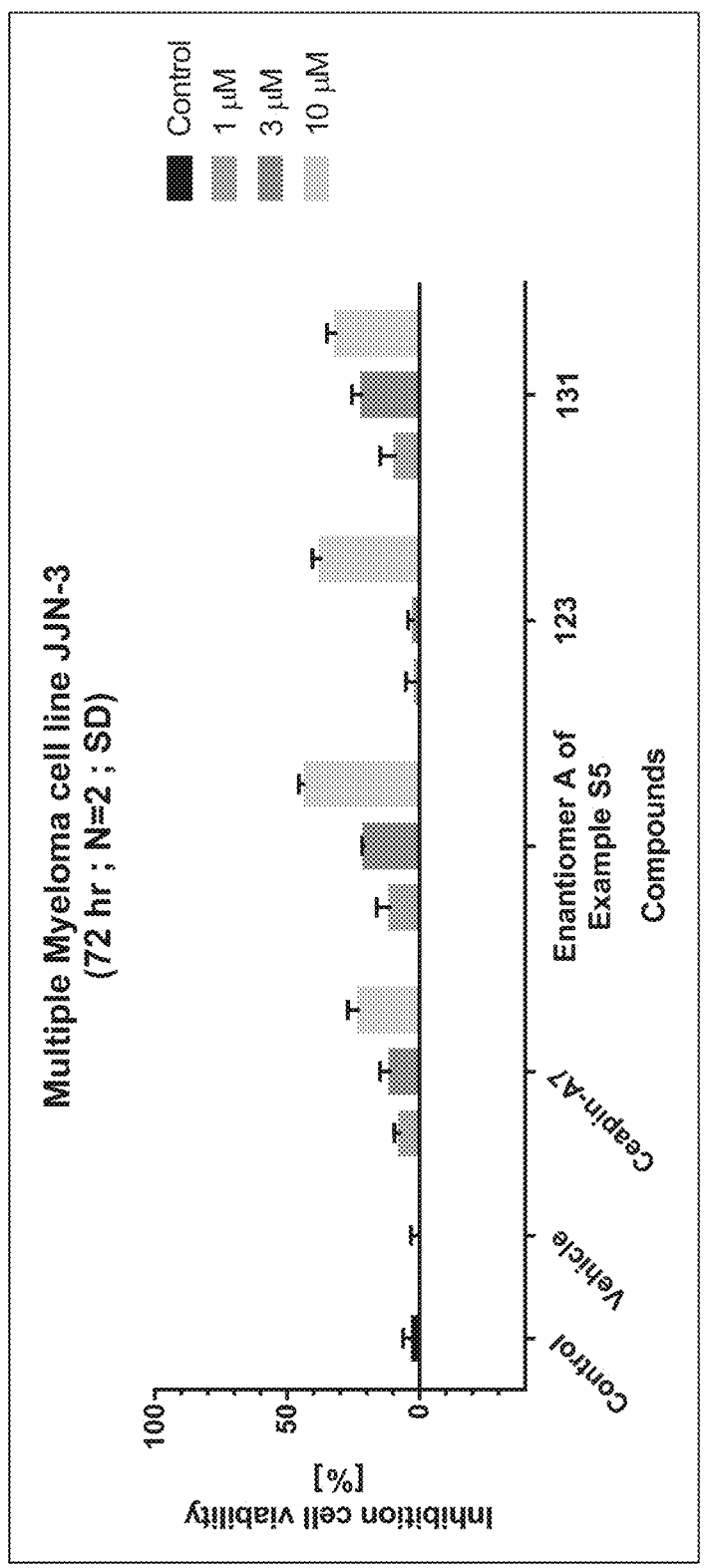
FIGS. 2A, 2B and 2C illustrate how modulation of ER proteostasis network using three exemplary compounds affects cell viability of MM cell lines.
Figure 2B:
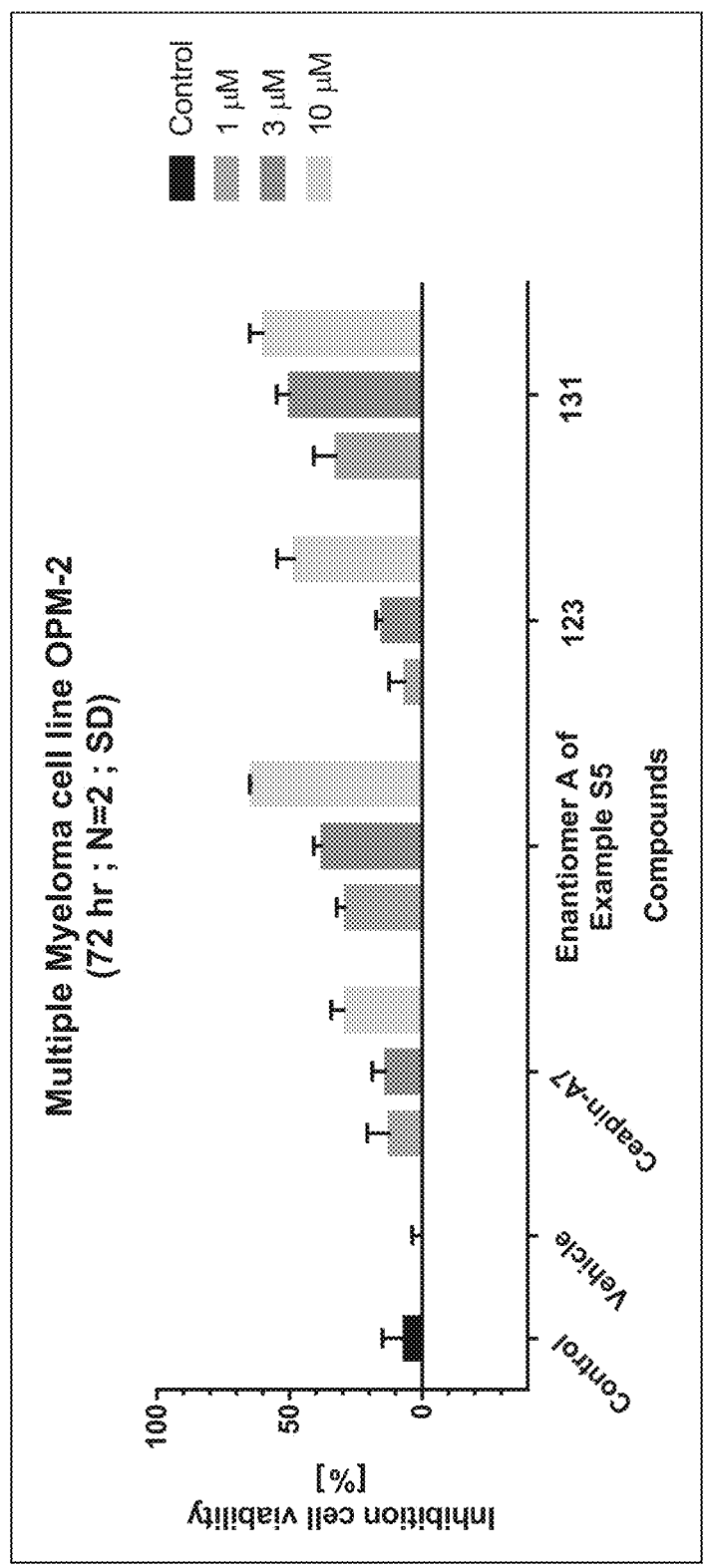
Figure 2C:
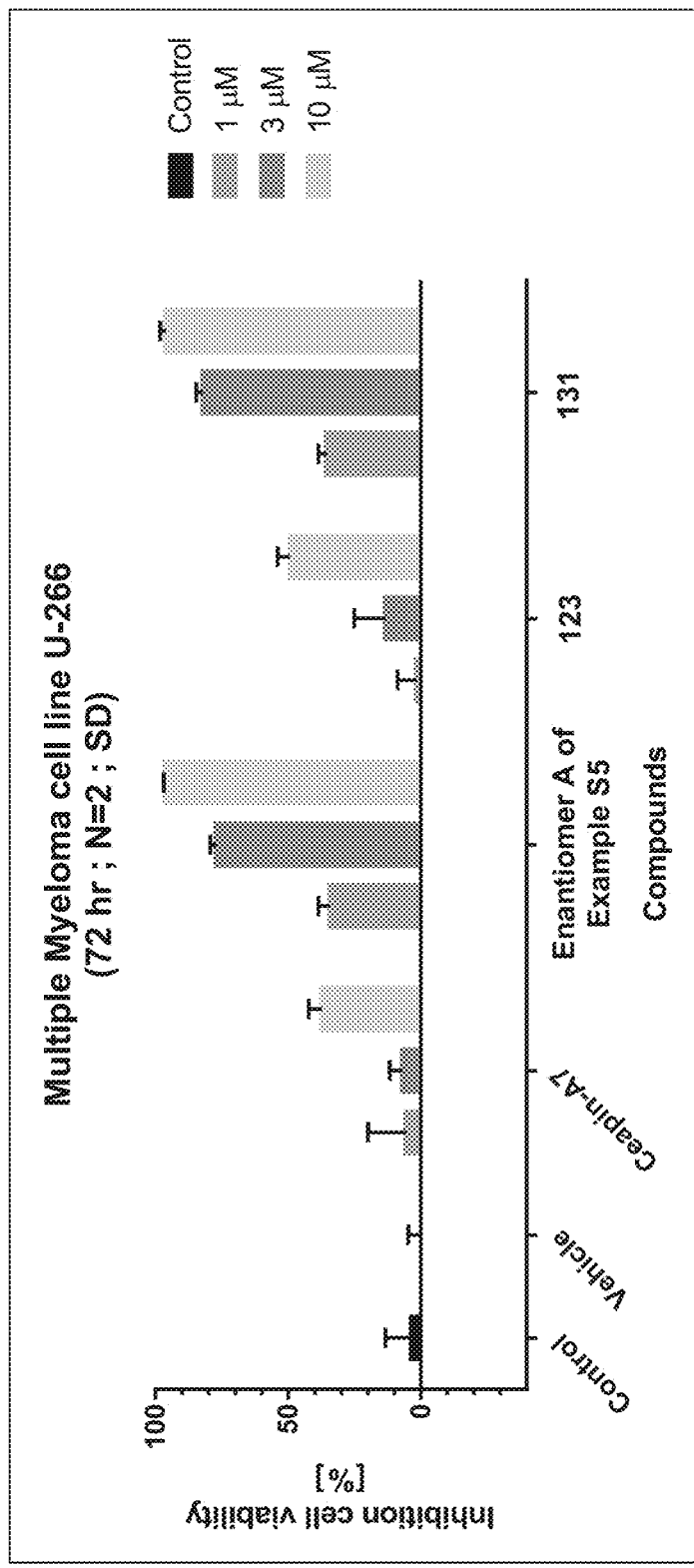

U-266, OPM-2, and JJN-3 cells were cultured as described above. At the day of the experiment, U-266 ($2 \times 10^4$ $^{cells}/_{well}$), OPM-2 ($1 \times 10^4$ $^{cells}/_{well}$), JJN3 ($4 \times 10^3$ $^{cells}/_{well}$) cells were seeded in white 96-well plate in 100 µL growing medium containing either vehicle (DMSO) or a compound of the invention at 1, 3 or 10 µM. After 72 hours post-treatment, luminescent-based cell viability was determined using Cell-Titer Glo (CTG) assay according to the manufacturer's instructions (Cat. No.: G7573, Promega). Percent of cell viability was calculated by normalizing luminescence signal to the average value from vehicle-treated wells, assumed as the maximum of viability (100%). In every experiment, all treatments were performed in triplicate and reported as % inhibition of viability±standard deviation (SD). Plots shown in FIG. 2 represent the average of two independent experiments.

Example B16: Subcutaneous Xenograft Growth and Efficacy Studies in Multiple Myeloma Models For tumor growth studies, MM cell lines (including RPMI-8226, H929, KMS-11, U-266, OPM-2, and JJN-3) are injected subcutaneously in the right flank of male NOD SCID mice. Tumors are monitored until they reached a mean tumor volume of approximately ~100 to 150 mm$^3$ and then randomized in one of the following groups: (i) Control group dosed with vehicle, (ii) Exemplary compound of the invention dosed orally, (iii) bortezomib (0.75 mg/kg, 100 µL total, intravenously, twice per week) or lenalidomide (50 mg/kg, 100 µL total, intraperitoneally, once daily for 5 consecutive days); and (iv) exemplary compound in combination with bortezomib or lenalidomide. Tumor size and body weight are measured twice per week. Subcutaneous tumor volumes are measured manually in two dimensions (length and width) using a digital caliper and analyzed using Excel, version 11.2 (Microsoft), or Prism 6 (GraphPad Software, Inc.). The tumor volume was calculated with the following formula:

Tumor size (mm$^3$)=(Longer measurement×Shorter measurement$^2$)×0.5

Animal body weights are measured also using a scale. Percent weight change is calculated using the following formula:

Group percent weight change=[(New weight−Initial weight)/Initial weight]×100

For the orthometastatic xenograft model, MM cell lines (including RPMI-8226, H929, KMS-11, U-266, OPM-2, and JJN-3) are injected intravenously via the tail vein of non-irradiated 8-week old NOD/SCID/IL2rγ−/− mice. The animals are imaged weekly under isoflurane anesthesia 5 min after intraperitoneal luciferin injection with 200 μl of 25 mg ml-1 D-luciferin (Invitrogen), and imaged on a Photon Imager (BioSpace Laboratory). During image acquisition, animals continued to receive anesthesia from a nosecone delivery system, while their body temperatures were maintained on a thermostatically controlled platform. Photon counts per min per cm² of observational area were calculated and compared using M3 Vision software (BioSpace Laboratory). After 6 weeks mice were grouped out into the following treatment groups: (i) Control group dosed with vehicle, (ii) Exemplary compound of the invention dosed orally, (iii) bortezomib (0.75 mg/kg, 100 μL total, intravenously, twice per week) or lenalidomide (50 mg/kg, 100 μL total, intraperitoneally, once daily for 5 consecutive days). After 14 days, mice were euthanized by cervical dislocation and bones harvested for fluorescence imaging using a Kodak In-Vivo FX system (Carestream Health Molecular Imaging, New Haven, Connecticut) and Carestream Molecular Imaging (MI) Software. Excitation and emission wavelengths were fixed at 550 nm and 600 nm, respectively. Fluorescence images were co-registered with X-ray images using the opensource software Image J (http://rsbweb.nih.gov/ij/).

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

$R^8$ is H or $C_1$-$C_6$alkyl, n is 0 or 1;

L is —$CH_2$— or is absent;

$R^2$, $R^3$, $R^4$, $R^5$, and $R^6$ are each independently H, halo, CN, $C_1$-$C_6$alkyl, or $C_1$-$C_6$haloalkyl;

or $R^2$, $R^4$, $R^5$, and $R^6$ are each independently H, halo, CN, $C_1$-$C_6$alkyl, or $C_1$-$C_6$haloalkyl and $R^3$ is taken together with an $R^1$ and the atoms to which they are attached to form a 5- or 6-membered ring, wherein the 5- or 6-membered ring is unsubstituted or substituted with one to three groups selected from the group consisting of halo, CN, —OH, $C_1$-$C_6$alkyl, and $C_1$-$C_6$haloalkyl;

provided that either:

$R^3$ is taken together with $R^1$ and the atoms to which they are attached to form a 5- or 6-membered ring; or at least two of $R^2$, $R^3$, $R^4$, $R^5$, and $R^6$ are other than H; or one of $R^2$, $R^3$, $R^4$, $R^5$, and $R^6$ is cyano;

A is 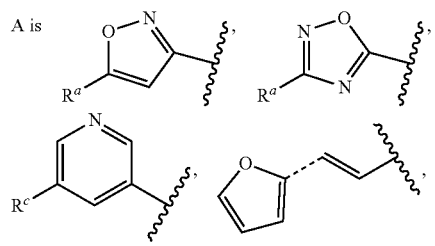

What is claimed is:

1. A method of treating a metabolic disorder in a subject in need thereof, comprising administering to the subject a compound of Formula (A):

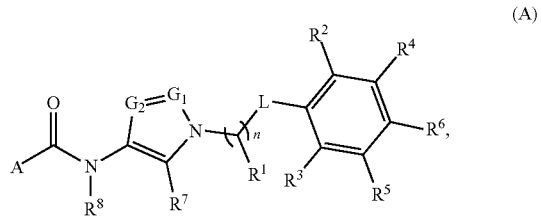

(A)

or a pharmaceutically acceptable salt thereof, wherein:
one of $G_1$ and $G_2$ is N and one of $G_1$ and $G_2$ is $CR^d$, wherein $R^d$ is H or $C_1$-$C_6$alkyl;
$R^1$ is H, $C_1$-$C_6$alkyl, or $C_3$-$C_8$cycloalkyl; or $R^1$ is H, $C_1$-$C_6$alkyl, $C_3$-$C_8$cycloalkyl, or $C_1$-$C_6$ haloalkyl;

-continued

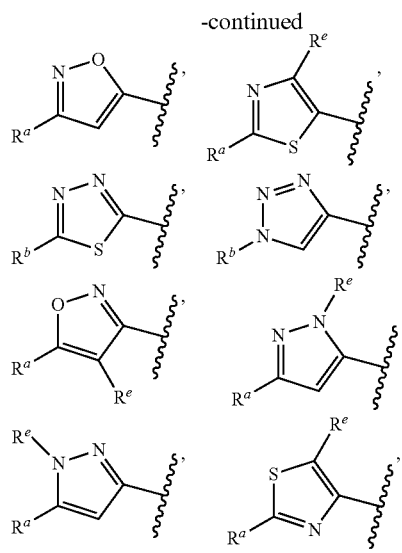

-continued

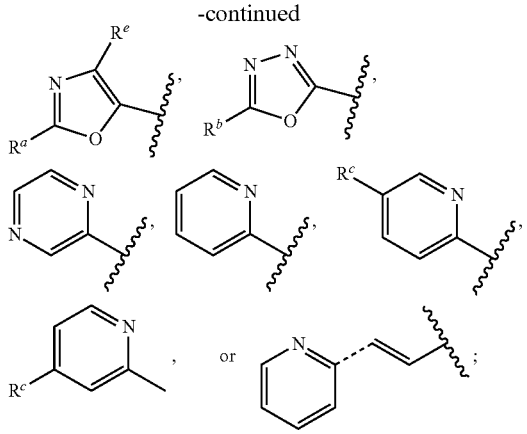

wherein --- indicates that

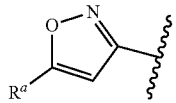 or 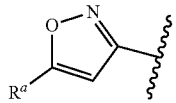

or is attached in either an E or Z configuration;

$R^a$ and $R^b$ are each independently H, $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^a$ and $R^b$ are unsubstituted or substituted with one to four groups selected from the group consisting of OH, halo, and $C_1$-$C_6$alkyl;

$R^c$ is $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^c$ is unsubstituted or substituted with one to four groups selected from the group consisting of OH, halo, and $C_1$-$C_6$alkyl;

$R^e$ is H or $C_1$-$C_6$alkyl;

provided that when A is

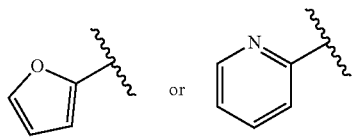 [SMILES: *c1ccco1 ; *c1ccccn1]

and $R^a$ is H, methyl, ethyl, n-Pr, i-Pr, i-Bu, 2-thiofuryl, 2-furyl, unsubstituted phenyl, 3-hydroxyphenyl, 4-hydroxyphenyl, 4-fluorophenyl, or 2,4-dichlorophenyl, at least one of (i)-(ix) applies:

(i) $G_2$ is N;
(ii) n is 1, L is absent, and $R^1$ is $C_1$-$C_6$alkyl;
(iii) n is 0, L is absent, and at least one of $R^2$, $R^3$, $R^4$, $R^5$, and $R^6$ is halo, CN, or $C_1$-$C_6$haloalkyl;
(iv) n is 1, and $R^3$ is taken together with $R^1$ and the atoms to which they are attached to form a 5- or 6-membered ring;
(v) one of $R^2$, $R^3$, $R^4$, $R^5$, and $R^6$ is CN; and
(vi) $R^4$ and $R^5$ are each independently Cl, Br, I, CN, $C_1$-$C_6$alkyl, or $C_1$-$C_6$haloalkyl;
(vii) one of $R^d$ and $R^7$ is $C_1$-$C_6$alkyl;
(viii) $R^2$ and $R^3$ are each Cl;
(ix) at least one of $R^2$, $R^3$, $R^4$, $R^5$, and $R^6$ is F, Br, I, CN, or $C_1$-$C_6$haloalkyl and $R^E$ is H or 2-thiofuryl;

provided that when A is

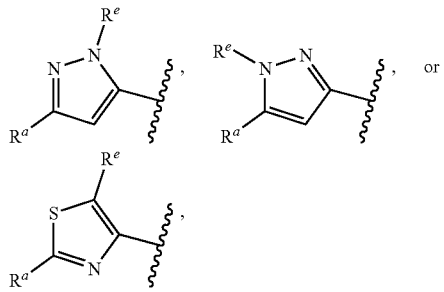

and n is 1, then $R^1$ is other than H;
provided that when A is

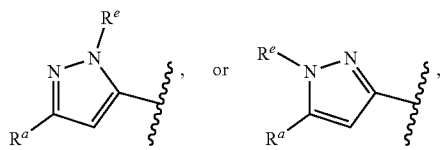

n is 0 and L is absent, then $R^a$ is other than H;
provided that when A is

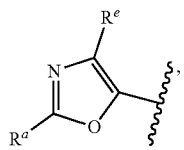

and $R^e$ is methyl, then $R^a$ is other than unsubstituted phenyl;
provided that when A

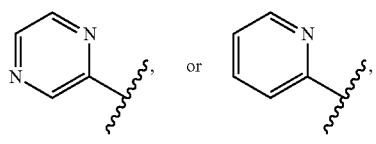 [SMILES: *c1cnccn1 ; *c1ccccn1]

n is 1 and L is absent, then $R^1$ is other than H;
and $R^7$ is H, $C_1$-$C_6$alkyl or $C_1$-$C_6$haloalkyl,
provided that when $R^d$ is $C_1$-$C_6$alkyl, $R^7$ is H, and when $R^7$ is $C_1$-$C_6$alkyl, $R^d$ is H.

2. The method of claim 1, wherein:

$R^1$ is H, $C_1$-$C_6$alkyl, or $C_3$-$C_8$cycloalkyl;
$R^8$ is H;
A is

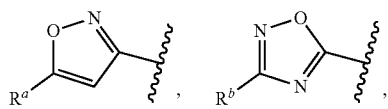

-continued

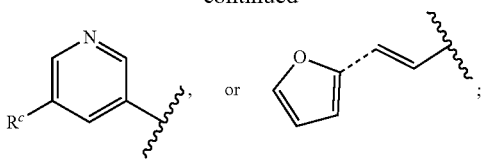

wherein --- indicates that

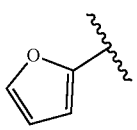

is attached in either an E or Z configuration;
$R^a$ and $R^b$ are each independently H, $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^E$ and $R^b$ are unsubstituted or substituted with one to four groups selected from the group consisting of OH, halo, and $C_1$-$C_6$alkyl;
and is represented by Formula (I):

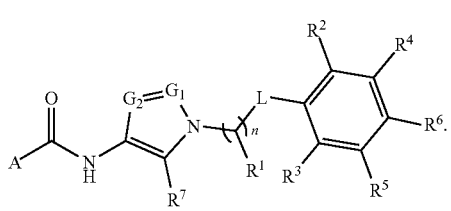

3. The method of claim 1, wherein $G_1$ is N and $G_2$ is $CR^d$.
4. The method of claim 1, wherein $R^d$ is H.
5. The method of claim 1, wherein n is 1.
6. The method of claim 1, wherein $R^3$ is taken together with $R^1$ and the atoms to which they are attached to form a 5- or 6-membered ring.
7. The method of claim 1, wherein L is absent.
8. The method of claim 1, wherein $R^2$, $R^3$, $R^4$, $R^5$, and $R^6$ are each independently H, Cl, CN, or $CF_3$.
9. The method of claim 1, wherein:
$R^2$ and $R^6$ are each $CF_3$, or
$R^4$ and $R^5$ are each $CF_3$, or
$R^3$ and $R^6$ are each $CF_3$.
10. The method of claim 1, wherein
A is

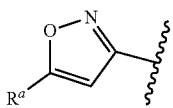

and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ are unsubstituted or substituted with one to four groups selected from the group consisting of OH, halo, and $C_1$-$C_6$alkyl.

11. The method of claim 1, wherein
A is

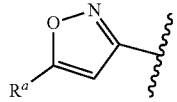

and $R^a$ is selected from the group consisting of $C_1$-$C_6$alkyl,

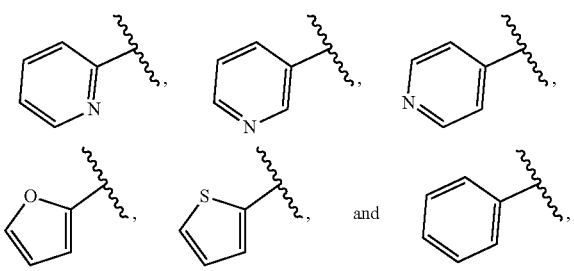

each of which is unsubstituted or is substituted with one to four groups selected from the group consisting of OH, halo, and $C_1$-$C_6$alkyl.

12. The method of claim 1, wherein
A is

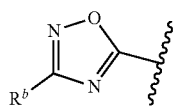

$R^b$ N and $R^b$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^b$ is unsubstituted or is substituted with one to four groups selected from the group consisting of OH, halo, and $C_1$-$C_6$alkyl.

13. The method of claim 1,
wherein A is

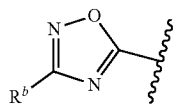

and $R^b$ is selected from the group consisting of $C_1$-$C_6$alkyl,

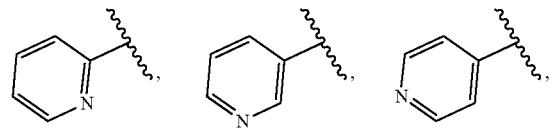

-continued

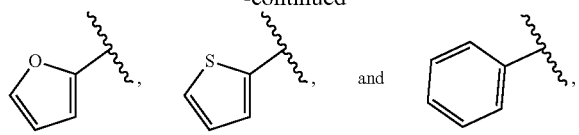

each of which is unsubstituted or is substituted with one to four groups selected from the group consisting of OH, halo, and $C_1$-$C_6$alkyl.

14. The method of claim 1, wherein A is

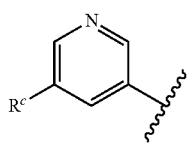

and $R^c$ is selected from the group consisting of $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^c$ is unsubstituted or is substituted with one to four groups selected from the group consisting of OH, halo, and $C_1$-$C_6$alkyl.

15. The method of claim 1, wherein A is

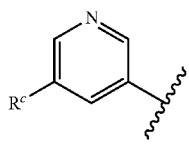

R and $R^c$ is selected from the group consisting of $C_1$-$C_6$alkyl

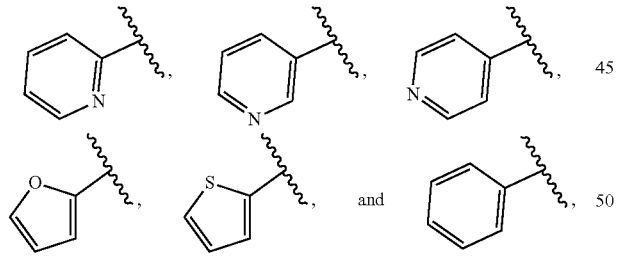

each of which is unsubstituted or is substituted with one to four groups selected from the group consisting of OH, halo, and $C_1$-$C_6$alkyl.

16. The method of claim 1, wherein A is

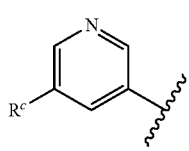

and $R^b$ is selected from the group consisting of H,

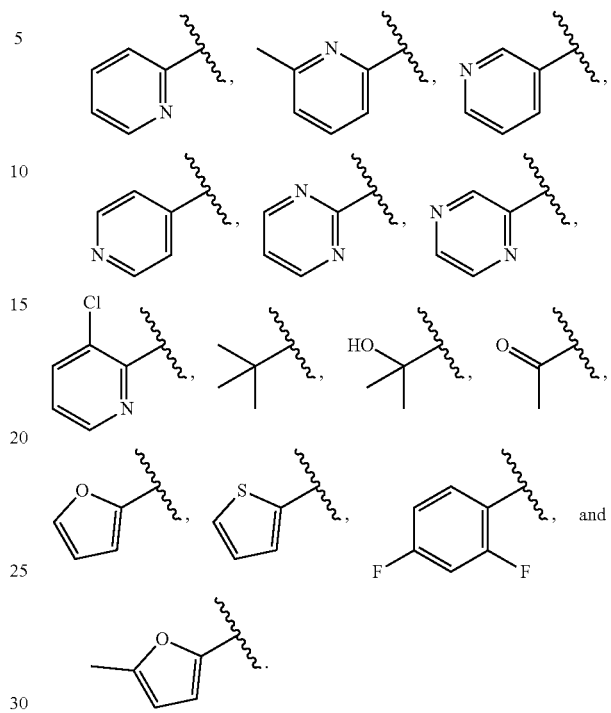

17. The method of claim 1, wherein $R^7$ is H.

18. The method of claim 1, wherein $R^7$ is $C_1$-$C_6$alkyl.

19. A method of treating a metabolic disorder in a subject in need thereof, comprising administering to the subject a compound selected from the group consisting of:

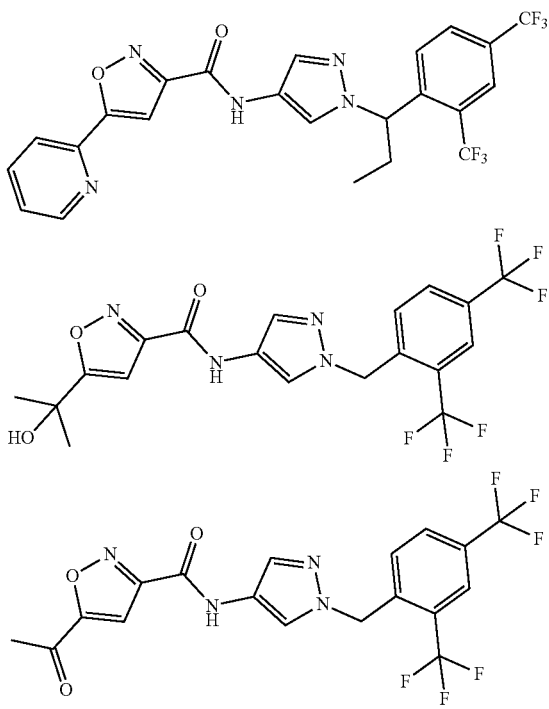

391
-continued
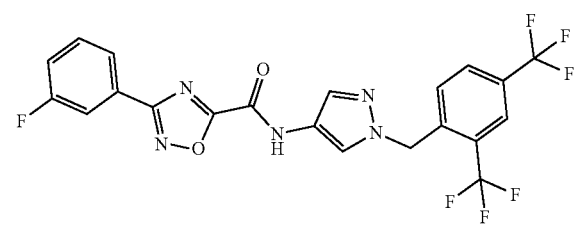
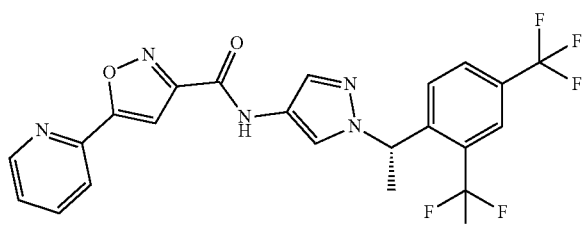
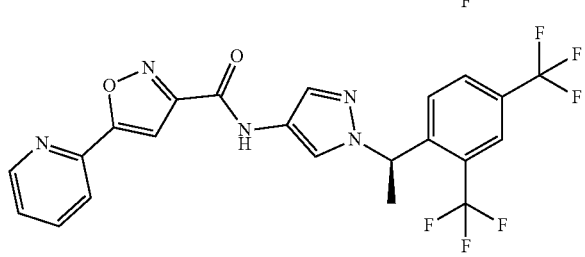
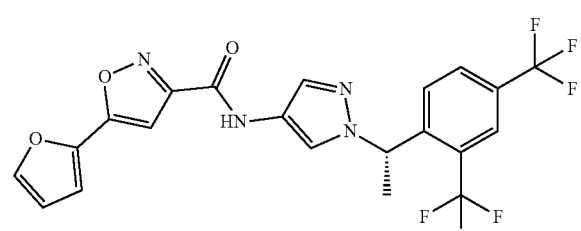
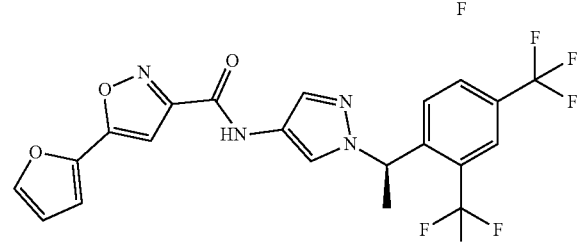
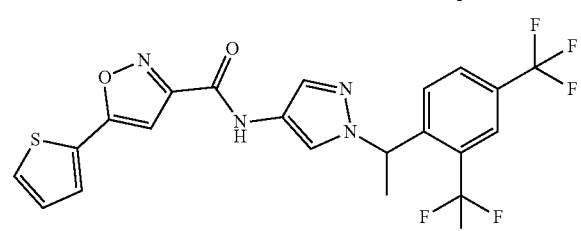
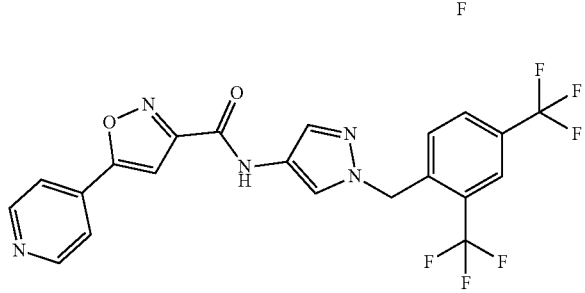
392
-continued
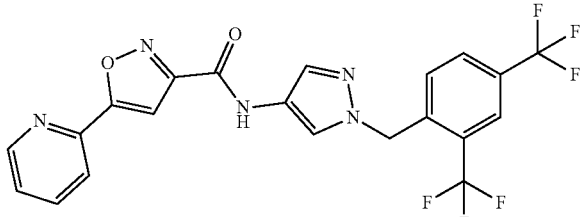
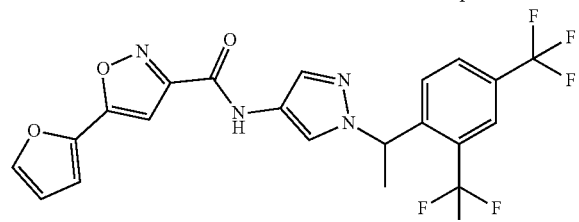
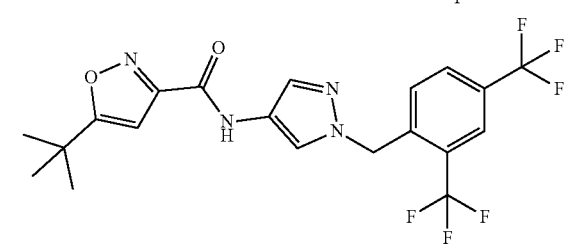
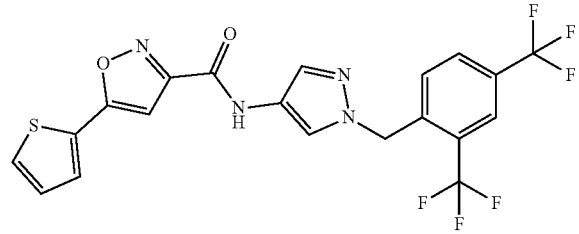
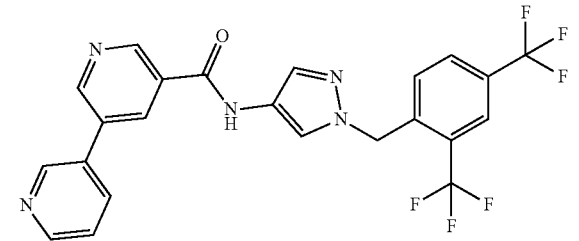
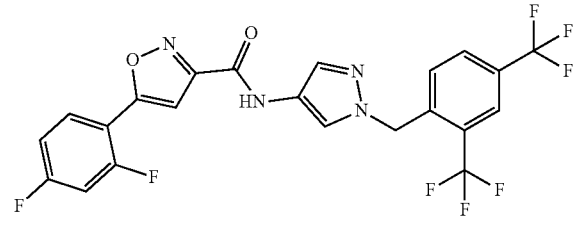
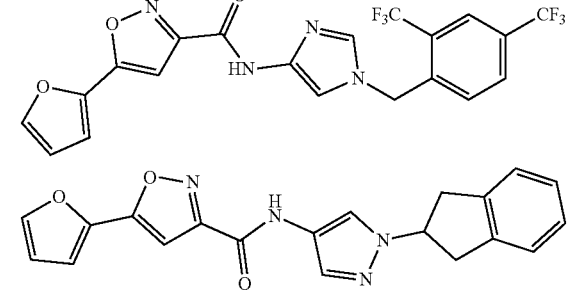

393
-continued
394
-continued
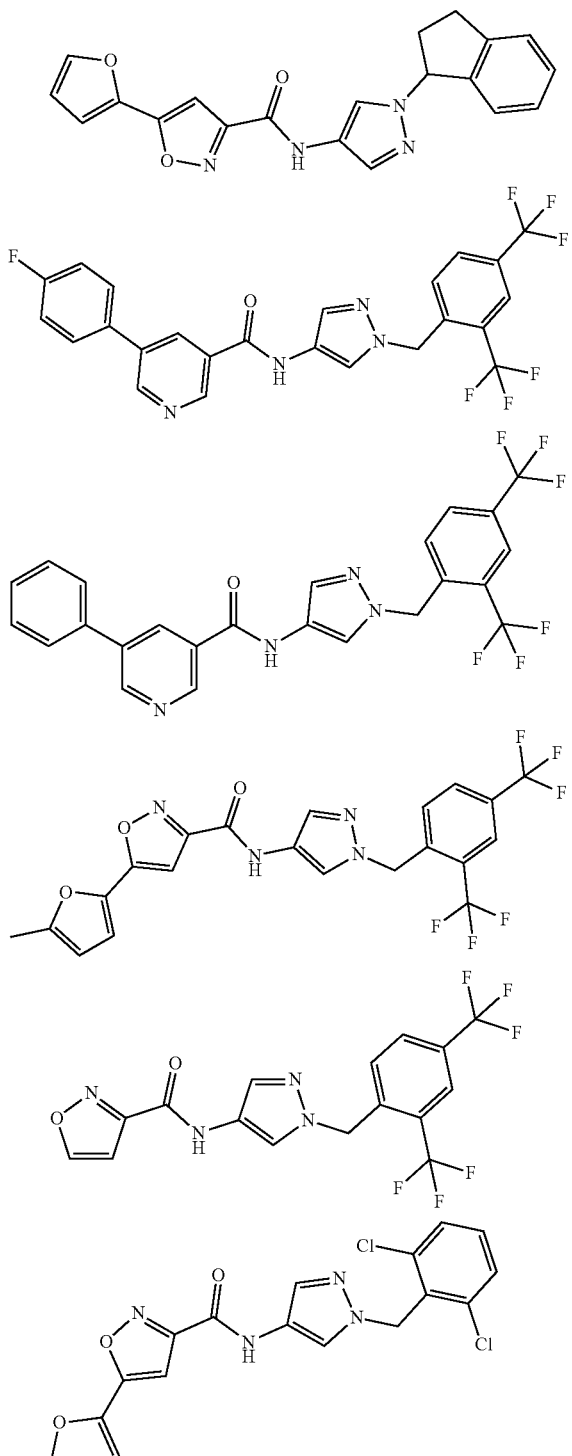
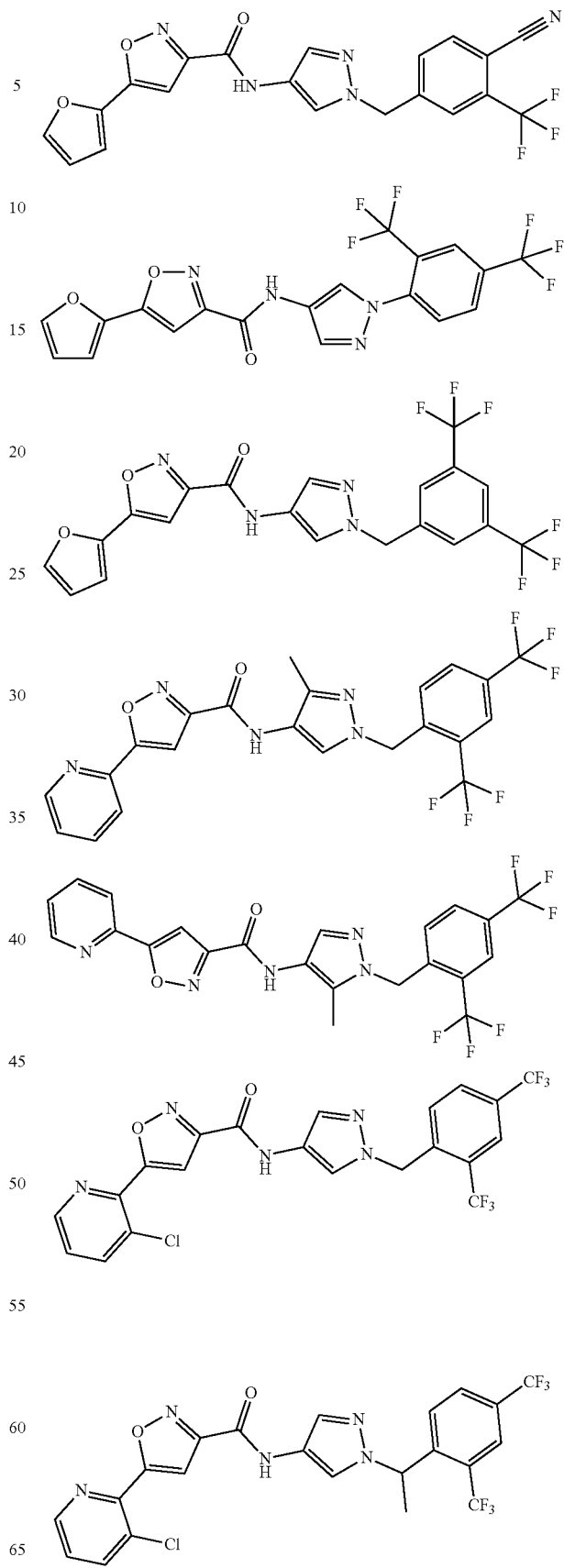

-continued
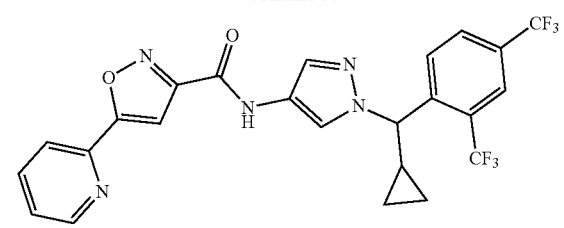
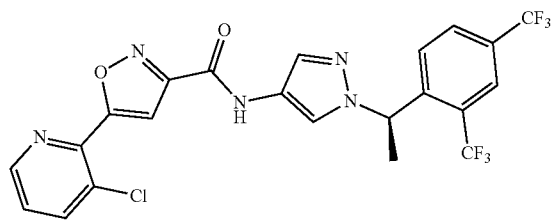
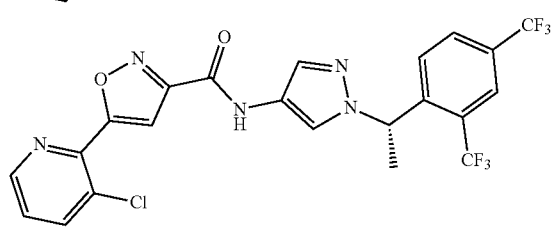
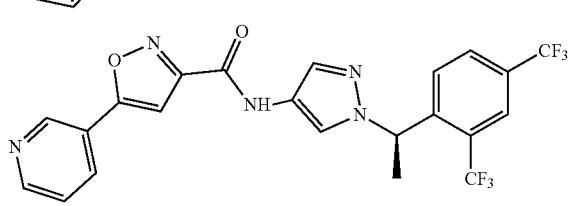
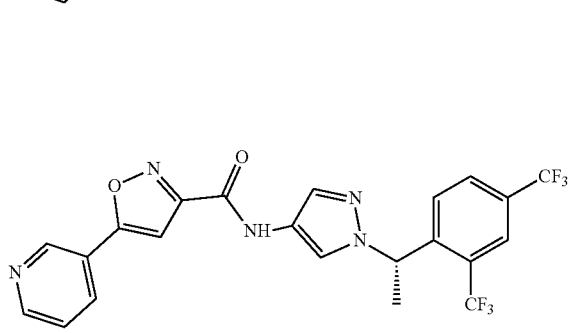
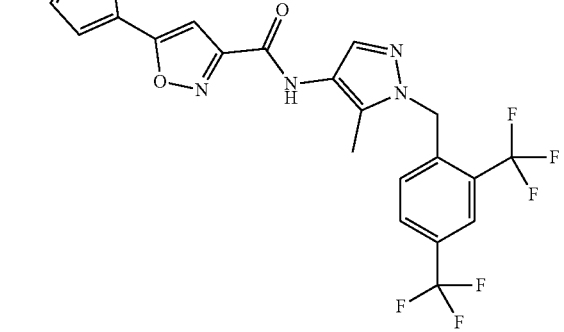
-continued
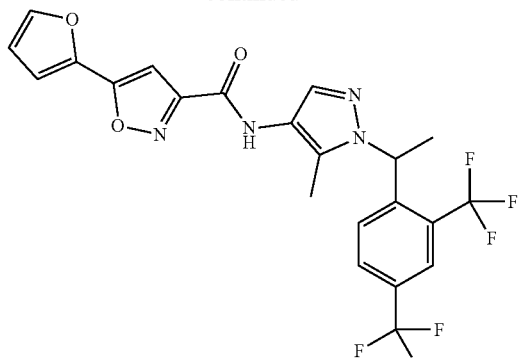
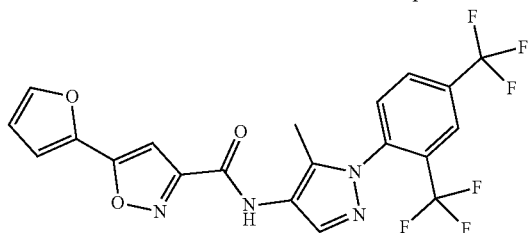
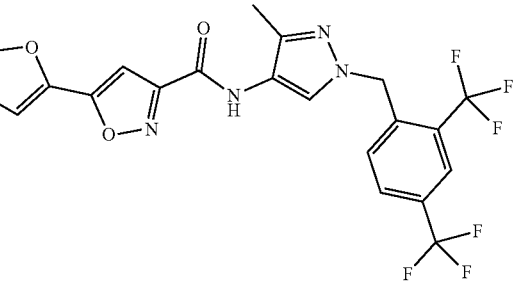
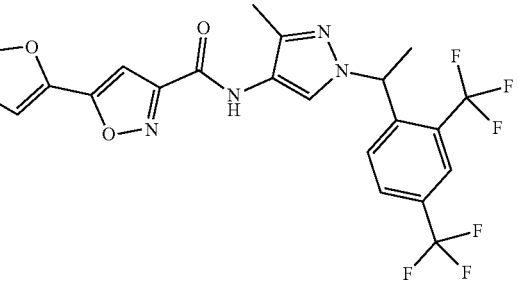
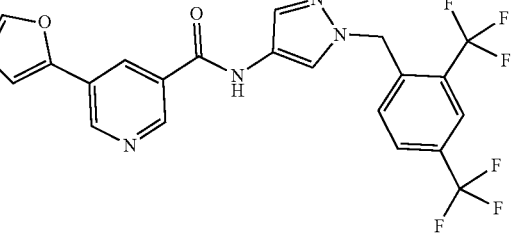
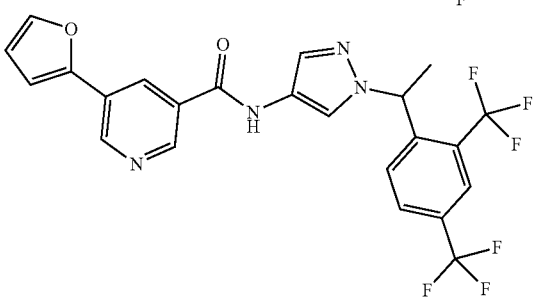

397
-continued
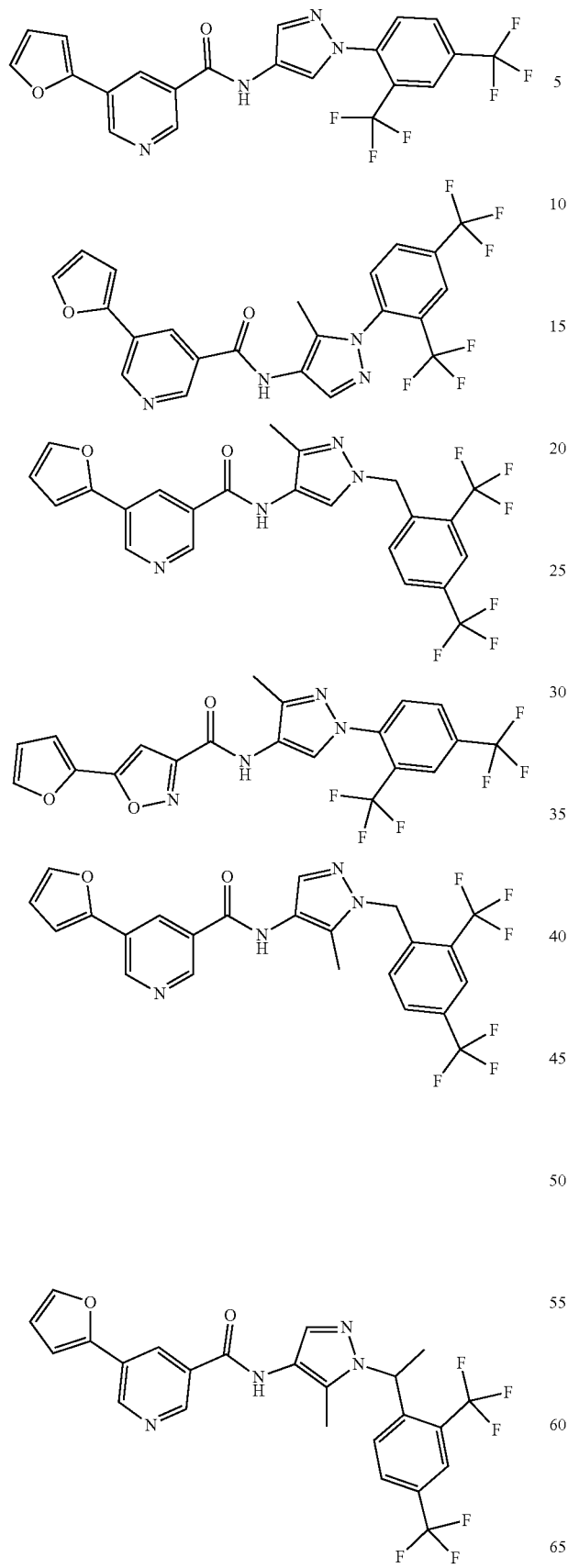
398
-continued
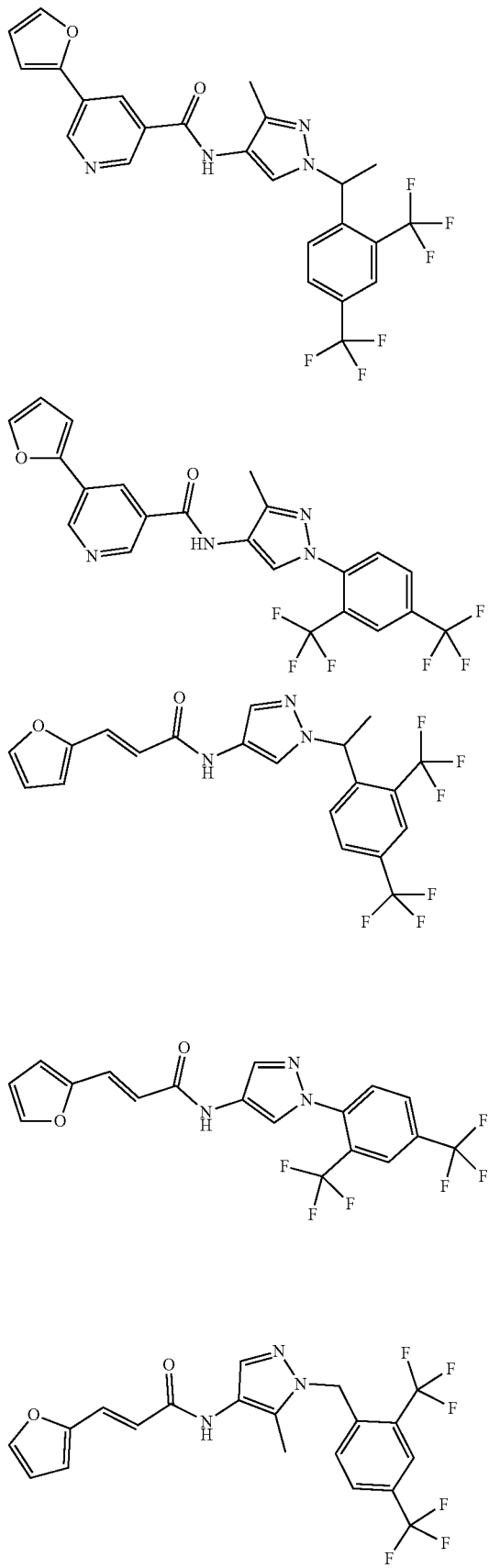

399
-continued
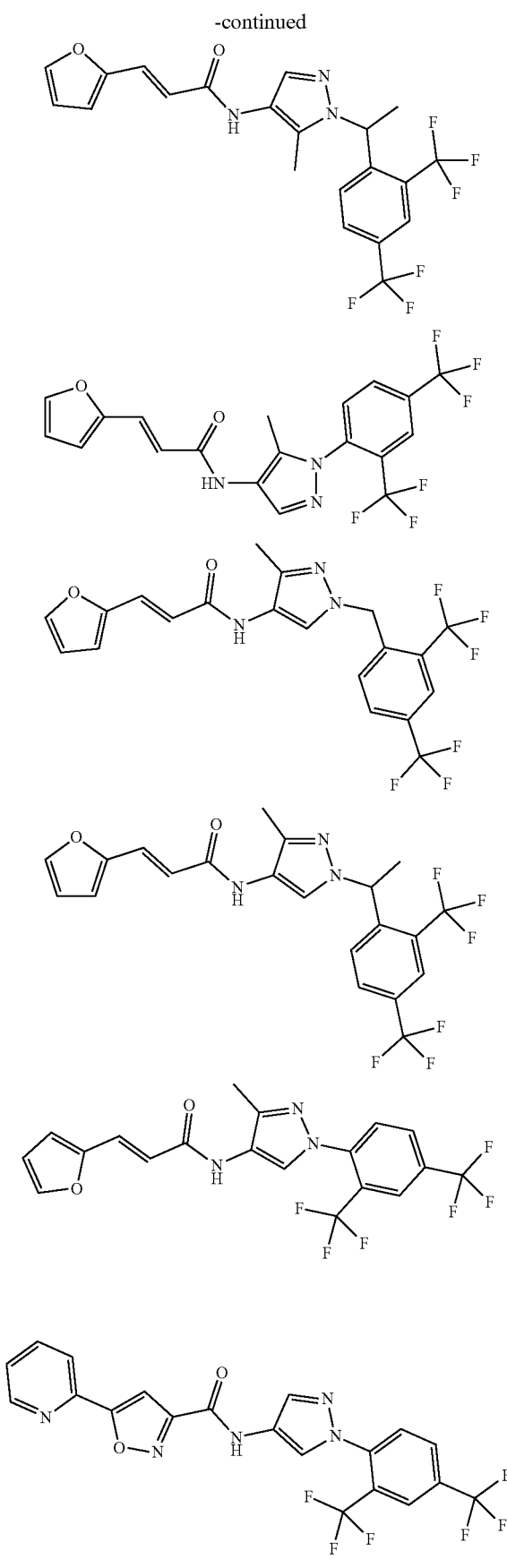
400
-continued
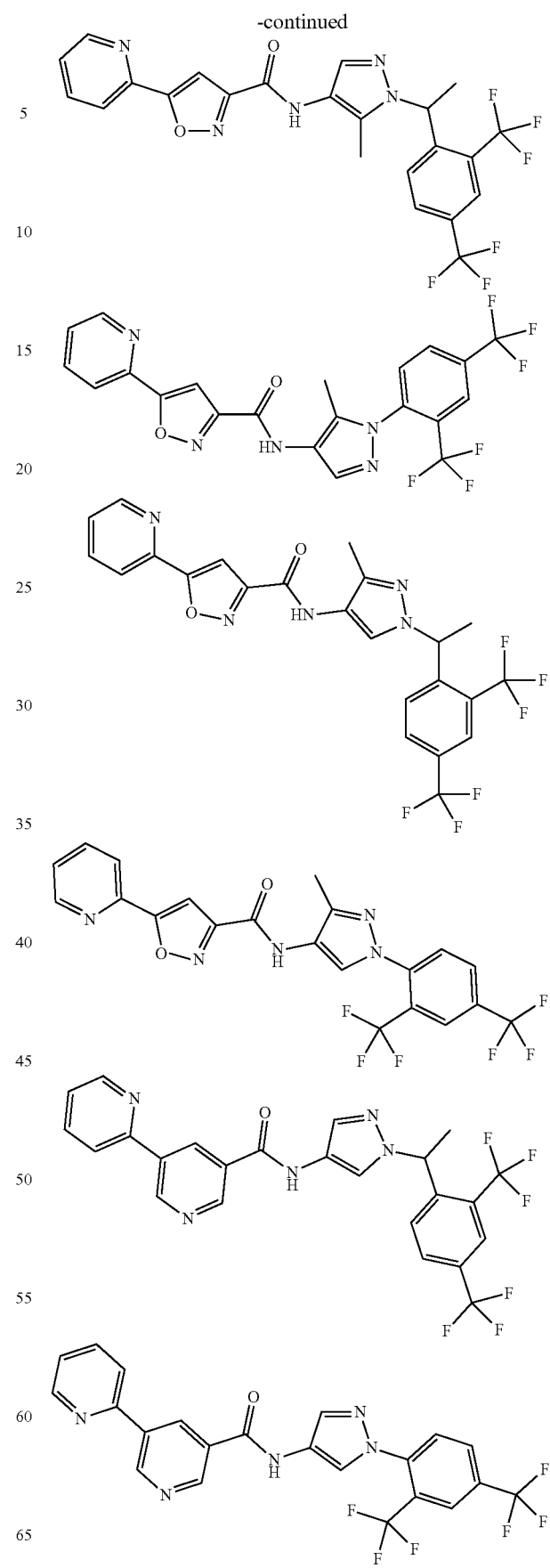

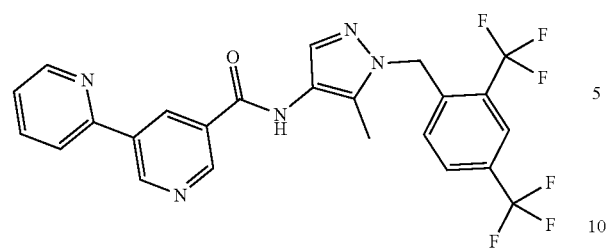
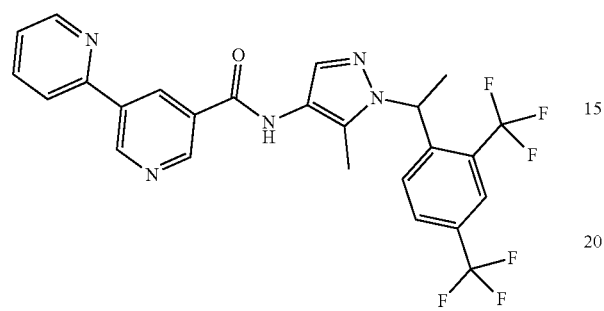
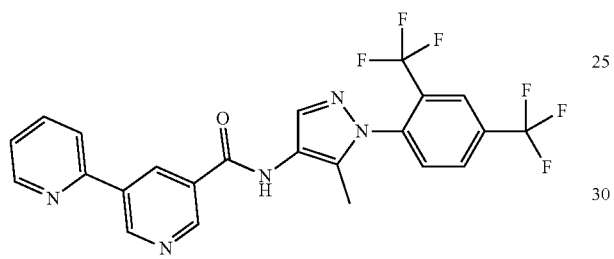
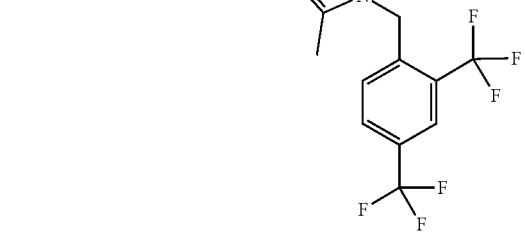
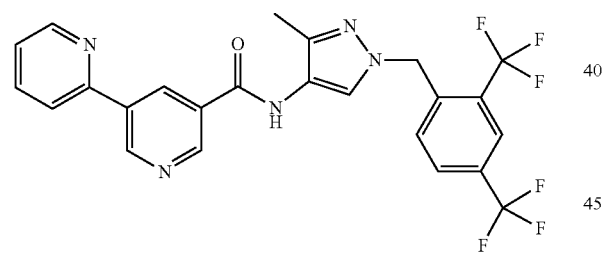
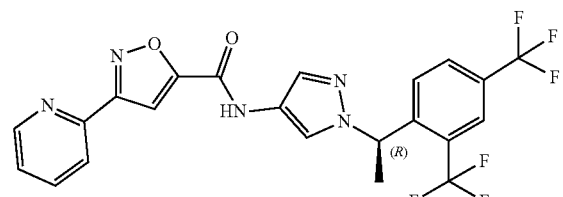
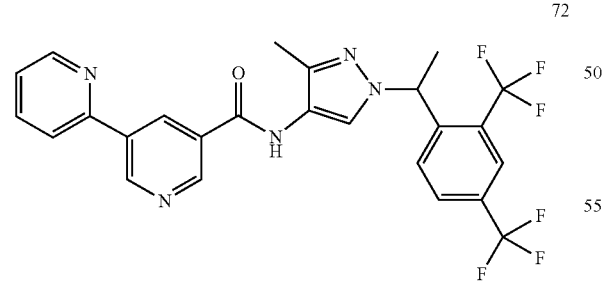
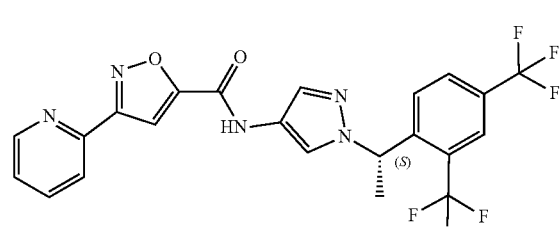
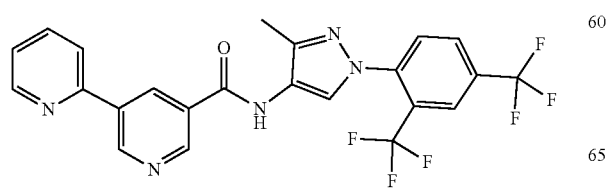
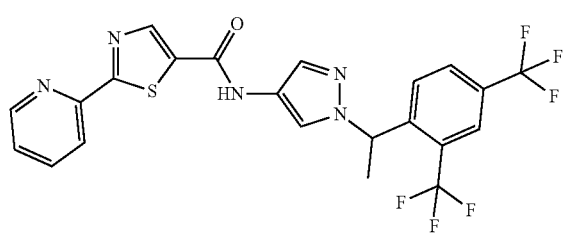

79
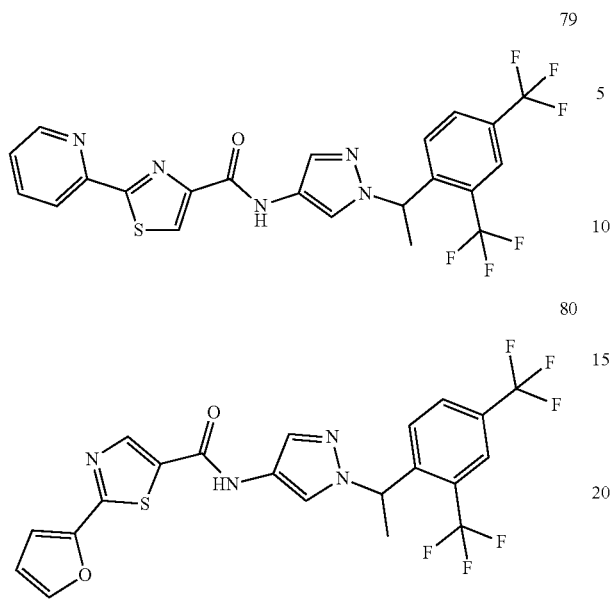
80
81
82
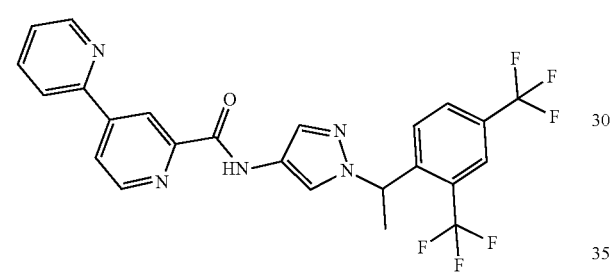
83
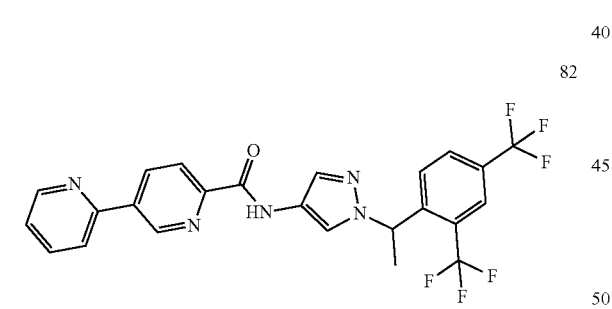
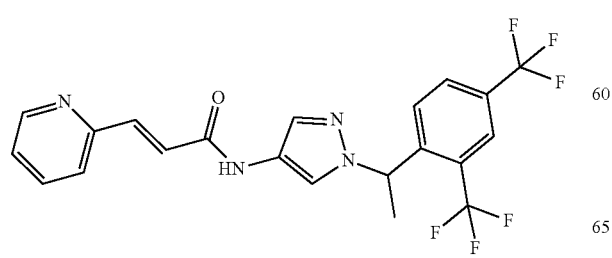
84
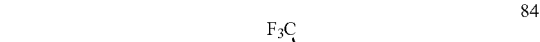
85
86
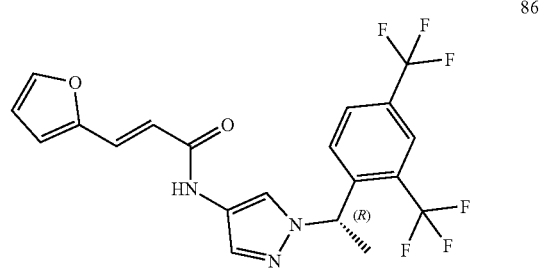
87
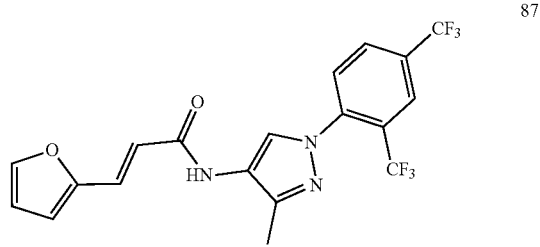
88
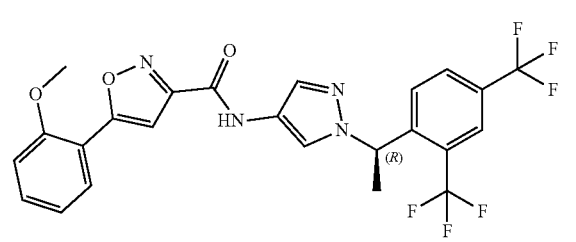
89
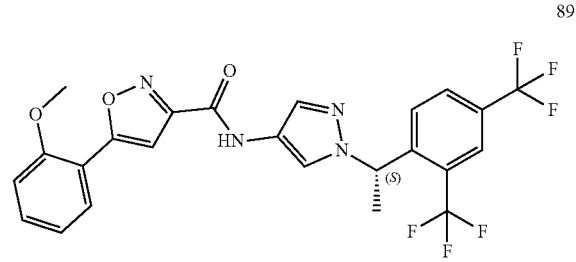

90
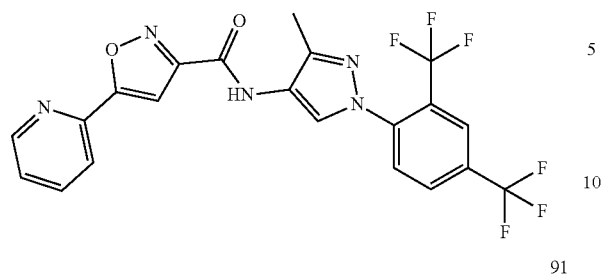
91
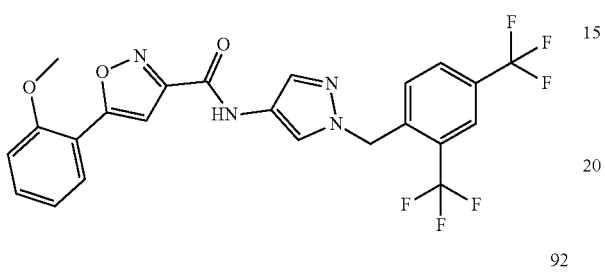
92
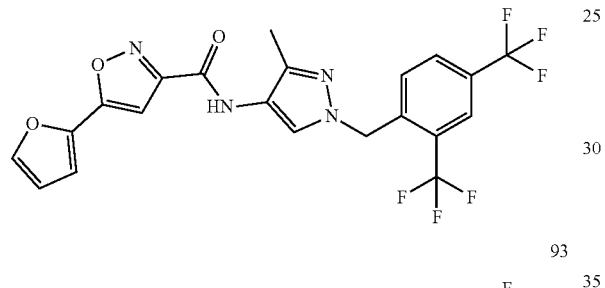
93
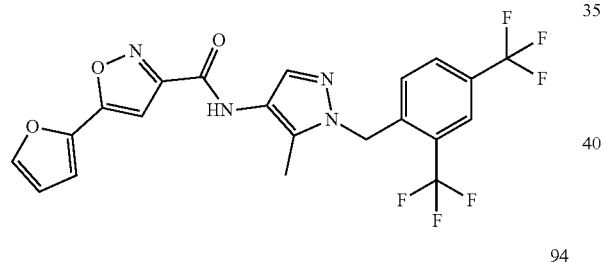
94
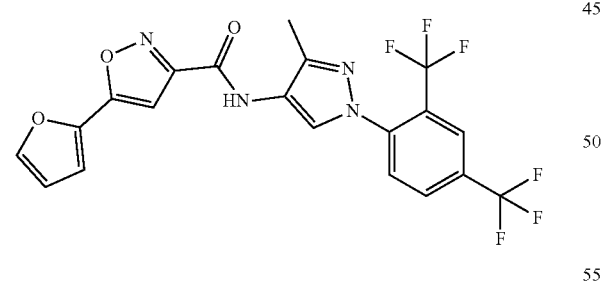
95
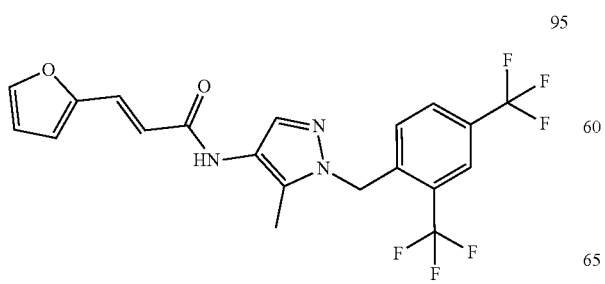
96
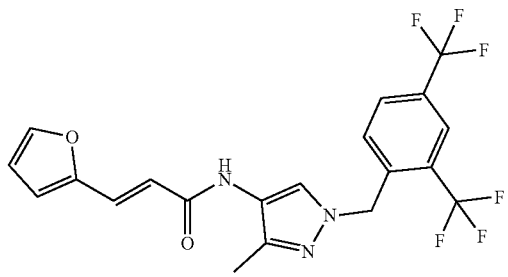
97
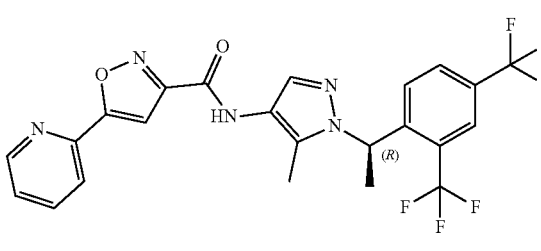
98
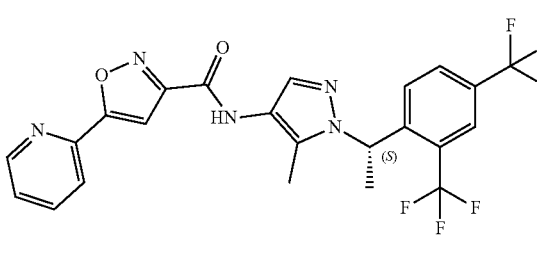
99
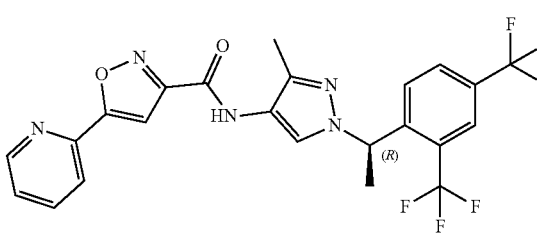
100
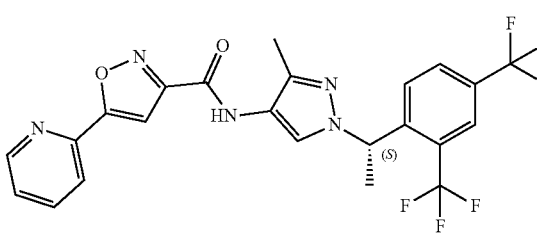
101
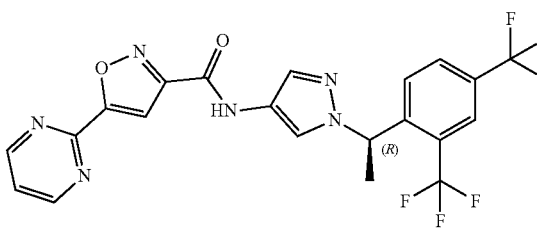

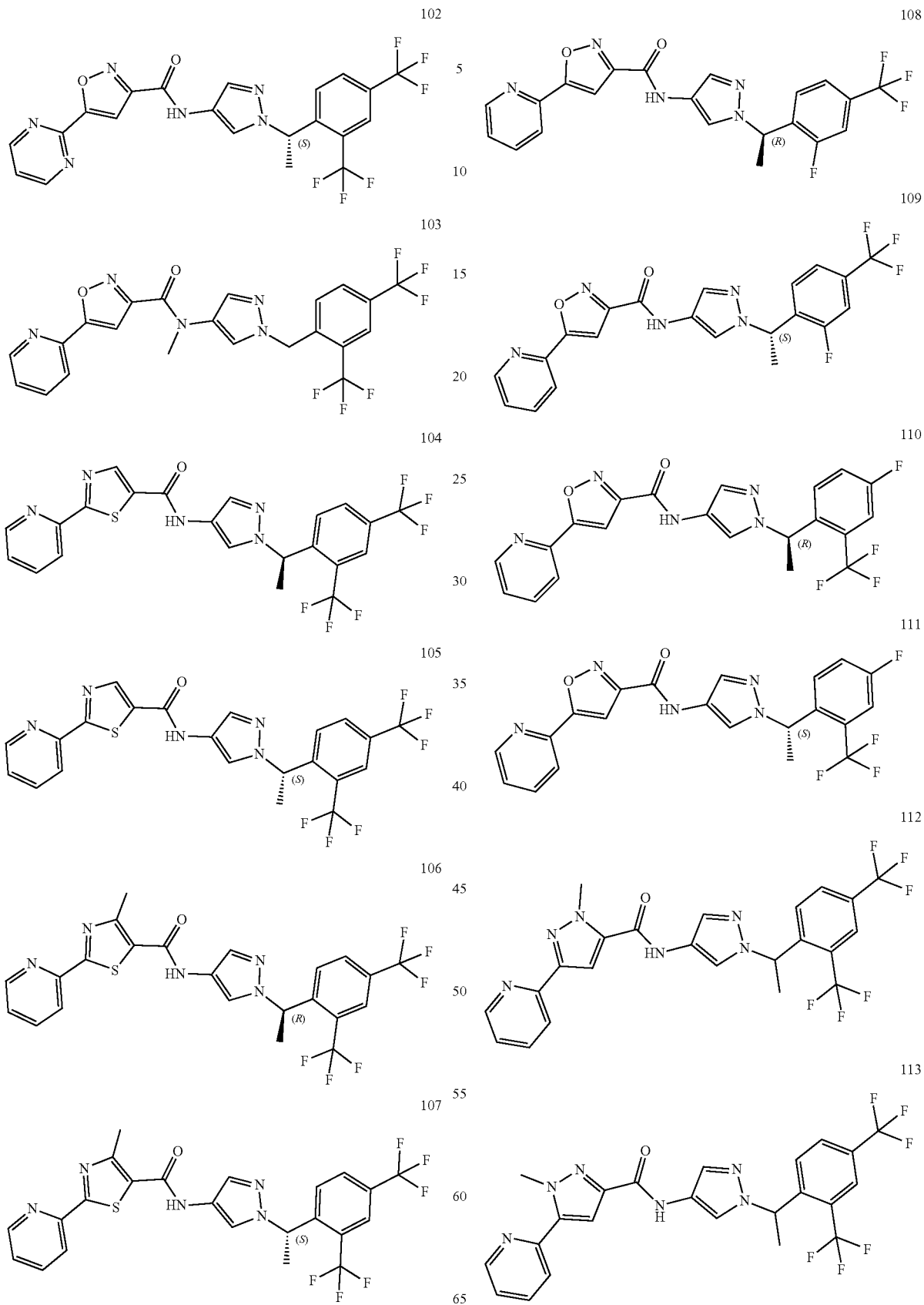

-continued

114

115

116

117

118

119

120

121

122

123

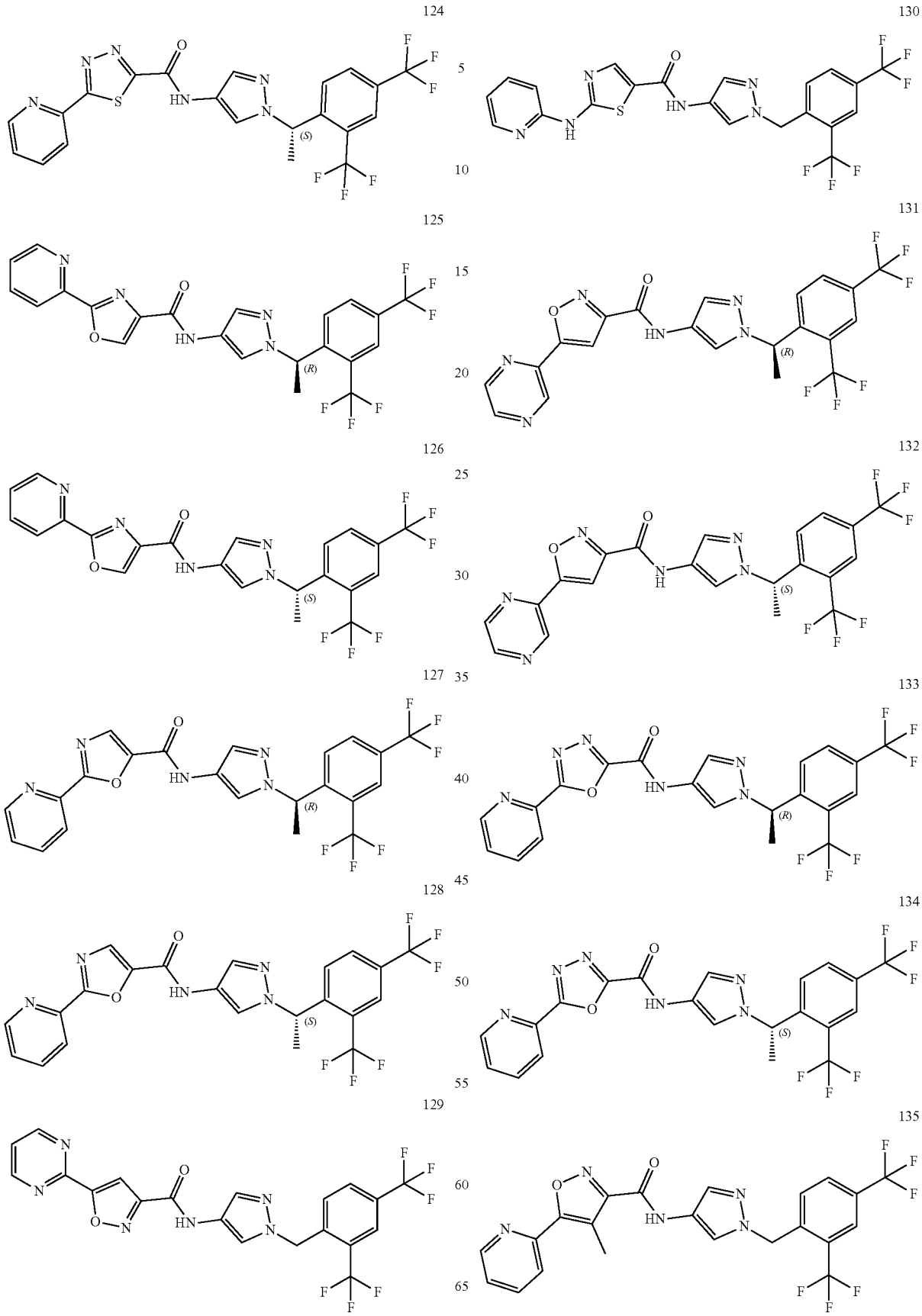

-continued
136
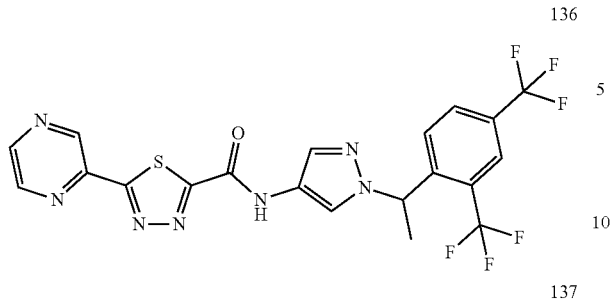
137
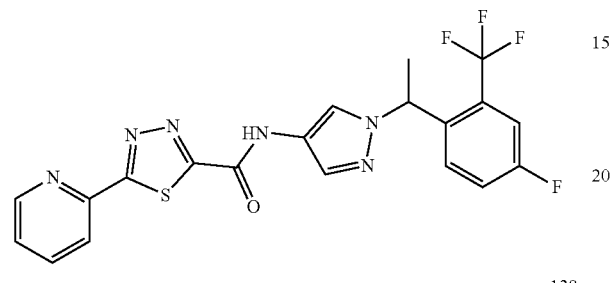
138
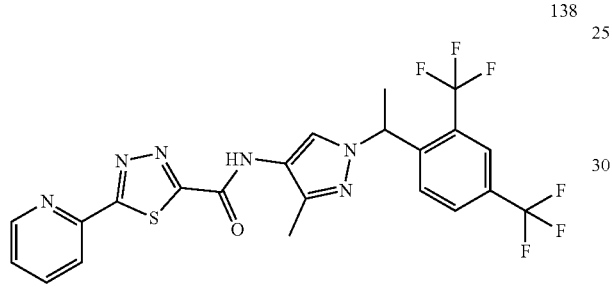
139
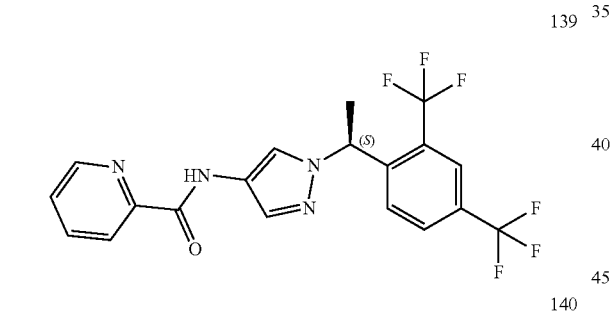
140
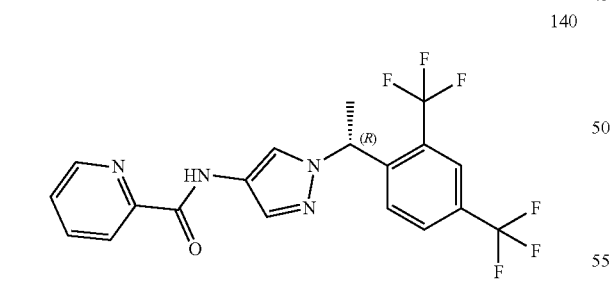
141
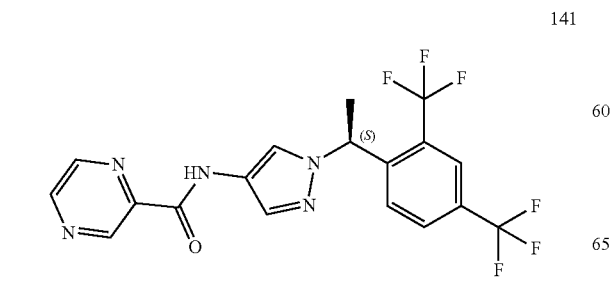
-continued
142
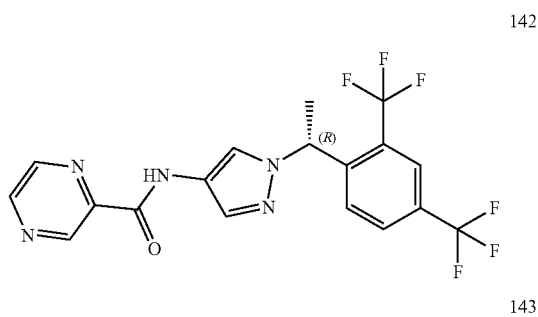
143
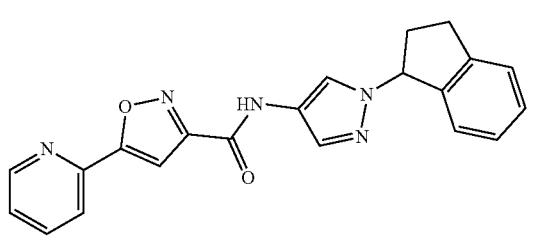
144
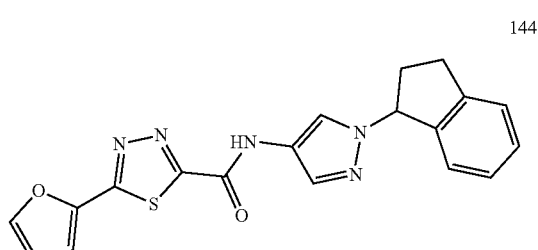
145
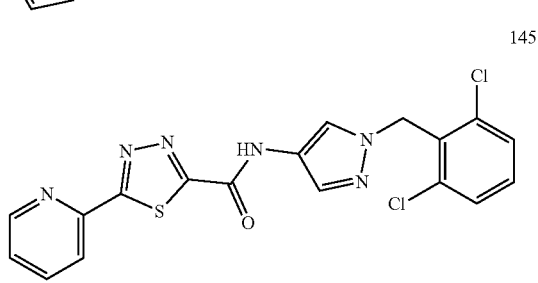
146
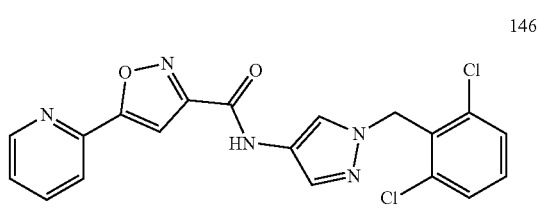
147
148
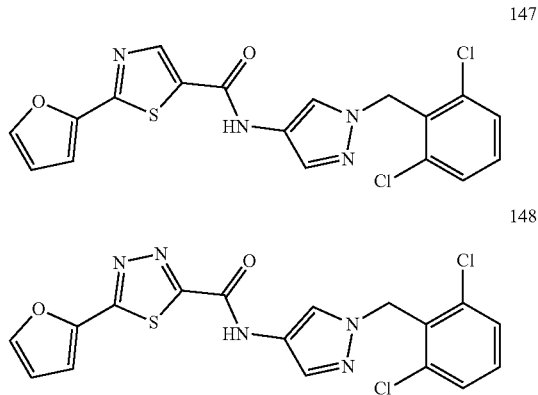

149
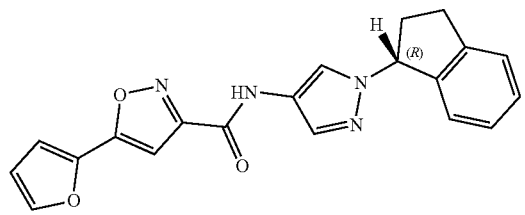
150
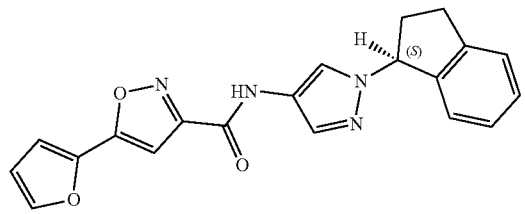
151
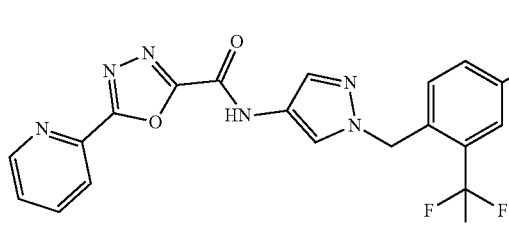
152
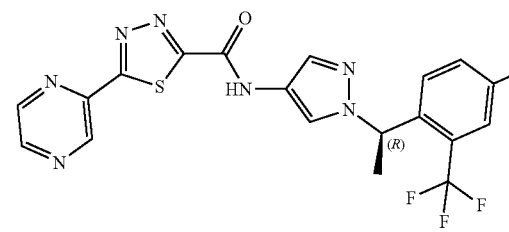
153
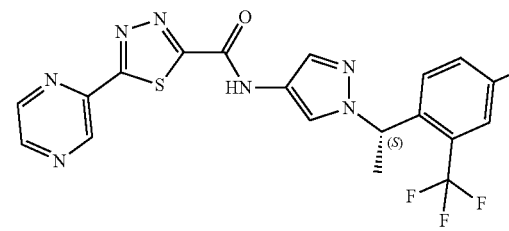
154
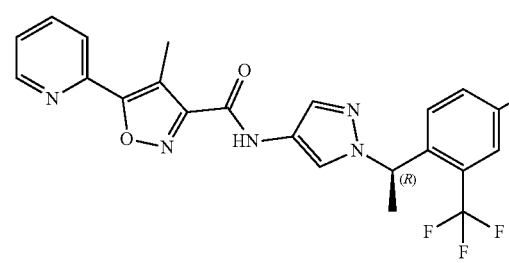
155
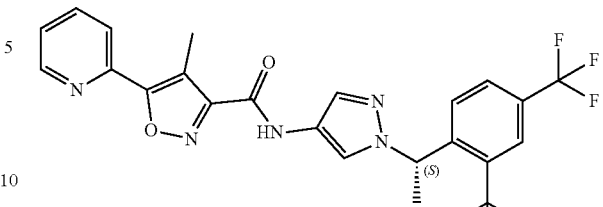
156
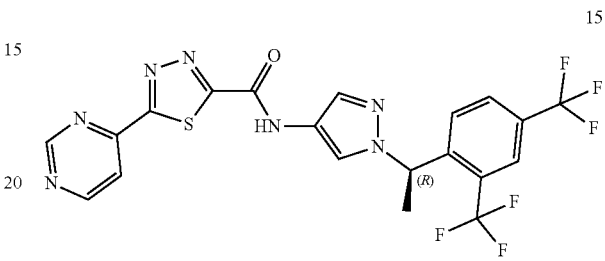
157
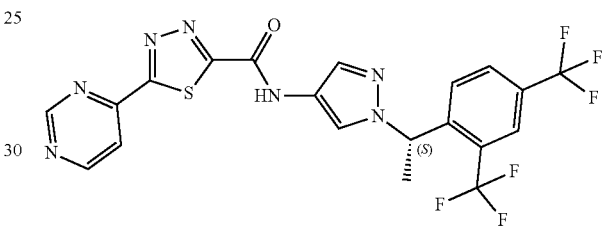
158
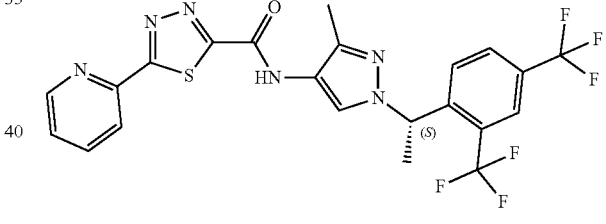
159
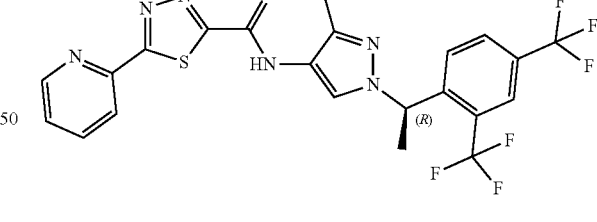
160

161

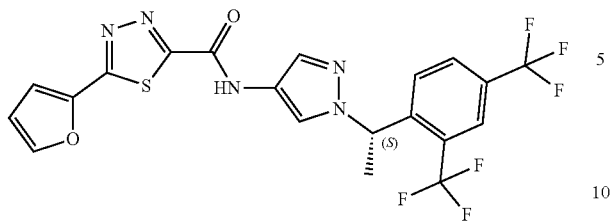

or a pharmaceutically acceptable salt thereof.

20. The method of claim 1, wherein the metabolic disease is non-alcoholic steatohepatitis.

21. A compound of Formula (A):

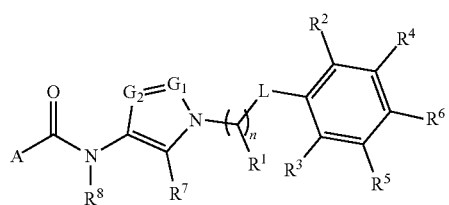

(A)

or a pharmaceutically acceptable salt thereof, wherein:
one of $G_1$ and $G_2$ is N and one of $G_1$ and $G_2$ is $CR^d$, wherein $R^d$ is H or $C_1$-$C_6$alkyl;
$R^1$ is H, $C_1$-$C_6$alkyl, or $C_3$-$C_6$cycloalkyl; or $R^1$ is H, $C_1$-$C_6$alkyl, $C_3$-$C_8$cycloalkyl, or $C_1$-$C_6$ haloalkyl;
$R^6$ is H or $C_1$-$C_6$alkyl,
n is 0 or 1;
L is —$CH_2$— or is absent;
$R^2$, $R^3$, $R^4$, $R^5$, and $R^6$ are each independently H, halo, CN, $C_1$-$C_6$alkyl, or $C_1$-$C_6$haloalkyl;
or $R^2$, $R^4$, $R^5$, and $R^6$ are each independently H, halo, CN, $C_1$-$C_6$alkyl, or $C_1$-$C_6$haloalkyl and $R^3$ is taken together with an $R^1$ and the atoms to which they are attached to form a 5- or 6-membered ring, wherein the 5- or 6-membered ring is unsubstituted or substituted with one to three groups selected from the group consisting of halo, CN, —OH, $C_1$-$C_6$alkyl, and $C_1$-$C_6$haloalkyl;
provided that either:
$R^3$ is taken together with $R^1$ and the atoms to which they are attached to form a 5- or 6-membered ring; or
at least two of $R^2$, $R^3$, $R^4$, $R^5$, and $R^6$ are other than H; or
one of $R^2$, $R^3$, $R^4$, $R^5$, and $R^6$ is cyano;

A is 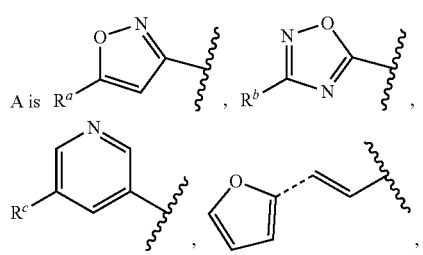

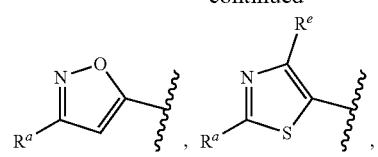

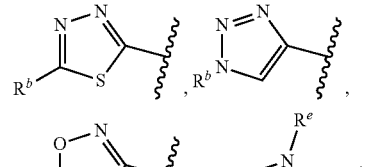

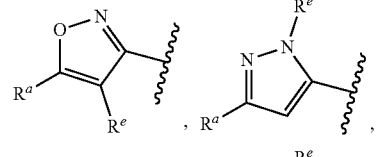

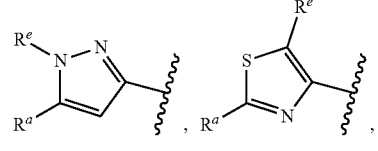

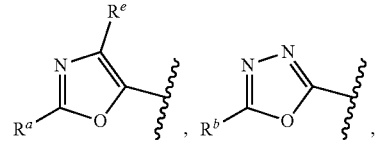

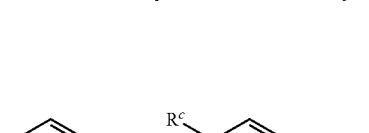

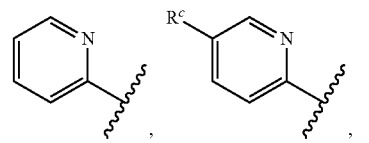

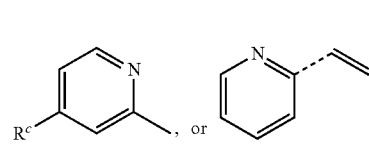

wherein --- indicates that

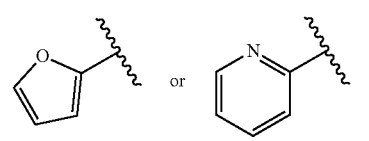 [SMILES: *c1ccco1 ; *c1ccccn1]

or is attached in either an E or Z configuration;

$R^a$ and $R^b$ are each independently H, $C_1$-$C_6$alkyl, —C(O) $C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^E$ and $R^b$ are unsubstituted or substituted with one to four groups selected from the group consisting of OH, halo, and $C_1$-$C_6$alkyl;

$R^c$ is $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^c$ is unsubstituted or substituted with one to four groups selected from the group consisting of OH, halo, and $C_1$-$C_6$alkyl;

$R^e$ is H or $C_1$-$C_6$alkyl;

provided that when A is

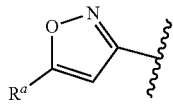

and $R^a$ is H, methyl, ethyl, n-Pr, i-Pr, i-Bu, 2-thio-furyl, 2-furyl, unsubstituted phenyl, 3-hydroxyphenyl, 4-hydroxyphenyl, 4-fluorophenyl, or 2,4-dichlorophenyl, at least one of (i)-(ix) applies:

(i) $G_2$ is N;
(ii) n is 1, L is absent, and $R^1$ is $C_1$-$C_6$alkyl;
(iii) n is 0, L is absent, and at least one of $R^2$, $R^3$, $R^4$, $R^5$, and $R^6$ is halo, CN, or $C_1$-$C_6$haloalkyl;
(iv) n is 1, and $R^3$ is taken together with $R^1$ and the atoms to which they are attached to form a 5- or 6-membered ring;
(v) one of $R^2$, $R^3$, $R^4$, $R^5$, and $R^6$ is CN; and
(vi) $R^4$ and $R^5$ are each independently Cl, Br, I, CN, $C_1$-$C_6$alkyl, or $C_1$-$C_6$haloalkyl;
(vii) one of $R^d$ and $R^7$ is $C_1$-$C_6$alkyl;
(viii) $R^2$ and $R^3$ are each Cl;
(ix) at least one of $R^2$, $R^3$, $R^4$, $R^5$, and $R^6$ is F, Br, I, CN, or $C_1$-$C_6$haloalkyl and $R^E$ is H or 2-thiofuryl;

provided that when A is

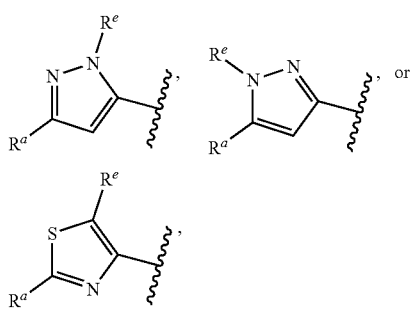

and n is 1, then $R^1$ is other than H;

provided that when A is

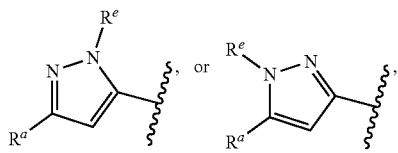

n is 0 and L is absent, then $R^e$ is other than H;

provided that when A is

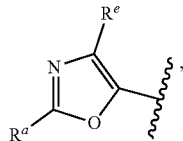

and $R^e$ is methyl, then $R^a$ is other than provided that when A is

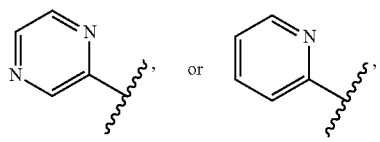 [SMILES: *c1cnccn1 ; *c1ccccn1]

n is 1 and L is absent, then $R^1$ is other than H;

and $R^7$ is H, $C_1$-$C_6$alkyl or $C_1$-$C_6$haloalkyl, provided that when $R^d$ is $C_1$-$C_6$alkyl, $R^7$ is H, and when $R^7$ is $C_1$-$C_6$alkyl, $R^d$ is H.

22. The compound of claim 21, wherein:

$R^1$ is H, $C_1$-$C_6$alkyl, or $C_3$-$C_8$cycloalkyl;

$R^8$ is H;

A is

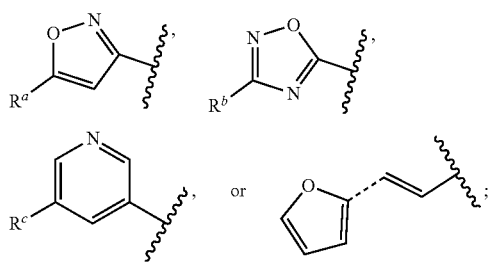

wherein --- indicates that

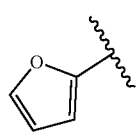 [SMILES: *c1ccco1]

is attached in either an E or Z configuration;

$R^a$, and $R^b$ are each independently H, $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^E$ and $R^b$ are unsubstituted or substituted with one to four groups selected from the group consisting of OH, halo, and $C_1$-$C_6$alkyl;

and is represented by Formula (I):

$$\text{(I)}$$

23. The compound of claim 21, wherein $G_1$ is N and $G_2$ is $CR^d$.
24. The compound of claim 21, wherein $R^d$ is H.
25. The compound of claim 21, wherein n is 1.
26. The compound of claim 21, wherein $R^3$ is taken together with $R^1$ and the atoms to which they are attached to form a 5- or 6-membered ring.
27. The compound of claim 21, wherein L is absent.
28. The compound of claim 21, wherein $R^2$, $R^3$, $R^4$, $R^5$, and $R^6$ are each independently H, Cl, CN, or $CF_3$.
29. The compound of claim 21, wherein:
$R^2$ and $R^6$ are each $CF_3$, or
$R^4$ and $R^5$ are each $CF_3$, or
$R^3$ and $R^6$ are each $CF_3$.
30. The compound of claim 21, wherein A is and $R^a$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^a$ are unsubstituted or substituted with one to four groups selected from the group consisting of OH, halo, and $C_1$-$C_6$alkyl.

31. The compound of claim 21, wherein A is

R and $R^a$ is selected from the group consisting of $C_1$-$C_6$alkyl, each of which is unsubstituted or is substituted with one to four groups selected from the group consisting of OH, halo, and $C_1$-$C_6$alkyl.

32. The compound of claim 21, wherein A is and $R^b$ is selected from the group consisting of H, $C_1$-$C_6$alkyl, —C(O)$C_1$-$C_6$alkyl, 6-membered aryl, and 5- or 6-membered heteroaryl, wherein each $C_1$-$C_6$alkyl, —C(O)$C_1$-$C_6$alkyl, 6-membered aryl, or 5- or 6-membered heteroaryl of $R^b$ is unsubstituted or is substituted with one to four groups selected from the group consisting of OH, halo, and $C_1$-$C_6$alkyl.

33. The compound of claim 21, wherein A is and $R^b$ is selected from the group consisting of $C_1$-$C_6$alkyl, each of which is unsubstituted or is substituted with one to four groups selected from the group consisting of OH, halo, and $C_1$-$C_6$alkyl.

34. The compound of claim 21, wherein A is

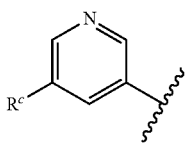

and $R^c$ is selected from the group consisting of $C_1$-$C_6$alkyl, —C(O)$C_1$-$C_6$alkyl, 6-membered aryl, or 5- or 6-membered heteroaryl, wherein each $C_1$-$C_6$alkyl, —C(O)$C_1$-$C_6$alkyl, 6-membered aryl, or 5- or 6-membered heteroaryl of $R^c$ is unsubstituted or is substituted with one to four groups selected from the group consisting of OH, halo, and $C_1$-$C_6$alkyl.

35. The compound of claim 21, wherein A is

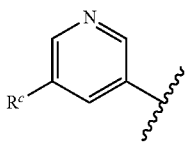

$R^c$ is selected from the group consisting of $C_1$-$C_6$alkyl,

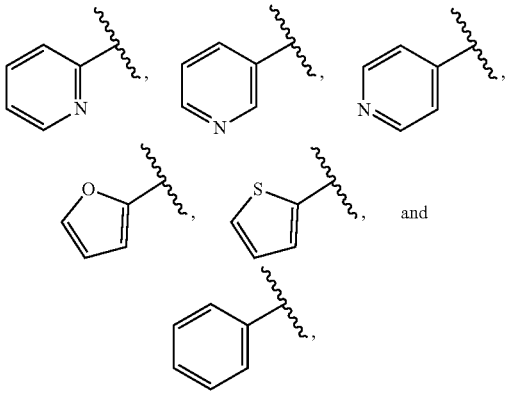

each of which is unsubstituted or is substituted with one to four groups selected from the group consisting of OH, halo, and $C_1$-$C_6$alkyl.

36. The compound of claim 21, wherein A is

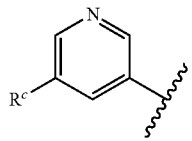

and $R^b$ is selected from the group consisting of H,

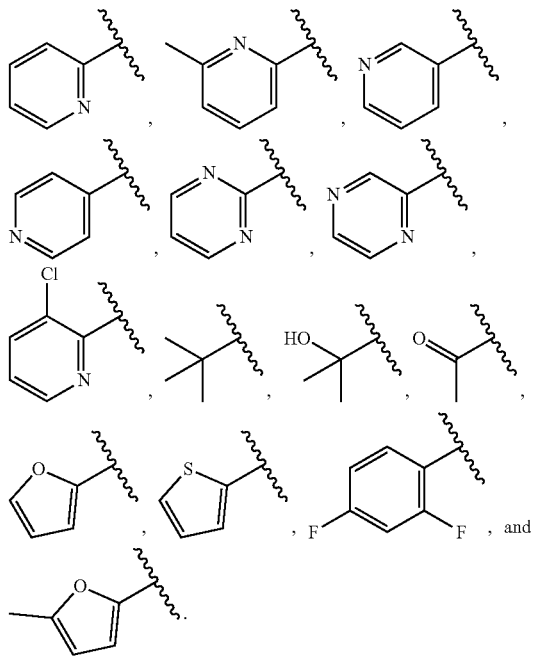

37. The compound of claim 21, wherein $R^7$ is H.

38. The compound of claim 21, wherein $R^7$ is $C_1$-$C_6$alkyl.

* * * * *

UNITED STATES PATENT AND TRADEMARK OFFICE
CERTIFICATE OF CORRECTION

PATENT NO. : 12,325,702 B2
APPLICATION NO. : 18/324826
DATED : June 10, 2025
INVENTOR(S) : Jennifer Alfaro et al.

Page 1 of 4

It is certified that error appears in the above-identified patent and that said Letters Patent is hereby corrected as shown below:

On the Title Page

Column 2, under References Cited; Foreign Patent Documents, Line 3, reading:
WO 2011/08776 A1 7/2011
Should read:
WO 2011/087776 A1 7/2011

In the Specification

Column 384, the second structure in Line 21 (approx.), reading:

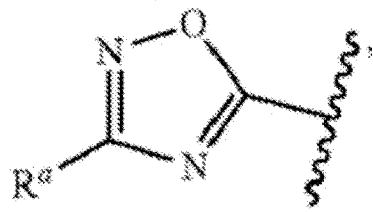

Should read:

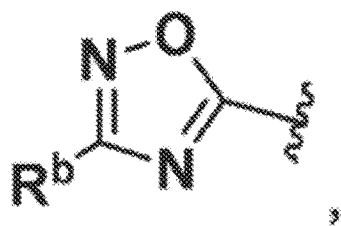

In the Claims

Column 385, Line 29, reading:
or is attached in either an E or Z configuration;
Should read:
is attached in either an E or Z configuration;

Signed and Sealed this
Ninth Day of September, 2025

Coke Morgan Stewart
*Acting Director of the United States Patent and Trademark Office*

CERTIFICATE OF CORRECTION (continued)
U.S. Pat. No. 12,325,702 B2

Column 386, Line 2, reading:
CN, or $C_1$-$C_6$haloalkyl and $R^E$ is H or 2-thiofuryl;
Should read:
CN, or $C_1$-$C_6$haloalkyl and $R^a$ is H or 2-thiofuryl;

Column 386, Line 42, reading:
provided that when A
Should read:
provided that when A is Column 387, Line 23, reading:
eroaryl of $R^E$ and $R^b$ are unsubstituted or substituted
Should read:
eroaryl of $R^a$ and $R^b$ are unsubstituted or substituted Column 388, Line 40, reading:
$R^b$ N and $R^b$ is selected from the group consisting of H,
Should read:
and $R^b$ is selected from the group consisting of H, Column 389, Line 39, reading:
R and $R^c$ is selected from the group consisting of
Should read:
and $R^c$ is selected from the group consisting of Column 404, Lines 25-35 (approx.), reading:

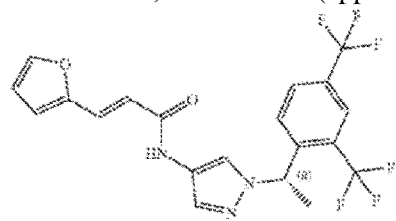

Should read:

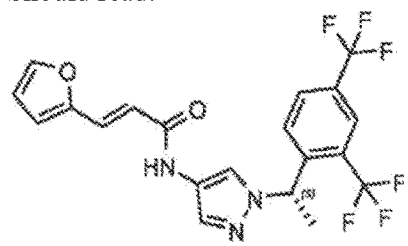

Column 417, Lines 33-35, reading:

CERTIFICATE OF CORRECTION (continued)
U.S. Pat. No. 12,325,702 B2

$R^1$ is H, $C_1$-$C_6$alkyl, or $C_3$-$C_6$cycloalkyl; or $R^1$ is H,
$C_1$-$C_6$alkyl, $C_3$-$C_8$cycloalkyl, or $C_1$-$C_6$ haloalkyl;
$R^6$ is H or $C_1$-$C_6$alkyl,
Should read:
$R^1$ is H, $C_1$-$C_6$alkyl, or $C_3$-$C_8$cycloalkyl; or $R^1$ is H,
$C_1$-$C_6$alkyl, $C_3$-$C_8$cycloalkyl, or $C_1$-$C_6$ haloalkyl;
$R^8$ is H or $C_1$-$C_6$alkyl, Column 418, Line 59, reading:
or is attached in either an E or Z configuration
Should read:
is attached in either an E or Z configuration Column 418, Line 65, reading:
eroaryl of $R^E$ and $R^b$ are unsubstituted or substituted
Should read:
eroaryl of $R^a$ and $R^b$ are unsubstituted or substituted Column 419, Line 39, reading:
CN, or $C_1$-$C_6$haloalkyl and $R^E$ is H or 2-thiofuryl;
Should read:
CN, or $C_1$-$C_6$haloalkyl and $R^a$ is H or 2-thiofuryl;

Column 420, Line 1, reading:
n is 0 and L is absent, then $R^e$ is other than H;
Should read:
n is 0 and L is absent, then $R^a$ is other than H;

Column 420, Line 13, reading:
and $R^e$ is methyl, then $R^a$ is other than provided that
Should read:
and $R^e$ is methyl, then $R^a$ is other than unsubstituted phenyl; provided that Column 420, Line 65, reading:
eroaryl of $R^E$ and $R^b$ are unsubstituted or substituted
Should read:
eroaryl of $R^a$ and $R^b$ are unsubstituted or substituted Column 421, Line 53, reading:
R and $R^a$ is selected from the group consisting of
Should read:
and $R^a$ is selected from the group consisting of Column 423, Line 29, reading:

$R^c$ is selected from the group consisting of $C_1$-$C_6$alkyl,

Should read:

and $R^c$ is selected from the group consisting of $C_1$-$C_6$alkyl,

SEQUENCE LISTING

```
Sequence total quantity: 1
SEQ ID NO: 1          moltype = DNA  length = 19
FEATURE               Location/Qualifiers
misc_feature          1..19
                      note = Synthetic Construct
source                1..19
                      mol_type = other DNA
                      organism = synthetic construct
SEQUENCE: 1
ccaatcggcg gcggccacg                                              19
```